US008048881B2

(12) United States Patent
Caroff et al.

(10) Patent No.: US 8,048,881 B2
(45) Date of Patent: Nov. 1, 2011

(54) PYRIMIDINE DERIVATIVES AND THEIR USE AS P2Y12 RECEPTOR ANTAGONISTS

(75) Inventors: Eva Caroff, Ranspach-le-Haut (FR); Heinz Fretz, Riehen (CH); Kurt Hilpert, Hofstetten (CH); Olivier Houille, Mulhouse (FR); Francis Hubler, Hégenheim (FR); Emmanuel Meyer, Aarau (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 1034 days.

(21) Appl. No.: 11/912,545

(22) PCT Filed: Apr. 27, 2006

(86) PCT No.: PCT/IB2006/051318
§ 371 (c)(1),
(2), (4) Date: Oct. 25, 2007

(87) PCT Pub. No.: WO2006/114774
PCT Pub. Date: Nov. 2, 2006

(65) Prior Publication Data
US 2008/0194576 A1 Aug. 14, 2008

(30) Foreign Application Priority Data
Apr. 28, 2005 (WO) ............... PCT/EP2005/004578
Nov. 10, 2005 (WO) ............... PCT/IB2005/053711

(51) Int. Cl.
*C07D 403/12* (2006.01)
*A61K 31/505* (2006.01)

(52) U.S. Cl. ........... 514/235.8; 514/252.11; 514/252.14; 514/252.18; 514/252.19; 514/252.2; 544/122; 544/295

(58) Field of Classification Search ................. 544/122, 544/295; 514/235.8, 252.11, 252.14, 252.18, 514/252.19, 252.2
See application file for complete search history.

(56) References Cited

FOREIGN PATENT DOCUMENTS

| JP | 53-073586 | 6/1978 |
|---|---|---|
| WO | WO-02/098856 A2 | 12/2002 |
| WO | WO-2004/052366 A1 | 6/2004 |
| WO | WO 2008/044217 | 4/2008 |
| WO | WO 2008/050301 | 5/2008 |
| WO | WO 2009/069100 | 6/2009 |
| WO | WO 2009/125365 | 10/2009 |
| WO | WO 2009/125366 | 10/2009 |
| WO | WO 2010/116328 | 10/2010 |
| WO | WO 2010/122504 | 10/2010 |

OTHER PUBLICATIONS

Vippagunta et al., Crystalline Solids, Advanced Drug Delivery Reviews, 48, pp. 3-26, 2001.*
West, Solid Solutions, Solid State Chemistry and its applications, pp. 358 & 365, 1988.*
Ulrich, Chapter 4: Crystallization, Kirk-Othmer Encyclopedia of Chemical Technology, pp. 1-7, Aug. 2002.*
Feokistov et al., Adenosine A2B receptors, Pharmacological Reviews, vol. 49, No. 4, pp. 381-402, 1997.*
Parlow J.J. et al. Bioorg Med Chem Lett. Aug. 15, 2009; 19, 6148-6156. Epub Sep. 10, 2009.
Bishop, Michael J.et al.; "3-($\alpha$R)-$\alpha$-((2S,5R)-4-Allyl-2,5-dimethyl-1-piperazinyl)-3-hydroxybenzyl)-$N$-alkyl-$N$-arylbenzamides: Potent, Non-Peptidic Agonists of Both the $\mu$ and $\delta$ Opioid Receptors"; J. Med. Chem. 2003, 46, pp. 623-633.
Fuerstner, Alois et al.; "Iron-Catalyzed Cross-Coupling Reactions"; J. Am. Chem. Soc., vol. 124, No. 46, 2002, pp. 13856-13863.
Gould, Philip L.; "Salt selection for basic drugs"; International Journal of Pharmaceutics, 33, 1986, pp. 201-217.
Parlow J.J. et al. Bioorg Med Chem Lett. Aug. 15, 2009; 19(16):4657-63. Epub Jun. 25, 2009.
Amir, J., et al., "Treatment of Thrombotic Thrombocytopenic Pupura with Antiplatelet Drugs", Blood, vol. 42, No. 1, pp. 27-33 Jul. 1973.
Antithrombotic Trialists' Collaboration, "Collaborative Meta-Analysis of Randomised Trials of Antiplatelet Therapy for Prevention of Death, Myocardial Infarction, and Stroke in High Risk Patients", British Medical Journal, vol. 324, pp. 71-86, 2002.
Balduini, C.L., et al., "Platelet Aggregation in Platelet-Rich Plasma and Whole Blood in 120 Patients with Myeloproliferative Disorders", Coagulation and Transfusion Medicine, vol. 95, No. 1, pp. 82-86, Jan. 1991.
Bertrand, Michel. E., "Randomized Multicenter Comparison of Conventional Anticoagulation Versus Antiplatelet Therapy in Unplanned and Elective Coronary Stenting: . . . " Circulation, vol. 98, pp. 1597-1603, 1998.
Brighton, T.A., et al., "Antiphospholipid Antibodies and Thrombosis", Bailliere's Clinical Haematology, vol. 7, No. 3, pp. 541-557, Sep. 1994.
Caprie Steering Committee, "A Randomized, Blinded, Trial of Clopidogrel Versus Asprin in Patients at Risk of Ischaemic Events (CAPRIE)", The Lancet, vol. 348, pp. 1329-1339, Nov. 16, 1996.
Collins, C.E. et al., "Review Article:Platelets in Inflammatory Bowel Diease-Pathogenic Role and Therapeutic Implications", Aliment Pharmacol. Ther., vol. 11, pp. 237-247, 1997.
Davies, M.J., et al., "Intramyocardial Platelet Aggregation in Patients with Unstable Angina Suffering Sudden Ischemic Cardiac Death", Pathophysiology and Natural History—Platelets, Circulation, vol. 73, No. 3, pp. 418-427, 1986. Felfernig-Boehm, D., et al., "Early Detection of Preeclampsia by Determination of Platelet Aggregability", Thrombosis Research, vol. 98, pp. 139-146, 2000.
Fox, K.A.A., et al. Benefits and Risks of the Combination of Clopidogrel and Aspirin in Patients Undergoing Surgical Revascularization for Non-ST-Elevation Acute Coronary Syndrome: The Clidogrel in Unstable Angina to Prevent Recurrent Ischemic Events (CURE) Trial, Circulation, vol. 110, pp. 1202-1208, 2004.
Halushka, P.V., et al., "Protective Effects of Aspirin in Endotoxic Shock", The Journal of Pharmacology and Experimental Therapeutics, vol. 218, No. 2, pp. 464-469, 1981.

(Continued)

*Primary Examiner* — Deepak Rao
(74) *Attorney, Agent, or Firm* — Hoxie & Associates LLC

(57) ABSTRACT

The invention relates to 4-aminocarbonyl-pyrimidine derivatives and their use as $P2Y_{12}$ receptor antagonists in the treatment and/or prevention and/or treatment of peripheral vascular, of visceral-, hepatic- and renal-vascular, of cardiovascular and of cerebrovascular diseases or conditions associated with platelet aggregation, including thrombosis in humans and other mammals.

16 Claims, No Drawings

OTHER PUBLICATIONS

Hovens, M.M.C., et al., "Aspirin in the Prevention and Treatment of Venous Thromboembolism", Journal of Thrombosis and Haemostasis, vol. 4, pp. 1470-1475, 2006.

Kharbanda, R.K., et al., "Prevention of Inflammation-Induced Endothelial Dysfunction: A Novel Vasculo-Protective Action of Aspirin", Circulation, vol. 105, pp. 2600-2604, 2002.

Megalopoulos, A., et al., "Recurrent Arterial Thromboses in a Woman with Heparin Induced Thrombocytopenia, Successfully Managed with Iloprost Followed by Clopidogrel. An Alternative Therapeutic Option for Heparin Induced Thrombocytopenia Type II Syndrome", International Angiology, vol. 25, No. 1, pp. 84-89, Mar. 2006.

Mehta, S.R., et al., "Effects of Pretreatment with Clopidogrel and Aspirin Followed by Long-Term Therapy in Patients Undergoing Percutaneous Coronary Intervention: The PCI-CURE Study", The Lancet, vol. 358, pp, 527-533, Aug. 18, 2001.

Payne, D.A., et al., "Beneficial Effects of Clopidogrel Combined with Aspirin in Reducing Cerebral Emboli in Patients Undergoing Carotid Endarterectomy", Circulation, vol. 109, pp. 1476-1481, 2004.

Stathakis, N.E., et al., Platelet Dysfunction in Essential Thrombocythaemia, Annals of Clinical Research, vol. 6, pp. 198-202, 1974.

Thorsen, C. A., et al., "The Treatment of the Hemolytic-Uremic Syndrome with Inhibitors, of Platelet Function", The American Journal of Medicine, vol. 66, pp. 711-716, Apr. 1979.

Triadou, P., et al., "Platelet Function in Sickle Cell Disease During Steady State", Nouvelle Revue Francaise Hematologie, vol. 32, pp. 137-142, 1990.

University of Perugia, "Aspirin for the Prevention of Recurrent Venous Thromboembolism and Cardiovascular Events", pp. 1-3, ClinicalTrials.gov/ct/show/NCT00222677, Sep. 13, 2005.

Yao, S., et al., "Clopidogrel is More Effective Than Aspirin as Adjuvant Treatment to Prevent Reocclusion After Thrombolysis", Am. J. Physiol., vol. 267, pp. H488-H493, 1994.

Amir, J., et al., "Treatment of Thrombotic Thrombocytopenic Pupura with Antiplatelet Drugs", Blood, vol. 42, No. 1, pp. 27-33 Jul. 1973.

Antithrombotic Trialists' Collaboration, "Collaborative Meta-Analysis of Randomised Trials of Antiplatelet Therapy for Prevention of Death, Myocardial Infarction, and Stroke in High Risk Patients", British Medical Journal, vol. 324, pp. 71-86, 2002.

Balduini, C.L., et al., "Platelet Aggregation in Platelet-Rich Plasma and Whole Blood in 120 Patients with Myeloproliferative Disorders", Coagulation and Transfusion Medicine, vol. 95, No. 1, pp. 82-86, Jan. 1991.

Bertrand, Michel. E., "Randomized Multicenter Comparison of Conventional Anticoagulation Versus Antiplatelet Therapy in Unplanned and Elective Coronary Stenting: . . . " Circulation, vol. 98, pp. 1597-1603, 1998.

Brighton, T.A., et al., "Antiphospholipid Antibodies and Thrombosis", Bailliere's Clinical Haematology, vol. 7, No. 3, pp. 541-557, Sep. 1994.

Caprie Steering Committee, "A Randomized, Blinded, Trial of Clopidogrel Versus Asprin in Patients at Risk of Ischaemic Events (CAPRIE)", The Lancet, vol. 348, pp. 1329-1339, Nov. 16, 1996.

Collins, C.E. et al., "Review Article:Platelets in Inflammatory Bowel Diease-Pathogenic Role and Therapeutic Implications", Aliment Pharmacol. Ther., vol. 11, pp. 237-247, 1997.

Davies, M.J., et al., "Intramyocardial Platelet Aggregation in Patients with Unstable Angina Suffering Sudden Ischemic Cardiac Death", Pathophysiology and Natural History—Platelets, Circulation, vol. 73, No. 3, pp. 418-427, 1986.

Felfernig-Boehm, D., et al., "Early Detection of Preeclampsia by Determination of Platelet Aggregability", Thrombosis Research, vol. 98, pp. 139-146, 2000.

Fox, K.A.A., et al. Benefits and Risks of the Combination of Clopidogrel and Aspirin in Patients Undergoing Surgical Revascularization for Non-ST-Elevation Acute Coronary Syndrome: The Clidogrel in Unstable Angina to Prevent Recurrent Ischemic Events (CURE) Trial, Circulation, vol. 110, pp. 1202-1208, 2004.

Halushka, P.V., et al., "Protective Effects of Aspirin in Endotoxic Shock", The Journal of Pharmacology and Experimental Therapeutics, vol. 218, No. 2, pp. 464-469, 1981.

Hovens, M.M.C., et al., "Aspirin in the Prevention and Treatment of Venous Thromboembolism", Journal of Thrombosis and Haemostasis, vol. 4, pp. 1470-1475, 2006.

Kharbanda, R.K., et al., "Prevention of Inflammation-Induced Endothelial Dysfunction: A Novel Vasculo-Protective Action of Aspirin", Circulation, vol. 105, pp. 2600-2604, 2002.

Megalopoulos, A., et al., "Recurrent Arterial Thromboses in a Woman with Heparin Induced Thrombocytopenia, Successfully Managed with Iloprost Followed by Clopidogrel. An Alternative Therapeutic Option for Heparin Induced Thrombocytopenia Type II Syndrome", International Angiology, vol. 25, No. 1, pp. 84-89, Mar. 2006.

Mehta, S.R., et al., "Effects of Pretreatment with Clopidogrel and Aspirin Followed by Long-Term Therapy in Patients Undergoing Percutaneous Coronary Intervention: The PCI-CURE Study", The Lancet, vol. 358, pp, 527-533, Aug. 18, 2001.

Payne, D.A., et al., "Beneficial Effects of Clopidogrel Combined with Aspirin in Reducing Cerebral Emboli in Patients Undergoing Carotid Endarterectomy", Circulation, vol. 109, pp. 1476-1481, 2004.

Stathakis, N.E., et al., Platelet Dysfunction in Essential Thrombocythaemia, Annals of Clinical Research, vol. 6, pp. 198-202, 1974.

Thorsen, C. A., et al., "The Treatment of the Hemolytic-Uremic Syndrome with Inhibitors, of Platelet Function", The American Journal of Medicine, vol. 66, pp. 711-716, Apr. 1979.

Triadou, P., et al., "Platelet Function in Sickle Cell Disease During Steady State", Nouvelle Revue Francaise Hematologie, vol. 32, pp. 137-142, 1990.

University of Perugia, "Aspirin for the Prevention of Recurrent Venous Thromboembolism and Cardiovascular Events", pp. 1-3, ClinicalTrials.gov/ct/show/NCT00222677, Sep. 13, 2005.

Yao, S., et al., "Clopidogrel is More Effective Than Aspirin as Adjuvant Treatment to Prevent Reocclusion After Thrombolysis", Am. J. Physiol., vol. 267, pp. H488-H493, 1994.

* cited by examiner

PYRIMIDINE DERIVATIVES AND THEIR USE AS P2Y12 RECEPTOR ANTAGONISTS

This application is a 371 of PCT/IB06/51318 filed Apr. 27, 2006.

FIELD OF THE INVENTION

The present invention relates to pyrimidine derivatives and their use as $P2Y_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals.

BACKGROUND OF THE INVENTION

Hemostasis is referred to as the natural balance of maintaining the fluidity of the blood in the vascular system and preventing excessive blood loss subsequent to blood vessel injury by rapid formation of a solid blood clot. After vascular damage, contraction of the vessels and platelet adhesion occur immediately followed by aggregation of the platelets, activation of the coagulation cascade and finally also of the fibrinolytic system. Haemostatic abnormalities can lead to excessive bleeding or thrombosis, both life-threatening situations.

A series of antiplatelet agents have been developed over the past several years based on different mechanisms of action. The most widely used agent in antiplatelet therapy is aspirin, which irreversibly inhibits cyclooxygenase-1 and thereby affecting the thromboxane pathway. Although not optimally efficacious, treatment with aspirin remains the standard therapy against which new therapeutics are compared and judged.

Other drugs like the phosphodiesterase inhibitors dipyridamole and cilostazol, as well as the vitamin K antagonists (warfarin), are marketed but do not show all desirable features for such drugs. Three intravenously applicable, potent GPIIb/IIIa receptor antagonists (abciximab, eptifibatide, and tirofiban) blocking platelet aggregation are available on the market. Besides, some orally active GPIIb/IIIa antagonists (e.g. sibrafiban, xemilofiban or orbofiban) have not been successful in clinical development so far.

Adenosine 5'-diphosphate (ADP) is a key mediator in platelet activation and aggregation interfering with two platelet ADP receptors $P2Y_1$ and $P2Y_{12}$.

Antagonists of the platelet ADP receptor have been identified and display inhibition of platelet aggregation and antithrombotic activity. The most effective antagonists known so far are the thienopyridines ticlopidine, clopidogrel and CS-747, which have been used clinically as antithrombotic agents. It could be shown that these drugs, via their reactive metabolites, irreversibly block the ADP receptor subtype $P2Y_{12}$.

Some $P2Y_{12}$ antagonists like AR-C69931MX (Cangrelor) or AZD6140 have reached phase II clinical studies. These inhibitors are selective platelet ADP receptor antagonists, which inhibit ADP-dependent platelet aggregation, and are effective in vivo.

Piperazino-carbonylmethylaminocarbonyl-naphtyl or -quinolyl derivatives have been described as ADP receptor antagonists in WO 02/098856 and WO 2004/052366.

However, only a few 2-phenyl-4-(carbonylmethylaminocarbonyl)-pyrimidine derivatives are known in the art: indeed, only JP 53073586 describes penicillin derivatives possessing such a motif (as antibiotic agents).

DESCRIPTION OF THE INVENTION

The present invention firstly relates to the compounds of formula I

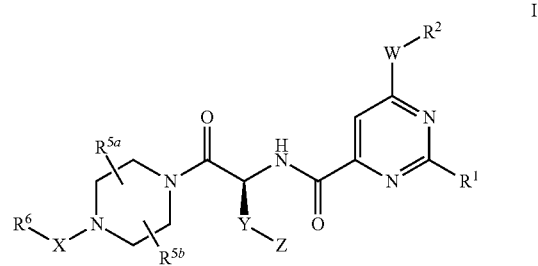

wherein
$R^1$ represents phenyl optionally substituted 1 to 3 times (preferably optionally substituted once or twice and more preferably optionally substituted once) by substituents each independently selected from the group consisting of halogen, methyl, methoxy, trifluoromethyl and trifluoromethoxy;
W represents a bond, and $R^2$ represents alkyl, haloalkyl, cyano, hydroxyalkyl, hydroxyalkyl substituted on its alkyl chain with an unsubstituted phenyl group, alkoxyalkyl, heterocyclyl, heterocyclylalkyl, cycloalkyl, cycloalkylalkyl, aryl, heteroaryl, or one of the radicals

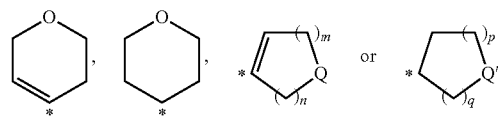

wherein:
m is 0 and n is 2 or 3 or m is 1 and n is 2,
p is 0 and q is 2 or 3, or p is 1 and q is 2 or also p is 2 or 3 and q is 0,
Q is —CO— or —CH(OR$^a$)—, R$^a$ being hydrogen or alkyl, and
Q' is —CO—; or
W represents —CH$_2$— and $R^2$ represents —NR$^7$R$^8$, —SR$^9$ or —SO$_2$R$^{10}$;
W represents —O— or —S— and $R^2$ represents alkyl, carboxyalkyl, alkoxycarbonylalkyl, hydroxyalkyl, alkoxyalkyl, heterocyclylalkyl, cycloalkyl, cycloalkylalkyl, aryl, aralkyl, heteroaryl or heteroarylalkyl;
W represents —NR$^3$— and $R^2$ represents hydrogen, alkyl, dialkylaminoalkyl, alkoxycarbonylalkyl, carboxyalkyl, carboxyalkyl substituted on its alkyl part with an unsubstituted phenyl group, hydroxyalkyl, alkoxyalkyl, heterocyclyl, heterocyclylalkyl, cycloalkyl, cycloalkylalkyl, aryl, 2-phenylcyclopropyl, aralkyl, diphenylalkyl, heteroarylalkyl wherein the heteroaryl is a monocyclic heteroaryl, —COR$^{11}$ or —SO$_2$R$^{12}$;
W represents —CH═CH— and $R^2$ represents alkyl, hydroxyalkyl, alkoxyalkyl, alkoxycarbonyl, phenyl or —CO—NR$^{13}$R$^{14}$; or
W represents —C≡C— and $R^2$ represents hydrogen, alkyl, hydroxyalkyl or alkoxyalkyl; or
W represents —CO— and $R^2$ represents alkyl;

R³ represents hydrogen or alkyl;

R⁷ represents alkyl or arylalkyl;

R⁸ represents alkyl;

or R⁷ and R⁸ form, together with the nitrogen that carries them, a heterocyclic ring of 4 to 7 members wherein the members needed to complete said heterocyclic ring are each independently selected from —CH₂—, —CH(CH₃)—, —CHR^y—, —O—, —S—, —CO— and —NR^z—, it being understood however that said heterocyclic ring does not contain more than one member selected from the group consisting of —CHR^y—, —O—, —S—, —CO— and —NR^z—, R^y representing hydroxy, hydroxymethyl, alkoxymethyl, alkoxycarbonyl or alkoxy and R^z representing hydrogen, alkyl or alkoxycarbonyl;

R⁹ represents cycloalkyl or aryl;

R¹⁰ represents alkyl, cycloalkyl or aryl;

R¹¹ represents alkyl, alkoxyalkyl, cycloalkyl, cycloalkylalkyl, aryl, monocyclic heteroaryl or aralkyl;

R¹² represents alkyl or aryl;

R¹³ represents alkyl;

R¹⁴ represents alkyl;

or W represents —NR³— and R² and R³ form, together with the nitrogen that carries them, a heterocyclic ring of 4 to 7 members wherein the members needed to complete said heterocyclic ring are each independently selected from —CH₂—, —CHR^x—, —O—, —S—, —CO— and —NR⁴—, it being understood however that said heterocyclic ring does not contain more than one member selected from the group consisting of —CHR^x—, —O—, —S—, —CO— and —NR⁴—, R^x representing hydroxy, hydroxymethyl, alkoxymethyl or alkoxy and R⁴ representing hydrogen or alkyl;

or also W represents —NR³— and R² and R³ form, together with the nitrogen that carries them, either an imidazolyl, pyrazolyl, 1,2,3-triazolyl or 1,2,4-triazolyl ring, which ring may be substituted by an alkyl group, or a 4-oxo-4H-pyridin-1-yl, 4,5-dihydro-pyrazol-1-yl, 2-methyl-4,5-dihydro-imidazol-1-yl or 3-methyl-5-oxo-2,5-dihydro-pyrazol-1-yl ring;

each of R^{5a} and R^{5b} represents independently hydrogen or methyl;

X represents —CO— and R⁶ represents alkyl, cycloalkyl, alkoxy, alkynyloxy, aryloxy, aralkoxy, aryl, monocyclic heteroaryl, aralkyl or NR¹⁵R¹⁶, or X represents —SO₂— and R⁶ represents alkyl R¹⁵ represents alkyl;

R¹⁶ represents hydrogen or alkyl;

or R¹⁵ and R¹⁶ form, together with the nitrogen that carries them, a heterocyclic ring of 4 to 7 members wherein the members needed to complete said heterocyclic ring are each independently selected from —CH₂—, —O—, —S— and —NR^w—, R^w representing hydrogen or alkyl, it being understood however that said heterocyclic ring does not contain more than one member selected from the group consisting of —O—, —S— and —NR^w—; and Y represents a bond and Z represents hydrogen or aryl substituted by carboxyalkoxy; or Y represents alkylene, alkoxyalkylene, phenylalkylene, alkoxyphenylene or alkoxyphenylalkylene and Z represents hydrogen, —OH, —NH₂, —COOH, tetrazolyl, —CO—NH₂, —COOR¹⁷, —NH—CO—R¹⁷, —NH—COOR¹⁷ or —NH—SO₂—R¹⁷, R¹⁷ representing alkyl.

A particular embodiment of this invention relates to compounds of formula $I_{P2}$

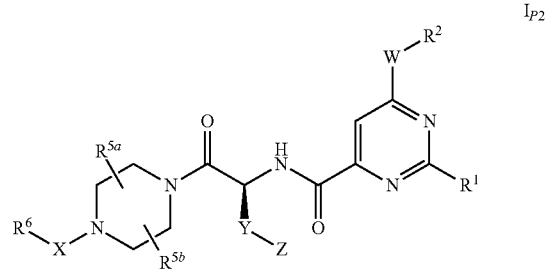

wherein

R¹ represents phenyl optionally substituted 1 to 3 times (preferably optionally substituted once or twice and more preferably optionally substituted once) by substituents each independently selected from the group consisting of halogen, methyl, methoxy, trifluoromethyl and trifluoromethoxy;

W represents a bond, —CH₂—, —O—, —S— or —NR³— and R² represents alkyl, dialkylaminoalkyl, alkoxycarbonylalkyl, carboxyalkyl, carboxyalkyl substituted with an unsubstituted phenyl group, hydroxyalkyl, alkoxyalkyl, heterocyclyl, heterocyclylalkyl, cycloalkyl, cycloalkylalkyl, aryl, 2-phenylcyclopropyl, aralkyl, diphenylalkyl, or one of the radicals

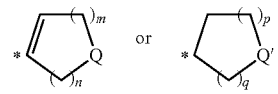

wherein:

m is 0 and n is 2 or 3 or m is 1 and n is 2, p is 0 and q is 2 or 3 or p is 1 and q is 2, Q is —CO— or —CH(OR^a)—, R^a being hydrogen or alkyl, and Q' is —CO—, it being understood that if W represents —O—, —S— or —NR³—, then R² may also represent heteroarylalkyl; or W represents —CH=CH— or —C≡C— and R² represents hydrogen, alkyl or hydroxyalkyl;

R³ represents hydrogen or alkyl;

or W represents —NR³— and R² and R³ form, together with the nitrogen that carries them, a heterocyclic ring of 4 to 7 members wherein the members needed to complete said heterocyclic ring are each independently selected from —CH₂—, —CHR^x—, —O—, —S—, —CO— and —NR⁴—, it being understood however that said heterocyclic ring does not contain more than one member selected from the group consisting of —CHR^x—, —O—, —S—, —CO— and —NR⁴—, R^x representing hydroxy, hydroxymethyl, alkoxymethyl or alkoxy and R⁴ representing hydrogen or alkyl;

or also W represents —NR³— and R² and R³ form, together with the nitrogen that carries them, an imidazolyl, pyrazolyl, 1,2,3-triazolyl or 1,2,4-triazolyl ring;

each of R^{5a} and R^{5b} represents independently hydrogen or methyl;

X represents —CO— and R⁶ represents alkoxy, alkynyloxy, aryloxy, aryl, heteroaryl or aralkyl or X represents —SO₂— and R⁶ represents alkyl; and Y represents a bond and Z represents hydrogen or aryl substituted by carboxyalkoxy;
or Y represents alkylene, alkoxyalkylene, phenylalkylene, alkoxyphenylene or alkoxyphenylalkylene and Z represents hydrogen, —OH, —NH$_2$, —COOH, tetrazolyl, —CO—NH$_2$, —COOR$^8$, —NH—CO—R$^8$, —NH—COOR$^8$ or —NH—SO$_2$—R$^8$, R$^8$ representing alkyl.

Another particular embodiment of this invention relates to compounds of formula I$_{P1}$

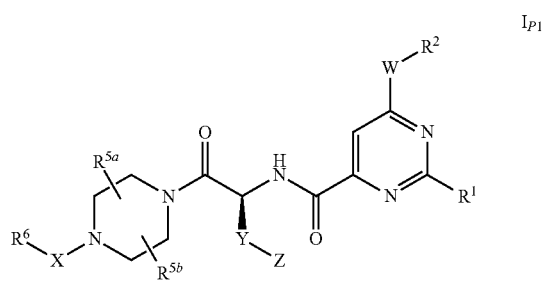

wherein
R$^1$ represents phenyl optionally substituted 1 to 3 times (preferably optionally substituted once or twice and more preferably optionally substituted once) by substituents each independently selected from the group consisting of halogen, methyl, methoxy, trifluoromethyl and trifluoromethoxy;
W represents a bond, —CH$_2$—, —O— or —NR$^3$—;
R$^2$ represents alkyl, dialkylaminoalkyl, alkoxycarbonylalkyl, carboxyalkyl, carboxyalkyl substituted with an unsubstituted phenyl group, hydroxyalkyl, heterocyclylalkyl, cycloalkyl, cycloalkylalkyl, aryl, phenylcyclopropyl, aralkyl, or diphenylalkyl;
R$^3$ represents hydrogen or alkyl;
or R$^2$ and R$^3$ can form, together with the nitrogen that carries them, a heterocyclic ring of 4 to 7 members wherein the members needed to complete said heterocyclic ring are each independently selected from —CH$_2$—, —O—, —S—, —CO— and —NR$^4$, it being understood however that said heterocyclic ring does not contain more than one member selected from the group consisting of —O—, —S— and —NR$^4$, R$^4$ representing hydrogen or alkyl;
each of R$^{5a}$ and R$^{5b}$ represents independently hydrogen or methyl;
X represents —CO— and R$^6$ represents alkoxy, alkynyloxy, aryloxy, aryl, heteroaryl or aralkyl or X represents —SO$_2$— and R$^6$ represents alkyl; and
Y represents a bond and Z represents hydrogen or aryl substituted by carboxyalkoxy;
or Y represents alkylene, alkoxyalkylene, phenylalkylene or alkoxyphenylalkylene and Z represents hydrogen, —OH, —NH$_2$, —COOH, tetrazolyl, —CO—NH$_2$, —COOR$^8$, —NH—CO—R$^8$, —NH—COOR$^8$ or —NH—SO$_2$—R$^8$, R$^8$ representing alkyl.

The compounds of formula I, I$_{P1}$ or I$_{P2}$ are P2Y$_{12}$ receptor antagonists. Accordingly, they are useful in therapy (including combination therapy), where they can be widely used as inhibitors of platelet activation, aggregation and degranulation, as promoters of platelet disaggregation or as anti-thrombotic agents.

Any reference to a compound of formula I, I$_{P1}$ or I$_{P2}$ is to be understood as referring also to optically pure enantiomers, mixtures of enantiomers, racemates, optically pure diastereoisomers, mixtures of diastereoisomers, diastereoisomeric racemates, mixture of diastereoisomeric racemates, meso forms, geometric isomers, as well as solvates and morphological forms and pharmaceutically acceptable salts thereof.

The invention in particular relates to a compound of formula I, I$_{P1}$ or I$_{P2}$ as defined above, or a salt of such a compound (and notably to a compound of formula I, I$_{P1}$ or I$_{P2}$ or a pharmaceutically acceptable salt of such a compound).

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids. When several basic groups are present mono- or polyacid addition salts may be formed.

Compounds having acidic groups, such as a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxy-ethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

The present invention also relates to pro-drugs of a compound of formula I, I$_{P1}$ or I$_{P2}$ that convert in vivo to the compound of formula I, I$_{P1}$ or I$_{P2}$ as such. Any reference to a compound of formula I, I$_{P1}$ or I$_{P2}$ is therefore to be understood as referring also to the corresponding pro-drugs of the compound of formula I, I$_{P1}$ or I$_{P2}$ as appropriate and expedient.

The following paragraphs provide definitions of the various chemical moieties for the compounds of formula I$_{P2}$ or I$_{CEP2}$ and are intended to apply to those compounds unless an otherwise expressly set out definition provides a broader or narrower definition:

Unless specified otherwise, the term "alkyl" (whether used alone or in combination) refers to a saturated straight or branched chain alkyl group containing 1 to 6 carbon atoms (e.g. methyl, ethyl, propyl, iso-propyl, butyl, iso-butyl, sec-butyl, tert-butyl, n-pentyl, neopentyl, iso-pentyl, n-hexyl or iso-hexyl), and preferably 1 to 4 carbon atoms.

The term "halogen" refers to fluorine, chlorine, bromine or iodine, preferably to fluorine, chlorine or bromine and more preferably to fluorine or chlorine.

The term "dialkylaminoalkyl", as used herein, refers to an alkyl group as previously defined wherein one hydrogen atom has been replaced by a dialkylamino group, the latter being an amino group substituted by 2 identical or different alkyl groups as previously defined. Dimethylaminoalkyl groups (examples of which are 2-dimethylamino-ethyl and 3-dimethylamino-propyl) are preferred among dialkylaminoalkyl groups.

The term "carboxyalkyl", as used herein, refers to an alkyl group as previously defined wherein one hydrogen atom has been replaced by a carboxy (i.e. —COOH) group. Examples of carboxyalkyl include, but are not limited to, carboxymethyl, 2-carboxyethyl and 3-carboxy-propyl.

The term "hydroxyalkyl", as used herein, refers to an alkyl group as previously defined wherein one hydrogen atom has been replaced by a hydroxy (i.e. —OH) group. Examples of hydroxyalkyl include, but are not limited to, hydroxymethyl, 2-hydroxy-ethyl, 2-hydroxy-propyl, 2-hydroxy-1-methyl-ethyl, 2-hydroxy-1,1-dimethyl-ethyl, 3-hydroxy-propyl, 3-hydroxy-butyl, 4-hydroxy-butyl, 3-hydroxy-pentyl and 3-hydroxy-3-methyl-butyl.

The term "alkoxyalkyl", as used herein, refers to an alkyl group as previously defined wherein one hydrogen atom has been replaced by an alkoxy group as defined hereafter. Examples of alkoxyalkyl include, but are not limited to, methoxymethyl and 2-methoxy-1-methyl-ethyl.

The term "alkynyl", as used herein, alone or in any combination, refers to a straight or branched hydrocarbon chain containing 2 to 6 carbon atoms with at least one carbon-carbon triple bond. Representative examples of alkynyl include, but are not limited to, ethynyl, 2-propynyl, 3-butynyl, 4-pentynyl and 5-hexynyl.

The term "cycloalkyl", as used herein, alone or in any combination, refers to a saturated cyclic hydrocarbon moiety containing 3 to 7 carbon atoms which may be substituted once by hydroxy or alkoxy (wherein the alkoxy is preferably methoxy or ethoxy and more preferably methoxy). Representative examples of cycloalkyl include, but are not limited to, cyclopropyl, cyclobutyl, cyclopentyl, cyclohexyl, 4-hydroxy-cyclohexyl and 2-hydroxy-cyclohexyl.

The term "cycloalkylalkyl", as used herein, refers to an alkyl group as previously defined wherein one hydrogen atom has been replaced by a cycloalkyl group as previously defined. An example of cycloalkylalkyl is cyclopropylmethyl.

The term "heterocyclyl", as used herein, alone or in any combination, refers to an unsubstituted saturated monocyclic moiety of 3 to 7 ring members containing 1 to 2 heteroatoms selected from nitrogen, oxygen and sulfur. Representative examples of heterocyclyl include, but are not limited to, azetidinyl, pyrrolidinyl, tetrahydrofuryl, piperidinyl, piperazinyl, morpholinyl and thiomorpholinyl.

The term "heterocyclylalkyl", as used herein, refers to an alkyl group as previously defined wherein one hydrogen atom has been replaced by a heterocyclyl group as previously defined. Representative examples of heterocyclylalkyl include, but are not limited to, 2-morpholin-4-yl-ethyl, 3-morpholin-4-yl-propyl and tetrahydrofuran-2-ylmethyl.

The term "alkylene", used alone or in combination, refers to a straight and branched divalent hydrocarbon chain group with one to six carbon atoms and preferably one to four carbon atoms. Representative examples of alkylene include, but are not limited to, methylene, ethylene, n-propylene and iso-propylene.

The term "alkoxy" (whether used alone or in combination) refers to a saturated straight or branched chain alkoxy group containing 1 to 6 carbon atoms (e.g. methoxy, ethoxy, propoxy, iso-propoxy, butoxy, iso-butoxy, sec-butoxy, tert-butoxy, n-pentoxy, neopentyloxy, iso-pentyloxy, n-hexyloxy or iso-hexyloxy), and preferably 1 to 4 carbon atoms.

The term "aryl" refers to an aromatic cyclic group with one, two or three rings, having from 6 to 14 carbon ring-atoms and preferably from 6 to 10 carbon ring-atoms, for example to phenyl or naphthyl groups (and notably to phenyl groups); in addition, the term "aryl" may also refer to the indanyl (e.g. indan-1-yl or indan-2-yl) and tetrahydronaphtalene groups. Any aryl group (and in particular any phenyl group) as defined herein may be substituted with one, two or more substituents (preferably with one to three and more preferably with one or two), each independently selected from the group consisting of halogen, alkyl, alkoxy, trifluoromethyl, trifluoromethoxy, carboxy, alkoxycarbonyl, amino, cyano and nitro. Specific examples of aryl groups are phenyl, 2-fluorophenyl, 3-fluorophenyl, 4-fluorophenyl, 2-chlorophenyl, 3-chlorophenyl, 4-chlorophenyl, 4-methoxyphenyl, 2-methylphenyl, 3-methylphenyl, 4-methylphenyl, 2-trifluoromethylphenyl, 3-trifluoromethylphenyl, 4-trifluoromethylphenyl, 4-trifluoromethoxy-phenyl, 2,4-difluorophenyl, 3,4-difluorophenyl, 2,4-dimethoxyphenyl, 3-carboxyphenyl, 4-carboxyphenyl, 5-amino-2,4-difluorophenyl and 2,4-dimethylphenyl.

The term "aralkyl", as used herein, alone or in any combination, refers to an aryl group appended to the parent molecular moiety through an alkyl group wherein however the aryl group may be unsubstituted or substituted with 1 to 3 substituents selected independently from the group consisting of halogen, alkyl, alkoxy, trifluoromethyl and trifluoromethoxy. Representative examples of arylalkyl include, but are not limited to, benzyl, 2-phenylethyl, 3-phenylpropyl and 2-naphth-2-ylethyl.

The term "phenylalkyl" as used herein refers to an alkyl group as previously defined wherein one hydrogen atom has been replaced by an unsubstituted phenyl group. Representative examples of phenylalkyl include, but are not limited to, benzyl, 2-phenylethyl and 3-phenylpropyl.

The term "heteroaryl", as used herein, alone or in any combination, refers to a mono-, bi- or tricyclic aromatic ring system containing up to 14 ring atoms wherein at least one of the rings contains at least one heteroatom independently selected from the group consisting of nitrogen, oxygen and sulfur. The heteroaryl group can be unsubstituted or substituted with 1 to 3 substituents (preferably 1 to 2 substituents and more preferably 1 substituent) selected independently from the group consisting of halogen, alkyl, alkoxy, trifluoromethyl and trifluoromethoxy. Representative examples of heteroaryl include, but are not limited to, thienyl, furanyl, pyrrolyl, thiazolyl, imidazolyl, oxazolyl, pyridyl, pyrimidinyl, quinolinyl, benzimidazolyl, benzothiazolyl, benzothienyl, benzoxazolyl, benzofuranyl, indolyl, carbazolyl, phenothiazin, phenoxazin, and the like.

The term "heteroaryl of 5 ring members", as used herein, refers to a monocyclic aromatic ring system containing 5 ring atoms among which 1 or 2 may be heteroatoms selected from O, N and S. Representative examples of heteroaryl of 5 ring members include, but are not limited to, thienyl, furanyl, pyrrolyl, thiazolyl, imidazolyl and oxazolyl.

The term "heteroarylalkyl", as used herein, refers to an alkyl group as previously defined wherein one hydrogen atom has been replaced by a heteroaryl group, said heteroaryl group being a mono- or bicyclic aromatic ring system containing up to 10 ring atoms wherein at least one of the rings contains at least one heteroatom independently selected from the group consisting of nitrogen, oxygen and sulfur. The heteroaryl of the heteroarylalkyl group can be unsubstituted or substituted with 1 to 2 substituents (and is preferably unsubstituted or substituted by 1 substituent) which are selected independently from the group consisting of alkyl groups. Representative examples of heteroarylalkyl include, but are not limited to, 2-furylmethyl, 2-pyrrolylmethyl and 2-thienylmethyl.

The term "heteroarylmethyl", as used herein, refers to a heteroarylalkyl group as previously defined wherein the alkyl group is a methyl. Representative examples of heteroarylmethyl include, but are not limited to, 2-furylmethyl, 2-pyrrolylmethyl and 2-thienylmethyl.

The term "diphenylalkyl", as used herein, alone or in any combination, refers to an alkyl group wherein two hydrogen atoms have each been replaced by an unsubstituted phenyl group. An example of diphenylalkyl is 1,2-diphenyl-ethyl.

The term "carboxyalkoxy", as used herein, refers to an alkoxy group as previously defined wherein one hydrogen atom has been replaced by a (i.e. —COOH) group. An example of carboxyalkoxy is carboxymethoxy.

The term "phenylalkylen", as used herein, refers to an unsubstituted divalent phenylalkyl group wherein the alkyl is as previously defined, said divalent group being attached to the rest of the molecule by, on the one side, one of the carbon atoms of the phenyl group and by, one the other side, one of the carbon atoms of the alkyl group.

The term "alkoxyalkylen", as used herein, refers to an unsubstituted divalent alkoxyalkyl group wherein the alkoxy and the alkyl are as previously defined, said divalent group being attached to the rest of the molecule by, on the one side, one of the carbon atoms of the alkyl group and by, one the other side, one of the carbon atoms of the alkoxy group. Representative examples of alkoxyalkylene include, but are not limited to, methoxyethylen and ethoxymethylen.

The term "alkoxyphenylalkylen" as used herein, refers to a group wherein the alkoxy and alkylene parts are as previously defined and the phenyl is an unsubstituted phenyl group. Representative examples of alkoxyphenylalkylene include, but are not limited to, 2-methoxyphenylmethylene and 3-methoxyphenylmethylene.

The following paragraphs provide definitions of the various chemical moieties for the compounds of formula $I_{P1}$ or $I_{CEP1}$ and are intended to apply to those compounds unless an otherwise expressly set out definition provides a broader or narrower definition:

Unless specified otherwise, the term "alkyl" (whether used alone or in combination) refers to a saturated straight or branched chain alkyl group containing 1 to 6 carbon atoms (e.g. methyl, ethyl, propyl, iso-propyl, butyl, iso-butyl, sec-butyl, tert-butyl, n-pentyl, neopentyl, iso-pentyl, n-hexyl or iso-hexyl), and preferably 1 to 4 carbon atoms.

The term "dialkylaminoalkyl", as used herein, refers to an alkyl group as previously defined wherein one hydrogen atom has been replaced by a dialkylamino group, the latter being an amino group substituted by 2 identical or different alkyl groups as previously defined. Dimethylaminoalkyl groups are preferred among dialkylaminoalkyl groups.

The term "carboxyalkyl", as used herein, refers to an alkyl group as previously defined wherein one hydrogen atom has been replaced by a carboxy (i.e. —COOH) group.

The term "hydroxyalkyl", as used herein, refers to an alkyl group as previously defined wherein one hydrogen atom has been replaced by a hydroxy (i.e. —OH) group.

The term "alkynyl", as used herein, alone or in any combination, refers to a straight or branched hydrocarbon chain containing 2 to 6 carbon atoms with at least one carbon-carbon triple bond. Representative examples of alkynyl include, but are not limited to, ethynyl, 2-propynyl, 3-butynyl, 4-pentynyl, 5-hexynyl and the like.

The term "cycloalkyl", as used herein, alone or in any combination, refers to a saturated cyclic hydrocarbon moiety containing 3 to 7 carbon atoms. Representative examples of cycloalkyl include, but are not limited to, cyclopropyl, cyclobutyl, cyclopentyl and cyclohexyl.

The term "cycloalkylalkyl", as used herein, refers to an alkyl group as previously defined wherein one hydrogen atom has been replaced by a cycloalkyl group as previously defined.

The term "heterocyclyl", as used herein, alone or in any combination, refers to an unsubstituted saturated monocyclic moiety of 3 to 7 ring members containing 1 to 2 heteroatoms selected from nitrogen, oxygen and sulfur. Representative examples of heterocyclyl include, but are not limited to, azetidine, pyrrolidine, piperidine, piperazine, morpholine and thiomorpholine.

The term "heterocyclylalkyl", as used herein, refers to an alkyl group as previously defined wherein one hydrogen atom has been replaced by a heterocyclyl group as previously defined.

The term "alkylene", used alone or in combination, refers to straight and branched divalent hydrocarbon chain groups with one to six carbon atoms and preferably one to four carbon atoms.

The term "alkoxy" (whether used alone or in combination) refers to a saturated straight or branched chain alkoxy group containing 1 to 6 carbon atoms (e.g. methoxy, ethoxy, propoxy, iso-propoxy, butoxy, iso-butoxy, sec-butoxy, tert-butoxy, n-pentoxy, neopentyloxy, iso-pentyloxy, n-hexyloxy or iso-hexyloxy), and preferably 1 to 4 carbon atoms.

The term "aryl" refers to an aromatic cyclic group with one, two or three rings, having from 6 to 14 carbon ring-atoms and preferably from 6 to 10 carbon ring-atoms, for example to phenyl or naphthyl groups (and notably to phenyl groups); in addition, the term "aryl" may also refer to the indanyl and tetrahydronaphtalene groups. Any aryl group (and in particular any phenyl group) as defined herein may be substituted with one, two or more substituents (and preferably one or two), each independently selected from the group consisting of halogen, alkyl, alkoxy, trifluoromethyl, trifluoromethoxy, carboxy, alkoxycarbonyl, amino, cyano and nitro. Specific examples of aryl groups are phenyl, 2-fluorophenyl, 3-fluorophenyl, 4-fluorophenyl, 2-chlorophenyl, 3-chlorophenyl, 4-chlorophenyl, 4-methoxyphenyl, 2-methylphenyl, 3-methylphenyl, 4-methylphenyl, 2-trifluoromethylphenyl, 3-trifluoromethylphenyl, 4-trifluoromethylphenyl, 4-trifluoromethoxy-phenyl, 2,4-difluorophenyl, 3,4-difluorophenyl, 2,4-dimethoxyphenyl, 3-carboxyphenyl, 4-carboxyphenyl, 5-amino-2,4-difluorophenyl and 2,4-dimethylphenyl.

The term "aralkyl", as used herein, alone or in any combination, refers to an aryl group appended to the parent molecular moiety through an alkyl group wherein however the aryl group may be unsubstituted or substituted with 1 to 3 substituents selected independently from the group consisting of halogen, alkyl, alkoxy, trifluoromethyl and trifluoromethoxy. Representative examples of arylalkyl include, but are not limited to, benzyl, 2-phenylethyl, 3-phenylpropyl, 2-naphth-2-ylethyl, and the like.

The term "heteroaryl", as used herein, alone or in any combination, refers to a mono-, bi- or tricyclic aromatic ring system containing up to 14 ring atoms wherein at least one of the rings contains at least one heteroatom independently selected from the group consisting of nitrogen, oxygen and sulfur. The heteroaryl group can be unsubstituted or substituted with 1 to 3 substituents (preferably 1 to 2 substituents and more preferably 1 substituent) selected independently from the group consisting of halogen, alkyl, alkoxy, trifluoromethyl and trifluoromethoxy. Representative examples of heteroaryl include, but are not limited to, thienyl, furanyl, pyrrolyl, thiazolyl, imidazolyl, oxazolyl, pyridyl, pyrimidinyl, quinolinyl, benzimidazolyl, benzothiazolyl, benzothienyl, benzoxazolyl, benzofuranyl, indolyl, carbazolyl, phenothiazin, phenoxazin, and the like.

The term "heteroaryl of 5 ring members", as used herein, refers to a monocyclic aromatic ring system containing 5 ring atoms among which 1 or 2 may be heteroatoms selected from O, N and S. Representative examples of heteroaryl of 5 ring members include, but are not limited to, thienyl, furanyl, pyrrolyl, thiazolyl, imidazolyl and oxazolyl.

The term "diphenylalkyl", as used herein, alone or in any combination, refers to an alkyl group wherein two hydrogen atoms have each been replaced by an unsubstituted phenyl group.

The term "phenylalkylen", as used herein, refers to an unsubstituted divalent phenylalkyl group wherein the alkyl is as previously defined, said divalent group being attached to the rest of the molecule by, on the one side, one of the carbon atoms of the phenyl group and by, one the other side, one of the carbon atoms of the alkyl group.

The term "alkoxyalkylen", as used herein, refers to an unsubstituted divalent alkoxyalkyl group wherein the alkoxy and the alkyl are as previously defined, said divalent group being attached to the rest of the molecule by, on the one side, one of the carbon atoms of the alkyl group and by, one the other side, one of the carbon atoms of the alkoxy group.

The term "alkoxyphenylalkylen" as used herein, refers to a group wherein the alkoxy and alkylene parts are as previously defined and the phenyl is an unsubstituted phenyl group.

The following paragraphs provide definitions of the various chemical moieties for the compounds according to the invention. Said definitions are intended to apply uniformly throughout the specification and claims (except for the compounds of formula $I_{P1}$ or $I_{CEP1}$ and the compounds of formula $I_{P2}$ or $I_{CEP2}$ that have their own definitions) unless an otherwise expressly set out definition provides a broader or narrower definition.

Unless specified otherwise, the term "alkyl" (whether used alone or in combination) refers to a saturated straight or branched chain alkyl group containing 1 to 7 carbon atoms (e.g. methyl, ethyl, propyl, iso-propyl, butyl, iso-butyl, sec-butyl, tert-butyl, n-pentyl, neopentyl, iso-pentyl, n-hexyl, iso-hexyl, n-heptyl or iso-heptyl), and more preferably 1 to 4 carbon atoms.

The term "halogen" refers to fluorine, chlorine, bromine or iodine, preferably to fluorine, chlorine or bromine and more preferably to fluorine or chlorine.

The term "haloalkyl", as used herein, refers to an alkyl group as previously defined wherein at least one hydrogen atom has been replaced by a halogen atom. Examples of haloalkyl include, but are not limited to, fluoromethyl and trifluoromethyl.

The term "dialkylaminoalkyl", as used herein, refers to an alkyl group as previously defined wherein one hydrogen atom has been replaced by a dialkylamino group, the latter being an amino group substituted by 2 identical or different alkyl groups as previously defined. Dimethylaminoalkyl groups (examples of which are 2-dimethylamino-ethyl and 3-dimethylamino-propyl) are preferred among dialkylaminoalkyl groups.

The term "carboxyalkyl", as used herein, refers to an alkyl group as previously defined wherein one hydrogen atom has been replaced by a carboxy (i.e. —COOH) group. Examples of carboxyalkyl include, but are not limited to, carboxymethyl, 2-carboxyethyl and 3-carboxy-propyl.

The term "hydroxyalkyl", as used herein, refers to an alkyl group as previously defined wherein one hydrogen atom has been replaced by a hydroxy (i.e. —OH) group. Examples of hydroxyalkyl include, but are not limited to, hydroxymethyl, 2-hydroxy-ethyl, 2-hydroxy-propyl, 2-hydroxy-1-methyl-ethyl, 2-hydroxy-1,1-dimethyl-ethyl, 1-hydroxy-propyl, 3-hydroxy-propyl, 1-hydroxy-butyl, 3-hydroxy-butyl, 4-hydroxy-butyl, 3-hydroxy-pentyl and 3-hydroxy-3-methyl-butyl.

The term "alkoxyalkyl", as used herein, refers to an alkyl group as previously defined wherein one hydrogen atom has been replaced by an alkoxy group as defined hereafter. Examples of alkoxyalkyl include, but are not limited to, methoxymethyl and 2-methoxy-1-methyl-ethyl.

The term "alkynyl", as used herein, alone or in any combination, refers to a straight or branched hydrocarbon chain containing 2 to 6 carbon atoms with at least one carbon-carbon triple bond. Representative examples of alkynyl include, but are not limited to, ethynyl, 2-propynyl, 3-butynyl, 4-pentynyl and 5-hexynyl.

The term "cycloalkyl", as used herein, alone or in any combination, refers to a saturated cyclic hydrocarbon moiety containing 3 to 7 carbon atoms which may be substituted once by hydroxy, hydroxymethyl, alkoxymethyl (preferably methoxymethyl or ethoxymethyl and more preferably methoxymethyl), alkoxy (preferably methoxy or ethoxy and more preferably methoxy) or alkoxycarbonyl (wherein the alkoxy is preferably methoxy or ethoxy and more preferably methoxy). Representative examples of cycloalkyl include, but are not limited to, cyclopropyl, cyclobutyl, cyclopentyl, cyclohexyl, 4-hydroxy-cyclohexyl, 2-hydroxy-cyclohexyl, 2-hydroxymethyl-cyclopropyl and 2-ethoxycarbonyl-cyclohexyl.

The term "cycloalkylalkyl", as used herein, refers to an alkyl group as previously defined wherein one hydrogen atom has been replaced by a cycloalkyl group as previously defined. An example of cycloalkylalkyl is cyclopropylmethyl.

The term "heterocyclyl", as used herein, alone or in any combination, refers to an unsubstituted saturated monocyclic moiety of 3 to 7 ring members containing 1 to 2 heteroatoms selected from nitrogen, oxygen and sulfur. Representative examples of heterocyclyl include, but are not limited to, azetidinyl, pyrrolidinyl, tetrahydrofuranyl, piperidinyl, piperazinyl, morpholinyl and thiomorpholinyl.

The term "heterocyclylalkyl", as used herein, refers to an alkyl group as previously defined wherein one hydrogen atom has been replaced by a heterocyclyl group as previously defined. Representative examples of heterocyclylalkyl include, but are not limited to, 2-morpholin-4-yl-ethyl, 3-morpholin-4-yl-propyl and tetrahydrofuran-2-ylmethyl.

The term "alkylene", used alone or in combination, refers to a straight and branched divalent saturated hydrocarbon chain group with one to six carbon atoms and preferably one to four carbon atoms. Representative examples of alkylene include, but are not limited to, methylene (—CH$_2$—), ethylene (—CH$_2$—CH$_2$—), n-propylene (—CH$_2$—CH$_2$—CH$_2$—) and iso-propylene (—CH$_2$—CH(CH$_3$)—).

The term "alkoxy" (whether used alone or in combination) refers to a saturated straight or branched chain alkoxy group containing 1 to 6 carbon atoms (e.g. methoxy, ethoxy, propoxy, iso-propoxy, butoxy, iso-butoxy, sec-butoxy, tert-butoxy, n-pentoxy, neopentyloxy, iso-pentyloxy, n-hexyloxy or iso-hexyloxy), and preferably 1 to 4 carbon atoms.

The term "aryl" refers to an aromatic cyclic group with one, two or three rings, having from 6 to 14 carbon ring-atoms and preferably from 6 to 10 carbon ring-atoms, for example to phenyl or naphthyl groups (and notably to phenyl groups); in addition, the term "aryl" may also refer to the indanyl (e.g. indan-1-yl or indan-2-yl), tetrahydronaphtalene, biphenyl-4-yl and benzo[1,3]dioxolyl groups. Any aryl group (and in particular any phenyl group) as defined herein may be substituted with one, two or more substituents (preferably with one to three substituents, more preferably with one or two substituents and notably with one substituent), each independently selected from the group consisting of halogen, alkyl, alkoxy, hydroxymethyl, acetyl, methanesulfonyl, trifluoromethyl, trifluoromethoxy, carboxy, alkoxycarbonyl, amino, cyano and nitro. Specific examples of aryl groups are phenyl, biphenyl-4-yl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-methylphenyl, 3-methylphenyl, 4-methylphenyl, 2-trifluoromethylphenyl, 3-trifluoromethylphenyl, 4-trifluoromethylphenyl, 4-trifluoromethoxy-phenyl, 2,4-difluorophenyl, 3,4-difluorophenyl, 2,4-dimethoxyphenyl, 3-carboxyphenyl, 4-carboxyphenyl, 4-hydroxymethylphenyl, 5-amino-2,4-difluorophenyl and 2,4-dimethylphenyl.

The term "aralkyl", as used herein, alone or in any combination, refers to an aryl group appended to the parent molecular moiety through an alkyl group wherein however the aryl group may be unsubstituted or substituted with 1 to 3 substituents selected independently from the group consisting of halogen, alkyl, alkoxy, trifluoromethyl and trifluoromethoxy. Representative examples of aralkyl include, but are not limited to, benzyl, 2-phenylethyl, 3-phenylpropyl and 2-naphth-2-ylethyl.

The term "aralkoxy", as used herein, alone or in any combination, refers to an aryl group appended to the parent molecular moiety through an alkoxy group wherein however the aryl group may be unsubstituted or substituted with 1 to 3 substituents selected independently from the group consisting of halogen, alkyl, alkoxy, trifluoromethyl and trifluoromethoxy. Representative examples of aralkoxy include, but are not limited to, benzyloxy, 2-phenylethoxy, 3-phenylpropoxy and 2-naphth-2-ylethoxy.

The term "phenylalkyl", as used herein, refers to an alkyl group as previously defined wherein one hydrogen atom has been replaced by an unsubstituted phenyl group. Representative examples of phenylalkyl include, but are not limited to, benzyl, 2-phenylethyl and 3-phenylpropyl.

The term "phenylalkoxy", as used herein, refers to an alkoxy group as previously defined wherein one hydrogen atom has been replaced by an unsubstituted phenyl group. Representative examples of phenylalkoxy include, but are not limited to, benzyloxy, 2-phenylethoxy and 3-phenylpropoxy.

The term "heteroaryl", as used herein, alone or in combination, refers to a mono-, bi- or tricyclic aromatic ring system containing up to 14 ring atoms wherein at least one of the rings contains at least one heteroatom independently selected from the group consisting of nitrogen, oxygen and sulfur; in addition, the term "heteroaryl" may also refer to 1-oxy-pyridinyl groups. The heteroaryl group can be unsubstituted or substituted with 1 to 3 substituents (preferably 1 to 2 substituents and more preferably 1 substituent) selected independently from the group consisting of halogen, alkyl, alkoxy, trifluoromethyl and trifluoromethoxy. Representative examples of heteroaryl include, but are not limited to, thienyl, furanyl, pyrrolyl, pyrazolyl, thiazolyl, imidazolyl, oxazolyl, pyridinyl, 1-oxy-4-pyridinyl, 1-oxy-3-pyridinyl, 1-oxy-2-pyridinyl, pyrimidinyl, quinolinyl, benzimidazolyl, benzothiazolyl, benzothienyl, benzoxazolyl, benzofuranyl, indolyl, carbazolyl, phenothiazinyl and phenoxazinyl.

The term "monocyclic heteroaryl", as used herein, refers to a monocyclic aromatic ring system containing 5 or 6 ring atoms among which 1 or 2 may be heteroatoms selected from O, N and S. The monocyclic heteroaryl group can be unsubstituted or substituted with 1 to 2 substituents (preferably 1 substituent) selected independently from the group consisting of halogen, alkyl, alkoxy, trifluoromethyl and trifluoromethoxy. Representative examples of monocyclic heteroaryl include, but are not limited to, thienyl, furanyl, pyrrolyl, pyrazolyl, thiazolyl, imidazolyl, oxazolyl, pyridinyl and pyrimidinyl.

The term "heteroaryl of 5 ring members", as used herein, refers to a monocyclic aromatic ring system containing 5 ring atoms among which 1 or 2 may be heteroatoms selected from O, N and S. Representative examples of heteroaryl of 5 ring members include, but are not limited to, thienyl, furanyl, pyrrolyl, pyrazolyl, thiazolyl, imidazolyl and oxazolyl.

The term "heteroarylalkyl", as used herein, refers to an alkyl group as previously defined wherein one hydrogen atom has been replaced by a heteroaryl group, said heteroaryl group being a mono- or bicyclic aromatic ring system containing up to 10 ring atoms wherein at least one of the rings contains at least one heteroatom independently selected from the group consisting of nitrogen, oxygen and sulfur. The heteroaryl of the heteroarylalkyl group can be unsubstituted or substituted with 1 to 2 substituents (and is preferably unsubstituted or substituted by 1 substituent) which are selected independently from the group consisting of alkyl groups. Representative examples of heteroarylalkyl include, but are not limited to, 2-furylmethyl, 2-pyrrolylmethyl and 2-thienylmethyl.

The term "heteroarylmethyl", as used herein, refers to a heteroarylalkyl group as previously defined wherein the alkyl group is a methyl. Representative examples of heteroarylmethyl include, but are not limited to, 2-furylmethyl, 2-pyrrolylmethyl and 2-thienylmethyl.

The term "diphenylalkyl", as used herein, alone or in any combination, refers to an alkyl group wherein two hydrogen atoms have each been replaced by an unsubstituted phenyl group. An example of diphenylalkyl is 1,2-diphenyl-ethyl.

The term "carboxyalkoxy", as used herein, refers to an alkoxy group as previously defined wherein one hydrogen atom has been replaced by a (i.e. —COOH) group. An example of carboxyalkoxy is carboxymethoxy.

The term "phenylalkylen", as used herein, refers to an unsubstituted divalent phenylalkyl group wherein the alkyl is as previously defined, said divalent group being attached to the rest of the molecule by, on the one side, one of the carbon atoms of the phenyl group and by, one the other side, one of the carbon atoms of the alkyl group.

The term "alkoxyalkylen", as used herein, refers to an unsubstituted divalent alkoxyalkyl group wherein the alkoxy and the alkyl are as previously defined, said divalent group being attached to the rest of the molecule by, on the one side, one of the carbon atoms of the alkyl group and by, one the other side, one of the carbon atoms of the alkoxy group. Representative examples of alkoxyalkylene include, but are not limited to, methoxyethylen and ethoxymethylen.

The term "alkoxyphenylalkylen" as used herein, refers to a group wherein the alkoxy and alkylene parts are as previously defined and the phenyl is an unsubstituted phenyl group. Representative examples of alkoxyphenylalkylene include, but are not limited to, 2-methoxyphenylmethylen and 3-methoxyphenylmethylen.

Besides, the following paragraphs provide definitions of various other terms. Said definitions are intended to apply uniformly throughout the specification and claims unless an otherwise expressly set out definition provides a broader or narrower definition.

The expression "pharmaceutically acceptable salt(S)" encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, pamoic acid, stearic acid, glutamic acid, aspartic acid, methanesulfonic acid, ethanedisulfonic acid, p-toluenesulfonic acid, salicylic acid, succinic acid, trifluoroacetic acid, and the like that are non toxic to living organisms or, in case the compound of formula I is acidic in nature, with an inorganic base like an alkali or earth alkali base, e.g. sodium hydroxide, potassium hydroxide, calcium hydroxide and the like. For other examples of pharmaceutically acceptable salts, reference can be made notably to "Salt selection for basic drugs", *Int. J. Pharm.* (1986), 33, 201-217.

The term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively the term "around") placed before a temperature "Y" refers in the current application to an interval extending from the temperature Y minus 10° C. to Y plus 10° C., and preferably to an interval extending from Y minus 5° C. to Y plus 5° C.

Moreover, the sign "*" placed near an atom will be used to designate the point of attachment of a radical to the rest of a molecule. For example:

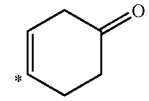

designates the 4-oxo-cyclohex-1-enyl radical.

The compounds of formula I will in particular be compounds of formula $I_{CE}$

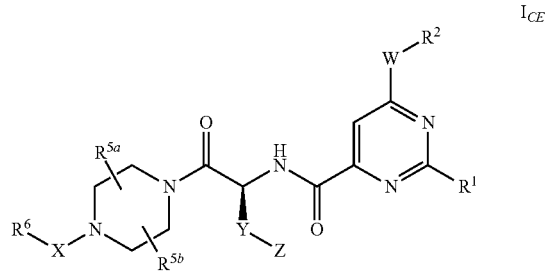

wherein

R$^1$ represents phenyl optionally substituted once by a substituent selected from the group consisting of halogen, methyl, methoxy, trifluoromethyl and trifluoromethoxy;

W represents a bond, and R$^2$ represents alkyl, haloalkyl, cyano, hydroxyalkyl, hydroxyalkyl substituted on its alkyl chain with an unsubstituted phenyl group, alkoxyalkyl, heterocyclyl, heterocyclylalkyl, cycloalkyl of 3 to 7 carbon atoms optionally substituted once by a group selected from hydroxy, hydroxymethyl, alkoxy and alkoxycarbonyl, phenyl optionally substituted once by a group selected from halogen, alkyl, alkoxy, hydroxymethyl, acetyl, methanesulfonyl, trifluoromethyl, carboxy and cyano, biphenyl-4-yl, an unsubstituted monocyclic heteroaryl, 1-oxy-pyridin-2-yl, 1-oxy-pyridin-3-yl, 1-oxy-pyridin-4-yl, benzo[1,3]dioxol-5-yl, or one of the radicals

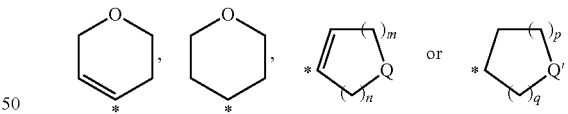

wherein:
m is 1 and n is 2,
p is 1 and q is 2,
Q is —CO— or —CH(OR$^a$)—, R$^a$ being hydrogen, and Q' is —CO—; or W represents —CH$_2$— and R$^2$ represents —NR$^7$R$^8$, —SR$^9$, or —SO$_2$R$^{10}$; or W represents —O— and R$^2$ represents alkyl, carboxyalkyl, hydroxyalkyl, cycloalkyl, cycloalkylalkyl, phenyl, phenylalkyl or an unsubstituted monocyclic heteroaryl; or W represents —S— and R$^2$ represents alkyl, carboxyalkyl, alkoxycarbonylalkyl, hydroxyalkyl, unsubstituted cycloalkyl of 3 to 7 carbon atoms, phenyl, phenylalkyl or heteroarylalkyl wherein the heteroaryl is an unsubstituted monocyclic heteroaryl; or W represents —NR³— and R² represents hydrogen, alkyl, dialkylaminoalkyl, alkoxycarbonylalkyl, carboxyalkyl, carboxyalkyl substituted on its alkyl part with an unsubstituted phenyl group, hydroxyalkyl, alkoxyalkyl, heterocyclyl, heterocyclylalkyl, cycloalkyl, phenyl optionally substituted once by halogen, indan-1-yl, indan-2-yl, 2-phenylcyclopropyl, phenylalkyl, diphenylalkyl, —COR¹¹ or —SO₂R¹²;

W represents —CH═CH— and R² represents hydroxyalkyl, alkoxycarbonyl, phenyl or —CO—NR¹³R¹⁴; or W represents —C≡C— and R² represents hydrogen or hydroxyalkyl; or W represents —CO— and R² represents alkyl;

R³ represents hydrogen or alkyl;

R⁷ represents alkyl or phenylalkyl;

R⁸ represents alkyl;

or R⁷ and R⁸ form, together with the nitrogen that carries them, a heterocyclic ring of 4 to 7 members wherein the members needed to complete said heterocyclic ring are each independently selected from —CH₂—, —CH(CH₃)—, —CHRʸ— or —O—, it being understood however that said heterocyclic ring does not contain more than one member selected from the group consisting of —CHRʸ— and —O—, Rʸ representing hydroxy, hydroxymethyl or alkoxycarbonyl;

R⁹ represents unsubstituted cycloalkyl of 3 to 7 carbon atoms or phenyl;

R¹⁰ represents alkyl, unsubstituted cycloalkyl of 3 to 7 carbon atoms or phenyl;

R¹¹ represents alkyl, alkoxyalkyl, unsubstituted cycloalkyl of 3 to 7 carbon atoms, cycloalkylalkyl wherein the cycloalkyl is an unsubstituted cycloalkyl of 3 to 7 carbon atoms, phenyl, monocyclic heteroaryl or phenylalkyl;

R¹² represents alkyl or phenyl;

R¹³ represents alkyl;

R¹⁴ represents alkyl;

or, when W represents —NR³—, R² and R³ can form, together with the nitrogen that carries them, a heterocyclic ring of 4 to 7 members wherein the members needed to complete said heterocyclic ring are each independently selected from —CH₂—, —CHRˣ—, —O—, —S— and —NR⁴—, it being understood however that said heterocyclic ring does not contain more than one member selected from the group consisting of —CHRˣ—, —O—, —S— and —NR⁴—, Rˣ representing hydroxy, methoxy, hydroxymethyl or methoxymethyl and R⁴ representing hydrogen; or also, when W represents —NR³—, R² and R³ can form, together with the nitrogen that carries them, either an imidazolyl, pyrazolyl, 1,2,3-triazolyl or 1,2,4-triazolyl ring, which ring may be substituted by an alkyl group, or a 4-oxo-4H-pyridin-1-yl, 4,5-dihydro-pyrazol-1-yl, 2-methyl-4,5-dihydro-imidazol-1-yl or 3-methyl-5-oxo-2,5-dihydro-pyrazol-1-yl;

each of R⁵ᵃ and R⁵ᵇ represents independently hydrogen or methyl;

X represents —CO— and R⁶ represents alkoxy, alkynyloxy, phenoxy, phenyl, heteroaryl of 5 ring members, phenylalkyl or NR¹⁵R¹⁶, or X represents —SO₂— and R⁶ represents alkyl;

R¹⁵ represents alkyl;

R¹⁶ represents hydrogen;

or R¹⁵ and R¹⁶ form, together with the nitrogen that carries them, a heterocyclic ring of 4 to 7 members wherein the members needed to complete said heterocyclic ring are each —CH₂—; and Y represents a bond and Z represents hydrogen or phenyl substituted by carboxyalkoxy; or Y represents alkylene, alkoxyalkylene, phenylalkylene, alkoxyphenylene or alkoxyphenylalkylene and Z represents hydrogen, —OH, —NH₂, —COOH, tetrazolyl, —CO—NH₂, —NH—CO—R⁷, —NH—COOR¹⁷ or —NH—SO₂—R¹⁷, R¹⁷ representing alkyl.

The compounds of formula $I_{P2}$ will in particular be compounds of formula $I_{CEP2}$

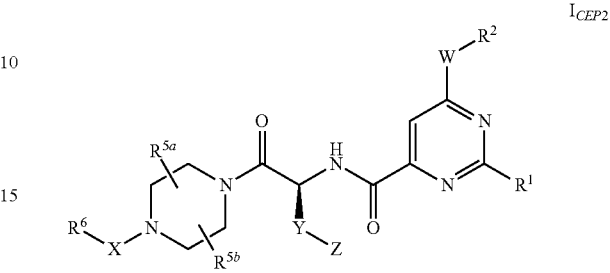

wherein

R¹ represents phenyl optionally substituted once by a substituent selected from the group consisting of halogen, methyl, methoxy, trifluoromethyl and trifluoromethoxy;

W represents a bond, —CH₂—, —O—, —S— or —NR³— and R² represents alkyl, dialkylaminoalkyl, alkoxycarbonylalkyl, carboxyalkyl, carboxyalkyl substituted with an unsubstituted phenyl group, hydroxyalkyl, alkoxyalkyl, heterocyclyl, heterocyclylalkyl, cycloalkyl optionally substituted once by a hydroxy group, cycloalkylalkyl, aryl, 2-phenylcyclopropyl, aralkyl, diphenylalkyl, or one of the radicals

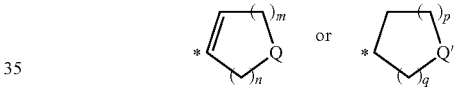

wherein:

m is 0 and n is 2 or 3 or m is 1 and n is 2, p is 0 and q is 2 or 3 or p is 1 and q is 2, Q is —CO— or —CH(OH)—, and Q' is —CO—, it being understood that if W represents —O—, —S— or —NR³—, then R² may also represent heteroarylalkyl wherein the heteroaryl is a 5-membered heteroaryl containing 1 to 2 heteroatoms selected independently from O, N and S; or W represents —CH═CH— or —C≡C— and R² represents hydrogen or hydroxyalkyl;

R³ represents hydrogen or alkyl;

or, when W represents —NR³—, R² and R³ can form, together with the nitrogen that carries them, a heterocyclic ring of 4 to 7 members wherein the members needed to complete said heterocyclic ring are each independently selected from —CH₂—, —CHRˣ—, —O—, —S— and —NR⁴—, it being understood however that said heterocyclic ring does not contain more than one member selected from the group consisting of —CHRˣ—, —O—, —S— and —NR⁴, Rˣ representing hydroxy or hydroxymethyl and R⁴ representing hydrogen;

or also, when W represents —NR³—, R² and R³ can form, together with the nitrogen that carries them, an imidazolyl or pyrazolyl ring;

each of R⁵ᵃ and R⁵ᵇ represents independently hydrogen or methyl;

X represents —CO— and R⁶ represents alkoxy, alkynyloxy, phenoxy, phenyl, heteroaryl of 5 ring members or phenylalkyl or X represents —SO₂— and R⁶ represents alkyl; and Y represents a bond and Z represents hydrogen or phenyl substituted by carboxyalkoxy; or Y represents alkylene, alkoxyalkylene, phenylalkylene, alkoxyphenylene or alkoxyphenylalkylene and Z represents hydrogen, —OH, —NH$_2$, —COOH, tetrazolyl, —CO—NH$_2$, —NH—CO—R$^8$, —NH—COOR$^8$ or —NH—SO$_2$—R$^8$, R$^8$ representing alkyl.

The compounds of formula I$_{P1}$ will in particular be compounds of formula I$_{CEP1}$

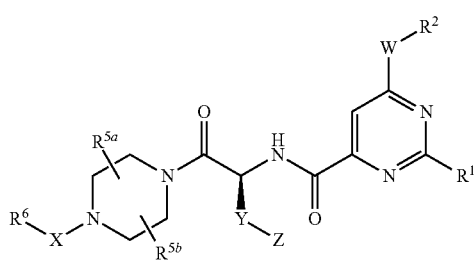

wherein
R$^1$ represents phenyl optionally substituted once by a substituent selected from the group consisting of halogen, methyl, methoxy, trifluoromethyl and trifluoromethoxy;
W represents a bond, —CH$_2$—, —O— or —NR$^3$—;
R$^2$ represents alkyl, dialkylaminoalkyl, alkoxycarbonylalkyl, carboxyalkyl, carboxyalkyl substituted with an unsubstituted phenyl group, hydroxyalkyl, heterocyclylalkyl, cycloalkyl, cycloalkylalkyl, phenyl optionally substituted once by a substituent selected from the group consisting of alkyl and carboxy, indanyl, phenylcyclopropyl, aralkyl, or diphenylalkyl;
R$^3$ represents hydrogen or alkyl;
or R$^2$ and R$^3$ can form, together with the nitrogen that carries them, a heterocyclic ring of 4 to 7 members wherein the members needed to complete said heterocyclic ring are each —CH$_2$—;
each of R$^{5a}$ and R$^{5b}$ represents independently hydrogen or methyl;
X represents —CO— and R$^6$ represents alkoxy, alkynyloxy, phenoxy, phenyl, heteroaryl of 5 ring members or phenylalkyl or X represents —SO$_2$— and R$^6$ represents alkyl; and
Y represents a bond and Z represents hydrogen or phenyl substituted by carboxyalkoxy; or Y represents alkylene, alkoxyalkylene, phenylalkylene or alkoxyphenylalkylene and Z represents hydrogen, —OH, —NH$_2$, —COOH, tetrazolyl, —CO—NH$_2$, —NH—CO—R$^8$, —NH—COOR$^8$ or —NH—SO$_2$—R$^8$, R$^8$ representing alkyl.

In a general manner, the compounds of formula I (or respectively of formula I$_{P1}$ or I$_{P2}$) wherein:
Y represents a bond and Z represents hydrogen or aryl substituted by carboxyalkoxy; or
Y represents alkylene, alkoxyalkylene, phenylalkylene or alkoxyphenylalkylene and Z represents hydrogen, —OH, —NH$_2$, —COOH, tetrazolyl, —CO—NH$_2$, —NH—CO—R$^{17}$, —NH—COOR$^{17}$ or —NH—SO$_2$—R$^{17}$, R$^{17}$ representing alkyl;
will be preferred over other compounds of formula I (or respectively of formula I$_{P1}$ or I$_{P2}$).

Preferred compounds of formula I will be those wherein at least one of the following characteristics is present:
R$^1$ represents phenyl optionally substituted once or twice by substituents each independently selected from the group consisting of halogen, methyl, methoxy, trifluoromethyl and trifluoromethoxy;

W represents a bond, and R$^2$ represents alkyl, haloalkyl, cyano, hydroxyalkyl, hydroxyalkyl substituted on its alkyl chain with an unsubstituted phenyl group, alkoxyalkyl, heterocyclyl, heterocyclylalkyl, cycloalkyl, cycloalkylalkyl, aryl, heteroaryl, or one of the radicals

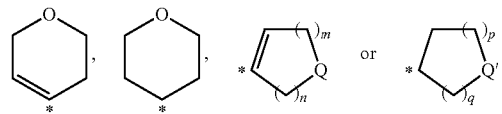

wherein:
m is 0 and n is 2 or 3 or m is 1 and n is 2,
p is 0 and q is 2 or 3, or p is 1 and q is 2 or also p is 2 or 3 and q is 0,
Q is —CO— or —CH(OR$^a$)—, R$^a$ being hydrogen or alkyl, and
Q' is —CO—; or
W represents —CH$_2$— and R$^2$ represents —NR$^7$R$^8$, —SR$^9$ or —SO$_2$R$^{10}$;
R$^7$ represents alkyl or phenylalkyl;
R$^8$ represents alkyl;
or R$^7$ and R$^9$ form, together with the nitrogen that carries them, a heterocyclic ring of 4 to 7 members wherein the members needed to complete said heterocyclic ring are each independently selected from —CH$_2$—, —CH(CH$_3$)—, —CHR$^y$—, —O—, —S—, —CO— and —NR$^z$—, it being understood however that said heterocyclic ring does not contain more than one member selected from the group consisting of —CHR$^y$—, —O—, —S—, —CO— and —NR$^z$—, R$^y$ representing hydroxy, hydroxymethyl, alkoxymethyl, alkoxycarbonyl or alkoxy and R$^z$ representing hydrogen, alkyl or alkoxycarbonyl;
R$^9$ represents unsubstituted cycloalkyl of 3 to 7 ring members or aryl;
R$^{10}$ represents alkyl, unsubstituted cycloalkyl of 3 to 7 ring members or aryl; or
W represents —O— or —S— and R$^2$ represents alkyl, carboxyalkyl, alkoxycarbonylalkyl, hydroxyalkyl, alkoxyalkyl, heterocyclylalkyl, cycloalkyl, cycloalkylalkyl, aryl, aralkyl, heteroaryl or heteroarylalkyl; or
W represents —NR$^3$— and R$^2$ represents hydrogen, alkyl, dialkylaminoalkyl, alkoxycarbonylalkyl, carboxyalkyl, carboxyalkyl substituted on its alkyl part with an unsubstituted phenyl group, hydroxyalkyl, alkoxyalkyl, heterocyclyl, heterocyclylalkyl, cycloalkyl, cycloalkylalkyl, aryl, 2-phenylcyclopropyl, aralkyl, diphenylalkyl, heteroarylalkyl wherein the heteroaryl is a monocyclic heteroaryl, —COR$^{11}$ or —SO$_2$R$^{12}$;
R$^3$ represents hydrogen or alkyl;
R$^{11}$ represents alkyl, alkoxyalkyl, cycloalkyl, cycloalkylalkyl, aryl, monocyclic heteroaryl or aralkyl;
R$^{12}$ represents alkyl or aryl; or
W represents —NR$^3$— and R$^2$ and R$^3$ form, together with the nitrogen that carries them, a heterocyclic ring of 4 to 7 members wherein the members needed to complete said heterocyclic ring are each independently selected from —CH$_2$—, —CHR$^x$—, —O—, —S—, —CO— and —NR$^4$—, it being understood however that said heterocyclic ring does not contain more than one member selected from the group consisting of —CHR$^x$—, —O—, —S—, —CO— and —NR$^4$—, R$^x$ representing hydroxy, hydroxymethyl, alkoxymethyl or alkoxy and R$^4$ representing hydrogen or alkyl; or also W represents —NR³— and R² and R³ form, together with the nitrogen that carries them, either an imidazolyl, pyrazolyl, 1,2,3-triazolyl or 1,2,4-triazolyl ring, which ring may be substituted by an alkyl group, or a 4-oxo-4H-pyridin-1-yl, 4,5-dihydro-pyrazol-1-yl, 2-methyl-4,5-dihydro-imidazol-1-yl or 3-methyl-5-oxo-2,5-dihydro-pyrazol-1-yl ring;

W represents —CH=CH— and R² represents alkyl, hydroxyalkyl, alkoxyalkyl, alkoxycarbonyl, phenyl or —CO—NR¹³R¹⁴;

R¹³ represents alkyl;

R¹⁴ represents alkyl; or

W represents —C≡C— and R² represents hydrogen, alkyl, hydroxyalkyl or alkoxyalkyl; or W represents —CO— and R² represents alkyl;

X represents —CO— and R⁶ represents alkyl, unsubstituted cycloalkyl of 3 to 7 ring members, alkoxy, alkynyloxy, aryloxy, aralkoxy, aryl, monocyclic heteroaryl, phenylalkyl or NR¹⁵R¹⁶, or X represents —SO₂— and R⁶ represents alkyl;

R¹⁵ represents alkyl;

R¹⁶ represents hydrogen or alkyl;

or R¹⁵ and R¹⁶ form, together with the nitrogen that carries them, a heterocyclic ring of 4 to 7 members wherein the members needed to complete said heterocyclic ring are each independently selected from —CH₂—, —O—, —S— and —NRʷ—, Rʷ representing hydrogen or alkyl, it being understood however that said heterocyclic ring does not contain more than one member selected from the group consisting of —O—, —S— and —NRʷ—;

Y represents a bond and Z represents hydrogen or phenyl substituted by carboxyalkoxy; or Y represents alkylene, alkoxyalkylene, phenylalkylene, alkoxyphenylene or alkoxyphenylalkylene and Z represents hydrogen, —OH, —NH₂, —COOH, tetrazolyl, —CO—NH₂, —COOR¹⁷, —NH—CO—R¹⁷, —NH—COOR⁷ or —NH—SO₂—R¹⁷, R¹⁷ representing alkyl.

More preferred compounds of formula I will be those wherein at least one of the following characteristics is present:

R¹ represents phenyl optionally substituted once by substituents each independently selected from the group consisting of halogen, methyl, methoxy, trifluoromethyl and trifluoromethoxy;

W represents a bond, and R² represents alkyl, haloalkyl, cyano, hydroxyalkyl, hydroxyalkyl substituted on its alkyl chain with an unsubstituted phenyl group, alkoxyalkyl, heterocyclyl, heterocyclylalkyl, cycloalkyl, aryl, heteroaryl, or one of the radicals

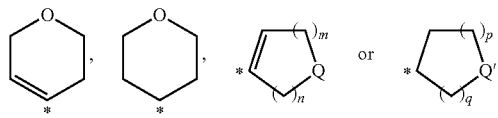

wherein:

m is 0 and n is 2 or 3 or m is 1 and n is 2, p is 0 and q is 2 or 3, or p is 1 and q is 2 or also p is 2 or 3 and q is 0, Q is —CO— or —CH(ORᵃ)—, Rᵃ being hydrogen or alkyl, and Q' is —CO—; or W represents —CH₂— and R² represents —NR⁷R⁸, —SR⁹ or —SO₂R¹⁰;

R⁷ represents alkyl or phenylalkyl;

R⁸ represents alkyl;

or R⁷ and R⁸ form, together with the nitrogen that carries them, a heterocyclic ring of 4 to 7 members wherein the members needed to complete said heterocyclic ring are each independently selected from —CH₂—, —CH(CH₃)—, —CHRʸ—, —O—, —S—, —CO— and —NR^z—, it being understood however that said heterocyclic ring does not contain more than one member selected from the group consisting of —CHRʸ—, —O—, —S—, —CO— and —NR^z—, Rʸ representing hydroxy, hydroxymethyl, alkoxymethyl, alkoxycarbonyl or alkoxy and R^z representing hydrogen, alkyl or alkoxycarbonyl;

R⁹ represents unsubstituted cycloalkyl of 3 to 7 ring members or aryl;

R¹⁰ represents alkyl, unsubstituted cycloalkyl of 3 to 7 ring members or aryl; or W represents —O— or —S— and R² represents alkyl, carboxyalkyl, alkoxycarbonylalkyl, hydroxyalkyl, alkoxyalkyl, heterocyclylalkyl, cycloalkyl, cycloalkylalkyl, aryl, aralkyl, heteroaryl or heteroarylalkyl; or W represents —NR³— and R² represents hydrogen, alkyl, alkoxycarbonylalkyl, carboxyalkyl, carboxyalkyl substituted on its alkyl part with an unsubstituted phenyl group, hydroxyalkyl, alkoxyalkyl, heterocyclyl, heterocyclylalkyl, cycloalkyl, cycloalkylalkyl, aryl, 2-phenylcyclopropyl, aralkyl, diphenylalkyl, heteroarylalkyl wherein the heteroaryl is a monocyclic heteroaryl, —COR¹¹ or —SO₂R¹²;

R³ represents hydrogen or alkyl;

R¹¹ represents alkyl, alkoxyalkyl, aryl, monocyclic heteroaryl or aralkyl;

R¹² represents alkyl or aryl; or

W represents —NR³— and R² and R³ form, together with the nitrogen that carries them, a heterocyclic ring of 4 to 7 members wherein the members needed to complete said heterocyclic ring are each independently selected from —CH₂—, —CHRˣ—, —O—, —S—, —CO— and —NR⁴—, it being understood however that said heterocyclic ring does not contain more than one member selected from the group consisting of —CHRˣ—, —O—, —S—, —CO— and —NR⁴—, Rˣ representing hydroxy, hydroxymethyl, alkoxymethyl or alkoxy and R⁴ representing hydrogen or alkyl; or also W represents —NR³— and R² and R³ form, together with the nitrogen that carries them, either an imidazolyl, pyrazolyl, 1,2,3-triazolyl or 1,2,4-triazolyl ring, which ring may be substituted by an alkyl group, or a 4-oxo-4H-pyridin-1-yl, 4,5-dihydro-pyrazol-1-yl, 2-methyl-4,5-dihydro-imidazol-1-yl or 3-methyl-5-oxo-2,5-dihydro-pyrazol-1-yl ring;

W represents —CH=CH— and R² represents alkyl, hydroxyalkyl, alkoxyalkyl, alkoxycarbonyl, phenyl or —CO—NR¹³R¹⁴;

R¹³ represents alkyl;

R¹⁴ represents alkyl; or

W represents —C≡C— and R² represents hydrogen, alkyl, hydroxyalkyl or alkoxyalkyl; or W represents —CO— and R² represents alkyl;

X represents —CO— and R⁶ represents alkyl, unsubstituted cycloalkyl of 3 to 7 ring members, alkoxy, alkynyloxy, phenoxy, phenylalkoxy, monocyclic heteroaryl, phenylalkyl or NR⁵R⁶, R¹⁵ represents alkyl;

R¹⁶ represents hydrogen or alkyl;

Y represents alkylene or alkoxyalkylene and Z represents —OH, —COOH, tetrazolyl or —COOR$^{17}$, R$^{17}$ representing alkyl.

Even more preferred compounds of formula I will be those wherein at least one of the following characteristics is present:

R$^1$ represents phenyl;

W represents a bond, and R$^2$ represents alkyl, hydroxyalkyl, alkoxyalkyl, heterocyclyl, heterocyclylalkyl, cycloalkyl of 3 to 7 ring members optionally substituted once by a hydroxy, hydroxymethyl or alkoxycarbonyl group, aryl, heteroaryl, or one of the radicals

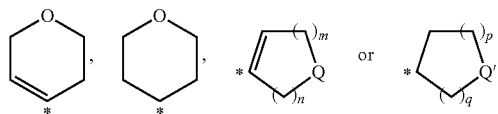

wherein:
m is 0 and n is 2 or 3 or m is 1 and n is 2,
p is 0 and q is 2 or 3, or p is 1 and q is 2 or also p is 2 or 3 and q is 0,
Q is —CO— or —CH(OR$^a$)—, R$^a$ being hydrogen, and Q' is —CO—; or
W represents —CH$_2$— and R$^2$ represents —NR$^7$R$^8$;
R$^7$ represents phenylalkyl;
R$^9$ represents alkyl; or
W represents —O— or —S— and R$^2$ represents cycloalkyl, phenylalkyl or heteroarylalkyl wherein the heteroaryl is a heteroaryl of 5 ring members; or
W represents —NR$^3$— and R$^2$ represents alkyl, carboxyalkyl substituted on its alkyl part with an unsubstituted phenyl group, hydroxyalkyl, alkoxyalkyl, heterocyclyl, heterocyclylalkyl, aryl, aralkyl;
R$^3$ represents hydrogen or methyl; or
W represents —NR$^3$— and R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl or alkoxy; or
W represents —NR$^3$— and R$^2$ and R$^3$ form, together with the nitrogen that carries them, either an imidazolyl, pyrazolyl, 1,2,3-triazolyl or 1,2,4-triazolyl ring, which ring may be substituted by an alkyl group, or a 4,5-dihydro-pyrazol-1-yl ring; or W represents —CH=CH— and R$^2$ represents hydroxyalkyl or alkoxycarbonyl; or
W represents —CO— and R$^2$ represents alkyl;
X represents —CO— and R$^6$ represents alkoxy, alkynyloxy or heteroaryl (and preferably alkoxy, alkynyloxy or heteroaryl of 5 ring members);
Y represents alkylene or alkoxyalkylene and Z represents —COOH.

Particularly preferred compounds of formula I will be those wherein at least one of the following characteristics is present:

R$^1$ represents phenyl;

W represents a bond, and R$^2$ represents alkyl, hydroxyalkyl, heterocyclylalkyl, cycloalkyl of 3 to 7 ring members optionally substituted once by a hydroxy, hydroxymethyl or alkoxycarbonyl group, phenyl optionally substituted once by a substituent selected from the group consisting of halogen, alkyl, alkoxy, hydroxymethyl, acetyl, methanesulfonyl and cyano, benzo[1,3]dioxolyl, monocyclic heteroaryl, 1-oxy-pyridin-2-yl, or the radical

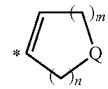

wherein:
m is 0 and n is 2 or 3 or m is 1 and n is 2,
Q is —CH(OH)—; or
W represents —S— and R$^2$ represents phenylalkyl; or
W represents —NR$^3$— and R$^2$ represents hydroxyalkyl, alkoxyalkyl, heterocyclyl, phenyl, indan-2-yl or phenylalkyl;
R$^3$ represents hydrogen; or
W represents —NR$^3$— and R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$-member, R$^x$ representing hydroxy, hydroxymethyl, alkoxymethyl or alkoxy; or
W represents —NR$^3$— and R$^2$ and R$^3$ form, together with the nitrogen that carries them, a pyrazolyl or 1,2,3-triazolyl ring, which ring may be substituted by an alkyl group; or
W represents —CH=CH— and R$^2$ represents alkoxycarbonyl; or
X represents —CO— and R$^6$ represents alkoxy or alkynyloxy;
Y represents —CH$_2$—, —CH$_2$—CH$_2$— or —CH$_2$—CH$_2$—CH$_2$— (and preferably —CH$_2$—CH$_2$—) and Z represents —COOH.

Furthermore, compounds of formula I wherein Y represents alkylene or alkoxyalkylene will generally be preferred over other compounds of formula I. Besides, compounds of formula I wherein Z represents —OH, —COOH, tetrazolyl or —COOR$^{17}$, R$^{17}$ representing alkyl will generally be preferred over other compounds of formula I.

The following main embodiments of compounds of formula I (or of salts thereof, in particular of pharmaceutically acceptable salts thereof) are particularly preferred.

According to a first main embodiment of this invention, the compounds of formula I will be such that W represents a bond; such compounds will be collectively designated by "compounds of formula I$_B$" throughout the specification and claims. In such case, the compounds of formula I$_B$ will preferably be such that:

R$^1$ represents phenyl optionally substituted once or twice by substituents each independently selected from the group consisting of halogen, methyl, methoxy, trifluoromethyl and trifluoromethoxy;

R$^2$ represents alkyl, hydroxyalkyl, alkoxyalkyl, heterocyclyl, heterocyclylalkyl, cycloalkyl of 3 to 7 ring members optionally substituted once by a hydroxy, hydroxymethyl or alkoxycarbonyl group, aryl, heteroaryl, or one of the radicals

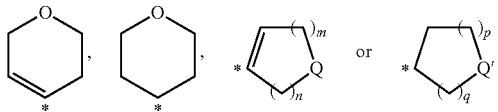

wherein:
m 0 and n is 2 or 3 or m is 1 and n is 2,
p is 0 and q is 2 or 3, or p is 1 and q is 2 or also p is 2 or 3 and q is 0,
Q is —CO— or —CH(OR$^a$)—, R$^a$ being hydrogen, and Q' is —CO—;
X represents —CO— and R$^6$ represents alkyl, unsubstituted cycloalkyl of 3 to 7 ring members, alkoxy, alkynyloxy, phenoxy, phenylalkoxy, monocyclic heteroaryl, phenylalkyl or NR$^{15}$R$^{16}$;
R$^{15}$ represents alkyl;
R$^{16}$ represents hydrogen or alkyl;
Y represents alkylene or alkoxyalkylene and Z represents —OH, —COOH, tetrazolyl or —COOR$^{17}$, R$^{17}$ representing alkyl.

Preferably, the compounds of formula I$_B$ will at least have one of the following characteristics:
R$^1$ represents phenyl optionally substituted once by a substituent selected from the group consisting of halogen, methyl, methoxy, trifluoromethyl and trifluoromethoxy;
R$^2$ represents alkyl, hydroxyalkyl, heterocyclylalkyl, cycloalkyl of 3 to 7 ring members optionally substituted once by a hydroxy, hydroxymethyl or alkoxycarbonyl group, phenyl optionally substituted once by a substituent selected from the group consisting of halogen, alkyl, alkoxy, hydroxymethyl, acetyl, methanesulfonyl and cyano, benzo[1,3]dioxolyl, monocyclic heteroaryl, 1-oxy-pyridin-2-yl, or the radical

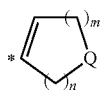

wherein:
m is 0 and n is 2 or 3 or m is 1 and n is 2, and
Q is —CH(OH)—;
each of R$^{5a}$ and R$^{5b}$ represents hydrogen;
X represents —CO— and R$^6$ represents alkoxy or alkynyloxy;
Y represents alkylene or alkoxyalkylene and Z represents —COOH.

More preferably, the compounds of formula I$_B$ will at least have one of the following characteristics:
R$^1$ represents phenyl optionally substituted once by a substituent selected from the group consisting of halogen, methyl and methoxy (and notably unsubstituted phenyl);
R$^2$ represents alkyl, hydroxyalkyl, heterocyclylalkyl, cycloalkyl of 3 to 7 ring members optionally substituted once by a hydroxy, hydroxymethyl or alkoxycarbonyl group, phenyl optionally substituted once by a substituent selected from the group consisting of halogen, alkyl, alkoxy, hydroxymethyl, acetyl, methanesulfonyl and cyano, benzo[1,3]dioxolyl, monocyclic heteroaryl, 1-oxy-pyridin-2-yl, or the radical

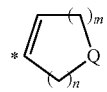

wherein:
m is 0 and n is 2 or 3 or m is 1 and n is 2, and
Q is —CH(OH)—;
each of R$^{5a}$ and R$^{5b}$ represents hydrogen;
X represents —CO— and R$^6$ represents alkoxy (in particular ethoxy);
Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

According to a second main embodiment of this invention, the compounds of formula I will be such that W represents —CH$_2$—; such compounds will be collectively designated by "compounds of formula I$_M$" throughout the specification and claims. In such case, the compounds of formula I$_M$ will preferably be such that:
R$^1$ represents phenyl optionally substituted once or twice by substituents each independently selected from the group consisting of halogen, methyl, methoxy, trifluoromethyl and trifluoromethoxy;
W represents —CH$_2$— and R$^2$ represents —NR$^7$R$^8$, —SR$^9$ or —SO$_2$R$^{10}$;
R$^7$ represents alkyl or phenylalkyl;
R$^8$ represents alkyl; or R$^7$ and R$^8$ form, together with the nitrogen that carries them, a heterocyclic ring of 4 to 7 members wherein the members needed to complete said heterocyclic ring are each independently selected from —CH$_2$—, —CH(CH$_3$)—, —CHR$^y$—, —O—, —S—, —CO— and —NR$^z$—, it being understood however that said heterocyclic ring does not contain more than one member selected from the group consisting of —CHR$^y$—, —O—, —S—, —CO— and —NR—, R$^y$ representing hydroxy, hydroxymethyl, alkoxymethyl, alkoxycarbonyl or alkoxy and R$^z$ representing hydrogen, alkyl or alkoxycarbonyl;
R$^9$ represents unsubstituted cycloalkyl of 3 to 7 ring members or aryl;
R$^{10}$ represents alkyl, unsubstituted cycloalkyl of 3 to 7 ring members or aryl;
X represents —CO— and R$^6$ represents alkyl, unsubstituted cycloalkyl of 3 to 7 ring members, alkoxy, alkynyloxy, phenoxy, phenylalkoxy, monocyclic heteroaryl, phenylalkyl or NR$^{15}$R$^{16}$,
R$^{15}$ represents alkyl;
R$^{16}$ represents hydrogen or alkyl;
Y represents alkylene or alkoxyalkylene and Z represents —OH, —COOH, tetrazolyl or —COOR$^{17}$, R$^{17}$ representing alkyl.

Preferably, the compounds of formula I$_M$ will at least have one of the following characteristics:
R$^1$ represents phenyl optionally substituted once by a substituent selected from the group consisting of halogen, methyl, methoxy, trifluoromethyl and trifluoromethoxy;
W represents —CH$_2$— and R$^2$ represents —NR$^7$R$^8$, —SR$^9$ or —SO$_2$R$^{10}$;
R$^7$ represents alkyl or phenylalkyl;
R$^8$ represents alkyl;
or R$^7$ and R$^8$ form, together with the nitrogen that carries them, a heterocyclic ring of 4 to 7 members wherein the members needed to complete said heterocyclic ring are each independently selected from —CH$_2$—, —CH (CH$_3$)—, —CHR$^y$—, —O—, —S—, —CO— and —NR$^z$—, it being understood however that said heterocyclic ring does not contain more than one member selected from the group consisting of —CHR$^y$—, —O—, —S—, —CO— and —NR$^z$—, R$^y$ representing hydroxy, hydroxymethyl, alkoxymethyl, alkoxycarbonyl or alkoxy and R$^z$ representing hydrogen, alkyl or alkoxycarbonyl;

R$^9$ represents unsubstituted cycloalkyl of 3 to 7 ring members or aryl;

R$^{10}$ represents alkyl, unsubstituted cycloalkyl of 3 to 7 ring members or aryl;

each of R$^{5a}$ and R$^{5b}$ represents hydrogen;

X represents —CO— and R$^6$ represents alkoxy or alkynyloxy;

Y represents alkylene or alkoxyalkylene and Z represents —COOH.

More preferably, the compounds of formula I$_M$ will at least have one of the following characteristics:

R$^1$ represents phenyl optionally substituted once by a substituent selected from the group consisting of halogen, methyl and methoxy (and notably unsubstituted phenyl);

R$^2$ represents —NR$^7$R$^8$;

R$^7$ represents phenylalkyl; and

R$^8$ represents alkyl;

each of R$^{5a}$ and R$^{5b}$ represents hydrogen;

X represents —CO— and R$^6$ represents alkoxy (in particular ethoxy);

Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

According to a third main embodiment of this invention, the compounds of formula I will be such that W represents —O—; such compounds will be collectively designated by "compounds of formula I$_O$" throughout the specification and claims. In such case, the compounds of formula I$_O$ will preferably be such that:

R$^1$ represents phenyl optionally substituted once or twice by substituents each independently selected from the group consisting of halogen, methyl, methoxy, trifluoromethyl and trifluoromethoxy;

R$^2$ represents alkyl, carboxyalkyl, alkoxycarbonylalkyl, hydroxyalkyl, alkoxyalkyl, heterocyclylalkyl, cycloalkyl, cycloalkylalkyl, aryl, aralkyl, heteroaryl or heteroarylalkyl;

X represents —CO— and R$^6$ represents alkyl, unsubstituted cycloalkyl of 3 to 7 ring members, alkoxy, alkynyloxy, phenoxy, phenylalkoxy, monocyclic heteroaryl, phenylalkyl or NR$^{15}$R$^{16}$;

R$^{15}$ represents alkyl;

R$^{16}$ represents hydrogen or alkyl;

Y represents alkylene or alkoxyalkylene and Z represents —OH, —COOH, tetrazolyl or —COOR$^{17}$, R$^{17}$ representing alkyl.

Preferably, the compounds of formula I$_O$ will at least have one of the following characteristics:

R$^1$ represents phenyl optionally substituted once by a substituent selected from the group consisting of halogen, methyl, methoxy, trifluoromethyl and trifluoromethoxy;

R$^2$ represents cycloalkyl, phenylalkyl or heteroarylalkyl wherein the heteroaryl is a heteroaryl of 5 ring members;

each of R$^{5a}$ and R$^{5b}$ represents hydrogen;

X represents —CO— and R$^6$ represents alkoxy or alkynyloxy;

Y represents alkylene or alkoxyalkylene and Z represents —COOH.

More preferably, the compounds of formula I$_O$ will at least have one of the following characteristics:

R$^1$ represents phenyl optionally substituted once by a substituent selected from the group consisting of halogen, methyl and methoxy (and notably unsubstituted phenyl);

R$^2$ represents cycloalkyl (in particular cyclopentyl);

each of R$^{5a}$ and R$^{5b}$ represents hydrogen;

X represents —CO— and R$^6$ represents alkoxy (in particular ethoxy);

Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

According to a fourth main embodiment of this invention, the compounds of formula I will be such that W represents —S—; such compounds will be collectively designated by "compounds of formula I$_S$" throughout the specification and claims. In such case, the compounds of formula I$_S$ will preferably be such that:

R$^1$ represents phenyl optionally substituted once or twice by substituents each independently selected from the group consisting of halogen, methyl, methoxy, trifluoromethyl and trifluoromethoxy;

R$^2$ represents alkyl, carboxyalkyl, alkoxycarbonylalkyl, hydroxyalkyl, alkoxyalkyl, heterocyclylalkyl, cycloalkyl, cycloalkylalkyl, aryl, aralkyl, heteroaryl or heteroarylalkyl;

X represents —CO— and R$^6$ represents alkyl, unsubstituted cycloalkyl of 3 to 7 ring members, alkoxy, alkynyloxy, phenoxy, phenylalkoxy, monocyclic heteroaryl, phenylalkyl or NR$^{15}$R$^{16}$;

R$^{15}$ represents alkyl;

R$^{16}$ represents hydrogen or alkyl;

Y represents alkylene or alkoxyalkylene and Z represents —OH, —COOH, tetrazolyl or —COOR$^{17}$, R$^{17}$ representing alkyl.

Preferably, the compounds of formula I$_S$ will at least have one of the following characteristics:

R$^1$ represents phenyl optionally substituted once by a substituent selected from the group consisting of halogen, methyl, methoxy, trifluoromethyl and trifluoromethoxy;

R$^2$ represents alkyl, carboxyalkyl, alkoxycarbonylalkyl, hydroxyalkyl, alkoxyalkyl, heterocyclylalkyl, cycloalkyl, cycloalkylalkyl, aryl, aralkyl, heteroaryl or heteroarylalkyl;

each of R$^{5a}$ and R$^{5b}$ represents hydrogen;

X represents —CO— and R$^6$ represents alkoxy or alkynyloxy;

Y represents alkylene or alkoxyalkylene and Z represents —COOH.

More preferably, the compounds of formula I$_S$ will at least have one of the following characteristics:

R$^1$ represents phenyl optionally substituted once by a substituent selected from the group consisting of halogen, methyl and methoxy (and notably unsubstituted phenyl);

R$^2$ represents phenylalkyl (notably benzyl);

each of R$^{5a}$ and R$^{5b}$ represents hydrogen;

X represents —CO— and R$^6$ represents alkoxy (in particular ethoxy);

Y represents alkylene (preferably —CH$_2$—, —CH$_2$—CH$_2$— or —CH$_2$—CH$_2$—CH$_2$— and more preferably —CH$_2$—CH$_2$—) and Z represents —COOH.

According to a fifth main embodiment of this invention, the compounds of formula I will be such that W represents —NR$^3$—; such compounds will be collectively designated by "compounds of formula $I_N$" throughout the specification and claims. In such case, the compounds of formula $I_N$ will preferably be such that:
- $R^1$ represents phenyl optionally substituted once or twice by substituents each independently selected from the group consisting of halogen, methyl, methoxy, trifluoromethyl and trifluoromethoxy;
- $R^2$ represents hydrogen, alkyl, dialkylaminoalkyl, alkoxycarbonylalkyl, carboxyalkyl, carboxyalkyl substituted on its alkyl part with an unsubstituted phenyl group, hydroxyalkyl, alkoxyalkyl, heterocyclyl, heterocyclylalkyl, cycloalkyl, cycloalkylalkyl, aryl, 2-phenylcyclopropyl, aralkyl, diphenylalkyl, heteroarylalkyl wherein the heteroaryl is a monocyclic heteroaryl, —$COR^{11}$ or —$SO_2R^{12}$;
- $R^3$ represents hydrogen or alkyl;
- $R^{11}$ represents alkyl, alkoxyalkyl, cycloalkyl, cycloalkylalkyl, aryl, monocyclic heteroaryl or aralkyl;
- $R^{12}$ represents alkyl or aryl; or
- $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^4$—, it being understood however that said heterocyclic ring does not contain more than one member selected from the group consisting of —$CHR^x$—, —O—, —S—, —CO— and —$NR^4$—, $R^x$ representing hydroxy, hydroxymethyl, alkoxymethyl or alkoxy and $R^4$ representing hydrogen or alkyl; or also
- $R^2$ and $R^3$ form, together with the nitrogen that carries them, either an imidazolyl, pyrazolyl, 1,2,3-triazolyl or 1,2,4-triazolyl ring, which ring may be substituted by an alkyl group, or a 4-oxo-4H-pyridin-1-yl, 4,5-dihydro-pyrazol-1-yl, 2-methyl-4,5-dihydro-imidazol-1-yl or 3-methyl-5-oxo-2,5-dihydro-pyrazol-1-yl ring;
- X represents —CO— and $R^6$ represents alkyl, unsubstituted cycloalkyl of 3 to 7 ring members, alkoxy, alkynyloxy, phenoxy, phenylalkoxy, monocyclic heteroaryl, phenylalkyl or $NR^{15}R^{16}$;
- $R^{15}$ represents alkyl;
- $R^{16}$ represents hydrogen or alkyl;
- Y represents alkylene or alkoxyalkylene and Z represents —OH, —COOH, tetrazolyl or —$COOR^{17}$, $R^{17}$ representing alkyl.

Preferably, the compounds of formula $I_N$ will at least have one of the following characteristics:
- $R^1$ represents phenyl optionally substituted once by a substituent selected from the group consisting of halogen, methyl, methoxy, trifluoromethyl and trifluoromethoxy;
- $R^2$ represents hydrogen, alkyl, alkoxycarbonylalkyl, carboxyalkyl, carboxyalkyl substituted on its alkyl part with an unsubstituted phenyl group, hydroxyalkyl, alkoxyalkyl, heterocyclyl, heterocyclylalkyl, cycloalkyl, cycloalkylalkyl, aryl, 2-phenylcyclopropyl, aralkyl, diphenylalkyl, heteroarylalkyl wherein the heteroaryl is a monocyclic heteroaryl, —$COR^{11}$ or —$SO_2R^{12}$;
- $R^3$ represents hydrogen or alkyl;
- $R^{11}$ represents alkyl, alkoxyalkyl, aryl, monocyclic heteroaryl or aralkyl;
- $R^{12}$ represents alkyl or aryl; or
- $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^4$—, it being understood however that said heterocyclic ring does not contain more than one member selected from the group consisting of —$CHR^x$—, —O—, —S—, —CO— and —$NR^4$—, $R^x$ representing hydroxy, hydroxymethyl, alkoxymethyl or alkoxy and $R^4$ representing hydrogen or alkyl; or also
- $R^2$ and $R^3$ form, together with the nitrogen that carries them, either an imidazolyl, pyrazolyl, 1,2,3-triazolyl or 1,2,4-triazolyl ring, which ring may be substituted by an alkyl group, or a 4-oxo-4H-pyridin-1-yl, 4,5-dihydro-pyrazol-1-yl, 2-methyl-4,5-dihydro-imidazol-1-yl or 3-methyl-5-oxo-2,5-dihydro-pyrazol-1-yl ring;
- each of $R^{5a}$ and $R^{5b}$ represents hydrogen;
- X represents —CO— and $R^6$ represents alkoxy or alkynyloxy;
- Y represents alkylene or alkoxyalkylene and Z represents —COOH.

More preferably, the compounds of formula $I_N$ will at least have one of the following characteristics:
- $R^1$ represents phenyl optionally substituted once by a substituent selected from the group consisting of halogen, methyl and methoxy (and notably unsubstituted phenyl);
- $R^2$ represents alkyl, carboxyalkyl substituted on its alkyl part with an unsubstituted phenyl group, hydroxyalkyl, alkoxyalkyl, heterocyclyl, heterocyclylalkyl, aryl or aralkyl;
- $R^3$ represents hydrogen or methyl; or
- $R^2$ and $R^3$ form, together with the nitrogen that carries them, a heterocyclic ring of 4 to 7 members wherein the members needed to complete said heterocyclic ring are each independently selected from —$CH_2$— and —$CHR^x$—, it being understood however that said heterocyclic ring does not contain more than one —$CHR^x$— member, $R^x$ representing hydroxy, hydroxymethyl, alkoxymethyl or alkoxy; or also
- W represents —$NR^3$— and $R^2$ and $R^3$ form, together with the nitrogen that carries them, either an imidazolyl, pyrazolyl, 1,2,3-triazolyl or 1,2,4-triazolyl ring, which ring may be substituted by an alkyl group, or a 4,5-dihydro-pyrazol-1-yl ring;
- each of $R^{5a}$ and $R^{5b}$ represents hydrogen;
- X represents —CO— and $R^6$ represents alkoxy (in particular ethoxy);
- Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

According to a variant of said fifth main embodiment, the compounds of formula $I_N$ will be such that the nitrogen atom of the —$NR^3$— radical is not member of a ring, i.e. such that $R^2$ represents hydrogen, alkyl, dialkylaminoalkyl, alkoxycarbonylalkyl, carboxyalkyl, carboxyalkyl substituted on its alkyl part with an unsubstituted phenyl group, hydroxyalkyl, alkoxyalkyl, heterocyclyl, heterocyclylalkyl, cycloalkyl, cycloalkylalkyl, aryl, 2-phenylcyclopropyl, aralkyl, diphenylalkyl, heteroarylalkyl wherein the heteroaryl is a monocyclic heteroaryl, —$COR^{11}$ or —$SO_2R^{12}$; such compounds will be collectively designated by "compounds of formula $I_{NL}$" throughout the specification and claims.

Preferably, the compounds of formula $I_{NL}$ will at least have one of the following characteristics:
- $R^1$ represents phenyl optionally substituted once by a substituent selected from the group consisting of halogen, methyl, methoxy, trifluoromethyl and trifluoromethoxy;
- $R^2$ represents hydrogen, alkyl, alkoxycarbonylalkyl, carboxyalkyl, carboxyalkyl substituted on its alkyl part with an unsubstituted phenyl group, hydroxyalkyl, alkoxyalkyl, heterocyclyl, heterocyclylalkyl, cycloalkyl, cycloalkylalkyl, aryl, 2-phenylcyclopropyl, aralkyl, diphenylalkyl, heteroarylalkyl wherein the heteroaryl is a monocyclic heteroaryl, —$COR^{11}$ or —$SO_2R^{12}$;

$R^3$ represents hydrogen or alkyl;

$R^{11}$ represents alkyl, alkoxyalkyl, aryl, monocyclic heteroaryl or aralkyl;

$R^{12}$ represents alkyl or aryl;

each of $R^{5a}$ and $R^{5b}$ represents hydrogen;

X represents —CO— and $R^6$ represents alkoxy or alkynyloxy;

Y represents alkylene or alkoxyalkylene and Z represents —COOH.

More preferably, the compounds of formula $I_N$ will at least have one of the following characteristics:

$R^1$ represents phenyl optionally substituted once by a substituent selected from the group consisting of halogen, methyl and methoxy (and notably unsubstituted phenyl);

$R^2$ represents alkyl, carboxyalkyl substituted on its alkyl part with an unsubstituted phenyl group, hydroxyalkyl, alkoxyalkyl, heterocyclyl, heterocyclylalkyl, aryl or aralkyl; $R^3$ represents hydrogen or methyl;

each of $R^{5a}$ and $R^{5b}$ represents hydrogen;

X represents —CO— and $R^6$ represents alkoxy (in particular ethoxy);

Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

According to another variant of said fifth main embodiment, the compounds of formula $I_N$ will be such that the nitrogen atom of the —$NR^3$— radical is member of a ring, i.e. either such that $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^4$—, it being understood however that said heterocyclic ring does not contain more than one member selected from the group consisting of —$CHR^x$—, —O—, —S—, —CO— and —$NR^4$—, $R^x$ representing hydroxy, hydroxymethyl, alkoxymethyl or alkoxy and $R^4$ representing hydrogen or alkyl, or such that $R^2$ and $R^3$ form, together with the nitrogen that carries them, either an imidazolyl, pyrazolyl, 1,2,3-triazolyl or 1,2,4-triazolyl ring, which ring may be substituted by an alkyl group, or a 4-oxo-4H-pyridin-1-yl, 4,5-dihydro-pyrazol-1-yl, 2-methyl-4,5-dihydro-imidazol-1-yl or 3-methyl-5-oxo-2,5-dihydro-pyrazol-1-yl ring; such compounds will be collectively designated by "compounds of formula $I_{NC}$" throughout the specification and claims.

Preferably, the compounds of formula $I_{NR}$ will at least have one of the following characteristics:

$R^1$ represents phenyl optionally substituted once by a substituent selected from the group consisting of halogen, methyl, methoxy, trifluoromethyl and trifluoromethoxy;

$R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^4$—, it being understood however that said heterocyclic ring does not contain more than one member selected from the group consisting of —$CHR^x$—, —O—, —S—, —CO— and —$NR^4$—, $R^x$ representing hydroxy, hydroxymethyl, alkoxymethyl or alkoxy and $R^4$ representing hydrogen or alkyl; or $R^2$ and $R^3$ form, together with the nitrogen that carries them, either an imidazolyl, pyrazolyl, 1,2,3-triazolyl or 1,2,4-triazolyl ring, which ring may be substituted by an alkyl group, or a 4-oxo-4H-pyridin-1-yl, 4,5-dihydro-pyrazol-1-yl, 2-methyl-4,5-dihydro-imidazol-1-yl or 3-methyl-5-oxo-2,5-dihydro-pyrazol-1-yl ring;

each of $R^{5a}$ and $R^{5b}$ represents hydrogen;

X represents —CO— and $R^6$ represents alkoxy or alkynyloxy;

Y represents alkylene or alkoxyalkylene and Z represents —COOH.

More preferably, the compounds of formula $I_{NR}$ will at least have one of the following characteristics:

$R^1$ represents phenyl optionally substituted once by a substituent selected from the group consisting of halogen, methyl and methoxy (and notably unsubstituted phenyl);

$R^2$ and $R^3$ form, together with the nitrogen that carries them, a heterocyclic ring of 4 to 7 members wherein the members needed to complete said heterocyclic ring are each independently selected from —$CH_2$— and —$CHR^x$—, it being understood however that said heterocyclic ring does not contain more than one —$CHR^x$— member, $R^x$ representing hydroxy, hydroxymethyl, alkoxymethyl or alkoxy; or W represents —$NR^3$— and $R^2$ and $R^3$ form, together with the nitrogen that carries them, either an imidazolyl, pyrazolyl, 1,2,3-triazolyl or 1,2,4-triazolyl ring, which ring may be substituted by an alkyl group, or a 4,5-dihydro-pyrazol-1-yl ring;

each of $R^{5a}$ and $R^{5b}$ represents hydrogen;

X represents —CO— and $R^6$ represents alkoxy (in particular ethoxy);

Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

According to a sixth main embodiment of this invention, the compounds of formula I will be such that W represents —CH═CH—; such compounds will be collectively designated by "compounds of formula $I_D$" throughout the specification and claims. In such case, the compounds of formula $I_D$ will preferably be such that:

$R^1$ represents phenyl optionally substituted once or twice by substituents each independently selected from the group consisting of halogen, methyl, methoxy, trifluoromethyl and trifluoromethoxy;

$R^2$ represents alkyl, hydroxyalkyl, alkoxyalkyl, alkoxycarbonyl, phenyl or —CO—$NR^{13}R^{14}$;

$R^{13}$ represents alkyl;

$R^{13}$ represents alkyl;

X represents —CO— and $R^6$ represents alkyl, unsubstituted cycloalkyl of 3 to 7 ring members, alkoxy, alkynyloxy, phenoxy, phenylalkoxy, monocyclic heteroaryl, phenylalkyl or $NR^{15}R^{16}$;

$R^{15}$ represents alkyl;

$R^{16}$ represents hydrogen or alkyl;

Y represents alkylene or alkoxyalkylene and Z represents —OH, —COOH, tetrazolyl or —$COOR^{17}$, $R^{17}$ representing alkyl.

Preferably, the compounds of formula $I_D$ will at least have one of the following characteristics:

$R^1$ represents phenyl optionally substituted once by a substituent selected from the group consisting of halogen, methyl, methoxy, trifluoromethyl and trifluoromethoxy;

$R^2$ represents alkyl, hydroxyalkyl, alkoxyalkyl, alkoxycarbonyl, phenyl or —CO—$NR^{13}R^{14}$; $R^{13}$ represents alkyl;

$R^{13}$ represents alkyl;

each of $R^{5a}$ and $R^{5b}$ represents hydrogen;

X represents —CO— and $R^6$ represents alkoxy or alkynyloxy;

Y represents alkylene or alkoxyalkylene and Z represents —COOH.

More preferably, the compounds of formula $I_D$ will at least have one of the following characteristics:

$R^1$ represents phenyl optionally substituted once by a substituent selected from the group consisting of halogen, methyl and methoxy (and notably unsubstituted phenyl);

$R^2$ represents hydroxyalkyl or alkoxycarbonyl;

each of $R^{5a}$ and $R^{5b}$ represents hydrogen;

X represents —CO— and $R^6$ represents alkoxy (in particular ethoxy);

Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

According to a seventh main embodiment of this invention, the compounds of formula I will be such that W represents —C≡C—; such compounds will be collectively designated by "compounds of formula $I_T$" throughout the specification and claims. In such case, the compounds of formula $I_T$ will preferably be such that:

$R^1$ represents phenyl optionally substituted once or twice by substituents each independently selected from the group consisting of halogen, methyl, methoxy, trifluoromethyl and trifluoromethoxy;

$R^2$ represents hydrogen, alkyl, hydroxyalkyl or alkoxyalkyl;

X represents —CO— and $R^6$ represents alkyl, unsubstituted cycloalkyl of 3 to 7 ring members, alkoxy, alkynyloxy, phenoxy, phenylalkoxy, monocyclic heteroaryl, phenylalkyl or $NR^{15}R^{16}$;

$R^{15}$ represents alkyl;

$R^{16}$ represents hydrogen or alkyl;

Y represents alkylene or alkoxyalkylene and Z represents —OH, —COOH, tetrazolyl or —$COOR^{17}$, $R^{17}$ representing alkyl.

Preferably, the compounds of formula $I_T$ will at least have one of the following characteristics:

$R^1$ represents phenyl optionally substituted once by a substituent selected from the group consisting of halogen, methyl, methoxy, trifluoromethyl and trifluoromethoxy;

$R^2$ represents hydrogen, alkyl, hydroxyalkyl or alkoxyalkyl;

each of $R^{5a}$ and $R^{5b}$ represents hydrogen;

X represents —CO— and $R^6$ represents alkoxy or alkynyloxy;

Y represents alkylene or alkoxyalkylene and Z represents —COOH.

More preferably, the compounds of formula $I_T$ will at least have one of the following characteristics:

$R^1$ represents phenyl optionally substituted once by a substituent selected from the group consisting of halogen, methyl and methoxy (and notably unsubstituted phenyl);

$R^2$ represents hydroxyalkyl;

each of $R^{5a}$ and $R^{5b}$ represents hydrogen;

X represents —CO— and $R^6$ represents alkoxy (in particular ethoxy);

Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

According to an eighth main embodiment of this invention, the compounds of formula I will be such that W represents —CO—; such compounds will be collectively designated by "compounds of formula $I_{CO}$" throughout the specification and claims. In such case, the compounds of formula $I_{CO}$ will preferably be such that:

$R^1$ represents phenyl optionally substituted once or twice by substituents each independently selected from the group consisting of halogen, methyl, methoxy, trifluoromethyl and trifluoromethoxy;

$R^2$ represents alkyl;

X represents —CO— and $R^6$ represents alkyl, unsubstituted cycloalkyl of 3 to 7 ring members, alkoxy, alkynyloxy, phenoxy, phenylalkoxy, monocyclic heteroaryl, phenylalkyl or $NR^{15}R^{16}$;

$R^{15}$ represents alkyl;

$R^{16}$ represents hydrogen or alkyl;

Y represents alkylene or alkoxyalkylene and Z represents —OH, —COOH, tetrazolyl or —$COOR^{17}$, $R^{17}$ representing alkyl.

Preferably, the compounds of formula $I_{CO}$ will at least have one of the following characteristics:

$R^1$ represents phenyl optionally substituted once by a substituent selected from the group consisting of halogen, methyl, methoxy, trifluoromethyl and trifluoromethoxy;

$R^2$ represents alkyl of 1 to 4 carbon atoms;

each of $R^{5a}$ and $R^{5b}$ represents hydrogen;

X represents —CO— and $R^6$ represents alkoxy or alkynyloxy;

Y represents alkylene or alkoxyalkylene and Z represents —COOH.

More preferably, the compounds of formula $I_{CO}$ will at least have one of the following characteristics:

$R^1$ represents phenyl optionally substituted once by a substituent selected from the group consisting of halogen, methyl and methoxy (and notably unsubstituted phenyl);

$R^2$ represents methyl;

each of $R^{5a}$ and $R^{5b}$ represents hydrogen;

X represents —CO— and $R^6$ represents alkoxy (in particular ethoxy);

Y represents alkylene (preferably —$CH_2$—, —$CH_2$—$CH_2$— or —$CH_2$—$CH_2$—$CH_2$— and more preferably —$CH_2$—$CH_2$—) and Z represents —COOH.

The following additional embodiments relate specifically to compounds of formula $I_{P2}$ and sometimes also to compounds of formula $I_{P1}$.

According to a particular embodiment of this invention, the compounds of formula I will be compounds of formula $I_{P2}$ that are such that:

i) W represents a bond, —$CH_2$—, —O—, —S— or —$NR^3$— and $R^2$ represents hydroxyalkyl, alkoxyalkyl, heterocyclyl, heterocyclylalkyl, cycloalkyl substituted once by a hydroxy group, cycloalkylalkyl wherein the cycloalkyl is substituted once by a hydroxy group, aralkyl, or one of the radicals

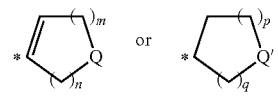

wherein:

m is 0 and n is 2 or 3 or m is 1 and n is 2, p is 0 and q is 2 or 3 or p is 1 and q is 2, Q is —CO— or —CH(OR$^a$)—, R$^a$ being hydrogen or alkyl, and
Q' is —CO—,
or W represents —O—, —S— or —NR$^3$— and R$^2$ represents heteroarylalkyl;

ii) W represents —NR$^3$— and R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy, hydroxymethyl, alkoxymethyl or alkoxy; or iii) W represents —NR$^3$— and R$^2$ and R$^3$ form, together with the nitrogen that carries them, an imidazolyl, pyrazolyl, 1,2,3-triazolyl or 1,2,4-triazolyl ring; or iv) W represents —CH=CH— or —C≡C— and R$^2$ represents hydroxyalkyl.

Preferably, according to the particular embodiment of this invention mentioned here above, the compounds of formula $I_{P2}$ will be such that:

i) W represents a bond, —CH$_2$—, —O—, —S— or —NR$^3$— and R$^2$ represents hydroxyalkyl, heterocyclyl, heterocyclylalkyl, cycloalkyl substituted once by a hydroxy group, cycloalkylalkyl wherein the cycloalkyl is substituted once by a hydroxy group, 4-oxo-cyclohex-1-enyl, 4-hydroxy-cyclohex-1-enyl or 4-oxo-cyclohexyl; or ii) W represents —NR$^3$— and R$^2$ and R$^3$ form, together with the nitrogen that carries them, a heterocyclic ring of 4 to 7 members wherein the members needed to complete said heterocyclic ring are each independently selected from —CH$_2$— and —CHR$^x$—, it being understood however that said heterocyclic ring does not contain more than one —CHR$^x$— member, R$^x$ representing hydroxy or hydroxymethyl; or iii) W represents —NR$^3$— and R$^2$ and R$^3$ form, together with the nitrogen that carries them, an imidazolyl or pyrazolyl ring; or iv) W represents —CH=CH— or —C≡C— and R$^2$ represents hydroxyalkyl.

More preferably, according to the particular embodiment of this invention mentioned here above, the compounds of formula $I_{P2}$ will be such that:

i) W represents a bond, —CH$_2$—, —O—, —S— or —NR$^3$— and R$^2$ represents hydroxyalkyl (and in particular hydroxymethyl, 1-hydroxy-ethyl, 1-hydroxy-propyl or 2-hydroxy-2-propyl), tetrahydrofuran-2-yl, tetrahydrofuran-3-yl, tetrahydrofuran-2-ylmethyl, 4-hydroxycyclohexyl, 2-hydroxycyclohexyl, 4-oxo-cyclohex-1-enyl, 4-hydroxy-cyclohex-1-enyl or 4-oxo-cyclohexyl; or ii) W represents —NR$^3$— and R$^2$ and R$^3$ form, together with the nitrogen that carries them, a heterocyclic ring such that the radical —NR$^2$R$^3$ represents 4-hydroxy-piperidin-1-yl, (R)-2-hydroxymethyl-pyrrolidin-1-yl, (S)-2-hydroxymethyl-pyrrolidin-1-yl, (R)-3-hydroxy-pyrrolidin-1-yl, (S)-3-hydroxy-pyrrolidin-1-yl, 3-hydroxy-piperidin-1-yl or 2-hydroxymethyl-piperidin-1-yl; or iii) W represents —NR$^3$— and R$^2$ and R$^3$ form, together with the nitrogen that carries them, an imidazolyl or pyrazolyl ring; or iv) W represents —CH=CH— or —C≡C— and R$^2$ represents hydroxymethyl, 1-hydroxy-ethyl, 1-hydroxy-propyl or 2-hydroxy-2-propyl.

According to a first variant of the particular embodiment mentioned here above, the compounds of formula $I_{P2}$ will be such that they have the features mentioned at point i) of one of the feature lists above. According to a second variant of the particular embodiment mentioned here above, the compounds of formula $I_{P2}$ will be such that they have the features mentioned at point ii) of one of the feature lists above. According to a third variant of the particular embodiment mentioned here above, the compounds of formula $I_{P2}$ will be such that they have the features mentioned at point iii) of one of the feature lists above. According to a fourth variant of the particular embodiment mentioned here above, the compounds of formula $I_{P2}$ will be such that they have the features mentioned at point iv). of one of the feature lists above.

Preferred compounds of formula $I_{P2}$ are also those wherein at least one of the following characteristics is present:

R$^1$ representing phenyl which may be substituted with one to two substituents, each independently selected from the group consisting of halogen, methyl, methoxy, trifluoromethyl and trifluoromethoxy (and preferably independently selected from the group consisting of halogen, methyl and methoxy);

W representing a bond, —CH$_2$—, —O—, —S— or —NR$^3$— and R$^2$ representing alkyl, alkoxycarbonylalkyl, carboxyalkyl, carboxyalkyl substituted with an unsubstituted phenyl group, hydroxyalkyl, heterocyclyl, heterocyclylalkyl, cycloalkyl, cycloalkylalkyl, aryl, aralkyl, diphenylalkyl or heteroarylmethyl (and preferably carboxyalkyl substituted with an unsubstituted phenyl group, hydroxyalkyl, heterocyclyl, heterocyclylalkyl, cycloalkyl, cycloalkylalkyl, aryl, aralkyl, diphenylalkyl or heteroarylmethyl);

R$^3$ representing hydrogen or methyl;

W representing —NR$^3$— and R$^2$ and R$^3$ forming, together with the nitrogen that carries them, a heterocyclic ring of 4 to 7 members wherein the members needed to complete said heterocyclic ring are each independently selected from —CH$_2$—, —CHR$^x$—, —O—, —S—, —CO— and —NR$^4$—, it being understood however that said heterocyclic ring does not contain more than one member selected from the group consisting of —CHR$^x$—, —O—, —S— and —NR$^4$—, R$^x$ representing hydroxy, hydroxymethyl, alkoxymethyl or alkoxy and R$^4$ representing hydrogen or alkyl (notably hydrogen or methyl and in particular hydrogen);

W representing —NR$^3$—, R$^2$ and R$^3$ can form, together with the nitrogen that carries them, an imidazolyl, pyrazolyl, 1,2,3-triazolyl or 1,2,4-triazolyl ring (and in particular an imidazolyl or pyrazolyl ring);

W represents —CH=CH— or —C≡C— and R$^2$ represents hydrogen or hydroxyalkyl;

at least one of R$^{5a}$ and R$^{5b}$ representing hydrogen;

X representing —CO— and R$^6$ representing alkoxy, alkynyloxy or heteroaryl (preferably alkoxy, notably methoxy or ethoxy and in particular ethoxy);

Y representing alkylene, alkoxyalkylene or phenylalkylene (preferably alkylene or alkoxyalkylene, notably alkylene and in particular alkylene of 1 to 3 carbon atoms);

Z representing —COOH or tetrazolyl (and in particular —COOH).

More preferred compounds of formula $I_{P2}$ (and preferred compounds of formula $I_{P1}$) are also those wherein at least one of the following characteristics is present:

R$^1$ representing phenyl which may be substituted with one to two substituents, each independently selected from the group consisting of halogen, methyl, methoxy, trifluoromethyl and trifluoromethoxy (and preferably independently selected from the group consisting of halogen, methyl and methoxy);

R² representing alkyl, alkoxycarbonylalkyl, carboxyalkyl, carboxyalkyl substituted with an unsubstituted phenyl group, hydroxyalkyl, heterocyclylalkyl, cycloalkyl, cycloalkylalkyl, aryl, aralkyl, or diphenylalkyl;

R³ representing hydrogen or methyl;

R² and R³ forming, together with the nitrogen that carries them, a heterocyclic ring of 4 to 6 members wherein the members needed to complete said heterocyclic ring are each independently selected from —CH₂—, —O—, —S— and —NR¹, it being understood however that said heterocyclic ring does not contain more than one member selected from the group consisting of —O—, —S— and —NR⁴, R⁴ representing hydrogen;

R⁴ representing hydrogen or methyl;

at least one of $R^{5a}$ and $R^{5b}$ representing hydrogen;

X representing —CO— and R⁶ representing alkoxy, alkynyloxy or heteroaryl;

Y representing alkylene, alkoxyalkylene or phenylalkylene;

Z representing —COOH or tetrazolyl.

Particularly preferred compounds of formula $I_{P2}$ (and more preferred compounds of formula $I_{P1}$) are those wherein at least one of the following characteristics is present:

R¹ representing unsubstituted phenyl;

R² representing alkyl, carboxyalkyl substituted with an unsubstituted phenyl group, cycloalkyl (notably unsubstituted alkyl), aryl or aralkyl;

R³ representing hydrogen;

R² and R³ forming, together with the nitrogen that carries them, a heterocyclic ring of 4 to 6 ring members (and preferably of 5 members) wherein each of the members needed to complete said heterocyclic ring is —CH₂—;

R⁴ representing hydrogen;

each of $R^{5a}$ and $R^{5b}$ representing hydrogen;

X representing —CO— and R⁶ representing alkoxy;

Y representing alkylene or alkoxyalkylene (and notably alkylene);

Z representing —COOH.

Besides, preferred combinations for the meanings of Y and Z in formula I (or in formula $I_{P2}$ or $I_{P1}$) will be as follows:

Y representing alkylene (and notably methylene, ethylene or propylene, in particular ethylene) and Z representing —COOH;

Y representing alkoxyalkylene and Z representing —COOH (in particular —Y—Z representing —(CH₂)₂—O—CH₂—COOH); or Y representing alkylene (and notably methylene) and Z representing tetrazolyl.

According to one particularly preferred embodiment, the compounds of formula $I_{P2}$ (or of formula $I_{P1}$) will be such that W represents a bond or —CH₂—; such compounds will be collectively designated by "compounds of formula $I_{CP2}$" (respectively "compounds of formula $I_{CP1}$") throughout the specification and claims. In such case, the compounds of formula $I_{P2}$ (or of formula $I_{P1}$) will preferably be such that:

R¹ represents unsubstituted phenyl;

R² represents alkyl, cycloalkyl or aryl;

each of $R^{5a}$ and $R^{5b}$ represents hydrogen;

X representing —CO— and R⁶ represents alkoxy;

Y represents alkylene; and

Z represents —COOH.

According to a preferred variant of the corresponding embodiment, the compounds of formula $I_{CP2}$ (or of formula $I_{CP1}$) will at least have one of the following characteristics:

R¹ represents phenyl optionally substituted once by a substituent selected from the group consisting of halogen, methyl and methoxy (and in particular unsubstituted phenyl);

R² represents alkyl, hydroxyalkyl, cycloalkyl or phenyl optionally substituted once by a substituent selected from the group consisting of halogen, methyl, methoxy and carboxy (and in particular hydroxyalkyl, unsubstituted cycloalkyl or cycloalkyl substituted once by hydroxy);

each of $R^{5a}$ and $R^{5b}$ represents hydrogen;

X represents —CO— and R⁶ represents alkoxy (and in particular ethoxy);

Y represents alkylene or alkoxyalkylene and Z represents —COOH or tetrazolyl (and preferably Y represents alkylene or alkoxyalkylene and Z represents —COOH, in particular Y representing methylene, ethylene or propylene and Z representing —COOH).

According to a preferred sub-variant of the corresponding embodiment, the compounds of formula $I_{CP2}$ (or of formula $I_{CP1}$) will be such that W represents a bond. Preferably, the compounds of this subvariant will at least have one of the following further characteristics:

R¹ represents phenyl optionally substituted once by a substituent selected from the group consisting of halogen, methyl and methoxy (and in particular unsubstituted phenyl);

R² represents alkyl, hydroxyalkyl, cycloalkyl or phenyl optionally substituted once by a substituent selected from the group consisting of halogen, methyl, methoxy and carboxy (and in particular hydroxyalkyl, unsubstituted cycloalkyl or cycloalkyl substituted once by hydroxy);

each of $R^{5a}$ and $R^{5b}$ represents hydrogen;

X represents —CO— and R⁶ represents alkoxy (and in particular ethoxy);

Y represents alkylene or alkoxyalkylene and Z represents —COOH or tetrazolyl (and preferably Y represents alkylene and Z represents —COOH, in particular Y representing methylene, ethylene or propylene and Z representing —COOH).

According to a preferred sub-variant of the corresponding embodiment, the compounds of formula $I_{CP2}$ (or of formula $I_{CP1}$) will be such that W represents —CH₂—. Preferably, the compounds of this subvariant will at least have one of the following further characteristics:

R¹ represents phenyl optionally substituted once by a substituent selected from the group consisting of halogen, methyl and methoxy (and in particular unsubstituted phenyl);

R² represents hydrogen or alkyl (and in particular alkyl);

each of $R^{5a}$ and $R^{5b}$ represents hydrogen;

X represents —CO— and R⁶ represents alkoxy (and in particular ethoxy);

Y represents alkylene or alkoxyalkylene and Z represents —COOH or tetrazolyl (and preferably Y represents alkylene or alkoxyalkylene and Z represents —COOH, in particular Y representing methylene, ethylene or propylene and Z representing —COOH).

According to another particularly preferred embodiment, the compounds of formula $I_{P2}$ (or of formula $I_{P1}$) will be such that W represents —O—; such compounds will be collectively designated by "compounds of formula $I_{OP2}$" (respectively "compounds of formula $I_{OP1}$") throughout the specification and claims. In such case, the compounds of formula $I_{P2}$ (or of formula $I_{P1}$) will preferably be such that:

$R^1$ represents unsubstituted phenyl;
$R^2$ represents cycloalkyl (and in particular cyclopentyl);
$R^5$ represents hydrogen;
X representing —CO— and $R^6$ represents alkoxy or alkenyloxy;
Y represents alkylene or alkoxyalkylene (and notably alkylene); and
Z represents —COOH.

According to a preferred variant of the corresponding embodiment, the compounds of formula $I_{OP2}$ (or of formula $I_{OP1}$) will at least have one of the following characteristics:
  $R^1$ represents phenyl optionally substituted once by a substituent selected from the group consisting of halogen, methyl and methoxy (and in particular unsubstituted phenyl);
  $R^2$ represents alkyl, hydroxyalkyl, cycloalkyl or phenyl optionally substituted once by a substituent selected from the group consisting of halogen, methyl, methoxy and carboxy (and in particular hydroxyalkyl, unsubstituted cycloalkyl or cycloalkyl substituted once by hydroxy);
  each of $R^{5a}$ and $R^{5b}$ represents hydrogen;
  X represents —CO— and $R^6$ represents alkoxy (and in particular ethoxy);
  Y represents alkylene or alkoxyalkylene and Z represents —COOH or tetrazolyl (and preferably Y represents alkylene or alkoxyalkylene and Z represents —COOH, in particular Y representing methylene, ethylene or propylene and Z representing —COOH).

Still another preferred embodiment regarding the compounds of formula $I_{P2}$ (or of formula $I_{P1}$) is that wherein the compounds of formula $I_{P2}$ (or of formula $I_{P1}$) are such that W represents —$NR^3$—; such compounds will be collectively designated by "compounds of formula $I_{NP2}$" (respectively "compounds of formula $I_{NP1}$") throughout the specification and claims. In such case, the compounds of formula $I_{P2}$ (or of formula $I_{P1}$) will preferably be such that:
  $R^1$ represents unsubstituted phenyl;
  $R^2$ represents aryl, aralkyl or carboxyalkyl substituted with an unsubstituted phenyl group;
  $R^3$ represents hydrogen;
  $R^5$ represents hydrogen;
  X representing —CO— and $R^6$ represents alkoxy;
  Y represents alkylene or alkoxyalkylene (and notably alkylene); and
  Z represents —COOH or tetrazolyl (and notably —COOH).

According to a preferred variant of the corresponding embodiment, the compounds of formula $I_{NP2}$ (or of formula $I_{NP1}$) will at least have one of the following characteristics:
  $R^1$ represents phenyl optionally substituted once by a substituent selected from the group consisting of halogen, methyl and methoxy (and in particular unsubstituted phenyl);
  $R^2$ represents alkyl, carboxyalkyl substituted with an unsubstituted phenyl group, hydroxyalkyl, cycloalkyl, phenyl optionally substituted once by a substituent selected from the group consisting of halogen, methyl, methoxy and carboxy, phenylalkyl (and in particular hydroxyalkyl, unsubstituted cycloalkyl or cycloalkyl substituted once by hydroxy) and $R^3$ represents hydrogen;
  $R^2$ and $R^3$ form, together with the nitrogen that carries them, a heterocyclic ring of 4 to 7 members wherein the members needed to complete said heterocyclic ring are each independently selected from —$CH_2$—, —$CHR^x$—, —O—, —S—, —CO— and —$NR^4$—, it being understood however that said heterocyclic ring does not contain more than one member selected from the group consisting of —$CHR^x$—, —O—, —S— and —$NR^4$—, $R^x$ representing hydroxy or hydroxymethyl and $R^4$ representing hydrogen or alkyl;
  $R^2$ and $R^3$ form, together with the nitrogen that carries them, an imidazolyl, pyrazolyl, 1,2,3-triazolyl or 1,2,4-triazolyl ring
  each of $R^{5a}$ and $R^{5b}$ represents hydrogen;
  X represents —CO— and $R^6$ represents alkoxy (and in particular ethoxy);
  Y represents alkylene or alkoxyalkylene and Z represents —COOH or tetrazolyl (and preferably Y represents alkylene or alkoxyalkylene and Z represents —COOH, in particular Y representing methylene, ethylene or propylene and Z representing —COOH).

Still another preferred embodiment regarding the compounds of general formula $I_{P2}$ (or of formula $I_{P1}$) is that wherein the compounds of general formula $I_{P2}$ (or of formula $I_{P1}$) are such that W represents —S—; such compounds will be collectively designated by "compounds of general formula $I_{SP2}$" (respectively "compounds of general formula $I_{SP1}$") throughout the specification and claims.

According to a preferred variant of the corresponding embodiment, the compounds of general formula $I_{SP2}$ will at least have one of the following characteristics:
  $R^1$ represents phenyl optionally substituted once by a substituent selected from the group consisting of halogen, methyl and methoxy (and in particular unsubstituted phenyl);
  $R^2$ represents alkyl, cycloalkyl, phenylalkyl or heteroarylalkyl (and in particular phenylalkyl or heteroarylalkyl, notably benzyl or tetrahydrofuran-2-ylmethyl);
  each of $R^{5a}$ and $R^{5b}$ represents hydrogen;
  X represents —CO— and $R^6$ represents alkoxy (and in particular ethoxy);
  Y represents alkylene or alkoxyalkylene and Z represents —COOH or tetrazolyl (and preferably Y represents alkylene or alkoxyalkylene and Z represents —COOH, in particular Y representing methylene, ethylene or propylene and Z representing —COOH).

Still another preferred embodiment regarding the compounds of formula $I_{P2}$ is that wherein the compounds of formula $I_{P2}$ are such that W represents —CH=CH— or —C≡C—; such compounds will be collectively designated by "compounds of formula $I_{DTP2}$" (respectively "compounds of formula $I_{DTP1}$") throughout the specification and claims.

According to a preferred variant of the corresponding embodiment, the compounds of formula $I_{DTP2}$ (or of formula $I_{DTP1}$) will be at least have one of the following characteristics: $R^2$ represents hydrogen or hydroxyalkyl (and in particular hydroxyalkyl).
  $R^1$ represents phenyl optionally substituted once by a substituent selected from the group consisting of halogen, methyl and methoxy (and in particular unsubstituted phenyl);
  $R^2$ represents hydrogen or hydroxyalkyl (and in particular hydroxyalkyl);
  each of $R^{5a}$ and $R^{5b}$ represents hydrogen;
  X represents —CO— and $R^6$ represents alkoxy (and in particular ethoxy);
  Y represents alkylene or alkoxyalkylene and Z represents —COOH or tetrazolyl (and preferably Y represents alkylene or alkoxyalkylene and Z represents —COOH, in particular Y representing methylene, ethylene or propylene and Z representing —COOH).

The following compounds of general formula I are especially preferred:

4-{(S)-4-carboxy-2-[(6-cyclopentyloxy-2-phenyl-pyrimidine-4-carbonyl)-amino]-butyryl}-piperazine-1-carboxylic acid ethyl ester;
4-{(S)-3-carboxy-2-[(6-cyclopentyloxy-2-phenyl-pyrimidine-4-carbonyl)-amino]-propionyl}-piperazine-1-carboxylic acid ethyl ester;
4-{(S)-5-carboxy-2-[(6-cyclopentyloxy-2-phenyl-pyrimidine-4-carbonyl)-amino]-pentanoyl}-piperazine-1-carboxylic acid ethyl ester;
4-{2-[(6-cyclopentyloxy-2-phenyl-pyrimidine-4-carbonyl)-amino]-acetyl}-piperazine-1-carboxylic acid ethyl ester;
4-{(S)-2-[(6-cyclopentyloxy-2-phenyl-pyrimidine-4-carbonyl)-amino]-3-methyl-butyryl}-piperazine-1-carboxylic acid ethyl ester;
4-{(S)-3-carbamoyl-2-[(6-cyclopentyloxy-2-phenyl-pyrimidine-4-carbonyl)-amino]-propionyl}-piperazine-1-carboxylic acid ethyl ester;
4-{(S)-4-carbamoyl-2-[(6-cyclopentyloxy-2-phenyl-pyrimidine-4-carbonyl)-amino]-butyryl}-piperazine-1-carboxylic acid ethyl ester;
4-{(S)-3-amino-2-[(6-cyclopentyloxy-2-phenyl-pyrimidine-4-carbonyl)-amino]-propionyl}-piperazine-1-carboxylic acid ethyl ester;
4-{(S)-6-amino-2-[(6-cyclopentyloxy-2-phenyl-pyrimidine-4-carbonyl)-amino]-hexanoyl}-piperazine-1-carboxylic acid ethyl ester;
4-{(S)-2-[(6-cyclopentyloxy-2-phenyl-pyrimidine-4-carbonyl)-amino]-3-hydroxy-propionyl}-piperazine-1-carboxylic acid ethyl ester;
4-{(S)-2-[(6-cyclopentyloxy-2-phenyl-pyrimidine-4-carbonyl)-amino]-4-hydroxy-butyryl}-piperazine-1-carboxylic acid ethyl ester;
4-{(S)-2-[(6-cyclopentyloxy-2-phenyl-pyrimidine-4-carbonyl)-amino]-5-hydroxy-pentanoyl}-piperazine-1-carboxylic acid ethyl ester;
4-{(S)-2-[(6-cyclopentyloxy-2-phenyl-pyrimidine-4-carbonyl)-amino]-6-hydroxy-hexanoyl}-piperazine-1-carboxylic acid ethyl ester;
4-{(S)-3-acetylamino-2-[(6-cyclopentyloxy-2-phenyl-pyrimidine-4-carbonyl)-amino]-propionyl}-piperazine-1-carboxylic acid ethyl ester;
4-{(S)-2-[(6-cyclopentyloxy-2-phenyl-pyrimidine-4-carbonyl)-amino]-3-methoxycarbonylamino-propionyl}-piperazine-1-carboxylic acid ethyl ester;
4-{(S)-2-[(6-cyclopentyloxy-2-phenyl-pyrimidine-4-carbonyl)-amino]-3-methanesulfonylamino-propionyl}-piperazine-1-carboxylic acid ethyl ester;
4-{(S)-4-carboxymethoxy-2-[(6-cyclopentyloxy-2-phenyl-pyrimidine-4-carbonyl)-amino]-butyryl}-piperazine-1-carboxylic acid ethyl ester;
4-[(S)-2-[(6-cyclopentyloxy-2-phenyl-pyrimidine-4-carbonyl)-amino]-3-(1H-tetrazol-5-yl)-propionyl]-piperazine-1-carboxylic acid ethyl ester;
4-[(S)-2-[(6-cyclopentyloxy-2-phenyl-pyrimidine-4-carbonyl)-amino]-4-(1H-tetrazol-5-yl)-butyryl]-piperazine-1-carboxylic acid ethyl ester;
4-{(S)-2-[(6-cyclopentyloxy-2-phenyl-pyrimidine-4-carbonyl)-amino]-3-[4-(1H-tetrazol-5-yl)-phenyl]-propionyl}-piperazine-1-carboxylic acid ethyl ester;
4-{(S)-3-(4-carboxy-phenyl)-2-[(6-cyclopentyloxy-2-phenyl-pyrimidine-4-carbonyl)-amino]-propionyl}-piperazine-1-carboxylic acid ethyl ester;
4-{(S)-3-(4-carboxymethoxy-phenyl)-2-[(6-cyclopentyloxy-2-phenyl-pyrimidine-4-carbonyl)-amino]-propionyl}-piperazine-1-carboxylic acid ethyl ester;
4-{(S)-4-carboxy-2-[(6-carboxymethoxy-2-phenyl-pyrimidine-4-carbonyl)-amino]-butyryl}-piperazine-1-carboxylic acid ethyl ester;
4-{(S)-4-carboxy-2-[(2-phenyl-6-propoxy-pyrimidine-4-carbonyl)-amino]-butyryl}-piperazine-1-carboxylic acid ethyl ester;
4-((S)-4-carboxy-2-{[6-(2-hydroxy-ethoxy)-2-phenyl-pyrimidine-4-carbonyl]-amino}-butyryl)-piperazine-1-carboxylic acid ethyl ester;
4-{(S)-2-[(6-benzyloxy-2-phenyl-pyrimidine-4-carbonyl)-amino]-4-carboxy-butyryl}-piperazine-1-carboxylic acid ethyl ester;
4-{(S)-4-carboxy-2-[(6-cyclopropylmethoxy-2-phenyl-pyrimidine-4-carbonyl)-amino]-butyryl}-piperazine-1-carboxylic acid ethyl ester;
4-{(S)-4-carboxy-2-[(6-cyclohexyloxy-2-phenyl-pyrimidine-4-carbonyl)-amino]-butyryl}-piperazine-1-carboxylic acid ethyl ester;
4-{(S)-4-carboxy-2-[(6-isopropoxy-2-phenyl-pyrimidine-4-carbonyl)-amino]-butyryl}-piperazine-1-carboxylic acid ethyl ester;
4-{(S)-4-carboxy-2-[(6-methoxy-2-phenyl-pyrimidine-4-carbonyl)-amino]-butyryl}-piperazine-1-carboxylic acid ethyl ester;
4-{3-(3-carboxymethoxy-phenyl)-2-[(6-cyclopentyloxy-2-phenyl-pyrimidine-4-carbonyl)-amino]-propionyl}-piperazine-1-carboxylic acid ethyl ester;
4-{3-(2-carboxymethoxy-phenyl)-2-[(6-cyclopentyloxy-2-phenyl-pyrimidine-4-carbonyl)-amino]-propionyl}-piperazine-1-carboxylic acid ethyl ester;
4-{(S)-2-(4-carboxymethoxy-phenyl)-2-[(6-cyclopentyloxy-2-phenyl-pyrimidine-4-carbonyl)-amino]-acetyl}-piperazine-1-carboxylic acid ethyl ester;
4-{(S)-4-carboxy-2-[(6-cyclopentyloxy-2-phenyl-pyrimidine-4 carbonyl)-amino]-butyryl}-piperazine-1-carboxylic acid prop-2-ynyl ester;
4-{(S)-4-carboxy-2-[(6-cyclopentyloxy-2-phenyl-pyrimidine-4-carbonyl)-amino]-butyryl}-piperazine-1-carboxylic acid butyl ester;
4-{(S)-4-carboxy-2-[(6-cyclopentyloxy-2-phenyl-pyrimidine-4-carbonyl)-amino]-butyryl}-piperazine-1-carboxylic acid isobutyl ester;
4-{(S)-4-carboxy-2-[(6-cyclopentyloxy-2-phenyl-pyrimidine-4-carbonyl)-amino]-butyryl}-piperazine-1-carboxylic acid 2,2-dimethyl-propyl ester;
4-{(S)-4-carboxy-2-[(6-cyclopentyloxy-2-phenyl-pyrimidine-4-carbonyl)-amino]-butyryl}-piperazine-1-carboxylic acid isopropyl ester;
(S)-4-[(6-cyclopentyloxy-2-phenyl-pyrimidine-4-carbonyl)-amino]-5-[4-(furan-2-carbonyl)-piperazin-1-yl]-5-oxo-pentanoic acid;
4-{(S)-4-carboxy-2-[(6-cyclopentyloxy-2-phenyl-pyrimidine-4-carbonyl)-amino]-butyryl}-piperazine-1-carboxylic acid phenyl ester;
(S)-5-(4-benzoyl-piperazin-1-yl)-4-[(6-cyclopentyloxy-2-phenyl-pyrimidine-4-carbonyl)-amino]-5-oxo-pentanoic acid;
4-{(S)-4-carboxy-2-[(6-cyclopentyloxy-2-phenyl-pyrimidine-4-carbonyl)-amino]-butyryl}-piperazine-1-carboxylic acid benzyl ester;
(S)-5-(4-butyryl-piperazin-1-yl)-4-[(6-cyclopentyloxy-2-phenyl-pyrimidine-4-carbonyl)-amino]-5-oxo-pentanoic acid;
(S)-4-[(6-cyclopentyloxy-2-phenyl-pyrimidine-4-carbonyl)-amino]-5-oxo-5-[4-(propane-1-sulfonyl)-piperazin-1-yl]-pentanoic acid;

4-{(S)-4-carboxy-2-[(6-cyclopentyloxy-2-phenyl-pyrimidine-4-carbonyl)-amino]-butyryl}-3-methyl-piperazine-1-carboxylic acid ethyl ester;
4-{(S)-4-carboxy-2-[(6-cyclopentyloxy-2-phenyl-pyrimidine-4-carbonyl)-amino]-butyryl}-2-methyl-piperazine-1-carboxylic acid ethyl ester;
4-{(S)-4-carboxy-2-[(6-cyclopentyloxy-2-phenyl-pyrimidine-4-carbonyl)-amino]-butyryl}-trans-2,5-dimethyl-piperazine-1-carboxylic acid ethyl ester;
4-{(S)-4-carboxy-2-[(6-methylamino-2-phenyl-pyrimidine-4-carbonyl)-amino]-butyryl}-piperazine-1-carboxylic acid ethyl ester;
4-{(S)-4-carboxy-2-[(2-phenyl-6-propylamino-pyrimidine-4-carbonyl)-amino]-butyryl}-piperazine-1-carboxylic acid ethyl ester;
4-{(S)-4-carboxy-2-[(6-isopropylamino-2-phenyl-pyrimidine-4-carbonyl)-amino]-butyryl}-piperazine-1-carboxylic acid ethyl ester;
4-{(S)-2-[(6-butylamino-2-phenyl-pyrimidine-4-carbonyl)-amino]-4-carboxy-butyryl}-piperazine-1-carboxylic acid ethyl ester;
4-{(S)-4-carboxy-2-[(6-isobutylamino-2-phenyl-pyrimidine-4-carbonyl)-amino]-butyryl}-piperazine-1-carboxylic acid ethyl ester;
4-{(S)-4-carboxy-2-[(6-cyclopropylamino-2-phenyl-pyrimidine-4-carbonyl)-amino]-butyryl}-piperazine-1-carboxylic acid ethyl ester;
4-{(S)-4-carboxy-2-[(6-cyclopentylamino-2-phenyl-pyrimidine-4-carbonyl)-amino]-butyryl}-piperazine-1-carboxylic acid ethyl ester;
4-{(S)-4-carboxy-2-[(6-cyclohexylamino-2-phenyl-pyrimidine-4-carbonyl)-amino]-butyryl}-piperazine-1-carboxylic acid ethyl ester;
4-((S)-4-carboxy-2-{[6-(ethoxycarbonylmethyl-amino)-2-phenyl-pyrimidine-4-carbonyl]-amino}-butyryl)-piperazine-1-carboxylic acid ethyl ester;
4-((S)-4-carboxy-2-{[6-(carboxymethyl-amino)-2-phenyl-pyrimidine-4-carbonyl]-amino}-butyryl)-piperazine-1-carboxylic acid ethyl ester;
4-((S)-4-carboxy-2-{[6-(2-hydroxy-ethylamino)-2-phenyl-pyrimidine-4-carbonyl]-amino}-butyryl)-piperazine-1-carboxylic acid ethyl ester;
4-((S)-4-carboxy-2-{[6-(2-ethoxycarbonyl-ethylamino)-2-phenyl-pyrimidine-4-carbonyl]-amino}-butyryl)-piperazine-1-carboxylic acid ethyl ester;
4-((S)-4-carboxy-2-{[6-(2-carboxy-ethylamino)-2-phenyl-pyrimidine-4-carbonyl]-amino}-butyryl)-piperazine-1-carboxylic acid ethyl ester;
4-((S)-4-carboxy-2-{[6-(3-hydroxy-propylamino)-2-phenyl-pyrimidine-4-carbonyl]-amino}-butyryl)-piperazine-1-carboxylic acid ethyl ester;
4-((S)-4-carboxy-2-{[6-(3-carboxy-propylamino)-2-phenyl-pyrimidine-4-carbonyl]-amino}-butyryl)-piperazine-1-carboxylic acid ethyl ester;
4-((S)-4-carboxy-2-{[6-(2-dimethylamino-ethylamino)-2-phenyl-pyrimidine-4-carbonyl]-amino}-butyryl)-piperazine-1-carboxylic acid ethyl ester;
4-((S)-4-carboxy-2-{[6-(3-dimethylamino-propylamino)-2-phenyl-pyrimidine-4-carbonyl]-amino}-butyryl)-piperazine-1-carboxylic acid ethyl ester;
4-((S)-4-carboxy-2-{[6-(2-morpholin-4-yl-ethylamino)-2-phenyl-pyrimidine-4-carbonyl]-amino}-butyryl)-piperazine-1-carboxylic acid ethyl ester;
4-((S)-4-carboxy-2-{[6-(3-morpholin-4-yl-propylamino)-2-phenyl-pyrimidine-4-carbonyl]-amino}-butyryl)-piperazine-1-carboxylic acid ethyl ester;
4-{(S)-2-[(6-benzylamino-2-phenyl-pyrimidine-4-carbonyl)-amino]-4-carboxy-butyryl}-piperazine-1-carboxylic acid ethyl ester;
4-((S)-4-carboxy-2-{[2-phenyl-6-((S)-1-phenyl-ethylamino)-pyrimidine-4-carbonyl]-amino}-butyryl)-piperazine-1-carboxylic acid ethyl ester;
4-((S)-4-carboxy-2-{[2-phenyl-6-((R)-1-phenyl-ethylamino)-pyrimidine-4-carbonyl]-amino}-butyryl)-piperazine-1-carboxylic acid ethyl ester;
4-((S)-4-carboxy-2-{[6-((S)-2-carboxy-1-phenyl-ethylamino)-2-phenyl-pyrimidine-4-carbonyl]-amino}-butyryl)-piperazine-1-carboxylic acid ethyl ester;
4-((S)-4-carboxy-2-{[6-((R)-2-carboxy-1-phenyl-ethylamino)-2-phenyl-pyrimidine-4-carbonyl]-amino}-butyryl)-piperazine-1-carboxylic acid ethyl ester;
4-{(S)-4-carboxy-2-[(6-phenethylamino-2-phenyl-pyrimidine-4-carbonyl)-amino]-butyryl}-piperazine-1-carboxylic acid ethyl ester;
4-((S)-4-carboxy-2-{[2-phenyl-6-(2-phenyl-propylamino)-pyrimidine-4-carbonyl]-amino}-butyryl)-piperazine-1-carboxylic acid ethyl ester;
4-((S)-4-carboxy-2-{[6-(1,2-diphenyl-ethylamino)-2-phenyl-pyrimidine-4-carbonyl]-amino}-butyryl)-piperazine-1-carboxylic acid ethyl ester;
4-(4-carboxy-2-{[2-phenyl-6-(trans-2-phenyl-cyclopropylamino)-pyrimidine-4-carbonyl]-amino}-butyryl)-piperazine-1-carboxylic acid ethyl ester;
4-((S)-4-carboxy-2-{[6-(indan-1-ylamino)-2-phenyl-pyrimidine-4-carbonyl]-amino}-butyryl)-piperazine-1-carboxylic acid ethyl ester;
4-((S)-4-carboxy-2-{[6-((R)-indan-1-ylamino)-2-phenyl-pyrimidine-4-carbonyl]-amino}-butyryl)-piperazine-1-carboxylic acid ethyl ester;
4-((S)-4-carboxy-2-{[6-(indan-2-ylamino)-2-phenyl-pyrimidine-4-carbonyl]-amino}-butyryl)-piperazine-1-carboxylic acid ethyl ester;
4-{(S)-4-carboxy-2-[(6-dimethylamino-2-phenyl-pyrimidine-4-carbonyl)-amino]-butyryl}-piperazine-1-carboxylic acid ethyl ester;
4-{(S)-2-[(6-azetidin-1-yl-2-phenyl-pyrimidine-4-carbonyl)-amino]-4-carboxy-butyryl}-piperazine-1-carboxylic acid ethyl ester;
4-{(S)-4-carboxy-2-[(2-phenyl-6-pyrrolidin-1-yl-pyrimidine-4-carbonyl)-amino]-butyryl}-piperazine-1-carboxylic acid ethyl ester;
4-{(S)-4-carboxy-2-[(2-phenyl-6-piperidin-1-yl-pyrimidine-4-carbonyl)-amino]-butyryl}-piperazine-1-carboxylic acid ethyl ester;
4-((S)-2-{[6-(butyl-methyl-amino)-2-phenyl-pyrimidine-4-carbonyl]-amino}-4-carboxy-butyryl)-piperazine-1-carboxylic acid ethyl ester;
4-{(S)-4-carboxy-2-[(2-phenyl-6-phenylamino-pyrimidine-4-carbonyl)-amino]-butyryl}-piperazine-1-carboxylic acid ethyl ester;
4-((S)-4-carboxy-2-{[6-(4-fluoro-phenylamino)-2-phenyl-pyrimidine-4-carbonyl]-amino}-butyryl)-piperazine-1-carboxylic acid ethyl ester;
4-{(S)-4-carboxy-2-[(6-methyl-2-phenyl-pyrimidine-4-carbonyl)-amino]-butyryl}-piperazine-1-carboxylic acid ethyl ester;
4-{(S)-4-carboxy-2-[(6-isopropyl-2-phenyl-pyrimidine-4-carbonyl)-amino]-butyryl}-piperazine-1-carboxylic acid ethyl ester;
4-{(S)-2-[(6-butyl-2-phenyl-pyrimidine-4-carbonyl)-amino]-4-carboxy-butyryl}-piperazine-1-carboxylic acid ethyl ester;

4-{(S)-4-carboxy-2-[(6-isobutyl-2-phenyl-pyrimidine-4-carbonyl)-amino]-butyryl}-piperazine-1-carboxylic acid ethyl ester;
4-{(S)-4-carboxy-2-[(6-cyclopropyl-2-phenyl-pyrimidine-4-carbonyl)-amino]-butyryl}-piperazine-1-carboxylic acid ethyl ester;
4-{(S)-4-carboxy-2-[(6-cyclopentyl-2-phenyl-pyrimidine-4-carbonyl)-amino]-butyryl}-piperazine-1-carboxylic acid ethyl ester;
4-{(S)-4-carboxy-2-[(2,6-diphenyl-pyrimidine-4-carbonyl)-amino]-butyryl}-piperazine-1-carboxylic acid ethyl ester;
4-{(S)-4-carboxy-2-[(2-phenyl-6-o-tolyl-pyrimidine-4-carbonyl)-amino]-butyryl}-piperazine-1-carboxylic acid ethyl ester;
4-{(S)-4-carboxy-2-[(2-phenyl-6-m-tolyl-pyrimidine-4-carbonyl)-amino]-butyryl}-piperazine-1-carboxylic acid ethyl ester;
4-{(S)-4-carboxy-2-[(2-phenyl-6-p-tolyl-pyrimidine-4-carbonyl)-amino]-butyryl}-piperazine-1-carboxylic acid ethyl ester;
4-((S)-4-carboxy-2-{[6-(3-carboxy-phenyl)-2-phenyl-pyrimidine-4-carbonyl]-amino}-butyryl)-piperazine-1-carboxylic acid ethyl ester;
4-((S)-4-carboxy-2-{[6-(4-carboxy-phenyl)-2-phenyl-pyrimidine-4-carbonyl]-amino}-butyryl)-piperazine-1-carboxylic acid ethyl ester;
4-((S)-4-carboxy-2-{[2-(4-fluoro-phenyl)-6-methyl-pyrimidine-4-carbonyl]-amino}-butyryl)-piperazine-1-carboxylic acid ethyl ester;
4-((S)-4-carboxy-2-{[2-(3-fluoro-phenyl)-6-methyl-pyrimidine-4-carbonyl]-amino}-butyryl)-piperazine-1-carboxylic acid ethyl ester;
4-((S)-4-carboxy-2-{[2-(2-fluoro-phenyl)-6-methyl-pyrimidine-4-carbonyl]-amino}-butyryl)-piperazine-1-carboxylic acid ethyl ester;
4-((S)-4-carboxy-2-{[2-(4-chloro-phenyl)-6-methyl-pyrimidine-4-carbonyl]-amino}-butyryl)-piperazine-1-carboxylic acid ethyl ester;
4-((S)-4-carboxy-2-{[2-(3-chloro-phenyl)-6-methyl-pyrimidine-4-carbonyl]-amino}-butyryl)-piperazine-1-carboxylic acid ethyl ester;
4-((S)-4-carboxy-2-{[2-(2-chloro-phenyl)-6-methyl-pyrimidine-4-carbonyl]-amino}-butyryl)-piperazine-1-carboxylic acid ethyl ester;
4-{(S)-4-carboxy-2-[(6-methyl-2-p-tolyl-pyrimidine-4-carbonyl)-amino]-butyryl}-piperazine-1-carboxylic acid ethyl ester;
4-{(S)-4-carboxy-2-[(6-methyl-2-m-tolyl-pyrimidine-4-carbonyl)-amino]-butyryl}-piperazine-1-carboxylic acid ethyl ester;
4-((S)-4-carboxy-2-{[2-(4-methoxy-phenyl)-6-methyl-pyrimidine-4-carbonyl]-amino}-butyryl)-piperazine-1-carboxylic acid ethyl ester;
4-((S)-4-carboxy-2-{[2-(3-methoxy-phenyl)-6-methyl-pyrimidine-4-carbonyl]-amino}-butyryl)-piperazine-1-carboxylic acid ethyl ester;
4-{2-[(6-isopropylamino-2-phenyl-pyrimidine-4-carbonyl)-amino]-acetyl}-piperazine-1-carboxylic acid ethyl ester;
4-{2-[(6-benzylamino-2-phenyl-pyrimidine-4-carbonyl)-amino]-acetyl}-piperazine-1-carboxylic acid ethyl ester;
4-{2-[(2,6-diphenyl-pyrimidine-4-carbonyl)-amino]-acetyl}-piperazine-1-carboxylic acid ethyl ester;
4-{2-[(6-cyclopropyl-2-phenyl-pyrimidine-4-carbonyl)-amino]-acetyl}-piperazine-1-carboxylic acid ethyl ester;
4-{(S)-2-[(6-isopropylamino-2-phenyl-pyrimidine-4-carbonyl)-amino]-3-methyl-butyryl}-piperazine-1-carboxylic acid ethyl ester;
4-{(S)-2-[(6-benzylamino-2-phenyl-pyrimidine-4-carbonyl)-amino]-3-methyl-butyryl}-piperazine-1-carboxylic acid ethyl ester;
4-{(S)-2-[(2,6-diphenyl-pyrimidine-4-carbonyl)-amino]-3-methyl-butyryl}-piperazine-1-carboxylic acid ethyl ester;
4-{(S)-3-(4-carboxy-phenyl)-2-[(6-isopropylamino-2-phenyl-pyrimidine-4-carbonyl)-amino]-propionyl}-piperazine-1-carboxylic acid ethyl ester;
4-{(S)-2-[(6-benzylamino-2-phenyl-pyrimidine-4-carbonyl)-amino]-3-(4-carboxy-phenyl)-propionyl}-piperazine-1-carboxylic acid ethyl ester;
4-{(S)-3-(4-carboxy-phenyl)-2-[(2,6-diphenyl-pyrimidine-4-carbonyl)-amino]-propionyl}-piperazine-1-carboxylic acid ethyl ester;
4-{(S)-3-(4-carboxy-phenyl)-2-[(6-cyclopropyl-2-phenyl-pyrimidine-4-carbonyl)-amino]-propionyl}-piperazine-1-carboxylic acid ethyl ester;
4-{(S)-5-carboxy-2-[(6-isopropylamino-2-phenyl-pyrimidine-4-carbonyl)-amino]-pentanoyl}-piperazine-1-carboxylic acid ethyl ester;
4-{(S)-2-[(6-benzylamino-2-phenyl-pyrimidine-4-carbonyl)-amino]-5-carboxy-pentanoyl}-piperazine-1-carboxylic acid ethyl ester;
4-{(S)-5-carboxy-2-[(2,6-diphenyl-pyrimidine-4-carbonyl)-amino]-pentanoyl}-piperazine-1-carboxylic acid ethyl ester;
4-{(S)-5-carboxy-2-[(6-cyclopropyl-2-phenyl-pyrimidine-4-carbonyl)-amino]-pentanoyl}-piperazine-1-carboxylic acid ethyl ester;
4-{(S)-2-[(6-benzylamino-2-phenyl-pyrimidine-4-carbonyl)-amino]-3-carbamoyl-propionyl}-piperazine-1-carboxylic acid ethyl ester;
4-[(S)-2-[(6-benzylamino-2-phenyl-pyrimidine-4-carbonyl)-amino]-3-(2H-tetrazol-5-yl)-propionyl]-piperazine-1-carboxylic acid ethyl ester;
4-{(S)-3-(4-hydroxy-phenyl)-2-[(6-isopropylamino-2-phenyl-pyrimidine-4-carbonyl)-amino]-propionyl}-piperazine-1-carboxylic acid ethyl ester;
4-{(S)-4-tert-butoxycarbonyl-2-[(6-cyclopentyloxy-2-phenyl-pyrimidine-4-carbonyl)-amino]-butyryl}-piperazine-1-carboxylic acid ethyl ester;
4-{(S)-3-tert-butoxycarbonyl-2-[(6-cyclopentyloxy-2-phenyl-pyrimidine-4-carbonyl)-amino]-propionyl}-piperazine-1-carboxylic acid ethyl ester;
4-{(S)-5-tert-butoxycarbonyl-2-[(6-cyclopentyloxy-2-phenyl-pyrimidine-4-carbonyl)-amino]-pentanoyl}-piperazine-1-carboxylic acid ethyl ester;
4-{(S)-2-[(6-cyclopentyloxy-2-phenyl-pyrimidine-4-carbonyl)-amino]-4-ethoxycarbonylmethoxy-butyryl}-piperazine-1-carboxylic acid ethyl ester;
4-[(S)-2-[(6-cyclopentyloxy-2-phenyl-pyrimidine-4-carbonyl)-amino]-3-(4-methoxycarbonyl-phenyl)-propionyl]-piperazine-1-carboxylic acid ethyl ester;
4-[(S)-2-[(6-cyclopentyloxy-2-phenyl-pyrimidine-4-carbonyl)-amino]-3-(4-methoxycarbonylmethoxy-phenyl)-propionyl]-piperazine-1-carboxylic acid ethyl ester;
4-{(S)-4-tert-butoxycarbonyl-2-[(6-carboxymethoxy-2-phenyl-pyrimidine-4-carbonyl)-amino]-butyryl}-piperazine-1-carboxylic acid ethyl ester;
4-{(S)-4-tert-butoxycarbonyl-2-[(2-phenyl-6-propoxy-pyrimidine-4-carbonyl)-amino]-butyryl}-piperazine-1-carboxylic acid ethyl ester;
4-((S)-4-tert-butoxycarbonyl-2-{[6-(2-hydroxy-ethoxy)-2-phenyl-pyrimidine-4-carbonyl]-amino}-butyryl)-piperazine-1-carboxylic acid ethyl ester;

4-{(S)-2-[(6-benzyloxy-2-phenyl-pyrimidine-4-carbonyl)-amino]-4-tert-butoxycarbonyl-butyryl}-piperazine-1-carboxylic acid ethyl ester;
4-{(S)-4-tert-butoxycarbonyl-2-[(6-cyclopropylmethoxy-2-phenyl-pyrimidine-4-carbonyl)-amino]-butyryl}-piperazine-1-carboxylic acid ethyl ester;
4-{(S)-4-tert-butoxycarbonyl-2-[(6-cyclohexyloxy-2-phenyl-pyrimidine-4-carbonyl)-amino]-butyryl}-piperazine-1-carboxylic acid ethyl ester;
4-{tert-butoxycarbonyl-2-[(6-isopropoxy-2-phenyl-pyrimidine-4-carbonyl)-amino]-butyryl}-piperazine-1-carboxylic acid ethyl ester;
4-{(S)-4-tert-butoxycarbonyl-2-[(6-methoxy-2-phenyl-pyrimidine-4-carbonyl)-amino]-butyryl}-piperazine-1-carboxylic acid ethyl ester;
4-[2-[(6-cyclopentyloxy-2-phenyl-pyrimidine-4-carbonyl)-amino]-3-(3-ethoxy-carbonylmethoxy-phenyl)-propionyl]-piperazine-1-carboxylic acid ethyl ester;
4-[2-[(6-cyclopentyloxy-2-phenyl-pyrimidine-4-carbonyl)-amino]-3-(2-ethoxy-carbonylmethoxy-phenyl)-propionyl]-piperazine-1-carboxylic acid ethyl ester;
4-[(S)-2-[(6-cyclopentyloxy-2-phenyl-pyrimidine-4-carbonyl)-amino]-2-(4-ethoxycarbonylmethoxy-phenyl)-acetyl]-piperazine-1-carboxylic acid ethyl ester;
4-{(S)-4-tert-butoxycarbonyl-2-[(6-cyclopentyloxy-2-phenyl-pyrimidine-4-carbonyl)-amino]-butyryl}-piperazine-1-carboxylic acid prop-2-ynyl ester;
4-{(S)-4-tert-butoxycarbonyl-2-[(6-cyclopentyloxy-2-phenyl-pyrimidine-4-carbonyl)-amino]-butyryl}-piperazine-1-carboxylic acid butyl ester;
4-{(S)-4-tert-butoxycarbonyl-2-[(6-cyclopentyloxy-2-phenyl-pyrimidine-4-carbonyl)-amino]-butyryl}-piperazine-1-carboxylic acid isobutyl ester;
4-{(S)-4-tert-butoxycarbonyl-2-[(6-cyclopentyloxy-2-phenyl-pyrimidine-4-carbonyl)-amino]-butyryl}-piperazine-1-carboxylic acid 2,2-dimethyl-propyl ester;
4-{(S)-4-tert-butoxycarbonyl-2-[(6-cyclopentyloxy-2-phenyl-pyrimidine-4-carbonyl)-amino]-butyryl}-piperazine-1-carboxylic acid isopropyl ester;
4-[(S)-(6-cyclopentyloxy-2-phenyl-pyrimidine-4-carbonyl)-amino]-5-[4-(furan-2-carbonyl)-piperazin-1-yl]-5-oxo-pentanoic acid tert-butyl ester;
4-{(S)-4-tert-butoxycarbonyl-2-[(6-cyclopentyloxy-2-phenyl-pyrimidine-4-carbonyl)-amino]-butyryl}-piperazine-1-carboxylic acid phenyl ester;
5-((S)-4-benzoyl-piperazin-1-yl)-4-[(6-cyclopentyloxy-2-phenyl-pyrimidine-4-carbonyl)-amino]-5-oxo-pentanoic acid tert-butyl ester;
4-{(S)-4-tert-butoxycarbonyl-2-[(6-cyclopentyloxy-2-phenyl-pyrimidine-4-carbonyl)-amino]-butyryl}-piperazine-1-carboxylic acid benzyl ester;
5-((S)-4-butyryl-piperazin-1-yl)-4-[(6-cyclopentyloxy-2-phenyl-pyrimidine-4-carbonyl)-amino]-5-oxo-pentanoic acid tert-butyl ester;
(S)-4-[(6-cyclopentyloxy-2-phenyl-pyrimidine-4-carbonyl)-amino]-5-oxo-5-[4-(propane-1-sulfonyl)-piperazin-1-yl]-pentanoic acid tert-butyl ester;
4-{(S)-4-tert-butoxycarbonyl-2-[(6-cyclopentyloxy-2-phenyl-pyrimidine-4-carbonyl)-amino]-butyryl}-3-methyl-piperazine-1-carboxylic acid ethyl ester;
4-{(S)-4-tert-butoxycarbonyl-2-[(6-cyclopentyloxy-2-phenyl-pyrimidine-4-carbonyl)-amino]-butyryl}-2-methyl-piperazine-1-carboxylic acid ethyl ester;
4-{(S)-4-tert-butoxycarbonyl-2-[(6-cyclopentyloxy-2-phenyl-pyrimidine-4-carbonyl)-amino]-butyryl}-trans-2,5-dimethyl-piperazine-1-carboxylic acid ethyl ester;
4-{(S)-4-tert-butoxycarbonyl-2-[(6-methylamino-2-phenyl-pyrimidine-4-carbonyl)-amino]-butyryl}-piperazine-1-carboxylic acid ethyl ester;
4-{(S)-4-tert-butoxycarbonyl-2-[(2-phenyl-6-propylamino-pyrimidine-4-carbonyl)-amino]-butyryl}-piperazine-1-carboxylic acid ethyl ester;
4-{(S)-4-tert-butoxycarbonyl-2-[(6-isopropylamino-2-phenyl-pyrimidine-4-carbonyl)-amino]-butyryl}-piperazine-1-carboxylic acid ethyl ester;
4-{(S)-4-tert-butoxycarbonyl-2-[(6-butylamino-2-phenyl-pyrimidine-4-carbonyl)-amino]-butyryl}-piperazine-1-carboxylic acid ethyl ester;
4-{(S)-4-tert-butoxycarbonyl-2-[(6-isobutylamino-2-phenyl-pyrimidine-4-carbonyl)-amino]-butyryl}-piperazine-1-carboxylic acid ethyl ester;
4-{(S)-4-tert-butoxycarbonyl-2-[(6-cyclopropylamino-2-phenyl-pyrimidine-4-carbonyl)-amino]-butyryl}-piperazine-1-carboxylic acid ethyl ester;
4-{(S)-4-tert-butoxycarbonyl-2-[(6-cyclopentylamino-2-phenyl-pyrimidine-4-carbonyl)-amino]-butyryl}-piperazine-1-carboxylic acid ethyl ester;
4-{(S)-4-tert-butoxycarbonyl-2-[(6-cyclohexylamino-2-phenyl-pyrimidine-4-carbonyl)-amino]-butyryl}-piperazine-1-carboxylic acid ethyl ester;
4-((S)-4-tert-butoxycarbonyl-2-{[6-(ethoxycarbonylmethyl-amino)-2-phenyl-pyrimidine-4-carbonyl]-amino}-butyryl)-piperazine-1-carboxylic acid ethyl ester;
4-((S)-4-tert-butoxycarbonyl-2-{[6-(2-hydroxy-ethylamino)-2-phenyl-pyrimidine-4-carbonyl]-amino}-butyryl)-piperazine-1-carboxylic acid ethyl ester;
4-((S)-4-tert-butoxycarbonyl-2-{[6-(2-ethoxycarbonyl-ethylamino)-2-phenyl-pyrimidine-4-carbonyl]-amino}-butyryl)-piperazine-1-carboxylic acid ethyl ester;
4-((S)-4-tert-butoxycarbonyl-2-{[6-(3-hydroxy-propylamino)-2-phenyl-pyrimidine-4-carbonyl]-amino}-butyryl)-piperazine-1-carboxylic acid ethyl ester;
4-((S)-4-tert-butoxycarbonyl-2-{[6-(3-tert-butoxycarbonyl-propylamino)-2-phenyl-pyrimidine-4-carbonyl]-amino}-butyryl)-piperazine-1-carboxylic acid ethyl ester;
4-((S)-4-tert-butoxycarbonyl-2-{[6-(2-dimethylamino-ethylamino)-2-phenyl-pyrimidine-4-carbonyl]-amino}-butyryl)-piperazine-1-carboxylic acid ethyl ester;
4-((S)-4-tert-butoxycarbonyl-2-{[6-(3-dimethylamino-propylamino)-2-phenyl-pyrimidine-4-carbonyl]-amino}-butyryl)-piperazine-1-carboxylic acid ethyl ester;
4-((S)-4-tert-butoxycarbonyl-2-{[6-(2-morpholin-4-yl-ethylamino)-2-phenyl-pyrimidine-4-carbonyl]-amino}-butyryl)-piperazine-1-carboxylic acid ethyl ester;
4-((S)-4-tert-butoxycarbonyl-2-{[6-(3-morpholin-4-yl-propylamino)-2-phenyl-pyrimidine-4-carbonyl]-amino}-butyryl)-piperazine-1-carboxylic acid ethyl ester;
4-{(S)-2-[(6-benzylamino-2-phenyl-pyrimidine-4-carbonyl)-amino]-4-tert-butoxycarbonyl-butyryl}-piperazine-1-carboxylic acid ethyl ester;
4-((S)-4-tert-butoxycarbonyl-2-{[2-phenyl-6-((S)-1-phenyl-ethylamino)-pyrimidine-4-carbonyl]-amino}-butyryl)-piperazine-1-carboxylic acid ethyl ester;
4-((S)-4-tert-butoxycarbonyl-2-{[2-phenyl-6-((R)-1-phenyl-ethylamino)-pyrimidine-4-carbonyl]-amino}-butyryl)-piperazine-1-carboxylic acid ethyl ester;
4-((S)-4-tert-butoxycarbonyl-2-{[6-((S)-2-tert-butoxycarbonyl-1-phenyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-((R)-2-tert-butoxycarbonyl-1-phenyl-ethylamino)-2-phenyl-pyrimidine-4-carbonyl]-amino}-butyryl)-piperazine-1-carboxylic acid ethyl ester;

4-{(S)-4-tert-butoxycarbonyl-2-[(6-phenethylamino-2-phenyl-pyrimidine-4-carbonyl)-amino]-butyryl}-piperazine-1-carboxylic acid ethyl ester;

4-((S)-4-tert-butoxycarbonyl-2-{[2-phenyl-6-(2-phenyl-propylamino)-pyrimidine-4-carbonyl]-amino}-butyryl)-piperazine-1-carboxylic acid ethyl ester;

4-((S)-4-tert-butoxycarbonyl-2-{[6-(1,2-diphenyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[2-phenyl-6-(trans-2-phenyl-cyclopropylamino)-pyrimidine-4-carbonyl]-amino}-butyryl)-piperazine-1-carboxylic acid ethyl ester;

4-((S)-4-tert-butoxycarbonyl-2-{[6-(indan-1-ylamino)-2-phenyl-pyrimidine-4-carbonyl]-amino}-butyryl)-piperazine-1-carboxylic acid ethyl ester;

4-((S)-4-tert-butoxycarbonyl-2-{[6-((R)-indan-1-ylamino)-2-phenyl-pyrimidine-4-carbonyl]-amino}-butyryl)-piperazine-1-carboxylic acid ethyl ester;

4-((S)-4-tert-butoxycarbonyl-2-{[6-(indan-2-ylamino)-2-phenyl-pyrimidine-4-carbonyl]-amino}-butyryl)-piperazine-1-carboxylic acid ethyl ester;

4-{(S)-4-tert-butoxycarbonyl-2-[(6-dimethylamino-2-phenyl-pyrimidine-4-carbonyl)-amino]-butyryl}-piperazine-1-carboxylic acid ethyl ester;

4-{(S)-2-[(6-azetidin-1-yl-2-phenyl-pyrimidine-4-carbonyl)-amino]-4-tert-butoxycarbonyl-butyryl}-piperazine-1-carboxylic acid ethyl ester;

4-{(S)-4-tert-butoxycarbonyl-2-[(2-phenyl-6-pyrrolidin-1-yl-pyrimidine-4-carbonyl)-amino]-butyryl}-piperazine-1-carboxylic acid ethyl ester;

4-{(S)-4-tert-butoxycarbonyl-2-[(2-phenyl-6-piperidin-1-yl-pyrimidine-4-carbonyl)-amino]-butyryl}-piperazine-1-carboxylic acid ethyl ester;

4-((S)-4-tert-butoxycarbonyl-2-{[6-(butyl-methyl-amino)-2-phenyl-pyrimidine-4-carbonyl]-amino}-butyryl)-piperazine-1-carboxylic acid ethyl ester;

4-{(S)-4-tert-butoxycarbonyl-2-[(2-phenyl-6-phenylamino-pyrimidine-4-carbonyl)-amino]-butyryl}-piperazine-1-carboxylic acid ethyl ester;

4-((S)-4-tert-butoxycarbonyl-2-{[6-(4-fluoro-phenylamino)-2-phenyl-pyrimidine-4-carbonyl]-amino}-butyryl)-piperazine-1-carboxylic acid ethyl ester;

4-{(S)-4-tert-butoxycarbonyl-2-[(6-methyl-2-phenyl-pyrimidine-4-carbonyl)-amino]-butyryl}-piperazine-1-carboxylic acid ethyl ester;

4-{(S)-4-tert-butoxycarbonyl-2-[(6-isopropyl-2-phenyl-pyrimidine-4-carbonyl)-amino]-butyryl}-piperazine-1-carboxylic acid ethyl ester;

4-{4-tert-butoxycarbonyl-2-[(6-butyl-2-phenyl-pyrimidine-4-carbonyl)-amino]-butyryl}-piperazine-1-carboxylic acid ethyl ester;

4-{(S)-4-tert-butoxycarbonyl-2-[(6-isobutyl-2-phenyl-pyrimidine-4-carbonyl)-amino]-butyryl}-piperazine-1-carboxylic acid ethyl ester;

4-{(S)-4-tert-butoxycarbonyl-2-[(6-cyclopropyl-2-phenyl-pyrimidine-4-carbonyl)-amino]-butyryl}-piperazine-1-carboxylic acid ethyl ester;

4-{(S)-4-tert-butoxycarbonyl-2-[(6-cyclopentyl-2-phenyl-pyrimidine-4-carbonyl)-amino]-butyryl}-piperazine-1-carboxylic acid ethyl ester;

4-{(S)-4-tert-butoxycarbonyl-2-[(2,6-diphenyl-pyrimidine-4-carbonyl)-amino]-butyryl}-piperazine-1-carboxylic acid ethyl ester;

4-{(S)-4-tert-butoxycarbonyl-2-[(2-phenyl-6-o-tolyl-pyrimidine-4-carbonyl)-amino]-butyryl}-piperazine-1-carboxylic acid ethyl ester;

4-{(S)-4-tert-butoxycarbonyl-2-[(2-phenyl-6-m-tolyl-pyrimidine-4-carbonyl)-amino]-butyryl}-piperazine-1-carboxylic acid ethyl ester;

4-{(S)-4-tert-butoxycarbonyl-2-[(2-phenyl-6-p-tolyl-pyrimidine-4-carbonyl)-amino]-butyryl}-piperazine-1-carboxylic acid ethyl ester;

4-((S)-4-tert-butoxycarbonyl-2-{[6-(3-carboxy-phenyl)-2-phenyl-pyrimidine-4-carbonyl]-amino}-butyryl)-piperazine-1-carboxylic acid ethyl ester;

4-((S)-4-tert-butoxycarbonyl-2-{[6-(4-carboxy-phenyl)-2-phenyl-pyrimidine-4-carbonyl]-amino}-butyryl)-piperazine-1-carboxylic acid ethyl ester;

4-((S)-4-tert-butoxycarbonyl-2-{[2-(4-fluoro-phenyl)-6-methyl-pyrimidine-4-carbonyl]-amino}-butyryl)-piperazine-1-carboxylic acid ethyl ester;

4-((S)-4-tert-butoxycarbonyl-2-{[2-(3-fluoro-phenyl)-6-methyl-pyrimidine-4-carbonyl]-amino}-butyryl)-piperazine-1-carboxylic acid ethyl ester;

4-((S)-4-tert-butoxycarbonyl-2-{[2-(2-fluoro-phenyl)-6-methyl-pyrimidine-4-carbonyl]-amino}-butyryl)-piperazine-1-carboxylic acid ethyl ester;

4-((S)-4-tert-butoxycarbonyl-2-{[2-(4-chloro-phenyl)-6-methyl-pyrimidine-4-carbonyl]-amino}-butyryl)-piperazine-1-carboxylic acid ethyl ester;

4-((S)-4-tert-butoxycarbonyl-2-{[2-(3-chloro-phenyl)-6-methyl-pyrimidine-4-carbonyl]-amino}-butyryl)-piperazine-1-carboxylic acid ethyl ester;

4-((S)-4-tert-butoxycarbonyl-2-{[2-(2-chloro-phenyl)-6-methyl-pyrimidine-4-carbonyl]-amino}-butyryl)-piperazine-1-carboxylic acid ethyl ester;

4-{(S)-4-tert-butoxycarbonyl-2-[(6-methyl-2-p-tolyl-pyrimidine-4-carbonyl)-amino]-butyryl}-piperazine-1-carboxylic acid ethyl ester;

4-{(S)-4-tert-butoxycarbonyl-2-[(6-methyl-2-m-tolyl-pyrimidine-4-carbonyl)-amino]-butyryl}-piperazine-1-carboxylic acid ethyl ester;

4-((S)-4-tert-butoxycarbonyl-2-{[2-(4-methoxy-phenyl)-6-methyl-pyrimidine-4-carbonyl]-amino}-butyryl)-piperazine-1-carboxylic acid ethyl ester;

4-((S)-4-tert-butoxycarbonyl-2-{[2-(3-methoxy-phenyl)-6-methyl-pyrimidine-4-carbonyl]-amino}-butyryl)-piperazine-1-carboxylic acid ethyl ester;

4-[(S)-2-[(6-isopropylamino-2-phenyl-pyrimidine-4-carbonyl)-amino]-3-(4-methoxycarbonyl-phenyl)-propionyl]-piperazine-1-carboxylic acid ethyl ester;

4-[(S)-2-[(6-benzylamino-2-phenyl-pyrimidine-4-carbonyl)-amino]-3-(4-methoxycarbonyl-phenyl)-propionyl]-piperazine-1-carboxylic acid ethyl ester;

4-(S)-[2-[(2,6-diphenyl-pyrimidine-4-carbonyl)-amino]-3-(4-methoxycarbonyl-phenyl)-propionyl]-piperazine-1-carboxylic acid ethyl ester;

4-[(S)-2-[(6-cyclopropyl-2-phenyl-pyrimidine-4-carbonyl)-amino]-3-(4-methoxycarbonyl-phenyl)-propionyl]-piperazine-1-carboxylic acid ethyl ester;

4-{(S)-5-tert-butoxycarbonyl-2-[(6-isopropylamino-2-phenyl-pyrimidine-4-carbonyl)-amino]-pentanoyl}-piperazine-1-carboxylic acid ethyl ester;

4-{(S)-2-[(6-benzylamino-2-phenyl-pyrimidine-4-carbonyl)-amino]-5-tert-butoxycarbonyl-pentanoyl}-piperazine-1-carboxylic acid ethyl ester;

4-{(S)-5-tert-butoxycarbonyl-2-[(2,6-diphenyl-pyrimidine-4-carbonyl)-amino]-pentanoyl}-piperazine-1-carboxylic acid ethyl ester;

4-{(S)-5-tert-butoxycarbonyl-2-[(6-cyclopropyl-2-phenyl-pyrimidine-4-carbonyl)-amino]-pentanoyl}-piperazine-1-carboxylic acid ethyl ester;

4-((S)-4-carboxy-2-{[6-(2-methoxy-1-methyl-ethylamino)-2-phenyl-pyrimidine-4-carbonyl]-amino}-butyryl)-piperazine-1-carboxylic acid ethyl ester;

4-((S)-4-carboxy-2-{[6-(isopropyl-methyl-amino)-2-phenyl-pyrimidine-4-carbonyl]-amino}-butyryl)-piperazine-1-carboxylic acid ethyl ester;

4-{(S)-4-carboxy-2-[(6-morpholin-4-yl-2-phenyl-pyrimidine-4-carbonyl)-amino]-butyryl}-piperazine-1-carboxylic acid ethyl ester;

4-{(S)-4-carboxy-2-[(2-phenyl-6-thiazolidin-3-yl-pyrimidine-4-carbonyl)-amino]-butyryl}-piperazine-1-carboxylic acid ethyl ester;

4-((S)-4-carboxy-2-{[6-(4-hydroxy-piperidin-1-yl)-2-phenyl-pyrimidine-4-carbonyl]-amino}-butyryl)-piperazine-1-carboxylic acid ethyl ester;

4-((S)-4-carboxy-2-{[6-(piperazin-1-yl)-2-phenyl-pyrimidine-4-carbonyl]-amino}-butyryl)-piperazine-1-carboxylic acid ethyl ester;

4-((S)-4-carboxy-2-{[6-(2-hydroxy-1-methyl-ethylamino)-2-phenyl-pyrimidine-4-carbonyl]-amino}-butyryl)-piperazine-1-carboxylic acid ethyl ester;

4-((S)-4-carboxy-2-{[6-(4-hydroxy-butylamino)-2-phenyl-pyrimidine-4-carbonyl]-amino}-butyryl)-piperazine-1-carboxylic acid ethyl ester;

4-((S)-4-carboxy-2-{[6-(2-hydroxy-propylamino)-2-phenyl-pyrimidine-4-carbonyl]-amino}-butyryl)-piperazine-1-carboxylic acid ethyl ester;

4-[(S)-4-carboxy-2-({2-phenyl-6-[(tetrahydro-furan-2-ylmethyl)-amino]-pyrimidine-4-carbonyl}-amino)-butyryl)-piperazine-1-carboxylic acid ethyl ester;

4-((S)-4-carboxy-2-{[6-((R)-2-hydroxymethyl-pyrrolidin-1-yl)-2-phenyl-pyrimidine-4-carbonyl]-amino}-butyryl)-piperazine-1-carboxylic acid ethyl ester;

4-((S)-4-carboxy-2-{[6-((S)-2-hydroxymethyl-pyrrolidin-1-yl)-2-phenyl-pyrimidine-4-carbonyl]-amino}-butyryl)-piperazine-1-carboxylic acid ethyl ester;

4-((S)-4-carboxy-2-{[6-((S)-3-hydroxy-pyrrolidin-1-yl)-2-phenyl-pyrimidine-4-carbonyl]-amino}-butyryl)-piperazine-1-carboxylic acid ethyl ester;

4-((S)-4-carboxy-2-{[6-((R)-3-hydroxy-pyrrolidin-1-yl)-2-phenyl-pyrimidine-4-carbonyl]-amino}-butyryl)-piperazine-1-carboxylic acid ethyl ester;

4-[(S)-4-carboxy-2-({2-phenyl-6-[(R)-(tetrahydro-furan-3-yl)amino]-pyrimidine-4-carbonyl}-amino)-butyryl]-piperazine-1-carboxylic acid ethyl ester;

4-{(S)-4-carboxy-2-[(6-imidazol-1-yl-2-phenyl-pyrimidine-4-carbonyl)-amino]-butyryl}-piperazine-1-carboxylic acid ethyl ester;

4-{(S)-4-carboxy-2-[(2-phenyl-6-pyrazol-1-yl-pyrimidine-4-carbonyl)-amino]-butyryl}-piperazine-1-carboxylic acid ethyl ester;

4-((S)-4-carboxy-2-{[6-((S)-2-hydroxy-1-methyl-ethylamino)-2-phenyl-pyrimidine-4-carbonyl]-amino}-butyryl)-piperazine-1-carboxylic acid ethyl ester;

4-((S)-4-carboxy-2-{[6-((R)-2-hydroxy-1-methyl-ethylamino)-2-phenyl-pyrimidine-4-carbonyl]-amino}-butyryl)-piperazine-1-carboxylic acid ethyl ester;

4-((S)-4-carboxy-2-{[6-(2-hydroxy-1,1-dimethyl-ethylamino)-2-phenyl-pyrimidine-4-carbonyl]-amino}-butyryl)-piperazine-1-carboxylic acid ethyl ester;

4-((S)-4-carboxy-2-{[6-(trans-4-hydroxy-cyclohexylamino)-2-phenyl-pyrimidine-4-carbonyl]-amino}-butyryl)-piperazine-1-carboxylic acid ethyl ester;

4-((S)-4-carboxy-2-{[6-(3-hydroxy-piperidin-1-yl)-2-phenyl-pyrimidine-4-carbonyl]-amino}-butyryl)-piperazine-1-carboxylic acid ethyl ester;

4-((S)-4-carboxy-2-{[6-(2-hydroxymethyl-piperidin-1-yl)-2-phenyl-pyrimidine-4-carbonyl]-amino}-butyryl)-piperazine-1-carboxylic acid ethyl ester;

4-((S)-4-carboxy-2-{[6-(trans-2-hydroxy-cyclohexylamino)-2-phenyl-pyrimidine-4 carbonyl]-amino}-butyryl)-piperazine-1-carboxylic acid ethyl ester;

4-{(S)-4-carboxy-2-[(2-phenyl-6-propylsulfanyl-pyrimidine-4-carbonyl)-amino]-butyryl}-piperazine-1-carboxylic acid ethyl ester;

4-{(S)-4-carboxy-2-[(6-isopropylsulfanyl-2-phenyl-pyrimidine-4-carbonyl)-amino]-butyryl}-piperazine-1-carboxylic acid ethyl ester;

4-{(S)-4-carboxy-2-[(6-cyclopentylsulfanyl-2-phenyl-pyrimidine-4-carbonyl)-amino]-butyryl}-piperazine-1-carboxylic acid ethyl ester;

4-{(S)-4-carboxy-2-[(6-isopropylsulfanyl-2-phenyl-pyrimidine-4-carbonyl)-amino]-butyryl}-piperazine-1-carboxylic acid ethyl ester;

4-{(S)-4-carboxy-2-[(6-cyclohexylsulfanyl-2-phenyl-pyrimidine-4-carbonyl)-amino]-butyryl}-piperazine-1-carboxylic acid ethyl ester;

4-{(S)-4-carboxy-2-[(6-ethoxycarbonylmethylsulfanyl-2-phenyl-pyrimidine-4-carbonyl)-amino]-butyryl}-piperazine-1-carboxylic acid ethyl ester;

4-((S)-4-carboxy-2-{[6-(2-ethoxycarbonyl-ethylsulfanyl)-2-phenyl-pyrimidine-4-carbonyl]-amino}-butyryl)-piperazine-1-carboxylic acid ethyl ester;

4-{(S)-4-carboxy-2-[(6-carboxymethylsulfanyl-2-phenyl-pyrimidine-4-carbonyl)-amino]-butyryl}-piperazine-1-carboxylic acid ethyl ester;

4-((S)-4-carboxy-2-{[6-(2-carboxy-ethylsulfanyl)-2-phenyl-pyrimidine-4-carbonyl]-amino}-butyryl)-piperazine-1-carboxylic acid ethyl ester;

4-{(S)-4-carboxy-2-[(2-phenyl-6-phenylsulfanyl-pyrimidine-4-carbonyl)-amino]-butyryl}-piperazine-1-carboxylic acid ethyl ester;

4-{(S)-2-[(6-benzylsulfanyl-2-phenyl-pyrimidine-4-carbonyl)-amino]-4-carboxy-butyryl}-piperazine-1-carboxylic acid ethyl ester;

4-{(S)-4-carboxy-2-[(6-ethynyl-2-phenyl-pyrimidine-4-carbonyl)-amino]-butyryl}-piperazine-1-carboxylic acid ethyl ester;

4-((S)-4-carboxy-2-{[6-(3-hydroxy-prop-1-ynyl)-2-phenyl-pyrimidine-4-carbonyl]-amino}-butyryl)-piperazine-1-carboxylic acid ethyl ester;

4-((S)-4-carboxy-2-{[6-(3-hydroxy-but-1-ynyl)-2-phenyl-pyrimidine-4-carbonyl]-amino}-butyryl)-piperazine-1-carboxylic acid ethyl ester;

4-((S)-4-carboxy-2-{[6-(3-hydroxy-pent-1-ynyl)-2-phenyl-pyrimidine-4-carbonyl]-amino}-butyryl)-piperazine-1-carboxylic acid ethyl ester;

4-((S)-4-carboxy-2-{[6-(3-hydroxy-3-methyl-but-1-ynyl)-2-phenyl-pyrimidine-4-carbonyl]-amino}-butyryl)-piperazine-1-carboxylic acid ethyl ester;

4-((S)-4-carboxy-2-{[6-(3-hydroxy-propyl)-2-phenyl-pyrimidine-4-carbonyl]-amino}-butyryl)-piperazine-1-carboxylic acid ethyl ester;

4-((S)-4-carboxy-2-{[6-(3-hydroxy-butyl)-2-phenyl-pyrimidine-4-carbonyl]-amino}-butyryl)-piperazine-1-carboxylic acid ethyl ester;

4-((S)-4-carboxy-2-{[6-(3-hydroxy-pentyl)-2-phenyl-pyrimidine-4-carbonyl]-amino}-butyryl)-piperazine-1-carboxylic acid ethyl ester;

4-((S)-4-carboxy-2-{[6-(3-hydroxy-3-methyl-butyl)-2-phenyl-pyrimidine-4-carbonyl]-amino}-butyryl)-piperazine-1-carboxylic acid ethyl ester;

4-((S)-4-carboxy-2-{[6-((E)-3-hydroxy-but-1-enyl)-2-phenyl-pyrimidine-4-carbonyl]-amino}-butyryl)-piperazine-1-carboxylic acid ethyl ester;

4-((S)-4-tert-butoxycarbonyl-2-{[6-(2-methoxy-1-methyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(isopropyl-methyl-amino)-2-phenyl-pyrimidine-4-carbonyl]-amino}-butyryl)-piperazine-1-carboxylic acid ethyl ester;

4-{(S)-4-tert-butoxycarbonyl-2-[(6-morpholin-4-yl-2-phenyl-pyrimidine-4-carbonyl)-amino]-butyryl}-piperazine-1-carboxylic acid ethyl ester;

4-{(S)-4-tert-butoxycarbonyl-2-[(2-phenyl-6-thiazolidin-3-yl-pyrimidine-4-carbonyl)-amino]-butyryl}-piperazine-1-carboxylic acid ethyl ester;

4-((S)-4-tert-butoxycarbonyl-2-{[6-(4-hydroxy-piperidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-(piperazin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-1-methyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(4-hydroxy-butylamino)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-propylamino)-2-phenyl-pyrimidine-4-carbonyl]-amino}-butyryl)-piperazine-1-carboxylic acid ethyl ester;

4-[(S)-4-tert-butoxycarbonyl-2-({2-phenyl-6-[(tetrahydrofuran-2-ylmethyl)-amino]-pyrimidine-4-carbonyl}-amino)-butyryl]-piperazine-1-carboxylic acid ethyl ester;

4-((S)-4-tert-butoxycarbonyl-2-{[6-((R)-2-hydroxymethyl-pyrrolidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-((S)-2-hydroxymethyl-pyrrolidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-((S)-3-hydroxy-pyrrolidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-((R)-3-hydroxy-pyrrolidin-1-yl)-2-phenyl-pyrimidine-4-carbonyl]-amino}-butyryl)-piperazine-1-carboxylic acid ethyl ester;

4-{(S)-4-tert-butoxycarbonyl-2-[2-phenyl-6-[(R)-(tetrahydro-furan-3-yl)amino]-pyrimidine-4-carbonyl}-amino)-butyryl]-piperazine-1-carboxylic acid ethyl ester;

4-{(S)-4-tert-butoxycarbonyl-2-[(6-imidazol-1-yl-2-phenyl-pyrimidine-4-carbonyl)-amino]-butyryl}-piperazine-1-carboxylic acid ethyl ester;

4-{(S)-4-tert-butoxycarbonyl-2-[(2-phenyl-6-pyrazol-1-yl-pyrimidine-4-carbonyl)-amino]-butyryl}-piperazine-1-carboxylic acid ethyl ester;

4-((S)-4-tert-butoxycarbonyl-2-{[6-((S)-2-hydroxy-1-methyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-((R)-2-hydroxy-1-methyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-1,1-dimethyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(trans-4-hydroxy-cyclohexylamino)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-piperidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxymethyl-piperidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-(trans-2-hydroxy-cyclohexylamino)-2-phenyl-pyrimidine-4-carbonyl]-amino}-butyryl)-piperazine-1-carboxylic acid ethyl ester;

4-{(S)-4-tert-butoxycarbonyl-2-[(2-phenyl-6-propylsulfanyl-pyrimidine-4-carbonyl)-amino]-butyryl}-piperazine-1-carboxylic acid ethyl ester;

4-{(S)-4-tert-butoxycarbonyl-2-[(6-isopropylsulfanyl-2-phenyl-pyrimidine-4-carbonyl)-amino]-butyryl}-piperazine-1-carboxylic acid ethyl ester;

4-{(S)-4-tert-butoxycarbonyl-2-[(6-cyclopentylsulfanyl-2-phenyl-pyrimidine-4-carbonyl)-amino]-butyryl}-piperazine-1-carboxylic acid ethyl ester;

4-{(S)-4-tert-butoxycarbonyl-2-[(6-isopropylsulfanyl-2-phenyl-pyrimidine-4-carbonyl)-amino]-butyryl}-piperazine-1-carboxylic acid ethyl ester;

4-{(S)-4-tert-butoxycarbonyl-2-[(6-cyclohexylsulfanyl-2-phenyl-pyrimidine-4-carbonyl)-amino]-butyryl}-piperazine-1-carboxylic acid ethyl ester;

4-{tert-butoxycarbonyl-2-[(6-ethoxyarbonylmethylsulfanyl-2-phenyl-pyrimidine-4-carbonyl)-amino]-butyryl}-piperazine-1-carboxylic acid ethyl ester;

4-((S)-4-tert-butoxycarbonyl-2-{[6-(2-ethoxycarbonyl-ethylsulfanyl)-2-phenyl-pyrimidine-4-carbonyl]-amino}-butyryl)-piperazine-1-carboxylic acid ethyl ester;

4-{(S)-4-tert-butoxycarbonyl-2-[(2-phenyl-6-phenylsulfanyl-pyrimidine-4-carbonyl)-amino]-butyryl}-piperazine-1-carboxylic acid ethyl ester;

4-{(S)-2-[(6-benzylsulfanyl-2-phenyl-pyrimidine-4-carbonyl)-amino]-4-tert-butoxycarbonyl-butyryl}-piperazine-1-carboxylic acid ethyl ester;

4-{(S)-4-tert-butoxycarbonyl-2-[(6-ethynyl-2-phenyl-pyrimidine-4-carbonyl)-amino]-butyryl}-piperazine-1-carboxylic acid ethyl ester;

4-((S)-4-tert-butoxycarbonyl-2-{[6-(3-hydroxy-prop-1-ynyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-but-1-ynyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-pent-1-ynyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-3-methyl-but-1-ynyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-propyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-butyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-pentyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-3-methyl-butyl)-2-phenyl-pyrimidine-4-carbonyl]-amino}-butyryl)-piperazine-1-carboxylic acid ethyl ester;

4-((S)-4-tert-butoxycarbonyl-2-{[6-((Z)-3-hydroxy-but-1-enyl)-2-phenyl-pyrimidine-4-carbonyl]-amino}-butyryl)-piperazine-1-carboxylic acid ethyl ester;

4-((S)-4-carboxy-2-{[6-(4-oxo-cyclohex-1-enyl)-2-phenyl-pyrimidine-4-carbonyl]-amino}-butyryl)-piperazine-1-carboxylic acid ethyl ester;

4-((S)-4-carboxy-2-{[6-(4-oxo-cyclohexyl)-2-phenyl-pyrimidine-4-carbonyl]-amino}-butyryl)-piperazine-1-carboxylic acid ethyl ester;

4-((S)-4-carboxy-2-{[6-(4-hydroxy-cyclohex-1-enyl)-2-phenyl-pyrimidine-4-carbonyl]-amino}-butyryl)-piperazine-1-carboxylic acid ethyl ester;

4-((S)-4-carboxy-2-{[6-(4-hydroxy-cyclohexyl)-2-phenyl-pyrimidine-4-carbonyl]-amino}-butyryl)-piperazine-1-carboxylic acid ethyl ester;

4-((S)-4-tert-butoxycarbonyl-2-{[6-(4-oxo-cyclohex-1-enyl)-2-phenyl-pyrimidine-4-carbonyl]-amino}-butyryl)-piperazine-1-carboxylic acid ethyl ester;

4-((S)-4-tert-butoxycarbonyl-2-{[6-(4-oxo-cyclohexyl)-2-phenyl-pyrimidine-4-carbonyl]-amino}-butyryl)-piperazine-1-carboxylic acid ethyl ester;

4-((S)-4-carboxy-2-{[6-((S)-3-methoxy-pyrrolidin-1-yl)-2-phenyl-pyrimidine-4-carbonyl]-amino}-butyryl)-piperazine-1-carboxylic acid ethyl ester;

4-((S)-4-carboxy-2-{[6-((S)-2-methoxy-1-methyl-ethylamino)-2-phenyl-pyrimidine-4-carbonyl]-amino}-butyryl)-piperazine-1-carboxylic acid ethyl ester;

4-((S)-4-carboxy-2-{[6-(4-methoxy-piperidin-1-yl)-2-phenyl-pyrimidine-4-carbonyl]-amino}-butyryl)-piperazine-1-carboxylic acid ethyl ester;

4-((S)-4-carboxy-2-{[6-((R)-3-methoxy-pyrrolidin-1-yl)-2-phenyl-pyrimidine-4-carbonyl]-amino}-butyryl)-piperazine-1-carboxylic acid ethyl ester;

4-((S)-4-carboxy-2-{[6-((R)-2-methoxy-1-methyl-ethylamino)-2-phenyl-pyrimidine-4-carbonyl]-amino}-butyryl)-piperazine-1-carboxylic acid ethyl ester;

4-((S)-4-carboxy-2-{[6-(2-methoxymethyl-piperidin-1-yl)-2-phenyl-pyrimidine-4-carbonyl]-amino}-butyryl)-piperazine-1-carboxylic acid ethyl ester;

4-((S)-4-carboxy-2-{[6-((S)-2-methoxymethyl-pyrrolidin-1-yl)-2-phenyl-pyrimidine-4-carbonyl]-amino}-butyryl)-piperazine-1-carboxylic acid ethyl ester;

4-((S)-4-carboxy-2-{[6-((R)-2-methoxymethyl-pyrrolidin-1-yl)-2-phenyl-pyrimidine-4-carbonyl]-amino}-butyryl)-piperazine-1-carboxylic acid ethyl ester;

4-((S)-4-carboxy-2-{[6-(2-methoxy-1,1-dimethyl-ethylamino)-2-phenyl-pyrimidine-4-carbonyl]-amino}-butyryl)-piperazine-1-carboxylic acid ethyl ester;

4-((S)-4-carboxy-2-{[6-(4,5-dihydro-pyrazol-1-yl)-2-phenyl-pyrimidine-4-carbonyl]-amino}-butyryl)-piperazine-1-carboxylic acid ethyl ester;

4-((S)-4-carboxy-2-{[6-(2-methyl-4,5-dihydro-imidazol-1-yl)-2-phenyl-pyrimidine-4-carbonyl]-amino}-butyryl)-piperazine-1-carboxylic acid ethyl ester;

4-{(S)-4-carboxy-2-[(2-phenyl-6-[1,2,4]triazol-1-yl-pyrimidine-4-carbonyl)-amino]-butyryl}-piperazine-1-carboxylic acid ethyl ester;

4-((S)-4-carboxy-2-{[6-(4-methyl-pyrazol-1-yl)-2-phenyl-pyrimidine-4-carbonyl]-amino}-butyryl)-piperazine-1-carboxylic acid ethyl ester;

4-((S)-4-carboxy-2-{[6-(3-methyl-pyrazol-1-yl)-2-phenyl-pyrimidine-4-carbonyl]-amino}-butyryl)-piperazine-1-carboxylic acid ethyl ester;

4-{(S)-4-carboxy-2-[(2-phenyl-6-[1,2,3]triazol-1-yl-pyrimidine-4-carbonyl)-amino]-butyryl}-piperazine-1-carboxylic acid ethyl ester;

4-((S)-2-{[6-(4-butyl-[1,2,3]triazol-1-yl)-2-phenyl-pyrimidine-4-carbonyl]-amino}-4-carboxy-butyryl)-piperazine-1-carboxylic acid ethyl ester;

4-{(S)-2-[(6-amino-2-phenyl-pyrimidine-4-carbonyl)-amino]-4-carboxy-butyryl}-piperazine-1-carboxylic acid ethyl ester;

4-((S)-4-carboxy-2-{[6-(cyclohexanecarbonyl-amino)-2-phenyl-pyrimidine-4-carbonyl]-amino}-butyryl)-piperazine-1-carboxylic acid ethyl ester;

4-[(S)-4-carboxy-2-({2-phenyl-6-[(thiophene-2-carbonyl)-amino]-pyrimidine-4-carbonyl}-amino)-butyryl]-piperazine-1-carboxylic acid ethyl ester;

4-[(S)-4-carboxy-2-({6-[(furan-2-carbonyl)-amino]-2-phenyl-pyrimidine-4-carbonyl}-amino)-butyryl]-piperazine-1-carboxylic acid ethyl ester;

4-{(S)-4-carboxy-2-[(2-phenyl-6-phenylacetylamino-pyrimidine-4-carbonyl)-amino]-butyryl}-piperazine-1-carboxylic acid ethyl ester;

4-((S)-4-carboxy-2-{[2-phenyl-6-(3-phenyl-propionylamino)-pyrimidine-4-carbonyl]-amino}-butyryl)-piperazine-1-carboxylic acid ethyl ester;

4-((S)-4-carboxy-2-{[6-(3-cyclopentyl-propionylamino)-2-phenyl-pyrimidine-4-carbonyl]-amino}-butyryl)-piperazine-1-carboxylic acid ethyl ester;

4-((S)-4-carboxy-2-{[6-(2,2-dimethyl-propionylamino)-2-phenyl-pyrimidine-4-carbonyl]-amino}-butyryl)-piperazine-1-carboxylic acid ethyl ester;

4-((S)-4-carboxy-2-{[2-phenyl-6-(2-propyl-pentanoylamino)-pyrimidine-4-carbonyl]-amino}-butyryl)-piperazine-1-carboxylic acid ethyl ester;

4-{(S)-2-[(6-benzoylamino-2-phenyl-pyrimidine-4-carbonyl)-amino]-4-carboxy-butyryl}-piperazine-1-carboxylic acid ethyl ester;

4-((S)-4-carboxy-2-{[6-(2-cyclopentyl-acetylamino)-2-phenyl-pyrimidine-4-carbonyl]-amino}-butyryl)-piperazine-1-carboxylic acid ethyl ester;

4-((S)-4-carboxy-2-{[6-(2-methoxy-acetylamino)-2-phenyl-pyrimidine-4-carbonyl]-amino}-butyryl)-piperazine-1-carboxylic acid ethyl ester;

4-((S)-4-carboxy-2-{[6-(cyclobutanecarbonyl-amino)-2-phenyl-pyrimidine-4-carbonyl]-amino}-butyryl)-piperazine-1-carboxylic acid ethyl ester;

4-((S)-4-carboxy-2-{[6-(cyclopentanecarbonyl-amino)-2-phenyl-pyrimidine-4-carbonyl]-amino}-butyryl)-piperazine-1-carboxylic acid ethyl ester;

4-{(S)-4-carboxy-2-[(6-pentanoylamino-2-phenyl-pyrimidine-4-carbonyl)-amino]-butyryl}-piperazine-1-carboxylic acid ethyl ester;

4-((S)-4-carboxy-2-{[6-(3-methyl-butyrylamino)-2-phenyl-pyrimidine-4-carbonyl]-amino}-butyryl)-piperazine-1-carboxylic acid ethyl ester;

4-((S)-4-carboxy-2-{[6-(cyclopropanecarbonyl-amino)-2-phenyl-pyrimidine-4-carbonyl]-amino}-butyryl)-piperazine-1-carboxylic acid ethyl ester;

4-{(S)-2-[(6-acetylamino-2-phenyl-pyrimidine-4-carbonyl)-amino]-4-carboxy-butyryl}-piperazine-1-carboxylic acid ethyl ester;

4-{(S)-2-[(6-butyrylamino-2-phenyl-pyrimidine-4-carbonyl)-amino]-4-carboxy-butyryl}-piperazine-1-carboxylic acid ethyl ester;

4-{(S)-4-carboxy-2-[(6-isobutyrylamino-2-phenyl-pyrimidine-4-carbonyl)-amino]-butyryl}-piperazine-1-carboxylic acid ethyl ester;

4-{(S)-4-carboxy-2-[(2-phenyl-6-propionylamino-pyrimidine-4-carbonyl)-amino]-butyryl}-piperazine-1-carboxylic acid ethyl ester;

4-((S)-4-carboxy-2-{[2-phenyl-6-(propane-1-sulfony-lamino)-pyrimidine-4-carbonyl]-amino}-butyryl)-piperazine-1-carboxylic acid ethyl ester;

4-(S)-4-carboxy-2-{[(6-ethanesulfonylamino-2-phenyl-pyrimidine-4-carbonyl)-amino]-butyryl}-piperazine-1-carboxylic acid ethyl ester;

4-{(S)-2-[(6-benzenesulfonylamino-2-phenyl-pyrimidine-4-carbonyl)-amino]-4-carboxy-butyryl}-piperazine-1-carboxylic acid ethyl ester;

4-((S)-4-carboxy-2-{[2-phenyl-6-(propane-2-sulfony-lamino)-pyrimidine-4-carbonyl]-amino}-butyryl)-piperazine-1-carboxylic acid ethyl ester;

4-((S)-4-carboxy-2-{[6-(4-oxo-4H-pyridin-1-yl)-2-phenyl-pyrimidine-4-carbonyl]-amino}-butyryl)-piperazine-1-carboxylic acid ethyl ester;

4-((S)-4-carboxy-2-{[6-(3-methyl-5-oxo-2,5-dihydro-pyrazol-1-yl)-2-phenyl-pyrimidine-4-carbonyl]-amino}-butyryl)-piperazine-1-carboxylic acid ethyl ester;

4-((S)-4-carboxy-2-{[6-(2-hydroxy-1-methyl-propylsulfanyl)-2-phenyl-pyrimidine-4-carbonyl]-amino}-butyryl)-piperazine-1-carboxylic acid ethyl ester;

4-((S)-4-carboxy-2-{[6-(2-hydroxy-propylsulfanyl)-2-phenyl-pyrimidine-4-carbonyl]-amino}-butyryl)-piperazine-1-carboxylic acid ethyl ester;

4-[(S)-2-({6-[(benzyl-methyl-amino)-methyl]-2-phenyl-pyrimidine-4-carbonyl}-amino)-4-carboxy-butyryl]-piperazine-1-carboxylic acid ethyl ester;

4-((S)-4-carboxy-2-{[6-(4-ethoxycarbonyl-piperidin-1-ylmethyl)-2-phenyl-pyrimidine-4-carbonyl]-amino}-butyryl)-piperazine-1-carboxylic acid ethyl ester;

4-((S)-4-carboxy-2-{[6-((S)-2-hydroxymethyl-pyrrolidin-1-ylmethyl)-2-phenyl-pyrimidine-4-carbonyl]-amino}-butyryl)-piperazine-1-carboxylic acid ethyl ester;

4-((S)-4-carboxy-2-{[6-(4-methoxycarbonyl-piperidin-1-ylmethyl)-2-phenyl-pyrimidine-4-carbonyl]-amino}-butyryl)-piperazine-1-carboxylic acid ethyl ester;

4-((S)-4-carboxy-2-{[6-(3-hydroxy-piperidin-1-ylmethyl)-2-phenyl-pyrimidine-4-carbonyl]-amino}-butyryl)-piperazine-1-carboxylic acid ethyl ester;

4-((S)-4-carboxy-2-{[6-(2-hydroxymethyl-piperidin-1-ylmethyl)-2-phenyl-pyrimidine-4-carbonyl]-amino}-butyryl)-piperazine-1-carboxylic acid ethyl ester;

4-{(S)-4-carboxy-2-[(6-morpholin-4-ylmethyl-2-phenyl-pyrimidine-4-carbonyl)-amino]-butyryl}-piperazine-1-carboxylic acid ethyl ester;

4-((S)-4-carboxy-2-{[6-((R)-3-hydroxy-pyrrolidin-1-ylmethyl)-2-phenyl-pyrimidine-4-carbonyl]-amino}-butyryl)-piperazine-1-carboxylic acid ethyl ester;

4-{(S)-4-carboxy-2-[(2-phenyl-6-piperidin-1-ylmethyl-pyrimidine-4-carbonyl)-amino]-butyryl}-piperazine-1-carboxylic acid ethyl ester;

4-((S)-4-carboxy-2-{[6-(2,6-dimethyl-morpholin-4-ylmethyl)-2-phenyl-pyrimidine-4-carbonyl]-amino}-butyryl)-piperazine-1-carboxylic acid ethyl ester;

4-[(S)-4-carboxy-2-({6-[(ethyl-methyl-amino)-methyl]-2-phenyl-pyrimidine-4-carbonyl}-amino)-butyryl]-piperazine-1-carboxylic acid ethyl ester;

4-{(S)-4-carboxy-2-[(6-diethylaminomethyl-2-phenyl-pyrimidine-4-carbonyl)-amino]-butyryl}-piperazine-1-carboxylic acid ethyl ester;

4-{(S)-4-carboxy-2-[(2-phenyl-6-pyrrolidin-1-ylmethyl-pyrimidine-4-carbonyl)-amino]-butyryl}-piperazine-1-carboxylic acid ethyl ester;

4-{(S)-4-carboxy-2-[(6-ethanesulfonylmethyl-2-phenyl-pyrimidine-4-carbonyl)-amino]-butyryl}-piperazine-1-carboxylic acid ethyl ester;

4-{(S)-4-carboxy-2-[(2-phenyl-6-phenylsulfanylmethyl-pyrimidine-4-carbonyl)-amino]-butyryl}-piperazine-1-carboxylic acid ethyl ester;

4-{(S)-2-[(6-benzenesulfonylmethyl-2-phenyl-pyrimidine-4-carbonyl)-amino]-4-carboxy-butyryl}-piperazine-1-carboxylic acid ethyl ester;

4-{(S)-4-carboxy-2-[(6-cyclopentylsulfanylmethyl-2-phenyl-pyrimidine-4-carbonyl)-amino]-butyryl}-piperazine-1-carboxylic acid ethyl ester;

4-{(S)-4-carboxy-2-[(6-cyclopentanesulfonylmethyl-2-phenyl-pyrimidine-4-carbonyl)-amino]-butyryl}-piperazine-1-carboxylic acid ethyl ester;

4-{(S)-4-carboxy-2-[(2-phenyl-6-thiophen-3-yl-pyrimidine-4-carbonyl)-amino]-butyryl}-piperazine-1-carboxylic acid ethyl ester;

4-((S)-4-carboxy-2-{[6-(2-methoxy-phenyl)-2-phenyl-pyrimidine-4-carbonyl]-amino}-butyryl)-piperazine-1-carboxylic acid ethyl ester;

4-((S)-4-carboxy-2-{[6-(4-methanesulfonyl-phenyl)-2-phenyl-pyrimidine-4-carbonyl]-amino}-butyryl)-piperazine-1-carboxylic acid ethyl ester;

4-((S)-2-{[6-(4-Acetyl-phenyl)-2-phenyl-pyrimidine-4-carbonyl]-amino}-4-carboxy-butyryl)-piperazine-1-carboxylic acid ethyl ester;

4-((S)-4-carboxy-2-{[6-(2-fluoro-phenyl)-2-phenyl-pyrimidine-4-carbonyl]-amino}-butyryl)-piperazine-1-carboxylic acid ethyl ester;

4-((S)-4-carboxy-2-{[6-(3-cyano-phenyl)-2-phenyl-pyrimidine-4-carbonyl]-amino}-butyryl)-piperazine-1-carboxylic acid ethyl ester;

4-((S)-4-carboxy-2-{[6-(3-fluoro-phenyl)-2-phenyl-pyrimidine-4-carbonyl]-amino}-butyryl)-piperazine-1-carboxylic acid ethyl ester;

4-((S)-4-carboxy-2-{[6-(4-methoxy-phenyl)-2-phenyl-pyrimidine-4-carbonyl]-amino}-butyryl)-piperazine-1-carboxylic acid ethyl ester;

4-{(S)-4-carboxy-2-[(6-furan-3-yl-2-phenyl-pyrimidine-4-carbonyl)-amino]-butyryl}-piperazine-1-carboxylic acid ethyl ester;

4-{(S)-2-[(6-benzo[1,3]dioxol-5-yl-2-phenyl-pyrimidine-4-carbonyl)-amino]-4-carboxy-butyryl}-piperazine-1-carboxylic acid ethyl ester;

4-((S)-4-carboxy-2-{[6-(3-methoxy-phenyl)-2-phenyl-pyrimidine-4-carbonyl]-amino}-butyryl)-piperazine-1-carboxylic acid ethyl ester;

4-((S)-4-carboxy-2-{[6-(4-hydroxymethyl-phenyl)-2-phenyl-pyrimidine-4-carbonyl]-amino}-butyryl)-piperazine-1-carboxylic acid ethyl ester;

4-{(S)-4-carboxy-2-[(2-phenyl-6-thiophen-2-yl-pyrimidine-4-carbonyl)-amino]-butyryl}-piperazine-1-carboxylic acid ethyl ester;

4-((S)-4-carboxy-2-{[6-(4-cyano-phenyl)-2-phenyl-pyrimidine-4-carbonyl]-amino}-butyryl)-piperazine-1-carboxylic acid ethyl ester;

4-((S)-4-carboxy-2-{[6-(3-chloro-phenyl)-2-phenyl-pyrimidine-4-carbonyl]-amino}-butyryl)-piperazine-1-carboxylic acid ethyl ester;

4-{(S)-2-[(6-biphenyl-4-yl-2-phenyl-pyrimidine-4-carbonyl)-amino]-4-carboxy-butyryl}-piperazine-1-carboxylic acid ethyl ester;

4-((S)-4-carboxy-2-{[2-phenyl-6-(1H-pyrazol-4-yl)-pyrimidine-4-carbonyl]-amino}-butyryl)-piperazine-1-carboxylic acid ethyl ester;
4-((S)-4-carboxy-2-{[2-phenyl-6-((E)-styryl)-pyrimidine-4-carbonyl]-amino}-butyryl)-piperazine-1-carboxylic acid ethyl ester;
4-((S)-4-carboxy-2-{[2-phenyl-6-(3-trifluoromethyl-phenyl)-pyrimidine-4-carbonyl]-amino}-butyryl)-piperazine-1-carboxylic acid ethyl ester;
4-{(S)-4-carboxy-2-[(2-phenyl-6-pyridin-3-yl-pyrimidine-4-carbonyl)-amino]-butyryl}-piperazine-1-carboxylic acid ethyl ester;
4-{(S)-4-carboxy-2-[(2-phenyl-6-pyridin-4-yl-pyrimidine-4-carbonyl)-amino]-butyryl}-piperazine-1-carboxylic acid ethyl ester;
4-{(S)-4-carboxy-2-[(2-phenyl-6-thiazol-2-yl-pyrimidine-4-carbonyl)-amino]-butyryl}-piperazine-1-carboxylic acid ethyl ester;
4-{(S)-2-[(6-acetyl-2-phenyl-pyrimidine-4-carbonyl)-amino]-4-carboxy-butyryl}-piperazine-1-carboxylic acid ethyl ester;
4-((S)-4-carboxy-2-{[6-(1-hydroxy-ethyl)-2-phenyl-pyrimidine-4-carbonyl]-amino}-butyryl)-piperazine-1-carboxylic acid ethyl ester;
4-((S)-4-carboxy-2-{[6-(1-methoxy-ethyl)-2-phenyl-pyrimidine-4-carbonyl]-amino}-butyryl)-piperazine-1-carboxylic acid ethyl ester;
4-((S)-4-carboxy-2-{[6-(1-ethoxy-ethyl)-2-phenyl-pyrimidine-4-carbonyl]-amino}-butyryl)-piperazine-1-carboxylic acid ethyl ester;
4-((S)-4-carboxy-2-{[6-(1-hydroxy-1-methyl-ethyl)-2-phenyl-pyrimidine-4-carbonyl]-amino}-butyryl)-piperazine-1-carboxylic acid ethyl ester;
4-((S)-4-ethoxycarbonyl-2-{[6-(1-hydroxy-1-methyl-ethyl)-2-phenyl-pyrimidine-4-carbonyl]-amino}-butyryl)-piperazine-1-carboxylic acid ethyl ester;
4-((S)-4-carboxy-2-{[6-(2-hydroxy-ethyl)-2-phenyl-pyrimidine-4-carbonyl]-amino}-butyryl)-piperazine-1-carboxylic acid ethyl ester;
4-((S)-4-carboxy-2-{[6-(2-methoxy-ethyl)-2-phenyl-pyrimidine-4-carbonyl]-amino}-butyryl)-piperazine-1-carboxylic acid ethyl ester;
4-((S)-4-carboxy-2-{[6-(2-hydroxy-cyclohexyl)-2-phenyl-pyrimidine-4-carbonyl]-amino}-butyryl)-piperazine-1-carboxylic acid ethyl ester;
4-((S)-4-carboxy-2-{[6-(2-methoxy-cyclohexyl)-2-phenyl-pyrimidine-4-carbonyl]-amino}-butyryl)-piperazine-1-carboxylic acid ethyl ester;
4-((S)-4-carboxy-2-{[6-(2-hydroxy-cyclopentyl)-2-phenyl-pyrimidine-4-carbonyl]-amino}-butyryl)-piperazine-1-carboxylic acid ethyl ester;
4-((S)-4-carboxy-2-{[6-(2-hydroxy-propyl)-2-phenyl-pyrimidine-4-carbonyl]-amino}-butyryl)-piperazine-1-carboxylic acid ethyl ester;
4-((S)-4-carboxy-2-{[6-(2-methoxy-propyl)-2-phenyl-pyrimidine-4-carbonyl]-amino}-butyryl)-piperazine-1-carboxylic acid ethyl ester;
4-((S)-4-carboxy-2-{[6-(3,6-dihydro-2H-pyran-4-yl)-2-phenyl-pyrimidine-4-carbonyl]-amino}-butyryl)-piperazine-1-carboxylic acid ethyl ester;
4-((S)-4-carboxy-2-{[2-phenyl-6-(tetrahydro-pyran-4-yl)-pyrimidine-4-carbonyl]-amino}-butyryl)-piperazine-1-carboxylic acid ethyl ester;
4-((S)-4-carboxy-2-{[6-(2-ethoxycarbonyl-cyclohexyl)-2-phenyl-pyrimidine-4-carbonyl]-amino}-butyryl)-piperazine-1-carboxylic acid ethyl ester;
4-((S)-4-carboxy-2-{[6-(1-oxy-pyridin-3-yl)-2-phenyl-pyrimidine-4-carbonyl]-amino}-butyryl)-piperazine-1-carboxylic acid ethyl ester;
4-((S)-4-carboxy-2-{[6-((E)-2-ethoxycarbonyl-vinyl)-2-phenyl-pyrimidine-4-carbonyl]-amino}-butyryl)-piperazine-1-carboxylic acid ethyl ester;
4-((S)-4-carboxy-2-{[2-phenyl-6-(tetrahydro-furan-2-ylmethyl)-pyrimidine-4-carbonyl]-amino}-butyryl)-piperazine-1-carboxylic acid ethyl ester;
4-((S)-4-carboxy-2-{[6-((E)-4-hydroxy-but-1-enyl)-2-phenyl-pyrimidine-4-carbonyl]-amino}-butyryl)-piperazine-1-carboxylic acid ethyl ester;
4-((S)-4-carboxy-2-{[6-(3-hydroxy-2-methyl-propyl)-2-phenyl-pyrimidine-4-carbonyl]-amino}-butyryl)-piperazine-1-carboxylic acid ethyl ester;
4-((S)-4-carboxy-2-{[2-phenyl-6-(tetrahydro-furan-3-yl)-pyrimidine-4-carbonyl]-amino}-butyryl)-piperazine-1-carboxylic acid ethyl ester;
4-((S)-4-carboxy-2-{[6-((E)-2-dimethylcarbamoyl-vinyl)-2-phenyl-pyrimidine-4-carbonyl]-amino}-butyryl)-piperazine-1-carboxylic acid ethyl ester;
4-{(S)-4-carboxy-2-[(6-cyano-2-phenyl-pyrimidine-4-carbonyl)-amino]-butyryl}-piperazine-1-carboxylic acid ethyl ester;
4-((S)-4-carboxy-2-{[6-(1-hydroxy-propyl)-2-phenyl-pyrimidine-4-carbonyl]-amino}-butyryl)-piperazine-1-carboxylic acid ethyl ester;
4-((S)-4-carboxy-2-{[6-(1-hydroxy-butyl)-2-phenyl-pyrimidine-4-carbonyl]-amino}-butyryl)-piperazine-1-carboxylic acid ethyl ester;
4-((S)-4-carboxy-2-{[6-(hydroxy-phenyl-methyl)-2-phenyl-pyrimidine-4-carbonyl]-amino}-butyryl)-piperazine-1-carboxylic acid ethyl ester;
4-((S)-4-carboxy-2-{[6-(2-hydroxy-2-phenyl-ethyl)-2-phenyl-pyrimidine-4-carbonyl]-amino}-butyryl)-piperazine-1-carboxylic acid ethyl ester;
4-{(S)-4-carboxy-2-[(6-ethoxymethyl-2-phenyl-pyrimidine-4-carbonyl)-amino]-butyryl}-piperazine-1-carboxylic acid ethyl ester;
4-{(S)-4-carboxy-2-[(2-phenyl-6-trifluoromethyl-pyrimidine-4-carbonyl)-amino]-butyryl}-piperazine-1-carboxylic acid ethyl ester;
4-{(S)-2-[(6-tert-butyl-2-phenyl-pyrimidine-4-carbonyl)-amino]-4-carboxy-butyryl}-piperazine-1-carboxylic acid ethyl ester;
4-{(S)-4-carboxy-2-[(6-phenoxy-2-phenyl-pyrimidine-4-carbonyl)-amino]-butyryl}-piperazine-1-carboxylic acid ethyl ester;
4-((S)-4-carboxy-2-{[2-phenyl-6-(pyridin-3-yloxy)-pyrimidine-4-carbonyl]-amino}-butyryl)-piperazine-1-carboxylic acid ethyl ester; —(S)-5-(4-tert-butylcarbamoyl-piperazin-1-yl)-4-[(6-cyclopentyloxy-2-phenyl-pyrimidine-4-carbonyl)-amino]-5-oxo-pentanoic acid;
(S)-4-[(6-cyclopentyloxy-2-phenyl-pyrimidine-4-carbonyl)-amino]-5-(4-isopropylcarbamoyl-piperazin-1-yl)-5-oxo-pentanoic acid;
(S)-4-[(6-cyclopentyloxy-2-phenyl-pyrimidine-4-carbonyl)-amino]-5-oxo-5-[4-(thiophene-2-carbonyl)-piperazin-1-yl]-pentanoic acid;
(S)-5-(4-cyclopentanecarbonyl-piperazin-1-yl)-4-[(6-cyclopentyloxy-2-phenyl-pyrimidine-4-carbonyl)-amino]-5-oxo-pentanoic acid;
(S)-4-[(6-cyclopentyloxy-2-phenyl-pyrimidine-4-carbonyl)-amino]-5-oxo-5-[4-(piperidine-1-carbonyl)-piperazin-1-yl]-pentanoic acid;

4-(4-tert-butoxycarbonyl-2-{[6-((S)-3-methoxy-pyrrolidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-((S)-2-methoxy-1-methyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(4-methoxy-piperidin-1-yl)-2-phenyl-pyrimidine-4-carbonyl]-amino}-butyryl)-piperazine-1-carboxylic acid ethyl ester;

4-(4-tert-butoxycarbonyl-2-{[6-((R)-3-methoxy-pyrrolidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-((R)-2-methoxy-1-methyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(2-methoxymethyl-piperidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-((S)-2-methoxymethyl-pyrrolidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-((R)-2-methoxymethyl-pyrrolidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-(2-methoxy-1,1-dimethyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(4,5-dihydro-pyrazol-1-yl)-2-phenyl-pyrimidine-4-carbonyl]-amino}-butyryl)-piperazine-1-carboxylic acid ethyl ester;

4-((S)-4-tert-butoxycarbonyl-2-{[6-(2-methyl-4,5-dihydro-imidazol-1-yl)-2-phenyl-pyrimidine-4-carbonyl]-amino}-butyryl)-piperazine-1-carboxylic acid ethyl ester;

4-{(S)-4-tert-butoxycarbonyl-2-[(2-phenyl-6-[1,2,4]triazol-1-yl-pyrimidine-4-carbonyl)-amino]-butyryl}-piperazine-1-carboxylic acid ethyl ester;

4-((S)-4-tert-butoxycarbonyl-2-{[6-(4-methyl-pyrazol-1-yl)-2-phenyl-pyrimidine-4-carbonyl]-amino}-butyryl)-piperazine-1-carboxylic acid ethyl ester;

4-((S)-4-tert-butoxycarbonyl-2-{[6-(3-methyl-pyrazol-1-yl)-2-phenyl-pyrimidine-4-carbonyl]-amino}-butyryl)-piperazine-1-carboxylic acid ethyl ester;

4-((S)-2-{[6-(4-butyl-[1,2,3]triazol-1-yl)-2-phenyl-pyrimidine-4-carbonyl]-amino}-4-tert-butoxycarbonyl-butyryl)-piperazine-1-carboxylic acid ethyl ester;

4-{(S)-2-[(6-amino-2-phenyl-pyrimidine-4-carbonyl)-amino]-4-tert-butoxycarbonyl-butyryl}-piperazine-1-carboxylic acid ethyl ester;

4-((S)-4-tert-butoxycarbonyl-2-{[6-(3-methyl-5-oxo-2,5-dihydro-pyrazol-1-yl)-2-phenyl-pyrimidine-4-carbonyl]-amino}-butyryl)-piperazine-1-carboxylic acid ethyl ester;

4-{(S)-4-tert-butoxycarbonyl-2-[(6-ethanesulfonylmethyl-2-phenyl-pyrimidine-4-carbonyl)-amino]-butyryl}-piperazine-1-carboxylic acid ethyl ester;

4-{(S)-4-tert-butoxycarbonyl-2-[(6-ethylsulfanylmethyl-2-phenyl-pyrimidine-4-carbonyl)-amino]-butyryl}-piperazine-1-carboxylic acid ethyl ester;

4-{(S)-2-[(6-benzenesulfonylmethyl-2-phenyl-pyrimidine-4-carbonyl)-amino]-4-tert-butoxycarbonyl-butyryl}-piperazine-1-carboxylic acid ethyl ester;

4-{(S)-4-tert-butoxycarbonyl-2-[(6-cyclopentylsulfanylmethyl-2-phenyl-pyrimidine-4-carbonyl)-amino]-butyryl}-piperazine-1-carboxylic acid ethyl ester;

4-{(S)-4-tert-butoxycarbonyl-2-[(6-cyclopentanesulfonylmethyl-2-phenyl-pyrimidine-4-carbonyl)-amino]-butyryl}-piperazine-1-carboxylic acid ethyl ester;

4-{(S)-4-tert-butoxycarbonyl-2-[(2-phenyl-6-pyridin-3-yl-pyrimidine-4-carbonyl)-amino]-butyryl}-piperazine-1-carboxylic acid ethyl ester;

4-{(S)-4-tert-butoxycarbonyl-2-[(2-phenyl-6-pyridin-4-yl-pyrimidine-4-carbonyl)-amino]-butyryl}-piperazine-1-carboxylic acid ethyl ester;

4-{(S)-4-tert-butoxycarbonyl-2-[(2-phenyl-6-thiazol-2-yl-pyrimidine-4-carbonyl)-amino]-butyryl}-piperazine-1-carboxylic acid ethyl ester;

4-{(S)-2-[(6-acetyl-2-phenyl-pyrimidine-4-carbonyl)-amino]-4-tert-butoxycarbonyl-butyryl}-piperazine-1-carboxylic acid ethyl ester;

4-((S)-4-tert-butoxycarbonyl-2-{[6-(1-hydroxy-ethyl)-2-phenyl-pyrimidine-4-carbonyl]-amino}-butyryl)-piperazine-1-carboxylic acid ethyl ester;

4-((S)-4-tert-butoxycarbonyl-2-{[6-(1-methoxy-ethyl)-2-phenyl-pyrimidine-4-carbonyl]-amino}-butyryl)-piperazine-1-carboxylic acid ethyl ester;

4-((S)-4-tert-butoxycarbonyl-2-{[6-(1-ethoxy-ethyl)-2-phenyl-pyrimidine-4-carbonyl]-amino}-butyryl)-piperazine-1-carboxylic acid ethyl ester;

4-((S)-4-tert-butoxycarbonyl-2-{[6-(1-hydroxy-1-methyl-ethyl)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-ethyl)-2-phenyl-pyrimidine-4-carbonyl]-amino}-butyryl)-piperazine-1-carboxylic acid ethyl ester;

4-((S)-4-tert-butoxycarbonyl-2-{[6-(2-methoxy-ethyl)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-cyclohexyl)-2-phenyl-pyrimidine-4-carbonyl]-amino}-butyryl)-piperazine-1-carboxylic acid ethyl ester;

4-((S)-4-tert-butoxycarbonyl-2-{[6-(2-methoxy-cyclohexyl)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-cyclopentyl)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-propyl)-2-phenyl-pyrimidine-4-carbonyl]-amino}-butyryl)-piperazine-1-carboxylic acid ethyl ester;

4-((S)-4-tert-butoxycarbonyl-2-{[6-(2-methoxy-propyl)-2-phenyl-pyrimidine-4-carbonyl]-amino}-butyryl)-piperazine-1-carboxylic acid ethyl ester;

4-((S)-4-tert-butoxycarbonyl-2-{[6-(3,6-dihydro-2H-pyran-4-yl)-2-phenyl-pyrimidine-4-carbonyl]-amino}-butyryl)-piperazine-1-carboxylic acid ethyl ester;

4-((S)-4-tert-butoxycarbonyl-2-{[2-phenyl-6-(tetrahydro-pyran-4-yl)-pyrimidine-4-carbonyl]-amino}-butyryl)-piperazine-1-carboxylic acid ethyl ester;

4-((S)-4-tert-butoxycarbonyl-2-{[6-(2-ethoxycarbonyl-cyclohexyl)-2-phenyl-pyrimidine-4-carbonyl]-amino}-butyryl)-piperazine-1-carboxylic acid ethyl ester;

4-((S)-4-tert-butoxycarbonyl-2-{[6-(1-oxy-pyridin-3-yl)-2-phenyl-pyrimidine-4-carbonyl]-amino}-butyryl)-piperazine-1-carboxylic acid ethyl ester;

4-((S)-4-tert-butoxycarbonyl-2-{[6-((E)-2-ethoxycarbonyl-vinyl)-2-phenyl-pyrimidine-4-carbonyl]-amino}-butyryl)-piperazine-1-carboxylic acid ethyl ester;

4-((S)-4-tert-butoxycarbonyl-2-{[2-phenyl-6-(tetrahydro-furan-2-ylmethyl)-pyrimidine-4-carbonyl]-amino}-butyryl)-piperazine-1-carboxylic acid ethyl ester;

4-((S)-4-tert-butoxycarbonyl-2-{[6-(3-hydroxy-2-methyl-propyl)-2-phenyl-pyrimidine-4-carbonyl]-amino}-butyryl)-piperazine-1-carboxylic acid ethyl ester;

4-((S)-4-tert-butoxycarbonyl-2-{[2-phenyl-6-(tetrahydro-furan-3-yl)-pyrimidine-4-carbonyl]-amino}-butyryl)-piperazine-1-carboxylic acid ethyl ester;

4-((S)-4-tert-butoxycarbonyl-2-{[6-((E)-2-dimethylcarbamoyl-vinyl)-2-phenyl-pyrimidine-4-carbonyl]-amino}-butyryl)-piperazine-1-carboxylic acid ethyl ester;

4-((S)-4-tert-butoxycarbonyl-2-{[6-(1-hydroxy-propyl)-2-phenyl-pyrimidine-4-carbonyl]-amino}-butyryl)-piperazine-1-carboxylic acid ethyl ester;

4-((S)-4-tert-butoxycarbonyl-2-{[6-(1-hydroxy-butyl)-2-phenyl-pyrimidine-4-carbonyl]-amino}-butyryl)-piperazine-1-carboxylic acid ethyl ester;

4-((S)-4-tert-butoxycarbonyl-2-{[6-(hydroxy-phenyl-methyl)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-2-phenyl-ethyl)-2-phenyl-pyrimidine-4-carbonyl]-amino}-butyryl)-piperazine-1-carboxylic acid ethyl ester;

4-{(S)-4-tert-butoxycarbonyl-2-[(2-phenyl-6-trifluoromethyl-pyrimidine-4-carbonyl)-amino]-butyryl}-piperazine-1-carboxylic acid ethyl ester;

4-{(S)-2-[(6-tert-butyl-2-phenyl-pyrimidine-4-carbonyl)-amino]-4-tert-butyloxycarbonyl-butyryl}-piperazine-1-carboxylic acid ethyl ester;

4-{(S)-4-tert-butoxycarbonyl-2-[(6-phenoxy-2-phenyl-pyrimidine-4-carbonyl)-amino]-butyryl}-piperazine-1-carboxylic acid ethyl ester;

4-((S)-4-carboxy-2-{[6-(1-oxy-pyridin-2-yl)-2-phenyl-pyrimidine-4-carbonyl]-amino}-butyryl)-piperazine-1-carboxylic acid ethyl ester;

4-((S)-4-carboxy-2-{[6-(1-oxy-pyridin-4-yl)-2-phenyl-pyrimidine-4-carbonyl]-amino}-butyryl)-piperazine-1-carboxylic acid ethyl ester;

4-((S)-4-carboxy-2-{[6-(2-hydroxy-1,1-dimethyl-ethyl)-2-phenyl-pyrimidine-4-carbonyl]-amino}-butyryl)-piperazine-1-carboxylic acid ethyl ester;

4-((S)-4-tert-butoxycarbonyl-2-{[6-(1-oxy-pyridin-2-yl)-2-phenyl-pyrimidine-4-carbonyl]-amino}-butyryl)-piperazine-1-carboxylic acid ethyl ester;

4-((S)-4-tert-butoxycarbonyl-2-{[6-(1-oxy-pyridin-4-yl)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-1,1-dimethyl-ethyl)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxymethyl-cyclopropyl)-2-phenyl-pyrimidine-4-carbonyl]-amino}-butyryl)-piperazine-1-carboxylic acid ethyl ester;

4-((S)-4-carboxy-2-{[6-(2-hydroxymethyl-cyclopropyl)-2-phenyl-pyrimidine-4-carbonyl]-amino}-butyryl)-piperazine-1-carboxylic acid ethyl ester; as well as the salts thereof (in particular the pharmaceutically acceptable salts thereof).

Particularly preferred among these compounds of formula I are the 316 first compounds of the above list (which are compounds of formula $I_{P2}$), in particular the 222 first compounds of the above list (which are compounds of formula $I_{P1}$). Besides, the 107 first compounds, the compounds named from the $115^{th}$ to the $122^{nd}$ position, the compound named in $124^{th}$ position, the compounds named from the $223^{rd}$ to the $267^{th}$ position, the compounds named from the $311^{th}$ to the $314^{th}$ position, the compounds named from the 317 to the $439^{th}$ position, the compounds named from the $493^{rd}$ to the $495^{th}$ position and the compound named in $500^{th}$ (last) position (and notably the 107 first compounds, the compounds named from the $223^{rd}$ to the $267^{th}$ position and the compounds named from the $311^{th}$ to the $314^{th}$ position) are preferred over the other compounds of the above list.

Compounds of formula I (or of formula $I_{P2}$ or $I_{P1}$) may be solvated, especially hydrated. The hydration can occur during the process of production or as a consequence of the hygroscopic nature of the initially water free compounds of formula I (or of formula $I_{P2}$ or $I_{P1}$).

A further object of the invention is the compounds of formula I (or of formula $I_{P2}$, $I_{P1}$, $I_{CE}$, $I_{CEP2}$ or $I_{CEP1}$) or their pharmaceutically acceptable salts as medicaments.

The invention also relates to pharmaceutical compositions containing at least one compound according to this invention (notably a compound of formula I, $I_{P2}$, $I_{P1}$, $I_{CE}$, $I_{CEP2}$ or $I_{CEP1}$), or a pharmaceutically acceptable salt thereof, and a pharmaceutically acceptable carrier, diluent or excipient. In particular, the invention relates to pharmaceutical compositions containing at least one compound of formula I (or of formula $I_{P2}$, $I_{P1}$, $I_{CE}$, $I_{CEP2}$ or $I_{CEP1}$) and a pharmaceutically acceptable carrier, diluent or excipient.

As mentioned above, therapeutically useful agents that contain compounds of formula I (or of formula $I_{P2}$, $I_{P1}$, $I_{CE}$, $I_{CEP2}$ or $I_{CEP1}$), their solvates, salts or formulations are also comprised in the scope of the present invention. In general, compounds of formula I can be administered, for example, perorally, e.g. as tablets, coated tablets, dragees, soft and hard gelatine capsules, pills, aqueous or oily solutions, emulsions, suspensions or syrups, rectally, e.g. in the form of suppositories, parenterally e.g. in the form of injection or infusion solutions, or topically, e.g. in the form of solutions, suspensions, ointments, creams, oils or aerosols.

Yet another object of this invention is the use of a compound of formula I (or of formula $I_{P2}$, $I_{P1}$, $I_{CE}$, $I_{CEP2}$ or $I_{CEP1}$), or of a pharmaceutically acceptable salt thereof, for the manufacture of a medicament for:

the treatment or prophylaxis of diseases including stable angina, unstable angina, myocardial infarction, embolism (including complications of atherosclerosis, notably embolic stroke), arterial thrombosis (including primary arterial thrombotic complications of atherosclerosis, notably thrombotic stroke), venous thrombosis (notably deep vein thrombosis), thrombosis secondary to vascular damage or to inflammation (including vasculitis, arteritis and glomerulonephritis), venoocclusive diseases, transient ischaemic attacks, peripheral vascular diseases, myocardial infarction with or without thrombolysis, myeloproliferative disease, thrombocytohaemia, sickle cell disease, inflammatory bowel disease, thrombotic thrombocytopaenic purpura, haemolytic uraemic syndrome;

for preventing thrombotic complications of septicaemia, adult respiratory distress syndrome, anti-phospholipid syndrome, heparin-induced thrombocytopaenia and pre-eclampsia/eclampsia;

for preventing cardiovascular complications after certain surgery procedures (notably coronary revascularisation like angioplasty (PTCA), other vascular graft surgery, endarterectomy or stent placement) or after accidental trauma;

for preventing organ graft rejection.

More generally, the invention relates to the use of a compound of formula I (or of formula $I_{P2}$, $I_{P1}$, $I_{CE}$, $I_{CEP2}$ or $I_{CEP1}$), or of a pharmaceutically acceptable salt thereof, for the manufacture of a medicament for the treatment and/or prevention of occlusive vascular disorders as well as to the use of a compound of formula I (or of formula $I_{P2}$, $I_{P1}$, $I_{CE}$, $I_{CEP2}$ or $I_{CEP1}$) for the manufacture of a medicament for the treatment and/or prevention of peripheral vascular, of visceral-, hepatic- and renal-vascular, of cardiovascular and of cerebrovascular diseases or conditions associated with platelet aggregation, including thrombosis in humans and other mammals.

Among the above-mentioned uses of compounds of formula I (or of formula $I_{P2}$, $I_{P1}$, $I_{CE}$, $I_{CEP2}$ or $I_{CEP1}$) or of pharmaceutically acceptable salts thereof for the manufacture of medicaments, the uses for manufacturing medicaments for the treatment or prophylaxis of myocardial infarction, arterial thrombosis (notably thrombotic stroke), transient ischaemic attacks, peripheral vascular disease and stable and unstable angina will be preferred.

The invention further relates to the use of a compound of formula I (or of formula $I_{P2}$, $I_{P1}$, $I_{CE}$, $I_{CEP2}$ or $I_{CEP1}$), or of a pharmaceutically acceptable salt thereof, for the preservation of blood products in vitro (e.g. the preservation of platelet concentrates), or for the prevention of occlusion in extracorporeal blood or blood product treatment machines (such as renal dialysis machines or plasmapheresis machines).

The invention also relates to methods of treatment for said disorders, said methods comprising the administration to a patient in need thereof of an effective amount of a compound of formula I (or of formula $I_{P2}$, $I_{P1}$, $I_{CE}$, $I_{CEP2}$ or $I_{CEP1}$) or of a pharmaceutically acceptable salt thereof.

The production of the pharmaceutical compositions can be effected in a manner which will be familiar to any person skilled in the art (see for example Mark Gibson, Editor, Pharmaceutical Preformulation and Formulation, 1HS Health Group, Englewood, Colo., USA, 2001; Remington, *The Science and Practice of Pharmacy*, 20th Edition, Philadelphia College of Pharmacy and Science) by bringing the described compounds of formula I (or of formula $I_{P2}$, $I_{P1}$, $I_{CE}$, $I_{CEP2}$ or $I_{CEP1}$) and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The preferences indicated for the compounds of formula I of course apply *mutatis mutandis* to the compounds of formula $I_{P2}$, of formula $I_{P1}$, of formula $I_{CE}$, of formula $I_{CEP2}$, of formula $I_{CEP1}$, of formula $I_B$, of formula $I_C$, of formula $I_M$, of formula $I_O$, of formula $I_S$, of formula $I_N$, of formula $I_{NL}$, of formula $I_{NR}$, of formula $I_D$, of formula $I_T$, of formula $I_{CO}$, of formula $I_{CP2}$, of formula $I_{CP1}$, of formula $I_{OP2}$, of formula $I_{OP1}$, of formula $I_{NP2}$, of formula $I_{NP1}$, of formula $I_{SP2}$, of formula $I_{SP1}$, of formula $I_{DTP2}$ or of formula $I_{DTP1}$, as well as to the optically pure enantiomers, mixtures of enantiomers, racemates, optically pure diastereoisomers, mixtures of diastereoisomers, diastereoisomeric racemates, mixture of diastereoisomeric racemates, meso forms, geometric isomers, solvates, morphological forms, salts and pharmaceutically acceptable salts of the compounds of formula I, of formula $I_{P2}$, of formula $I_{P1}$, of formula $I_{CE}$, of formula $I_{CEP2}$, of formula $I_{CEP1}$, of formula $I_B$, of formula $I_C$, of formula $I_M$, of formula $I_O$, of formula $I_S$, of formula $I_N$, of formula $I_{NL}$, of formula $I_{NR}$, of formula $I_D$, of formula $I_T$, of formula $I_{CO}$, of formula $I_{CP2}$, of formula $I_{CP1}$, of formula $I_{OP2}$, of formula $I_{OP1}$, of formula $I_{NP2}$, of formula $I_{NP1}$, of formula $I_{SP2}$, of formula $I_{SP1}$, of formula $I_{DTP2}$ or of formula $I_{DTP1}$. The same applies to these compounds as medicaments, to pharmaceutical compositions containing these compounds as active principles or to the uses of these compounds for the manufacture of a medicament for the treatment of the diseases according to this invention.

According to the invention, the compounds of formula I (or of formula $I_{P2}$, $I_{P1}$, $I_{CE}$, $I_{CEP2}$ or $I_{CEP1}$) can be prepared by the process described below.

Preparation of the Compounds of Formula I

Abbreviations:

The following abbreviations are used throughout the specification and the examples:

| | |
|---|---|
| AcOH | acetic acid |
| aq. | aqueous |
| cHex | cyclohexane |
| DCM | dichloromethane |
| DIPEA | diisopropylethylamine |
| DMF | N,N-dimethylformamide |
| EA | ethyl acetate |
| EDCI | N-(3-dimethylaminopropyl)-N-ethylcarbodiimide |
| EtOH | ethanol |
| Et$_2$O | diethyl ether |
| Hept | heptane |
| Hex | hexane |
| HOBT | 1-hydroxybenzotriazole |
| HV | high vacuum |
| MCPBA | meta-chloroperbenzoic acid |
| MeCN | acetonitile |
| MeOH | methanol |
| NEt$_3$ | triethylamine |
| org. | organic |
| Pd/C | palladium on carbon |
| PyBOP | benzotriazole-1-yl-oxy-tris-pyrrolidino-phosphonium hexafluorophosphate |
| TBAF | tetrabutylammonium fluoride |
| TFA | trifluoroacetic acid |
| THF | tetrahydrofuran |
| TLC | thin layer chromatography |
| RT | room temperature |
| t$_R$ | retention time |

General Preparation Routes:

The various compounds of formula I can be prepared using the general routes summarized in Scheme 1 hereafter. In all compounds of formula I.1, formula I.2, formula I.3, formula I.4, formula I.5, formula I.6, formula I.7, formula I.8 or formula II represented in Scheme 1, W, X, R$^1$, R$^2$, R$^{5a}$, R$^{5b}$ and R$^6$ have the same meaning as in formula I and Y' represents alkylene, alkoxyalkylen, phenylalkylene or alkoxyphenylalkylen.

Scheme 1
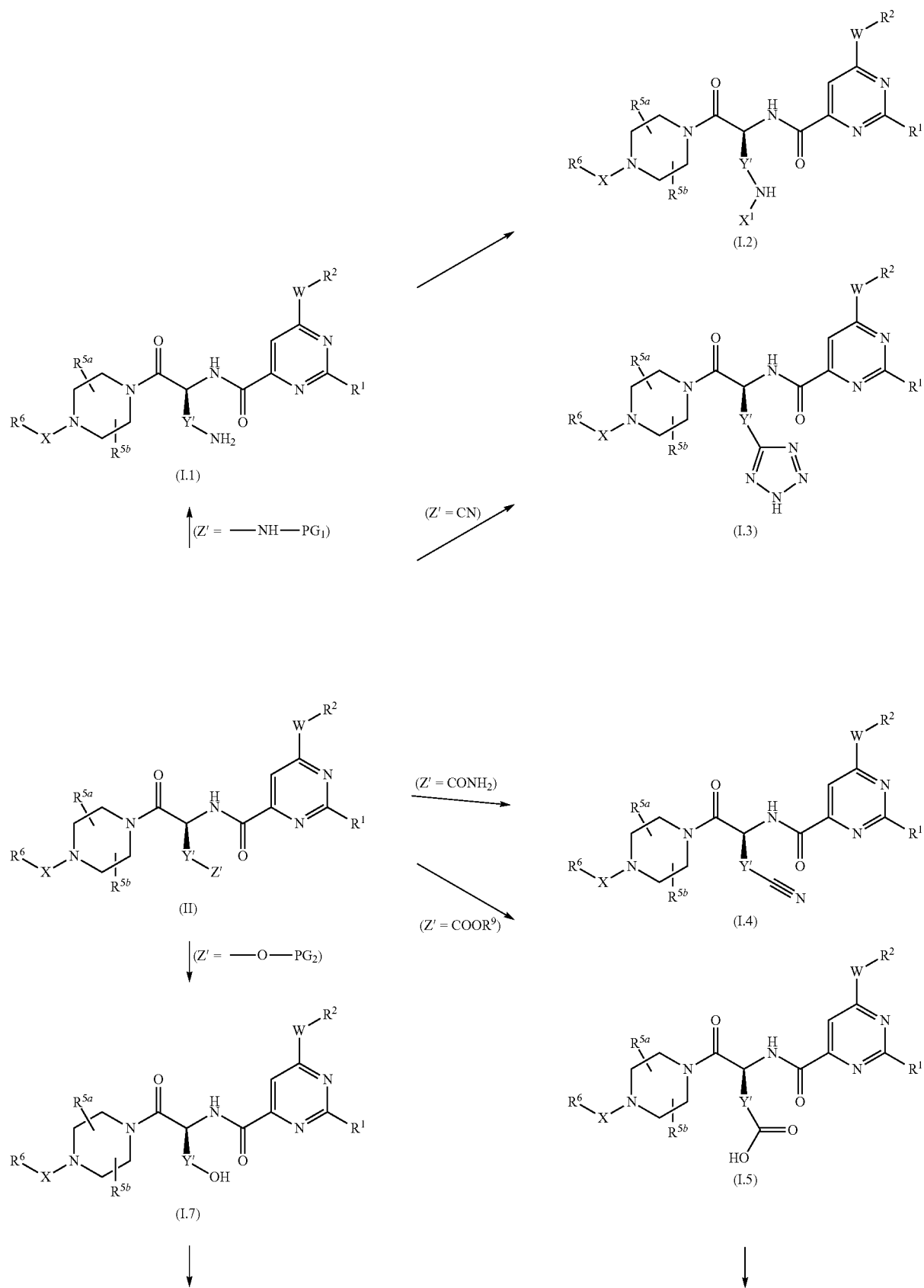

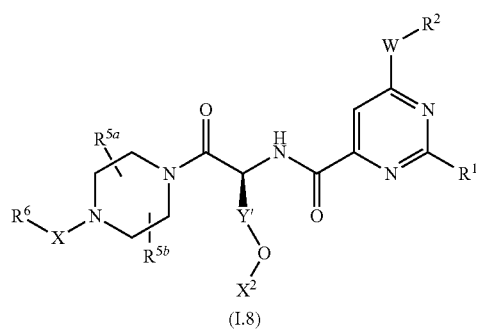

(I.8)

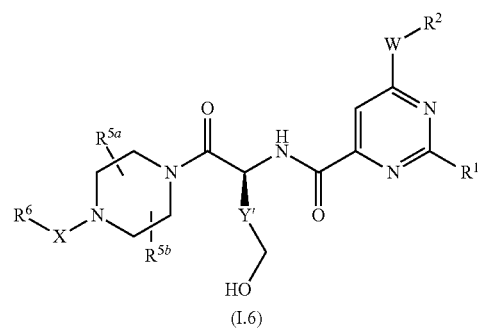

(I.6)

The amines of formula I.1 can be obtained (Scheme 1) by conversion of the corresponding protected amines of general formula II wherein Z' is —NH-$PG_1$ and $PG_1$ is a suitable protecting group for an amine function. Suitable amine function protection groups and protection and deprotection methods are well known to one skilled in the art (see notably "Protective groups in organic synthesis", Greene T. W. and Wuts P. G. M., Wiley-Interscience, 1999).

The compounds of formula I.2, wherein $X^1$ may represent —$SO_2$—$R^{17}$, —$COR^{17}$ or —$COOR^{17}$ (wherein $R^{17}$ is as defined in formula I), can be obtained (Scheme 1) by conversion of the corresponding amines of formula I.1 wherein Z' is —$NH_2$ carrying out standard reactions with a sulfonyl chloride of formula $R^{17}$—$SO_2$—Cl, acid chloride of formula $R^{17}$—CO—Cl or chloroformate $R^{17}$—O—CO—Cl in the presence of a suitable base such as $NEt_3$, DIPEA or N-methylmorpholine, in a suitable solvent such as DCM, THF or DMF, and preferably at RT.

The tetrazole derivatives of formula I.3 can be prepared (Scheme 1) by conversion of the corresponding cyano derivatives of formula II wherein Z' is —CN using the well-known methodology with sodium azide.

The compounds of formula I.4 can be prepared (Scheme 1) by reaction of the corresponding amide derivatives of general formula II wherein Z' is —$CONH_2$ with the well-known Burgess reagent.

The compounds of formula I.5 can be prepared (Scheme 1) by hydrolysis of the corresponding compounds of formula II wherein Z' is —$COOR^{17}$ ($R^{17}$ being alkyl) under standard conditions well known to one skilled in the art. The compounds of formula I.6 can then be prepared (Scheme 1) by reduction of the acids of formula I.5. Such reduction can be carried out by reacting the acids of formula I.5 with ethyl chloroformate in the presence of a suitable base such as $NEt_3$, DIPEA, N-methylmorpholine, in a suitable solvent such as DCM, THF or DMF, between −10 and 0° C., and by adding a reducing agent such as $NaBH_4$.

The compounds of formula I.7 can be prepared (Scheme 1) by deprotection of the corresponding compounds of formula II wherein Z' is —O-$PG_2$ and $PG_2$ is a suitable protecting group for an alcohol function. Suitable alcohol function protection groups and protection and deprotection methods are well known to one skilled in the art (see notably "Protective groups in organic synthesis", Greene T. W. and Wuts P. G. M., Wiley-Interscience, 1999).

The compounds of formula I.8, wherein $X^2$ represents alkylene substituted by a Z group as defined in formula I (if necessary protected using standard techniques known to one skilled in the art), can be prepared (Scheme 1) according to standard alkylation techniques, reacting the alcohols of formula I.7 with bromide derivatives of formula $X^2$—Br in presence of a suitable base such as potassium hexamethyldisilazane, cesium carbonate or $K_2CO_3$, in a suitable solvent such as THF or DMF, at a temperature preferably comprised between 0° C. and RT.

Besides, whenever the compounds of formula I are obtained in the form of mixtures of enantiomers, the enantiomers can be separated using methods known to one skilled in the art (e.g. by formation and separation of diastereomeric salts or by chromatography over a chiral stationary phase). Whenever the compounds of formula I are obtained in the form of mixtures of diasteromers they may be separated by an appropriate combination of silica gel chromatography, HPLC and crystallisation techniques.

Preparation of the Various Synthesis Intermediates:
Preparation of the Compounds of Formula II The compounds of formula II can be prepared (Scheme 2) by coupling a compound of formula III wherein X, $R^{5a}$, $R^{5b}$, $R^6$, Y' and Z' have the same meanings as in formula II with a compound of formula IV wherein W, $R^1$ and $R^2$ have the same meanings as in formula II, using standard peptide coupling methods such as HOBT, EDCI hydrochloride, 1,3-dicyclohexylcarbodiimide, benzotriazole-1-yl-oxy-tris-pyrrolidino-phosphonium hexafluorophosphate, benzotriazole-1-yl-oxy-tris-(dimethylamino)-phosphoniumhexafluorophosphate, optionally in the presence of a suitable base such as $NEt_3$, DIPEA or N-methylmorpholine and in a suitable solvent such as DCM, THF or DMF, preferably at a temperature around RT.

Scheme 2

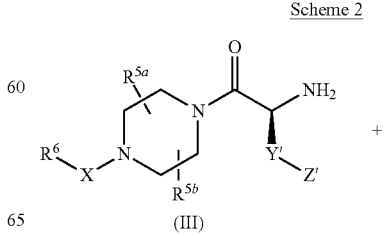

(III)

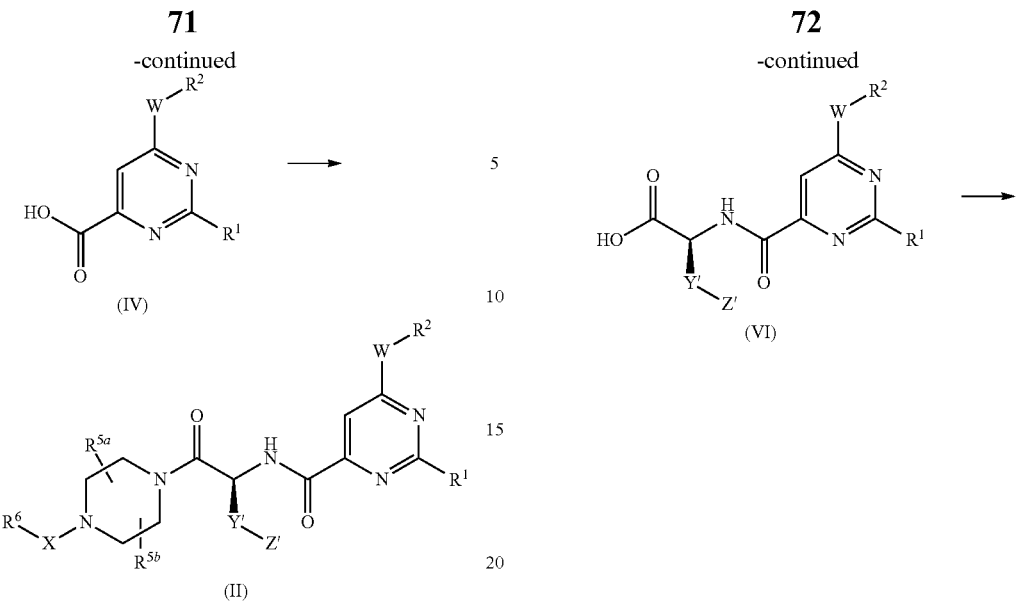

Alternatively, the compounds of formula II can be prepared (Scheme 2a) by coupling a compound of formula V wherein X, $R^{5a}$, $R^{5b}$ and $R^6$ have the same meanings as in formula II with a compound of formula VI wherein W, $R^1$, $R^2$, Y' and Z' have the same meanings as in formula II, using the same standard coupling methods as those described above for the coupling reaction involving compounds of formulae III and IV.

Scheme 2a

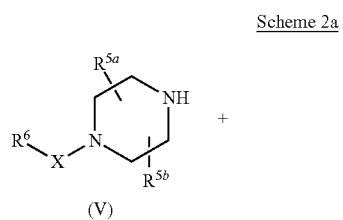

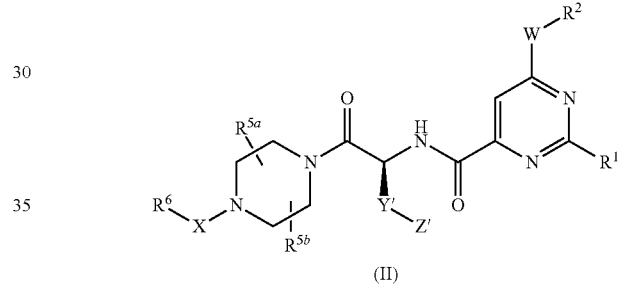

A further route towards the compounds of formula II is shown in Scheme 2b hereafter.

Scheme 2b

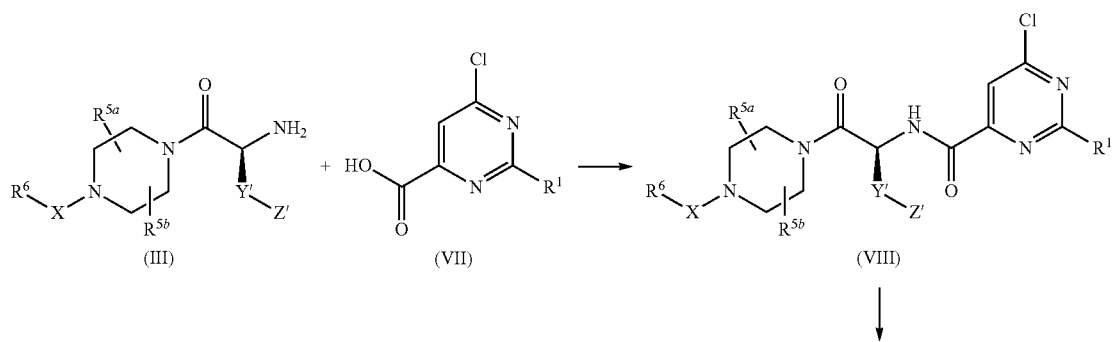

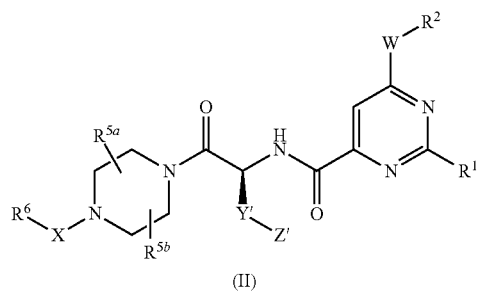

(II)

According to this further route, the compounds of formula III wherein Z' is H, —NH-PG₁ or —O-PG₂ can be coupled with the chloropyrimidine derivatives of formula VII wherein R¹ has the same meaning as in formula II, using the same standard coupling methods as those described above for the coupling reaction involving compounds of formulae III and IV. The resulting intermediate of formula VIII can then be converted into a compound of formula II wherein W is —NR³— by aromatic substitution reaction with an amine of formula HNR²R³ optionally in the presence of a suitable base such as NEt₃, DIPEA or N-methylmorpholine, the reaction being carried out in a suitable solvent such as DCM, THF, MeCN or DMF and preferably between RT and 60° C.

The resulting intermediate of formula VIII can also be converted into a compound of formula II wherein W is —O— and R² is aryl or heteroaryl by aromatic substitution reaction with a alcohol of formula R²OH in the presence of a suitable base such as NaH, the reaction being carried out in a suitable solvent such as THF, MeCN or DMF and preferably around RT.

The resulting intermediate of formula VIII can also be converted into a compound of formula II wherein W is —S— by aromatic substitution reaction with a thiol of formula HSR² in the presence of a suitable base such as NaH, the reaction being carried out in a suitable solvent such as THF, MeCN or DMF and preferably around RT.

The intermediate of formula VIII can also be converted into a compound of formula II wherein W is a —NR³— and R² and R³ form, together with the nitrogen that carries them, an imidazolyl, pyrazolyl, 1,2,3-triazolyl or 1,2,4-triazolyl ring by aromatic substitution reaction with the appropriate heteroaryl in the presence of a suitable base such as NaH, in a suitable solvent such as THF, MeCN or DMF and preferably around RT. Alternatively, the intermediate of formula VIII can also be converted into a compound of formula II wherein W is —NR³— and R² and R³ form, together with the nitrogen that carries them a substituted 1,2,3-triazolyl ring by an aromatic substitution reaction with sodium azide, in a suitable solvent such as DMF and preferably at 0° C. The azide derivative can then be converted into the substituted 1,2,3-triazolyl ring by reaction with the appropriate alkyne, using standard methods known to the skilled artisan.

The intermediate of formula VIII can also be converted into a compound of formula II wherein W is —CH₂— or a bond, using a reagent of formula R²—CH₂—B(OR)₂ (if W is —CH₂—) or a reagent of formula R²—B(OR)₂ (if W is a bond), R being hydrogen or alkyl, using standard conditions for a Suzuki reaction, and preferably a boronic acid or ester derivative in the presence of a suitable base such as potassium phosphate or K₂CO₃, in the presence of a suitable palladium catalyst such as tetrakis(triphenylphosphine) palladium or tris(dibenzylideneacetone)dipalladium, optionally in the presence of a suitable catalyst such as triphenylphosphine, in a suitable solvent such as dioxane or a toluene/EtOH mixture, and preferably heating at about 100° C.; alternatively, the intermediate of formula VIII can also be converted into a compound of formula II wherein W is —CH₂— or a bond, using a magnesium derivative of formula R²—CH₂—MgBr (if W is —CH₂—) or R²—MgBr (if W is a bond), in the presence of a suitable iron catalyst such as iron(III) acetylacetonate, in a suitable solvent such as THF and at a temperature preferably around RT (see Furstner A. et al. in *J. Am. Chem. Soc.* (2002), 13856-13863). Besides, the intermediate of formula VIII can also be converted into a compound of formula II wherein W is a bond, using a reagent of formula R₂—SnBu₃, using standard conditions for a Stille reaction, and preferably a tributylstannane derivative in a suitable solvent such as toluene, and preferably heating at about 110° C.

The intermediate of formula VIII can furthermore be converted into a compound of formula II wherein W is —CH=CH—, using a reagent of formula R₂—CH=CH₂, using standard conditions for a Heck reaction, and preferably an alkene derivative in the presence of a suitable base such as DIPEA, in the presence of a suitable palladium catalyst such as palladium (II) acetate, in the presence of a suitable ligand such as tri-(ortho-tolyl)-phosphine, in a suitable solvent such as MeCN, and preferably heating at about 90° C.

Alternatively, the intermediate of formula VIII can also be converted into a compound of formula II wherein W is —C≡C—, using a reagent of formula R²—C≡CH, using standard conditions for a Sonogashira reaction, and preferably an alkyne derivative in the presence of a suitable base such as NEt₃, in the presence of a suitable palladium catalyst such as bis-(triphenylphosphine) palladium(II)-dichloride, in the presence of a suitable copper catalyst such as copper(I) iodide, in a suitable solvent such as DMF, and at RT. The compound of formula II wherein W is —C≡C— can also be converted into a compound of formula II wherein W is —CH=CH— or —CH₂—, reducing the triple bond to the double bond or to the single bond. The triple bond can be reduced to the double bond in the presence of a suitable catalyst such as palladium on barium sulfate, in a suitable solvent such as pyridine, at a temperature preferably around RT and under hydrogen; alternatively the triple bond can be reduced to the single bond in the presence of a suitable catalyst such as Raney Nickel, in a suitable solvent such as MeOH, at a temperature preferably around RT and under hydrogen.

Still another route towards the compounds of formula II wherein —W—R² represents methyl is shown in Scheme 2c hereafter.

Scheme 2c

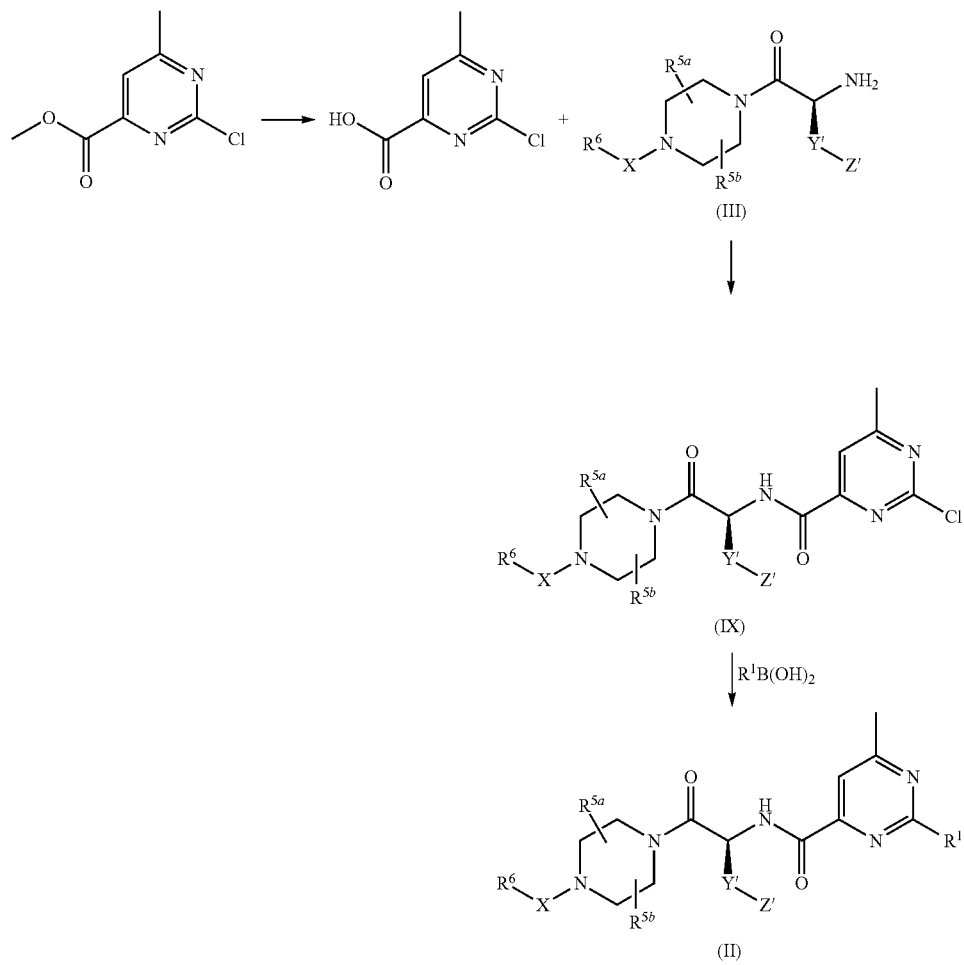

According to the route shown in Scheme 2c, the commercially available methyl-2-chloro-6-methylpyrimidine-4-carboxylate is saponified using standard conditions such as LiOH or NaOH in a suitable solvent such as water, MeOH, THF, at RT to yield the corresponding acid which is then coupled with the compound of formula III previously mentioned, using the same standard coupling methods as those described above for the coupling reaction involving compounds of formulae III and IV. The chloro derivative of formula IX can then be converted into the compound of formula II by a Suzuki reaction with a boronic acid derivative of formula $R^1B(OH)_2$, using standard conditions for such reaction (e.g. as described above for the conversion of the compound of formula VIII into the corresponding compound of formula II).

Still another route towards the compounds of formula II wherein W represents —$CH_2$— and $R^2$ represents —$NR^7R^8$, —$SR^9$ or —$SO_2R^{10}$ is shown in Scheme 2d hereafter.

Scheme 2d

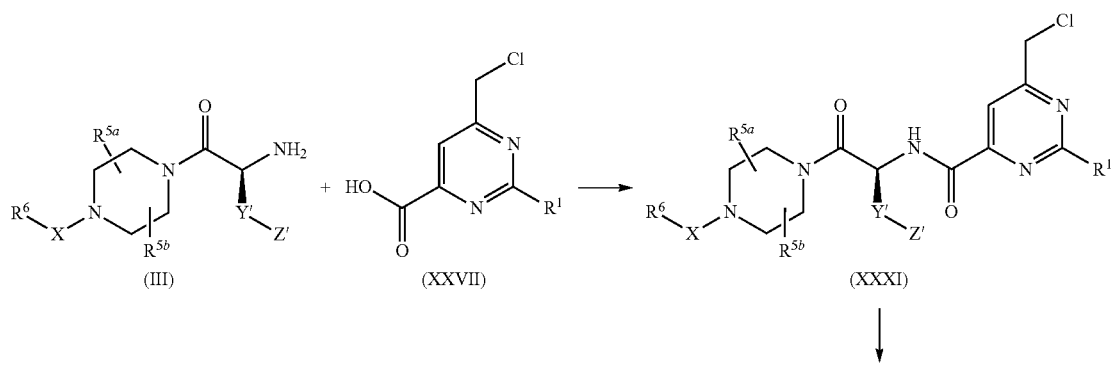

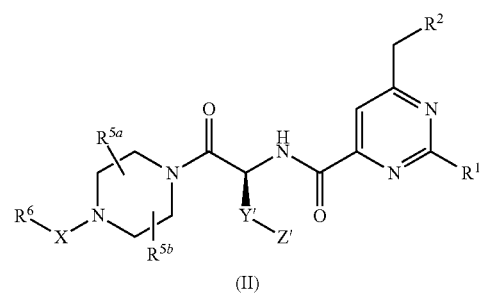

According to this route, the compounds of formula III can be coupled with the chloropyrimidine derivatives of formula XXVII using the same standard coupling methods as those described above for the coupling reaction involving compounds of formulae III and IV. The resulting intermediate of formula XXXI can then be converted into a compound of formula II wherein $R^2$ is —$NR^7R^8$ by nucleophilic substitution reaction with an amine of formula $HNR^7R^8$ using the same method as the one described above for the compounds of formula II wherein W is —$NR^3$.

The resulting intermediate of formula XXXI can also be converted into a compound of formula II wherein $R^2$ is —$SR^9$ by nucleophilic substitution reaction with a thiol of formula $HSR^9$ using the same method as the one described above for the compounds of formula II wherein W is —S—.

The resulting compound of formula II wherein W is —$CH_2$— and $R^2$ is —$SR^9$ can be converted into a compound of formula II wherein $R^2$ is —$SO_2R^{10}$ by oxidising the thiol using standard oxidising agents such as MCPBA, in a suitable solvent such as DCM, and at a temperature between 0° C. and RT.

The resulting intermediate of formula XXXI can also be converted into a compound of formula II wherein W is a bond and $R^2$ is —$CH_2OR$, R being alkyl, by nucleophilic substitution reaction with an alcohol of formula R—$CH_2OH$ in the presence of a base such as NaH, in a suitable solvent such as THF or DMF, and at a temperature preferably between 0° C. and RT.

Still another route towards the compounds of formula II wherein W is —NH— is shown in Scheme 2e hereafter.

Scheme 2e

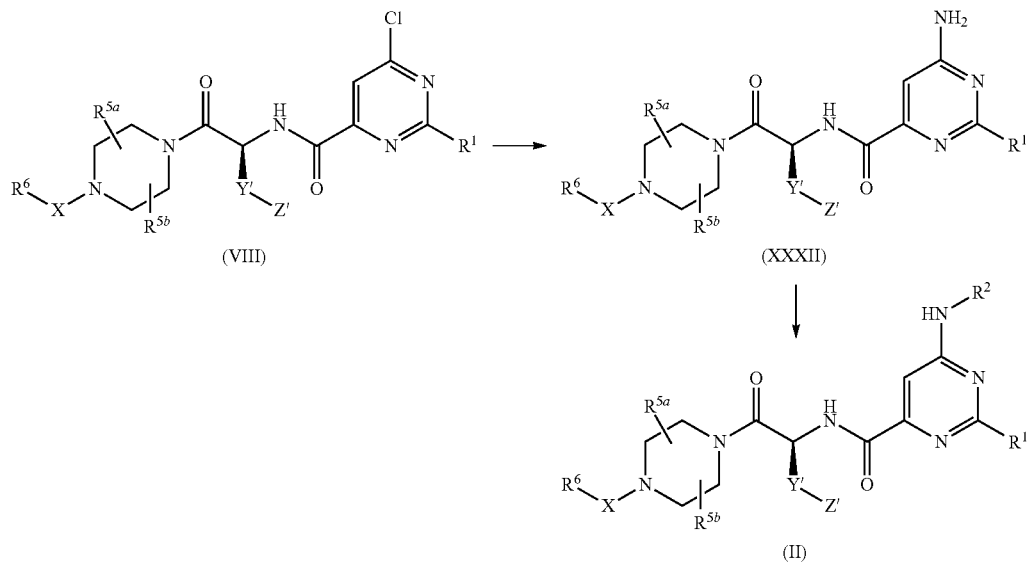

According to this further route, the compounds of formula VIII can be reacted with ammonia in MeOH, preferably heating at a temperature about 90° C. The resulting intermediate of formula XXXII can be converted into a compound of formula II wherein W is —NH— and $R^2$ represents —$COR^1$ by coupling with an acid chloride of formula $R^{11}COCl$, in a suitable solvent such as pyridine, preferably heating at a temperature about 70° C. Alternatively, the resulting intermediate of formula XXXII can be converted into a compound of formula II wherein W is —NH— and $R^2$ is —$SO_2R^{12}$ by coupling with a sulfonyl chloride of formula $R^{12}SO_2Cl$, in the presence of a suitable base such as NaH, in a suitable solvent such as THF or DMF, preferably heating at a temperature about 70° C.

In particular cases, the intermediate of formula VIII bearing a chloro as leaving group may be replaced by the intermediate of formula XXXIV bearing a phenylsulfonyl as leaving group, for further reaction (Scheme 2f). The intermediate of formula XXXIV may be synthesised using the same method as the one described above for the compounds of formula II wherein W is —S—. The thiol intermediate of formula XXXIII may then be oxidised into the intermediate XXXIV using the same method as the one described above for the compounds of formula II wherein W is —$CH_2$— and $R^2$ is —$SR^9$.

Scheme 2f

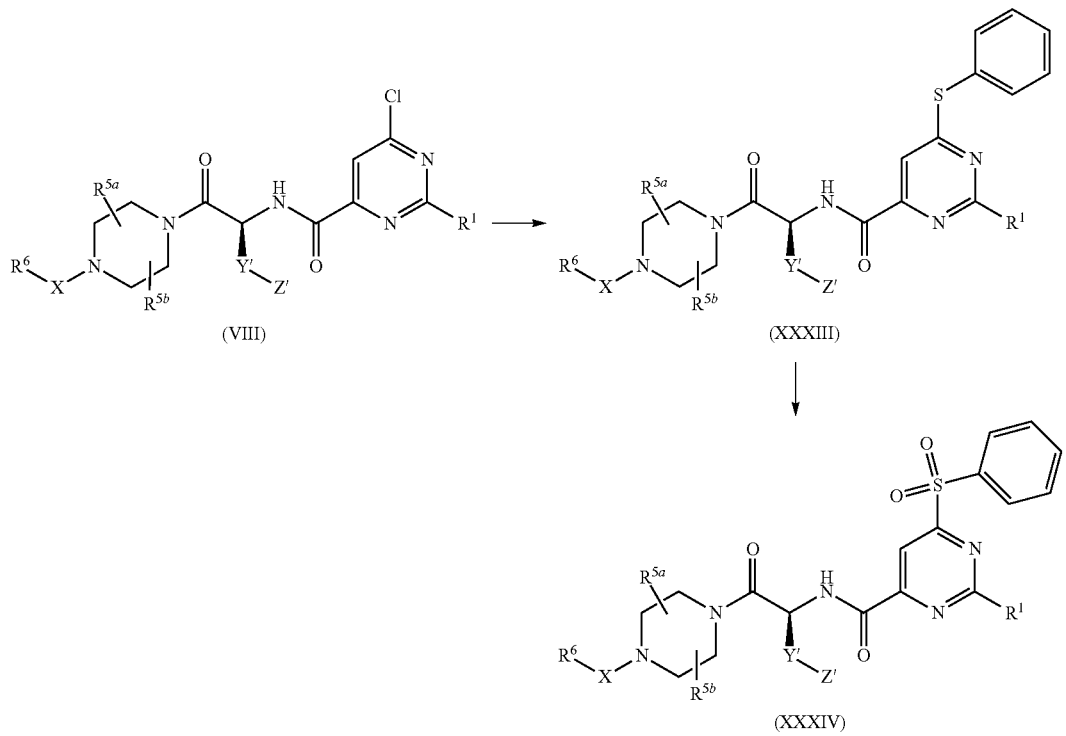

Preparation of the Compounds of Formula III

The compounds of formula III can be prepared (Scheme 3) by coupling the piperazine derivative of formula V wherein X, $R^{5a}$, $R^{5b}$ and $R^6$ have the same meanings as in formula III with a compound of formula X wherein Y' and Z' have the same meanings as in formula III, using the same standard peptide coupling methods as those described above for the coupling reaction involving compounds of formulae III and IV. The resulting intermediate of formula XI is then deprotected using standard methods (see e.g. "Protective groups in organic synthesis", Greene T. W. and Wuts P. G. M., Wiley-Interscience, 1999) to yield the compound of formula III.

-continued

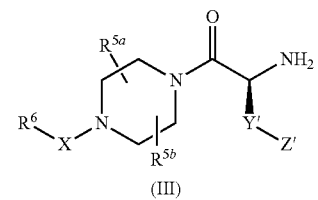

Preparation of the Compounds of Formula IV

The carboxypyrimidine derivatives of formula IV wherein W represents an oxygen atom can be prepared as summarized in Scheme 4 hereafter.

Scheme 3

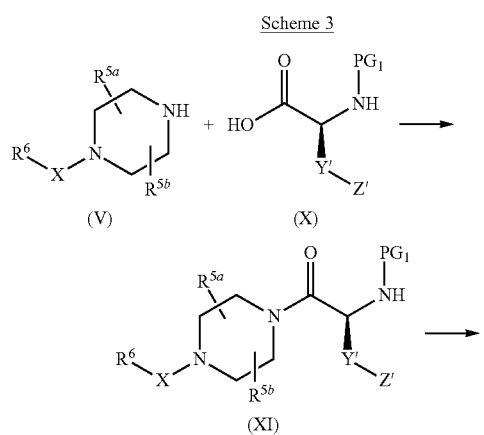

Scheme 4

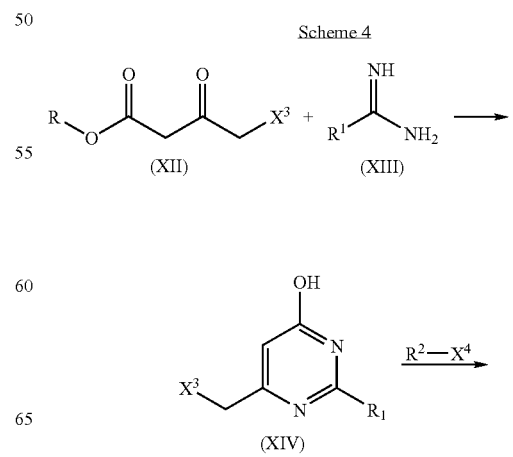

-continued

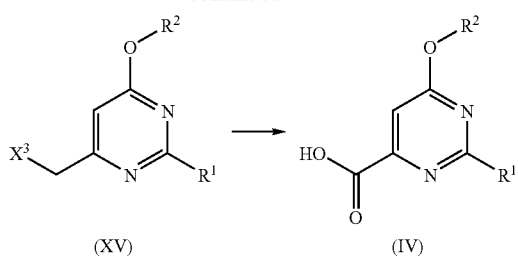

The acetoacetate derivative of formula XII (wherein $X^3$ is hydrogen or methoxy and R is alkyl) is reacted with an amidine of formula XIII, optionally in the presence of a suitable base such as sodium methoxide, in a suitable solvent such as EtOH, the mixture being preferably heated at a temperature between 60 and 90° C. The pyrimidine derivative of formula XIV thus obtained can be alkylated using an alkylating agent of formula $R^2$—$X^4$ (wherein $X^4$ could be halogen), in the presence of an appropriate base such as cesium or potassium carbonate, in a suitable solvent such as DMF, THF or MeCN and at a temperature preferably between RT and 70° C. The intermediate of formula XV thus obtained can then be oxidised using standard methods known to the skilled artisan. If $X^3$ is hydrogen (preferred case), the compound of formula XV may be oxidised by refluxing it in pyridine in the presence of selenium dioxide. If $X^3$ is methoxy, the compound of formula XV may be demethylated using standard reagents such as boron tribromide, in a suitable solvent such as DCM, preferably at a temperature between −10 and 10° C.; the intermediate alcohol thus obtained can then be oxidised, directly to the acid in one step or through the aldehyde in two steps, using standard oxidising agents such as $KMnO_4$, silver nitrate, Dess-Martin periodinane, in a suitable solvent such as water, dioxane, MeCN or DCM and at a suitable temperature. For the particular case wherein, in the compound of formula XII, —OR is —$CF_3$ and $X^3$ is hydrogen, the same synthetic route as described above in Scheme 4 may be followed, the alkylation step being omitted.

Alternatively, the carboxypyrimidine derivatives of formula IV wherein W represents an oxygen atom can be prepared as summarized in Scheme 4a hereafter:

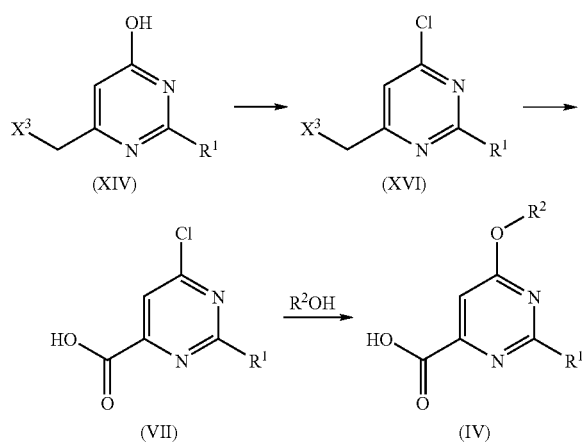

According to this alternative route, the compound of formula XIV is chlorinated to yield the compound of formula XVI using standard conditions (e.g. phosphoryl chloride at reflux). In the preferred case wherein $X^3$ is a methoxy group, the compounds of formula XV are converted into the corresponding acids of formula VII using the same procedures as those described above to convert the compounds of formula XIV into the acids of formula IV. The compound of formula VII can then be substituted (aromatic nucleophilic substitution) by an alcohol of formula $R^2OH$ in the presence of a base such as NaH, in a suitable solvent such as THF, and at a temperature preferably between 0° C. and RT.

For the particular case wherein —W—$R^2$ represents a methyl group, the preparation route summarized in Scheme 4b hereafter may be used.

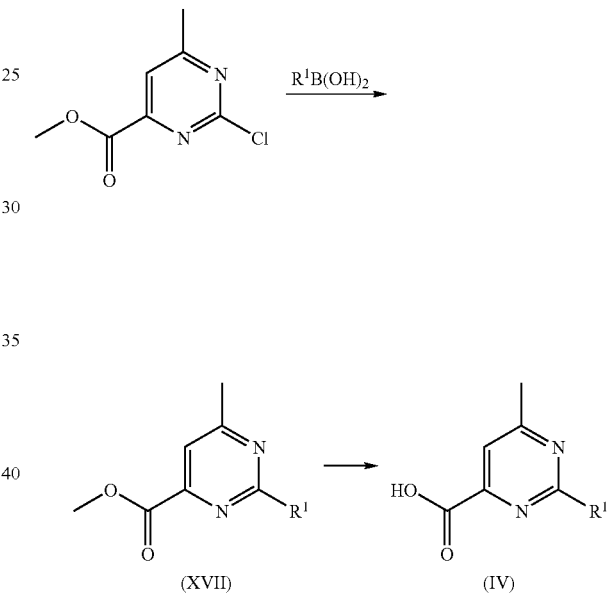

The intermediate of formula XVII may be synthesised starting from commercially available methyl-2-chloro-6-methylpyrimidine-4-carboxylate using standard Suzuki conditions, preferentially using a boronic acid derivative of formula $R_1B(OH)_2$ in the presence of a suitable base such as potassium phosphate, in the presence of a suitable palladium catalyst such as tetrakis(triphenylphosphine) palladium, in a suitable solvent such as dioxane, preferably heating at about 100° C. The compound of formula XVII can then be saponified using standard conditions such as LiOH or NaOH in a suitable solvent such as water, MeOH or THF, at a temperature preferably around RT.

The carboxypyrimidine derivatives of formula IV wherein W represents —$CH_2$— can be prepared as summarized in Scheme 4c hereafter.

Scheme 4c

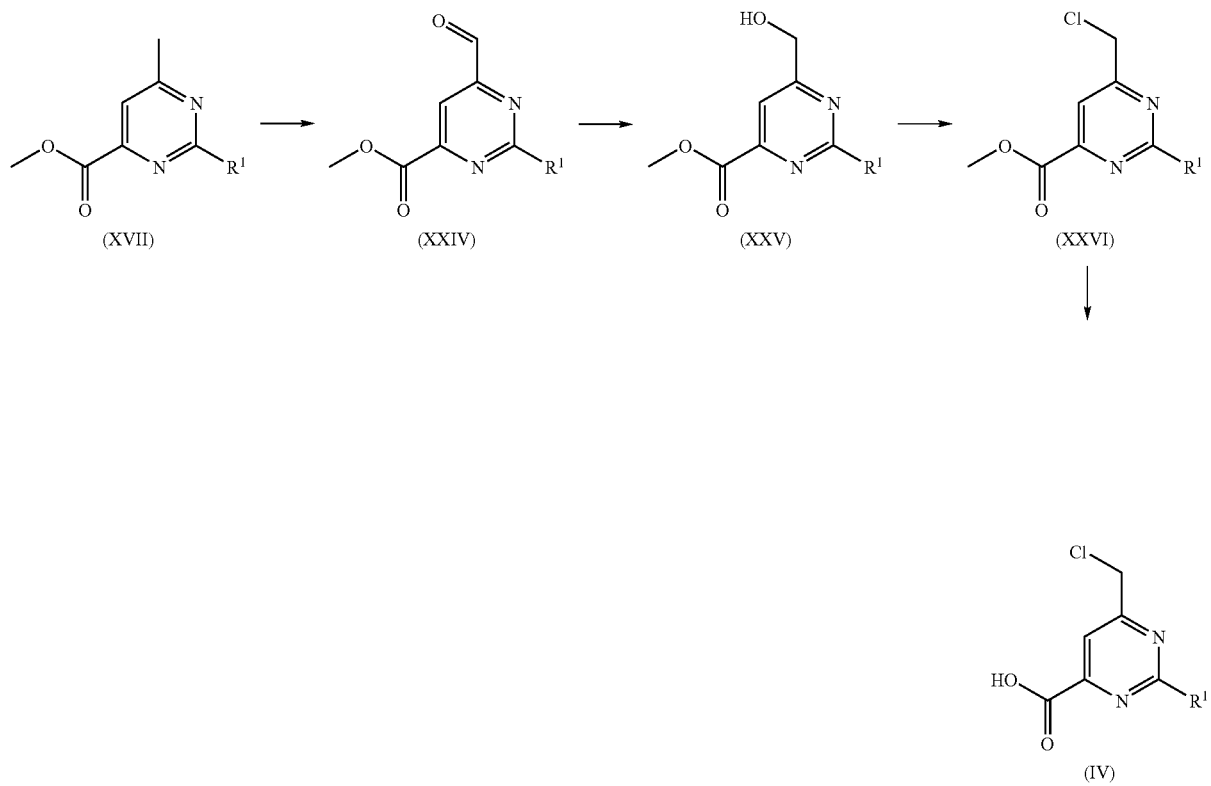

The intermediate of formula XXIV can be synthesised by oxidising intermediate XVII, for example by refluxing it in dioxane in the presence of selenium dioxide. The intermediate of formula XXIV can be reduced using standard reduction conditions such as $NaBH_4$ in a mixture of MeOH and DCM, at a temperature preferably between 0° C. and RT. The hydroxy derivative of formula XXV can then be chlorinated using conditions described above for the intermediate of formula XVI. The compound of formula XXVI can then be saponified using conditions described above for the intermediate of formula XVII.

Still another route for the preparation of the carboxypyrimidine derivatives of formula IV wherein W represents a bond and $R^2$ represents an alkyl or alkoxyalkyl group is summarized in Scheme 4d hereafter.

Scheme 4d

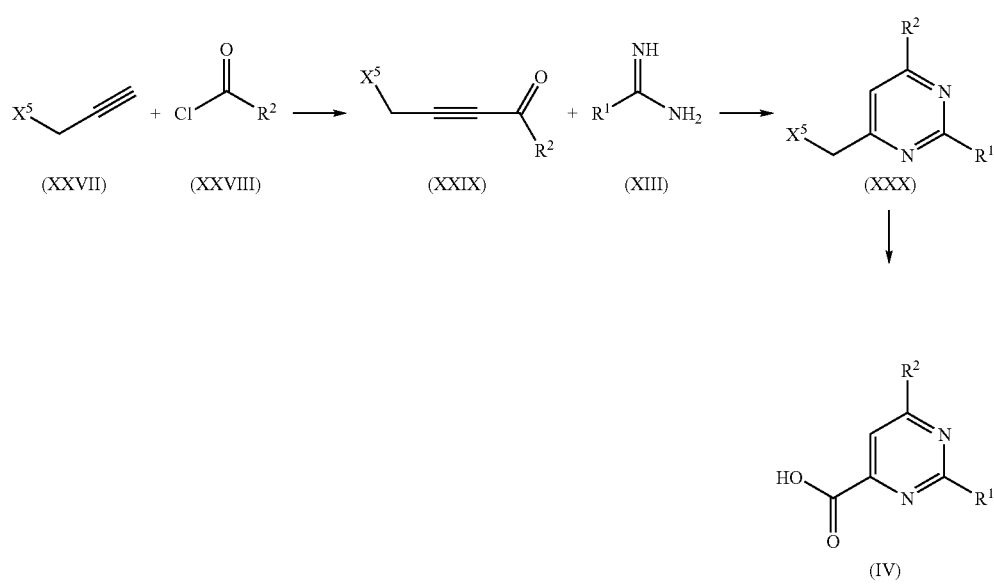

According to this further route, a monosubstituted alkyne reagent of formula XXVII wherein $X^5$ is a suitably protected oxygen can be coupled to an acid chloride reagent of formula XXVIII, in the presence of a palladium catalyst such as bis-(triphenylphosphine) palladium(II)-dichloride, in the presence of a suitable copper catalyst such as copper(I) iodide, in a suitable solvent such as $NEt_3$, preferably at RT. The intermediate of formula XXIX thus obtained can then be coupled to an amidine of formula XIII using the same conditions as the ones described above for the synthesis of the intermediate of formula XIV. The intermediate of formula XXX can then be cleaved off from the oxygen protecting group, using an appropriate method known to the skilled artisan, and the free hydroxy further oxidised, using the same method as the one described above for the oxidation of the intermediate of formula XV.

For the particular case wherein W represents a bond and $R^2$ represents —CH(OH)R or —$CH_2$—CH(OH)R, R being alkyl or phenyl, the carboxypyrimidine derivatives of formula IV can be prepared as summarized in Scheme 4e hereafter.

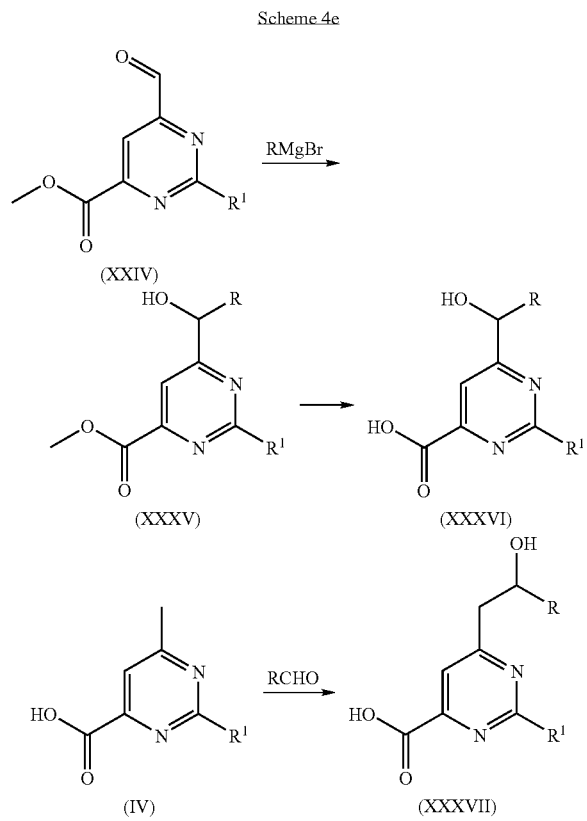

Scheme 4e (XXIV) (XXXV) (XXXVI) (IV) (XXXVII)

The intermediate of formula XXIV can be converted into the intermediate of formula XXXV by reaction with a magnesium bromide derivative of formula RMgBr, in a suitable solvent such as THF, preferably at a temperature of −78° C. The intermediate of formula XXXV can then be saponified to the intermediate of formula XXXVI using conditions described above for the intermediate of formula XVII.

Alternatively, the intermediate of formula IV can be converted into the intermediate of formula XXXVII by reaction with an aldehyde derivative of formula RCHO, in the presence of a suitable base such as sodium bis(trimethylsilyl) amide solution, in a suitable solvent such as THF, preferably at a temperature of 0° C.

Preparation of the Compounds of Formula V

Three situations have to be distinguished for the preparation of compounds of formula V, namely the case wherein $R^{5a}$ and $R^{5b}$ are both hydrogen (Scheme 5), the cases wherein one of $R^{5a}$ and $R^{5b}$ is hydrogen whereas the other is methyl (Scheme 5a) and eventually the case wherein $R^{5a}$ and $R^{5b}$ are both methyl.

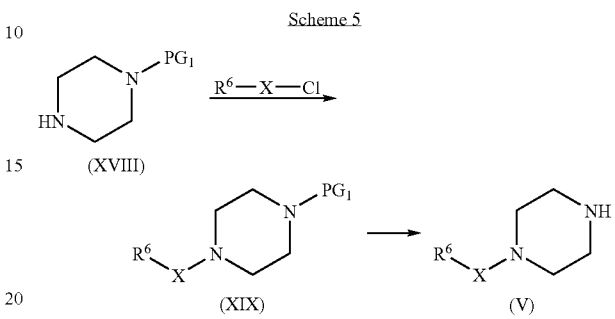

Scheme 5

(XVIII) (XIX) (V)

The compounds of formula V wherein $R^{5a}$ and $R^{5b}$ are both hydrogen can be prepared (Scheme 5) by reacting the piperazine derivative of formula XVIII (wherein $PG_1$ is a suitable protecting group for an amine function) with the chloro derivative of formula $R^6$—X—Cl (wherein X and $R^6$ have the same meaning as in formula V) in the presence of a suitable base such as $NEt_3$, DIPEA or N-methylmorpholine, in a suitable solvent such as DCM, THF or DMF, and at a temperature preferably around RT. The intermediates of formula XIX are converted into the compounds of formula V by cleaving off the protecting group $PG_1$ using standard conditions for the deprotection of amines, and preferentially palladium on carbon in a suitable solvent such as MeOH, EtOH, THF or EA, or TFA or HCl in a suitable solvent such as DCM, $Et_2O$, dioxane or EA.

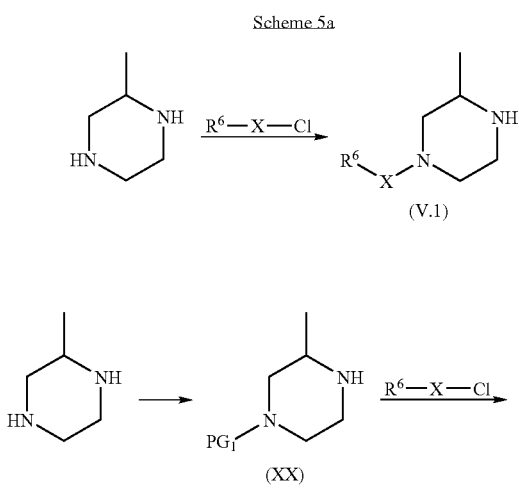

Scheme 5a (V.1)

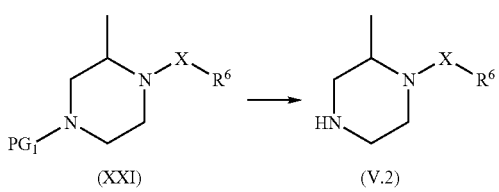

(XX) (XXI) (V.2)

The two cases wherein one of $R^{5a}$ and $R^{5b}$ is hydrogen whereas the other is methyl are represented in Scheme 5a above:

The compounds of formula V.1 can be prepared (top of Scheme 5a) by direct coupling with a chloro derivative of formula $R^6$—X—Cl.

In the case of the compounds of formula V.2 (bottom of Scheme 5a), a protection by an amine protecting group $PG_1$ is first carried out. The intermediate of formula XX thus obtained is then coupled with a chloro derivative of formula $R^6$—X—Cl and the coupling product of formula XXI is then deprotected as described above for the compounds of formula XIX.

For the particular case wherein $R^{5a}$ and $R^{5b}$ are both methyl and X is —CO—, the disubstituted piperazine may be coupled to the chloro derivative $R^6$—CO—Cl according to a procedure described by Bishop M. J., et al. in *J. Med. Chem.* (2003), 623-633, yielding the corresponding piperazine derivative of formula V.

Preparation of the Compounds of Formula VI

The substituted pyrimidine derivatives of formula VI can be prepared as summarized in Scheme 6 hereafter.

Particular embodiments of the invention are described in the following Examples, which serve to illustrate the invention in more detail without limiting its scope in any way.

EXAMPLES

Characterization Methods Used

The LC-MS retention times have been obtained using the following elution conditions:

A) LC-MS (A):

A X-terra® column (MS C18 5 μm, 4.6×50 mm) was used. The two elution solvents were as follows: solvent A=water+0.06% formic acid; solvent B=acetonitrile+0.06% formic acid. The eluent flow rate was 3 ml/min and the characteristics of the eluting mixture proportion in function of the time t from start of the elution are summarized in the table below (a linear gradient being used between two consecutive time points):

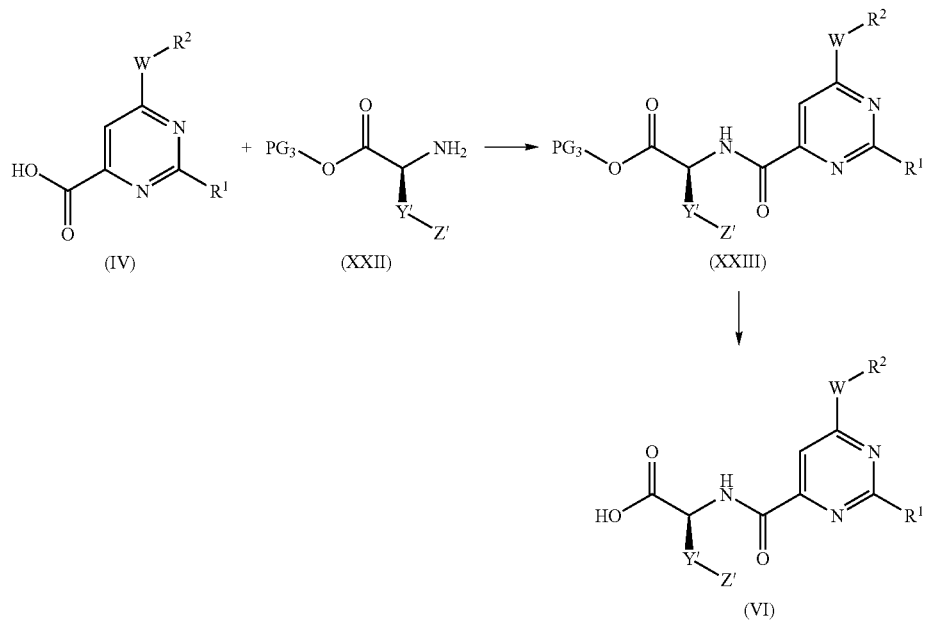

Scheme 6

The carboxypyrimidine derivative of formula IV wherein W, $R^1$ and $R^2$ have the same meanings as in formula VI, can be coupled to the amino acid of formula XXII wherein Y' and Z' have the same meaning as in formula VI and $PG_3$ is a suitable protecting group for a carboxy group, using standard coupling methods already described above for the coupling reaction regarding the compounds of formulae III and IV. The protecting group $PG_2$ of the compound of formula XXIII can then be cleaved off using standard conditions for deprotection of amino acids to yield the compound of formula VI.

Preparation of the Compounds of Formula VII

These compounds can be prepared as described above (see "Preparation of compounds of formula IV", Scheme 4a).

Preparation of the Compounds of Formula X, XII or XIII:

If not commercially available, these compounds can be prepared according to standard methods by the skilled artisan from commercially available compounds.

|  | t (min) | | | | |
| --- | --- | --- | --- | --- | --- |
|  | 0 | 1 | 1.25 | 1.30 | 1.75 |
| Solvent A (%) | 95 | 5 | 5 | 95 | 95 |
| Solvent B (%) | 5 | 95 | 95 | 5 | 5 |

B) LC-MS (B):

A Zorbax® column (Agilent SB.Aq 5 μm, 4.6×50 mm) was used. The two elution solvents were as follows: solvent A=water+0.06% formic acid; solvent B=acetonitrile+0.06% formic acid. The eluent flow rate was 3 ml/min and the characteristics of the eluting mixture proportion in function of the time t from start of the elution are summarized in the table below (a linear gradient being used between two consecutive time points):

| | t (min) | | | | |
|---|---|---|---|---|---|
| | 0 | 1 | 1.25 | 1.30 | 1.75 |
| Solvent A (%) | 95 | 5 | 5 | 95 | 95 |
| Solvent B (%) | 5 | 95 | 95 | 5 | 5 |

C) LC-MS (C):

A Zorbax® column (Agilent SB.Aq 5 μm, 4.6×50 mm) was used. The two elution solvents were as follows: solvent A=water+0.05% TFA; solvent B=acetonitrile. The eluent flow rate was 4.5 ml/min and the characteristics of the eluting mixture proportion in function of the time t from start of the elution are summarized in the table below (a linear gradient being used between two consecutive time points):

| | t (min) | | | |
|---|---|---|---|---|
| | 0 | 1 | 1.45 | 1.55 |
| Solvent A (%) | 95 | 5 | 5 | 95 |
| Solvent B (%) | 5 | 95 | 95 | 5 |

Preparative LC-MS Methods Used:

The purifications by preparative LC-MS have been performed using the conditions described hereafter.

A Zorbax® column (PrepHT SB.Aq 5 mm, 21.2×50 mm) was used. The two elution solvents were as follows: solvent A=water+0.2% formic acid; solvent B=acetonitrile+0.2% formic acid. The eluent flow rate was 95 ml/min and the characteristics of the eluting mixture proportion in function of the time t from start of the elution are summarized in the tables below (a linear gradient being used between two consecutive time points):

I) Preparative LC-MS (I):

| | t (min) | | | | | | | |
|---|---|---|---|---|---|---|---|---|
| | 0 | 0.6 | 3.3 | 3.9 | 4.5 | 5.1 | 5.2 | 6 |
| Solvent A (%) | 89.5 | 89.5 | 68.5 | 68.5 | 0 | 0 | 89.5 | 89.5 |
| Solvent B (%) | 10.5 | 10.5 | 31.5 | 31.5 | 100 | 100 | 10.5 | 10.5 |

II) Preparative LC-MS (II):

| | t (min) | | | | | | | |
|---|---|---|---|---|---|---|---|---|
| | 0 | 0.6 | 3.3 | 3.9 | 4.5 | 5.1 | 5.2 | 6 |
| Solvent A (%) | 79 | 79 | 58 | 58 | 0 | 0 | 79 | 79 |
| Solvent B (%) | 21 | 21 | 42 | 42 | 100 | 100 | 21 | 21 |

III) Preparative LC-MS (III):

| | t (min) | | | | | | | |
|---|---|---|---|---|---|---|---|---|
| | 0 | 0.6 | 3.3 | 3.9 | 4.5 | 5.1 | 5.2 | 6 |
| Solvent A (%) | 68.5 | 68.5 | 42 | 42 | 0 | 0 | 68.5 | 68.5 |
| Solvent B (%) | 31.5 | 31.5 | 58 | 58 | 100 | 100 | 31.5 | 31.5 |

IV) Preparative LC-MS (IV):

| | t (min) | | | | | | | |
|---|---|---|---|---|---|---|---|---|
| | 0 | 0.6 | 3.3 | 3.9 | 4.5 | 5.1 | 5.2 | 6 |
| Solvent A (%) | 58 | 58 | 31.6 | 31.6 | 0 | 0 | 58 | 58 |
| Solvent B (%) | 42 | 42 | 68.4 | 68.4 | 100 | 100 | 42 | 42 |

V) Preparative LC-MS (V):

| | t (min) | | | | | | | |
|---|---|---|---|---|---|---|---|---|
| | 0 | 0.6 | 3.3 | 3.9 | 4.5 | 5.1 | 5.2 | 6 |
| Solvent A (%) | 42 | 42 | 21 | 21 | 0 | 0 | 42 | 42 |
| Solvent B (%) | 58 | 58 | 79 | 79 | 100 | 100 | 58 | 58 |

Example 1

4-{(S)-4-carboxy-2-[(6-cyclopentyloxy-2-phenyl-pyrimidine-4-carbonyl)-amino]-butyryl}-piperazine-1-carboxylic acid ethyl ester 1.1. 4-((S)-2-benzyloxycarbonylamino-4-tert-butoxycarbonyl-butyryl)-piperazine-1-carboxylic acid ethyl ester Z-(L)Glu(OtBu)—OH (5 g), HOBT hydrate (2.5 g) and EDCI hydrochloride (3.1 g) were dissolved in DCM/THF (1/1, 42 ml). After 15 min stirring, 1-ethoxycarbonylpiperazine (2.6 g) was added and the stirring was continued overnight at RT. 150 ml of EA and 60 ml of a $NaHCO_3$ solution were added to the mixture and the phases were separated. The org. phase was washed with 60 ml of a 1M $NaHSO_4$ solution and 60 ml of a NaCl solution, was dried ($Na_2SO_4$) and evaporated off. After HV drying, 7 g of the desired compound were obtained.

LC-MS (A): $t_R$=1.12 min; $[M+H]^+$: 478.12.

1.2. 4-((S)-2-amino-4-tert-butoxycarbonyl-butyryl)-piperazine-1-carboxylic acid ethyl ester Intermediate 1.1 (7 g) was hydrogenated in EtOH (17 ml) with Pd/C (10%, 350 mg) for 24 h. The mixture was filtered through celite and evaporated off. HV drying afforded 5.3 g of a colourless oil.

LC-MS (A): $t_R$=0.66 min; $[M+H]^+$: 344.06.

1.3. 6-methoxymethyl-2-phenyl-pyrimidin-4-ol

Benzamidine (15 g), methyl-4-methoxyacetate (18.2 g) and sodium methoxide (30% in MeOH, 23.1 ml) were dissolved in EtOH (130 ml) and the resulting mixture was refluxed overnight. It was cooled down and filtered off. The solid was washed with EtOH. The resulting ethanolic solutions were evaporated off and the residue high-vacuum dried. 27 g of a brown-yellow solid were obtained.

LC-MS (A): $t_R$=0.79 min; $[M+H]^+$: 217.02; $[M-H]^-$: 215.08.

1.4. 4-cyclopentyloxy-6-methoxymethyl-2-phenyl-pyrimidine

To a solution of intermediate 1.3 (27 g) in DMF (780 ml) were added $Cs_2CO_3$ (203.4 g) and bromocyclopentane (66.9 ml). The mixture was heated at 60° C. for 2 h. Water (1.5 l) and EA (1.5 l) were added after cooling down. After separation, the org. phase was washed with water (1 l). The aq. phases were extracted with EA (0.5 l) and the resulting org. phases were dried over $Na_2SO_4$ and evaporated off. After HV drying, 35.5 g of the desired compound were obtained.

LC-MS (A): $t_R$=1.46 min; $[M+H]^+$: 285.13.

1.5. (6-cyclopentyloxy-2-phenyl-pyrimidin-4-yl)-methanol

A solution of intermediate 1.4 (35.5 g) in DCM (660 ml) was cooled down to 5° C. A solution of $BBr_3$ (11.8 ml) in DCM (500 ml) was added into it slowly in order that the temperature of the reaction mixture did not rise above 10° C. After 15 min at 5° C., the ice bath was removed and the mixture was stirred at RT for 1 h. The reaction mixture was cooled down and carefully quenched by adding water (1.3 l) and a 1M NaOH solution (1.7 l). The mixture was allowed to stand at RT overnight, and was diluted with DCM (600 ml). The phases were separated and the aq. phase extracted with DCM (0.5 l). The org. phases were washed with water (0.5 l), dried over $Na_2SO_4$ and evaporated off. After HV drying, 31 g of the desired compound were obtained.

LC-MS (A): $t_R$=1.24 min; $[M+H]^+$: 271.15.

1.6. 6-cyclopentyloxy-2-phenyl-pyrimidine-4-carbaldehyde

Dess Martin periodinane solution (15 wt % in DCM, 150 ml) was added to a solution of intermediate 1.5 (16.5 g) in DCM (350 ml) so that the temperature did not rise above 20° C. The mixture was stirred at RT for 2 h under argon, and was quenched by adding successively DCM (600 ml) and a 1M NaOH solution (600 ml). After 30 min stirring, the two phases were separated and the org. layer was washed with a 1M NaOH solution (100 ml), water and dried over $Na_2SO_4$. It was evaporated off and dried under HV to afford 16 g of the desired compound.

$^1$H-NMR ($CDCl_3$): 10 (s, 1H); 8.5 (d, 2H); 7.5 (m, 3H); 7.05 (s, 1H); 5.6 (m, 1H); 2.05 (m, 2H); 1.9 (m, 4H); 1.65 (m, 2H).

1.7. 6-cyclopentyloxy-2-phenyl-pyrimidine-4-carboxylic acid

Silver nitrate (23.7 g) was added to a solution of intermediate 1.6 (15 g) and NaOH (17.9 g) in EtOH (1.4 l)/water (1 l). The mixture was stirred at RT for 3 h before being acidified with a 1M HCl solution until pH 1, and silver was filtered off. The filtrate was evaporated and the resulting aq. mixture was extracted twice with DCM. The org. layers were dried over $Na_2SO_4$ and evaporated off. The residue was recrystallised in cHex. After HV drying, 12.5 g of a pale yellow powder were obtained.

LC-MS (A): $t_R$=1.26 min; $[M+H]^+$: 285.06; $[M-H]^-$: 283.26.

1.8. 4-{(S)-4-tert-butoxycarbonyl-2-[(6-cyclopentyloxy-2-phenyl-pyrimidine-4-carbonyl)-amino]-butyryl}-piperazine-1-carboxylic acid ethyl ester Intermediate 1.7 (57 mg), HOBT hydrate (40.6 mg), DIPEA (70 µl) and EDCI hydrochloride (58 mg) were dissolved in DMF (1.5 ml). After 15 min stirring, intermediate 1.2 (103 mg) was added and stirring maintained for 3 h 30 at RT. A saturated $NH_4Cl$ solution was added and the mixture extracted with EA. The org. phases were dried ($Na_2SO_4$) and evaporated off. Column chromatography (EA/Hept 1/3) of the crude yielded 40 mg of the desired compound.

LC-MS (A): $t_R$=1.47 min; $[M+H]^+$: 610.23.

1.9. 4-{(S)-4-carboxy-2-[(6-cyclopentyloxy-2-phenyl-pyrimidine-4-carbonyl)-amino]-butyryl}-piperazine-1-carboxylic acid ethyl ester 40 mg of intermediate 1.8 were dissolved in TFA/DCM (1/1, 2 ml). After 1 h stirring at RT, the solvent was removed, the residue taken up in toluene and evaporated off. After lyophilisation, 24 mg of compound were obtained.

LC-MS (A): $t_R$=1.23 min; $[M+H]^+$: 554.02; $[M-H]^-$: 552.25.

Example 2

4-{(S)-3-carboxy-2-[(6-cyclopentyloxy-2-phenyl-pyrimidine-4-carbonyl)-amino]-propionyl}-piperazine-1-carboxylic acid ethyl ester

2.1. 4-((S)-2-benzyloxycarbonylamino-3-tert-butoxycarbonyl-propionyl)-piperazine-1-carboxylic acid ethyl ester This compound was prepared using a method analogous to that of Example 1, step 1.1, Z-(L)-Asp(OtBu)—OH replacing Z-(L)Glu(OtBu)—OH.

LC-MS (B): $t_R$=0.96 min; $[M+H]^+$: 464.36.

2.2. 4-((S)-2-amino-3-tert-butoxycarbonyl-propionyl)-piperazine-1-carboxylic acid ethyl ester 4-((S)-2-benzyloxycarbonylamino-3-tert-butoxycarbonyl-propionyl)-piperazine-1-carboxylic acid ethyl ester (3.27 g) was hydrogenated in EA (25 ml) with Pd/C (10%, 327 mg) overnight. The mixture was filtered through celite and evaporated off. HV drying afforded 2.29 g of the desired compound.

$^1$H-NMR ($CDCl_3$): 4.15 (q, 2H); 4.05 (dd, 1H); 3.6 to 3.4 (m, 8H); 2.6 (dd, 1H); 2.4 (dd, 1H); 1.6 (s, 2H); 1.45 (s, 9H); 1.25 (t, 3H).

2.3. 4-{(S)-3-tert-butoxycarbonyl-2-[(6-cyclopentyloxy-2-phenyl-pyrimidine-4-carbonyl)-amino]-propionyl}-piperazine-1-carboxylic acid ethyl ester This compound was prepared using a method analogous to that of Example 1, step 1.8, intermediate 2.2 replacing intermediate 1.2, and no DIPEA being used.

LC-MS (B): $t_R$=1.26 min; $[M+H]^+$: 596.25.

2.4. 4-{(S)-3-carboxy-2-[(6-cyclopentyloxy-2-phenyl-pyrimidine-4-carbonyl)-amino]-propionyl}-piperazine-1-carboxylic acid ethyl ester This compound was prepared using a method analogous to that of Example 1, step 1.9, intermediate 2.3 replacing intermediate 1.8.

LC-MS (B): $t_R$=1.10 min; $[M+H]^+$: 540.02; $[M-H]^-$: 538.22.

Example 3

4-{(S)-5-carboxy-2-[(6-cyclopentyloxy-2-phenyl-pyrimidine-4-carbonyl)-amino]-pentanoyl}-piperazine-1-carboxylic acid ethyl ester

3.1. 4-((S)-2-benzyloxycarbonylamino-5-tert-butoxycarbonyl-pentanoyl)-piperazine-1-carboxylic acid ethyl ester This compound was prepared using a method analogous to that of Example 1, step 1.1, Z-(L)-Aad(OtBu)—OH replacing Z-(L)Glu(OtBu)—OH.

LC-MS (B): $t_R$=0.98 min; [M+H]$^+$: 492.46.

3.2. 4-((S)-2-amino-5-tert-butoxycarbonyl-pentanoyl)-piperazine-1-carboxylic acid ethyl ester This compound was prepared using a method analogous to that of Example 1, step 1.2, intermediate 3.1 replacing intermediate 1.1.

$^1$H-NMR (CDCl$_3$): 4.15 (q, 2H); 3.7 (m, 1H); 3.6 to 3.4 (m, 8H); 2.25 (m, 2H); 1.9 (br s, 2H); 1.7 (m, 3H); 1.5 (m, 1H); 1.45 (s, 9H); 1.25 (t, 3H).

3.3. 4-{(S)-5-tert-butoxycarbonyl-2-[(6-cyclopentyloxy-2-phenyl-pyrimidine-4-carbonyl)-amino]-pentanoyl}-piperazine-1-carboxylic acid ethyl ester This compound was prepared using a method analogous to that of Example 1, step 1.8, intermediate 3.2 replacing intermediate 1.2, and no DIPEA being used.

LC-MS (B): $t_R$=1.27 min; [M+H]$^+$: 624.16.

3.4. 4-{(S)-3-carboxy-2-[(6-cyclopentyloxy-2-phenyl-pyrimidine-4-carbonyl)-amino]-propionyl}-piperazine-1-carboxylic acid ethyl ester This compound was prepared using a method analogous to that of Example 1, step 1.9, intermediate 3.3 replacing intermediate 1.8.

LC-MS (B): $t_R$=1.12 min; [M+H]$^+$: 568.13; [M−H]$^-$: 566.26.

Example 4

4-{2-[(6-cyclopentyloxy-2-phenyl-pyrimidine-4-carbonyl)-amino]-acetyl}-piperazine-1-carboxylic acid ethyl ester

4.1. 4-(2-benzyloxycarbonylamino-acetyl)-piperazine-1-carboxylic acid ethyl ester Z-Gly-OH (2.09 g), HOBT hydrate (1.57 g), DIPEA (1.76 ml) and EDCI hydrochloride (1.96 g) were dissolved in DCM/DMF (60 ml/15 ml). After 15 min stirring, 1-ethoxycarbonylpiperazine (1.49 ml) was added and the stirring was continued overnight at RT. EA and a NaHCO$_3$ solution were added to the mixture and the phases were separated. The org. phase was washed with a 1M NaHSO$_4$ solution and a NaCl solution, dried (Na$_2$SO$_4$) and evaporated off. After HV drying, 3.5 g of the desired product were obtained.

LC-MS (A): $t_R$=0.91 min; [M+H]$^+$: 350.14; [M−H]$^-$: 349.11.

4.2. 4-(2-amino-acetyl)-piperazine-1-carboxylic acid ethyl ester

This compound was prepared using a method analogous to that of Example 2, step 2.2, intermediate 4.1 replacing intermediate 1.1.

LC-MS (A): $t_R$=0.70 min; [M+H]$^+$: 216.13.

4.3. 4-{2-[(6-cyclopentyloxy-2-phenyl-pyrimidine-4-carbonyl)-amino]-acetyl}-piperazine-1-carboxylic acid ethyl ester 6-cyclopentyloxy-2-phenyl-pyrimidine-4-carboxylic acid (57 mg), HOBT hydrate (34 mg) and EDCI hydrochloride (44 mg) were dissolved in DMF (1 ml). After 15 min stirring, Intermediate 4.2 (47 mg) in DMF (0.5 ml) was added and the stirring was continued for 6 h at RT. A saturated NH$_4$Cl solution was added and the mixture was extracted with EA. The org. phases were dried (Na$_2$SO$_4$) and evaporated off. Column chromatography (EA/Hept 1/2) followed by a preparative TLC (EA) of the crude offered 42 mg of the desired compound.

LC-MS (A): $t_R$=1.27 min; [M+H]$^+$: 481.99.

Example 5

4-{(S)-2-[(6-cyclopentyloxy-2-phenyl-pyrimidine-4-carbonyl)-amino]-3-methyl-butyryl}-piperazine-1-carboxylic acid ethyl ester

5.1. 4-((S)-2-tert-butoxycarbonylamino-3-methyl-butyryl)-piperazine-1-carboxylic acid ethyl ester This compound was prepared using a method analogous to that of Example 1, step 1.1, Boc-(L)-Val-OH replacing Z-(L)Glu(OtBu)—OH.

LC-MS (C): $t_R$=0.89 min; [M+H-Boc]$^+$: 258.26.

5.2. 4-((S)-2-amino-3-methyl-butyryl)-piperazine-1-carboxylic acid ethyl ester hydrochloride Intermediate 5.1 (329 mg) was dissolved in EA (5 ml) and a 4M HCl solution in dioxane was added. After completion, the solvents were removed and the residue lyophilised to give 280 mg of the desired hydrochloride salt.

LC-MS (B): $t_R$=0.57 min; [M+H]$^+$: 258.25.

5.3. 4-{(S)-2-[(6-cyclopentyloxy-2-phenyl-pyrimidine-4-carbonyl)-amino]-3-methyl-butyryl}-piperazine-1-carboxylic acid ethyl ester 6-cyclopentyloxy-2-phenyl-pyrimidine-4-carboxylic acid (20 mg), 1-HOBT hydrate (10.4 mg), DIPEA (21 µl) and EDCI hydrochloride (14.8 mg) were dissolved in THF/DCM (1/4, 5 ml). After 15 min stirring, intermediate 5.2 (20.6 mg) was added and the stirring was continued at RT until completion. DCM and a NaHCO$_3$ solution were added to the mixture and the phases were separated. The org. phase was washed with a 1M NaHSO$_4$ solution and a NaCl solution, dried (Na$_2$SO$_4$) and evaporated off. Preparative TLC (DCM/MeOH 5%) offered 20 mg of the desired compound.
LC-MS (B): t$_R$=1.25 min; [M+H]$^+$: 524.06.

Example 6

4-{(S)-3-carbamoyl-2-[(6-cyclopentyloxy-2-phenyl-pyrimidine-4-carbonyl)-amino]-propionyl}-piperazine-1-carboxylic acid ethyl ester

6.1. 4-((S)-2-benzyloxycarbonylamino-3-carbamoyl-propionyl)-piperazine-1-carboxylic acid ethyl ester This compound was prepared using a method analogous to that of Example 1, step 1.1, Z-(L)-Asn-OH replacing Z-(L)Glu(OtBu)—OH.
LC-MS (B): t$_R$=0.84 min; [M+Na]$^+$: 428.97.

6.2. 4-((S)-2-amino-3-carbamoyl-propionyl)-piperazine-1-carboxylic acid ethyl ester This compound was prepared using a method analogous to that of Example 1, step 1.2, intermediate 6.1 replacing intermediate 1.1.
$^1$H-NMR (CDCl$_3$): 7 (br s, 1H); 5.5 (br s, 1H); 4.15 (q, 2H); 3.7 to 3.4 (m, 8H); 2.45 (m, 2H); 2.1 (br s, 2H); 1.25 (t, 3H).

6.3. 4-{(S)-3-carbamoyl-2-[(6-cyclopentyloxy-2-phenyl-pyrimidine-4-carbonyl)-amino]-propionyl}-piperazine-1-carboxylic acid ethyl ester This compound was prepared using a method analogous to that of Example 5, step 5.3, intermediate 6.2 replacing intermediate 5.2.
LC-MS (B): t$_R$=1.07 min; [M+H]$^+$: 539.29; [M−H]$^-$: 537.21.

Example 7

4-{(S)-4-carbamoyl-2-[(6-cyclopentyloxy-2-phenyl-pyrimidine-4-carbonyl)-amino]-butyryl}-piperazine-1-carboxylic acid ethyl ester

7.1. 4-((S)-2-tert-butoxycarbonylamino-4-carbamoyl-butyryl)-piperazine-1-carboxylic acid ethyl ester This compound was prepared using a method analogous to that of Example 1, step 1.1, Boc-(L)-Gln-OH replacing Z-(L)Glu(OtBu)—OH.
LC-MS (C): t$_R$=0.71 min; [M+H]$^+$: 387.33.

7.2. 4-((S)-2-amino-4-carbamoyl-butyryl)-piperazine-1-carboxylic acid ethyl ester hydrochloride This compound was prepared using a method analogous to that of Example 5, step 5.2, intermediate 7.1 replacing intermediate 5.1.
LC-MS (B): t$_R$=0.46 min; [M+H]$^+$: 287.27.

7.3. 4-{(S)-4-carbamoyl-2-[(6-cyclopentyloxy-2-phenyl-pyrimidine-4-carbonyl)-amino]-butyryl}-piperazine-1-carboxylic acid ethyl ester
This compound was prepared using a method analogous to that of Example 5, step 5.3, intermediate 7.2 replacing intermediate 5.2.
LC-MS (B): t$_R$=1.10 min; [M+H]$^+$: 552.96; [M−H]$^-$: 551.28.

Example 8

4-{(S)-3-amino-2-[(6-cyclopentyloxy-2-phenyl-pyrimidine-4-carbonyl)-amino]-propionyl}-piperazine-1-carboxylic acid ethyl ester hydrochloride

8.1. 4-((S)-2-Benzyloxycarbonylamino-3-tert-butoxycarbonylamino-propionyl)-piperazine-1-carboxylic acid ethyl ester This compound was prepared using a method analogous to that of Example 1, step 1.1, Z-(L)-Dap(Boc)-OH replacing Z-(L)Glu(OtBu)—OH.
LC-MS (B): t$_R$=1.03 min; [M+H]$^+$: 479.11.

8.2. 4-((S)-2-amino-3-tert-butoxycarbonylamino-propionyl)-piperazine-1-carboxylic acid ethyl ester This compound was prepared using a method analogous to that of Example 1, step 1.2, intermediate 8.1 replacing intermediate 1.1.
$^1$H-NMR (CDCl$_3$): 5.35 (m, 1H); 4.15 (q, 2H); 3.9 (m, 1H); 3.7 (m, 1H); 3.65 to 3.5 (m, 8H); 3.05 (m, 1H); 2.05 (br s, 2H); 1.4 (s, 9H); 1.25 (t, 3H).

8.3. 4-{(S)-3-tert-butoxycarbonylamino-2-[(6-cyclopentyloxy-2-phenyl-pyrimidine-4-carbonyl)-amino]-propionyl}-piperazine-1-carboxylic acid ethyl ester This compound was prepared using a method analogous to that of Example 5, step 5.3, intermediate 8.2 replacing intermediate 5.2 and no DIPEA being used.
LC-MS (B): 1.22 min; 611.17 [M+H]$^+$; 609.26 [M−H]$^-$.

8.4. 4-{(S)-3-amino-2-[(6-cyclopentyloxy-2-phenyl-pyrimidine-4-carbonyl)-amino]-propionyl}-piperazine-1-carboxylic acid ethyl ester hydrochloride This compound was prepared using a method analogous to that of Example 5, step 5.2, intermediate 8.3 replacing intermediate 5.1.
LC-MS (B): t$_R$=0.87 min; [M+H]$^+$: 511.11.

Example 9

4-{(S)-6-amino-2-[(6-cyclopentyloxy-2-phenyl-pyrimidine-4-carbonyl)-amino]-hexanoyl}-piperazine-1-carboxylic acid ethyl ester

9.1. 4-((S)-6-benzyloxycarbonylamino-2-tert-butoxycarbonylamino-hexanoyl)-piperazine-1-carboxylic acid ethyl ester This compound was prepared using a method analogous to that of Example 1, step 1.1, Boc-(L)-Lys(Z)—OH replacing Z-(L)Glu(OtBu)—OH.
LC-MS (C): t$_R$=0.96 min; [M+H]$^+$: 520.62.

9.2. 4-((S)-2-amino-6-benzyloxycarbonylamino-hexanoyl)-piperazine-1-carboxylic acid ethyl ester hydrochloride This compound was prepared using a method analogous to that of Example 5, step 5.2, intermediate 9.1 replacing intermediate 5.1.

LC-MS (B): $t_R$=0.73 min; [M+H]$^+$: 421.33.

9.3. 4-{(S)-6-benzyloxycarbonylamino-2-[(6-cyclopentyloxy-2-phenyl-pyrimidine-4-carbonyl)-amino]-hexanoyl}-piperazine-1-carboxylic acid ethyl ester This compound was prepared using a method analogous to that of Example 5, step 5.3, intermediate 9.2 replacing intermediate 5.2.

LC-MS (B): $t_R$=1.25 min; [M+H]$^+$: 687.27; [M−H]$^-$: 685.33.

9.4. 4-{(S)-6-amino-2-[(6-cyclopentyloxy-2-phenyl-pyrimidine-4-carbonyl)-amino]-hexanoyl}-piperazine-1-carboxylic acid ethyl ester This compound was prepared using a method analogous to that of Example 1, step 1.2, intermediate 9.3 replacing intermediate 1.1.

LC-MS (B): $t_R$=0.88 min; [M+H]$^+$: 553.03.

Example 10

4-{(S)-2-[(6-cyclopentyloxy-2-phenyl-pyrimidine-4-carbonyl)-amino]-3-hydroxy-propionyl}-piperazine-1-carboxylic acid ethyl ester

10.1. 4-((S)-3-benzyloxy-2-tert-butoxycarbonylamino-propionyl)-piperazine-1-carboxylic acid ethyl ester This compound was prepared using a method analogous to that of Example 1, step 1.1, Boc-(L)-Ser(Bzl)-OH replacing Z-(L)Glu(OtBu)—OH.

LC-MS (B): $t_R$=1.07 min; [M+H−Boc]$^+$: 335.87.

10.2. 4-((S)-2-amino-3-benzyloxy-propionyl)-piperazine-1-carboxylic acid ethyl ester hydrochloride This compound was prepared using a method analogous to that of Example 5, step 5.2, intermediate 10.1 replacing intermediate 5.1.

LC-MS (B): $t_R$=0.65 min; [M+H]$^+$: 335.97.

10.3. 4-{(S)-3-benzyloxy-2-[(6-cyclopentyloxy-2-phenyl-pyrimidine-4-carbonyl)-amino]-propionyl}-piperazine-1-carboxylic acid ethyl ester This compound was prepared using a method analogous to that of Example 5, step 5.3, intermediate 10.2 replacing intermediate 5.2.

LC-MS (B): $t_R$=1.26 min; [M+H]$^+$: 602.14.

10.4. 4-{(S)-2-[(6-cyclopentyloxy-2-phenyl-pyrimidine-4-carbonyl)-amino]-3-hydroxy-propionyl}-piperazine-1-carboxylic acid ethyl ester This compound was prepared using a method analogous to that of Example 1, step 1.2, intermediate 10.3 replacing intermediate 1.1.

LC-MS (B): $t_R$=1.11 min; [M+H]$^+$: 512.11; [M−H]$^-$: 510.31.

Example 11

4-{(S)-2-[(6-cyclopentyloxy-2-phenyl-pyrimidine-4-carbonyl)-amino]-4-hydroxy-butyryl}-piperazine-1-carboxylic acid ethyl ester 4-{(S)-3-carboxy-2-[(6-cyclopentyloxy-2-phenyl-pyrimidine-4-carbonyl)-amino]-propionyl}-piperazine-1-carboxylic acid ethyl ester (64 mg) was dissolved in THF (1 ml) and cooled down to −10° C. N-methylmorpholine (13 μl) and ethyl chloroformate (11 μl) were added and, after 10 min at −10° C., sodium borohydride (13.5 mg). After 5 min, the mixture was warmed to 0° C., and MeOH was added over 10 min. Solvents were removed. The residue was taken up in EA, washed with a 1M HCl solution, water, a 10% solution of NaHCO$_3$ and a NaCl solution. The org. phase was dried (Na$_2$SO$_4$) and evaporated off. Preparative TLC (DCM/MeOH 5%) offered 31 mg of the desired compound.

LC-MS (B): $t_R$=1.14 min; [M+H]$^+$: 525.99.

The compounds of Examples 12 and 13 were prepared using a method analogous to that of Example 11, starting from 4-{(S)-4-carboxy-2-[(6-cyclopentyloxy-2-phenyl-pyrimidine-4-carbonyl)-amino]-butyryl}-piperazine-1-carboxylic acid ethyl ester and 4-{(S)-5-carboxy-2-[(6-cyclopentyloxy-2-phenyl-pyrimidine-4-carbonyl)-amino]-pentanoyl}-piperazine-1-carboxylic acid ethyl ester respectively.

Example 12

4-{(S)-2-[(6-cyclopentyloxy-2-phenyl-pyrimidine-4-carbonyl)-amino]-5-hydroxy-pentanoyl}-piperazine-1-carboxylic acid ethyl ester LC-MS (B): $t_R$=1.12 min; [M+H]$^+$: 540.09.

Example 13

4-{(S)-2-[(6-cyclopentyloxy-2-phenyl-pyrimidine-4-carbonyl)-amino]-6-hydroxy-hexanoyl}-piperazine-1-carboxylic acid ethyl ester LC-MS (B): $t_R$=1.15 min; [M+H]$^+$: 554.14; [M−H]$^-$: 552.41.

Example 14

4-{(S)-3-acetylamino-2-[(6-cyclopentyloxy-2-phenyl-pyrimidine-4-carbonyl)-amino]-propionyl}-piperazine-1-carboxylic acid ethyl ester 4-{(S)-3-amino-2-[(6-cyclopentyloxy-2-phenyl-pyrimidine-4-carbonyl)-amino]-propionyl}-piperazine-1-carboxylic acid ethyl ester hydrochloride (80 mg) was dissolved in DCM (2 ml) and NEt$_3$ (45 μl) was added. The mixture was cooled down to 0° C. and acetylchloride (11 μl) was added. After 15 min stirring it was allowed to warm to RT. After 45 min, the solution was evaporated off and the residue taken up in EA/water. The org. phase was washed with a NaCl solution, and the aq. phases were extracted back with EA. The org.

layers were dried (Na$_2$SO$_4$) and evaporated off. Preparative TLC (DCM/MeOH 10%) offered 41 mg of the desired compound.

LC-MS (B): t$_R$=1.12 min; [M+H]$^+$: 552.97; [M−H]$^-$: 551.21.

The compounds of Examples 15 and 16 were prepared using a method analogous to that of Example 14, using respectively methylchloroformate and mesylchloride instead of acetyl chloride.

Example 15

4-{(S)-2-[(6-cyclopentyloxy-2-phenyl-pyrimidine-4-carbonyl)-amino]-3-methoxycarbonylamino-propionyl}-piperazine-1-carboxylic acid ethyl ester LC-MS (B): t$_R$=1.15 min; [M+H]$^+$: 568.99; [M−H]$^-$: 567.28.

Example 16

4-{(S)-2-[(6-cyclopentyloxy-2-phenyl-pyrimidine-4-carbonyl)-amino]-3-methanesulfonylamino-propionyl}-piperazine-1-carboxylic acid ethyl ester LC-MS (B): t$_R$=1.13 min; [M+H]$^+$: 589.00; [M−H]$^-$: 587.23.

Example 17

4-{(S)-4-carboxymethoxy-2-[(6-cyclopentyloxy-2-phenyl-pyrimidine-4-carbonyl)-amino]-butyryl}-piperazine-1-carboxylic acid ethyl ester

17.1. 4-{(S)-2-[(6-cyclopentyloxy-2-phenyl-pyrimidine-4-carbonyl)-amino]-4-ethoxycarbonylmethoxy-butyryl}-piperazine-1-carboxylic acid ethyl ester 4-{(S)-2-[(6-cyclopentyloxy-2-phenyl-pyrimidine-4-carbonyl)-amino]-4-hydroxy-butyryl}-piperazine-1-carboxylic acid ethyl ester (16.8 mg) was dissolved in THF (1 ml) under argon and cooled to 0° C. A solution of potassium bis-(trimethylsilyl)-amide (0.5 M in toluene, 8 µl) and, 5 min later, ethylbromoacetate (5 µl) were added. The mixture was stirred at 0° C. for 1 h and evaporated off. The residue was taken up in water and extracted twice with EA. The org. layers were washed with water, a NaCl solution, dried (Na$_2$SO$_4$) and evaporated off to give 19 mg of the desired compound.

LC-MS (B): t$_R$=1.21 min; [M+H]$^+$: 612.38.

17.2. 4-{(S)-4-carboxymethoxy-2-[(6-cyclopentyloxy-2-phenyl-pyrimidine-4-carbonyl)-amino]-butyryl}-piperazine-1-carboxylic acid ethyl ester Intermediate 17.1 (19 mg) and LiOH (2.6 mg) were dissolved in THF/water (1/1, 1 ml). After stirring overnight at RT, the THF was evaporated off. The remaining aq. phase was extracted with EA and acidified (1M HCl solution). It was extracted with EA and the resulting org. layers were washed with a NaCl solution, dried (Na$_2$SO$_4$) and evaporated off. Purification by preparative LC-MS (IV) offered 1 mg of the desired compound.

LC-MS (B): t$_R$=1.12 min; [M+H]$^+$: 584.32; [M−H]$^-$: 582.38.

Example 18

4-[(S)-2-[(6-cyclopentyloxy-2-phenyl-pyrimidine-4-carbonyl)-amino]-3-(1H-tetrazol-5-yl)-propionyl]-piperazine-1-carboxylic acid ethyl ester

18.1. 4-{(S)-3-cyano-2-[(6-cyclopentyloxy-2-phenyl-pyrimidine-4-carbonyl)-amino]-propionyl}-piperazine-1-carboxylic acid ethyl ester 4-{(S)-3-carbamoyl-2-[(6-cyclopentyloxy-2-phenyl-pyrimidine-4-carbonyl)-amino]-propionyl}-piperazine-1-carboxylic acid ethyl ester (67 mg) was dissolved in DCM (2 ml) under argon and Burgess reagent (103 mg) was added portionwise. After 1 h stirring at RT, the solvent was removed and the crude was purified by preparative TLC (EA/Hept 1/1) to offer 35 mg of the desired compound.

LC-MS (C): t$_R$=1.06 min; [M+H]$^+$: 521.08.

18.2. 4-{(S)-2-[(6-cyclopentyloxy-2-phenyl-pyrimidine-4-carbonyl)-amino]-3-(H-tetrazol-5-yl)-propionyl}-piperazine-1-carboxylic acid ethyl ester Intermediate 18.1 (35 mg), sodium azide (52 mg) and NH$_4$Cl (43 mg) were suspended in DMF (1 ml). The mixture was heated at 150° C. in a microwave oven for 1 h. A 1M HCl solution was added to make it acidic and the mixture was extracted with EA. The org. layers were dried (Na$_2$SO$_4$) and evaporated off. Preparative TLC (DCM/MeOH 5%/AcOH 1%) offered 20 mg of the desired compound.

LC-MS (C): t$_R$=1.00 min; [M+H]$^+$: 564.06.

Example 19

4-[(S)-2-[(6-cyclopentyloxy-2-phenyl-pyrimidine-4-carbonyl)-amino]-4-(1H-tetrazol-5-yl)-butyryl]-piperazine-1-carboxylic acid ethyl ester

19.1. 4-{(S)-4-cyano-2-[(6-cyclopentyloxy-2-phenyl-pyrimidine-4-carbonyl)-amino]-butyryl}-piperazine-1-carboxylic acid ethyl ester This compound was prepared using a method analogous to that of Example 18, step 18.1, starting from 4-{(S)-4-carbamoyl-2-[(6-cyclopentyloxy-2-phenyl-pyrimidine-4-carbonyl)-amino]-butyryl}-piperazine-1-carboxylic acid ethyl ester, but no purification being performed.

LC-MS (B): t$_R$=1.18 min; [M+H]$^+$: 535.27.

19.2. 4-[(S)-2-[(6-cyclopentyloxy-2-phenyl-pyrimidine-4-carbonyl)-amino]-3-(2H-tetrazol-5-yl)-propionyl]-piperazine-1-carboxylic acid ethyl ester This compound was prepared using a method analogous to that of Example 18, step 18.2, intermediate 19.1 replacing intermediate 18.1.

LC-MS (B): t$_R$=1.12 min; [M+H]$^+$: 578.29; [M−H]$^-$: 576.28.

Example 20

4-{(S)-2-[(6-cyclopentyloxy-2-phenyl-pyrimidine-4-carbonyl)-amino]-3-[4-(1H-tetrazol-5-yl)-phenyl]-propionyl}-piperazine-1-carboxylic acid ethyl ester

20.1. 4-[(S)-2-tert-butoxyarbonylamino-3-(4-cyano-phenyl)-propionyl]-piperazine-1-carboxylic acid ethyl ester This compound was prepared using a method analogous to that of Example 1, step 1.1, Boc-(L)-4-cyano-Phe-OH replacing Z-(L)Glu(OtBu)—OH.

LC-MS (B): $t_R$=1.16 min; [M+H]$^+$: 431.09.

20.2. 4-[(S)-2-amino-3-(4-cyano-phenyl)-propionyl]-piperazine-1-carboxylic acid ethyl ester hydrochloride This compound was prepared using a method analogous to that of Example 5, step 5.2, intermediate 20.1 replacing intermediate 5.1.

LC-MS (B): $t_R$=0.68 min; [M+H]$^+$: 331.17.

20.03. 4-{(S)-3-(4-cyano-phenyl)-2-[(6-cyclopentyloxy-2-phenyl-pyrimidine-4-carbonyl)-amino]-propionyl}-piperazine-1-carboxylic acid ethyl ester This compound was prepared using a method analogous to that of Example 5, step 5.3, intermediate 20.2 replacing intermediate 5.2.

LC-MS (B): $t_R$=1.25 min; [M+H]$^+$: 597.34; [M−H]$^-$: 595.40.

20.4. 4-{(S)-2-[(6-cyclopentyloxy-2-phenyl-pyrimidine-4-carbonyl)-amino]-3-[4-(1H-tetrazol-5-yl)-phenyl]-propionyl}-piperazine-1-carboxylic acid ethyl ester This compound was prepared using a method analogous to that of Example 18, step 18.2, intermediate 20.3 replacing intermediate 18.1.

LC-MS (B): $t_R$=1.16 min; [M+H]$^+$: 640.11; [M−H]$^-$: 638.36.

Example 21

4-{(S)-3-(4-carboxy-phenyl)-2-[(6-cyclopentyloxy-2-phenyl-pyrimidine-4-carbonyl)-amino]-propionyl}-piperazine-1-carboxylic acid ethyl ester

21.1. 4-[(S)-2-tert-butoxycarbonylamino-3-(4-tert-butoxycarbonyl-phenyl)-propionyl]-piperazine-1-carboxylic acid ethyl ester This compound was prepared using a method analogous to that of Example 1, step 1.1, Boc-(L)-p-carboxy-Phe(OtBu)—OH. replacing Z-(L)Glu(OtBu)—OH.

21.2. 4-[(S)-2-amino-3-(4-carboxy-phenyl)-propionyl]-piperazine-1-carboxylic acid ethyl ester hydrochloride This compound was prepared using a method analogous to that of Example 5, step 5.2, intermediate 21.1 replacing intermediate 5.1.

LC-MS (B): $t_R$=0.63 min; [M+H]$^+$: 350.14.

21.3. 4-[(S)-2-amino-3-(4-methoxycarbonyl-phenyl)-propionyl]-piperazine-1-carboxylic acid ethyl ester hydrochloride Intermediate 21.2 (375 mg) was esterified by dissolving in a 3M solution of HCl in MeOH (3 ml). After 2 h at RT, the solvent was removed and the residue was lyophilised to give 413 mg of the desired compound.

LC-MS (B): $t_R$=0.67 min; [M+H]$^+$: 364.13.

21.4. 4-[(S)-2-[(6-cyclopentyloxy-2-phenyl-pyrimidine-4-carbonyl)-amino]-3-(4-methoxycarbonyl-phenyl)-propionyl]-piperazine-1-carboxylic acid ethyl ester This compound was prepared using a method analogous to that of Example 5, step 5.3, intermediate 21.3 replacing intermediate 5.2.

LC-MS (B): $t_R$=1.26 min; [M+H]$^+$: 630.39; [M−H]$^-$: 628.31.

21.5. 4-{(S)-3-(4-carboxy-phenyl)-2-[(6-cyclopentyloxy-2-phenyl-pyrimidine-4-carbonyl)-amino]-propionyl}-piperazine-1-carboxylic acid ethyl ester This compound was prepared using a method analogous to that of Example 17, step 17.2, intermediate 21.4 replacing intermediate 17.1. The title compound was however purified by preparative LC-MS (IV).

LC-MS (B): $t_R$=1.17 min; [M+H]$^+$: 616.16; [M−H]$^-$: 614.32.

Example 22

4-{(S)-3-(4-carboxymethoxy-phenyl)-2-[(6-cyclopentyloxy-2-phenyl-pyrimidine-4-carbonyl)-amino]-propionyl}-piperazine-1-carboxylic acid ethyl ester

22.1. 4-[(S)-3-(4-benzyloxy-phenyl)-2-tert-butoxycarbonylamino-propionyl]-piperazine-1-carboxylic acid ethyl ester This compound was prepared using a method analogous to that of Example 1, step 1.1, Boc-(L)-Tyr(Bzl)-OH replacing Z-(L)Glu(OtBu)—OH.

LC-MS (C): $t_R$=1.04 min; [M+H]$^+$: 512.36.

22.2. 4-[(S)-2-amino-3-(4-benzyloxy-phenyl)-propionyl]-piperazine-1-carboxylic acid ethyl ester hydrochloride This compound was prepared using a method analogous to that of Example 5, step 5.2, intermediate 22.1 replacing intermediate 5.1.

LC-MS (B): $t_R$=0.77 min; [M+H]$^+$: 412.31.

22.3. 4-{(S)-3-(4-benzyloxy-phenyl)-2-[(6-cyclopentyloxy-2-phenyl-pyrimidine-4-carbonyl)-amino]-propionyl}-piperazine-1-carboxylic acid ethyl ester This compound was prepared using a method analogous to that of Example 5, step 5.3, intermediate 22.2 replacing intermediate 5.2.

LC-MS (B): $t_R$=1.32 min; [M+H]$^+$: 678.18.

22.4. 4-[(S)-2-[(6-cyclopentyloxy-2-phenyl-pyrimidine-4-carbonyl)-amino]-3-(4-hydroxy-phenyl)-propionyl]-piperazine-1-carboxylic acid ethyl ester This compound was prepared using a method analogous to that of Example 1, step 1.2, intermediate 22.3 replacing intermediate 1.1.

LC-MS (B): $t_R$=1.18 min; [M+H]$^+$: 588.20; [M−H]$^-$: 586.13.

22.5. 4-[(S)-2-[(6-cyclopentyloxy-2-phenyl-pyrimidine-4-carbonyl)-amino]-3-(4-methoxycarbonyl-methoxy-phenyl)-propionyl]-piperazine-1-carboxylic acid ethyl ester Intermediate 22.4 (41 mg) and cesium carbonate (47 mg) were dissolved in DMF (1 ml), and methylbromoacetate (12 ml) was added. After stirring at RT overnight, 5 ml of water were added and the mixture was extracted with EA. The org. layers were washed with water, with a NaCl solution, dried (Na$_2$SO$_4$) and evaporated off to give 38 mg of the desired product.

LC-MS (B): $t_R$=1.24 min; [M+H]$^+$: 660.18.

22.6. 4-{(S)-3-(4-carboxymethoxy-phenyl)-2-[(6-cyclopentyloxy-2-phenyl-pyrimidine-4-carbonyl)-amino]-propionyl}-piperazine-1-carboxylic acid ethyl ester This compound was prepared using a method analogous to that of Example 17, step 17.2, intermediate 22.5 replacing intermediate 17.1. The title compound was however purified by preparative LC-MS (V).

LC-MS (B): $t_R$=1.16 min; [M+H]$^+$: 646.40; [M−H]$^-$: 644.39.

Example 23

4-{(S)-4-carboxy-2-[(6-carboxymethoxy-2-phenyl-pyrimidine-4-carbonyl)-amino]-butyryl}-piperazine-1-carboxylic acid ethyl ester

23.1. 6-methyl-2-phenyl-pyrimidin-4-ol

Benzamidine hydrochloride (1.56 g), ethyl acetoacetate (1.26 ml) and sodium methoxide (30% in MeOH, 3.7 ml) were dissolved in EtOH (10 ml) and the resulting mixture was refluxed overnight. It was cooled down and the white suspension was filtered off. The solid was washed with water and high-vacuum dried. 1.83 g of a white solid were obtained.

LC-MS (A): $t_R$=0.75 min; 187.07 [M+H]$^+$; 185.20 [M−H]$^-$.

23.2. 4-chloro-6-methyl-2-phenyl-pyrimidine

Phosphorous pentoxide (8 ml) was slowly added to a stirred powder of intermediate 23.1 (935 mg). The solution was refluxed for 2 h, cooled down, and carefully added onto crushed ice. After 30 min stirring, the obtained suspension was extracted with EA twice. The org. layers were washed twice with a NaHCO$_3$ solution, dried (Na$_2$SO$_4$) and evaporated off. After HV, 960 mg of the desired compound were obtained.

LC-MS (A): $t_R$=1.28 min; [M+H]$^+$: 204.96; [M+H]$^-$: 203.21.

23.3. (6-methyl-2-phenyl-pyrimidin-4-yloxy)-acetic acid methyl ester

Methyl glycolate (188 μl) was added to a suspension of NaH (100 mg) in anhydrous DMF (3 ml). After 30 min stirring, intermediate 23.2 (510 mg) dissolved in DMF (1 ml) was added. The mixture was stirred overnight. A NH$_4$Cl solution was added and the resulting mixture was extracted with EA. The org. phases were dried (Na$_2$SO$_4$) and evaporated off. The crude (580 mg, 85% pure) was directly used in the next step.

23.4. 6-methoxycarbonylmethoxy-2-phenyl-pyrimidine-4-carboxylic acid

A mixture of selenium dioxide (290 mg) and intermediate 23.3 (458 mg) in pyridine (18 ml) was refluxed for 64 h. After cooling down, a solution of citric acid was added until pH 3-4. The mixture was extracted with EA. The org. layers were washed with a solution of citric acid, dried (Na$_2$SO$_4$) and evaporated off. The NMR analysis indicated that the desired was around 50% pure. It was nonetheless used directly into the next step.

LC-MS (A): $t_R$=0.99 min; [M+H]$^+$: 289.01; [M−H]$^-$: 287.00.

23.5. 4-{(S)-4-tert-butoxycarbonyl-2-[(6-methoxycarbonylmethoxy-2-phenyl-pyrimidine-4-carbonyl)-amino]-butyryl}-piperazine-1-carboxylic acid ethyl ester Intermediate 23.3 (115 mg, 50% pure), HOBT hydrate (40 mg) and EDCI hydrochloride (58 mg) were dissolved in DMF (1 ml) at 0° C. After 15 min stirring at 0° C., 4-((S)-2-amino-4-tert-butoxycarbonyl-butyryl)-piperazine-1-carboxylic acid ethyl ester (103 mg) in DMF (0.5 ml) was added and the stirring was continued for 16 h at RT. A saturated NH$_4$Cl solution was added and the mixture was extracted with EA. The org. phases were dried (Na$_2$SO$_4$) and evaporated off. Column chromatography (EA/Hept 1/4 to 1/1) afforded 37 mg of the desired compound.

LC-MS (A): $t_R$=1.23 min; [M+H]$^+$: 614.19.

23.6. 4-{(S)-4-tert-butoxycarbonyl-2-[(6-carboxymethoxy-2-phenyl-pyrimidine-4-carbonyl)-amino]-butyryl}-piperazine-1-carboxylic acid ethyl ester This compound was prepared using a method analogous to that of Example 17, step 17.2, intermediate 23.5 replacing intermediate 17.1 but no purification being performed.

LC-MS (A): $t_R$=1.15 min; [M+H]$^+$: 600.13; [M−H]$^-$: 598.26.

23.7. 4-{(S)-4-carboxy-2-[(6-carboxymethoxy-2-phenyl-pyrimidine-4-carbonyl)-amino]-butyryl}-piperazine-1-carboxylic acid ethyl ester This compound was prepared using a method analogous to that of Example 1, step 1.9, intermediate 23.6 replacing intermediate 1.8.

LC-MS (A): $t_R$=0.94 min; $[M+H]^+$: 544.03; $[M-H]^-$: 542.09.

Example 24

4-{(S)-4-carboxy-2-[(2-phenyl-6-propoxy-pyrimidine-4-carbonyl)-amino]-butyryl}-piperazine-1-carboxylic acid ethyl ester

24.1. 4-chloro-6-methoxymethyl-2-phenyl-pyrimidine

Phosphorous pentoxide (20 ml) was slowly added to a stirred powder of 6-methoxymethyl-2-phenyl-pyrimidin-4-ol (4.3 g). The solution was refluxed for 1 h 30, cooled down, and carefully added onto crushed ice. After 30 min stirring, the obtained suspension was extracted twice with EA. The org. layers were washed twice with a $NaHCO_3$ solution, dried ($Na_2SO_4$) and evaporated off. After high vaccuum, 4.17 g of the desired compound were obtained.

LC-MS (A): $t_R$=1.28 min; $[M+H]^+$: 237.03; $[M-H]^-$: 235.09.

24.2. (6-chloro-2-phenyl-pyrimidin-4-yl)-methanol

A solution of $BBr_3$ (1.83 ml) in DCM (25 ml) was syringed into a solution of intermediate 24.1 (4.17 g) in DCM (90 ml) under argon at 0° C. After 30 min at 0° C., the reaction was complete. It was quenched by the addition of $Et_2O$ (100 ml), water (100 ml) and 1M NaOH solution (100 ml). After 1 h stirring at RT, the mixture was extracted with DCM, and the org. layers were washed with water, dried ($Na_2SO_4$) and evaporated. The resulting oil crushed out, and the solid obtained was washed with Hept. After HV drying, 3.29 g of a beige powder were obtained.

LC-MS (A): $t_R$=1.05 min; $[M+H]^+$: 223.12; $[M-H]^-$: 221.11.

24.3. 6-chloro-2-phenyl-pyrimidine-4-carboxylic acid

Intermediate 24.2 (2.2 g) was dissolved in dioxane (50 ml) and a solution of NaOH (398 mg) in water (350 ml) was added, followed by $KMnO_4$ (4.7 g). The mixture was stirred at RT for 2 h 30. 2M aq. HCl solution (50 ml) was added to the solution. It was stirred for 1 h and filtered off. The solution was extracted twice with EA. The org. phases were dried ($Na_2SO_4$) and evaporated. After HV drying, 2.24 g of a pale yellow powder were obtained.

LC-MS (A): $t_R$=1.10 min; $[M+H]^+$: 235.02; $[M+H]^+$: 237.03; $[M-H]^-$: 233.08.

24.4. 2-phenyl-6-propoxy-pyrimidine-4-carboxylic acid 1-propanol (46 µl) was added to a suspension of NaH (24 mg) in anhydrous THF (1 ml) at 0° C. After 30 min stirring at 0° C., intermediate 24.3 (47 mg) dissolved in THF (0.6 ml) was added. The mixture was allowed to warm to RT and stirred overnight. A 1M solution of HCl was added and the resulting mixture was extracted with EA. The org. phases were dried ($Na_2SO_4$) and evaporated off. The crude was directly used in the next step.

LC-MS (A): $t_R$=1.18 min; $[M+H]^+$: 258.75; $[M-H]^-$: 257.07.

24.5. 4-{(S)-4-tert-butoxycarbonyl-2-[(2-phenyl-6-propoxy-pyrimidine-4-carbonyl)-amino]-butyryl}-piperazine-1-carboxylic acid ethyl ester This compound was prepared using a method analogous to that of Example 1, step 1.8, intermediate 24.4 replacing intermediate 1.7, the reaction being left overnight, and no purification being carried out.

LC-MS (A): $t_R$=1.40 min; $[M+H]^+$: 584.14.

24.6. 4-{(S)-4-carboxy-2-[(2-phenyl-6-propoxy-pyrimidine-4-carbonyl)-amino]-butyryl}-piperazine-1-carboxylic acid ethyl ester This compound was prepared using a method analogous to that of Example 1, step 1.9, intermediate 24.5 replacing intermediate 1.8.

LC-MS (A): $t_R$=1.16 min; $[M+H]^+$: 528.08; $[M-H]^-$: 526.21.

Example 25

4-((S)-4-carboxy-2-{[6-(2-hydroxy-ethoxy)-2-phenyl-pyrimidine-4-carbonyl]-amino}-butyryl)-piperazine-1-carboxylic acid ethyl ester

25.1. 6-(2-hydroxy-ethoxy)-2-phenyl-pyrimidine-4-carboxylic acid

Ethylene glycol (34 µl) was added to a suspension of sodium hydride (24 mg) in anhydrous THF (2 ml) at 0° C. After 30 min stirring at 0° C., 6-chloro-2-phenyl-pyrimidine-4-carboxylic acid (47 mg) dissolved in THF (1.2 ml) was added. The mixture was allowed to warm to RT and stirred overnight. A 1M HCl solution was added and the resulting mixture was extracted with EA. The org. phases were dried ($Na_2SO_4$) and evaporated off.

LC-MS (A): $t_R$=0.84 min; $[M+H]^+$: 260.87; $[M-H]^-$: 259.14.

25.2. 4-((S)-4-tert-butoxycarbonyl-2-{[6-(2-hydroxy-ethoxy)-2-phenyl-pyrimidine-4-carbonyl]-amino}-butyryl)-piperazine-1-carboxylic acid ethyl ester This compound was prepared using a method analogous to that of Example 1, step 1.8, intermediate 25.1 replacing intermediate 1.7.

LC-MS (A): $t_R$=1.14 min; $[M+H]^+$: 586.20; $[M-H]^-$: 584.26.

25.3. 4-((S)-4-carboxy-2-{[6-(2-hydroxy-ethoxy)-2-phenyl-pyrimidine-4 carbonyl]-amino}-butyryl)-piperazine-1-carboxylic acid ethyl ester This compound was prepared using a method analogous to that of Example 1, step 1.9, intermediate 25.2 replacing intermediate 1.8 and the title compound being purified by preparative LC-MS (IV).

LC-MS (A): $t_R$=0.92 min; $[M+H]^+$: 529.91; $[M-H]^-$: 528.22.

Example 26

4-{(S)-2-[(6-benzyloxy-2-phenyl-pyrimidine-4-carbonyl)-amino]-4-carboxy-butyryl}-piperazine-1-carboxylic acid ethyl ester

26.1. 6-benzyloxy-2-phenyl-pyrimidine-4-carboxylic acid

This compound was prepared using a method analogous to that of Example 25, step 25.1, benzyl alcohol replacing ethylene glycol.
LC-MS (A): $t_R$=1.22 min; [M+H]$^+$: 306.74; [M–H]$^-$: 305.12.

262. 4-{(S)-2-[(6-benzyloxy-2-phenyl-pyrimidine-4-carbonyl)-amino]-4-tert-butoxycarbonyl-butyryl}-piperazine-1-carboxylic acid ethyl ester This compound was prepared using a method analogous to that of Example 1, step 1.8, intermediate 26.1 replacing intermediate 1.7.
LC-MS (A): $t_R$=1.39 min; [M+H]$^+$: 632.19.

26.3. 4-{(S)-2-[(6-benzyloxy-2-phenyl-pyrimidine-4-carbonyl)-amino]-4 carboxy-butyryl}-piperazine-1-carboxylic acid ethyl ester This compound was prepared using a method analogous to that of Example 1, step 1.9, intermediate 26.2 replacing intermediate 1.8 and the title compound being purified by preparative LC-MS (IV).
LC-MS (A): $t_R$=1.19 min; [M+H]$^+$: 576.29; [M–H]$^-$: 574.35.

Example 27

4-{(S)-4-carboxy-2-[(6-cyclopropylmethoxy-2-phenyl-pyrimidine-4-carbonyl)-amino]-butyryl}-piperazine-1-carboxylic acid ethyl ester

27.1. 6-cyclopropylmethoxy-2-phenyl-pyrimidine-4-carboxylic acid

This compound was prepared using a method analogous to that of Example 25, step 25.1, cyclopropylmethanol replacing ethylene glycol.
LC-MS (A): $t_R$=1.17 min; [M+H]$^+$: 270.89; [M–H]$^-$: 269.10.

27.2. 4-{(S)-4-tert-butoxycarbonyl-2-[(6-cyclopropylmethoxy-2-phenyl-pyrimidine-4-carbonyl)-amino]-butyryl}-piperazine-1-carboxylic acid ethyl ester This compound was prepared using a method analogous to that of Example 1, step 1.8, intermediate 27.1 replacing intermediate 1.7.
LC-MS (A): $t_R$=1.39 min; [M+H]$^+$: 596.24.

27.3. 4-{(S)-4-carboxy-2-[(6-cyclopropylmethoxy-2-phenyl-pyrimidine-4 carbonyl)-amino]-butyryl}-piperazine-1-carboxylic acid ethyl ester This compound was prepared using a method analogous to that of Example 1, step 1.9, intermediate 27.2 replacing intermediate 1.8 and the title compound being purified by preparative LC-MS (III).
LC-MS (A): $t_R$=1.19 min; [M+H]$^+$: 540.27; [M–H]$^-$: 538.33.

Example 28

4-{(S)-4-carboxy-2-[(6-cyclohexyloxy-2-phenyl-pyrimidine-4-carbonyl)-amino]-butyryl}-piperazine-1-carboxylic acid ethyl ester

28.1. 6-cyclohexyloxy-2-phenyl-pyrimidine-4-carboxylic acid

This compound was prepared using a method analogous to that of Example 25, step 25.1, cyclohexyl alcohol replacing ethylene glycol.
LC-MS (A): $t_R$=1.32 min; [M+H]$^+$: 298.78; [M–H]$^-$: 297.17.

28.2. 4-{(S)-4-tert-butoxycarbonyl-2-[(6-cyclohexyloxy-2-phenyl-pyrimidine-4-carbonyl)-amino]-butyryl}-piperazine-1-carboxylic acid ethyl ester This compound was prepared using a method analogous to that of Example 1, step 1.8, intermediate 28.1 replacing intermediate 1.7.
LC-MS (A): $t_R$=1.54 min; [M+H]$^+$: 624.11.

28.3. 4-{(S)-4-carboxy-2-[(6-cyclohexyloxy-2-phenyl-pyrimidine-4 carbonyl)-amino]-butyryl}-piperazine-1-carboxylic acid ethyl ester This compound was prepared using a method analogous to that of Example 1, step 1.9, intermediate 28.2 replacing intermediate 1.8 and the title compound being purified by preparative LC-MS (IV).
LC-MS (A): $t_R$=1.27 min; [M+H]$^+$: 568.32; [M–H]$^-$: 566.38.

Example 29

4-{(S)-4-carboxy-2-[(6-isopropoxy-2-phenyl-pyrimidine-4-carbonyl)-amino]-butyryl}-piperazine-1-carboxylic acid ethyl ester

29.1. 6-isopropoxy-2-phenyl-pyrimidine-4-carboxylic acid

This compound was prepared using a method analogous to that of Example 25, step 25.1, isopropyl alcohol replacing ethylene glycol.
LC-MS (A): $t_R$=1.17 min; [M+H]$^+$: 258.93; [M–H]$^-$: 257.14.

29.2. 4-{(S)-4-tert-butoxycarbonyl-2-[(6-isopropoxy-2-phenyl-pyrimidine-4-carbonyl)-amino]-butyryl}-piperazine-1-carboxylic acid ethyl ester This compound was prepared using a method analogous to that of Example 1, step 1.8, intermediate 29.1 replacing intermediate 1.7.
LC-MS (A): $t_R$=1.39 min; [M+H]$^+$: 584.06.

29.93. 4-{(S)-4-carboxy-2-[(6-isopropoxy-2-phenyl-pyrimidine-4-carbonyl)-amino]-butyryl}-piperazine-1-carboxylic acid ethyl ester This compound was prepared using a method analogous to that of Example 1, step 1.9, intermediate 29.2 replacing intermediate 1.8.

LC-MS (A): $t_R$=1.15 min; [M+H]$^+$: 528.08; [M−H]$^-$: 526.21.

Example 30

4-{(S)-4-carboxy-2-[(6-methoxy-2-phenyl-pyrimidine-4-carbonyl)-amino]-butyryl}-piperazine-1-carboxylic acid ethyl ester 30.1. 6-methoxy-2-phenyl-pyrimidine-4-carboxylic acid This compound was prepared using a method analogous to that of Example 25, step 25.1, MeOH replacing ethylene glycol.
LC-MS (A): $t_R$=1.03 min; [M+H]$^+$: 231.08; [M−H]$^-$: 229.49.

30.2. 4-{(S)-4-tert-butoxycarbonyl-2-[(6-methoxy-2-phenyl-pyrimidine-4-carbonyl)-amino]-butyryl}-piperazine-1-carboxylic acid ethyl ester This compound was prepared using a method analogous to that of Example 1, step 1.8, intermediate 30.1 replacing intermediate 1.7.
LC-MS (A): $t_R$=1.30 min; [M+H]$^+$: 556.26.

30.3. 4-{(S)-4-carboxy-2-[(6-methoxy-2-phenyl-pyrimidine-4-carbonyl)-amino]-butyryl}-piperazine-1-carboxylic acid ethyl ester This compound was prepared using a method analogous to that of Example 1, step 1.9, intermediate 30.2 replacing intermediate 1.8.
LC-MS (A): $t_R$=1.37 min; [M+H]$^+$: 500.04; [M−H]$^-$: 498.14.

Example 31

4-{3-(3-carboxymethoxy-phenyl)-2-[(6-cyclopentyloxy-2-phenyl-pyrimidine-4-carbonyl)-amino]-propionyl}-piperazine-1-carboxylic acid ethyl ester 31.1. 2-amino-3-(3-hydroxy-phenyl)-propionic acid methyl ester DL-m-Tyrosine (1 g) was stirred in a 3M solution of HCl in MeOH (10 ml) for 2 h at RT The solvent was removed and HV drying afforded 1.43 g of the desired compound.
LC-MS (B): $t_R$=0.49 min; [M−H]$^-$: 230.32.

31.2. 2-tert-butoxycarbonylamino-3-(3-hydroxy-phenyl)-propionic acid methyl ester Intermediate 31.1 (1.43 g) and NEt$_3$ (1.72 ml) were dissolved in THF (10 ml) and Boc anhydride (1.35 g) was added. The mixture was stirred overnight at RT. 20 ml of DCM were added and the mixture was washed with water and a NaCl solution. The aq. phase was extracted back with DCM, the org. layers were dried (Na$_2$SO$_4$) and evaporated off to give 1.77 g of the desired compound.
LC-MS (B): $t_R$=0.96 min; [M−H]$^-$: 294.20.

31.3. 3-(3-benzyloxy-phenyl)-2-tert-butoxycarbonylamino-propionic acid methyl ester This compound was prepared using a method analogous to that of Example 22, step 22.5, intermediate 31.2 replacing intermediate 22.4 and benzyl bromide replacing methylbromoacetate.
LC-MS (B): $t_R$=1.17 min; [M+H−Boc]$^+$: 286.10.

31.4. 3-(3-benzyloxy-phenyl)-2-tert-butoxycarbonylamino-propionic acid

This compound was prepared using a method analogous to that of Example 17, step 17.2, intermediate 31.3 replacing intermediate 17.1 but no purification being performed.
LC-MS (C): $t_R$=0.98 min.

31.5. 4-[3-(3-benzyloxy-phenyl)-2-tert-butoxycarbonylamino-propionyl]-piperazine-1-carboxylic acid ethyl ester This compound was prepared using a method analogous to that of Example 1, step 1.1, 3-(3-benzyloxy-phenyl)-2-tert-butoxycarbonylamino-propionic acid replacing Z-(L)Glu(OtBu)—OH.
LC-MS (B): $t_R$=1.15 min; [M+H+Na]$^+$: 534.16.

31.6. 4-[2-amino-3-(3-benzyloxy-phenyl)-propionyl]-piperazine-1-carboxylic acid ethyl ester hydrochloride This compound was prepared using a method analogous to that of Example 5, step 5.2, intermediate 31.5 replacing intermediate 5.1.
LC-MS (B): $t_R$=0.76 min; [M+H]$^+$: 412.19.

31.7. 4-{3-(3-benzyloxy-phenyl)-2-[(6-cyclopentyloxy-2-phenyl-pyrimidine-4-carbonyl)-amino]-propionyl}-piperazine-1-carboxylic acid ethyl ester This compound was prepared using a method analogous to that of Example 5, step 5.3, intermediate 31.6 replacing intermediate 5.2.
LC-MS (C): $t_R$=1.20 min; [M+H]$^+$: 678.07.

31.8. 4-[2-[(6-cyclopentyloxy-2-phenyl-pyrimidine-4-carbonyl)-amino]-(3-hydroxy-phenyl)-propionyl]-piperazine-1-carboxylic acid ethyl ester This compound was prepared using a method analogous to that of Example 1, step 1.2, intermediate 31.7 replacing intermediate 1.1. The title compound was purified by preparative TLC (EA/Hept 1/1).
LC-MS (B): $t_R$=1.19 min; [M+H]$^+$: 588.27; [M−H]$^-$: 586.63.

31.9. 4-[2-[(6-cyclopentyloxy-2-phenyl-pyrimidine-4-carbonyl)-amino]-3-(3-ethoxycarbonylmethoxy-phenyl)-propionyl]-piperazine-1-carboxylic acid ethyl ester This compound was prepared using a method analogous to that of Example 22, step 22.5, intermediate 31.8 replacing intermediate 22.4 and ethylbromoacetate replacing methylbromoacetate.
LC-MS (B): $t_R$=1.26 min; [M+H]$^+$: 674.53.

31.10. 4-{3-(3-carboxymethoxy-phenyl)-2-[(6-cyclopentyloxy-2-phenyl-pyrimidine-4-carbonyl)-amino]-propionyl}-piperazine-1-carboxylic acid ethyl ester This compound was prepared using a method analogous to that of Example 17, step 17.2, intermediate 31.9 replacing intermediate 17.1 but no purification being performed.
LC-MS (B): $t_R$=1.17 min; [M+H]$^+$: 646.40; [M−H]$^-$: 644.46.

Example 32

4-{3-(2-carboxymethoxy-phenyl)-2-[(6-cyclopentyloxy-2-phenyl-pyrimidine-4-carbonyl)-amino]-propionyl}-piperazine-1-carboxylic acid ethyl ester Intermediates 32.1 to 32.9 and the compound of Example 32 (=compound 32.10) were prepared using methods analogous to that used for respectively the intermediates 31.1 to 31.9 and the compound of Example 31 (=compound 31.10), except that DL-o-Tyrosine replaced DL-m-Tyrosine in stage 32.1.

32.1. 2-amino-3-(2-hydroxy-phenyl)-propionic acid methyl ester

LC-MS (C): $t_R$=0.50 min.

32.2. 2-tert-butoxycarbonylamino-3-(2-hydroxy-phenyl)-propionic acid methyl ester LC-MS (B): $t_R$=1.00 min; [M+H-Boc]$^+$: 196.14.

32.3. 3-(2-benzyloxy-phenyl)-2-tert-butoxycarbonylamino-propionic acid methyl ester LC-MS (B): $t_R$=1.19 min; [M+H-Boc]$^+$: 286.10.

32.4. 3-(2-benzyloxy-phenyl)-2-tert-butoxycarbonylamino-propionic acid

LC-MS (C): 0.99 min; [M+H-Boc]$^+$: 272.14.

32.5. 4-[3-(2-benzyloxy-phenyl)-2-tert-butoxycarbonylamino-propionyl]-piperazine-1-carboxylic acid ethyl ester LC-MS (C): $t_R$=1.05 min; [M+H]$^+$: 512.31.

32.6. 4-[2-amino-3-(2-benzyloxy-phenyl)-propionyl]-piperazine-1-carboxylic acid ethyl ester hydrochloride LC-MS (B): $t_R$=0.78 min; [M+H]$^+$: 412.19.

32.7. 4-{3-(2-benzyloxy-phenyl)-2-[(6-cyclopentyloxy-2-phenyl-pyrimidine-4-carbonyl)-amino]-propionyl}-piperazine-1-carboxylic acid ethyl ester LC-MS (C): $t_R$=1.21 min; [M+H]$^+$: 678.09.

32.8. 4-[2-[(6-cyclopentyloxy-2-phenyl-pyrimidine-4-carbonyl)-amino]-3-(2-hydroxy-phenyl)-propionyl]-piperazine-1-carboxylic acid ethyl ester LC-MS (B): $t_R$=1.21 min; [M+H]$^+$: 588.34; [M−H]$^-$: 586.33.

32.9. 4-[2-[(6-cyclopentyloxy-2-phenyl-pyrimidine-4-carbonyl)-amino]-3-(2-ethoxycarbonylmethoxy-phenyl)-propionyl]-piperazine-1-carboxylic acid ethyl ester LC-MS (B): $t_R$=1.27 min; [M+H]$^+$: 674.73.

32.10. 4-{3-(2-carboxymethoxy-phenyl)-2-[(6-cyclopentyloxy-2-phenyl-pyrimidine-4-carbonyl)-amino]-propionyl}-piperazine-1-carboxylic acid ethyl ester LC-MS (B): $t_R$=1.19 min; [M+H]$^+$: 646.33; [M−H]$^-$: 644.32.

Example 33

4-{(S)-2-(4-carboxymethoxy-phenyl)-2-[(6-cyclopentyloxy-2-phenyl-pyrimidine-4-carbonyl)-amino]-acetyl}-piperazine-1-carboxylic acid ethyl ester Intermediates 33.1 to 33.9 and the compound of Example 33 (=compound 33.10) were prepared using methods analogous to that used for respectively the intermediates 31.10 to 31.9 and the compound of Example 31 (=compound 31.10), except that 4-hydroxy-L-phenylglycine replaced DL-m-Tyrosine in stage 33.1.

33.1. (S)-amino-(4-hydroxy-phenyl)-acetic acid methyl ester

LC-MS (B): $t_R$=0.37 min; [M+H-Me]$^+$: 165.07.

33.2. (S)-tert-butoxycarbonylamino-(4-hydroxy-phenyl)-acetic acid methyl ester

LC-MS (B): $t_R$=0.93 min; [M−H]$^-$: 280.15.

33.3. (S)-(4-benzyloxy-phenyl)-tert-butoxycarbonylamino-acetic acid methyl ester LC-MS (B): $t_R$=1.16 min; [M+H-Boc]$^+$: 270.11.

33.4. (S)-(4-benzyloxy-phenyl)-tert-butoxycarbonylamino-acetic acid

LC-MS (B): $t_R$=1.08 min; [M−H]$^-$: 356.16.

33.5. 4-[(S)-2-(4-benzyloxy-phenyl)-2-tert-butoxycarbonylamino-acetyl]-piperazine-1-carboxylic acid ethyl ester LC-MS (C): $t_R$=1.03 min; [M+H]$^+$: 498.27.

33.6. 4-[(S)-2-amino-2-(4-benzyloxy-phenyl)-acetyl]-piperazine-1-carboxylic acid ethyl ester hydrochloride LC-MS (B): $t_R$=0.77 min; [M+H]$^+$: 399.37.

33.7. 4-{(S)-2-(4-benzyloxy-phenyl)-2-[(6-cyclopentyloxy-2-phenyl-pyrimidine-4-carbonyl)-amino]-acetyl}-piperazine-1-carboxylic acid ethyl ester LC-MS (C): $t_R$=1.19 min; [M+H]$^+$: 664.07.

33.8. 4-[(S)-2-[(6-cyclopentyloxy-2-phenyl-pyrimidine-4-carbonyl)-amino]-2-(4-hydroxy-phenyl)-acetyl]-piperazine-1-carboxylic acid ethyl ester LC-MS (B): $t_R$=1.18 min; [M+H]$^+$: 574.34.

33.9. 4-[(S)-2-[(6-cyclopentyloxy-2-phenyl-pyrimidine-4-carbonyl)-amino]-2-(4-ethoxycarbonylmethoxy-phenyl)-acetyl]-piperazine-1-carboxylic acid ethyl ester LC-MS (B): $t_R$=1.24 min; [M+H]$^+$: 660.53.

33.10. 4-{(S)-2-(4-carboxymethoxy-phenyl)-2-[(6-cyclopentyloxy-2-phenyl-pyrimidine-4-carbonyl)-amino]-acetyl}-piperazine-1-carboxylic acid ethyl ester LC-MS (B): $t_R$=1.17 min; [M+H]$^+$: 632.61; [M−H]$^-$: 630.32.

Example 34

4-{(S)-4-carboxy-2-[(6-cyclopentyloxy-2-phenyl-pyrimidine-4 carbonyl)-amino]-butyryl}-piperazine-1-carboxylic acid prop-2-ynyl ester

34.1. 2-[(S)-(6-cyclopentyloxy-2-phenyl-pyrimidine-4-carbonyl)-amino]-pentanedioic acid 5-tert-butyl ester 1-methyl ester This compound was prepared using a method analogous to that of Example 5, step 5.3, H-Glu(OtBu)-OMe replacing intermediate 5.2. The compound was however purified by column chromatography (EA/Hex 1/4).
LC-MS (A): $t_R$=1.46 min; [M+H]$^+$: 484.07.

34.2. 2-[(S)-(6-cyclopentyloxy-2-phenyl-pyrimidine-4-carbonyl)-amino]-pentanedioic acid 5-tert-butyl ester This compound was prepared using a method analogous to that of Example 17, step 17.2, intermediate 34.1 replacing intermediate 17.1. The compound was however purified by column chromatography (DCM/MeOH/AcOH, 100/10/1).
LC-MS (A): $t_R$=1.37 min; [M+H]$^+$: 470.02; [M−H]$^-$: 468.22.

34.3. 4-{(S)-4-tert-butoxycarbonyl-2-[(6-cyclopentyloxy-2-phenyl-pyrimidine-4-carbonyl)-amino]-butyryl}-piperazine-1-carboxylic acid benzyl ester This compound was prepared using a method analogous to that of Example 5, step 5.3, intermediate 34.2 replacing 6-cyclopentyloxy-2-phenyl-pyrimidine-4-carboxylic acid and piperazine-1-carboxylic acid benzyl ester replacing intermediate 5.2, but using no DIPEA.
LC-MS (A): $t_R$=1.54 min; [M+H]$^+$: 672.24.

34.4. 4-[(S)-(6-cyclopentyloxy-2-phenyl-pyrimidine-4-carbonyl)-amino]-5-oxo-5-piperazin-1-yl-pentanoic acid tert-butyl ester This compound was prepared using a method analogous to that of Example 1, step 1.2, intermediate 34.3 replacing intermediate 1.1. The compound was however purified by column chromatography (DCM/MeOH, 10/1).
LC-MS (A): $t_R$=0.95 min; [M+H]$^+$: 538.08.

34.5. 4-{(S)-4-tert-butoxycarbonyl-2-[(6-cyclopentyloxy-2-phenyl-pyrimidine-4-carbonyl)-amino]-butyryl}-piperazine-1-carboxylic acid prop-2-ynyl ester Intermediate 34.4 (30 mg) was dissolved in DCM (500 μl) and propargyl chloroformate (6 μl) and triethylamine (9 μl) were added. The mixture was stirred overnight, diluted with DCM, washed with water, dried (Na$_2$SO$_4$) and evaporated off. After HV, 27 mg of the desired compound were obtained.
LC-MS (A): $t_R$=1.39 min; [M+H]$^+$: 651.25.

34.6. 4-{(S)-4-carboxy-2-[(6-cyclopentyloxy-2-phenyl-pyrimidine-4 carbonyl)-amino]-butyryl}-piperazine-1-carboxylic acid prop-2-ynyl ester This compound was prepared using a method analogous to that of Example 1, step 1.9, intermediate 34.5 replacing intermediate 1.8.
LC-MS (A): $t_R$=1.21 min; [M+H]$^+$: 564.12; [M−H]$^-$: 562.32.

Example 35

4-{(S)-4-carboxy-2-[(6-cyclopentyloxy-2-phenyl-pyrimidine-4-carbonyl)-amino]-butyryl}-piperazine-1-carboxylic acid butyl ester

35.1. 4-{(S)-4-tert-butoxycarbonyl-2-[(6-cyclopentyloxy-2-phenyl-pyrimidine-4-carbonyl)-amino]-butyryl}-piperazine-1-carboxylic acid butyl ester This compound was prepared using a method analogous to that of Example 34, step 34.5, butyl chloroformate replacing propargyl chloroformate.
LC-MS (A): $t_R$=1.56 min; [M+H]$^+$: 638.23.

35.2. 4-{(S)-4-carboxy-2-[(6-cyclopentyloxy-2-phenyl-pyrimidine-4-carbonyl)-amino]-butyryl}-piperazine-1-carboxylic acid butyl ester This compound was prepared using a method analogous to that of Example 1, step 1.9, intermediate 35.1 replacing intermediate 1.8.
LC-MS (A): $t_R$=1.32 min; [M+H]$^+$: 582.12; [M−H]$^-$: 580.32.

Example 36

4-{(S)-4-carboxy-2-[(6-cyclopentyloxy-2-phenyl-pyrimidine-4-carbonyl)-amino]-butyryl}-piperazine-1-carboxylic acid isobutyl ester

36.1. 4-{(S)-4-tert-butoxycarbonyl-2-[(6-cyclopentyloxy-2-phenyl-pyrimidine-4-carbonyl)-amino]-butyryl}-piperazine-1-carboxylic acid isobutyl ester This compound was prepared using a method analogous to that of Example 34, step 34.5, isobutyl chloroformate replacing propargyl chloroformate.
LC-MS (A): $t_R$=1.56 min; [M+H]$^+$: 638.16.

36.2. 4-{(S)-4-carboxy-2-[(6-cyclopentyloxy-2-phenyl-pyrimidine-4 carbonyl)-amino]-butyryl}-piperazine-1-carboxylic acid isobutyl ester This compound was prepared using a method analogous to that of Example 1, step 1.9, intermediate 36.1 replacing intermediate 1.8.

LC-MS (A): $t_R$=1.31 min; [M+H]$^+$: 582.12; [M−H]$^−$: 580.32.

Example 37

4-{(S)-4-carboxy-2-[(6-cyclopentyloxy-2-phenyl-pyrimidine-4-carbonyl)-amino]-butyryl}-piperazine-1-carboxylic acid 2,2-dimethyl-propyl ester

37.1. 4-{(S)-4-tert-butoxycarbonyl-2-[(6-cyclopentyloxy-2-phenyl-pyrimidine-4-carbonyl)-amino]-butyryl}-piperazine-1-carboxylic acid 2,2-dimethyl-propyl ester This compound was prepared using a method analogous to that of Example 34, step 34.5, neopentyl chloroformate replacing propargyl chloroformate.

LC-MS (A): $t_R$=1.60 min; [M+H]$^+$: 652.14.

37.2. 4-{(S)-4-carboxy-2-[(6-cyclopentyloxy-2-phenyl-pyrimidine-4 carbonyl)-amino]-butyryl}-piperazine-1-carboxylic acid 2,2-dimethyl-propyl ester This compound was prepared using a method analogous to that of Example 1, step 1.9, intermediate 37.1 replacing intermediate 1.8.

LC-MS (A): $t_R$=1.34 min; [M+H]$^+$: 596.18; [M−H]$^−$: 594.24.

Example 38

4-{(S)-4-carboxy-2-[(6-cyclopentyloxy-2-phenyl-pyrimidine-4-carbonyl)-amino]-butyryl}-piperazine-1-carboxylic acid isopropyl ester

38.1. 4-{(S)-4-tert-butoxy-carbonyl-2-[(6-cyclopentyloxy-2-phenyl-pyrimidine-4-carbonyl)-amino]-butyryl}-piperazine-1-carboxylic acid isopropyl ester This compound was prepared using a method analogous to that of Example 34, step 34.5, isopropyl chloroformate replacing propargyl chloroformate.

LC-MS (A): $t_R$=1.53 min; [M+H]$^+$: 624.24.

38.2. 4-{(S)-4-carboxy-2-[(6-cyclopentyloxy-2-phenyl-pyrimidine-4 carbonyl)-amino]-butyryl}-piperazine-1-carboxylic acid isopropyl ester This compound was prepared using a method analogous to that of Example 1, step 1.9, intermediate 38.1 replacing intermediate 1.8.

LC-MS (A): $t_R$=1.27 min; [M+H]$^+$: 568.06; [M−H]$^−$: 566.26.

Example 39

(S)-4-[(6-cyclopentyloxy-2-phenyl-pyrimidine-4-carbonyl)-amino]-5-[4-(furan-2-carbonyl)-piperazin-1-yl]-5-oxo-pentanoic acid

39.1. 4-[(S)-(6-cyclopentyloxy-2-phenyl-pyrimidine-4-carbonyl)-amino]-5-[4-furan-2-carbonyl)-piperazin-1-yl]-5-oxo-pentanoic acid tert-butyl ester This compound was prepared using a method analogous to that of Example 5, step 5.3, 2-[(S)-(6-cyclopentyloxy-2-phenyl-pyrimidine-4-carbonyl)-amino]-pentanedioic acid 5-tert-butyl ester replacing 6-cyclopentyloxy-2-phenyl-pyrimidine-4-carboxylic acid, 1-(2-furoyl)piperazine replacing intermediate 5.2 and no DIPEA being used.

LC-MS (A): $t_R$=1.40 min; [M+H]$^+$: 632.27.

39.2. (S)-4-[(6-cyclopentyloxy-2-phenyl-pyrimidine-4-carbonyl)-amino]-5[4-(furan-2-carbonyl)-piperazin-1-yl]-5-oxo-pentanoic acid This compound was prepared using a method analogous to that of Example 1, step 1.9, intermediate 39.1 replacing intermediate 1.8. The title compound was however purified by column chromatography (DCM/MeOH/AcOH, 100/10/1) followed by preparative LC-MS (III).

LC-MS (A): $t_R$=1.18 min; [M+H]$^+$: 576.10; [M−H]$^−$: 574.16.

Example 40

4-{(S)-4-carboxy-2-[(6-cyclopentyloxy-2-phenyl-pyrimidine-4-carbonyl)-amino]-butyryl}-piperazine-1-carboxylic acid phenyl ester

40.1. Piperazine-1,4-dicarboxylic acid benzyl ester phenyl ester

This compound was prepared using a method analogous to that of Example 34, step 34.5, phenyl chloroformate replacing propargyl chloroformate.

LC-MS (A): $t_R$=1.13 min; [M+H]$^+$: 340.81.

40.2. Piperazine-1-carboxylic acid phenyl ester

This compound was prepared using a method analogous to that of Example 1, step 1.2, intermediate 40.1 replacing intermediate 1.1.

LC-MS (C): $t_R$=0.67 min; [M+MeCN+H]$^+$: 248.24.

40.3. 4-{(S)-4-tert-butoxycarbonyl-2-[(6-cyclopentyloxy-2-phenyl-pyrimidine-4-carbonyl)-amino]-butyryl}-piperazine-1-carboxylic acid phenyl ester This compound was prepared using a method analogous to that of Example 5, step 5.3, 2-[(S)-(6-cyclopentyloxy-2-phenyl-pyrimidine-4-carbonyl)-amino]-pentanedioic acid 5-tert-butyl ester replacing 6-cyclopentyloxy-2-phenyl-pyrimidine-4-carboxylic acid and intermediate 40.2 replacing intermediate 5.2, but using no DIPEA.

LC-MS (A): $t_R$=1.51 min; [M+H]$^+$: 658.32.

40.4. 4-{(S)-4-carboxy-2-[(6-cyclopentyloxy-2-phenyl-pyrimidine-4 carbonyl)-amino]-butyryl}-piperazine-1-carboxylic acid phenyl ester This compound was prepared using a method analogous to that of Example 1, step 1.9, intermediate 40.3 replacing intermediate 1.8. The title compound was however purified by column chromatography (DCM/MeOH/AcOH, 100/10/1).

LC-MS (A): $t_R$=1.26 min; [M+H]$^+$: 602.14; [M−H]$^−$: 600.27.

Example 41

(S)-5-(4-benzoyl-piperazin-1-yl)-4-[(6-cyclopentyloxy-2-phenyl-pyrimidine-4-carbonyl)-amino]-5-oxo-pentanoic acid

41.1. 4-benzoyl-piperazine-1-carboxylic acid benzyl ester

Piperazine-1-carboxylic acid benzyl ester (500 mg) was dissolved in DCM (5 ml) and the mixture was cooled down to 0° C. Benzoyl chloride (290 µl) and NEt$_3$ (379 µl) were added. The mixture was stirred for 48 h, diluted with DCM, washed with water, dried (Na$_2$SO$_4$) and evaporated off. After HV, 650 mg of the desired compound were obtained.

LC-MS (A): t$_R$=1.05 min; [M+H]$^+$: 324.87.

41.2. Phenyl-piperazin-1-yl-methanone

This compound was prepared using a method analogous to that of Example 1, step 1.2, intermediate 41.1 replacing intermediate 1.1.

LC-MS (A): t$_R$=0.47 min; [M+H]$^+$: 191.01.

41.3. 5-((S)-4-benzoyl-piperazin-1-yl)-4-[(6-cyclopentyloxy-2-phenyl-pyrimidine-4-carbonyl)-amino]-5-oxo-pentanoic acid tert-butyl ester This compound was prepared using a method analogous to that of Example 5, step 5.3, 2-[(S)-(6-cyclopentyloxy-2-phenyl-pyrimidine-4-carbonyl)-amino]-pentanedioic acid 5-tert-butyl ester replacing 6-cyclopentyloxy-2-phenyl-pyrimidine-4-carboxylic acid and intermediate 41.2 replacing intermediate 5.2, but using no DIPEA.

LC-MS (A): t$_R$=1.41 min; [M+H]$^+$: 642.25.

41.4. (S)-5-(4-benzoyl-piperazin-1-yl)-4-[(6-cyclopentyloxy-2-phenyl-pyrimidine-4-carbonyl)-amino]-5-oxo-pentanoic acid This compound was prepared using a method analogous to that of Example 1, step 1.9, intermediate 41.3 replacing intermediate 1.8. The title compound was however purified by column chromatography (DCM/MeOH/AcOH, 100/10/1).

LC-MS (A): t$_R$=1.19 min; [M+H]$^+$: 586.07; [M−H]$^-$: 584.20.

Example 42

4-{(S)-4-carboxy-2-[(6-cyclopentyloxy-2-phenyl-pyrimidine-4-carbonyl)-amino]-butyryl}-piperazine-1-carboxylic acid benzyl ester

42.1. 4-{(S)-4-tert-butoxycarbonyl-2-[(6-cyclopentyloxy-2-phenyl-pyrimidine-4-carbonyl)-amino]-butyryl}-piperazine-1-carboxylic acid benzyl ester This compound was prepared using a method analogous to that of Example 5, step 5.3, 2-[(S)-(6-cyclopentyloxy-2-phenyl-pyrimidine-4-carbonyl)-amino]-pentanedioic acid 5-tert-butyl ester replacing 6-cyclopentyloxy-2-phenyl-pyrimidine-4-carboxylic acid and benzyl-piperazine carboxylate replacing intermediate 5.2, but using no DIPEA.

LC-MS (A): t$_R$=1.53 min; [M+H]$^+$: 672.31.

42.2. 4-{(S)-4-carboxy-2-[(6-cyclopentyloxy-2-phenyl-pyrimidine-4 carbonyl)-amino]-butyryl}-piperazine-1-carboxylic acid benzyl ester This compound was prepared using a method analogous to that of Example 1, step 1.9, intermediate 42.1 replacing intermediate 1.8. The title compound was however purified by preparative LC-MS (IV).

LC-MS (A): t$_R$=1.32 min; [M+H]$^+$: 616.20; [M−H]$^-$: 614.26.

Example 43

(S)-5-(4-butyryl-piperazin-1-yl)-4-[(6-cyclopentyloxy-2-phenyl-pyrimidine-4-carbonyl)-amino]-5-oxo-pentanoic acid

43.1. 4-butyryl-piperazine-1-carboxylic acid tert-butyl ester

This compound was prepared using a method analogous to that of Example 41, step 41.1, 1-Boc-piperazine replacing piperazine-1-carboxylic acid benzyl ester and butyryl chloride replacing benzoyl chloride.

$^1$H-NMR (DMSO-d$_6$): 3.35 (m, 8H); 2.25 (t, 2H); 1.5 (q, 2H); 1.4 (s, 9H); 0.85 (t, 3H).

43.2. 1-piperazin-1-yl-butan-1-one hydrochloride

This compound was prepared using a method analogous to that of Example 5, step 5.2, intermediate 43.1 replacing intermediate 5.1 and Et$_2$O replacing EA.

LC-MS (C): t$_R$=0.93 min; [M+CF$_3$COOH+H]$^+$: 268.31.

43.3. 5-((S)-4-butyryl-piperazin-1-yl)-4-[(6-cyclopentyloxy-2-phenyl-pyrimidine-4-carbonyl)-amino]-5-oxo-pentanoic acid tert-butyl ester This compound was prepared using a method analogous to that of Example 5, step 5.3, intermediate 43.2 replacing 6-cyclopentyloxy-2-phenyl-pyrimidine-4-carboxylic acid and 1-piperazin-1-yl-butan-1-one hydrochloride replacing intermediate 5.2.

LC-MS (A): t$_R$=1.39 min; [M+H]$^+$: 608.30.

43.4. (S)-5-(4-butyryl-piperazin-1-yl)-4-[(6-cyclopentyloxy-2-phenyl-pyrimidine-4-carbonyl)-amino]-5-oxo-pentanoic acid This compound was prepared using a method analogous to that of Example 1, step 1.9, intermediate 43.3 replacing intermediate 1.8. The title compound was however purified by preparative LC-MS (III).

LC-MS (A): t$_R$=1.19 min; [M+H]$^+$: 552.14; [M−H]$^-$: 550.34.

Example 44

(S)-4-[(6-cyclopentyloxy-2-phenyl-pyrimidine-4-carbonyl)-amino]-5-oxo-5-[4-(propane-1-sulfonyl)-piperazin-1-yl]-pentanoic acid

44.1. 4-(propane-1-sulfonyl)-piperazine-1-carboxylic acid tert-butyl ester

This compound was prepared using a method analogous to that of Example 41, step 41.1, 1-Boc-piperazine replacing piperazine-1-carboxylic acid benzyl ester and 1-propanesulfonyl chloride replacing benzoyl chloride.

¹H-NMR (DMSO-d₆): 3.85 (br s, 2H); 3.35 (m, 4H); 3.1 (m, 4H); 1.65 (q, 2H); 1.4 (s, 9H); 0.95 (t, 3H).

44.2. 1-(propane-1-sulfonyl)-piperazine hydrochloride

This compound was prepared using a method analogous to that of Example 5, step 5.2, intermediate 44.1 replacing intermediate 5.1 and Et₂O replacing EA.

LC-MS (C): $t_R$=0.45 min; [M+MeCN+H]⁺: 234.38.

44.3. (S)-4-[(6-cyclopentyloxy-2-phenyl-pyrimidine-4-carbonyl)-amino]-5-oxo-5-[4-(propane-1-sulfonyl)-piperazin-1-yl]-pentanoic acid tert-butyl ester This compound was prepared using a method analogous to that of Example 5, step 5.3, 2-[(S)-(6-cyclopentyloxy-2-phenyl-pyrimidine-4-carbonyl)-amino]-pentanedioic acid 5-tert-butyl ester replacing 6-cyclopentyloxy-2-phenyl-pyrimidine-4-carboxylic acid and intermediate 44.2 replacing intermediate 5.2.

LC-MS (A): $t_R$=1.45 min; [M+H]⁺: 644.18; [M−H]⁻: 643.91.

44.4. (S)-4-[(6-cyclopentyloxy-2-phenyl-pyrimidine-4-carbonyl)-amino]-5 oxo-5-[4-(propane-1-sulfonyl)-piperazin-1-yl]-pentanoic acid This compound was prepared using a method analogous to that of Example 1, step 1.9, intermediate 44.3 replacing intermediate 1.8. The title compound was however purified by preparative LC-MS (IV).

LC-MS (A): $t_R$=1.20 min; [M+H]⁺: 588.15; [M−H]⁻: 586.21.

Example 45

4-{(S)-4-carboxy-2-[(6-cyclopentyloxy-2-phenyl-pyrimidine-4-carbonyl)-amino]-butyryl}-3-methyl-piperazine-1-carboxylic acid ethyl ester

45.1. 3-methyl-piperazine-1-carboxylic acid ethyl ester 2-methylpiperazine (1 g) was dissolved in MeOH (12 ml) and AcOH (1.8 ml) was added. The mixture was cooled down to 0° C., ethyl chloroformate (0.95 ml) was added over 60 min. The mixture was allowed to warm to RT and was stirred overnight. Water was added and MeOH was evaporated off. The residue was extracted with toluene and the org. layers were washed with water. The combined aq. layers were basified to pH 14 with a 2M NaOH solution and extracted with toluene. The combined org. layers were washed with a NaCl solution, dried (Na₂SO₄) and evaporated off to give 936 mg of the desired compound.

¹H-NMR (CDCl₃): 4.1 (q, 2H); 3.95 (br s, 2H); 2.9 (d, 1H); 2.75 (m, 3H); 2.4 (t, 1H); 1.6 (br s, 1H); 1.25 (t, 3H); 1.05 (t, 3H).

45.2. 4-{(S)-4-tert-butoxycarbonyl-2-[(6-cyclopentyloxy-2-phenyl-pyrimidine-4-carbonyl)-amino]-butyryl}-3-methyl-piperazine-1-carboxylic acid ethyl ester This compound was prepared using a method analogous to that of Example 5, step 5.3, 2-[(S)-(6-cyclopentyloxy-2-phenyl-pyrimidine-4-carbonyl)-amino]-pentanedioic acid 5-tert-butyl ester replacing 6-cyclopentyloxy-2-phenyl-pyrimidine-4-carboxylic acid and intermediate 45.1 replacing intermediate 5.2, but using no DIPEA.

LC-MS (A): $t_R$=1.49 min; [M+H]⁺: 624.19.

45.3. 4-{(S)-4-carboxy-2-[(6-cyclopentyloxy-2-phenyl-pyrimidine-4 carbonyl)-amino]-butyryl}-3-methyl-piperazine-1-carboxylic acid ethyl ester This compound was prepared using a method analogous to that of Example 1, step 1.9, intermediate 45.2 replacing intermediate 1.8. The title compound was however purified by preparative LC-MS (IV).

LC-MS (A): $t_R$=1.25 min; [M+H]⁺: 568.13; [M−H]⁻: 566.40.

Example 46

4-{(S)-4-carboxy-2-[(6-cyclopentyloxy-2-phenyl-pyrimidine-4-carbonyl)-amino]-butyryl}-2-methyl-piperazine-1-carboxylic acid ethyl ester

46.1. 3-methyl-piperazine-1-carboxylic acid benzyl ester

This compound was prepared using a method analogous to that of Example 45, step 45.1, benzyl chloroformate replacing ethyl chloroformate.

¹H-NMR (CDCl₃): 7.35 (m, 5H); 5.1 (s, 2H); 4 (br s, 2H); 2.8 (m, 4H); 2.45 (br s, 1H); 1.6 (s, 1H); 1.05 (t, 3H).

46.2. 2-methyl-piperazine-1,4-dicarboxylic acid 4-benzyl ester 1-ethyl ester This compound was prepared using a method analogous to that of Example 41, step 41.1, intermediate 46.1 replacing piperazine-1-carboxylic acid benzyl ester and ethyl chloroformate replacing benzoyl chloride.

¹H-NMR (DMSO-d₆): 7.35 (m, 5H); 5.1 (s, 2H); 4.2 (br s, 1H); 4.1 (q, 2H); 3.9 (d, 1H); 3.75 (m, 2H); 3 (m, 3H); 1.2 (t, 3H); 1.05 (t, 3H).

46.3. 2-methyl-piperazine-1-carboxylic acid ethyl ester

This compound was prepared using a method analogous to that of Example 1, step 1.2, intermediate 46.2 replacing intermediate 1.1.

¹H-NMR (CDCl₃): 4.2 (m, 1H); 4.1 (q, 2H); 3.8 (d, 1H); 2.9 (m, 3H); 2.7 (m, 2H); 1.6 (br s, 1H); 1.2 (2t, 6H).

46.4. 4-{(S)-4-tert-butoxycarbonyl-2-[(6-cyclopentyloxy-2-phenyl-pyrimidine-4-carbonyl)-amino]-butyryl}-2-methyl-piperazine-1-carboxylic acid ethyl ester This compound was prepared using a method analogous to that of Example 5, step 5.3, 2-[(S)-(6-cyclopentyloxy-2-phenyl-pyrimidine-4-carbonyl)-amino]-pentanedioic acid 5-tert-butyl ester replacing 6-cyclopentyloxy-2-phenyl-pyrimidine-4-carboxylic acid and intermediate 46.3 replacing intermediate 5.2, but using no DIPEA.

LC-MS (A): $t_R$=1.50 min; [M+H]⁺: 624.17.

46.5. 4-{(S)-4-carboxy-2-[(6-cyclopentyloxy-2-phenyl-pyrimidine-4 carbonyl)-amino]-butyryl}-2-methyl-piperazine-1-carboxylic acid ethyl ester This compound was prepared using a method analogous to that of Example 1, step 1.9, intermediate 46.4 replacing intermediate 1.8. The title compound was however purified by preparative LC-MS (IV).

LC-MS (A): $t_R$=1.25 min; [M+H]$^+$: 568.06; [M−H]$^-$: 566.33.

Example 47

4-{(S)-4-carboxy-2-[(6-cyclopentyloxy-2-phenyl-pyrimidine-4-carbonyl)-amino]-butyryl}-trans-2,5-dimethyl-piperazine-1-carboxylic acid ethyl ester 47.1. trans-2,5-dimethyl-piperazine-1-carboxylic acid ethyl ester Methanesulfonic acid (1.136 ml) dissolved in water (1 ml) was added to trans-2,5-dimethylpiperazine (1 g). It was cooled down in an ice bath so that the temperature did not rise above 40° C. At 25° C., EtOH (1.2 ml) was added to the mixture and the pH was adjusted to 4-5 by adding a 50% solution of potassium acetate. Finally, ethyl chloroformate dissolved in THF was added. The pH was again adjusted to 4 by adding a 50% solution of potassium acetate. The mixture was stirred for another hour at RT and evaporated off. The residue was diluted with EA, the org. phase was separated, washed with a 1M HCl solution. The aq. layers were basified with a NaOH solution till pH 10 and extracted with EA. The combined org. layers were dried (Na$_2$SO$_4$) and evaporated off. 740 mg of the desired compound were obtained.

$^1$H-NMR (DMSO-d$_6$): 4 (q, 2H); 3.95 (m, 1H); 3.4 (d, 1H); 3.1 (dd, 1H); 2.95 (dd, 2H); 2.3 (dd, 1H); 1.15 (d and t, 6H); 1 (d, 3H).

47.2. 4-{(S)-4-tert-butoxycarbonyl-2-[(6-cyclopentyloxy-2-phenyl-pyrimidine-4-carbonyl)-amino]-butyryl}-trans-2,5-dimethyl-piperazine-1-carboxylic acid ethyl ester This compound was prepared using a method analogous to that of Example 5, step 5.3, 2-[(S)-(6-cyclopentyloxy-2-phenyl-pyrimidine-4-carbonyl)-amino]-pentanedioic acid 5-tert-butyl ester replacing 6-cyclopentyloxy-2-phenyl-pyrimidine-4-carboxylic acid and intermediate 47.1 replacing intermediate 5.2, but using no DIPEA.

LC-MS (A): $t_R$=1.52 min; [M+H]$^+$: 638.23.

47.3. 4-{(S)-4-carboxy-2-[(6-cyclopentyloxy-2-phenyl-pyrimidine-4 carbonyl)-amino]-butyryl}-trans-2,5-dimethyl-piperazine-1-carboxylic acid ethyl ester This compound was prepared using a method analogous to that of Example 1, step 1.9, intermediate 41.3 replacing intermediate 1.8. The title compound was however purified by preparative LC-MS (IV).

LC-MS (A): $t_R$=1.27 min; [M+H]$^+$: 582.12; [M−H]$^-$: 580.46.

Example 48

4-{(S)-4-carboxy-2-[(6-methylamino-2-phenyl-pyrimidine-4-carbonyl)-amino]-butyryl}-piperazine-1-carboxylic acid ethyl ester triflate salt 48.1. 4-{(S)-4-tert-butoxycarbonyl-2-[(6-chloro-2-phenyl-pyrimidine-4-carbonyl)-amino]-butyryl}-piperazine-1-carboxylic acid ethyl ester Under argon, oxalyl chloride (0.843 ml) was added to a solution of 6-chloro-2-phenyl-pyrimidine-4-carboxylic acid (1.17 g) in acetonitrile (50 ml) and it was refluxed for 3 h. The reaction mixture was cooled down to 0° C. and NEt$_3$ (2.07 ml) was added, followed by 4-((S)-2-amino-4-tert-butoxycarbonyl-butyryl)-piperazine-1-carboxylic acid ethyl ester (1.7 g) in 10 ml acetonitrile. It was stirred at RT under argon for 1 h. Water was added and the reaction mixture was extracted with EA. The org. layers were dried (Na$_2$SO$_4$) and evaporated off. Purification by column chromatography (EA/Hept 1/3 to 1/2) offered 1.61 g of the desired compound.

LC-MS (A): $t_R$=1.32 min; [M−H]$^-$: 558.30.

48.2. 4-{(S)-4-tert-butoxycarbonyl-2-[(6-methylamino-2-phenyl-pyrimidine-4-carbonyl)-amino]-butyryl}-piperazine-1-carboxylic acid ethyl ester Intermediate 48.1 (56 mg) was dissolved in THF (0.3 ml) and 0.4 ml of 2M solution of methylamine in THF was added. The mixture was stirred for 4 h at RT. Water was added and the mixture extracted with EA. The org. layers were dried (Na$_2$SO$_4$) and evaporated off to give 60 mg of the desired pure compound.

LC-MS (A): $t_R$=1.21 min; [M+H]$^+$: 555.11; [M−H]$^-$: 553.45.

48.3. 4-{(S)-4-carboxy-2-[(6-methylamino-2-phenyl-pyrimidine-4 carbonyl)-amino]-butyryl}-piperazine-1-carboxylic acid ethyl ester triflate salt This compound was prepared using a method analogous to that of Example 1, step 1.9, intermediate 48.2 replacing intermediate 1.8.

LC-MS (A): $t_R$=0.97 min; [M+H]$^+$: 498.96; [M−H]$^-$: 497.15.

Example 49

4-{(S)-4-carboxy-2-[(2-phenyl-6-propylamino-pyrimidine-4-carbonyl)-amino]-butyryl}-piperazine-1-carboxylic acid ethyl ester triflate salt 49.1. 4-{(S)-4-tert-butoxycarbonyl-2-[(2-phenyl-6-propylamino-pyrimidine-4-carbonyl)-amino]-butyryl}-piperazine-1-carboxylic acid ethyl ester 4-{(S)-4-tert-butoxycarbonyl-2-[(6-chloro-2-phenyl-pyrimidine-4-carbonyl)-amino]-butyryl}-piperazine-1-carboxylic acid ethyl ester (53 mg) and propylamine (31 µl) were dissolved in THF (0.5 ml). The mixture was stirred at 40° C. until reaction completion. Water was added and it was extracted with EA. The org. layers were dried (Na$_2$SO$_4$) and evaporated off to give 60 mg of the desired pure compound.

LC-MS (A): $t_R$=1.32 min; [M+H]$^+$: 583.23; [M−H]$^-$: 581.50.

49.2. 4-{(S)-4-carboxy-2-[(2-phenyl-6-propylamino-pyrimidine-4 carbonyl)-amino]-butyryl}-piperazine-1-carboxylic acid ethyl ester triflate salt This compound was prepared using a method analogous to that of Example 1, step 1.9, intermediate 49.1 replacing intermediate 1.8.
LC-MS (A): $t_R$=1.10 min; [M+H]$^+$: 527.07; [M+H]$^-$: 525.27.

Example 50

4-{(S)-4-carboxy-2-[(6-isopropylamino-2-phenyl-pyrimidine-4-carbonyl)-amino]-butyryl}-piperazine-1-carboxylic acid ethyl ester triflate salt 50.1. 4-{(S)-4-tert-butoxycarbonyl-2-[(6-isopropylamino-2-phenyl-pyrimidine-4-carbonyl)-amino]-butyryl}-piperazine-1-carboxylic acid ethyl ester This compound was prepared using a method analogous to that of Example 49, step 49.1, isopropylamine replacing propylamine.
LC-MS (A): $t_R$=1.31 min; [M+H]$^+$: 583.30; [M+H]$^-$: 581.57.

50.2. 4-{(S)-4-carboxy-2-[(6-isopropylamino-2-phenyl-pyrimidine-4 carbonyl)-amino]-butyryl}-piperazine-1-carboxylic acid ethyl ester triflate salt This compound was prepared using a method analogous to that of Example 1, step 1.9, intermediate 50.1 replacing intermediate 1.8.
LC-MS (A): $t_R$=1.08 min; [M+H]$^+$: 527.07; [M+H]$^-$: 525.27.

Example 51

4-{(S)-2-[(6-butylamino-2-phenyl-pyrimidine-4-carbonyl)-amino]-4-carboxy-butyryl}-piperazine-1-carboxylic acid ethyl ester triflate salt 51.1. 4-{(S)-4-tert-butoxycarbonyl-2-[(6-butylamino-2-phenyl-pyrimidine-4-carbonyl)-amino]-butyryl}-piperazine-1-carboxylic acid ethyl ester This compound was prepared using a method analogous to that of Example 49, step 49.1, butylamine replacing propylamine.
LC-MS (A): $t_R$=1.37 min; [M+H]$^+$: 597.22.

51.2. 4-{(S)-2-[(6-butylamino-2-phenyl-pyrimidine-4-carbonyl)-amino]-4 carboxy-butyryl}-piperazine-1-carboxylic acid ethyl ester triflate salt This compound was prepared using a method analogous to that of Example 1, step 1.9, intermediate 51.1 replacing intermediate 1.8.
LC-MS (A): $t_R$=1.15 min; [M+H]$^+$: 541.06; [M+H]$^-$: 539.32.

Example 52

4-{(S)-4-carboxy-2-[(6-isobutylamino-2-phenyl-pyrimidine-4-carbonyl)-amino]-butyryl}-piperazine-1-carboxylic acid ethyl ester triflate salt 52.1. 4-{(S)-4-tert-butoxycarbonyl-2-[(6-isobutylamino-2-phenyl-pyrimidine-4-carbonyl)-amino]-butyryl}-piperazine-1-carboxylic acid ethyl ester This compound was prepared using a method analogous to that of Example 49, step 49.1, isobutylamine replacing propylamine.
LC-MS (A): $t_R$=1.37 min; [M+H]$^+$: 597.22.

52.2. 4-{(S)-4-carboxy-2-[(6-isobutylamino-2-phenyl-pyrimidine-4 carbonyl)-amino]-butyryl}-piperazine-1-carboxylic acid ethyl ester triflate salt This compound was prepared using a method analogous to that of Example 1, step 1.9, intermediate 52.1 replacing intermediate 1.8.
LC-MS (A): $t_R$=1.15 min; [M+H]$^+$: 541.13; [M+H]$^-$: 539.39.

Example 53

4-{(S)-4-carboxy-2-[(6-cyclopropylamino-2-phenyl-pyrimidine-4-carbonyl)-amino]-butyryl}-piperazine-1-carboxylic acid ethyl ester triflate salt 53.1. 4-{(S)-4-tert-butoxycarbonyl-2-[(6-cyclopropylamino-2-phenyl-pyrimidine-4-carbonyl)-amino]-butyryl}-piperazine-1-carboxylic acid ethyl ester This compound was prepared using a method analogous to that of Example 49, step 49.1, cyclopropylamine replacing propylamine.
LC-MS (A): $t_R$=1.25 min; [M+H]$^+$: 581.15; [M+H]$^-$: 579.49.

53.2. 4-{(S)-4-carboxy-2-[(6-cyclopropylamino-2-phenyl-pyrimidine-4-carbonyl)-amino]-butyryl}-piperazine-1-carboxylic acid ethyl ester triflate salt This compound was prepared using a method analogous to that of Example 1, step 1.9, intermediate 53.1 replacing intermediate 1.8.
LC-MS (A): $t_R$=1.03 min; [M+H]$^+$: 525.06; [M+H]$^-$: 523.33.

Example 54

4-{(S)-4-carboxy-2-[(6-cyclopentylamino-2-phenyl-pyrimidine-4-carbonyl)-amino]-butyryl}-piperazine-1-carboxylic acid ethyl ester triflate salt 54.1. 4-{(S)-4-tert-butoxycarbonyl-2-[(6-cyclopentylamino-2-phenyl-pyrimidine-4-carbonyl)-amino]-butyryl}-piperazine-1-carboxylic acid ethyl ester This compound was prepared using a method analogous to that of Example 49, step 49.1, cyclopentylamine replacing propylamine.
LC-MS (A): $t_R$=1.39 min; [M+H]$^+$: 609.21; [M+H]$^-$: 607.54.

54.2. 4-{(S)-4-carboxy-2-[(6-cyclopentylamino-2-phenyl-pyrimidine-4 carbonyl)-amino]-butyryl}-piperazine-1-carboxylic acid ethyl ester triflate salt This compound was prepared using a method analogous to that of Example 1, step 1.9, intermediate 54.1 replacing intermediate 1.8.

LC-MS (A): $t_R$=1.16 min; [M+H]$^+$: 553.11; [M+H]$^-$: 551.17.

Example 55

4-{(S)-4-carboxy-2-[(6-cyclohexylamino-2-phenyl-pyrimidine-4-carbonyl)-amino]-butyryl}-piperazine-1-carboxylic acid ethyl ester triflate salt

55.1. 4-{(S)-4-tert-butoxycarbonyl-2-[(6-cyclohexylamino-2-phenyl-pyrimidine-4-carbonyl)-amino]-butyryl}-piperazine-1-carboxylic acid ethyl ester This compound was prepared using a method analogous to that of Example 49, step 49.1, cyclohexylamine replacing propylamine.

LC-MS (A): $t_R$=1.43 min; [M+H]$^+$: 623.27.

55.2. 4-{(S)-4-carboxy-2-[(6-cyclohexylamino-2-phenyl-pyrimidine-4 carbonyl)-amino]-butyryl}-piperazine-1-carboxylic acid ethyl ester triflate salt This compound was prepared using a method analogous to that of Example 1, step 1.9, intermediate 55.1 replacing intermediate 1.8.

LC-MS (A): $t_R$=1.21 min; [M+H]$^+$: 567.16; [M+H]$^-$: 565.29.

Example 56

4-((S)-4-carboxy-2-{[6-(ethoxycarbonylmethyl-amino)-2-phenyl-pyrimidine-4-carbonyl]-amino}-butyryl)-piperazine-1-carboxylic acid ethyl ester triflate salt

56.1. 4-((S)-4-tert-butoxycarbonyl-2-{[6-(ethoxycarbonylmethyl-amino)-2-phenyl-pyrimidine-4-carbonyl]-amino}-butyryl)-piperazine-1-carboxylic acid ethyl ester 4-{(S)-4-tert-butoxycarbonyl-2-[(6-chloro-2-phenyl-pyrimidine-4-carbonyl)-amino]-butyryl}-piperazine-1-carboxylic acid ethyl ester (40 mg), glycine ethyl ester hydrochloride (23.8 mg) and NEt$_3$ (20 l) were dissolved in THF (0.5 ml). The mixture was stirred at 40° C. until reaction completion. Water was added to the reaction mixture which was extracted with EA. The org. layers were dried (Na$_2$SO$_4$) and evaporated off to give 41 mg of the desired pure compound.

LC-MS (A): $t_R$=1.22 min; [M+H]$^+$: 627.15; [M+H]$^-$: 625.34.

56.2. 4-((S)-4-carboxy-2-{[6-(ethoxycarbonylmethyl-amino)-2-phenyl-pyrimidine-4-carbonyl]-amino}-butyryl)-piperazine-1-carboxylic acid ethyl ester triflate salt This compound was prepared using a method analogous to that of Example 1, step 1.9, intermediate 56.1 replacing intermediate 1.8.

LC-MS (A): $t_R$=1.02 min; [M+H]$^+$: 571.04; [M+H]$^-$: 569.24.

Example 57

4-((S)-4-carboxy-2-{[6-(carboxymethyl-amino)-2-phenyl-pyrimidine-4-carbonyl]-amino}-butyryl)-piperazine-1-carboxylic acid ethyl ester hydrochloride The triflate salt of Example 56 (40 mg) and LiOH (40 mg) were dissolved in THF/water (1/1, 1 ml). After stirring 2 h at RT, the mixture was acidified (1M HCl solution). It was extracted with EA and the resulting org. layers were dried (Na$_2$SO$_4$) and evaporated off to give 36 mg the desired compound.

LC-MS (A): $t_R$=0.90 min; [M+H]$^+$: 543.06; [M+H]$^-$: 541.19.

Example 58

4-((S)-4-carboxy-2-{[6-(2-hydroxy-ethylamino)-2-phenyl-pyrimidine-4-carbonyl]-amino}-butyryl)-piperazine-1-carboxylic acid ethyl ester hydrochloride

58.1. 4-((S)-4-tert-butoxycarbonyl-2-{[6-(2-hydroxy-ethylamino)-2-phenyl-pyrimidine-4-carbonyl]-amino}-butyryl)-piperazine-1-carboxylic acid ethyl ester This compound was prepared using a method analogous to that of Example 49, step 49.1, ethanolamine replacing propylamine.

LC-MS (A): $t_R$=1.10 min; [M+H]$^+$: 585.17; [M+H]$^-$: 583.37.

58.2. 4-((S)-4-carboxy-2-{[6-(2-hydroxy-ethylamino)-2-phenyl-pyrimidine-4-carbonyl]-amino}-butyryl)-piperazine-1-carboxylic acid ethyl ester hydrochloride Intermediate 58.1 (40 mg) was dissolved in TFA/DCM (1/1, 1 ml), and it was stirred at RT for 6 h. The mixture was evaporated off and the residue taken up in THF/solution of LiOH in order to cleave off the trifluoroacetic ester. After 1 h, the desired compound was obtained. The mixture was acidified and extracted twice with EA. The org. phases were dried and evaporated off to afford 14 mg of the desired hydrochloride salt.

LC-MS (A): $t_R$=0.90 min; [M+H]$^+$: 529.15; [M+H]$^-$: 527.21.

Example 59

4-((S)-4-carboxy-2-{[6-(2-ethoxycarbonyl-ethylamino)-2-phenyl-pyrimidine-4-carbonyl]-amino}-butyryl)-piperazine-1-carboxylic acid ethyl ester triflate salt

59.1. 4-((S)-4-tert-butoxycarbonyl-2-{[6-(2-ethoxycarbonyl-ethylamino)-2-phenyl-pyrimidine-4-carbonyl]-amino}-butyryl)-piperazine-1-carboxylic acid ethyl ester This compound was prepared using a method analogous to that of Example 56, step 56.1, beta-alanine ethyl ester hydrochloride ethanolamine replacing glycine ethyl ester hydrochloride.

LC-MS (A): $t_R$=1.25 min; [M+H]$^+$: 641.34.

59.2. 4-((S)-4-carboxy-2-{[6-(2-ethoxycarbonyl-ethylamino)-2-phenyl-pyrimidine-4-carbonyl]-amino}-butyryl)-piperazine-1-carboxylic acid ethyl ester triflate salt This compound was prepared using a method analogous to that of Example 1, step 1.9, intermediate 59.1 replacing intermediate 1.8.
LC-MS (A): $t_R$=1.02 min; [M+H]$^+$: 585.10; [M+H]$^-$: 583.30.

Example 60

4-((S)-4-carboxy-2-{[6-(2-carboxy-ethylamino)-2-phenyl-pyrimidine-4-carbonyl]-amino}-butyryl)-piperazine-1-carboxylic acid ethyl ester hydrochloride This compound was prepared using a method analogous to that of Example 57, starting however from the triflate salt of Example 59.
LC-MS (A): $t_R$=0.92 min; [M+H]$^+$: 556.97; [M+H]$^-$: 555.25.

Example 61

4-((S)-4-carboxy-2-{[6-(3-hydroxy-propylamino)-2-phenyl-pyrimidine-4-carbonyl]-amino}-butyryl)-piperazine-1-carboxylic acid ethyl ester hydrochloride

61.1. 4-((S)-4-tert-butoxycarbonyl-2-{[6-(3-hydroxy-propylamino)-2-phenyl-pyrimidine-4-carbonyl]-amino}-butyryl)-piperazine-1-carboxylic acid ethyl ester This compound was prepared using a method analogous to that of Example 49, step 49.1, 3-amino-propan-1-ol replacing propylamine.
LC-MS (A): $t_R$=1.10 min; [M+H]$^+$: 599.30; [M+H]$^-$: 597.43.

61.2. 4-((S)-4-carboxy-2-{[6-(3-hydroxy-propylamino)-2-phenyl-pyrimidine-4-carbonyl]-amino}-butyryl)-piperazine-1-carboxylic acid ethyl ester hydrochloride This compound was prepared using a method analogous to that of Example 58, step 58.2, intermediate 61.1 replacing intermediate 58.1.
LC-MS (A): $t_R$=0.90 min; [M+H]$^+$: 543.06; [M+H]$^-$: 541.40.

Example 62

4-((S)-4-carboxy-2-{[6-(3-carboxy-propylamino)-2-phenyl-pyrimidine-4-carbonyl]-amino}-butyryl)-piperazine-1-carboxylic acid ethyl ester triflate salt

62.1. 4-((S)-4-tert-butoxycarbonyl-2-{[6-(3-tert-butoxycarbonyl-propylamino)-2-phenyl-pyrimidine-4-carbonyl]-amino}-butyryl)-piperazine-1-carboxylic acid ethyl ester This compound was prepared using a method analogous to that of Example 56, step 56.1, H-γ-Abu-OtBu.HCl replacing glycine ethyl ester hydrochloride.
LC-MS (A): $t_R$=1.35 min; [M+H]$^+$: 683.15; [M+H]$^-$: 681.38.

62.2. 4-((S)-4-carboxy-2-{[6-(3-carboxy-propylamino)-2-phenyl-pyrimidine-4-carbonyl]-amino}-butyryl)-piperazine-1-carboxylic acid ethyl ester triflate salt This compound was prepared using a method analogous to that of Example 1, step 1.9, intermediate 62.1 replacing intermediate 1.8.
LC-MS (A): $t_R$=0.92 min; [M+H]$^+$: 570.97; [M+H]$^-$: 569.31.

Example 63

4-((S)-4-carboxy-2-{[6-(2-dimethylamino-ethylamino)-2-phenyl-pyrimidine-4-carbonyl]-amino}-butyryl)-piperazine-1-carboxylic acid ethyl ester triflate salt

63.1. 4-((S)-4-tert-butoxycarbonyl-2-{[6-(2-dimethylamino-ethylamino)-2-phenyl-pyrimidine-4-carbonyl]-amino}-butyryl)-piperazine-1-carboxylic acid ethyl ester This compound was prepared using a method analogous to that of Example 49, step 49.1, 2-dimethylaminoethylamine replacing propylamine.
LC-MS (A): $t_R$=0.81 min; [M+H]$^+$: 612.11.

63.2. 4-((S)-4-carboxy-2-{[6-(2-dimethylamino-ethylamino)-2-phenyl-pyrimidine-4-carbonyl]-amino}-butyryl)-piperazine-1-carboxylic acid ethyl ester triflate salt This compound was prepared using a method analogous to that of Example 1, step 1.9, intermediate 63.1 replacing intermediate 1.8.
LC-MS (A): $t_R$=0.72 min; [M+H]$^+$: 556.01; [M+H]$^-$: 554.35.

Example 64

4-((S)-4-carboxy-2-{[6-(3-dimethylamino-propylamino)-2-phenyl-pyrimidine-4-carbonyl]-amino}-butyryl)-piperazine-1-carboxylic acid ethyl ester triflate salt

64.1. 4-((S)-4-tert-butoxycarbonyl-2-{[6-(3-dimethylamino-propylamino)-2-phenyl-pyrimidine-4-carbonyl]-amino}-butyryl)-piperazine-1-carboxylic acid ethyl ester This compound was prepared using a method analogous to that of Example 49, step 49.1, 3-dimethylamino-1-propylamine replacing propylamine.
LC-MS (A): $t_R$=0.83 min; [M+H]$^+$: 626.07; [M+H]$^-$: 624.17.

64.2. 4-((S)-4-carboxy-2-{[6-(3-dimethylamino-propylamino)-2-phenyl-pyrimidine-4-carbonyl]-amino}-butyryl)-piperazine-1-carboxylic acid ethyl ester triflate salt This compound was prepared using a method analogous to that of Example 1, step 1.9, intermediate 64.1 replacing intermediate 1.8.

LC-MS (A): $t_R$=0.73 min; [M+H]$^+$: 570.07; [M+H]$^-$: 568.13.

Example 65

4-((S)-4-carboxy-2-{[6-(2-morpholin-4-yl-ethylamino)-2-phenyl-pyrimidine-4-carbonyl]-amino}-butyryl)-piperazine-1-carboxylic acid ethyl ester triflate salt 65.1. 4-((S)-4-tert-butoxycarbonyl-2-{[6-(2-morpholin-4-yl-ethylamino)-2-phenyl-pyrimidine-4-carbonyl]-amino}-butyryl)-piperazine-1-carboxylic acid ethyl ester This compound was prepared using a method analogous to that of Example 49, step 49.1, 4-(2-aminoethyl)-morpholine replacing propylamine.

LC-MS (A): $t_R$=0.81 min; [M+H]$^+$: 654.23; [M+H]$^-$: 652.50.

65.2. 4-((S)-4-carboxy-2-{[6-(2-morpholin-4-yl-ethylamino)-2-phenyl-pyrimidine-4-carbonyl]-amino}-butyryl)-piperazine-1-carboxylic acid ethyl ester triflate salt This compound was prepared using a method analogous to that of Example 1, step 1.9, intermediate 65.1 replacing intermediate 1.8.

LC-MS (A): $t_R$=0.73 min; [M+H]$^+$: 598.05; [M+H]$^-$: 596.32.

Example 66

4-((S)-4-carboxy-2-{[6-(3-morpholin-4-yl-propylamino)-2-phenyl-pyrimidine-4-carbonyl]-amino}-butyryl)-piperazine-1-carboxylic acid ethyl ester triflate salt 66.1. 4-((S)-4-tert-butoxycarbonyl-2-{[6-(3-morpholin-4-yl-propylamino)-2-phenyl-pyrimidine-4-carbonyl]-amino}-butyryl)-piperazine-1-carboxylic acid ethyl ester This compound was prepared using a method analogous to that of Example 49, step 49.1, 4-(3-aminopropyl)-morpholine replacing propylamine.

LC-MS (A): $t_R$=0.82 min; [M+H]$^+$: 668.22; [M+H]$^-$: 666.63.

66.2. 4-((S)-4-carboxy-2-{[6-(3-morpholin-4-yl-propylamino)-2-phenyl-pyrimidine-4-carbonyl]-amino}-butyryl)-piperazine-1-carboxylic acid ethyl ester triflate salt This compound was prepared using a method analogous to that of Example 1, step 1.9, intermediate 66.1 replacing intermediate 1.8.

LC-MS (A): $t_R$=0.73 min; [M+H]$^+$: 612.02; [M+H]$^-$: 611.42.

Example 67

4-{(S)-2-[(6-benzylamino-2-phenyl-pyrimidine-4-carbonyl)-amino]-4-carboxy-butyryl}-piperazine-1-carboxylic acid ethyl ester triflate salt 67.1. 4-{(S)-2-[(6-benzylamino-2-phenyl-pyrimidine-4-carbonyl)-amino]-4-tert-butoxycarbonyl-butyryl}-piperazine-1-carboxylic acid ethyl ester This compound was prepared using a method analogous to that of Example 49, step 49.1, benzylamine replacing propylamine.

LC-MS (A): $t_R$=1.32 min; [M+H]$^+$: 631.30; [M+H]$^-$: 629.57.

67.2. 4-{(S)-2-[(6-benzylamino-2-phenyl-pyrimidine-4-carbonyl)-amino]-4 carboxy-butyryl}-piperazine-1-carboxylic acid ethyl ester triflate salt This compound was prepared using a method analogous to that of Example 1, step 1.9, intermediate 67.1 replacing intermediate 1.8.

LC-MS (A): $t_R$=1.11 min; [M+H]$^+$: 575.13; [M+H]$^-$: 573.33.

Example 68

4-((S)-4-carboxy-2-{[2-phenyl-6-((S)-1-phenyl-ethylamino)-pyrimidine-4-carbonyl]-amino}-butyryl)-piperazine-1-carboxylic acid ethyl ester hydrochloride 68.1. 4-((S)-4-tert-butoxycarbonyl-2-{[2-phenyl-6-((S)-1-phenyl-ethylamino)-pyrimidine-4-carbonyl]-amino}-butyryl)-piperazine-1-carboxylic acid ethyl ester This compound was prepared using a method analogous to that of Example 49, step 49.1, (S)-methylbenzylamine replacing propylamine.

LC-MS (A): $t_R$=1.35 min; [M+H]$^+$: 645.22; [M+H]$^-$: 643.42.

68.2. 4-((S)-4-carboxy-2-{[2-phenyl-6-((S)-1-phenyl-ethylamino)-pyrimidine-4-carbonyl]-amino}-butyryl)-piperazine-1-carboxylic acid ethyl ester hydrochloride This compound was prepared using a method analogous to that of Example 1, step 1.9, intermediate 68.1 replacing intermediate 1.8, with a work up being however performed as follows. The residue was dissolved in EA. The solution was washed with a 1M LiOH solution, dried ($Na_2SO_4$) and evaporated off. The residue was again taken up in EA and a 2M solution of HCl in $Et_2O$ was added. The hydrochloride salt of the compound crushed out within seconds, was filtered off and HV dried.

LC-MS (A): $t_R$=1.12 min; [M+H]$^+$: 589.12; [M+H]$^-$: 587.25.

Example 69

4-((S)-4-carboxy-2-{[2-phenyl-6-((R)-1-phenyl-ethylamino)-pyrimidine-4-carbonyl]-amino}-butyryl)-piperazine-1-carboxylic acid ethyl ester hydrochloride 69.1. 4-((S)-4-tert-butoxycarbonyl-2-{[2-phenyl-6-((R)-1-phenyl-ethylamino)-pyrimidine-4-carbonyl]-amino}-butyryl)-piperazine-1-carboxylic acid ethyl ester This compound was prepared using a method analogous to that of Example 49, step 49.1, (R)-methylbenzylamine replacing propylamine.
LC-MS (A): $t_R$=1.34 min; [M+H]$^+$: 645.29; [M+H]$^-$: 643.49.

69.2. 4-((S)-4-carboxy-2-{[2-phenyl-6-((R)-1-phenyl-ethylamino)-pyrimidine-4-carbonyl]-amino}-butyryl)-piperazine-1-carboxylic acid ethyl ester hydrochloride This compound was prepared using a method analogous to that of Example 68, step 68.2, intermediate 69.1 replacing intermediate 68.1.
LC-MS (A): $t_R$=1.14 min; [M+H]$^+$: 589.12; [M+H]$^-$: 587.25.

Example 70

4-((S)-4-carboxy-2-{[6-((S)-2-carboxy-1-phenyl-ethylamino)-2-phenyl-pyrimidine-4-carbonyl]-amino}-butyryl)-piperazine-1-carboxylic acid ethyl ester formate salt 70.1. 4-((S)-4-tert-butoxycarbonyl-2-{[6-((S)-2-tert-butoxycarbonyl-1-phenyl-ethylamino)-2-phenyl-pyrimidine-4-carbonyl]-amino}-butyryl)-piperazine-1-carboxylic acid ethyl ester This compound was prepared using a method analogous to that of Example 49, step 49.1, tert-butyl (3S)-3-amino-3-phenylpropanoate replacing propylamine.
LC-MS (A): $t_R$=1.39 min; [M+H]$^+$: 745.32.

70.2. 4-((S)-4-carboxy-2-{[6-((S)-2-carboxy-1-phenyl-ethylamino)-2 phenyl-pyrimidine-4-carbonyl]-amino}-butyryl)-piperazine-1-carboxylic acid ethyl ester formate salt This compound was prepared using a method analogous to that of Example 1, step 1.9, intermediate 70.1 replacing intermediate 1.8. The title compound was however purified by preparative LC-MS (II).

LC-MS (A): $t_R$=1.00 min; [M+H]$^+$: 633.10; [M+H]$^-$: 631.30.

Example 71

4-((S)-4-carboxy-2-{[6-((R)-2-carboxy-1-phenyl-ethylamino)-2-phenyl-pyrimidine-4-carbonyl]-amino}-butyryl)-piperazine-1-carboxylic acid ethyl ester formate salt 71.1. 4-((S)-4-tert-butoxycarbonyl-2-{[6-((R)-2-tert-butoxycarbonyl-1-phenyl-ethylamino)-2-phenyl-pyrimidine-4-carbonyl]-amino}-butyryl)-piperazine-1-carboxylic acid ethyl ester This compound was prepared using a method analogous to that of Example 49, step 49.1, tert-butyl (3R)-3-amino-3-phenylpropanoate replacing propylamine.
LC-MS (A): $t_R$=1.39 min; [M+H]$^+$: 745.25.

71.2. 4-((S)-4-carboxy-2-{[6-((R)-2-carboxy-1-phenyl-ethylamino)-2 phenyl-pyrimidine-4-carbonyl]-amino}-butyryl)-piperazine-1-carboxylic acid ethyl ester formate salt This compound was prepared using a method analogous to that of Example 1, step 1.9, intermediate 71.1 replacing intermediate 1.8. The title compound was however purified by preparative LC-MS (II).
LC-MS (A): $t_R$=0.99 min; [M+H]$^+$: 633.00; [M+H]$^-$: 631.37.

Example 72

4-{(S)-4-carboxy-2-[(6-phenethylamino-2-phenyl-pyrimidine-4-carbonyl)-amino]-butyryl}-piperazine-1-carboxylic acid ethyl ester triflate salt 72.1. 4-{(S)-4-tert-butoxycarbonyl-2-[(6-phenethylamino-2-phenyl-pyrimidine-4-carbonyl)-amino]-butyryl}-piperazine-1-carboxylic acid ethyl ester This compound was prepared using a method analogous to that of Example 49, step 49.1, phenylethylamine replacing propylamine.
LC-MS (A): $t_R$=1.36 min; [M+H]$^+$: 645.15; [M+H]$^-$: 643.42.

72.2. 4-{(S)-4-carboxy-2-[(6-phenethylamino-2-phenyl-pyrimidine-4 carbonyl)-amino]-butyryl}-piperazine-1-carboxylic acid ethyl ester triflate salt This compound was prepared using a method analogous to that of Example 1, step 1.9, intermediate 71.1 replacing intermediate 1.8.
LC-MS (A): $t_R$=1.16 min; [M+H]$^+$: 589.05; [M+H]$^-$: 587.32.

Example 73

4-((S)-4-carboxy-2-{[2-phenyl-6-(2-phenyl-propylamino)-pyrimidine-4-carbonyl]-amino}-butyryl)-piperazine-1-carboxylic acid ethyl ester formate salt 73.1. 4-((S)-4-tert-butoxycarbonyl-2-{[2-phenyl-6-(2-phenyl-propylamino)-pyrimidine-4-carbonyl]-amino}-butyryl)-piperazine-1-carboxylic acid ethyl ester This compound was prepared using a method analogous to that of Example 49, step 49.1, A methylphenethylamine replacing propylamine.

73.2. 4-((S)-4-carboxy-2-{[2-phenyl-6-(2-phenyl-propylamino)-pyrimidine-4-carbonyl]-amino}-butyryl)-piperazine-1-carboxylic acid ethyl ester formate salt This compound was prepared using a method analogous to that of Example 1, step 1.9, intermediate 73.1 replacing intermediate 1.8. The title compound was however purified by preparative LC-MS (IV).

LC-MS (A): $t_R$=1.19 min; $[M+H]^+$: 603.06; $[M+H]^-$: 601.30.

Example 74

4-((S)-4-carboxy-2-{[6-(1,2-diphenyl-ethylamino)-2-phenyl-pyrimidine-4-carbonyl]-amino}-butyryl)-piperazine-1-carboxylic acid ethyl ester formate salt

74.1. 4-((S)-4-tert-butoxycarbonyl-2-{[6-(1,2-diphenyl-ethylamino)-2-phenyl-pyrimidine-4-carbonyl]-amino}-butyryl)-piperazine-1-carboxylic acid ethyl ester This compound was prepared using a method analogous to that of Example 49, step 49.1, 1,2-diphenylethylamine replacing propylamine.

LC-MS (A): $t_R$=1.40 min; $[M+H]^+$: 721.35; $[M+H]^-$: 719.48.

74.2. 4-((S)-4-carboxy-2-{[6-(1,2-diphenyl-ethylamino)-2-phenyl-pyrimidine-4-carbonyl]-amino}-butyryl)-piperazine-1-carboxylic acid ethyl ester formate salt This compound was prepared using a method analogous to that of Example 1, step 1.9, intermediate 74.1 replacing intermediate 1.8. The compound was however purified by preparative LC-MS (IV).

LC-MS (A): $t_R$=1.23 min; $[M+H]^+$: 665.13; $[M+H]^-$: 663.30.

Example 75

4-(4-carboxy-2-{[2-phenyl-6-(trans-2-phenyl-cyclopropylamino)-pyrimidine-4-carbonyl]-amino}-butyryl)-piperazine-1-carboxylic acid ethyl ester formate salt

75.1. 4-((S)-4-tert-butoxycarbonyl-2-{[2-phenyl-6-(trans-2-phenyl-cyclopropylamino)-pyrimidine-4-carbonyl]-amino}-butyryl)-piperazine-1-carboxylic acid ethyl ester This compound was prepared using a method analogous to that of Example 56, step 56.1, trans-2-phenylcyclopropylamine hydrochloride replacing glycine ethyl ester hydrochloride.

LC-MS (A): $t_R$=1.36 min; $[M+H]^+$: 657.16; $[M+H]^-$: 655.40.

75.2. 4-(4-carboxy-2-{[2-phenyl-6-(trans-2-phenyl-cyclopropylamino)-pyrimidine-4-carbonyl]-amino}-butyryl)-piperazine-1-carboxylic acid ethyl ester formate salt This compound was prepared using a method analogous to that of Example 1, step 1.9, intermediate 75.1 replacing intermediate 1.8. The title compound was however purified by preparative LC-MS (IV).

LC-MS (A): $t_R$=1.16 min; $[M+H]^+$: 601.05; $[M+H]^-$: 599.22.

Example 76

4-((S)-4-carboxy-2-{[6-(indan-1-ylamino)-2-phenyl-pyrimidine-4-carbonyl]-amino}-butyryl)-piperazine-1-carboxylic acid ethyl ester hydrochloride

76.1. 4-((S)-4-tert-butoxycarbonyl-2-{[6-(indan-1-ylamino)-2-phenyl-pyrimidine-4-carbonyl]-amino}-butyryl)-piperazine-1-carboxylic acid ethyl ester This compound was prepared using a method analogous to that of Example 49, step 49.1, 1-aminoindan replacing propylamine.

LC-MS (A): $t_R$=1.39 min; $[M+H]^+$: 657.28.

76.2. 4-((S)-4-carboxy-2-{[6-(indan-1-ylamino)-2-phenyl-pyrimidine-4 carbonyl]-amino}-butyryl)-piperazine-1-carboxylic acid ethyl ester hydrochloride This compound was prepared using a method analogous to that of Example 68, step 68.2, intermediate 76.1 replacing intermediate 68.1.

LC-MS (A): $t_R$=1.19 min; $[M+H]^+$: 601.17; $[M+H]^-$: 599.99.

Example 77

4-((S)-4-carboxy-2-{[6-((R)-indan-1-ylamino)-2-phenyl-pyrimidine-4-carbonyl]-amino}-butyryl)-piperazine-1-carboxylic acid ethyl ester formate salt

77.1. 4-((S)-4-tert-butoxycarbonyl-2-{[6-((R)-indan-1-ylamino)-2-phenyl-pyrimidine-4-carbonyl]-amino}-butyryl)-piperazine-1-carboxylic acid ethyl ester This compound was prepared using a method analogous to that of Example 49, step 49.1, (R)-1-aminoindan replacing propylamine.

LC-MS (A): $t_R$=1.40 min; $[M+H]^+$: 657.34; $[M+H]^-$: 655.26.

77.2. 4-((S)-4-carboxy-2-{[6-((R)-indan-1-ylamino)-2-phenyl-pyrimidine-4 carbonyl]-amino}-butyryl)-piperazine-1-carboxylic acid ethyl ester formate salt This compound was prepared using a method analogous to that of Example 1, step 1.9, intermediate 77.1 replacing intermediate 1.8. The title compound was however purified by preparative LC-MS (IV).

LC-MS (A): $t_R$=1.20 min; $[M+H]^+$: 601.06; $[M+H]^-$: 599.15.

Example 78

4-((S)-4-carboxy-2-{[6-(indan-2-ylamino)-2-phenyl-pyrimidine-4-carbonyl]-amino}-butyryl)-piperazine-1-carboxylic acid ethyl ester formate salt

78.1. 4-((S)-4-tert-butoxycarbonyl-2-{[6-(indan-2-ylamino)-2-phenyl-pyrimidine-4-carbonyl]-amino}-butyryl)-piperazine-1-carboxylic acid ethyl ester This compound was prepared using a method analogous to that of Example 56, step 56.1, 2-aminoindan hydrochloride replacing glycine ethyl ester hydrochloride.

LC-MS (A): $t_R$=1.40 min; $[M+H]^+$: 657.27; $[M+H]^-$: 655.33.

78.2. 4-((S)-4-carboxy-2-{[6-(indan-2-ylamino)-2-phenyl-pyrimidine-4-carbonyl]-amino}-butyryl)-piperazine-1-carboxylic acid ethyl ester formate salt This compound was prepared using a method analogous to that of Example 1, step 1.9, intermediate 78.1 replacing intermediate 1.8. The title compound was however purified by preparative LC-MS (IV).

LC-MS (A): $t_R$=1.20 min; $[M+H]^+$: 601.05; $[M+H]^-$: 599.15.

Example 79

4-{(S)-4-carboxy-2-[(6-dimethylamino-2-phenyl-pyrimidine-4-carbonyl)-amino]-butyryl}-piperazine-1-carboxylic acid ethyl ester triflate salt

79.1. 4-{(S)-4-tert-butoxycarbonyl-2-[(6-dimethylamino-2-phenyl-pyrimidine-4-carbonyl)-amino]-butyryl}-piperazine-1-carboxylic acid ethyl ester This compound was prepared using a method analogous to that of Example 49, step 49.1, dimethylamine replacing propylamine.

LC-MS (A): $t_R$=1.29 min; $[M+H]^+$: 569.10.

79.2. 4-{(S)-4-carboxy-2-[(6-dimethylamino-2-phenyl-pyrimidine-4 carbonyl)-amino]-butyryl}-piperazine-1-carboxylic acid ethyl ester triflate salt This compound was prepared using a method analogous to that of Example 1, step 1.9, intermediate 79.1 replacing intermediate 1.8.

LC-MS (A): $t_R$=1.05 min; $[M+H]^+$: 513.08; $[M+H]^-$: 511.14.

Example 80

4-{(S)-2-[(6-azetidin-1-yl-2-phenyl-pyrimidine-4-carbonyl)-amino]-4-carboxy-butyryl}-piperazine-1-carboxylic acid ethyl ester triflate salt

80.1. 4-{(S)-2-[(6-azetidin-1-yl-2-phenyl-pyrimidine-4-carbonyl)-amino]-4-tert-butoxycarbonyl-butyryl}-piperazine-1-carboxylic acid ethyl ester This compound was prepared using a method analogous to that of Example 49, step 49.1, azetidine replacing propylamine.

LC-MS (A): $t_R$=1.29 min; $[M+H]^+$: 581.15.

80.2. 4-{(S)-2-[(6-azetidin-1-yl-2-phenyl-pyrimidine-4-carbonyl)-amino]-4 carboxy-butyryl}-piperazine-1-carboxylic acid ethyl ester triflate salt This compound was prepared using a method analogous to that of Example 1, step 1.9, intermediate 80.1 replacing intermediate 1.8.

LC-MS (A): $t_R$=1.05 min; $[M+H]^+$: 525.06; $[M+H]^-$: 523.19.

Example 81

4-{(S)-4-carboxy-2-[(2-phenyl-6-pyrrolidin-1-yl-pyrimidine-4-carbonyl)-amino]-butyryl}-piperazine-1-carboxylic acid ethyl ester triflate salt

81.1. 4-{(S)-4-tert-butoxycarbonyl-2-[(2-phenyl-6-pyrrolidin-1-yl-pyrimidine-4-carbonyl)-amino]-butyryl}-piperazine-1-carboxylic acid ethyl ester This compound was prepared using a method analogous to that of Example 49, step 49.1, pyrrolidine replacing propylamine.

LC-MS (A): $t_R$=1.36 min; $[M+H]^+$: 595.21.

81.2. 4-{(S)-4-carboxy-2-[(2-phenyl-6-pyrrolidin-1-yl-pyrimidine-4 carbonyl)-amino]-butyryl}-piperazine-1-carboxylic acid ethyl ester triflate salt This compound was prepared using a method analogous to that of Example 1, step 1.9, intermediate 81.1 replacing intermediate 1.8.

LC-MS (A): $t_R$=1.11 min; $[M+H]^+$: 539.12; $[M+H]^-$: 537.25.

Example 82

4-{(S)-4-carboxy-2-[(2-phenyl-6-piperidin-1-yl-pyrimidine-4-carbonyl)-amino]-butyryl}-piperazine-1-carboxylic acid ethyl ester triflate salt

82.1. 4-{(S)-4-tert-butoxycarbonyl-2-[(2-phenyl-6-piperidin-1-yl-pyrimidine-4-carbonyl)-amino]-butyryl}-piperazine-1-carboxylic acid ethyl ester This compound was prepared using a method analogous to that of Example 49, step 49.1, piperidine replacing propylamine.

LC-MS (A): $t_R$=1.40 min; $[M+H]^+$: 609.21.

82.2. 4-{(S)-4-carboxy-2-[(2-phenyl-6-piperidin-1-yl-pyrimidine-4 carbonyl)-amino]-butyryl}-piperazine-1-carboxylic acid ethyl ester triflate salt This compound was prepared using a method analogous to that of Example 1, step 1.9, intermediate 82.1 replacing intermediate 1.8.

LC-MS (A): $t_R$=1.18 min; $[M+H]^+$: 553.11; $[M+H]^-$: 551.31.

Example 83

4-((S)-2-{[6-(butyl-methyl-amino)-2-phenyl-pyrimidine-4-carbonyl]-amino}-4-carboxy-butyryl)-piperazine-1-carboxylic acid ethyl ester triflate salt

83.1. 4-((S)-4-tert-butoxycarbonyl-2-{[6-(butyl-methyl-amino)-2-phenyl-pyrimidine-4-carbonyl]-amino}-butyryl)-piperazine-1-carboxylic acid ethyl ester This compound was prepared using a method analogous to that of Example 49, step 49.1, methylbutylamine replacing propylamine.
LC-MS (A): $t_R$=1.43 min; [M+H]$^+$: 611.28.

83.2. 4-((S)-2-{[6-(butyl-methyl-amino)-2-phenyl-pyrimidine-4-carbonyl]-amino}-4-carboxy-butyryl)-piperazine-1-carboxylic acid ethyl ester triflate salt This compound was prepared using a method analogous to that of Example 1, step 1.9, intermediate 80.1 replacing intermediate 1.8.
LC-MS (A): $t_R$=1.21 min; [M+H]$^+$: 555.18; [M+H]$^-$: 553.31.

Example 84

4-{(S)-4-carboxy-2-[(2-phenyl-6-phenylamino-pyrimidine-4-carbonyl)-amino]-butyryl}-piperazine-1-carboxylic acid ethyl ester triflate salt

84.1. 4-{(S)-4-tert-butoxycarbonyl-2-[(2-phenyl-6-phenylamino-pyrimidine-4-carbonyl)-amino]-butyryl}-piperazine-1-carboxylic acid ethyl ester This compound was prepared using a method analogous to that of Example 56, step 56.1, azetidine replacing glycine ethyl ester hydrochloride.
LC-MS (A): $t_R$=1.32 min; [M+H]$^+$: 617.30; [M+H]$^-$: 615.29.

84.2. 4-{(S)-4-carboxy-2-[(2-phenyl-6-phenylamino-pyrimidine-4 carbonyl)-amino]-butyryl}-piperazine-1-carboxylic acid ethyl ester triflate salt This compound was prepared using a method analogous to that of Example 1, step 1.9, intermediate 84.1 replacing intermediate 1.8. The title compound was however purified by preparative LC-MS (IV).
LC-MS (C): $t_R$=0.97 min; [M+H]$^+$: 561.23.

Example 85

4-((S)-4-carboxy-2-{[6-(4-fluoro-phenylamino)-2-phenyl-pyrimidine-4-carbonyl]-amino}-butyryl)-piperazine-1-carboxylic acid ethyl ester

85.1. 4-((S)-4-tert-butoxycarbonyl-2-{[6-(4-fluoro-phenylamino)-2-phenyl-pyrimidine-4-carbonyl]-amino}-butyryl)-piperazine-1-carboxylic acid ethyl ester This compound was prepared using a method analogous to that of Example 84, step 84.1, 4-fluoroaniline replacing aniline.
[M+H]$^+$: 635.56.

85.2. 4-((S)-4-carboxy-2-{[6-(4-fluoro-phenylamino)-2-phenyl-pyrimidine-4-carbonyl]-amino}-butyryl)-piperazine-1-carboxylic acid ethyl ester This compound was prepared using a method analogous to that of Example 1, step 1.9, intermediate 85.1 replacing intermediate 1.8. The title compound was however purified by preparative LC-MS (IV).
LC-MS (C): $t_R$=1.13 min; [M+H]$^+$: 579.26.

Example 86

4-{(S)-4-carboxy-2-[(6-methyl-2-phenyl-pyrimidine-4-carbonyl)-amino]-butyryl}-piperazine-1-carboxylic acid ethyl ester

86.1. 6-methyl-2-phenyl-pyrimidine-4-carboxylic acid methyl ester 2-chloro-6-methyl-pyrimidine-4-carboxylic acid methyl ester (930 mg), phenylboronic acid (610 mg), tetrakis(triphenylphosphine)palladium (265 mg) and potassium phosphate (2.12 g) were dissolved in anhydrous dioxane (25 ml) under argon. The mixture was refluxed overnight and worked up with water/EA. The org. phases were dried (Na$_2$SO$_4$) and evaporated off. Column chromatography (EA/Hept 1/5) offered 875 mg of the desired compound.
LC-MS (A): $t_R$=1.12 min; [M+H]$^+$: 229.01.

86.2. 6-methyl-2-phenyl-pyrimidine-4-carboxylic acid

Intermediate 86.1 (456 mg) was dissolved in a solution of NaOH (400 mg) in MeOH/water (4/1, 5 ml). After stirring 4 h at RT, MeOH was removed, a 1M HCl solution was added and the mixture was extracted with EA. The org. phases were dried (Na$_2$SO$_4$) and evaporated off to offer 409 mg of the desired compound.
LC-MS (A): $t_R$=0.96 min; [M+H]$^+$: 214.91; [M–H]$^-$: 213.25.

86.3. 4-{(S)-4-tert-butoxycarbonyl-2-[(6-methyl-2-phenyl-pyrimidine-4-carbonyl)-amino]-butyryl}-piperazine-1-carboxylic acid ethyl ester Intermediate 86.2 (214 mg), HOBT hydrate (168 mg) and EDCI hydrochloride (210 mg) were dissolved in DMF (7 ml). After 15 min stirring, 4-((S)-2-amino-4-tert-butoxycarbonyl-butyryl)-piperazine-1-carboxylic acid ethyl ester (377 mg) was added and the stirring was continued overnight at RT. A saturated NH$_4$Cl solution was added and the mixture was extracted with EA. The org. phases were dried (Na$_2$SO$_4$) and evaporated off. Column chromatography (EA/Hept 1/3 to 1/1) of the crude offered the compound still contaminated by some starting material. It was then taken up in EA and washed with a Na$_2$CO$_3$ solution, dried and evaporated off to give 462 mg of the pure desired compound.
LC-MS (A): $t_R$=1.26 min; [M+H]$^+$: 540.09; [M–H]$^-$: 538.36.

86.4. 4-{(S)-4-carboxy-2-[(6-methyl-2-phenyl-pyrimidine-4-carbonyl)-amino]-butyryl}-piperazine-1-carboxylic acid ethyl ester Intermediate 86.3 (444 mg) was dissolved in TFA/DCM (1/1, 12 ml), and it was stirred at RT for 2 h. The mixture was evaporated off and HV dried to give 391 mg of the desired compound.

LC-MS (A): $t_R$=1.01 min; [M+H]$^+$: 484.00; [M–H]$^-$: 482.27.

Example 87

4-{(S)-4-carboxy-2-[(6-isopropyl-2-phenyl-pyrimidine-4-carbonyl)-amino]-butyryl}-piperazine-1-carboxylic acid ethyl ester

87.1. 4-{(S)-4-tert-butoxycarbonyl-2-[(6-isopropyl-2-phenyl-pyrimidine-4-carbonyl)-amino]-butyryl}-piperazine-1-carboxylic acid ethyl ester Isopropylmagnesium bromide (29.5 mg) was added to an orange solution of 4-{(S)-4-tert-butoxycarbonyl-2-[(6-chloro-2-phenyl-pyrimidine-4-carbonyl)-amino]-butyryl}-piperazine-1-carboxylic acid ethyl ester (56 mg) and iron(III) acetylacetonate (1.8 mg) in anhydrous THF (1 ml) under argon. After stirring at RT for 30 min, it was quenched with a 1M HCl solution and extracted with EA. The org. phases were dried (Na$_2$SO$_4$) and evaporated off to give 50 mg of the desired compound.

LC-MS (A): $t_R$=1.40 min; [M+H]$^+$: 568.08; [M+H-Boc]$^+$: 511.87.

87.2. 4-{(S)-4-carboxy-2-[(6-isopropyl-2-phenyl-pyrimidine-4-carbonyl)-amino]-butyryl}-piperazine-1-carboxylic acid ethyl ester This compound was prepared using a method analogous to that of Example 1, step 1.9, intermediate 87.1 replacing intermediate 1.8.

LC-MS (A): $t_R$=1.14 min; [M+H]$^+$: 511.97; [M–H]$^-$: 510.17.

Example 88

4-{(S)-2-[(6-butyl-2-phenyl-pyrimidine-4-carbonyl)-amino]-4-carboxy-butyryl}-piperazine-1-carboxylic acid ethyl ester

88.1. 4-{(4-tert-butoxycarbonyl-2-[(6-butyl-2-phenyl-pyrimidine-4-carbonyl)-amino]-butyryl}-piperazine-1-carboxylic acid ethyl ester This compound was prepared using a method analogous to that of Example 86, step 86.1, 4-{(S)-4-tert-butoxycarbonyl-2-[(6-chloro-2-phenyl-pyrimidine-4-carbonyl)-amino]-butyryl}-piperazine-1-carboxylic acid ethyl ester replacing 2-chloro-6-methyl-pyrimidine-4-carboxylic acid methyl ester and butylboronic acid replacing phenylboronic acid.

LC-MS (A): $t_R$=1.42 min; [M+H]$^+$: 582.19.

88.2. 4-{(S)-2-[(6-butyl-2-phenyl-pyrimidine-4-carbonyl)-amino]-4 carboxy-butyryl}-piperazine-1-carboxylic acid ethyl ester This compound was prepared using a method analogous to that of Example 1, step 1.9, intermediate 88.1 replacing intermediate 1.8.

LC-MS (A): $t_R$=1.19 min; [M+H]$^+$: 526.10; [M–H]$^-$: 524.23.

Example 89

4-{(S)-4-carboxy-2-[(6-isobutyl-2-phenyl-pyrimidine-4-carbonyl)-amino]-butyryl}-piperazine-1-carboxylic acid ethyl ester

89.1. 4-{(S)-4-tert-butoxycarbonyl-2-[(6-isobutyl-2-phenyl-pyrimidine-4-carbonyl)-amino]-butyryl}-piperazine-1-carboxylic acid ethyl ester This compound was prepared using a method analogous to that of Example 86, step 86.1, 4-{(S)-4-tert-butoxycarbonyl-2-[(6-chloro-2-phenyl-pyrimidine-4-carbonyl)-amino]-butyryl}-piperazine-1-carboxylic acid ethyl ester replacing 2-chloro-6-methyl-pyrimidine-4-carboxylic acid methyl ester and isobutylboronic acid replacing phenylboronic acid.

LC-MS (A): $t_R$=1.43 min; [M+H]$^+$: 582.33.

89.2. 4-{(S)-4-carboxy-2-[(6-isobutyl-2-phenyl-pyrimidine-4-carbonyl)-amino]-butyryl}-piperazine-1-carboxylic acid ethyl ester This compound was prepared using a method analogous to that of Example 1, step 1.9, intermediate 89.1 replacing intermediate 1.8.

LC-MS (A): $t_R$=1.18 min; [M+H]$^+$: 526.10; [M–H]$^-$: 524.30.

Example 90

4-{(S)-4-carboxy-2-[(6-cyclopropyl-2-phenyl-pyrimidine-4-carbonyl)-amino]-butyryl}-piperazine-1-carboxylic acid ethyl ester

90.1. 4-{(S)-4-tert-butoxycarbonyl-2-[(6-cyclopropyl-2-phenyl-pyrimidine-4-carbonyl)-amino]-butyryl}-piperazine-1-carboxylic acid ethyl ester This compound was prepared using a method analogous to that of Example 86, step 86.1, 4-{(S)-4-tert-butoxycarbonyl-2-[(6-chloro-2-phenyl-pyrimidine-4-carbonyl)-amino]-butyryl}-piperazine-1-carboxylic acid ethyl ester replacing 2-chloro-6-methyl-pyrimidine-4-carboxylic acid methyl ester and cyclopropylboronic acid replacing phenylboronic acid.

LC-MS (A): $t_R$=1.35 min; [M+H]$^+$: 566.06.

90.2. 4-{(S)-4-carboxy-2-[(6-cyclopropyl-2-phenyl-pyrimidine-4-carbonyl)-amino]-butyryl}-piperazine-1-carboxylic acid ethyl ester This compound was prepared using a method analogous to that of Example 1, step 1.9, intermediate 90.1 replacing intermediate 1.8.

LC-MS (A): $t_R$=1.10 min; [M+H]$^+$: 510.03; [M–H]$^-$: 508.23.

Example 91

4-{(S)-4-carboxy-2-[(6-cyclopentyl-2-phenyl-pyrimidine-4-carbonyl)-amino]-butyryl}-piperazine-1-carboxylic acid ethyl ester

91.1. 4-{(S)-4-tert-butoxycarbonyl-2-[(6-cyclopentyl-2-phenyl-pyrimidine-4-carbonyl)-amino]-butyryl}-piperazine-1-carboxylic acid ethyl ester This compound was prepared using a method analogous to that of Example 87, step 87.1, cyclopentylmagnesium bromide replacing isopropylmagnesium bromide.

LC-MS (A): $t_R$=1.47 min; [M+H]$^+$: 594.18.

91.2. 4-{(S)-4-carboxy-2-[(6-cyclopentyl-2-phenyl-pyrimidine-4-carbonyl)-amino]-butyryl}-piperazine-1-carboxylic acid ethyl ester This compound was prepared using a method analogous to that of Example 1, step 1.9, intermediate 91.1 replacing intermediate 1.8.

LC-MS (A): $t_R$=1.22 min; [M+H]$^+$: 538.08; [M−H]$^−$: 536.21.

Example 92

4-{(S)-4-carboxy-2-[(2,6-diphenyl-pyrimidine-4-carbonyl)-amino]-butyryl}-piperazine-1-carboxylic acid ethyl ester

92.1. 4-{(S)-4-tert-butoxycarbonyl-2-[(2,6-diphenyl-pyrimidine-4-carbonyl)-amino]-butyryl}-piperazine-1-carboxylic acid ethyl ester This compound was prepared using a method analogous to that of Example 86, step 86.1, 4-{(S)-4-tert-butoxycarbonyl-2-[(6-chloro-2-phenyl-pyrimidine-4-carbonyl)-amino]-butyryl}-piperazine-1-carboxylic acid ethyl ester replacing 2-chloro-6-methyl-pyrimidine-4-carboxylic acid methyl ester.

LC-MS (A): $t_R$=1.41 min; [M+H]$^+$: 602.21.

92.2. 4-{(S)-4-carboxy-2-[(2,6-diphenyl-pyrimidine-4-carbonyl)-amino]-butyryl}-piperazine-1-carboxylic acid ethyl ester This compound was prepared using a method analogous to that of Example 1, step 1.9, intermediate 92.1 replacing intermediate 1.8.

LC-MS (A): $t_R$=1.17 min; [M+H]$^+$: 546.11.

Example 93

4-{(S)-4-carboxy-2-[(2-phenyl-6-o-tolyl-pyrimidine-4-carbonyl)-amino]-butyryl}-piperazine-1-carboxylic acid ethyl ester

93.1. 4-{(S)-4-tert-butoxycarbonyl-2-[(2-phenyl-6-o-tolyl-pyrimidine-4-carbonyl)-amino]-butyryl}-piperazine-1-carboxylic acid ethyl ester This compound was prepared using a method analogous to that of Example 86, step 86.1, 4-{(S)-4-tert-butoxycarbonyl-2-[(6-chloro-2-phenyl-pyrimidine-4-carbonyl)-amino]-butyryl}-piperazine-1-carboxylic acid ethyl ester replacing 2-chloro-6-methyl-pyrimidine-4-carboxylic acid methyl ester and 2-tolylboronic acid replacing phenylboronic acid.

LC-MS (A): $t_R$=1.41 min; [M+H]$^+$: 616.15.

93.2. 4-{(S)-4-carboxy-2-[(2-phenyl-6-o-tolyl-pyrimidine-4-carbonyl)-amino]-butyryl}-piperazine-1-carboxylic acid ethyl ester This compound was prepared using a method analogous to that of Example 1, step 1.9, intermediate 93.1 replacing intermediate 1.8.

LC-MS (A): $t_R$=1.20 min; [M+H]$^+$: 560.08; [M−H]$^−$: 558.21.

Example 94

4-{(S)-4-carboxy-2-[(2-phenyl-6-m-tolyl-pyrimidine-4-carbonyl)-amino]-butyryl}-piperazine-1-carboxylic acid ethyl ester

94.1. 4-{(S)-4-tert-butoxycarbonyl-2-[(2-phenyl-6-m-tolyl-pyrimidine-4-carbonyl)-amino]-butyryl}-piperazine-1-carboxylic acid ethyl ester This compound was prepared using a method analogous to that of Example 86, step 86.1, 4-{(S)-4-tert-butoxycarbonyl-2-[(6-chloro-2-phenyl-pyrimidine-4-carbonyl)-amino]-butyryl}-piperazine-1-carboxylic acid ethyl ester replacing 2-chloro-6-methyl-pyrimidine-4-carboxylic acid methyl ester and 3-tolylboronic acid replacing phenylboronic acid.

LC-MS (A): $t_R$=1.48 min; [M+H]$^+$: 616.19.

94.2. 4-{(S)-4-carboxy-2-[(2-phenyl-6-m-tolyl-pyrimidine-4-carbonyl)-amino]-butyryl}-piperazine-1-carboxylic acid ethyl ester This compound was prepared using a method analogous to that of Example 1, step 1.9, intermediate 94.1 replacing intermediate 1.8.

LC-MS (A): $t_R$=1.24 min; [M+H]$^+$: 559.98; [M−H]$^−$: 558.21.

Example 95

4-{(S)-4-carboxy-2-[(2-phenyl-6-p-tolyl-pyrimidine-4-carbonyl)-amino]-butyryl}-piperazine-1-carboxylic acid ethyl ester

95.1. 4-{(S)-4-tert-butoxycarbonyl-2-[(2-phenyl-6-p-tolyl-pyrimidine-4-carbonyl)-amino]-butyryl}-piperazine-1-carboxylic acid ethyl ester This compound was prepared using a method analogous to that of Example 86, step 86.1, 4-{(S)-4-tert-butoxycarbonyl-2-[(6-chloro-2-phenyl-pyrimidine-4-carbonyl)-amino]-butyryl}-piperazine-1-carboxylic acid ethyl ester replacing 2-chloro-6-methyl-pyrimidine-4-carboxylic acid methyl ester and 4-tolylboronic acid replacing phenylboronic acid.

LC-MS (A): $t_R$=1.47 min; [M+H]$^+$: 616.19.

95.2. 4-{(S)-4-carboxy-2-[(2-phenyl-6-p-tolyl-pyrimidine-4-carbonyl)-amino]-butyryl}-piperazine-1-carboxylic acid ethyl ester This compound was prepared using a method analogous to that of Example 1, step 1.9, intermediate 95.1 replacing intermediate 1.8.

LC-MS (A): $t_R$=1.23 min; [M+H]$^+$: 559.98; [M−H]$^−$: 558.21.

Example 96

4-((S)-4-carboxy-2-{[6-(3-carboxy-phenyl)-2-phenyl-pyrimidine-4-carbonyl]-amino}-butyryl)-piperazine-1-carboxylic acid ethyl ester

96.1. 4-((S)-4-tert-butoxycarbonyl-2-{[6-(3-carboxy-phenyl)-2-phenyl-pyrimidine-4-carbonyl]-amino}-butyryl)-piperazine-1-carboxylic acid ethyl ester This compound was prepared using a method analogous to that of Example 86, step 86.1, 4-{(S)-4-tert-butoxycarbonyl- 2-[(6-chloro-2-phenyl-pyrimidine-4-carbonyl)-amino]-butyryl}-piperazine-1-carboxylic acid ethyl ester replacing 2-chloro-6-methyl-pyrimidine-4-carboxylic acid methyl ester and 3-carboxyphenylboronic acid replacing phenylboronic acid.

LC-MS (A): $t_R$=1.24 min; [M+H]$^+$: 646.19.

96.2. 4-((S)-4-carboxy-2-{[6-(3-carboxy-phenyl)-2-phenyl-pyrimidine-4 carbonyl]-amino}-butyryl)-piperazine-1-carboxylic acid ethyl ester This compound was prepared using a method analogous to that of Example 1, step 1.9, intermediate 96.1 replacing intermediate 1.8.

LC-MS (A): $t_R$=1.02 min; [M+H]$^+$: 589.96; [M−H]$^−$: 588.20.

Example 97

4-((S)-4-carboxy-2-{[6-(4-carboxy-phenyl)-2-phenyl-pyrimidine-4-carbonyl]-amino}-butyryl)-piperazine-1-carboxylic acid ethyl ester

97.1. 4-((S)-4-tert-butoxycarbonyl-2-{[6-(4-carboxy-phenyl)-2-phenyl-pyrimidine-4-carbonyl]-amino}-butyryl)-piperazine-1-carboxylic acid ethyl ester This compound was prepared using a method analogous to that of Example 86, step 86.1, 4-{(S)-4-tert-butoxycarbonyl-2-[(6-chloro-2-phenyl-pyrimidine-4-carbonyl)-amino]-butyryl}-piperazine-1-carboxylic acid ethyl ester replacing 2-chloro-6-methyl-pyrimidine-4-carboxylic acid methyl ester and 4-carboxyphenylboronic acid replacing phenylboronic acid.

LC-MS (A): $t_R$=1.22 min; [M+H]$^+$: 646.12; [M−H]$^−$: 644.25.

97.2. 4-((S)-4-carboxy-2-{[6-(4-carboxy-phenyl)-2-phenyl-pyrimidine-4 carbonyl]-amino}-butyryl)-piperazine-1-carboxylic acid ethyl ester This compound was prepared using a method analogous to that of Example 1, step 1.9, intermediate 93.1 replacing intermediate 1.8.

LC-MS (A): $t_R$=1.03 min; [M+H]$^+$: 590.03; [M−H]$^−$: 588.20.

Example 98

4-((S)-4-carboxy-2-{[2-(4-fluoro-phenyl)-6-methyl-pyrimidine-4-carbonyl]-amino}-butyryl)-piperazine-1-carboxylic acid ethyl ester

98.1. 2-chloro-6-methyl-pyrimidine-4-carboxylic acid

This compound was prepared using a method analogous to that of Example 17, step 17.2, methyl 2-chloro-6-methylpyrimidine-4-carboxylate replacing intermediate 17.1 but no purification being performed.

LC-MS (A): $t_R$=0.66 min; [M−H]$^−$: 171.18.

98.2. 4-{(S)-4-tert-butoxycarbonyl-2-[(2-chloro-6-methyl-pyrimidine-4-carbonyl)-amino]-butyryl}-piperazine-1-carboxylic acid ethyl ester Intermediate 98.1 (863 mg) was dissolved in dry acetonitrile (25 ml). Oxalyl chloride (635 mg) was added and the reaction mixture was refluxed 2 h. The solvent was removed and the product dried under HV. The residue was taken up in acetonitrile (20 ml), NEt$_3$ (0.696 ml) was added followed by 4-((S)-2-amino-4-tert-butoxycarbonyl-butyryl)-piperazine-1-carboxylic acid ethyl ester (1.72 g) dissolved in DMF (5 ml). After stirring for 1 h at RT, EA was added and the mixture was washed with a NH$_4$Cl solution, a diluted AcOH solution and a solution of NaHCO$_3$. The org. layer was dried and evaporated off to offer 1.65 g of the desired compound.

LC-MS (A): $t_R$=1.11 min; [M+Na$^+$H]$^+$: 519.85.

98.3. 4-((S)-4-tert-butoxycarbonyl-2-{[2-(4-fluoro-phenyl)-6-methyl-pyrimidine-4-carbonyl]-amino}-butyryl)-piperazine-1-carboxylic acid ethyl ester This compound was prepared using a method analogous to that of Example 86, step 86.1, intermediate 98.2 replacing 2-chloro-6-methyl-pyrimidine-4-carboxylic acid methyl ester and 4-fluorophenylboronic acid replacing phenylboronic acid.

LC-MS (A): $t_R$=1.28 min; [M+H]$^+$: 558.09; [M−H]$^−$: 556.22.

98.4. 4-((S)-4-carboxy-2-{[2-(4-fluoro-phenyl)-6-methyl-pyrimidine-4 carbonyl]-amino}-butyryl)-piperazine-1-carboxylic acid ethyl ester This compound was prepared using a method analogous to that of Example 1, step 1.9, intermediate 98.3 replacing intermediate 1.8.

LC-MS (A): $t_R$=1.04 min; [M+H]$^+$: 502.00; [M−H]$^−$: 500.20.

Example 99

4-((S)-4-carboxy-2-{[2-(3-fluoro-phenyl)-6-methyl-pyrimidine-4-carbonyl]-amino}-butyryl)-piperazine-1-carboxylic acid ethyl ester

99.1. 4-((S)-4-tert-butoxycarbonyl-2-{[2-(3-fluoro-phenyl)-6-methyl-pyrimidine-4-carbonyl]-amino}-butyryl)-piperazine-1-carboxylic acid ethyl ester This compound was prepared using a method analogous to that of Example 98, step 98.3, 3-fluorophenylboronic acid replacing 4-fluorophenylboronic acid.

LC-MS (A): $t_R$=1.29 min; [M+H]$^+$: 558.09.

99.2. 4-((S)-4-carboxy-2-{[2-(3-fluoro-phenyl)-6-methyl-pyrimidine-4 carbonyl]-amino}-butyryl)-piperazine-1-carboxylic acid ethyl ester This compound was prepared using a method analogous to that of Example 1, step 1.9, intermediate 99.1 replacing intermediate 1.8.

LC-MS (A): $t_R$=1.04 min; [M+H]$^+$: 501.93; [M−H]$^−$: 500.27.

Example 100

4-((S)-4-carboxy-2-{[2-(2-fluoro-phenyl)-6-methyl-pyrimidine-4-carbonyl]-amino}-butyryl)-piperazine-1-carboxylic acid ethyl ester

100.1. 4-((S)-4-tert-butoxycarbonyl-2-{[2-(2-fluoro-phenyl)-6-methyl-pyrimidine-4-carbonyl]-amino}-butyryl)-piperazine-1-carboxylic acid ethyl ester This compound was prepared using a method analogous to that of Example 98, step 98.3, 2-fluorophenylboronic acid replacing 4-fluorophenylboronic acid.

LC-MS (A): $t_R$=1.20 min; [M+H]$^+$: 558.09.

100.2. 4-((S)-4-carboxy-2-{[2-(2-fluoro-phenyl)-6-methyl-pyrimidine-4 carbonyl]-amino}-butyryl)-piperazine-1-carboxylic acid ethyl ester This compound was prepared using a method analogous to that of Example 1, step 1.9, intermediate 100.1 replacing intermediate 1.8.
LC-MS (A): $t_R$=0.95 min; [M+H]$^+$: 502.00; [M−H]$^−$: 500.13.

Example 101

4-((S)-4-carboxy-2-{[2-(4-chloro-phenyl)-6-methyl-pyrimidine-4-carbonyl]-amino}-butyryl)-piperazine-1-carboxylic acid ethyl ester 101.1. 4-((S)-4-tert-butoxycarbonyl-2-{[2-(4-chloro-phenyl)-6-methyl-pyrimidine-4-carbonyl]-amino}-butyryl)-piperazine-1-carboxylic acid ethyl ester This compound was prepared using a method analogous to that of Example 98, step 98.3, 4-chlorophenylboronic acid replacing 4-fluorophenylboronic acid.
LC-MS (A): $t_R$=1.36 min; [M+H]$^+$: 573.93.

101.2. 4-((S)-4-carboxy-2-{[2-(4-chloro-phenyl)-6-methyl-pyrimidine-4 carbonyl]-amino}-butyryl)-piperazine-1-carboxylic acid ethyl ester This compound was prepared using a method analogous to that of Example 1, step 1.9, intermediate 101.1 replacing intermediate 1.8.
LC-MS (A): $t_R$=1.08 min; [M+H]$^+$: 518.00; [M−H]$^−$: 516.20.

Example 102

4-((S)-4-carboxy-2-{[2-(3-chloro-phenyl)-6-methyl-pyrimidine-4-carbonyl]-amino}-butyryl)-piperazine-1-carboxylic acid ethyl ester 102.1. 4-((S)-4-tert-butoxycarbonyl-2-{[2-(3-chloro-phenyl)-6-methyl-pyrimidine-4-carbonyl]-amino}-butyryl)-piperazine-1-carboxylic acid ethyl ester This compound was prepared using a method analogous to that of Example 98, step 98.3, 3-chlorophenylboronic acid replacing 4-fluorophenylboronic acid.
LC-MS (A): $t_R$=1.35 min; [M+H]$^+$: 574.09.

102.2. 4-((S)-4-carboxy-2-{[2-(3-chloro-phenyl)-6-methyl-pyrimidine-4 carbonyl]-amino}-butyryl)-piperazine-1-carboxylic acid ethyl ester This compound was prepared using a method analogous to that of Example 1, step 1.9, intermediate 102.1 replacing intermediate 1.8.
LC-MS (A): $t_R$=1.09 min; [M+H]$^+$: 517.93; [M−H]$^−$: 516.20.

Example 103

4-((S)-4-carboxy-2-{[2-(2-chloro-phenyl)-6-methyl-pyrimidine-4-carbonyl]-amino}-butyryl)-piperazine-1-carboxylic acid ethyl ester 103.1. 4-((S)-4-tert-butoxycarbonyl-2-{[2-(2-chloro-phenyl)-6-methyl-pyrimidine-4-carbonyl]-amino}-butyryl)-piperazine-1-carboxylic acid ethyl ester This compound was prepared using a method analogous to that of Example 98, step 98.3, 2-chlorophenylboronic acid replacing 4-fluorophenylboronic acid.
LC-MS (A): $t_R$=1.23 min; [M+H]$^+$: 574.09.

103.2. 4-((S)-4-carboxy-2-{[2-(2-chloro-phenyl)-6-methyl-pyrimidine-4 carbonyl]-amino}-butyryl)-piperazine-1-carboxylic acid ethyl ester This compound was prepared using a method analogous to that of Example 1, step 1.9, intermediate 103.1 replacing intermediate 1.8.
LC-MS (A): $t_R$=0.97 min; [M+H]$^+$: 518.00; [M−H]$^−$: 516.20.

Example 104

4-{(S)-4-carboxy-2-[(6-methyl-2-p-tolyl-pyrimidine-4-carbonyl)-amino]-butyryl}-piperazine-1-carboxylic acid ethyl ester 104.1. 4-{(S)-4-tert-butoxycarbonyl-2-[(6-methyl-2-p-tolyl-pyrimidine-4-carbonyl)-amino]-butyryl}-piperazine-1-carboxylic acid ethyl ester This compound was prepared using a method analogous to that of Example 98, step 98.3, p-tolylboronic acid replacing 4-fluorophenylboronic acid.
LC-MS (A): $t_R$=1.33 min; [M+H]$^+$: 553.98.

104.2. 4-{(S)-4-carboxy-2-[(6-methyl-2-p-tolyl-pyrimidine-4-carbonyl)-amino]-butyryl}-piperazine-1-carboxylic acid ethyl ester This compound was prepared using a method analogous to that of Example 1, step 1.9, intermediate 104.1 replacing intermediate 1.8.
LC-MS (A): $t_R$=1.06 min; [M+H]$^+$: 497.99; [M−H]$^−$: 496.19.

Example 105

4-{(S)-4-carboxy-2-[(6-methyl-2-m-tolyl-pyrimidine-4-carbonyl)-amino]-butyryl}-piperazine-1-carboxylic acid ethyl ester 105.1. 4-{(S)-4-tert-butoxycarbonyl-2-[(6-methyl-2-m-tolyl-pyrimidine-4-carbonyl)-amino]-butyryl}-piperazine-1-carboxylic acid ethyl ester This compound was prepared using a method analogous to that of Example 98, step 98.3, m-tolylboronic acid replacing 4-fluorophenylboronic acid.
LC-MS (A): $t_R$=1.30 min; [M+H]$^+$: 553.98.

105.2. 4-{(S)-4-carboxy-2-[(6-methyl-2-m-tolyl-pyrimidine-4-carbonyl)-amino]-butyryl}-piperazine-1-carboxylic acid ethyl ester This compound was prepared using a method analogous to that of Example 1, step 1.9, intermediate 105.1 replacing intermediate 1.8.
LC-MS (A): $t_R$=1.05 min; [M+H]$^+$: 497.99; [M−H]$^−$: 496.19.

Example 106

4-((S)-4-carboxy-2-{[2-(4-methoxy-phenyl)-6-methyl-pyrimidine-4-carbonyl]-amino}-butyryl)-piperazine-1-carboxylic acid ethyl ester

106.1. 4-((S)-4-tert-butoxycarbonyl-2-{[2-(4-methoxy-phenyl)-6-methyl-pyrimidine-4-carbonyl]-amino}-butyryl)-piperazine-1-carboxylic acid ethyl ester This compound was prepared using a method analogous to that of Example 98, step 98.3, 4-methoxyphenylboronic acid replacing 4-fluorophenylboronic acid.
LC-MS (A): $t_R$=1.25 min; [M+H]$^+$: 570.14.

106.2. 4-((S)-4-carboxy-2-{[2-(4-methoxy-phenyl)-6-methyl-pyrimidine-4 carbonyl]-amino}-butyryl)-piperazine-1-carboxylic acid ethyl ester This compound was prepared using a method analogous to that of Example 1, step 1.9, intermediate 106.1 replacing intermediate 1.8.
LC-MS (A): $t_R$=1.00 min; [M+H]$^+$: 514.05; [M−H]$^−$: 512.18.

Example 107

4-((S)-4-carboxy-2-{[2-(3-methoxy-phenyl)-6-methyl-pyrimidine-4-carbonyl]-amino}-butyryl)-piperazine-1-carboxylic acid ethyl ester

107.1. 4-((S)-4-tert-butoxycarbonyl-2-{[2-(3-methoxy-phenyl)-6-methyl-pyrimidine-4-carbonyl]-amino}-butyryl)-piperazine-1-carboxylic acid ethyl ester This compound was prepared using a method analogous to that of Example 98, step 98.3, 3-methoxyphenylboronic acid replacing 4-fluorophenylboronic acid.
LC-MS (A): $t_R$=1.26 min; [M+H]$^+$: 570.14.

107.2. 4-((S)-4-carboxy-2-{[2-(3-methoxy-phenyl)-6-methyl-pyrimidine-4 carbonyl]-amino}-butyryl)-piperazine-1-carboxylic acid ethyl ester This compound was prepared using a method analogous to that of Example 1, step 1.9, intermediate 107.1 replacing intermediate 1.8.
LC-MS (A): $t_R$=1.00 min; [M+H]$^+$: 514.05; [M−H]$^−$: 512.18.

Example 108

4-{2-[(6-isopropylamino-2-phenyl-pyrimidine-4-carbonyl)-amino]-acetyl}-piperazine-1-carboxylic acid ethyl ester

108.1. 4-{2-[(6-chloro-2-phenyl-pyrimidine-4-carbonyl)-amino]-acetyl}-piperazine-1-carboxylic acid ethyl ester Intermediate 24.3 (150 mg), intermediate 4.2 (163 mg), DIPEA (0.12 ml) and PyBOP (435 mg) were dissolved in DCM (10 ml) at 0° C. The mixture was stirred overnight in an ice bath. The solvent was removed and the residue taken up in EA. It was washed with a NH$_4$Cl solution, a NaHCO$_3$ solution and a NaCl solution. The aq. phases were back extracted with EA, the org. layers were combined, dried (Na$_2$SO$_4$) and evaporated off. Column chromatography (EA/Hept 1/2) offered 173 mg of the desired compound.
LC-MS (B): $t_R$=1.08 min; [M+H]$^+$: 432.13; [M−H]$^−$: 430.19.

108.2. 4-{2-[(6-isopropylamino-2-phenyl-pyrimidine-4-carbonyl)-amino]-acetyl}-piperazine-1-carboxylic acid ethyl ester This compound was prepared using a method analogous to that of Example 49, step 49.1, intermediate 108.1 replacing intermediate 48.1 and isopropylamine replacing propylamine.
LC-MS (B): $t_R$=1.9 min; [M+H]$^+$: 454.92.

Example 109

4-{2-[(6-benzylamino-2-phenyl-pyrimidine-4-carbonyl)-amino]-acetyl}-piperazine-1-carboxylic acid ethyl ester This compound was prepared using a method analogous to that of Example 49, step 49.1, intermediate 108.1 replacing intermediate 48.1 and benzylamine replacing propylamine.
LC-MS (B): $t_R$=1.11 min; [M+H]$^+$: 503.07; [M−H]$^−$: 502.57.

Example 110

4-{2-[(2,6-diphenyl-pyrimidine-4-carbonyl)-amino]-acetyl}-piperazine-1-carboxylic acid ethyl ester This compound was prepared using a method analogous to that of Example 86, step 86.1, intermediate 108.1 replacing 2-chloro-6-methyl-pyrimidine-4-carboxylic acid methyl ester.
LC-MS (B): $t_R$=1.15 min; [M+H]$^+$: 474.15.

Example 111

4-{2-[(6-cyclopropyl-2-phenyl-pyrimidine-4-carbonyl)-amino]-acetyl}-piperazine-1-carboxylic acid ethyl ester This compound was prepared using a method analogous to that of Example 86, step 86.1, intermediate 108.1 replacing 2-chloro-6-methyl-pyrimidine-4-carboxylic acid methyl ester and cyclopropylboronic acid replacing phenylboronic acid.
LC-MS (B): $t_R$=1.11 min; [M+H]$^+$: 438.04.

Example 112

4-{(S)-2-[(6-isopropylamino-2-phenyl-pyrimidine-4-carbonyl)-amino]-3-methyl-butyryl}-piperazine-1-carboxylic acid ethyl ester

112.1. 4-{(S)-2-[(6-chloro-2-phenyl-pyrimidine-4-carbonyl)-amino]-methyl-butyryl}-piperazine-1-carboxylic acid ethyl ester This compound was prepared using a method analogous to that of Example 108, step 108.1, intermediate 5.2 replacing intermediate 4.2.

LC-MS (B): $t_R$=1.16 min; [M+H]$^+$: 474.17; [M–H]$^-$: 472.58.

112.2. 4-{(S)-2-[(6-isopropylamino-2-phenyl-pyrimidine-4-carbonyl)-amino]-3-methyl-butyryl}-piperazine-1-carboxylic acid ethyl ester This compound was prepared using a method analogous to that of Example 49, step 49.1, intermediate 112.1 replacing intermediate 48.1 and isopropylamine replacing propylamine.
LC-MS (B): $t_R$=1.16 min; [M+H]$^+$: 497.24.

Example 113

4-{(S)-2-[(6-benzylamino-2-phenyl-pyrimidine-4-carbonyl)-amino]-3-methyl-butyryl}-piperazine-1-carboxylic acid ethyl ester This compound was prepared using a method analogous to that of Example 49, step 49.1, intermediate 112.1 replacing intermediate 48.1 and benzylamine replacing propylamine.
LC-MS (B): $t_R$=1.18 min; [M+H]$^+$: 545.32; [M–H]$^-$: 543.24.

Example 114

4-{(S)-2-[(2,6-diphenyl-pyrimidine-4-carbonyl)-amino]-3-methyl-butyryl}-piperazine-1-carboxylic acid ethyl ester This compound was prepared using a method analogous to that of Example 86, step 86.1, intermediate 112.1 replacing 2-chloro-6-methyl-pyrimidine-4-carboxylic acid methyl ester.
LC-MS (B): $t_R$=1.23 min; [M+H]$^+$: 516.57.

Example 115

4-{(S)-3-(4-carboxy-phenyl)-2-[(6-isopropylamino-2-phenyl-pyrimidine-4-carbonyl)-amino]-propionyl}-piperazine-1-carboxylic acid ethyl ester 115.1. 4-[(S)-2-[(6-chloro-2-phenyl-pyrimidine-4-carbonyl)-amino]-3-(4-methoxycarbonyl-phenyl)-propionyl]-piperazine-1-carboxylic acid ethyl ester This compound was prepared using a method analogous to that of Example 108, step 108.1, intermediate 21.3 replacing intermediate 4.2.
LC-MS (B): $t_R$=1.18 min; [M+H]$^+$: 580.02; [M–H]$^-$: 578.36.

115.2. 4-{(S)-2-[(6-isopropylamino-2-phenyl-pyrimidine-4-carbonyl)-amino]-3-(4-methoxycarbonyl-phenyl)-propionyl}-piperazine-1-carboxylic acid ethyl ester This compound was prepared using a method analogous to that of Example 49, step 49.1, intermediate 115.1 replacing intermediate 48.1 and isopropylamine replacing propylamine.
[M+H]$^+$: 603.21.

115.3. 4-{(S)-3-(4-carboxy-phenyl)-2-[(6-isopropylamino-2-phenyl-pyrimidine-4-carbonyl)-amino]-propionyl}-piperazine-1-carboxylic acid ethyl ester This compound was prepared using a method analogous to that of Example 17, step 17.2, intermediate 115.2 replacing intermediate 17.1, the title compound being purified by preparative TLC (DCM/MeOH 2%/AcOH 1%).
LC-MS (B): $t_R$=1.09 min; [M–H]$^-$: 587.37.

Example 116

4-{(S)-2-[(6-benzylamino-2-phenyl-pyrimidine-4-carbonyl)-amino]-3-(4-carboxy-phenyl)-propionyl}-piperazine-1-carboxylic acid ethyl ester 116.1. 4-[(S)-2-[(6-benzylamino-2-phenyl-pyrimidine-4-carbonyl)-amino]-3-(4-methoxycarbonyl-phenyl)-propionyl]-piperazine-1-carboxylic acid ethyl ester This compound was prepared using a method analogous to that of Example 49, step 49.1, intermediate 115.1 replacing intermediate 48.1 and benzylamine replacing propylamine.
[M+H]$^+$: 651.33.

116.2. 4-[(S)-2-[(6-benzylamino-2-phenyl-pyrimidine-4-carbonyl)-amino]-3-(4-carboxy-phenyl)-propionyl]-piperazine-1-carboxylic acid ethyl ester This compound was prepared using a method analogous to that of Example 17, step 17.2, intermediate 116.1 replacing intermediate 17.1, the title compound being purified by preparative TLC (DCM/MeOH 2%/AcOH 1%).
LC-MS (B): $t_R$=1.12 min; [M+H]$^+$: 637.46; [M–H]$^-$: 635.31.

Example 117

4-{(S)-3-(4-carboxy-phenyl)-2-[(2,6-diphenyl-pyrimidine-4-carbonyl)-amino]-propionyl}-piperazine-1-carboxylic acid ethyl ester 117.1. 4-(S)-[2-[(2,6-diphenyl-pyrimidine-4-carbonyl)-amino]-3-(4-methoxycarbonyl-phenyl)-propionyl]-piperazine-1-carboxylic acid ethyl ester This compound was prepared using a method analogous to that of Example 86, step 86.1, intermediate 115.1 replacing 2-chloro-6-methyl-pyrimidine-4-carboxylic acid methyl ester.
LC-MS (B): $t_R$=1.25 min; [M+H]$^+$: 622.22.

117.2. 4-{(S)-3-(4-carboxy-phenyl)-2-[(2,6-diphenyl-pyrimidine-4-carbonyl)-amino]-propionyl}-piperazine-1-carboxylic acid ethyl ester This compound was prepared using a method analogous to that of Example 17, step 17.2, intermediate 117.1 replacing intermediate 17.1, the title compound being purified by preparative TLC (DCM/MeOH 5%/AcOH 1%).
LC-MS (B): $t_R$=1.15 min; [M+H]$^+$: 608.36; [M–H]$^-$: 606.35.

Example 118

4-{(S)-3-(4-carboxy-phenyl)-2-[(6-cyclopropyl-2-phenyl-pyrimidine-4-carbonyl)-amino]-propionyl}-piperazine-1-carboxylic acid ethyl ester 118.1. 4-[(S)-2-[(6-cyclopropyl-2-phenyl-pyrimidine-4-carbonyl)-amino]-3-(4-methoxycarbonyl-phenyl)-propionyl]-piperazine-1-carboxylic acid ethyl ester This compound was prepared using a method analogous to that of Example 86, step 86.1, intermediate 115.1 replacing 2-chloro-6-methyl-pyrimidine-4-carboxylic acid methyl ester and cyclopropylboronic acid replacing phenylboronic acid.

LC-MS (B): $t_R$=1.20 min; [M+H]$^+$: 586.40.

118.12. 4-{(S)-3-(4-carboxy-phenyl)-2-[(6-cyclopropyl-2-phenyl-pyrimidine-4-carbonyl)-amino]-propionyl}-piperazine-1-carboxylic acid ethyl ester This compound was prepared using a method analogous to that of Example 17, step 17.2, intermediate 118.1 replacing intermediate 17.1, the title compound being purified by preparative TLC (DCM/MeOH 5%/AcOH 1%).

LC-MS (B): $t_R$=1.11 min; [M+H]$^+$: 572.40; [M–H]$^-$: 570.39.

Example 119

4-{(S)-5-carboxy-2-[(6-isopropylamino-2-phenyl-pyrimidine-4-carbonyl)-amino]-pentanoyl}-piperazine-1-carboxylic acid ethyl ester

119.1. 4-{(S)-5-tert-butoxycarbonyl-2-[(6-chloro-2-phenyl-pyrimidine-4-carbonyl)-amino]-pentanoyl}-piperazine-1-carboxylic acid ethyl ester This compound was prepared using a method analogous to that of Example 108, step 108.1, intermediate 3.2 replacing intermediate 4.2.

LC-MS (A): $t_R$=1.33 min; [M+H]$^+$: 574.34.

119.2. 4-{(S)-5-tert-butoxycarbonyl-2-[(6-isopropylamino-2-phenyl-pyrimidine-4-carbonyl)-amino]-pentanoyl}-piperazine-1-carboxylic acid ethyl ester This compound was prepared using a method analogous to that of Example 49, step 49.1, intermediate 119.1 replacing intermediate 48.1 and isopropylamine replacing propylamine.

LC-MS (A): $t_R$=1.33 min; [M+H]$^+$: 597.32.

119.3. 4-{(S)-5-carboxy-2-[(6-isopropylamino-2-phenyl-pyrimidine-4-carbonyl)-amino]-pentanoyl}-piperazine-1-carboxylic acid ethyl ester This compound was prepared using a method analogous to that of Example 1, step 1.9, intermediate 119.2 replacing intermediate 1.8.

LC-MS (A): $t_R$=1.10 min; [M+H]$^+$: 541.30; [M–H]$^-$: 539.29.

Example 120

4-{(S)-2-[(6-benzylamino-2-phenyl-pyrimidine-4-carbonyl)-amino]-5-carboxy-pentanoyl}-piperazine-1-carboxylic acid ethyl ester

120.1. 4-{(S)-2-[(6-benzylamino-2-phenyl-pyrimidine-4-carbonyl)-amino]-5-tert-butoxycarbonyl-pentanoyl}-piperazine-1-carboxylic acid ethyl ester This compound was prepared using a method analogous to that of Example 49, step 49.1, intermediate 119.1 replacing intermediate 48.1 and benzylamine replacing propylamine.

LC-MS (A): $t_R$=1.34 min; [M+H]$^+$: 645.70; [M–H]$^-$: 643.35.

120.2. 4-{(S)-2-[(6-benzylamino-2-phenyl-pyrimidine-4-carbonyl)-amino]-5-carboxy-pentanoyl}-piperazine-1-carboxylic acid ethyl ester This compound was prepared using a method analogous to that of Example 1, step 1.9, intermediate 120.1 replacing intermediate 1.8.

LC-MS (A): $t_R$=1.12 min; [M+H]$^+$: 589.31; [M–H]$^-$: 587.37.

Example 121

4-{(S)-5-carboxy-2-[(2,6-diphenyl-pyrimidine-4-carbonyl)-amino]-pentanoyl}-piperazine-1-carboxylic acid ethyl ester

121.1. 4-{(S)-5-tert-butoxycarbonyl-2-[(2,6-diphenyl-pyrimidine-4-carbonyl)-amino]-pentanoyl}-piperazine-1-carboxylic acid ethyl ester This compound was prepared using a method analogous to that of Example 86, step 86.1, intermediate 119.1 replacing 2-chloro-6-methyl-pyrimidine-4-carboxylic acid methyl ester.

LC-MS (A): $t_R$=1.42 min; [M+H]$^+$: 616.81.

121.2. 4-{(S)-5-carboxy-2-[(2,6-diphenyl-pyrimidine-4-carbonyl)-amino]-pentanoyl}-piperazine-1-carboxylic acid ethyl ester This compound was prepared using a method analogous to that of Example 1, step 1.9, intermediate 121.1 replacing intermediate 1.8.

LC-MS (A): $t_R$=1.19 min; [M+H]$^+$: 560.28; [M–H]$^-$: 558.41.

Example 122

4-{(S)-5-carboxy-2-[(6-cyclopropyl-2-phenyl-pyrimidine-4-carbonyl)-amino]-pentanoyl}-piperazine-1-carboxylic acid ethyl ester

122.1. 4-{(S)-5-tert-butoxycarbonyl-2-[(6-cyclopropyl-2-phenyl-pyrimidine-4-carbonyl)-amino]-pentanoyl}-piperazine-1-carboxylic acid ethyl ester This compound was prepared using a method analogous to that of Example 86, step 86.1, intermediate 119.1 replacing 2-chloro-6-methyl-pyrimidine-4-carboxylic acid methyl ester and cyclopropylboronic acid replacing phenylboronic acid.

LC-MS (A): $t_R$=1.38 min; [M+H]$^+$: 580.30.

122.2. 4-{(S)-5-carboxy-2-[(6-cyclopropyl-2-phenyl-pyrimidine-4-carbonyl)-amino]-pentanoyl}-piperazine-1-carboxylic acid ethyl ester This compound was prepared using a method analogous to that of Example 1, step 1.9, intermediate 122.1 replacing intermediate 1.8.

LC-MS (A): $t_R$=1.12 min; [M+H]$^+$: 524.26; [M–H]$^-$: 522.25.

Example 123

4-{(S)-2-[(6-benzylamino-2-phenyl-pyrimidine-4-carbonyl)-amino]-3-carbamoyl-propionyl}-piperazine-1-carboxylic acid ethyl ester 123.1. 4-{(S)-3-carbamoyl-2-[(6-chloro-2-phenyl-pyrimidine-4-carbonyl)-amino]-propionyl}-piperazine-1-carboxylic acid ethyl ester This compound was prepared using a method analogous to that of Example 108, step 108.1, intermediate 6.2 replacing intermediate 4.2.
LC-MS (A): $t_R$=0.99 min; [M+H]$^+$: 489.21; [M–H]$^-$: 487.20.

123.2. 4-{(S)-2-[(6-benzylamino-2-phenyl-pyrimidine-4-carbonyl)-amino]-3-carbamoyl-propionyl}-piperazine-1-carboxylic acid ethyl ester This compound was prepared using a method analogous to that of Example 49, step 49.1, intermediate 123.1 replacing intermediate 48.1 and benzylamine replacing propylamine.
LC-MS (A): $t_R$=1.05 min; [M+H]$^+$: 560.14; [M–H]$^-$: 558.41.

Example 124

4-[(S)-2-[(6-benzylamino-2-phenyl-pyrimidine-4-carbonyl)-amino]-3-(2H-tetrazol-5-yl)-propionyl]-piperazine-1-carboxylic acid ethyl ester 124.1. 4-{(S)-2-[(6-benzylamino-2-phenyl-pyrimidine-4-carbonyl)-amino]-3-cyano-propionyl}-piperazine-1-carboxylic acid ethyl ester This compound was prepared using a method analogous to that of Example 18, step 18.1, intermediate 123.2 replacing 4-{(S)-3-carbamoyl-2-[(6-cyclopentyloxy-2-phenyl-pyrimidine-4-carbonyl)-amino]-propionyl}-piperazine-1-carboxylic acid ethyl ester.
LC-MS (A): $t_R$=1.17 min; [M+H]$^+$: 542.27; [M–H]$^-$: 540.40.

124.2. 4-[(S)-2-[(6-benzylamino-2-phenyl-pyrimidine-4-carbonyl)-amino]-3-(2H-tetrazol-5-yl)-propionyl]-piperazine-1-carboxylic acid ethyl ester This compound was prepared using a method analogous to that of Example 18, step 18.2, intermediate 124.1 replacing intermediate 18.1.
LC-MS (A): $t_R$=1.09 min; [M+H]$^+$: 585.22; [M–H]$^-$: 583.35.

Example 125

4-{(S)-3-(4-hydroxy-phenyl)-2-[(6-isopropylamino-2-phenyl-pyrimidine-4-carbonyl)-amino]-propionyl}-piperazine-1-carboxylic acid ethyl ester 125.1. 4-{(S)-3-(4-benzyloxy-phenyl)-2-[(6-chloro-2-phenyl-pyrimidine-4-carbonyl)-amino]-propionyl}-piperazine-1-carboxylic acid ethyl ester This compound was prepared using a method analogous to that of Example 108, step 108.1, intermediate 22.2 replacing intermediate 4.2.
LC-MS (B): $t_R$=1.26 min; [M+H]$^+$: 628.52.

125.2. 4-{(S)-3-(4-benzyloxy-phenyl)-2-[(6-isopropylamino-2-phenyl-pyrimidine-4-carbonyl)-amino]-propionyl}-piperazine-1-carboxylic acid ethyl ester This compound was prepared using a method analogous to that of Example 49, step 49.1, intermediate 125.1 replacing intermediate 48.1 and isopropylamine replacing propylamine.
LC-MS (B): $t_R$=1.25 min; [M+H]$^+$: 699.26; [M–H]$^-$: 697.39.

125.3. 4-{(S)-3-(4-hydroxy-phenyl)-2-[(6-isopropylamino-2-phenyl-pyrimidine-4-carbonyl)-amino]-propionyl}-piperazine-1-carboxylic acid ethyl ester This compound was prepared using a method analogous to that of Example 1, step 1.2, intermediate 125.2 replacing intermediate 1.1.
LC-MS (B): $t_R$=1.10 min; [M+H]$^+$: 561.32.

The compounds of Examples 126 to 222 were prepared using a method analogous to that of the Example indicated between brackets, except that the last step of the corresponding Example was not carried out.

Example 126

4-{(S)-4-tert-butoxycarbonyl-2-[(6-cyclopentyloxy-2-phenyl-pyrimidine-4-carbonyl)-amino]-butyryl}-piperazine-1-carboxylic acid ethyl ester (Example 1). LC-MS (A): $t_R$=1.47 min; [M+H]$^+$: 610.23.

Example 127

4-{(S)-3-tert-butoxycarbonyl-2-[(6-cyclopentyloxy-2-phenyl-pyrimidine-4-carbonyl)-amino]-propionyl}-piperazine-1-carboxylic acid ethyl ester (Example 2). LC-MS (B): $t_R$=1.26 min; [M+H]$^+$: 596.25.

Example 128

4-{(S)-5-tert-butoxycarbonyl-2-[(6-cyclopentyloxy-2-phenyl-pyrimidine-4-carbonyl)-amino]-pentanoyl}-piperazine-1-carboxylic acid ethyl ester (Example 3). LC-MS (B): $t_R$=1.27 min; [M+H]$^+$: 624.16.

Example 129

4-{(S)-2-[(6-cyclopentyloxy-2-phenyl-pyrimidine-4-carbonyl)-amino]-4-ethoxycarbonylmethoxy-butyryl}-piperazine-1-carboxylic acid ethyl ester (Example 17). LC-MS (B): $t_R$=1.21 min; [M+H]$^+$: 612.38.

Example 130

4-[(S)-2-[(6-cyclopentyloxy-2-phenyl-pyrimidine-4-carbonyl)-amino]-3-(4-methoxycarbonyl-phenyl)-propionyl]-piperazine-1-carboxylic acid ethyl ester (Example 21). LC-MS (B): $t_R$=1.26 min; [M+H]$^+$: 630.39; [M–H]$^-$: 628.31.

Example 131

4-[(S)-2-[(6-cyclopentyloxy-2-phenyl-pyrimidine-4-carbonyl)-amino]-3-(4-methoxycarbonylmethoxy-phenyl)-propionyl]-piperazine-1-carboxylic acid ethyl ester (Example 22). LC-MS (B): $t_R$=1.24 min; $[M+H]^+$: 660.18.

Example 132

4-{(S)-4-tert-butoxycarbonyl-2-[(6-carboxymethoxy-2-phenyl-pyrimidine-4-carbonyl)-amino]-butyryl}-piperazine-1-carboxylic acid ethyl ester (Example 23). LC-MS (A): $t_R$=1.15 min; $[M+H]^+$: 600.13; $[M-H]^-$: 598.26.

Example 133

4-{(S)-4-tert-butoxycarbonyl-2-[(2-phenyl-6-propoxy-pyrimidine-4-carbonyl)-amino]-butyryl}-piperazine-1-carboxylic acid ethyl ester (Example 24). LC-MS (A): $t_R$=1.40 min; $[M+H]^+$: 584.14.

Example 134

4-((S)-4-tert-butoxycarbonyl-2-{[6-(2-hydroxy-ethoxy)-2-phenyl-pyrimidine-4-carbonyl]-amino}-butyryl)-piperazine-1-carboxylic acid ethyl ester (Example 25). LC-MS (A): $t_R$=1.14 min; $[M+H]^+$: 586.20; $[M-H]^-$: 584.26.

Example 135

4-{(S)-2-[(6-benzyloxy-2-phenyl-pyrimidine-4-carbonyl)-amino]-4-tert-butoxycarbonyl-butyryl}-piperazine-1-carboxylic acid ethyl ester (Example 26). LC-MS (A): $t_R$=1.39 min; $[M+H]^+$: 632.19.

Example 136

4-{(S)-4-tert-butoxycarbonyl-2-[(6-cyclopropylmethoxy-2-phenyl-pyrimidine-4-carbonyl)-amino]-butyryl}-piperazine-1-carboxylic acid ethyl ester (Example 27). LC-MS (A): $t_R$=1.39 min; $[M+H]^+$: 596.24.

Example 137

4-{(S)-4-tert-butoxycarbonyl-2-[(6-cyclohexyloxy-2-phenyl-pyrimidine-4-carbonyl)-amino]-butyryl}-piperazine-1-carboxylic acid ethyl ester (Example 28). LC-MS (A): $t_R$=1.54 min; $[M+H]^+$: 624.11.

Example 138

4-{(S)-4-tert-butoxycarbonyl-2-[(6-isopropoxy-2-phenyl-pyrimidine-4-carbonyl)-amino]-butyryl}-piperazine-1-carboxylic acid ethyl ester (Example 29). LC-MS (A): $t_R$=1.39 min; $[M+H]^+$: 584.06.

Example 139

4-{(S)-4-tert-butoxycarbonyl-2-[(6-methoxy-2-phenyl-pyrimidine-4-carbonyl)-amino]-butyryl}-piperazine-1-carboxylic acid ethyl ester (Example 30). LC-MS (A): $t_R$=1.30 min; $[M+H]^+$: 556.26.

Example 140

4-[2-[(6-cyclopentyloxy-2-phenyl-pyrimidine-4-carbonyl)-amino]-3-(3-ethoxycarbonylmethoxy-phenyl)-propionyl]-piperazine-1-carboxylic acid ethyl ester (Example 31). LC-MS (B): $t_R$=1.26 min; $[M+H]^+$: 674.53.

Example 141

4-[2-[(6-cyclopentyloxy-2-phenyl-pyrimidine-4-carbonyl)-amino]-3-(2-ethoxycarbonylmethoxy-phenyl)-propionyl]-piperazine-1-carboxylic acid ethyl ester (Example 32). LC-MS (B): $t_R$=1.27 min; $[M+H]^+$: 674.73.

Example 142

4-[(S)-2-[(6-cyclopentyloxy-2-phenyl-pyrimidine-4-carbonyl)-amino]-2-(4-ethoxycarbonylmethoxy-phenyl)-acetyl]-piperazine-1-carboxylic acid ethyl ester (Example 33). LC-MS (B): $t_R$=1.24 min; $[M+H]^+$: 660.53.

Example 143

4-{(S)-4-tert-butoxycarbonyl-2-[(6-cyclopentyloxy-2-phenyl-pyrimidine-4-carbonyl)-amino]-butyryl}-piperazine-1-carboxylic acid prop-2-ynyl ester (Example 34). LC-MS (A): $t_R$=1.39 min; $[M+H]^+$: 651.25.

Example 144

4-{(S)-4-tert-butoxycarbonyl-2-[(6-cyclopentyloxy-2-phenyl-pyrimidine-4-carbonyl)-amino]-butyryl}-piperazine-1-carboxylic acid butyl ester (Example 35). LC-MS (A): $t_R$=1.56 min; $[M+H]^+$: 638.23.

Example 145

4-{(S)-4-tert-butoxycarbonyl-2-[(6-cyclopentyloxy-2-phenyl-pyrimidine-4-carbonyl)-amino]-butyryl}-piperazine-1-carboxylic acid isobutyl ester (Example 36). LC-MS (A): $t_R$=1.56 min; $[M+H]^+$: 638.16.

Example 146

4-{(S)-4-tert-butoxycarbonyl-2-[(6-cyclopentyloxy-2-phenyl-pyrimidine-4-carbonyl)-amino]-butyryl}-piperazine-1-carboxylic acid 2,2-dimethyl-propyl ester (Example 37). LC-MS (A): $t_R$=1.60 min; $[M+H]^+$: 652.14.

Example 147

4-{(S)-4-tert-butoxycarbonyl-2-[(6-cyclopentyloxy-2-phenyl-pyrimidine-4-carbonyl)-amino]-butyryl}-piperazine-1-carboxylic acid isopropyl ester (Example 38). LC-MS (A): $t_R$=1.53 min; [M+H]$^+$: 624.24.

Example 148

4-[(S)-(6-cyclopentyloxy-2-phenyl-pyrimidine-4-carbonyl)-amino]-5-[4-(furan-2-carbonyl)-piperazin-1-yl]-5-oxo-pentanoic acid tert-butyl ester (Example 39). LC-MS (A): $t_R$=1.40 min; [M+H]$^+$: 632.27.

Example 149

4-{(S)-4-tert-butoxycarbonyl-2-[(6-cyclopentyloxy-2-phenyl-pyrimidine-4-carbonyl)-amino]-butyryl}-piperazine-1-carboxylic acid phenyl ester (Example 40). LC-MS (A): $t_R$=1.51 min; [M+H]$^+$: 658.32.

Example 150

5-((S)-4-benzoyl-piperazin-1-yl)-4-[(6-cyclopentyloxy-2-phenyl-pyrimidine-4-carbonyl)-amino]-5-oxo-pentanoic acid tert-butyl ester (Example 41). LC-MS (A): $t_R$=1.41 min; [M+H]$^+$: 642.25.

Example 151

4-{(S)-4-tert-butoxycarbonyl-2-[(6-cyclopentyloxy-2-phenyl-pyrimidine-4-carbonyl)-amino]-butyryl}-piperazine-1-carboxylic acid benzyl ester (Example 42). LC-MS (A): $t_R$=1.53 min; [M+H]$^+$: 672.31.

Example 152

5-((S)-4-butyryl-piperazin-1-yl)-4-[(6-cyclopentyloxy-2-phenyl-pyrimidine-4-carbonyl)-amino]-5-oxo-pentanoic acid tert-butyl ester (Example 43). LC-MS (A): $t_R$=1.39 min; [M+H]$^+$: 608.30.

Example 153

(S)-4-[(6-cyclopentyloxy-2-phenyl-pyrimidine-4-carbonyl)-amino]-5-oxo-5-[4-(propane-1-sulfonyl)-piperazin-1-yl]-pentanoic acid tert-butyl ester (Example 44). LC-MS (A): $t_R$=1.45 min; [M+H]$^+$: 644.18; [M−H]$^-$: 643.91.

Example 154

4-{(S)-4-tert-butoxycarbonyl-2-[(6-cyclopentyloxy-2-phenyl-pyrimidine-4-carbonyl)-amino]-butyryl}-3-methyl-piperazine-1-carboxylic acid ethyl ester (Example 45). LC-MS (A): $t_R$=1.49 min; [M+H]$^+$: 624.19.

Example 155

4-{(S)-4-tert-butoxycarbonyl-2-[(6-cyclopentyloxy-2-phenyl-pyrimidine-4-carbonyl)-amino]-butyryl}-2-methyl-piperazine-1-carboxylic acid ethyl ester (Example 46). LC-MS (A): $t_R$=1.50 min; [M+H]$^+$: 624.17.

Example 156

4-{(S)-4-tert-butoxycarbonyl-2-[(6-cyclopentyloxy-2-phenyl-pyrimidine-4-carbonyl)-amino]-butyryl}-trans-2,5-dimethyl-piperazine-1-carboxylic acid ethyl ester (Example 47). LC-MS (A): $t_R$=1.52 min; [M+H]$^+$: 638.23.

Example 157

4-{(S)-4-tert-butoxycarbonyl-2-[(6-methylamino-2-phenyl-pyrimidine-4-carbonyl)-amino]-butyryl}-piperazine-1-carboxylic acid ethyl ester (Example 48). LC-MS (A): $t_R$=1.21 min; [M+H]$^+$: 555.11; [M−H]$^-$: 553.45.

Example 158

4-{(S)-4-tert-butoxycarbonyl-2-[(2-phenyl-6-propylamino-pyrimidine-4-carbonyl)-amino]-butyryl}-piperazine-1-carboxylic acid ethyl ester (Example 49). LC-MS (A): $t_R$=1.32 min; [M+H]$^+$: 583.23; [M−H]$^-$: 581.50.

Example 159

4-{(S)-4-tert-butoxycarbonyl-2-[(6-isopropylamino-2-phenyl-pyrimidine-4-carbonyl)-amino]-butyryl}-piperazine-1-carboxylic acid ethyl ester (Example 50). LC-MS (A): $t_R$=1.31 min; [M+H]$^+$: 583.30; [M+H]$^-$: 581.57.

Example 160

4-{(S)-4-tert-butoxycarbonyl-2-[(6-butylamino-2-phenyl-pyrimidine-4-carbonyl)-amino]-butyryl}-piperazine-1-carboxylic acid ethyl ester (Example 51). LC-MS (A): $t_R$=1.37 min; [M+H]$^+$: 597.22.

Example 161

4-{(S)-4-tert-butoxycarbonyl-2-[(6-isobutylamino-2-phenyl-pyrimidine-4-carbonyl)-amino]-butyryl}-piperazine-1-carboxylic acid ethyl ester (Example 52). LC-MS (A): $t_R$=1.37 min; [M+H]$^+$: 597.22.

Example 162

4-{(S)-4-tert-butoxycarbonyl-2-[(6-cyclopropylamino-2-phenyl-pyrimidine-4-carbonyl)-amino]-butyryl}-piperazine-1-carboxylic acid ethyl ester (Example 53). LC-MS (A): $t_R$=1.25 min; [M+H]$^+$: 581.15; [M+H]$^-$: 579.49.

Example 163

4-{(S)-4-tert-butoxycarbonyl-2-[(6-cyclopentylamino-2-phenyl-pyrimidine-4-carbonyl)-amino]-butyryl}-piperazine-1-carboxylic acid ethyl ester (Example 54). LC-MS (A): $t_R$=1.39 min; [M+H]$^+$: 609.21; [M+H]$^-$: 607.54.

Example 164

4-{(S)-4-tert-butoxycarbonyl-2-[(6-cyclohexylamino-2-phenyl-pyrimidine-4-carbonyl)-amino]-butyryl}-piperazine-1-carboxylic acid ethyl ester (Example 55). LC-MS (A): $t_R$=1.43 min; [M+H]$^+$: 623.27.

Example 165

4-((S)-4-tert-butoxycarbonyl-2-{[6-(ethoxycarbonyl-methyl-amino)-2-phenyl-pyrimidine-4-carbonyl]-amino}-butyryl)-piperazine-1-carboxylic acid ethyl ester (Example 56). LC-MS (A): $t_R$=1.22 min; [M+H]$^+$: 627.15; [M+H]$^-$: 625.34.

Example 166

4-((S)-4-tert-butoxycarbonyl-2-{[6-(2-hydroxy-ethylamino)-2-phenyl-pyrimidine-4-carbonyl]-amino}-butyryl)-piperazine-1-carboxylic acid ethyl ester (Example 58). LC-MS (A): $t_R$=1.10 min; [M+H]$^+$: 585.17; [M+H]$^-$: 583.37.

Example 167

4-((S)-4-tert-butoxycarbonyl-2-{[6-(2-ethoxycarbonyl-ethylamino)-2-phenyl-pyrimidine-4-carbonyl]-amino}-butyryl)-piperazine-1-carboxylic acid ethyl ester (Example 59). LC-MS (A): $t_R$=1.25 min; [M+H]$^+$: 641.34.

Example 168

4-((S)-4-tert-butoxycarbonyl-2-{[6-(3-hydroxy-propylamino)-2-phenyl-pyrimidine-4-carbonyl]-amino}-butyryl)-piperazine-1-carboxylic acid ethyl ester (Example 61). LC-MS (A): $t_R$=1.10 min; [M+H]$^+$: 599.30; [M+H]$^-$: 597.43.

Example 169

4-((S)-4-tert-butoxycarbonyl-2-{[6-(3-tert-butoxycarbonyl-propylamino)-2-phenyl-pyrimidine-4-carbonyl]-amino}-butyryl)-piperazine-1-carboxylic acid ethyl ester (Example 62). LC-MS (A): $t_R$=1.35 min; [M+H]$^+$: 683.15; [M+H]$^-$: 681.38.

Example 170

4-((S)-4-tert-butoxycarbonyl-2-{[6-(2-dimethylamino-ethylamino)-2-phenyl-pyrimidine-4-carbonyl]-amino}-butyryl)-piperazine-1-carboxylic acid ethyl ester (Example 63). LC-MS (A): $t_R$=0.81 min; [M+H]$^+$: 612.11.

Example 171

4-((S)-4-tert-butoxycarbonyl-2-{[6-(3-dimethylamino-propylamino)-2-phenyl-pyrimidine-4-carbonyl]-amino}-butyryl)-piperazine-1-carboxylic acid ethyl ester (Example 64). LC-MS (A): $t_R$=0.83 min; [M+H]$^+$: 626.07; [M+H]$^-$: 624.17.

Example 172

4-((S)-4-tert-butoxycarbonyl-2-{[6-(2-morpholin-4-yl-ethylamino)-2-phenyl-pyrimidine-4-carbonyl]-amino}-butyryl)-piperazine-1-carboxylic acid ethyl ester (Example 65). LC-MS (A): $t_R$=0.81 min; [M+H]$^+$: 654.23; [M+H]$^-$: 652.50.

Example 173

4-((S)-4-tert-butoxycarbonyl-2-{[6-(3-morpholin-4-yl-propylamino)-2-phenyl-pyrimidine-4-carbonyl]-amino}-butyryl)-piperazine-1-carboxylic acid ethyl ester (Example 66). LC-MS (A): $t_R$=0.82 min; [M+H]$^+$: 668.22; [M+H]$^-$: 666.63.

Example 174

4-{(S)-2-[(6-benzylamino-2-phenyl-pyrimidine-4-carbonyl)-amino]-4-tert-butoxycarbonyl-butyryl}-piperazine-1-carboxylic acid ethyl ester (Example 67). LC-MS (A): $t_R$=1.32 min; [M+H]$^+$: 631.30; [M+H]$^-$: 629.57.

Example 175

4-((S)-4-tert-butoxycarbonyl-2-{[2-phenyl-6-((S)-1-phenyl-ethylamino)-pyrimidine-4-carbonyl]-amino}-butyryl)-piperazine-1-carboxylic acid ethyl ester (Example 68). LC-MS (A): $t_R$=1.35 min; [M+H]$^+$: 645.22; [M+H]$^-$: 643.42.

Example 176

4-((S)-4-tert-butoxycarbonyl-2-{[2-phenyl-6-((R)-1-phenyl-ethylamino)-pyrimidine-4-carbonyl]-amino}-butyryl)-piperazine-1-carboxylic acid ethyl ester (Example 69). LC-MS (A): $t_R$=1.34 min; $[M+H]^+$: 645.29; $[M+H]^-$: 643.49.

Example 177

4-((S)-4-tert-butoxycarbonyl-2-{[6-((S)-2-tert-butoxycarbonyl-1-phenyl-ethylamino)-2-phenyl-pyrimidine-4-carbonyl]-amino}-butyryl)-piperazine-1-carboxylic acid ethyl ester (Example 70). LC-MS (A): $t_R$=1.39 min; $[M+H]^+$: 745.32.

Example 178

4-((S)-4-tert-butoxycarbonyl-2-{[6-((R)-2-tert-butoxycarbonyl-1-phenyl-ethylamino)-2-phenyl-pyrimidine-4-carbonyl]-amino}-butyryl)-piperazine-1-carboxylic acid ethyl ester (Example 71). LC-MS (A): $t_R$=1.39 min; $[M+H]^+$: 745.25.

Example 179

4-{(S)-4-tert-butoxycarbonyl-2-[(6-phenethylamino-2-phenyl-pyrimidine-4-carbonyl)-amino]-butyryl}-piperazine-1-carboxylic acid ethyl ester (Example 72). LC-MS (A): $t_R$=1.36 min; $[M+H]^+$: 645.15; $[M+H]^-$: 643.42.

Example 180

4-((S)-4-tert-butoxycarbonyl-2-{[2-phenyl-6-(2-phenyl-propylamino)-pyrimidine-4-carbonyl]-amino}-butyryl)-piperazine-1-carboxylic acid ethyl ester (Example 73). LC-MS (A): $t_R$=1.41 min; $[M+H]^+$: 659.28; $[M+H]^-$: 657.13.

Example 181

4-((S)-4-tert-butoxycarbonyl-2-{[6-(1,2-diphenyl-ethylamino)-2-phenyl-pyrimidine-4-carbonyl]-amino}-butyryl)-piperazine-1-carboxylic acid ethyl ester (Example 74). LC-MS (A): $t_R$=1.40 min; $[M+H]^+$: 721.35; $[M+H]^-$: 719.48.

Example 182

4-((S)-4-tert-butoxycarbonyl-2-{[2-phenyl-6-(trans-2-phenyl-cyclopropylamino)-pyrimidine-4-carbonyl]-amino}-butyryl)-piperazine-1-carboxylic acid ethyl ester (Example 75). LC-MS (A): $t_R$=1.36 min; $[M+H]^+$: 657.16; $[M+H]^-$: 655.40.

Example 183

4-((S)-4-tert-butoxycarbonyl-2-{[6-(indan-1-ylamino)-2-phenyl-pyrimidine-4-carbonyl]-amino}-butyryl)-piperazine-1-carboxylic acid ethyl ester (Example 76). LC-MS (A): $t_R$=1.39 min; $[M+H]^+$: 657.28.

Example 184

4-((S)-4-tert-butoxycarbonyl-2-{[6-((R)-indan-1-ylamino)-2-phenyl-pyrimidine-4-carbonyl]-amino}-butyryl)-piperazine-1-carboxylic acid ethyl ester (Example 77). LC-MS (A): $t_R$=1.40 min; $[M+H]^+$: 657.34; $[M+H]^-$: 655.26.

Example 185

4-((S)-4-tert-butoxycarbonyl-2-{[6-(indan-2-ylamino)-2-phenyl-pyrimidine-4-carbonyl]-amino}-butyryl)-piperazine-1-carboxylic acid ethyl ester (Example 78). LC-MS (A): $t_R$=1.40 min; $[M+H]^+$: 657.27; $[M+H]^-$: 655.33.

Example 186

4-{(S)-4-tert-butoxycarbonyl-2-[(6-dimethylamino-2-phenyl-pyrimidine-4-carbonyl)-amino]-butyryl}-piperazine-1-carboxylic acid ethyl ester (Example 79). LC-MS (A): $t_R$=1.29 min; $[M+H]^+$: 569.10.

Example 187

4-{(S)-2-[(6-azetidin-1-yl-2-phenyl-pyrimidine-4-carbonyl)-amino]-4-tert-butoxycarbonyl-butyryl}-piperazine-1-carboxylic acid ethyl ester (Example 80). LC-MS (A): $t_R$=1.29 min; $[M+H]^+$: 581.15.

Example 188

4-{(S)-4-tert-butoxycarbonyl-2-[(2-phenyl-6-pyrrolidin-1-yl-pyrimidine-4-carbonyl)-amino]-butyryl}-piperazine-1-carboxylic acid ethyl ester (Example 81). LC-MS (A): $t_R$=1.36 min; $[M+H]^+$: 595.21.

Example 189

4-{(S)-4-tert-butoxycarbonyl-2-[(2-phenyl-6-piperidin-1-yl-pyrimidine-4-carbonyl)-amino]-butyryl}-piperazine-1-carboxylic acid ethyl ester (Example 82). LC-MS (A): $t_R$=1.40 min; $[M+H]^+$: 609.21.

Example 190

4-((S)-4-tert-butoxycarbonyl-2-{[6-(butyl-methyl-amino)-2-phenyl-pyrimidine-4-carbonyl]-amino}-butyryl)-piperazine-1-carboxylic acid ethyl ester (Example 83). LC-MS (A): $t_R$=1.43 min; $[M+H]^+$: 611.28.

Example 191

4-{(S)-4-tert-butoxycarbonyl-2-[(2-phenyl-6-phenylamino-pyrimidine-4-carbonyl)-amino]-butyryl}-piperazine-1-carboxylic acid ethyl ester (Example 84). LC-MS (A): $t_R$=1.32 min; $[M+H]^+$: 617.30; $[M+H]^-$: 615.29.

Example 192

4-((S)-4-tert-butoxycarbonyl-2-{[6-(4-fluoro-phenylamino)-2-phenyl-pyrimidine-4-carbonyl]-amino}-butyryl)-piperazine-1-carboxylic acid ethyl ester (Example 85). $[M+H]^+$: 635.56.

Example 193

4-{(S)-4-tert-butoxycarbonyl-2-[(6-methyl-2-phenyl-pyrimidine-4-carbonyl)-amino]-butyryl}-piperazine-1-carboxylic acid ethyl ester (Example 86). LC-MS (A): $t_R$=1.26 min; $[M+H]^+$: 540.09; $[M-H]^-$: 538.36.

Example 194

4-{(S)-4-tert-butoxycarbonyl-2-[(6-isopropyl-2-phenyl-pyrimidine-4-carbonyl)-amino]-butyryl}-piperazine-1-carboxylic acid ethyl ester (Example 87). LC-MS (A): $t_R$=1.40 min; $[M+H]^+$: 568.08; $[M+H-Boc]^+$: 511.87.

Example 195

4-{4-tert-butoxycarbonyl-2-[(6-butyl-2-phenyl-pyrimidine-4-carbonyl)-amino]-butyryl}-piperazine-1-carboxylic acid ethyl ester (Example 88). LC-MS (A): $t_R$=1.42 min; $[M+H]^+$: 582.19.

Example 196

4-{(S)-4-tert-butoxycarbonyl-2-[(6-isobutyl-2-phenyl-pyrimidine-4-carbonyl)-amino]-butyryl}-piperazine-1-carboxylic acid ethyl ester (Example 89). LC-MS (A): $t_R$=1.43 min; $[M+H]^+$: 582.33.

Example 197

4-{(S)-4-tert-butoxycarbonyl-2-[(6-cyclopropyl-2-phenyl-pyrimidine-4-carbonyl)-amino]-butyryl}-piperazine-1-carboxylic acid ethyl ester (Example 90). LC-MS (A): $t_R$=1.35 min; $[M+H]^+$: 566.06.

Example 198

4-{(S)-4-tert-butoxycarbonyl-2-[(6-cyclopentyl-2-phenyl-pyrimidine-4-carbonyl)-amino]-butyryl}-piperazine-1-carboxylic acid ethyl ester (Example 91). LC-MS (A): $t_R$=1.47 min; $[M+H]^+$: 594.18.

Example 199

4-{(S)-4-tert-butoxycarbonyl-2-[(2,6-diphenyl-pyrimidine-4-carbonyl)-amino]-butyryl}-piperazine-1-carboxylic acid ethyl ester (Example 92). LC-MS (A): $t_R$=1.41 min; $[M+H]^+$: 602.21.

Example 200

4-{(S)-4-tert-butoxycarbonyl-2-[(2-phenyl-6-o-tolyl-pyrimidine-4-carbonyl)-amino]-butyryl}-piperazine-1-carboxylic acid ethyl ester (Example 93). LC-MS (A): $t_R$=1.41 min; $[M+H]^+$: 616.15.

Example 201

4-{(S)-4-tert-butoxycarbonyl-2-[(2-phenyl-6-m-tolyl-pyrimidine-4-carbonyl)-amino]-butyryl}-piperazine-1-carboxylic acid ethyl ester (Example 94). LC-MS (A): $t_R$=1.48 min; $[M+H]^+$: 616.19.

Example 202

4-{(S)-4-tert-butoxycarbonyl-2-[(2-phenyl-6-p-tolyl-pyrimidine-4-carbonyl)-amino]-butyryl}-piperazine-1-carboxylic acid ethyl ester (Example 95). LC-MS (A): $t_R$=1.47 min; $[M+H]^+$: 616.19.

Example 203

4-((S)-4-tert-butoxycarbonyl-2-{[6-(3-carboxy-phenyl)-2-phenyl-pyrimidine-4-carbonyl]-amino}-butyryl)-piperazine-1-carboxylic acid ethyl ester (Example 96). LC-MS (A): $t_R$=1.24 min; $[M+H]^+$: 646.19.

Example 204

4-((S)-4-tert-butoxycarbonyl-2-{[6-(4-carboxy-phenyl)-2-phenyl-pyrimidine-4-carbonyl]-amino}-butyryl)-piperazine-1-carboxylic acid ethyl ester (Example 97). LC-MS (A): $t_R$=1.22 min; $[M+H]^+$: 646.12; $[M-H]^-$: 644.25.

Example 205

4-((S)-4-tert-butoxycarbonyl-2-{[2-(4-fluoro-phenyl)-6-methyl-pyrimidine-4-carbonyl]-amino}-butyryl)-piperazine-1-carboxylic acid ethyl ester (Example 98). LC-MS (A): $t_R$=1.28 min; $[M+H]^+$: 558.09; $[M-H]^-$: 556.22.

Example 206

4-((S)-4-tert-butoxycarbonyl-2-{[2-(3-fluoro-phenyl)-6-methyl-pyrimidine-4-carbonyl]-amino}-butyryl)-piperazine-1-carboxylic acid ethyl ester (Example 99). LC-MS (A): $t_R$=1.29 min; $[M+H]^+$: 558.09.

Example 207

4-((S)-4-tert-butoxycarbonyl-2-{[2-(2-fluoro-phenyl)-6-methyl-pyrimidine-4-carbonyl]-amino}-butyryl)-piperazine-1-carboxylic acid ethyl ester (Example 100). LC-MS (A): $t_R$=1.20 min; [M+H]$^+$: 558.09.

Example 208

4-((S)-4-tert-butoxycarbonyl-2-{[2-(4-chloro-phenyl)-6-methyl-pyrimidine-4-carbonyl]-amino}-butyryl)-piperazine-1-carboxylic acid ethyl ester (Example 101). LC-MS (A): $t_R$=1.36 min; [M+H]$^+$: 573.93.

Example 209

4-((S)-4-tert-butoxycarbonyl-2-{[2-(3-chloro-phenyl)-6-methyl-pyrimidine-4-carbonyl]-amino}-butyryl)-piperazine-1-carboxylic acid ethyl ester (Example 102). LC-MS (A): $t_R$=1.35 min; [M+H]$^+$: 574.09.

Example 210

4-((S)-4-tert-butoxycarbonyl-2-{[2-(2-chloro-phenyl)-6-methyl-pyrimidine-4-carbonyl]-amino}-butyryl)-piperazine-1-carboxylic acid ethyl ester (Example 103). LC-MS (A): $t_R$=1.23 min; [M+H]$^+$: 574.09.

Example 211

4-{(S)-4-tert-butoxycarbonyl-2-[(6-methyl-2-p-tolyl-pyrimidine-4-carbonyl)-amino]-butyryl}-piperazine-1-carboxylic acid ethyl ester (Example 104). LC-MS (A): $t_R$=1.33 min; [M+H]$^+$: 553.98.

Example 212

4-{(S)-4-tert-butoxycarbonyl-2-[(6-methyl-2-m-tolyl-pyrimidine-4-carbonyl)-amino]-butyryl}-piperazine-1-carboxylic acid ethyl ester (Example 105). LC-MS (A): $t_R$=1.30 min; [M+H]$^+$: 553.98.

Example 213

4-((S)-4-tert-butoxycarbonyl-2-{[2-(4-methoxy-phenyl)-6-methyl-pyrimidine-4-carbonyl]-amino}-butyryl)-piperazine-1-carboxylic acid ethyl ester (Example 106). LC-MS (A): $t_R$=1.25 min; [M+H]$^+$: 570.14.

Example 214

4-((S)-4-tert-butoxycarbonyl-2-{[2-(3-methoxy-phenyl)-6-methyl-pyrimidine-4-carbonyl]-amino}-butyryl)-piperazine-1-carboxylic acid ethyl ester (Example 107). LC-MS (A): $t_R$=1.26 min; [M+H]$^+$: 570.14.

Example 215

4-[(S)-2-[(6-isopropylamino-2-phenyl-pyrimidine-4-carbonyl)-amino]-3-(4-methoxycarbonyl-phenyl)-propionyl]-piperazine-1-carboxylic acid ethyl ester (Example 115). [M+H]$^+$: 603.21.

Example 216

4-[(S)-2-[(6-benzylamino-2-phenyl-pyrimidine-4-carbonyl)-amino]-3-(4-methoxycarbonyl-phenyl)-propionyl]-piperazine-1-carboxylic acid ethyl ester (Example 116). [M+H]$^+$: 651.33.

Example 217

4-(S)-[2-[(2,6-diphenyl-pyrimidine-4-carbonyl)-amino]-3-(4-methoxycarbonyl-phenyl)-propionyl]-piperazine-1-carboxylic acid ethyl ester (Example 117). LC-MS (B): $t_R$=1.25 min; [M+H]$^+$: 622.22.

Example 218

4-[(S)-2-[(6-cyclopropyl-2-phenyl-pyrimidine-4-carbonyl)-amino]-3-(4-methoxycarbonyl-phenyl)-propionyl]-piperazine-1-carboxylic acid ethyl ester (Example 118). LC-MS (B): $t_R$=1.20 min; [M+H]$^+$: 586.40.

Example 219

4-{(S)-5-tert-butoxycarbonyl-2-[(6-isopropylamino-2-phenyl-pyrimidine-4-carbonyl)-amino]-pentanoyl}-piperazine-1-carboxylic acid ethyl ester (Example 119). LC-MS (A): $t_R$=1.33 min; [M+H]$^+$: 597.32.

Example 220

4-{(S)-2-[(6-benzylamino-2-phenyl-pyrimidine-4-carbonyl)-amino]-5-tert-butoxycarbonyl-pentanoyl}-piperazine-1-carboxylic acid ethyl ester (Example 120). LC-MS (A): $t_R$=1.34 min; [M+H]$^+$: 645.70; [M−H]$^-$: 643.35.

Example 221

4-{(S)-5-tert-butoxycarbonyl-2-[(2,6-diphenyl-pyrimidine-4-carbonyl)-amino]-pentanoyl}-piperazine-1-carboxylic acid ethyl ester (Example 121). LC-MS (A): $t_R$=1.42 min; [M+H]$^+$: 616.81.

Example 222

4-{(S)-5-tert-butoxycarbonyl-2-[(6-cyclopropyl-2-phenyl-pyrimidine-4-carbonyl)-amino]-pentanoyl}-piperazine-1-carboxylic acid ethyl ester (Example 122). LC-MS (A): $t_R$=1.38 min; [M+H]$^+$: 580.30.

Example 223

4-((S)-4-carboxy-2-{[6-(2-methoxy-1-methyl-ethylamino)-2-phenyl-pyrimidine-4-carbonyl]-amino}-butyryl)-piperazine-1-carboxylic acid ethyl ester formate salt 223.1. 4-((S)-4-tert-butoxycarbonyl-2-{[6-(2-methoxy-1-methyl-ethylamino)-2-phenyl-pyrimidine-4-carbonyl]-amino}-butyryl)-piperazine-1-carboxylic acid ethyl ester This compound was prepared using a method analogous to that of Example 49, step 49.1, 2-amino-1-methoxypropane replacing propylamine.

LC-MS (B): $t_R$=1.16 min; [M+H]$^+$: 613.49; [M−H]$^-$: 611.76.

223.2. 4-((S)-4-carboxy-2-{[6-(2-methoxy-1-methyl-ethylamino)-2-phenyl-pyrimidine-4-carbonyl]-amino}-butyryl)-piperazine-1-carboxylic acid ethyl ester formate salt This compound was prepared using a method analogous to that of Example 1, step 1.9, intermediate 223.1 replacing intermediate 1.8. The compound was however purified by preparative LC-MS (water/acetonitrile/formic acid).

LC-MS (B): $t_R$=1.03 min; [M+H]$^+$: 557.38; [M−H]$^-$: 556.82.

Example 224

4-((S)-4-carboxy-2-{[6-(isopropyl-methyl-amino)-2-phenyl-pyrimidine-4-carbonyl]-amino}-butyryl)-piperazine-1-carboxylic acid ethyl ester formate salt 224.1. 4-((S)-4-tert-butoxycarbonyl-2-{[6-(isopropyl-methyl-amino)-2-phenyl-pyrimidine-4-carbonyl]-amino}-butyryl)-piperazine-1-carboxylic acid ethyl ester This compound was prepared using a method analogous to that of Example 49, step 49.1, N-isopropylmethylamine replacing propylamine.

LC-MS (B): $t_R$=1.23 min; [M+H]$^+$: 597.49.

224.2. 4-((S)-4-carboxy-2-{[6-(isopropyl-methyl-amino)-2-phenyl-pyrimidine-4-carbonyl]-amino}-butyryl)-piperazine-1-carboxylic acid ethyl ester formate salt This compound was prepared using a method analogous to that of Example 1, step 1.9, intermediate 224.1 replacing intermediate 1.8. The compound was however purified by preparative LC-MS (water/acetonitrile/formic acid).

LC-MS (B): $t_R$=1.07 min; [M+H]$^+$: 541.45; [M−H]$^-$: 539.51.

Example 225

4-{(S)-4-carboxy-2-[(6-morpholin-4-yl-2-phenyl-pyrimidine-4-carbonyl)-amino]-butyryl}-piperazine-1-carboxylic acid ethyl ester formate salt 225.1. 4-{(S)-4-tert-butoxycarbonyl-2-[(6-morpholin-4-yl-2-phenyl-pyrimidine-4-carbonyl)-amino]-butyryl}-piperazine-1-carboxylic acid ethyl ester This compound was prepared using a method analogous to that of Example 49, step 49.1, morpholine replacing propylamine.

LC-MS (B): $t_R$=1.17 min; [M+H]$^+$: 611.55; [M−H]$^-$: 609.75.

225.2. 4-{(S)-4-carboxy-2-[(6-morpholin-4-yl-2-phenyl-pyrimidine-4-carbonyl)-amino]-butyryl}-piperazine-1-carboxylic acid ethyl ester formate salt This compound was prepared using a method analogous to that of Example 1, step 1.9, intermediate 225.1 replacing intermediate 1.8. The compound was however purified by preparative LC-MS (water/acetonitrile/formic acid).

LC-MS (B): $t_R$=1.00 min; [M+H]$^+$: 555.44; [M−H]$^-$: 553.57.

Example 226

4-{(S)-4-carboxy-2-[(2-phenyl-6-thiazolidin-3-yl-pyrimidine-4-carbonyl)-amino]-butyryl}-piperazine-1-carboxylic acid ethyl ester formate salt 226.1. 4-{(S)-4-tert-butoxycarbonyl-2-[(2-phenyl-6-thiazolidin-3-yl-pyrimidine-4-carbonyl)-amino]-butyryl}-piperazine-1-carboxylic acid ethyl ester This compound was prepared using a method analogous to that of Example 49, step 49.1, thiazolidine replacing propylamine.

LC-MS (B): $t_R$=1.21 min; [M+H]$^+$: 613.49.

226.2. 4-{(S)-4-carboxy-2-[(2-phenyl-6-thiazolidin-3-yl-pyrimidine-4-carbonyl)-amino]-butyryl}-piperazine-1-carboxylic acid ethyl ester formate salt This compound was prepared using a method analogous to that of Example 1, step 1.9, intermediate 226.1 replacing intermediate 1.8. The compound was however purified by preparative LC-MS (water/acetonitrile/formic acid).

LC-MS (B): $t_R$=1.06 min; [M+H]$^+$: 557.38; [M−H]$^-$: 555.58.

Example 227

4-((S)-4-carboxy-2-{[6-(4-hydroxy-piperidin-1-yl)-2-phenyl-pyrimidine-4-carbonyl]-amino}-butyryl)-piperazine-1-carboxylic acid ethyl ester hydrochloride

227.1. 4-((S)-4-tert-butoxycarbonyl-2-{[6-(4-hydroxy-piperidin-1-yl)-2-phenyl-pyrimidine-4-carbonyl]-amino}-butyryl)-piperazine-1-carboxylic acid ethyl ester This compound was prepared using a method analogous to that of Example 49, step 49.1, 4-hydroxypiperidine replacing propylamine.
LC-MS (B): $t_R$=1.11 min; [M+H]$^+$: 625.54.

227.2. 4-((S)-4-carboxy-2-{[6-(4-hydroxy-piperidin-1-yl)-2-phenyl-pyrimidine-4-carbonyl]-amino}-butyryl)-piperazine-1-carboxylic acid ethyl ester hydrochloride This compound was prepared using a method analogous to that of Example 58, step 58.2, intermediate 227.1 replacing intermediate 58.1. The compound was however purified by preparative LC-MS (water/acetonitrile/formic acid) giving the desired compound and 4-((S)-4-carboxy-2-{[6-(4-formyloxy-piperidin-1-yl)-2-phenyl-pyrimidine-4-carbonyl]-amino}-butyryl)-piperazine-1-carboxylic acid ethyl ester. The mixture was taken up in THF/solution of LiOH in order to cleave off the formyl group. After reaction completion, the mixture was acidified and extracted twice with DCM. The org. phases were dried and evaporated off to afford 9 mg of the desired hydrochloride salt.
LC-MS (B): $t_R$=0.95 min; [M+H]$^+$: 569.43; [M−H]$^-$: 567.63.

Example 228

4-((S)-4-carboxy-2-{[6-(piperazin-1-yl)-2-phenyl-pyrimidine-4-carbonyl]-amino}-butyryl)-piperazine-1-carboxylic acid ethyl ester dihydrochloride

228.1. 4-((S)-4-tert-butoxycarbonyl-2-{[6-(piperazin-1-yl)-2-phenyl-pyrimidine-4-carbonyl]-amino}-butyryl)-piperazine-1-carboxylic acid ethyl ester This compound was prepared using a method analogous to that of Example 49, step 49.1, piperazine replacing propylamine.
LC-MS (B): $t_R$=0.85 min; [M+H]$^+$: 610.51; [M−H]$^-$: 608.78.

228.2. 4-((S)-4-carboxy-2-{[6-(piperazin-1-yl)-2-phenyl-pyrimidine-4-carbonyl]-amino}-butyryl)-piperazine-1-carboxylic acid ethyl ester dihydrochloride This compound was prepared using a method analogous to that of Example 1, step 1.9, intermediate 228.1 replacing intermediate 1.8. The compound was however purified by preparative LC-MS (water/acetonitrile/formic acid) giving a mixture of the desired compound and 4-((S)-4-carboxy-2-{[6-(4-formyl-piperazin-1-yl)-2-phenyl-pyrimidine-4-carbonyl]-amino}-butyryl)-piperazine-1-carboxylic acid ethyl ester. The mixture was taken up in a 1M solution of NaOH in order to cleave off the formyl group. It was evaporated off and the residue was taken up in DCM and the resulting suspension filtered off. A 3M solution of HCl in EA was added to the obtained solution, which induced the precipitation of the desired compound as hydrochloride salt (1.3 mg).
LC-MS (B): $t_R$=0.76 min; [M+H]$^+$: 554.47; [M−H]$^-$: 552.67.

Example 229

4-((S)-4-carboxy-2-{[6-(2-hydroxy-1-methyl-ethylamino)-2-phenyl-pyrimidine-4-carbonyl]-amino}-butyryl)-piperazine-1-carboxylic acid ethyl ester hydrochloride

229.1. 4-((S)-4-tert-butoxycarbonyl-2-{[6-(2-hydroxy-1-methyl-ethylamino)-2-phenyl-pyrimidine-4-carbonyl]-amino}-butyryl)-piperazine-1-carboxylic acid ethyl ester This compound was prepared using a method analogous to that of Example 49, step 49.1, DL-2-amino-propanol replacing propylamine.
LC-MS (B): $t_R$=1.08 min; [M+H]$^+$: 599.49; [M−H]$^-$: 597.86.

229.2. 4-((S)-4-carboxy-2-{[6-(2-hydroxy-1-methyl-ethylamino)-2-phenyl-pyrimidine-4-carbonyl]-amino}-butyryl)-piperazine-1-carboxylic acid ethyl ester hydrochloride This compound was prepared using a method analogous to that of Example A5, step A5.2, intermediate 229.1 replacing intermediate A5.1.
LC-MS (B): $t_R$=0.93 min; [M+H]$^+$: 543.45; [M−H]$^-$: 541.58.

Example 230

4-((S)-4-carboxy-2-{[6-(4-hydroxy-butylamino)-2-phenyl-pyrimidine-4-carbonyl]-amino}-butyryl)-piperazine-1-carboxylic acid ethyl ester

230.1. 4-((S)-4-tert-butoxycarbonyl-2-{[6-(4-hydroxy-butylamino)-2-phenyl-pyrimidine-4-carbonyl]-amino}-butyryl)-piperazine-1-carboxylic acid ethyl ester This compound was prepared using a method analogous to that of Example 49, step 49.1, 4-amino-1-butanol replacing propylamine.
LC-MS (B): $t_R$=1.09 min; [M+H]$^+$: 613.56; [M−H]$^-$: 611.62.

230.2. 4-((S)-4-carboxy-2-{[6-(4-hydroxy-butylamino)-2-phenyl-pyrimidine-4-carbonyl]-amino}-butyryl)-piperazine-1-carboxylic acid ethyl ester Intermediate 230.1 (35 mg) was dissolved in TFA/DCM (1/1, 1 ml), and it was stirred at RT overnight. The mixture was evaporated off and the residue taken up in THF/solution of LiOH in order to cleave off the trifluoroacetic ester. After 3 h, the desired compound was obtained. The mixture was neutralized to pH 7 and extracted twice with EA. The org. phases were dried and evaporated off to afford 19 mg of the desired compound.

Example 231

4-((S)-4-carboxy-2-{[6-(2-hydroxy-propylamino)-2-phenyl-pyrimidine-4-carbonyl]-amino}-butyryl)-piperazine-1-carboxylic acid ethyl ester 231.1. 4-((S)-4-tert-butoxycarbonyl-2-{[6-(2-hydroxy-propylamino)-2-phenyl-pyrimidine-4-carbonyl]-amino}-butyryl)-piperazine-1-carboxylic acid ethyl ester This compound was prepared using a method analogous to that of Example 49, step 49.1, 1-amino-2-propanol replacing propylamine.

LC-MS (B): $t_R$=1.07 min; [M+H]$^+$: 599.49; [M−H]$^−$: 597.76.

231.2. 4-((S)-4-carboxy-2-{[6-(2-hydroxy-propylamino)-2-phenyl-pyrimidine-4-carbonyl]-amino}-butyryl)-piperazine-1-carboxylic acid ethyl ester This compound was prepared using a method analogous to that of Example 230, step 230.2, intermediate 231.1 replacing intermediate 230.1.

LC-MS (B): $t_R$=0.92 min; [M+H]$^+$: 543.32; [M−H]$^−$: 541.45.

Example 232

4-[(S)-4-carboxy-2-({2-phenyl-6-[(tetrahydro-furan-2-ylmethyl)-amino]-pyrimidine-4-carbonyl}-amino)-butyryl]-piperazine-1-carboxylic acid ethyl ester formate salt 232.1. 4-[(S)-4-tert-butoxycarbonyl-2-({(2-phenyl-6-[(tetrahydro-furan-2-ylmethyl)-amino]-pyrimidine-4-carbonyl}-amino)-butyryl]-piperazine-1-carboxylic acid ethyl ester This compound was prepared using a method analogous to that of Example 49, step 49.1, tetrahydrofurfurylamine replacing propylamine.

LC-MS (B): $t_R$=1.16 min; [M+H]$^+$: 625.54; [M−H]$^−$: 623.74.

232.2. 4-{(S)-4-carboxy-2-[(2-phenyl-6-[(tetrahydro-furan-2-ylmethyl)-amino]-pyrimidine-4-carbonyl}-amino)-butyryl]-piperazine-1-carboxylic acid ethyl ester formate salt This compound was prepared using a method analogous to that of Example 1, step 1.9, intermediate 232.1 replacing intermediate 1.8. The compound was however purified by preparative LC-MS (water/acetonitrile/formic acid).

LC-MS (B): $t_R$=1.01 min; [M+H]$^+$: 569.29; [M−H]$^−$: 567.56.

Example 233

4-((S)-4-carboxy-2-{[6-((R)-2-hydroxymethyl-pyrrolidin-1-yl)-2-phenyl-pyrimidine-4-carbonyl]-amino}-butyryl)-piperazine-1-carboxylic acid ethyl ester 233.1. 4-((S)-4-tert-butoxycarbonyl-2-{[6-((R)-2-hydroxymethyl-pyrrolidin-1-yl)-2-phenyl-pyrimidine-4-carbonyl]-amino}-butyryl)-piperazine-1-carboxylic acid ethyl ester This compound was prepared using a method analogous to that of Example 49, step 49.1, D-prolinol replacing propylamine.

LC-MS (B): $t_R$=1.14 min; [M+H]$^+$: 625.61.

233.2. 4-((S)-4-carboxy-2-{[6-((R)-2-hydroxymethyl-pyrrolidin-1-yl)-2-phenyl-pyrimidine-4-carbonyl]-amino}-butyryl)-piperazine-1-carboxylic acid ethyl ester This compound was prepared using a method analogous to that of Example 230, step 230.2, intermediate 233.1 replacing intermediate 230.1.

LC-MS (B): $t_R$=0.97 min; [M+H]$^+$: 569.36; [M−H]$^−$: 567.42.

Example 234

4-((S)-4-carboxy-2-{[6-((S)-2-hydroxymethyl-pyrrolidin-1-yl)-2-phenyl-pyrimidine-4-carbonyl]-amino}-butyryl)-piperazine-1-carboxylic acid ethyl ester 234.1. 4-((S)-4-tert-butoxycarbonyl-2-{[6-((S)-2-hydroxymethyl-pyrrolidin-1-yl)-2-phenyl-pyrimidine-4-carbonyl]-amino}-butyryl)-piperazine-1-carboxylic acid ethyl ester This compound was prepared using a method analogous to that of Example 49, step 49.1, L-prolinol replacing propylamine.

LC-MS (B): $t_R$=1.13 min; [M+H]$^+$: 625.61; [M−H]$^−$: 623.95.

234.2. 4-((S)-4-carboxy-2-{[6-((S)-2-hydroxymethyl-pyrrolidin-1-yl)-2-phenyl-pyrimidine-4-carbonyl]-amino}-butyryl)-piperazine-1-carboxylic acid ethyl ester This compound was prepared using a method analogous to that of Example 230, step 230.2, intermediate 234.1 replacing intermediate 230.1.

LC-MS (B): $t_R$=0.97 min; [M+H]$^+$: 569.36; [M−H]$^−$: 567.56.

Example 235

4-((S)-4-carboxy-2-{[6-((S)-3-hydroxy-pyrrolidin-1-yl)-2-phenyl-pyrimidine-4-carbonyl]-amino}-butyryl)-piperazine-1-carboxylic acid ethyl ester 235.1. 4-((S)-4-tert-butoxycarbonyl-2-{[6-((S)-3-hydroxy-pyrrolidin-1-yl)-2-phenyl-pyrimidine-4-carbonyl]-amino}-butyryl)-piperazine-1-carboxylic acid ethyl ester This compound was prepared using a method analogous to that of Example 49, step 49.1, (S)-3-hydroxypyrrolidine replacing propylamine.

LC-MS (B): $t_R$=1.10 min; [M+H]$^+$: 611.48; [M–H]$^-$: 610.79.

235.2. 4-((S)-4-carboxy-2-{[6-((S)-3-hydroxy-pyrrolidin-1-yl)-2-phenyl-pyrimidine-4-carbonyl]-amino}-butyryl)-piperazine-1-carboxylic acid ethyl ester This compound was prepared using a method analogous to that of Example 230, step 230.2, intermediate 235.1 replacing intermediate 230.1.
LC-MS (B): $t_R$=0.94 min; [M+H]$^+$: 55.37; [M–H]$^-$: 553.50.

Example 236

4-((S)-4-carboxy-2-{[6-((R)-3-hydroxy-pyrrolidin-1-yl)-2-phenyl-pyrimidine-4-carbonyl]-amino}-butyryl)-piperazine-1-carboxylic acid ethyl ester 236.1. 4-((S)-4-tert-butoxycarbonyl-2-{[6-((R)-3-hydroxy-pyrrolidin-1-yl)-2-phenyl-pyrimidine-4-carbonyl]-amino}-butyryl)-piperazine-1-carboxylic acid ethyl ester This compound was prepared using a method analogous to that of Example 49, step 49.1, (R)-3-hydroxypyrrolidine replacing propylamine.
LC-MS (B): $t_R$=1.10 min; [M+H]$^+$: 611.55.

236.2. 4-((S)-4-carboxy-2-{[6-((R)-3-hydroxy-pyrrolidin-1-yl)-2-phenyl-pyrimidine-4-carbonyl]-amino}-butyryl)-piperazine-1-carboxylic acid ethyl ester This compound was prepared using a method analogous to that of Example 230, step 230.2, intermediate 236.1 replacing intermediate 230.1.
LC-MS (B): $t_R$=0.92 min; [M+H]$^+$: 555.30; [M–H]$^-$: 553.43.

Example 237

4-[(S)-4-carboxy-2-({2-phenyl-6-[(R)-(tetrahydro-furan-3-yl)amino]-pyrimidine-4-carbonyl}-amino)-butyryl]-piperazine-1-carboxylic acid ethyl ester formate salt 237.1. 4-[(S)-4-tert-butoxycarbonyl-2-({2-phenyl-6-[(R)-(tetrahydro-furan-3-yl)amino]-pyrimidine-4-carbonyl}-amino)-butyryl]-piperazine-1-carboxylic acid ethyl ester This compound was prepared using a method analogous to that of Example 49, step 49.1, (R)-3-aminotetrahydrofuran replacing propylamine.
LC-MS (B): $t_R$=1.13 min; [M+H]$^+$: 611.27.

237.2. 4-[(S)-4-carboxy-2-({2-phenyl-6-[(R)-(tetrahydro-furan-3-yl)amino]-pyrimidine-4-carbonyl}-amino)-butyryl]-piperazine-1-carboxylic acid ethyl ester formate salt This compound was prepared using a method analogous to that of Example 230, step 230.2, intermediate 237.1 replacing intermediate 230.1.
LC-MS (B): $t_R$=0.97 min; [M+H]$^+$: 555.37; [M–H]$^-$: 553.36.

Example 238

4-{(S)-4-carboxy-2-[(6-imidazol-1-yl-2-phenyl-pyrimidine-4-carbonyl)-amino]-butyryl}-piperazine-1-carboxylic acid ethyl ester 238.1. 4-{(S)-4-tert-butoxycarbonyl-2-[(6-imidazol-1-yl-2-phenyl-pyrimidine-4-carbonyl)-amino]-butyryl}-piperazine-1-carboxylic acid ethyl ester Imidazole (3 mg) was added to a suspension of NaH (1.7 mg) in anhydrous THF (0.2 ml) at RT. After 30 min stirring at RT, 4-{(S)-4-tert-butoxycarbonyl-2-[(6-chloro-2-phenyl-pyrimidine-4-carbonyl)-amino]-butyryl}-piperazine-1-carboxylic acid ethyl ester (25 mg) dissolved in THF (0.2 ml) was added. The mixture was allowed to stir at RT overnight. Water was added and the resulting mixture was extracted with DCM. The org. phases were dried (Na$_2$SO$_4$) and evaporated off.
LC-MS (B): $t_R$=1.14 min; [M+H]$^+$: 592.50; [M–H]$^-$: 590.63.

238.2. 4-{(S)-4-carboxy-2-[(6-imidazol-1-yl-2-phenyl-pyrimidine-4-carbonyl)-amino]-butyryl}-piperazine-1-carboxylic acid ethyl ester This compound was prepared using a method analogous to that of Example 1, step 1.9, intermediate 238.1 replacing intermediate 1.8. The compound was however purified by preparative LC-MS (water/acetonitrile/formic acid).
LC-MS (B): $t_R$=1.04 min; [M+H]$^+$: 536.46; [M–H]$^-$: 534.59.

Example 239

4-{(S)-4-carboxy-2-[(2-phenyl-6-pyrazol-1-yl-pyrimidine-4-carbonyl)-amino]-butyryl}-piperazine-1-carboxylic acid ethyl ester 239.1. 4-{(S)-4-tert-butoxycarbonyl-2-[(2-phenyl-6-pyrazol-1-yl-pyrimidine-4-carbonyl)-amino]-butyryl}-piperazine-1-carboxylic acid ethyl ester This compound was prepared using a method analogous to that of Example 238, step 238.1, pyrazole replacing imidazole.
LC-MS (B): $t_R$=1.20 min; [M+H]$^+$: 592.50.

239.2. 4-{(S)-4-carboxy-2-[(2-phenyl-6-pyrazol-1-yl-pyrimidine-4-carbonyl)-amino]-butyryl}-piperazine-1-carboxylic acid ethyl ester This compound was prepared using a method analogous to that of Example 1, step 1.9, intermediate 239.1 replacing intermediate 1.8. The compound was however purified by preparative LC-MS (water/acetonitrile/formic acid).
LC-MS (B): $t_R$=0.93 min; [M+H]$^+$: 536.32; [M–H]$^-$: 534.45.

Example 240

4-((S)-4-carboxy-2-{[6-((S)-2-hydroxy-1-methyl-ethylamino)-2-phenyl-pyrimidine-4-carbonyl]-amino}-butyryl)-piperazine-1-carboxylic acid ethyl ester 240.1. 4-((S)-4-tert-butoxycarbonyl-2-{[6-((S)-2-hydroxy-1-methyl-ethylamino)-2-phenyl-pyrimidine-4-carbonyl]-amino}-butyryl)-piperazine-1-carboxylic acid ethyl ester This compound was prepared using a method analogous to that of Example 49, step 49.1, (S)-(+)-2-amino-1-propanol replacing propylamine.
LC-MS (B): $t_R$=1.09 min; [M+H]$^+$: 599.36; [M−H]$^-$: 597.49.

240.2. 4-((S)-4-carboxy-2-{[6-((S)-2-hydroxy-1-methyl-ethylamino)-2-phenyl-pyrimidine-4-carbonyl]-amino}-butyryl)-piperazine-1-carboxylic acid ethyl ester This compound was prepared using a method analogous to that of Example 230, step 230.2, intermediate 240.1 replacing intermediate 230.1.
LC-MS (B): $t_R$=0.93 min; [M+H]$^+$: 543.45; [M−H]$^-$: 541.45.

Example 241

4-((S)-4-carboxy-2-{[6-((R)-2-hydroxy-1-methyl-ethylamino)-2-phenyl-pyrimidine-4-carbonyl]-amino}-butyryl)-piperazine-1-carboxylic acid ethyl ester 241.1. 4-((S)-4-tert-butoxycarbonyl-2-{[6-((R)-2-hydroxy-1-methyl-ethylamino)-2-phenyl-pyrimidine-4-carbonyl]-amino}-butyryl)-piperazine-1-carboxylic acid ethyl ester This compound was prepared using a method analogous to that of Example 49, step 49.1, (R)-(−)-2-amino-1-propanol replacing propylamine.
LC-MS (B): $t_R$=1.08 min; [M+H]$^+$: 599.43; [M−H]$^-$: 597.55.

241.2. 4-((S)-4-carboxy-2-{[6-((R)-2-hydroxy-1-methyl-ethylamino)-2-phenyl-pyrimidine-4-carbonyl]-amino}-butyryl)-piperazine-1-carboxylic acid ethyl ester
This compound was prepared using a method analogous to that of Example 230, step 230.2, intermediate 241.1 replacing intermediate 230.1.
LC-MS (B): $t_R$=0.92 min; [M+H]$^+$: 543.32; [M−H]$^-$: 541.45.

Example 242

4-((S)-4-carboxy-2-{[6-(2-hydroxy-1,1-dimethyl-ethylamino)-2-phenyl-pyrimidine-4-carbonyl]-amino}-butyryl)-piperazine-1-carboxylic acid ethyl ester 242.1. 4-((S)-4-tert-butoxycarbonyl-2-{[6-(2-hydroxy-1,1-dimethyl-ethylamino)-2-phenyl-pyrimidine-4-carbonyl]-amino}-butyryl)-piperazine-1-carboxylic acid ethyl ester This compound was prepared using a method analogous to that of Example 49, step 49.1, 2-amino-2-methyl-1-propanol replacing propylamine.
LC-MS (B): $t_R$=1.11 min; [M+H]$^+$: 613.42; [M−H]$^-$: 611.55.

242.2. 4-((S)-4-carboxy-2-{[6-(2-hydroxy-1,1-dimethyl-ethylamino)-2-phenyl-pyrimidine-4-carbonyl]-amino}-butyryl)-piperazine-1-carboxylic acid ethyl ester This compound was prepared using a method analogous to that of Example 230, step 230.2, intermediate 242.1 replacing intermediate 230.1.
LC-MS (B): $t_R$=0.97 min; [M+H]$^+$: 557.38; [M−H]$^-$: 555.51.

Example 243

4-((S)-4-carboxy-2-{[6-(trans-4-hydroxy-cyclohexylamino)-2-phenyl-pyrimidine-4-carbonyl]-amino}-butyryl)-piperazine-1-carboxylic acid ethyl ester 243.1. 4-((S)-4-tert-butoxycarbonyl-2-{[6-(trans-4-hydroxy-cyclohexylamino)-2-phenyl-pyrimidine-4-carbonyl]-amino}-butyryl)-piperazine-1-carboxylic acid ethyl ester This compound was prepared using a method analogous to that of Example 49, step 49.1, trans-4-aminocyclohexanol replacing propylamine.
LC-MS (B): $t_R$=1.19 min; [M+H]$^+$: 639.54; [M−H]$^-$: 637.53.

243.2. 4-((S)-4-carboxy-2-2-{[6-(trans-4-hydroxy-cyclohexylamino)-2-phenyl-pyrimidine-4-carbonyl]-amino}-butyryl)-piperazine-1-carboxylic acid ethyl ester This compound was prepared using a method analogous to that of Example 230, step 230.2, intermediate 243.1 replacing intermediate 230.1.
LC-MS (B): $t_R$=0.92 min; [M+H]$^+$: 583.42; [M−H]$^-$: 581.55.

Example 244

4-((S)-4-carboxy-2-{[6-(3-hydroxy-piperidin-1-yl)-2-phenyl-pyrimidine-4-carbonyl]-amino}-butyryl)-piperazine-1-carboxylic acid ethyl ester 244.1. 4-((S)-4-tert-butoxycarbonyl-2-{[6-(3-hydroxy-piperidin-1-yl)-2-phenyl-pyrimidine-4-carbonyl]-amino}-butyryl)-piperazine-1-carboxylic acid ethyl ester This compound was prepared using a method analogous to that of Example 49, step 49.1, 3-hydroxypiperidine replacing propylamine.
LC-MS (B): $t_R$=1.12 min; [M+H]$^+$: 625.47; [M−H]$^-$: 623.53.

244.2. 4-((S)-4-carboxy-2-{[6-(3-hydroxy-piperidin-1-yl)-2-phenyl-pyrimidine-4-carbonyl]-amino}-butyryl)-piperazine-1-carboxylic acid ethyl ester This compound was prepared using a method analogous to that of Example 230, step 230.2, intermediate 244.1 replacing intermediate 230.1. The compound was however purified by preparative LC-MS (water/acetonitrile/formic acid). The

Example 245

4-((S)-4-carboxy-2-{[6-(2-hydroxymethyl-piperidin-1-yl)-2-phenyl-pyrimidine-4-carbonyl]-amino}-butyryl)-piperazine-1-carboxylic acid ethyl ester 245.1. 4-((S)-4-tert-butoxycarbonyl-2-{[6-(2-hydroxymethyl-piperidin-1-yl)-2-phenyl-pyrimidine-4-carbonyl]-amino}-butyryl)-piperazine-1-carboxylic acid ethyl ester This compound was prepared using a method analogous to that of Example 49, step 49.1, 2-hydroxymethylpiperidine replacing propylamine.

LC-MS (B): $t_R$=1.15 min; [M+H]$^+$: 639.47; [M−H]$^-$: 637.60.

245.2. 4-((S)-4-carboxy-2-{[6-(2-hydroxymethyl-piperidin-1-yl)-2-phenyl-pyrimidine-4-carbonyl]-amino}-butyryl)-piperazine-1-carboxylic acid ethyl ester This compound was prepared using a method analogous to that of Example 230, step 230.2, intermediate 245.1 replacing intermediate 230.1.

LC-MS (B): $t_R$=1.02 min; [M+H]$^+$: 583.35; [M−H]$^-$: 581.48.

Example 246

4-((S)-4-carboxy-2-{[6-(trans-2-hydroxy-cyclohexylamino)-2-phenyl-pyrimidine-4-carbonyl]-amino}-butyryl)-piperazine-1-carboxylic acid ethyl ester 246.1. 4-((S)-4-tert-butoxycarbonyl-2-{[6-(trans-2-hydroxy-cyclohexylamino)-2-phenyl-pyrimidine-4-carbonyl]-amino}-butyryl)-piperazine-1-carboxylic acid ethyl ester This compound was prepared using a method analogous to that of Example 56, step 56.1, trans-2-aminocyclohexanol hydrochloride replacing glycine ethyl ester hydrochloride, and DIPEA replacing NEt$_3$.

LC-MS (B): $t_R$=1.20 min; [M+H]$^+$: 639.54.

246.2. 4-((S)-4-carboxy-2-{[6-(trans-2-hydroxy-cyclohexylamino)-2-phenyl-pyrimidine-4-carbonyl]-amino}-butyryl)-piperazine-1-carboxylic acid ethyl ester This compound was prepared using a method analogous to that of Example 230, step 230.2, intermediate 246.1 replacing intermediate 230.1.

LC-MS (B): $t_R$=1.01 min; [M+H]$^+$: 583.22; [M−H]$^-$: 581.48.

fraction containing the compound was neutralized with NaOH and acetonitrile was evaporated off. The remaining aq. solution was extracted with DCM. The org. phases were dried (Na$_2$SO$_4$) and evaporated off giving the desired compound.

LC-MS (B): $t_R$=0.97 min; [M+H]$^+$: 569.36; [M−H]$^-$: 567.49.

Example 247

4-{(S)-4-carboxy-2-[(2-phenyl-6-propylsulfanyl-pyrimidine-4-carbonyl)-amino]-butyryl}-piperazine-1-carboxylic acid ethyl ester 247.1. 4-{(S)-4-tert-butoxycarbonyl-2-[(2-phenyl-6-propylsulfanyl-pyrimidine-4-carbonyl)-amino]-butyryl}-piperazine-1-carboxylic acid ethyl ester 1-propanethiol (11 μl) was added to a suspension of NaH (4 mg) in anhydrous DMF (0.3 ml) at 0° C. After 1 h stirring at 0° C., 4-{(S)-4-tert-butoxycarbonyl-2-[(6-chloro-2-phenyl-pyrimidine-4-carbonyl)-amino]-butyryl}-piperazine-1-carboxylic acid ethyl ester (50 mg) dissolved in DMF (0.1 ml) was added. The mixture was allowed to warm to RT and was stirred at RT until completion. A NaHCO$_3$ solution was added and the resulting mixture was extracted with DCM. The org. phases were dried (Na$_2$SO$_4$) and evaporated off. The crude was directly used in the next step.

LC-MS (B): $t_R$=1.26 min; [M+H]$^+$: 600.39; [M−H]$^-$: 599.63.

247.2. 4-{(S)-4-carboxy-2-[(2-phenyl-6-propylsulfanyl-pyrimidine-4-carbonyl)-amino]-butyryl}-piperazine-1-carboxylic acid ethyl ester This compound was prepared using a method analogous to that of Example 1, step 1.9, intermediate 247.1 replacing intermediate 1.8. The compound was however purified by preparative LC-MS (water/acetonitrile/formic acid).

LC-MS (B): $t_R$=1.11 min; [M+H]$^+$: 544.29; [M−H]$^-$: 542.48.

Example 248

4-{(S)-4-carboxy-2-[(6-isopropylsulfanyl-2-phenyl-pyrimidine-4-carbonyl)-amino]-butyryl}-piperazine-1-carboxylic acid ethyl ester 248.1. 4-{(S)-4-tert-butoxycarbonyl-2-[(6-isopropylsulfanyl-2-phenyl-pyrimidine-4-carbonyl)-amino]-butyryl}-piperazine-1-carboxylic acid ethyl ester This compound was prepared using a method analogous to that of Example 247, step 247.1, 2-propanethiol replacing 1-propanethiol, and the reaction being carried out at RT instead of 0° C.

LC-MS (B): $t_R$=1.26 min; [M+H]$^+$: 600.53; [M−H]$^-$: 600.46.

248.2. 4-{(S)-4-carboxy-2-[(6-isopropylsulfanyl-2-phenyl-pyrimidine-4-carbonyl)-amino]-butyryl}-piperazine-1-carboxylic acid ethyl ester This compound was prepared using a method analogous to that of Example 1, step 1.9, intermediate 248.1 replacing intermediate 1.8. The compound was however purified by preparative LC-MS (water/acetonitrile/formic acid).

LC-MS (B): $t_R$=1.12 min; [M+H]$^+$: 544.29; [M−H]$^-$: 542.55.

Example 249

4-{(S)-4-carboxy-2-[(6-cyclopentylsulfanyl-2-phenyl-pyrimidine-4-carbonyl)-amino]-butyryl}-piperazine-1-carboxylic acid ethyl ester

249.1. 4-{(S)-4-tert-butoxycarbonyl-2-[(6-cyclopentylsulfanyl-2-phenyl-pyrimidine-4-carbonyl)-amino]-butyryl}-piperazine-1-carboxylic acid ethyl ester This compound was prepared using a method analogous to that of Example 247, step 247.1, cyclopentylmercaptan replacing 1-propanethiol.

LC-MS (B): $t_R$=1.29 min; [M+H]$^+$: 626.51; [M−H]$^-$: 624.64.

249.2. 4-{(S)-4-carboxy-2-[(6-cyclopentylsulfanyl-2-phenyl-pyrimidine-4-carbonyl)-amino]-butyryl}-piperazine-1-carboxylic acid ethyl ester This compound was prepared using a method analogous to that of Example 1, step 1.9, intermediate 249.1 replacing intermediate 1.8. The compound was however purified by preparative LC-MS (water/acetonitrile/formic acid).

LC-MS (B): $t_R$=1.15 min; [M+H]$^+$: 570.40; [M−H]$^-$: 568.39.

Example 250

4-{(S)-4-carboxy-2-[(6-isopropylsulfanyl-2-phenyl-pyrimidine-4-carbonyl)-amino]-butyryl}-piperazine-1-carboxylic acid ethyl ester

250.1. 4-{(S)-4-tert-butoxycarbonyl-2-[(6-isopropylsulfanyl-2-phenyl-pyrimidine-4-carbonyl)-amino]-butyryl}-piperazine-1-carboxylic acid ethyl ester This compound was prepared using a method analogous to that of Example 247, step 247.1, furfurylmercaptan replacing 1-propanethiol.

LC-MS (B): $t_R$=1.23 min; [M+H]$^+$: 638.50; [M−H]$^-$: 637.46.

250.2. 4-{(S)-4-carboxy-2-[(6-isopropylsulfanyl-2-phenyl-pyrimidine-4-carbonyl)-amino]-butyryl}-piperazine-1-carboxylic acid ethyl ester This compound was prepared using a method analogous to that of Example 1, step 1.9, intermediate 250.1 replacing intermediate 1.8. The compound was however purified by preparative LC-MS (water/acetonitrile/formic acid).

LC-MS (B): $t_R$=1.10 min; [M+H]$^+$: 582.38; [M−H]$^-$: 580.44.

Example 251

4-{(S)-4-carboxy-2-[(6-cyclohexylsulfanyl-2-phenyl-pyrimidine-4-carbonyl)-amino]-butyryl}-piperazine-1-carboxylic acid ethyl ester

251.1. 4-{(S)-4-tert-butoxycarbonyl-2-[(6-cyclohexylsulfanyl-2-phenyl-pyrimidine-4-carbonyl)-amino]-butyryl}-piperazine-1-carboxylic acid ethyl ester This compound was prepared using a method analogous to that of Example 248, step 248.1, cyclohexanethiol replacing 2-propanethiol.

LC-MS (B): $t_R$=1.32 min; [M+H]$^+$: 640.51.

251.2. 4-{(S)-4-carboxy-2-[(6-cyclohexylsulfanyl-2-phenyl-pyrimidine-4-carbonyl)-amino]-butyryl}-piperazine-1-carboxylic acid ethyl ester This compound was prepared using a method analogous to that of Example 1, step 1.9, intermediate 251.1 replacing intermediate 1.8. The compound was however purified by preparative LC-MS (water/acetonitrile/formic acid).

LC-MS (B): $t_R$=1.18 min; [M+H]$^+$: 584.46; [M−H]$^-$: 582.73.

Example 252

4-{(S)-4-carboxy-2-[(6-ethoxycarbonylmethylsulfanyl-2-phenyl-pyrimidine-4-carbonyl)-amino]-butyryl}-piperazine-1-carboxylic acid ethyl ester

252.1. 4-{(S)-4-tert-butoxycarbonyl-2-[(6-ethoxycarbonylmethylsulfanyl-2-phenyl-pyrimidine-4-carbonyl)-amino]-butyryl}-piperazine-1-carboxylic acid ethyl ester This compound was prepared using a method analogous to that of Example 248, step 248.1, ethyl 2-mercaptoacetate replacing 2-propanethiol.

LC-MS (B): $t_R$=1.23 min; [M+H]$^+$: 644.45.

252.2. 4-{(S)-4-carboxy-2-[(6-ethoxycarbonylmethylsulfanyl-2-phenyl-pyrimidine-4-carbonyl)-amino]-butyryl}-piperazine-1-carboxylic acid ethyl ester This compound was prepared using a method analogous to that of Example 1, step 1.9, intermediate 252.1 replacing intermediate 1.8. The compound was however purified by preparative LC-MS (water/acetonitrile/formic acid).

LC-MS (B): $t_R$=1.05 min; [M+H]$^+$: 588.41; [M−H]$^-$: 586.54.

Example 253

4-((S)-4-carboxy-2-{[6-(2-ethoxycarbonyl-ethylsulfanyl)-2-phenyl-pyrimidine-4-carbonyl]-amino}-butyryl)-piperazine-1-carboxylic acid ethyl ester

253.1. 4-((S)-4-tert-butoxycarbonyl-2-{[6-(2-ethoxycarbonyl-ethylsulanyl)-2-phenyl-pyrimidine-4-carbonyl]-amino}-butyryl)-piperazine-1-carboxylic acid ethyl ester This compound was prepared using a method analogous to that of Example 248, step 248.1, ethyl 3-mercaptopropionate replacing 2-propanethiol.

LC-MS (B): $t_R$=1.22 min; [M+H]$^+$: 658.52; [M−H]$^-$: 657.83.

253.2. 4-((S)-4-carboxy-2-{[6-(2-ethoxycarbonyl-ethylsulfanyl)-2-phenyl-pyrimidine-4-carbonyl]-amino}-butyryl)-piperazine-1-carboxylic acid ethyl ester This compound was prepared using a method analogous to that of Example 1, step 1.9, intermediate 253.1 replacing intermediate 1.8. The compound was however purified by preparative LC-MS (water/acetonitrile/formic acid).

LC-MS (B): $t_R$=1.08 min; [M+H]$^+$: 602.47; [M–H]$^-$: 600.67.

Example 254

4-{(S)-4-carboxy-2-[(6-carboxymethylsulfanyl-2-phenyl-pyrimidine-4-carbonyl)-amino]-butyryl}-piperazine-1-carboxylic acid ethyl ester This compound was prepared using a method analogous to that of Example 57, starting from Example 252. The compound was however purified by preparative LC-MS (water/acetonitrile/formic acid).
LC-MS (B): $t_R$=0.94 min; [M+H]$^+$: 560.42; [M–H]$^-$: 558.76.

Example 255

4-((S)-4-carboxy-2-{[6-(2-carboxy-ethylsulfanyl)-2-phenyl-pyrimidine-4-carbonyl]-amino}-butyryl)-piperazine-1-carboxylic acid ethyl ester This compound was prepared using a method analogous to that of Example 57, starting from Example 253. The compound was however purified by preparative LC-MS (water/acetonitrile/formic acid).
LC-MS (B): $t_R$=0.96 min; [M+H]$^+$: 574.42; [M–H]$^-$: 572.62.

Example 256

4-{(S)-4-carboxy-2-[(2-phenyl-6-phenylsulfanyl-pyrimidine-4-carbonyl)-amino]-butyryl}-piperazine-1-carboxylic acid ethyl ester 256.1. 4-{(S)-4-tert-butoxycarbonyl-2-[(2-phenyl-6-phenylsulfanyl-pyrimidine-4-carbonyl)-amino]-butyryl}-piperazine-1-carboxylic acid ethyl ester This compound was prepared using a method analogous to that of Example 248, step 248.1, thiophenol replacing 2-propanethiol.
LC-MS (B): $t_R$=1.27 min; [M+H]$^+$: 634.41.

256.2. 4-((S)-4-carboxy-2-[(2-phenyl-6-phenylsulfanyl-pyrimidine-4-carbonyl)-amino-butyryl]-piperazine-1-carboxylic acid ethyl ester This compound was prepared using a method analogous to that of Example 1, step 1.9, intermediate 256.1 replacing intermediate 1.8. The compound was however purified by preparative LC-MS (water/acetonitrile/formic acid).
LC-MS (B): $t_R$=1.13 min; [M+H]$^+$: 578.44; [M–H]$^-$: 576.63.

Example 257

4-{(S)-2-[(6-benzylsulfanyl-2-phenyl-pyrimidine-4-carbonyl)-amino]-4-carboxy-butyryl}-piperazine-1-carboxylic acid ethyl ester 257.1. 4-{(S)-2-[(6-benzylsulfanyl-2-phenyl-pyrimidine-4-carbonyl)-amino]-4-tert-butoxycarbonyl-butyryl}-piperazine-1-carboxylic acid ethyl ester This compound was prepared using a method analogous to that of Example 248, step 248.1, benzylmercaptan replacing 2-propanethiol.

LC-MS (B): $t_R$=1.27 min; [M+H]$^+$: 648.47; [M–H]$^-$: 581.50.

257.2. 4-{(S)-2-[(6-benzylsulfanyl-2-phenyl-pyrimidine-4-carbonyl)-amino]-4-carboxy-butyryl}-piperazine-1-carboxylic acid ethyl ester This compound was prepared using a method analogous to that of Example 1, step 1.9, intermediate 257.1 replacing intermediate 1.8. The compound was however purified by preparative LC-MS (water/acetonitrile/formic acid).
LC-MS (B): $t_R$=1.12 min; [M+H]$^+$: 592.43; [M–H]$^-$: 590.63.

Example 258

4-{(S)-4-carboxy-2-[(6-ethynyl-2-phenyl-pyrimidine-4-carbonyl)-amino]-butyryl}-piperazine-1-carboxylic acid ethyl ester 258.1. 4-{(S)-4-tert-butoxycarbonyl-2-[(2-phenyl-6-trimethylsilanylethynyl-pyrimidine-4-carbonyl)-amino]-butyryl}-piperazine-1-carboxylic acid ethyl ester NEt$_3$ (0.249 ml) and trimethylsilylacetylene (0.254 ml) in DMF (4.5 ml) were syringed into a flask containing cupper iodide (8.9 mg), bis-(triphenylphosphine) palladium(II)-dichloride (22.5 mg) and 4-{(S)-4-tert-butoxycarbonyl-2-[(6-chloro-2-phenyl-pyrimidine-4-carbonyl)-amino]-butyryl}-piperazine-1-carboxylic acid ethyl ester (500 mg) under argon. The mixture was allowed to stir at RT overnight. A saturated NH$_4$Cl solution was added and the resulting mixture was extracted with EA. The org. phases were dried (Na$_2$SO$_4$) and evaporated off. Column chromatography (EA/Hept 1/2 to 1/1.5) afforded 339 mg of the desired compound.
$^1$H-NMR (CDCl$_3$): 8.95 (d, 1H); 8.55 (br s, 2H); 8.00 (s, 1H); 7.55 (br s, 3H); 5.25 (m, 1H); 4.20 (q, 2H); 3.8 to 3.5 (m, 8H); 2.4 (m, 2H); 2.2 (m, 1H); 1.95 (m, 1H); 1.5 (s, 9H); 1.3 (t, 3H); 0.35 (s, 9H).

258.2. 4-{(S)-4-tert-butoxycarbonyl-2-[(6-ethynyl-2-phenyl-pyrimidine-4-carbonyl)-amino]-butyryl}-piperazine-1-carboxylic acid ethyl ester Intermediate 258.1 (339 mg) was dissolved in a 7M ammonia solution in MeOH. The mixture was allowed to stir at RT for 30 min. The solvent was evaporated off. Column chromatography (EA/Hept 1/1 to EA) afforded 297 mg of the desired compound.
$^1$H-NMR (CDCl$_3$): 8.95 (d, 1H); 8.55 (br s, 2H); 8.05 (s, 1H); 7.55 (br s, 3H); 5.25 (m, 1H); 4.20 (q, 2H); 3.75 to 3.5 (m, 8H); 3.45 (s, 1H); 2.4 (m, 2H); 2.2 (m, 1H); 1.9 (m, 1H); 1.45 (s, 9H); 1.3 (t, 3H).

258.3. 4-{(S)-4-carboxy-2-[(6-ethynyl-2-phenyl-pyrimidine-4-carbonyl)-amino]-butyryl}-piperazine-1-carboxylic acid ethyl ester This compound was prepared using a method analogous to that of Example 1, step 1.9, intermediate 258.2 replacing intermediate 1.8. The compound was however purified by preparative TLC (EA).

LC-MS (A): $t_R$=1.01 min; [M–H]⁻: 492.41.

Example 259

4-((S)-4-carboxy-2-{[6-(3-hydroxy-prop-1-ynyl)-2-phenyl-pyrimidine-4-carbonyl]-amino}-butyryl)-piperazine-1-carboxylic acid ethyl ester

259.1. 4-((S)-4-tert-butoxycarbonyl-2-{[6-(3-hydroxy-prop-1-ynyl)-2-phenyl-pyrimidine-4-carbonyl]-amino}-butyryl)-piperazine-1-carboxylic acid ethyl ester This compound was prepared using a method analogous to that of Example 258, step 258.1, propargylalkohol replacing trimethylsilylacetylene.
LC-MS (A): $t_R$=1.12 min; [M+H]⁺: 580.17; [M–H]⁻: 578.50.

259.2. 4-((S)-4-carboxy-2-{[6-(3-hydroxy-prop-1-ynyl)-2-phenyl-pyrimidine-4-carbonyl]-amino}-butyryl)-piperazine-1-carboxylic acid ethyl ester This compound was prepared using a method analogous to that of Example 1, step 1.9, intermediate 259.1 replacing intermediate 1.8. The compound was however purified by preparative LC-MS (water/acetonitrile/formic acid).
LC-MS (A): $t_R$=0.93 min; [M+H]⁺: 524.34; [M–H]⁻: 522.33.

Example 260

4-((S)-4-carboxy-2-{[6-(3-hydroxy-but-1-ynyl)-2-phenyl-pyrimidine-4-carbonyl]-amino}-butyryl)-piperazine-1-carboxylic acid ethyl ester

260.1. 4-((S)-4-tert-butoxycarbonyl-2-{[6-(3-hydroxy-but-1-ynyl)-2-phenyl-pyrimidine-4-carbonyl]-amino}-butyryl)-piperazine-1-carboxylic acid ethyl ester This compound was prepared using a method analogous to that of Example 258, step 258.1, 3-butyn-2-ol replacing trimethylsilylacetylene.
LC-MS (A): $t_R$=1.16 min; [M+H]⁺: 594.71.

260.2. 4-((S)-4-carboxy-2-{[6-(3-hydroxy-but-1-ynyl)-2-phenyl-pyrimidine-4-carbonyl]-amino}-butyryl)-piperazine-1-carboxylic acid ethyl ester This compound was prepared using a method analogous to that of Example 1, step 1.9, intermediate 260.1 replacing intermediate 1.8. The compound was however purified by preparative LC-MS (water/acetonitrile/formic acid).
LC-MS (A): $t_R$=0.95 min; [M+H]⁺: 538.33; [M–H]⁻: 536.39.

Example 261

4-((S)-4-carboxy-2-{[6-(3-hydroxy-pent-1-ynyl)-2-phenyl-pyrimidine-4-carbonyl]-amino}-butyryl)-piperazine-1-carboxylic acid ethyl ester

261.1. 4-((S)-4-tert-butoxycarbonyl-2-{[6-(3-hydroxy-pent-1-ynyl)-2-phenyl-pyrimidine-4-carbonyl]-amino}-butyryl)-piperazine-1-carboxylic acid ethyl ester This compound was prepared using a method analogous to that of Example 258, step 258.1, ethyl ethynyl carbinol replacing trimethylsilylacetylene.
LC-MS (A): $t_R$=1.21 min; [M+H]⁺: 608.57; [M–H]⁻: 606.49.

261.2. 4-((S)-4-carboxy-2-{[6-(3-hydroxy-pent-1-ynyl)-2-phenyl-pyrimidine-4-carbonyl]-amino}-butyryl)-piperazine-1-carboxylic acid ethyl ester This compound was prepared using a method analogous to that of Example 1, step 1.9, intermediate 261.1 replacing intermediate 1.8. The compound was however purified by preparative LC-MS (water/acetonitrile/formic acid).
LC-MS (A): $t_R$=0.99 min; [M+H]⁺: 552.32; [M–H]⁻: 550.45.

Example 262

4-((S)-4-carboxy-2-{[6-(3-hydroxy-3-methyl-but-1-ynyl)-2-phenyl-pyrimidine-4-carbonyl]-amino}-butyryl)-piperazine-1-carboxylic acid ethyl ester

262.1. 4-((S)-4-tert-butoxycarbonyl-2-{[6-(3-hydroxy-3-methyl-but-1-ynyl)-2-phenyl-pyrimidine-4-carbonyl]-amino}-butyryl)-piperazine-1-carboxylic acid ethyl ester This compound was prepared using a method analogous to that of Example 258, step 258.1, 2-methyl-3-butyn-2-ol replacing trimethylsilylacetylene.
LC-MS (A): $t_R$=1.20 min; [M+H]⁺: 608.36; [M–H]⁻: 606.49.

262.2. 4-((S)-4-carboxy-2-{[6-(3-hydroxy-3-methyl-but-1-ynyl)-2-phenyl-pyrimidine-4-carbonyl]-amino}-butyryl)-piperazine-1-carboxylic acid ethyl ester This compound was prepared using a method analogous to that of Example 1, step 1.9, intermediate 262.1 replacing intermediate 1.8.
LC-MS (A): $t_R$=0.98 min; [M+H]⁺: 552.39; [M–H]⁻: 550.38.

Example 263

4-((S)-4-carboxy-2-{[6-(3-hydroxy-propyl)-2-phenyl-pyrimidine-4-carbonyl]-amino}-butyryl)-piperazine-1-carboxylic acid ethyl ester

263.1. 4-((S)-4-tert-butoxycarbonyl-2-{[6-(3-hydroxy-propyl)-2-phenyl-pyrimidine-4-carbonyl]-amino}-butyryl)-piperazine-1-carboxylic acid ethyl ester Raney Nickel in water was decanted, the supernatant was removed and MeOH was added. The process was repeated three times and the resulting Raney Nickel in MeOH was added to a solution of intermediate 259.1 (249 mg) in MeOH (15 ml). The mixture was stirred under hydrogen overnight, filtered through celite and the solution evaporated off. Preparative TLC (EA/Hept 5/1) afforded 111 mg of the desired compound.
LC-MS (A): $t_R$=1.13 min; [M–H]⁻: 582.59.

263.2. 4-((S)-4-carboxy-2-{[6-(3-hydroxy-propyl)-2-phenyl-pyrimidine-4-carbonyl]-amino}-butyryl)-piperazine-1-carboxylic acid ethyl ester This compound was prepared using a method analogous to that of Example 58, step 58.2, intermediate 263.1 replacing intermediate 58.1.

LC-MS (A): $t_R$=0.91 min; [M+H]⁺: 528.28; [M−H]⁻: 526.35.

Example 264

4-((S)-4-carboxy-2-{[6-(3-hydroxy-butyl)-2-phenyl-pyrimidine-4-carbonyl]-amino}-butyryl)-piperazine-1-carboxylic acid ethyl ester

264.1. 4-((S)-4-tert-butoxycarbonyl-2-{[6-(3-hydroxy-butyl)-2-phenyl-pyrimidine-4-carbonyl]-amino}-butyryl)-piperazine-1-carboxylic acid ethyl ester This compound was prepared using a method analogous to that of Example 263, step 263.1, intermediate 260.1 replacing intermediate 259.1.

LC-MS (A): $t_R$=1.16 min; [M+H]⁺: 598.52; [M−H]⁻: 596.58.

264.2. 4-((S)-4-carboxy-2-{[6-(3-hydroxy-butyl)-2-phenyl-pyrimidine-4-carbonyl]-amino}-butyryl)-piperazine-1-carboxylic acid ethyl ester This compound was prepared using a method analogous to that of Example 58, step 58.2, intermediate 264.1 replacing intermediate 58.1.

LC-MS (A): $t_R$=0.94 min; [M+H]⁺: 542.18; [M−H]⁻: 540.54.

Example 265

4-((S)-4-carboxy-2-{[6-(3-hydroxy-pentyl)-2-phenyl-pyrimidine-4-carbonyl]-amino}-butyryl)-piperazine-1-carboxylic acid ethyl ester

265.1. 4-((S)-4-tert-butoxycarbonyl-2-{[6-(3-hydroxy-pentyl)-2-phenyl-pyridine-4-carbonyl]-amino}-butyryl)-piperazine-1-carboxylic acid ethyl ester This compound was prepared using a method analogous to that of Example 263, step 263.1, intermediate 261.1 replacing intermediate 259.1.

LC-MS (A): $t_R$=1.22 min; [M−H]⁻: 610.65.

265.2. 4-((S)-4-carboxy-2-{[6-(3-hydroxy-pentyl)-2-phenyl-pyrimidine-4-carbonyl]-amino}-butyryl)-piperazine-1-carboxylic acid ethyl ester This compound was prepared using a method analogous to that of Example 58, step 58.2, intermediate 265.1 replacing intermediate 58.1.

LC-MS (A): $t_R$=1.00 min; [M+H]⁺: 556.41; [M−H]⁻: 554.47.

Example 266

4-((S)-4-carboxy-2-{[6-(3-hydroxy-3-methyl-butyl)-2-phenyl-pyrimidine-4-carbonyl]-amino}-butyryl)-piperazine-1-carboxylic acid ethyl ester

266.1. 4-((S)-4-tert-butoxycarbonyl-2-{[6-(3-hydroxy-3-methyl-butyl)-2-phenyl-pyrimidine-4-carbonyl]-amino}-butyryl)-piperazine-1-carboxylic acid ethyl ester This compound was prepared using a method analogous to that of Example 263, step 263.1, intermediate 262.1 replacing intermediate 259.1.

LC-MS (A): $t_R$=1.19 min; [M−H]⁻: 610.65.

266.2. 4-((S)-4-carboxy-2-{[6-(3-hydroxy-3-methyl-butyl)-2-phenyl-pyrimidine-4-carbonyl]-amino}-butyryl)-piperazine-1-carboxylic acid ethyl ester This compound was prepared using a method analogous to that of Example 58, step 58.2, intermediate 266.1 replacing intermediate 58.1.

LC-MS (A): $t_R$=0.97 min; [M+H]⁺: 556.34; [M−H]⁻: 554.40.

Example 267

4-((S)-4-carboxy-2-{[6-((E)-3-hydroxy-but-1-enyl)-2-phenyl-pyrimidine-4-carbonyl]-amino}-butyryl)-piperazine-1-carboxylic acid ethyl ester

267.1. 4-((S)-4-tert-butoxycarbonyl-2-{[6-((Z)-3-hydroxy-but-1-enyl)-2-phenyl-pyrimidine-4-carbonyl]-amino}-butyryl)-piperazine-1-carboxylic acid ethyl ester A solution of intermediate 260.1 (40 mg) in pyridine (0.2 ml) was added to palladium on barium sulfate (5% Pd, 10 mg). The suspension was stirred under hydrogen for 4 h, filtered through Celite, the cake washed with MeOH and the solution evaporated off. Preparative TLC (EA/Hept 5/1) afforded 13 mg of the desired compound as Z isomer.

LC-MS (A): $t_R$=1.18 min; [M+H]⁺: 596.38; [M−H]⁻: 594.44.

¹H-NMR (CDCl₃): 8.95 (d, 1H); 8.45 (br s, 2H); 7.85 (s, 1H); 7.55 (br s, 3H); 6.95 (d, 1H, 12.3 Hz); 6.35 (dd, 1H, 6.4 and 12.9 Hz); 5.25 (m, 1H); 5.1 (m, 1H); 4.15 (q, 2H); 3.75-3.45 (m, 8H); 2.4 (m, 2H); 2.2 (m, 1H); 1.9 (m, 1H); 1.65 (s, 1H); 1.50 (d, 3H); 1.45 (s, 9H); 1.25 (t, 3H).

267.2. 4-((S)-4-carboxy-2-{[6-((E)-3-hydroxy-but-1-enyl)-2-phenyl-pyrimidine-4-carbonyl]-amino}-butyryl)-piperazine-1-carboxylic acid ethyl ester This compound was prepared using a method analogous to that of Example 1, step 1.9, intermediate 267.1 replacing intermediate 1.8. The compound was however purified by preparative LC-MS (water/acetonitrile/formic acid).

LC-MS (A): $t_R$=0.96 min; [M+H]⁺: 539.99; [M−H]⁻: 538.47.

¹H-NMR (CDCl₃): 9.1 (d, 1H); 8.55 (br s, 2H); 7.85 (s, 1H); 7.55 (br s, 3H); 7.3 (dd, 1H, 5 Hz); 6.75 (d, 1H, 15.5 Hz); 5.3 (m, 1H); 4.6 (m, 1H); 4.15 (q, 2H); 3.75 to 3.45 (m, 8H); 2.5 (m, 2H); 2.2 (m, 1H); 1.9 (m, 1H); 1.45 (d, 3H); 1.25 (t, 3H).

The compounds of Examples 268 to 310 were prepared using a method analogous to that of the Example indicated between brackets, except that the last step of the corresponding Example was not carried out.

Example 268

4-((S)-4-tert-butoxycarbonyl-2-{[6-(2-methoxy-1-methyl-ethylamino)-2-phenyl-pyrimidine-4-carbonyl]-amino}-butyryl)-piperazine-1-carboxylic acid ethyl ester (Example 223). LC-MS (B): $t_R$=1.16 min; [M+H]⁺: 613.49; [M−H]⁻: 611.76.

Example 269

4-((S)-4-tert-butoxycarbonyl-2-{[6-(isopropyl-methyl-amino)-2-phenyl-pyrimidine-4-carbonyl]-amino}-butyryl)-piperazine-1-carboxylic acid ethyl ester (Example 224). LC-MS (B): $t_R$=1.23 min; [M+H]$^+$: 597.49.

Example 270

4-{(S)-4-tert-butoxycarbonyl-2-[(6-morpholin-4-yl-2-phenyl-pyrimidine-4-carbonyl)-amino]-butyryl}-piperazine-1-carboxylic acid ethyl ester (Example 225). LC-MS (B): $t_R$=1.17 min; [M+H]$^+$: 611.55; [M−H]$^-$: 609.75.

Example 271

4-{(S)-4-tert-butoxycarbonyl-2-[(2-phenyl-6-thiazolidin-3-yl-pyrimidine-4-carbonyl)-amino]-butyryl}-piperazine-1-carboxylic acid ethyl ester (Example 226). LC-MS (B): $t_R$=1.21 min; [M+H]$^+$: 613.49.

Example 272

4-((S)-4-tert-butoxycarbonyl-2-{[6-(4-hydroxy-piperidin-1-yl)-2-phenyl-pyrimidine-4-carbonyl]-amino}-butyryl)-piperazine-1-carboxylic acid ethyl ester (Example 227). LC-MS (B): $t_R$=1.11 min; [M+H]$^+$: 625.54.

Example 273

4-((S)-4-tert-butoxycarbonyl-2-{[6-(piperazin-1-yl)-2-phenyl-pyrimidine-4-carbonyl]-amino}-butyryl)-piperazine-1-carboxylic acid ethyl ester (Example 228). LC-MS (B): $t_R$=0.85 min; [M+H]$^+$: 610.51; [M−H]$^-$: 608.78.

Example 274

4-((S)-4-tert-butoxycarbonyl-2-{[6-(2-hydroxy-1-methyl-ethylamino)-2-phenyl-pyrimidine-4-carbonyl]-amino}-butyryl)-piperazine-1-carboxylic acid ethyl ester (Example 229). LC-MS (B): $t_R$=1.08 min; [M+H]$^+$: 599.49; [M−H]$^-$: 597.86.

Example 275

4-((S)-4-tert-butoxycarbonyl-2-{[6-(4-hydroxy-butylamino)-2-phenyl-pyrimidine-4-carbonyl]-amino}-butyryl)-piperazine-1-carboxylic acid ethyl ester (Example 230). LC-MS (B): $t_R$=1.09 min; [M+H]$^+$: 613.56; [M−H]$^-$: 611.62.

Example 276

4-((S)-4-tert-butoxycarbonyl-2-{[6-(2-hydroxy-propylamino)-2-phenyl-pyrimidine-4-carbonyl]-amino}-butyryl)-piperazine-1-carboxylic acid ethyl ester (Example 231). LC-MS (B): $t_R$=1.07 min; [M+H]$^+$: 599.49; [M−H]$^-$: 597.76.

Example 277

4-[(S)-4-tert-butoxycarbonyl-2-({2-phenyl-6-[(tetrahydro-furan-2-ylmethyl)-amino]-pyrimidine-4-carbonyl}-amino)-butyryl]-piperazine-1-carboxylic acid ethyl ester (Example 232). LC-MS (B): $t_R$=1.16 min; [M+H]$^+$: 625.54; [M−H]$^-$: 623.74.

Example 278

4-((S)-4-tert-butoxycarbonyl-2-{[6-((R)-2-hydroxymethyl-pyrrolidin-1-yl)-2-phenyl-pyrimidine-4-carbonyl]-amino}-butyryl)-piperazine-1-carboxylic acid ethyl ester (Example 233). LC-MS (B): $t_R$=1.14 min; [M+H]$^+$: 625.61.

Example 279

4-((S)-4-tert-butoxycarbonyl-2-{[6-((S)-2-hydroxymethyl-pyrrolidin-1-yl)-2-phenyl-pyrimidine-4-carbonyl]-amino}-butyryl)-piperazine-1-carboxylic acid ethyl ester (Example 234). LC-MS (B): $t_R$=1.13 min; [M+H]$^+$: 625.61; [M−H]$^-$: 623.95.

Example 280

4-((S)-4-tert-butoxycarbonyl-2-{[6-((S)-3-hydroxy-pyrrolidin-1-yl)-2-phenyl-pyrimidine-4-carbonyl]-amino}-butyryl)-piperazine-1-carboxylic acid ethyl ester (Example 235). LC-MS (B): $t_R$=1.10 min; [M+H]$^+$: 611.48; [M−H]$^-$: 610.79.

Example 281

4-((S)-4-tert-butoxycarbonyl-2-{[6-((R)-3-hydroxy-pyrrolidin-1-yl)-2-phenyl-pyrimidine-4-carbonyl]-amino}-butyryl)-piperazine-1-carboxylic acid ethyl ester (Example 236). LC-MS (B): $t_R$=1.10 min; [M+H]$^+$: 611.55.

Example 282

4-[(S)-4-tert-butoxycarbonyl-2-({2-phenyl-6-[(R)-(tetrahydro-furan-3-yl)amino]-pyrimidine-4-carbonyl}-amino)-butyryl]-piperazine-1-carboxylic acid ethyl ester (Example 237). LC-MS (B): $t_R$=1.13 min; [M+H]$^+$: 611.27.

Example 283

4-{(S)-4-tert-butoxycarbonyl-2-[(6-imidazol-1-yl-2-phenyl-pyrimidine-4-carbonyl)-amino]-butyryl}-piperazine-1-carboxylic acid ethyl ester (Example 238). LC-MS (B): $t_R$=1.14 min; [M+H]$^+$: 592.50; [M−H]$^-$: 590.63.

Example 284

4-{(S)-4-tert-butoxycarbonyl-2-[(2-phenyl-6-pyrazol-1-yl-pyrimidine-4-carbonyl)-amino]-butyryl}-piperazine-1-carboxylic acid ethyl ester (Example 239). LC-MS (B): $t_R$=1.20 min; [M+H]$^+$: 592.50.

Example 285

4-((S)-4-tert-butoxycarbonyl-2-{[6-((S)-2-hydroxy-1-methyl-ethylamino)-2-phenyl-pyrimidine-4-carbonyl]-amino}-butyryl)-piperazine-1-carboxylic acid ethyl ester (Example 240). LC-MS (B): $t_R$=1.09 min; [M+H]$^+$: 599.36; [M−H]$^-$: 597.49.

Example 286

4-((S)-4-tert-butoxycarbonyl-2-{[6-((R)-2-hydroxy-1-methyl-ethylamino)-2-phenyl-pyrimidine-4-carbonyl]-amino}-butyryl)-piperazine-1-carboxylic acid ethyl ester (Example 241). LC-MS (B): $t_R$=1.08 min; [M+H]$^+$: 599.43; [M−H]$^-$: 597.55.

Example 287

4-((S)-4-tert-butoxycarbonyl-2-{[6-(2-hydroxy-1,1-dimethyl-ethylamino)-2-phenyl-pyrimidine-4-carbonyl]-amino}-butyryl)-piperazine-1-carboxylic acid ethyl ester (Example 242). LC-MS (B): $t_R$=1.11 min; [M+H]$^+$: 613.42; [M−H]$^-$: 611.55.

Example 288

4-((S)-4-tert-butoxycarbonyl-2-{[6-(trans-4-hydroxy-cyclohexylamino)-2-phenyl-pyrimidine-4-carbonyl]-amino}-butyryl)-piperazine-1-carboxylic acid ethyl ester (Example 243). LC-MS (B): $t_R$=1.19 min; [M+H]$^+$: 639.54; [M−H]$^-$: 637.53.

Example 289

4-((S)-4-tert-butoxycarbonyl-2-{[6-(3-hydroxy-piperidin-1-yl)-2-phenyl-pyrimidine-4-carbonyl]-amino}-butyryl)-piperazine-1-carboxylic acid ethyl ester (Example 244). LC-MS (B): $t_R$=1.12 min; [M+H]$^+$: 625.47; [M−H]$^-$: 623.53.

Example 290

4-((S)-4-tert-butoxycarbonyl-2-{[6-(2-hydroxymethyl-piperidin-1-yl)-2-phenyl-pyrimidine-4-carbonyl]-amino}-butyryl)-piperazine-1-carboxylic acid ethyl ester (Example 245). LC-MS (B): $t_R$=1.15 min; [M+H]$^+$: 639.47; [M−H]$^-$: 637.60.

Example 291

4-((S)-4-tert-butoxycarbonyl-2-{[6-(trans-2-hydroxy-cyclohexylamino)-2-phenyl-pyrimidine-4-carbonyl]-amino}-butyryl)-piperazine-1-carboxylic acid ethyl ester (Example 246). LC-MS (B): $t_R$=1.20 min; [M+H]$^+$: 639.54.

Example 292

4-{(S)-4-tert-butoxycarbonyl-2-[(2-phenyl-6-propylsulfanyl-pyrimidine-4-carbonyl)-amino]-butyryl}-piperazine-1-carboxylic acid ethyl ester (Example 247). LC-MS (B): $t_R$=1.26 min; [M+H]$^+$: 600.39; [M−H]$^-$: 599.63.

Example 293

4-{(S)-4-tert-butoxycarbonyl-2-[(6-isopropylsulfanyl-2-phenyl-pyrimidine-4-carbonyl)-amino]-butyryl}-piperazine-1-carboxylic acid ethyl ester (Example 248). LC-MS (B): $t_R$=1.26 min; [M+H]$^+$: 600.53; [M−H]$^-$: 600.46.

Example 294

4-{(S)-4-tert-butoxycarbonyl-2-[(6-cyclopentylsulfanyl-2-phenyl-pyrimidine-4-carbonyl)-amino]-butyryl}-piperazine-1-carboxylic acid ethyl ester (Example 249). LC-MS (B): $t_R$=1.29 min; [M+H]$^+$: 626.51; [M−H]$^-$: 624.64.

Example 295

4-{(S)-4-tert-butoxycarbonyl-2-[(6-isopropylsulfanyl-2-phenyl-pyrimidine-4-carbonyl)-amino]-butyryl}-piperazine-1-carboxylic acid ethyl ester (Example 250). LC-MS (B): $t_R$=1.23 min; [M+H]$^+$: 638.50; [M−H]$^-$: 637.46.

Example 296

4-{(S)-4-tert-butoxycarbonyl-2-[(6-cyclohexylsulfanyl-2-phenyl-pyrimidine-4-carbonyl)-amino]-butyryl}-piperazine-1-carboxylic acid ethyl ester (Example 251). LC-MS (B): $t_R$=1.32 min; [M+H]$^+$: 640.51.

Example 297

4-{(S)-4-tert-butoxycarbonyl-2-[(6-ethoxycarbonyl-methylsulfanyl-2-phenyl-pyrimidine-4-carbonyl)-amino]-butyryl}-piperazine-1-carboxylic acid ethyl ester (Example 252). LC-MS (B): $t_R$=1.23 min; [M+H]$^+$: 644.45.

Example 298

4-((S)-4-tert-butoxycarbonyl-2-{[6-(2-ethoxycarbonyl-ethylsulfanyl)-2-phenyl-pyrimidine-4-carbonyl]-amino}-butyryl)-piperazine-1-carboxylic acid ethyl ester (Example 253). LC-MS (B): $t_R$=1.22 min; [M+H]$^+$: 658.52; [M−H]$^-$: 657.83.

Example 299

4-{(S)-4-tert-butoxycarbonyl-2-[(2-phenyl-6-phenyl-sulfanyl-pyrimidine-4-carbonyl)-amino]-butyryl}-piperazine-1-carboxylic acid ethyl ester (Example 256). LC-MS (B): $t_R$=1.27 min; [M+H]$^+$: 634.41.

Example 300

4-{(S)-2-[(6-benzylsulfanyl-2-phenyl-pyrimidine-4-carbonyl)-amino]-4-tert-butoxycarbonyl-butyryl}-piperazine-1-carboxylic acid ethyl ester (Example 257). LC-MS (B): $t_R$=1.27 min; [M+H]$^+$: 648.47; [M−H]$^-$: 581.50.

Example 301

4-{(S)-4-tert-butoxycarbonyl-2-[(6-ethynyl-2-phenyl-pyrimidine-4-carbonyl)-amino]-butyryl}-piperazine-1-carboxylic acid ethyl ester (Example 258). $^1$H-NMR (CDCl$_3$): 8.95 (d, 1H); 8.55 (br s, 2H); 8.05 (s, 1H); 7.55 (br s, 3H); 5.25 (m, 1H); 4.20 (q, 2H); 3.75 to 3.5 (m, 8H); 3.45 (s, 1H); 2.4 (m, 2H); 2.2 (m, 1H); 1.9 (m, 1H); 1.45 (s, 9H); 1.3 (t, 3H).

Example 302

4-((S)-4-tert-butoxycarbonyl-2-{[6-(3-hydroxy-prop-1-ynyl)-2-phenyl-pyrimidine-4-carbonyl]-amino}-butyryl)-piperazine-1-carboxylic acid ethyl ester (Example 259). LC-MS (A): $t_R$=1.12 min; [M+H]$^+$: 580.17; [M−H]$^-$: 578.50.

Example 303

4-((S)-4-tert-butoxycarbonyl-2-{[6-(3-hydroxy-but-1-ynyl)-2-phenyl-pyrimidine-4-carbonyl]-amino}-butyryl)-piperazine-1-carboxylic acid ethyl ester (Example 260). LC-MS (A): $t_R$=1.16 min; [M+H]$^+$: 594.71.

Example 304

4-((S)-4-tert-butoxycarbonyl-2-{[6-(3-hydroxy-pent-1-ynyl)-2-phenyl-pyrimidine-4-carbonyl]-amino}-butyryl)-piperazine-1-carboxylic acid ethyl ester (Example 261). LC-MS (A): $t_R$=1.21 min; [M+H]$^+$: 608.57; [M−H]$^-$: 606.49.

Example 305

4-((S)-4-tert-butoxycarbonyl-2-{[6-(3-hydroxy-3-methyl-but-1-ynyl)-2-phenyl-pyrimidine-4-carbonyl]-amino}-butyryl)-piperazine-1-carboxylic acid ethyl ester (Example 262). LC-MS (A): $t_R$=1.20 min; [M+H]$^+$: 608.36; [M−H]$^-$: 606.49.

Example 306

4-((S)-4-tert-butoxycarbonyl-2-{[6-(3-hydroxy-propyl)-2-phenyl-pyrimidine-4-carbonyl]-amino}-butyryl)-piperazine-1-carboxylic acid ethyl ester (Example 263). LC-MS (A): $t_R$=1.13 min; [M−H]$^-$: 582.59.

Example 307

4-((S)-4-tert-butoxycarbonyl-2-{[6-(3-hydroxy-butyl)-2-phenyl-pyrimidine-4-carbonyl]-amino}-butyryl)-piperazine-1-carboxylic acid ethyl ester (Example 264). LC-MS (A): $t_R$=1.16 min; [M+H]$^+$: 598.52; [M−H]$^-$: 596.58.

Example 308

4-((S)-4-tert-butoxycarbonyl-2-{[6-(3-hydroxy-pentyl)-2-phenyl-pyrimidine-4-carbonyl]-amino}-butyryl)-piperazine-1-carboxylic acid ethyl ester (Example 265). LC-MS (A): $t_R$=1.22 min; [M−H]$^-$: 610.65.

Example 309

4-((S)-4-tert-butoxycarbonyl-2-{[6-(3-hydroxy-3-methyl-butyl)-2-phenyl-pyrimidine-4-carbonyl]-amino}-butyryl)-piperazine-1-carboxylic acid ethyl ester (Example 266). LC-MS (A): $t_R$=1.19 min; [M−H]$^-$: 610.65.

Example 310

4-((S)-4-tert-butoxycarbonyl-2-{[6-((Z)-3-hydroxy-but-1-enyl)-2-phenyl-pyrimidine-4-carbonyl]-amino}-butyryl)-piperazine-1-carboxylic acid ethyl ester (Example 267). LC-MS (A): $t_R$=1.18 min; [M+H]$^+$: 596.38; [M−H]$^-$: 594.44.

Example 311

4-((S)-4-carboxy-2-{[6-(4-oxo-cyclohex-1-enyl)-2-phenyl-pyrimidine-4-carbonyl]-amino}-butyryl)-piperazine-1-carboxylic acid ethyl ester

311.1. Trifluoro-methanesulfonic acid 1,4-dioxa-spiro[4.5]dec-7-en-8-yl ester A lithium bis(trimethysilyl)amide solution (1M in THF, 7 ml) in THF (20 ml) was cooled down to −78° C. and 1,4-dioxaspiro[4,5]decan-8-one (1 g) in THF (7 ml) was added slowly. The mixture was stirred for 2 h 30 at −78° C. N-phenyl-bis(trifluoromethanesulfonimide) (2.45 g) in THF (8 ml) was added slowly. The temperature was then allowed to increase to 0° C. It was further stirred at 0° C. for 2 h. The solvent was evaporated off (water bath temperature: 25° C.) and HV dried. The crude was used without purification.
$^1$H-NMR (CDCl$_3$): 7.05 (m, 4H); 5.6 (s, 1H); 3.9 (s, 4H); 2.5 (s, 2H); 2.3 (s, 2H); 1.8 (m, 2H).

311.2. 8-(4,4,5,5-tetramethyl-[1, 3, 2]dioxaborolan-2-yl)-1,4-dioxa-spiro[4.5]dec-7-ene Intermediate 311.1 (922 mg), bis(pinacolato)diboron (894 mg), chloro(1,1'-bis(diphenylphosphino) ferrocene) palladium (II) dichloromethane adduct (78 mg) and potassium acetate (941 mg) were dissolved in anhydrous DMSO under argon and refluxed for 48 h. After cooling down, water was added and the mixture was extracted with EA. The org. layers were washed with a NaCl solution, dried (Na$_2$SO$_4$) and evaporated off. The compound was used in the next step without purification or characterisation.

311.3. 4-((S)-4-tert-butoxycarbonyl-2-{[6-(1,4-dioxa-spiro[4.5]dec-7-en-8-yl)-2-phenyl-pyrimidine-4-carbonyl]-amino}-butyryl)-piperazine-1-carboxylic acid ethyl ester Intermediate 311.2 (1 mmol), 4-{(S)-4-tert-butoxycarbonyl-2-[(6-chloro-2-phenyl-pyrimidine-4-carbonyl)-amino]-butyryl}-piperazine-1-carboxylic acid ethyl ester (1 mmol, 560 mg), tris-(dibenzylidenaceton)-dipalladium (0.025 mmol, 23 mg) and triphenylphosphine (0.2 mmol, 55 mg) were dissolved in toluene (1.2 ml), EtOH (0.3 ml) and a 1M solution of sodium carbonate (0.3 ml). The mixture was refluxed for 48 h under argon. After cooling down, water was added and the mixture was extracted with chloroform. The org. layers were dried (Na$_2$SO$_4$) and evaporated off. Column chromatography (EA/Hept 1/2 to 1/0) afforded 155 mg of the desired compound.
LC-MS (A): $t_R$=1.33 min; [M+H]$^+$: 664.27.

311.4. 4-((S)-4-tert-butoxycarbonyl-2-{[6-(4-oxo-cyclohex-1-enyl)-2-phenyl-pyrimidine-4-carbonyl]-amino}-butyryl)-piperazine-1-carboxylic acid ethyl ester Intermediate 311.3 (30 mg) was dissolved in dioxane (0.4 ml) and the solution was cooled down to 5° C. A mixture of sulfuric acid (50 ml) and water (50 ml) was added and the mixture was further stirred at 5° C. for 15 min. Water was added and the mixture extracted with EA. The org. layers were dried (Na$_2$SO$_4$) and evaporated off to afford the desired compound (25 mg).
LC-MS (A): $t_R$=1.26 min; [M+H]$^+$: 620.28; [M−H]$^-$: 618.48.

311.5. 4-((S)-4-carboxy-2-{[6-(4-oxo-cyclohex-1-enyl)-2-phenyl-pyrimidine-4-carbonyl]-amino}-butyryl)-piperazine-1-carboxylic acid ethyl ester This compound was prepared using a method analogous to that of Example 1, step 1.9, intermediate 311.4 replacing intermediate 1.8. The compound was however purified by preparative TLC (EA).
LC-MS (A): $t_R$=1.03 min; [M+H]$^+$: 564.23; [M−H]$^-$: 562.36.

Example 312

4-((S)-4-carboxy-2-{[6-(4-oxo-cyclohexyl)-2-phenyl-pyrimidine-4-carbonyl]-amino}-butyryl)-piperazine-1-carboxylic acid ethyl ester

312.1. 4-((S)-4-tert-butoxycarbonyl-2-{[6-(1,4-dioxa-spiro[4.5]dec-8-yl)-2-phenyl-pyrimidine-4-carbonyl]-amino}-butyryl)-piperazine-1-carboxylic acid ethyl ester Intermediate 311.3 (40 mg) was hydrogenated in EtOH (1 ml) with platinum dioxide (10 mg) for 16 h. The mixture was filtered through celite and evaporated off. HV drying afforded 38 mg of the desired product.
LC-MS (A): $t_R$=1.32 min; [M+H]$^+$: 666.35.

312.2. 4-((S)-4-tert-butoxycarbonyl-2-{[6-(4-oxo-cyclohexyl)-2-phenyl-pyrimidine-4-carbonyl]-amino}-butyryl)-piperazine-1-carboxylic acid ethyl ester This compound was prepared using a method analogous to that of Example 311, step 311.4, intermediate 312.1 replacing intermediate 311.3.
LC-MS (C): $t_R$=1.06 min; [M+H]$^+$: 622.20.

312.3. 4-((S)-4-carboxy-2-{[6-(4-oxo-cyclohexyl)-2-phenyl-pyrimidine-4-carbonyl]-amino}-butyryl)-piperazine-1-carboxylic acid ethyl ester This compound was prepared using a method analogous to that of Example 1, step 1.9, intermediate 312.2 replacing intermediate 1.8. The compound was however purified by preparative TLC (EA).
LC-MS (C): $t_R$=0.91 min; [M+H]$^+$: 566.15.

Example 313

4-((S)-4-carboxy-2-{[6-(4-hydroxy-cyclohex-1-enyl)-2-phenyl-pyrimidine-4-carbonyl]-amino}-butyryl)-piperazine-1-carboxylic acid ethyl ester The compound of Example 311 (20 mg) was dissolved in ice-cold MeOH (0.4 ml) and NaBH$_4$ (1.4 mg) was added. The mixture was stirred at 0° C. for 3 h. Water was added and the mixture extracted with EA. The aq. phase was acidified with a 2M HCl solution (0.2 ml) and extracted again with EA. The last org. layers were dried (Na$_2$SO$_4$) and evaporated off. Preparative TLC (EA/MeOH, 9/1) afforded 3 mg of the desired compound.
LC-MS (C): $t_R$=0.87 min; [M+H]$^+$: 566.12.

Example 314

4-((S)-4-carboxy-2-{[6-(4-hydroxy-cyclohexyl)-2-phenyl-pyrimidine-4-carbonyl]-amino}-butyryl)-piperazine-1-carboxylic acid ethyl ester This compound was prepared using a method analogous to that of Example 313, the compound of Example 312 replacing that of Example 311.

LC-MS (C): $t_R$=0.86 min; [M+H]$^+$: 568.16.

The compounds of Examples 315 and 316 were prepared using a method analogous to that of the Example indicated between brackets, except that the last step of the corresponding Example was not carried out.

Example 315

4-((S)-4-tert-butoxycarbonyl-2-{[6-(4-oxo-cyclohex-1-enyl)-2-phenyl-pyrimidine-4-carbonyl]-amino}-butyryl)-piperazine-1-carboxylic acid ethyl ester (Example 311). LC-MS (A): $t_R$=1.26 min; [M+H]$^+$: 620.28; [M−H]$^-$: 618.48.

Example 316

4-((S)-4-tert-butoxycarbonyl-2-{[6-(4-oxo-cyclohexyl)-2-phenyl-pyrimidine-4-carbonyl]-amino}-butyryl)-piperazine-1-carboxylic acid ethyl ester (Example 312). LC-MS (C): $t_R$=1.06 min; [M+H]$^+$: 622.20.

Example 317

4-((S)-4-carboxy-2-{[6-((S)-3-methoxy-pyrrolidin-1-yl)-2-phenyl-pyrimidine-4-carbonyl]-amino}-butyryl)-piperazine-1-carboxylic acid ethyl ester formate salt 317.1. 4-(4-tert-butoxycarbonyl-2-{[6-((S)-3-hydroxy-pyrrolidin-1-yl)-2-phenyl-pyrimidine-4-carbonyl]-amino}-butyryl)-piperazine-1-carboxylic acid ethyl ester Intermediate 48.1 (50 mg), (S)-3-hydroxypyrrolidine (15.5 mg) and DIPEA (30 µl) were dissolved in THF (1 ml). The mixture was stirred at RT until reaction completion. Water was added to the reaction mixture which was extracted with DCM. The org. layers were dried (Na$_2$SO$_4$) and evaporated off to give 54 mg of the desired crude compound.

LC-MS (B): $t_R$=1.0 min; [M+H]$^+$: 611.27.

317.2. 4-(4-tert-butoxycarbonyl-2-{[6-((S)-3-methoxy-pyrrolidin-1-yl)-2-phenyl-pyrimidine-4-carbonyl]-amino}-butyryl)-piperazine-1-carboxylic acid ethyl ester NaH (4.3 mg) was added to a solution of intermediate 317.1 (54 mg) in THF (1 ml). After 10 min stirring at RT, methyl iodide (7 µl) was added. The mixture was stirred at RT overnight and quenched with MeOH. It was extracted with water/DCM. The org. phase was evaporated off and purified by preparative LC-MS (III).

LC-MS (C): $t_R$=1.07 min; [M+H]$^+$: 625.25.

317.3. 4-((S)-4-carboxy-2-{[6-((S)-3-methoxy-pyrrolidin-1-yl)-2-phenyl-pyrimidine-4-carbonyl]-amino}-butyryl)-piperazine-1-carboxylic acid ethyl ester formate salt This compound was prepared using a method analogous to that of Example 1, step 1.9, intermediate 317.2 replacing intermediate 1.8. The compound was however purified by preparative LC-MS (III).

LC-MS (B): $t_R$=1.03 min; [M+H]$^+$: 569.43.

Example 318

4-((S)-4-carboxy-2-{[6-((S)-2-methoxy-1-methyl-ethylamino)-2-phenyl-pyrimidine-4-carbonyl]-amino}-butyryl)-piperazine-1-carboxylic acid ethyl ester formate salt 318.1. 4-((S)-4-tert-butoxycarbonyl-2-{[6-((S)-2-hydroxy-1-methyl-ethylamino)-2-phenyl-pyrimidine-4-carbonyl]-amino}-butyryl)-piperazine-1-carboxylic acid ethyl ester This compound was prepared using a method analogous to that of Example 317, step 317.1, (S)-(+)-2-amino-1-propanol replacing (S)-3-hydroxypyrrolidine.

LC-MS (B): $t_R$=1.09 min; [M+H]$^+$: 599.31.

318.2. 4-((S)-4-tert-butoxycarbonyl-2-{[6-((S)-2-methoxy-1-methyl-ethylamino)-2-phenyl-pyrimidine-4-carbonyl]-amino}-butyryl)-piperazine-1-carboxylic acid ethyl ester This compound was prepared using a method analogous to that of Example 317, step 317.2, intermediate 318.1 replacing intermediate 317.1.

LC-MS (C): $t_R$=1.05 min; [M+H]$^+$: 613.23.

318.3. 4-((S)-4-carboxy-2-{[6-((S)-2-methoxy-1-methyl-ethylamino)-2-phenyl-pyrimidine-4-carbonyl]-amino}-butyryl)-piperazine-1-carboxylic acid ethyl ester formate salt This compound was prepared using a method analogous to that of Example 317, step 317.3, intermediate 318.2 replacing intermediate 317.2.

LC-MS (B): $t_R$=1.02 min; [M+H]$^+$: 557.45.

Example 319

4-((S)-4-carboxy-2-{[6-(4-methoxy-piperidin-1-yl)-2-phenyl-pyrimidine-4-carbonyl]-amino}-butyryl)-piperazine-1-carboxylic acid ethyl ester formate salt 319.1. 4-((S)-4-tert-butoxycarbonyl-2-{[6-(4-hydroxy-piperidin-1-yl)-2-phenyl-pyrimidine-4-carbonyl]-amino}-butyryl)-piperazine-1-carboxylic acid ethyl ester This compound was prepared using a method analogous to that of Example 317, step 317.1, 4-hydroxypiperidine replacing (S)-3-hydroxypyrrolidine.

LC-MS (B): $t_R$=1.11 min; [M+H]$^+$: 625.42.

319.2. 4-((S)-4-tert-butoxycarbonyl-2-{[6-(4-methoxy-piperidin-1-yl)-2-phenyl-pyrimidine-4-carbonyl]-amino}-butyryl)-piperazine-1-carboxylic acid ethyl ester This compound was prepared using a method analogous to that of Example 317, step 317.2, intermediate 319.1 replacing intermediate 317.1.
LC-MS (C): $t_R$=1.08 min; [M+H]$^+$: 639.28.

319.3. 4-((S)-4-carboxy-2-{[6-(4-methoxy-piperidin-1-yl)-2-phenyl-pyrimidine-4-carbonyl]-amino}-butyryl)-piperazine-1-carboxylic acid ethyl ester formate salt This compound was prepared using a method analogous to that of Example 317, step 317.3, intermediate 319.2 replacing intermediate 317.2.
LC-MS (B): $t_R$=1.04 min; [M+H]$^+$: 583.25.

Example 320

4-((S)-4-carboxy-2-{[6-((R)-3-methoxy-pyrrolidin-1-yl)-2-phenyl-pyrimidine-4-carbonyl]-amino}-butyryl)-piperazine-1-carboxylic acid ethyl ester formate salt 320.1. 4-(4-tert-butoxycarbonyl-2-{[6-((R)-3-hydroxy-pyrrolidin-1-yl)-2-phenyl-pyrimidine-4-carbonyl]-amino}-butyryl)-piperazine-1-carboxylic acid ethyl ester This compound was prepared using a method analogous to that of Example 317, step 317.1, (R)-3-hydroxypyrrolidine replacing (S)-3-hydroxypyrrolidine.
LC-MS (B): $t_R$=1.11 min; [M+H]$^+$: 611.21.

320.2. 4-(4-tert-butoxycarbonyl-2-{[6-((R)-3-methoxy-pyrrolidin-1-yl)-2-phenyl-pyrimidine-4-carbonyl]-amino}-butyryl)-piperazine-1-carboxylic acid ethyl ester This compound was prepared using a method analogous to that of Example 317, step 317.2, intermediate 320.1 replacing intermediate 317.1.
LC-MS (C): $t_R$=1.07 min; [M+H]$^+$: 625.25.

320.3. 4-((S)-4-carboxy-2-{[6-((R)-3-methoxy-pyrrolidin-1-yl)-2-phenyl-pyrimidine-4-carbonyl]-amino}-butyryl)-piperazine-1-carboxylic acid ethyl ester formate salt This compound was prepared using a method analogous to that of Example 317, step 317.3, intermediate 320.2 replacing intermediate 317.2.
LC-MS (B): $t_R$=1.03 min; [M+H]$^+$: 569.17.

Example 321

4-((S)-4-carboxy-2-{[6-((R)-2-methoxy-1-methyl-ethylamino)-2-phenyl-pyrimidine-4-carbonyl]-amino}-butyryl)-piperazine-1-carboxylic acid ethyl ester formate salt 321.1. 4-((S)-4-tert-butoxycarbonyl-2-{[6-((R)-2-hydroxy-1-methyl-ethylamino)-2-phenyl-pyrimidine-4-carbonyl]-amino}-butyryl)-piperazine-1-carboxylic acid ethyl ester This compound was prepared using a method analogous to that of Example 317, step 317.1, (R)-(−)-2-amino-1-propanol replacing (S)-3-hydroxypyrrolidine.
LC-MS (B): $t_R$=1.09 min; [M+H]$^+$: 599.43.

321.2. 4-((S)-4-tert-butoxycarbonyl-2-{[6-((R)-2-methoxy-1-methyl-ethylamino)-2-phenyl-pyrimidine-4-carbonyl]-amino}-butyryl)-piperazine-1-carboxylic acid ethyl ester This compound was prepared using a method analogous to that of Example 317, step 317.2, intermediate 321.1 replacing intermediate 317.1.
LC-MS (C): $t_R$=1.04 min; [M+H]$^+$: 613.22.

321.3. 4-((S)-4-carboxy-2-{[6-((R)-2-methoxy-1-methyl-ethylamino)-2-phenyl-pyrimidine-4-carbonyl]-amino}-butyryl)-piperazine-1-carboxylic acid ethyl ester formate salt This compound was prepared using a method analogous to that of Example 317, step 317.3, intermediate 321.2 replacing intermediate 317.2.
LC-MS (B): $t_R$=1.01 min; [M+H]$^+$: 557.58.

Example 322

4-((S)-4-carboxy-2-{[6-(2-methoxymethyl-piperidin-1-yl)-2-phenyl-pyrimidine-4-carbonyl]-amino}-butyryl)-piperazine-1-carboxylic acid ethyl ester formate salt 322.1. 4-((S)-4-tert-butoxycarbonyl-2-{[6-(2-hydroxymethyl-piperidin-1-yl)-2-phenyl-pyrimidine-4-carbonyl]-amino}-butyryl)-piperazine-1-carboxylic acid ethyl ester This compound was prepared using a method analogous to that of Example 317, step 317.1, 2-(hydroxymethyl)-piperidine replacing (S)-3-hydroxypyrrolidine.
LC-MS (B): $t_R$=1.15 min; [M+H]$^+$: 639.47.

322.2. 4-((S)-4-tert-butoxycarbonyl-2-{[6-(2-methoxymethyl-piperidin-1-yl)-2-phenyl-pyrimidine-4-carbonyl]-amino}-butyryl)-piperazine-1-carboxylic acid ethyl ester This compound was prepared using a method analogous to that of Example 317, step 317.2, intermediate 322.1 replacing intermediate 317.1.
LC-MS (C): $t_R$=1.11 min; [M+H]$^+$: 653.28.

322.3. 4-((S)-4-carboxy-2-{[6-(2-methoxymethyl-piperidin-1-yl)-2-phenyl-pyrimidine-4-carbonyl]-amino}-butyryl)-piperazine-1-carboxylic acid ethyl ester formate salt This compound was prepared using a method analogous to that of Example 317, step 317.3, intermediate 322.2 replacing intermediate 317.2.
LC-MS (B): $t_R$=1.08 min; [M+H]$^+$: 597.42.

Example 323

4-((S)-4-carboxy-2-{[6-((S)-2-methoxymethyl-pyrrolidin-1-yl)-2-phenyl-pyrimidine-4-carbonyl]-amino}-butyryl)-piperazine-1-carboxylic acid ethyl ester formate salt

323.1. 4-((S)-4-tert-butoxycarbonyl-2-{[6-((S)-2-hydroxymethyl-pyrrolidin-1-yl)-2-phenyl-pyrimidine-4-carbonyl]-amino}-butyryl)-piperazine-1-carboxylic acid ethyl ester This compound was prepared using a method analogous to that of Example 317, step 317.1, L-prolinol replacing (S)-3-hydroxypyrrolidine.

LC-MS (B): $t_R$=1.14 min; [M+H]$^+$: 625.24.

323.2. 4-((S)-4-tert-butoxycarbonyl-2-{[6-((S)-2-methoxymethyl-pyrrolidin-1-yl)-2-phenyl-pyrimidine-4-carbonyl]-amino}-butyryl)-piperazine-1-carboxylic acid ethyl ester This compound was prepared using a method analogous to that of Example 317, step 317.2, intermediate 323.1 replacing intermediate 317.1.

LC-MS (C): $t_R$=1.10 min; [M+H]$^+$: 639.28.

323.3. 4-((S)-4-carboxy-2-{[6-((S)-2-methoxymethyl-pyrrolidin-1-yl)-2-phenyl-pyrimidine-4-carbonyl]-amino}-butyryl)-piperazine-1-carboxylic acid ethyl ester formate salt This compound was prepared using a method analogous to that of Example 317, step 317.3, intermediate 323.2 replacing intermediate 317.2.

LC-MS (B): $t_R$=1.06 min; [M+H]$^+$: 583.24.

Example 324

4-((S)-4-carboxy-2-{[6-((R)-2-methoxymethyl-pyrrolidin-1-yl)-2-phenyl-pyrimidine-4-carbonyl]-amino}-butyryl)-piperazine-1-carboxylic acid ethyl ester formate salt

324.1. 4-((S)-4-tert-butoxycarbonyl-2-{[6-((R)-2-hydroxymethyl-pyrrolidin-1-yl)-2-phenyl-pyrimidine-4-carbonyl]-amino}-butyryl)-piperazine-1-carboxylic acid ethyl ester This compound was prepared using a method analogous to that of Example 317, step 317.1, D-prolinol replacing (S)-3-hydroxypyrrolidine.

LC-MS (B): $t_R$=1.14 min; [M+H]$^+$: 625.22.

324.2. 4-((S)-4-tert-butoxycarbonyl-2-{[6-((R)-2-methoxymethyl-pyrrolidin-1-yl)-2-phenyl-pyrimidine-4-carbonyl]-amino}-butyryl)-piperazine-1-carboxylic acid ethyl ester This compound was prepared using a method analogous to that of Example 317, step 317.2, intermediate 324.1 replacing intermediate 317.1.

LC-MS (C): $t_R$=1.09 min; [M+H]$^+$: 639.28.

324.3. 4-((S)-4-carboxy-2-{[6-((R)-2-methoxymethyl-pyrrolidin-1-yl)-2-phenyl-pyrimidine-4-carbonyl]-amino}-butyryl)-piperazine-1-carboxylic acid ethyl ester formate salt This compound was prepared using a method analogous to that of Example 317, step 317.3, intermediate 324.2 replacing intermediate 317.2.

LC-MS (B): $t_R$=1.06 min; [M+H]$^+$: 583.30.

Example 325

4-((S)-4-carboxy-2-{[6-(2-methoxy-1,1-dimethyl-ethylamino)-2-phenyl-pyrimidine-4-carbonyl]-amino}-butyryl)-piperazine-1-carboxylic acid ethyl ester hydrochloride

325.1. 4-((S)-4-tert-butoxycarbonyl-2-{[6-(2-hydroxy-1,1-dimethyl-ethylamino)-2-phenyl-pyrimidine-4-carbonyl]-amino}-butyryl)-piperazine-1-carboxylic acid ethyl ester This compound was prepared using a method analogous to that of Example 317, step 317.1, 2-amino-2-methyl-1-propanol replacing (S)-3-hydroxypyrrolidine and the reaction taking place at 60° C. instead of RT.

LC-MS (C): $t_R$=1.00 min; [M+H]$^+$: 613.21.

325.2. 4-((S)-4-tert-butoxycarbonyl-2-{[6-(2-methoxy-1,1-dimethyl-ethylamino)-2-phenyl-pyrimidine-4-carbonyl]-amino}-butyryl)-piperazine-1-carboxylic acid ethyl ester This compound was prepared using a method analogous to that of Example 317, step 317.2, intermediate 325.1 replacing intermediate 317.1. The compound was purified by preparative LC-MS (IV) instead of (III).

LC-MS (B): $t_R$=1.19 min; [M+H]$^+$: 627.29.

325.3. 4-((S)-4-carboxy-2-{[6-(2-methoxy-1,1-dimethyl-ethylamino)-2-phenyl-pyrimidine-4-carbonyl]-amino}-butyryl)-piperazine-1-carboxylic acid ethyl ester hydrochloride This compound was prepared using a method analogous to that of Example 1, step 1.9, intermediate 325.2 replacing intermediate 1.8, with a work up being however performed as follows. The residue was dissolved in DCM. The solution was washed with a 1M NaOH solution, dried (Na$_2$SO$_4$) and evaporated off. The residue was taken up in a 3M solution of HCl in EA and the solvent evaporated off, giving the hydrochloride salt of the desired compound.

LC-MS (B): $t_R$=1.05 min; [M+H]$^+$: 571.15.

Example 326

4-((S)-4-carboxy-2-{[6-(4,5-dihydro-pyrazol-1-yl)-2-phenyl-pyrimidine-4-carbonyl]-amino}-butyryl)-piperazine-1-carboxylic acid ethyl ester hydrochloride

326.1. 4-((S)-4-tert-butoxycarbonyl-2-{[6-(4,5-dihydro-pyrazol-1-yl)-2-phenyl-pyrimidine-4-carbonyl]-amino}-butyryl)-piperazine-1-carboxylic acid ethyl ester This compound was prepared using a method analogous to that of Example 317, step 317.1, 2-pyrazoline replacing (S)-3-hydroxypyrrolidine and the reaction taking place at 60° C. instead of RT.

LC-MS (B): $t_R$=1.18 min; [M+H]$^+$: 594.26.

326.2. 4-((S)-4-carboxy-2-{[6-(4,5-dihydro-pyrazol-1-yl)-2-phenyl-pyrimidine-4-carbonyl]-amino}-butyryl)-piperazine-1-carboxylic acid ethyl ester hydrochloride This compound was prepared using a method analogous to that of Example 1, step 1.9, intermediate 326.1 replacing intermediate 1.8, with a work up being however performed as follows. The residue was dissolved in DCM. The solution was washed with a 1M NaOH solution, dried ($Na_2SO_4$) and evaporated off. The residue was taken up in a 3M solution of HCl in EA and the solvent evaporated off, giving the hydrochloride salt of the desired compound.
LC-MS (B): $t_R$=1.02 min; $[M+H]^+$: 538.16.

Example 327

4-((S)-4-carboxy-2-{[6-(2-methyl-4,5-dihydro-imidazol-1-yl)-2-phenyl-pyrimidine-4-carbonyl]-amino}-butyryl)-piperazine-1-carboxylic acid ethyl ester formate salt 327.1. 4-((S)-4-tert-butoxycarbonyl-2-{[6-(2-methyl-4,5-dihydro-imidazol-1-yl)-2-phenyl-pyrimidine-4-carbonyl]-amino}-butyryl)-piperazine-1-carboxylic acid ethyl ester This compound was prepared using a method analogous to that of Example 317, step 317.1, 2-methyl-2-imidazoline replacing (S)-3-hydroxypyrrolidine, the reaction taking place at 60° C. instead of RT.
LC-MS (B): $t_R$=0.86 min; $[M+H]^+$: 608.32.

327.2. 4-((S)-4-carboxy-2-{[6-(2-methyl-4,5-dihydro-imidazol-1-yl)-2-phenyl-pyrimidine-4-carbonyl]-amino}-butyryl)-piperazine-1-carboxylic acid ethyl ester formate salt This compound was prepared using a method analogous to that of Example 326, step 326.2, intermediate 327.1 replacing intermediate 326.1. The compound was however purified by preparative LC-MS (I).
LC-MS (B): $t_R$=0.73 min; $[M+H]^+$: 552.15.

Example 328

4-{(S)-4-carboxy-2-[(2-phenyl-6-[1,2,4]triazol-1-yl-pyrimidine-4-carbonyl)-amino]-butyryl}-piperazine-1-carboxylic acid ethyl ester formate salt 328.1. 4-{(S)-4-tert-butoxycarbonyl-2-[(2-phenyl-6-[1, 2, 4]triazol-1-yl-pyrimidine-4-carbonyl)-amino]-butyryl}-piperazine-1-carboxylic acid ethyl ester This compound was prepared using a method analogous to that of Example 238, step 238.1, 1,2,4-triazole replacing imidazole and the reaction taking place at 70° C. instead of RT. The compound was purified by preparative LC-MS (III).
LC-MS (C): $t_R$=1.17 min; $[M+H]^+$: 593.24.

328.2. 4-{(S)-4-carboxy-2-[(2-phenyl-6-[1,2,4]triazol-1-yl-pyrimidine-4-carbonyl)-amino]-butyryl}-piperazine-1-carboxylic acid ethyl ester formate salt This compound was prepared using a method analogous to that of Example 326, step 326.2, intermediate 328.1 replacing intermediate 326.1. The compound was however purified by preparative LC-MS (III).
LC-MS (B): $t_R$=0.99 min; $[M+H]^+$: 537.36.

Example 329

4-((S)-4-carboxy-2-{[6-(4-methyl-pyrazol-1-yl)-2-phenyl-pyrimidine-4-carbonyl]-amino}-butyryl)-piperazine-1-carboxylic acid ethyl ester 329.1. 4-((S)-4-tert-butoxycarbonyl-2-{[6-(4-methyl-pyrazol-1-yl)-2-phenyl-pyrimidine-4-carbonyl]-amino}-butyryl)-piperazine-1-carboxylic acid ethyl ester This compound was prepared using a method analogous to that of Example 238, step 238.1, 4-methylpyrazole replacing imidazole.
LC-MS (B): $t_R$=1.27 min; $[M+H]^+$: 606.24.

329.2. 4-((S)-4-carboxy-2-{[6-(4-methyl-pyrazol-1-yl)-2-phenyl-pyrimidine-4-carbonyl]-amino}-butyryl)-piperazine-1-carboxylic acid ethyl ester This compound was prepared using a method analogous to that of Example 1, step 1.9, intermediate 329.1 replacing intermediate 1.8. The compound was however purified by preparative LC-MS (III).
LC-MS (B): $t_R$=1.13 min; $[M+H]^+$: 549.98.

Example 330

4-((S)-4-carboxy-2-{[6-(3-methyl-pyrazol-1-yl)-2-phenyl-pyrimidine-4-carbonyl]-amino}-butyryl)-piperazine-1-carboxylic acid ethyl ester 330.1. 4-((S)-4-tert-butoxycarbonyl-2-{[6-(3-methyl-pyrazol-1-yl)-2-phenyl-pyrimidine-4-carbonyl]-amino}-butyryl)-piperazine-1-carboxylic acid ethyl ester This compound was prepared using a method analogous to that of Example 238, step 238.1, 3-methylpyrazole replacing imidazole.
LC-MS (B): $t_R$=1.26 min; $[M+H]^+$: 606.24.

330.2. 4-((S)-4-carboxy-2-{[6-(3-methyl-pyrazol-1-yl)-2-phenyl-pyrimidine-4-carbonyl]-amino}-butyryl)-piperazine-1-carboxylic acid ethyl ester This compound was prepared using a method analogous to that of Example 326, step 326.2, intermediate 330.1 replacing intermediate 326.1. The compound was however purified by preparative LC-MS (III).
LC-MS (B): $t_R$=1.12 min; $[M+H]^+$: 550.14.

Example 331

4-{(S)-4-carboxy-2-[(2-phenyl-6-[1,2,3]triazol-1-yl-pyrimidine-4-carbonyl)-amino]-butyryl}-piperazine-1-carboxylic acid ethyl ester 331.1. 4-{(S)-4-carboxy-2-[(6-chloro-2-phenyl-pyrimidine-4-carbonyl)-amino]-butyryl}-piperazine-1-carboxylic acid ethyl ester This compound was prepared using a method analogous to that of Example 1, step 1.9, intermediate 48.1 replacing intermediate 1.8.
LC-MS (C): $t_R$=0.92 min; $[M+H]^+$: 504.21.

331.2. 4-{(S)-4-tert-carboxy-2-[(2-phenyl-6-[1,2,3]triazol-1-yl-pyrimidine-4-carbonyl)-amino]-butyryl}-piperazine-1-carboxylic acid ethyl ester 1H-1,2,3-triazole (34.5 mg) was added to a suspension of NaH (20 mg) in anhydrous DMF (2 ml) at RT. After 5 min stirring at RT, intermediate 331.1 (50 mg) was added. The mixture was allowed to stir at RT for 1 h. A NH$_4$Cl solution was added and the resulting mixture was extracted with EA. The organic phases were dried (Na$_2$SO$_4$) and evaporated off. The compound was purified by preparative LC-MS (III).
LC-MS (C): t$_R$=0.91 min; [M+H]$^+$: 537.39.

Example 332

4-((S)-2-{[6-(4-butyl-[1,2,3]triazol-1-yl)-2-phenyl-pyrimidine-4-carbonyl]-amino}-4-carboxy-butyryl)-piperazine-1-carboxylic acid ethyl ester 332.1. 4-((S)-2-{[(6-azido-2-phenyl-pyrimidine-4-carbonyl)-amino]-4-tert-butoxycarbonyl-butyryl}-piperazine-1-carboxylic acid ethyl ester To a solution of intermediate 48.1 (150 mg) in DMF (3 ml) was added at 0° C. NaN$_3$ (50 mg). The reaction mixture was allowed to warm to RT and was stirred over weekend at RT. It was poured into water and extracted with Et$_2$O. The organic phases were washed with a NaCl solution, dried (Na$_2$SO$_4$) and evaporated off to afford 80 mg of the desired product.
LC-MS (C): t$_R$=1.08 min; [M+H]$^+$: 567.36.

332.2. 4-((S)-2-{[6-(4-butyl-[1,2,3]triazol-1-yl)-2-phenyl-pyrimidine-4-carbonyl]-amino}-4-tert-butoxycarbonyl-butyryl)-piperazine-1-carboxylic acid ethyl ester Intermediate 332.1 (80 mg) and 1-hexine (16 µl) were suspended in a 1:1 mixture of water and t-butanol (1 ml). Ascorbic acid (27.3 mg) was added, followed by the copper (II) sulfate pentahydrate (7 mg). The heterogeneous mixture was stirred at RT overnight. A NaHCO$_3$ solution was added and the mixture was extracted with DCM. The organic phases were washed with a NaCl solution, dried (Na$_2$SO$_4$) and evaporated off. Preparative TLC (EA/Hept 3/7 to 1/1) of the crude yielded 22 mg of the desired compound.
LC-MS (C): t$_R$=1.14 min; [M+H]$^+$: 649.30.

332.3. 4-((S)-2-{[6-(4-butyl-[1,2,3]triazol-1-yl)-2-phenyl-pyrimidine-4-carbonyl]-amino}-4-carboxy-butyryl)-piperazine-1-carboxylic acid ethyl ester This compound was prepared using a method analogous to that of Example 1, step 1.9, intermediate 332.2 replacing intermediate 1.8. The compound was however purified by preparative LC-MS (IV).
LC-MS (C): t$_R$=1.01 min; [M+H]$^+$: 593.16.

Example 333

4-{(S)-2-[(6-amino-2-phenyl-pyrimidine-4-carbonyl)-amino]-4-carboxy-butyryl}-piperazine-1-carboxylic acid ethyl ester triflate salt 333.1. 4-{(S)-2-[(6-amino-2-phenyl-pyrimidine-4-carbonyl)-amino]-4-tert-butoxycarbonyl-butyryl}-piperazine-1-carboxylic acid ethyl ester Intermediate 48.1 (4.9 g) was dissolved in MeOH (15 ml) and a 7M solution of ammonia in MeOH (15 ml). The mixture was heated at 90° C. in a microwave oven (Emrys Optimizer, Biotage) overnight. DCM was added. The organic solution was washed with water, dried (Na$_2$SO$_4$) and evaporated off. Column chromatography (EA/Hept 1/1 to 1/0) afforded 3.03 g of the desired compound.
LC-MS (C): t$_R$=0.96 min; [M+H]$^+$: 541.13.

333.2. 4-{(S)-2-[(6-amino-2-phenyl-pyrimidine-4-carbonyl)-amino]-4-carboxy-butyryl}-piperazine-1-carboxylic acid ethyl ester triflate salt This compound was prepared using a method analogous to that of Example 1, step 1.9, intermediate 333.1 replacing intermediate 1.8.
LC-MS (C): t$_R$=0.80 min; [M+H]$^+$: 485.03.

Example 334

4-((S)-4-carboxy-2-{[6-(cyclohexanecarbonyl-amino)-2-phenyl-pyrimidine-4-carbonyl]-amino}-butyryl)-piperazine-1-carboxylic acid ethyl ester Intermediate 333.1 (70 mg) and cyclohexanecarboxylic acid chloride (1 eq) were dissolved in pyridine (0.5 ml) and the mixture was heated at 70° C. overnight. The mixture was evaporated off and the residue taken up in TFA (1 ml). After 3 h stirring at RT, the solvent was removed and the residue purified by preparative LC-MS (IV).
LC-MS (C): t$_R$=0.97 min; [M+H]$^+$: 595.32.

Example 335

4-[(S)-4-carboxy-2-({2-phenyl-6-[(thiophene-2-carbonyl)-amino]-pyrimidine-4-carbonyl}-amino)-butyryl]-piperazine-1-carboxylic acid ethyl ester This compound was prepared using a method analogous to that of Example 334, 2-thiophenecarbonyl chloride replacing cyclohexanecarboxylic acid chloride.
LC-MS (C): t$_R$=0.94 min; [M+H]$^+$: 595.22.

Example 336

4-{(S)-4-carboxy-2-({6-[(furan-2-carbonyl)-amino]-2-phenyl-pyrimidine-4-carbonyl}-amino)-butyryl}-piperazine-1-carboxylic acid ethyl ester This compound was prepared using a method analogous to that of Example 334, 2-furoyl chloride replacing cyclohexanecarboxylic acid chloride.
LC-MS (C): t$_R$=0.91 min; [M+H]$^+$: 579.25.

Example 337

4-{(S)-4-carboxy-2-[(2-phenyl-6-phenylacetylamino-pyrimidine-4-carbonyl)-amino]-butyryl}-piperazine-1-carboxylic acid ethyl ester This compound was prepared using a method analogous to that of Example 334, phenylacetyl chloride replacing cyclohexanecarboxylic acid chloride.
LC-MS (C): t$_R$=0.94 min; [M+H]$^+$: 603.28.

Example 338

4-((S)-4-carboxy-2-{[2-phenyl-6-(3-phenyl-propionylamino)-pyrimidine-4-carbonyl]-amino}-butyryl)-piperazine-1-carboxylic acid ethyl ester This compound was prepared using a method analogous to that of Example 334, 3-phenylpropionyl chloride replacing cyclohexanecarboxylic acid chloride.
LC-MS (C): $t_R$=0.99 min; [M+H]$^+$: 617.55.

Example 339

4-((S)-4-carboxy-2-{[6-(3-cyclopentyl-propionylamino)-2-phenyl-pyrimidine-4-carbonyl]-amino}-butyryl)-piperazine-1-carboxylic acid ethyl ester This compound was prepared using a method analogous to that of Example 334, 3-cyclopentylpropionyl chloride replacing cyclohexanecarboxylic acid chloride, using preparative LC-MS (IV) instead of (III).
LC-MS (C): $t_R$=1.00 min; [M+H]$^+$: 609.35.

Example 340

4-((S)-4-carboxy-2-{[6-(2,2-dimethyl-propionylamino)-2-phenyl-pyrimidine-4-carbonyl]-amino}-butyryl)-piperazine-1-carboxylic acid ethyl ester This compound was prepared using a method analogous to that of Example 334, pivaloyl chloride replacing cyclohexanecarboxylic acid chloride.
LC-MS (C): $t_R$=0.94 min; [M+H]$^+$: 569.30.

Example 341

4-((S)-4-carboxy-2-{[2-phenyl-6-(2-propyl-pentanoylamino)-pyrimidine-4-carbonyl]-amino}-butyryl)-piperazine-1-carboxylic acid ethyl ester This compound was prepared using a method analogous to that of Example 334, 2,2-di-n-propylacetyl chloride replacing cyclohexanecarboxylic acid chloride.
LC-MS (C): $t_R$=1.02 min; [M+H]$^+$: 611.40.

Example 342

4-{(S)-2-[(6-benzoylamino-2-phenyl-pyrimidine-4-carbonyl)-amino]-4-carboxy-butyryl}-piperazine-1-carboxylic acid ethyl ester This compound was prepared using a method analogous to that of Example 334, benzoyl chloride replacing cyclohexanecarboxylic acid chloride.
LC-MS (C): $t_R$=0.94 min; [M+H]$^+$: 589.26.

Example 343

4-((S)-4-carboxy-2-{[6-(2-cyclopentyl-acetylamino)-2-phenyl-pyrimidine-4-carbonyl]-amino}-butyryl)-piperazine-1-carboxylic acid ethyl ester This compound was prepared using a method analogous to that of Example 334, cyclopentylacetyl chloride replacing cyclohexanecarboxylic acid chloride.
LC-MS (C): $t_R$=0.97 min; [M+H]$^+$: 595.32.

Example 344

4-((S)-4-carboxy-2-{[6-(2-methoxy-acetylamino)-2-phenyl-pyrimidine-4-carbonyl]-amino}-butyryl)-piperazine-1-carboxylic acid ethyl ester This compound was prepared using a method analogous to that of Example 334, methoxyacetyl chloride replacing cyclohexanecarboxylic acid chloride.
LC-MS (C): $t_R$=0.87 min; [M+H]$^+$: 557.27.

Example 345

4-((S)-4-carboxy-2-{[6-(cyclobutanecarbonyl-amino)-2-phenyl-pyrimidine-4-carbonyl]-amino}-butyryl)-piperazine-1-carboxylic acid ethyl ester This compound was prepared using a method analogous to that of Example 334, cyclobutanecarboxylic acid chloride replacing cyclohexanecarboxylic acid chloride.
LC-MS (C): $t_R$=0.92 min; [M+H]$^+$: 567.28.

Example 346

4-((S)-4-carboxy-2-{[6-(cyclopentanecarbonyl-amino)-2-phenyl-pyrimidine-4-carbonyl]-amino}-butyryl)-piperazine-1-carboxylic acid ethyl ester This compound was prepared using a method analogous to that of Example 334, cyclopentanecarboxylic acid chloride replacing cyclohexanecarboxylic acid chloride, using preparative LC-MS (IV) instead of (III).
LC-MS (C): $t_R$=0.94 min; [M+H]$^+$: 581.29.

Example 347

4-{(S)-4-carboxy-2-[(6-pentanoylamino-2-phenyl-pyrimidine-4-carbonyl)-amino]-butyryl}-piperazine-1-carboxylic acid ethyl ester This compound was prepared using a method analogous to that of Example 334, valeryl chloride replacing cyclohexanecarboxylic acid chloride.
LC-MS (C): $t_R$=0.96 min; [M+H]$^+$: 569.38.

Example 348

4-((S)-4-carboxy-2-{[6-(3-methyl-butyrylamino)-2-phenyl-pyrimidine-4-carbonyl]-amino}-butyryl)-piperazine-1-carboxylic acid ethyl ester This compound was prepared using a method analogous to that of Example 334, isovaleryl chloride replacing cyclohexanecarboxylic acid chloride.
LC-MS (C): $t_R$=0.94 min; [M+H]$^+$: 569.29.

Example 349

4-((S)-4-carboxy-2-{[6-(cyclopropanecarbonyl-amino)-2-phenyl-pyrimidine-4-carbonyl]-amino}-butyryl)-piperazine-1-carboxylic acid ethyl ester This compound was prepared using a method analogous to that of Example 334, cyclopropanecarboxylic acid chloride replacing cyclohexanecarboxylic acid chloride.
LC-MS (C): $t_R$=0.89 min; [M+H]$^+$: 553.28.

Example 350

4-{(S)-2-[(6-acetylamino-2-phenyl-pyrimidine-4-carbonyl)-amino]-4-carboxy-butyryl}-piperazine-1-carboxylic acid ethyl ester This compound was prepared using a method analogous to that of Example 334, acetyl chloride replacing cyclohexanecarboxylic acid chloride, using preparative LC-MS (IV) instead of (II).
LC-MS (C): $t_R$=0.84 min; [M+H]$^+$: 527.27.

Example 351

4-{(S)-2-[(6-butyrylamino-2-phenyl-pyrimidine-4-carbonyl)-amino]-4-carboxy-butyryl}-piperazine-1-carboxylic acid ethyl ester This compound was prepared using a method analogous to that of Example 334, butyryl chloride replacing cyclohexanecarboxylic acid chloride.
LC-MS (C): $t_R$=0.91 min; [M+H]$^+$: 555.28.

Example 352

4-{(S)-4-carboxy-2-[(6-isobutyrylamino-2-phenyl-pyrimidine-4-carbonyl)-amino]-butyryl}-piperazine-1-carboxylic acid ethyl ester This compound was prepared using a method analogous to that of Example 334, isobutyryl chloride replacing cyclohexanecarboxylic acid chloride.
LC-MS (C): $t_R$=0.90 min; [M+H]$^+$: 555.29.

Example 353

4-{(S)-4-carboxy-2-[(2-phenyl-6-propionylamino-pyrimidine-4-carbonyl)-amino]-butyryl}-piperazine-1-carboxylic acid ethyl ester This compound was prepared using a method analogous to that of Example 334, propionyl chloride replacing cyclohexanecarboxylic acid chloride.
LC-MS (C): $t_R$=0.87 min; [M+H]$^+$: 541.28.

Example 354

4-((S)-4-carboxy-2-{[2-phenyl-6-(propane-1-sulfonylamino)-pyrimidine-4-carbonyl]-amino}-butyryl)-piperazine-1-carboxylic acid ethyl ester Intermediate 333.1 (100 mg) was added to a suspension of NaH (11 mg) in anhydrous THF (0.5 ml) at RT. After 30 min stirring at RT, 1-propanesulfonyl chloride (26.4 mg) dissolved in THF (0.5 ml) was added. The mixture was stirred at 70° C. overnight. The mixture was evaporated off and the residue taken up in TFA (0.5 ml) and stir at RT for 2 h. After removal of the solvent, the crude was purified by preparative LC-MS (III) to afford 30 mg of the desired compound.
LC-MS (C): $t_R$=0.90 min; [M+H]$^+$: 591.47.

Example 355

4-{(S)-4-carboxy-2-[(6-ethanesulfonylamino-2-phenyl-pyrimidine-4-carbonyl)-amino]-butyryl}-piperazine-1-carboxylic acid ethyl ester This compound was prepared using a method analogous to that of Example 354, ethanesulfonyl chloride replacing 1-propanesulfonyl chloride.
LC-MS (C): $t_R$=0.87 min; [M+H]$^+$: 577.36.

Example 356

4-{(S)-2-[(6-benzenesulfonylamino-2-phenyl-pyrimidine-4-carbonyl)-amino]-4-carboxy-butyryl}-piperazine-1-carboxylic acid ethyl ester This compound was prepared using a method analogous to that of Example 354, benzenesulfonyl chloride replacing 1-propanesulfonyl chloride.
LC-MS (C): $t_R$=0.93 min; [M+H]$^+$: 625.35.

Example 357

4-((S)-4-carboxy-2-{[2-phenyl-6-(propane-2-sulfonylamino)-pyrimidine-4-carbonyl]-amino}-butyryl)-piperazine-1-carboxylic acid ethyl ester This compound was prepared using a method analogous to that of Example 354, 2-propanesulfonyl chloride replacing 1-propanesulfonyl chloride.
LC-MS (C): $t_R$=0.90 min; [M+H]$^+$: 591.40.

Example 358

4-((S)-4-carboxy-2-{[6-(4-oxo-4H-pyridin-1-yl)-2-phenyl-pyrimidine-4-carbonyl]-amino}-butyryl)-piperazine-1-carboxylic acid ethyl ester This compound was prepared using a method analogous to that of Example 331, step 331.2, 4-pyridinol replacing 1H-1,2,3-triazole. The crude was directly purified by preparative LC-MS (II).
LC-MS (C): $t_R$=0.89 min; [M+H]$^+$: 563.53.

Example 359

4-((S)-4-carboxy-2-{[6-(3-methyl-5-oxo-2,5-dihydro-pyrazol-1-yl)-2-phenyl-pyrimidine-4-carbonyl]-amino}-butyryl)-piperazine-1-carboxylic acid ethyl ester 359.1. 4-((S)-4-tert-butoxycarbonyl-2-{[6-(3-methyl-5-oxo-2,5-dihydro-pyrazol-1-yl)-2-phenyl-pyrimidine-4-carbonyl]-amino}-butyryl)-piperazine-1-carboxylic acid ethyl ester This compound was prepared using a method analogous to that of Example 331, step 331.2, intermediate 48.1 replacing intermediate 331.1, 3-methyl-3-pyrazoline-5-one replacing 1H-1,2,3-triazole. The compound was however purified by column chromatography (EA/Hept 3/7).
LC-MS (C): $t_R$=1.01 min; [M+H]$^+$: 622.08.

359.2. 4-((S)-carboxy-2-{[6-(3-methyl-5-oxo-2,5-dihydro-pyrazol-1-yl)-2-phenyl-pyrimidine-4-carbonyl]-amino}-butyryl)-piperazine-1-carboxylic acid ethyl ester This compound was prepared using a method analogous to that of Example 1, step 1.9, intermediate 359.1 replacing intermediate 1.8. The compound was however purified by preparative LC-MS (I).
LC-MS (C): $t_R$=0.87 min; [M+H]$^+$: 565.97.

Example 360

4-((S)-4-carboxy-2-{[6-(2-hydroxy-1-methyl-propyl-sulfanyl)-2-phenyl-pyrimidine-4-carbonyl]-amino}-butyryl)-piperazine-1-carboxylic acid ethyl ester

360.1. 3-(tert-butyl-dimethyl-silanyloxy)-butane-2-thiol 2,6-lutidine (163 μl) was added to a solution of 3-mercapto-2-butanol (68 mg) in DCM (5 ml) and the mixture was cooled down to −20° C. Tert-butyldimethylsilyl trifluoromethanesulfonate (163 μl) was slowly added and it was stirred 1 h at −20° C. Another 163 μl of the silyl reagent was added and the mixture was allowed to warm to RT and stirred one might at RT. The mixture was evaporated off and used without purification and characterization.

360.2. 4-[(S)-4-tert-butoxycarbonyl-2-({6-[2-(tert-butyl-dimethyl-silanyloxy)-1-methyl-propylsulfanyl]-2-phenyl-pyrimidine-4-carbonyl}-amino)-butyryl]-piperazine-1-carboxylic acid ethyl ester This compound was prepared using a method analogous to that of Example 247, step 247.1, intermediate 360.1 replacing 1-propanethiol and the reaction being carried out at RT instead of 0° C.

LC-MS (C): $t_R$=1.28 min; [M+H]$^+$: 744.45.

360.3. 4-[(S)-2-({6-[2-(tert-butyl-dimethyl-silanyloxy)-1-methyl-propylsulfanyl]-2-phenyl-pyrimidine-4-carbonyl}-amino)-4-carboxy-butyryl]-piperazine-1-carboxylic acid ethyl ester This compound was prepared using a method analogous to that of Example 1, step 1.9, intermediate 360.2 replacing intermediate 1.8.

LC-MS (B): $t_R$=1.30 min; [M+H]$^+$: 688.38.

360.4. 4-((S)-4-carboxy-2-{[6-(2-hydroxy-1-methyl-propylsulfanyl)-2-phenyl-pyrimidine-4-carbonyl]-amino}-butyryl)-piperazine-1-carboxylic acid ethyl ester Intermediate 360.3 (63 mg) was dissolved in THF (1 ml) and a 1M solution of TBAF in THF (356 μl) was added. After stirring 48 h at RT, the mixture was evaporated off and the residue taken up in DCM/NH$_4$Cl solution. The org. phase was dried (Na$_2$SO$_4$) and evaporated off. Preparative LC-MS (III) gave 14 mg of the desired product.

LC-MS (C): $t_R$=0.91 min; [M+H]$^+$: 574.31.

Example 361

4-((S)-4-carboxy-2-{[6-(2-hydroxy-propylsulfanyl)-2-phenyl-pyrimidine-4-carbonyl]-amino}-butyryl)-piperazine-1-carboxylic acid ethyl ester

361.1. 2-(tert-butyl-dimethyl-silanyloxy)-propane-1-thiol

This compound was prepared using a method analogous to that of Example 360, step 360.1, 1-mercapto-2-propanol replacing 3-mercapto-2-butanol.

361.2. 4-[(S)-4-tert-butoxycarbonyl-2-({6-[2-(tert-butyl-dimethyl-silanyloxy)-propylsulfanyl]-2-phenyl-pyrimidine-4-carbonyl]-amino)-butyryl}-piperazine-1-carboxylic acid ethyl ester This compound was prepared using a method analogous to that of Example 360, step 360.2, intermediate 361.1 replacing intermediate 360.1.

LC-MS (C): $t_R$=1.27 min; [M+H]$^+$: 730.43.

361.3. 4-((S)-4-carboxy-2-{[6-(2-hydroxy-propylsulfanyl)-2-phenyl-pyrimidine-4-carbonyl]-amino}-butyryl)-piperazine-1-carboxylic acid ethyl ester This compound was prepared using a method analogous to that of Example 1, step 1.9, intermediate 361.2 replacing intermediate 1.8. The compound was however purified by preparative LC-MS (II).

LC-MS (B): $t_R$=0.98 min; [M+H]$^+$: 560.20.

Example 362

4-[(S)-2-({6-[(benzyl-methyl-amino)-methyl]-2-phenyl-pyrimidine-4-carbonyl}-amino)-4-carboxy-butyryl]-piperazine-1-carboxylic acid ethyl ester

362.1. 6-formyl-2-phenyl-pyrimidine-4-carboxylic acid methyl ester

A mixture of intermediate 86.1 (5 g) and selenium dioxide (HOW MUCH?) in dioxane was refluxed overnight. It was filtered through Celite and evaporated off. Column chromatography (EA/Hept 1/9) afforded 4 g of the desired product.

LC-MS (C): $t_R$=0.74 min; [M+H$_2$O+H]$^+$: 261.21.

362.2. 6-hydroxymethyl-2-phenyl-pyrimidine-4-carboxylic acid methyl ester

Intermediate 362.1 (1.57 g) was dissolved in MeOH/DCM (31 ml/4 ml) and cooled down to 0° C. NaBH$_4$ (62 mg) was added portionwise. After 1 h 30 stirring at 0° C., water and a 1M HCl solution were added and the org. solvents were removed. The remaining solution was extracted with DCM. The org. phases were washed with a NaCl solution, dried (Na$_2$SO$_4$) and evaporated off to afford 1.57 g of the desired product.

LC-MS (C): $t_R$=0.81 min; [M+H]$^+$: 244.97.

362.3. 6-chloromethyl-2-phenyl-pyrimidine-4-carboxylic acid methyl ester

This compound was prepared using a method analogous to that of Example 23, step 23.2, intermediate 362.2 replacing intermediate 23.1.

LC-MS (C): $t_R$=0.99 min; [M+H]$^+$: 262.95.

362.4. 6-chloromethyl-2-phenyl-pyrimidine-4-carboxylic acid

This compound was prepared using a method analogous to that of Example 86, step 86.2, intermediate 362.3 replacing intermediate 86.1.

LC-MS (C): $t_R$=0.88 min; [M+H]$^+$: 248.93.

362.5. 4-{(S)-4-tert-butoxycarbonyl-2-[(6-chloromethyl-2-phenyl-pyrimidine-4-carbonyl)-amino]-butyryl}-piperazine-1-carboxylic acid ethyl ester This compound was prepared using a method analogous to that of Example 1, step 1.1, intermediate 362.4 replacing Z-(L)Glu(OtBu)—OH, intermediate 1.2 replacing 1-ethoxycarbonylpiperazine and DCM being used as solvent.
LC-MS (C): $t_R$=1.08 min; [M+H]$^+$: 574.34.

362.6 4-[(S)-2-({6-[(benzyl-methyl-amino)-methyl]-2-phenyl-pyrimidine-4-carbonyl}-amino)-4-tert-butoxycarbonyl-butyryl]-piperazine-1-carboxylic acid ethyl ester Intermediate 362.5 (70 mg) was dissolved in THF (1 ml) and N-benzylmethylamine (121 mg) was added. The mixture was heated at 100° C. in a sealed tube until reaction completion and was evaporated off. The residue was taken up in TFA (1 ml) and stirred for 48 h at RT. The solution was partially evaporated and purified by preparative LC-MS (I) to afford 31 mg of the desired compound.
LC-MS (C): $t_R$=0.79 min; [M+H]$^+$: 603.18.

Example 363

4-((S)-4-carboxy-2-{[6-(4-ethoxycarbonyl-piperidin-1-ylmethyl)-2-phenyl-pyrimidine-4-carbonyl]-amino}-butyryl)-piperazine-1-carboxylic acid ethyl ester This compound was prepared using a method analogous to that of Example 362, step 362.6, ethyl isonipecotate replacing N-benzylmethylamine.
LC-MS (C): $t_R$=0.76 min; [M+H]$^+$: 639.22.

Example 364

4-((S)-4-carboxy-2-{[6-((S)-2-hydroxymethyl-pyrrolidin-1-ylmethyl)-2-phenyl-pyrimidine-4-carbonyl]-amino}-butyryl)-piperazine-1-carboxylic acid ethyl ester This compound was prepared using a method analogous to that of Example 362, step 362.6, L-prolinol replacing N-benzylmethylamine.
LC-MS (C): $t_R$=0.72 min; [M+H]$^+$: 583.17.

Example 365

4-((S)-4-carboxy-2-{[6-(4-methoxycarbonyl-piperidin-1-ylmethyl)-2-phenyl-pyrimidine-4-carbonyl]-amino}-butyryl)-piperazine-1-carboxylic acid ethyl ester This compound was prepared using a method analogous to that of Example 362, step 362.6, methyl isonipecotate replacing N-benzylmethylamine.
LC-MS (C): $t_R$=0.74 min; [M+H]$^+$: 625.19.

Example 366

4-((S)-4-carboxy-2-{[6-(3-hydroxy-piperidin-1-ylmethyl)-2-phenyl-pyrimidine-4-carbonyl]-amino}-butyryl)-piperazine-1-carboxylic acid ethyl ester This compound was prepared using a method analogous to that of Example 362, step 362.6, 3-hydroxypiperidine replacing N-benzylmethylamine.
LC-MS (C): $t_R$=0.70 min; [M+H]$^+$: 583.20.

Example 367

4-((S)-4-carboxy-2-{[6-(2-hydroxymethyl-piperidin-1-ylmethyl)-2-phenyl-pyrimidine-4-carbonyl]-amino}-butyryl)-piperazine-1-carboxylic acid ethyl ester This compound was prepared using a method analogous to that of Example 362, step 362.6, 2-(hydroxymethyl)piperidine replacing N-benzylmethylamine.
LC-MS (C): $t_R$=0.72 min; [M+H]$^+$: 597.18.

Example 368

4-{(S)-4-carboxy-2-[(6-morpholin-4-ylmethyl-2-phenyl-pyrimidine-4-carbonyl)-amino]-butyryl}-piperazine-1-carboxylic acid ethyl ester This compound was prepared using a method analogous to that of Example 362, step 362.6, morpholine replacing N-benzylmethylamine.
LC-MS (C): $t_R$=0.71 min; [M+H]$^+$: 569.17.

Example 369

4-((S)-4-carboxy-2-{[6-((R)-3-hydroxy-pyrrolidin-1-ylmethyl)-2-phenyl-pyrimidine-4-carbonyl]-amino}-butyryl)-piperazine-1-carboxylic acid ethyl ester This compound was prepared using a method analogous to that of Example 362, step 362.6, (R)-3-pyrrolidinol replacing N-benzylmethylamine.
LC-MS (C): $t_R$=0.69 min; [M+H]$^+$: 569.16.

Example 370

4-{(S)-4-carboxy-2-[(2-phenyl-6-piperidin-1-ylmethyl-pyrimidine-4-carbonyl)-amino]-butyryl}-piperazine-1-carboxylic acid ethyl ester This compound was prepared using a method analogous to that of Example 362, step 362.6, piperidine replacing N-benzylmethylamine.
LC-MS (C): $t_R$=0.74 min; [M+H]$^+$: 567.20.

Example 371

4-((S)-4-carboxy-2-{[6-(2,6-dimethyl-morpholin-4-ylmethyl)-2-phenyl-pyrimidine-4-carbonyl]-amino}-butyryl)-piperazine-1-carboxylic acid ethyl ester This compound was prepared using a method analogous to that of Example 362, step 362.6, 2,6-dimethylmorpholine replacing N-benzylmethylamine.
LC-MS (C): $t_R$=0.74 min; [M+H]$^+$: 597.19.

Example 372

4-[(S)-4-carboxy-2-({6-[(ethyl-methyl-amino)-methyl]-2-phenyl-pyrimidine-4-carbonyl}-amino)-butyryl]-piperazine-1-carboxylic acid ethyl ester This compound was prepared using a method analogous to that of Example 362, step 362.6, ethylmethylamine replacing N-benzylmethylamine.
LC-MS (C): $t_R$=0.72 min; [M+H]$^+$: 541.17.

Example 373

4-{(S)-4-carboxy-2-[(6-diethylaminomethyl-2-phenyl-pyrimidine-4-carbonyl)-amino]-butyryl}-piperazine-1-carboxylic acid ethyl ester This compound was prepared using a method analogous to that of Example 362, step 362.6, diethylamine replacing N-benzylmethylamine.

LC-MS (C): $t_R$=0.74 min; [M+H]$^+$: 555.17.

Example 374

4-{(S)-4-carboxy-2-[(2-phenyl-6-pyrrolidin-1-ylmethyl-pyrimidine-4-carbonyl)-amino]-butyryl}-piperazine-1-carboxylic acid ethyl ester This compound was prepared using a method analogous to that of Example 362, step 362.6, pyrrolidine replacing N-benzylmethylamine.

LC-MS (C): $t_R$=0.72 min; [M+H]$^+$: 553.13.

Example 375

4-{(S)-4-carboxy-2-[(6-ethanesulfonylmethyl-2-phenyl-pyrimidine-4-carbonyl)-amino]-butyryl}-piperazine-1-carboxylic acid ethyl ester

375.1. 4-{(S)-4-tert-butoxycarbonyl-2-[(6-ethylsulfanylmethyl-2-phenyl-pyrimidine-4-carbonyl)-amino]-butyryl}-piperazine-1-carboxylic acid ethyl ester This compound was prepared using a method analogous to that of Example 331, step 331.2, intermediate 362.5 replacing intermediate 331.1, ethanethiol replacing 1H-1,2,3-triazole, the reaction being carried out at 0° C. instead of RT.

LC-MS (A): $t_R$=1.34 min; [M+H]$^+$: 600.26.

375.2. 4-{(S)-4-tert-butoxycarbonyl-2-[(6-ethanesulfonylmethyl-2-phenyl-pyrimidine-4-carbonyl)-amino]-butyryl}-piperazine-1-carboxylic acid ethyl ester MCPBA (49 mg) was added to an ice cold solution of intermediate 375.1 (60 mg) in DCM (1 ml). The mixture was stirred at 0° C. for 2 h, then at RT overnight. A NaHCO$_3$ solution was added and the mixture was extracted with EA. The org. phase was dried (Na$_2$SO$_4$) and evaporated off. Preparative TLC (CHCl$_3$/MeOH 9/1) afforded 48 mg of the desired product.

LC-MS (A): $t_R$=1.16 min; [M+H]$^+$: 630.39.

375.3. 4-{(S)-4-carboxy-2-[(6-ethanesulfonylmethyl-2-phenyl-pyrimidine-4-carbonyl)-amino]-butyryl}-piperazine-1-carboxylic acid ethyl ester This compound was prepared using a method analogous to that of Example 1, step 1.9, intermediate 375.2 replacing intermediate 1.8. The compound was however purified by preparative TLC (DCM/MeOH/AcOH 9/1/0.1).

LC-MS (B): $t_R$=0.96 min; [M+H]$^+$: 576.22.

Example 376

4-{(S)-4-carboxy-2-[(2-phenyl-6-phenylsulfanylmethyl-pyrimidine-4-carbonyl)-amino]-butyryl}-piperazine-1-carboxylic acid ethyl ester

376.1. 4-{(S)-4-tert-butoxycarbonyl-2-[(6-ethylsulfanylmethyl-2-phenyl-pyrimidine-4-carbonyl)-amino]-butyryl}-piperazine-1-carboxylic acid ethyl ester This compound was prepared using a method analogous to that of Example 331, step 331.2, intermediate 362.5 replacing intermediate 331.1, thiophenol replacing 1H-1,2,3-triazole and the reaction being started at 0° C. instead of RT and continued overnight at RT. Besides, the compound was purified by preparative TLC (EA/Hept 1/1).

LC-MS (B): $t_R$=1.27 min; [M+H]$^+$: 648.56.

376.2. 4-{(S)-4-carboxy-2-[(2-phenyl-6-phenylsulfanylmethyl-pyrimidine-4-carbonyl)-amino]-butyryl}-piperazine-1-carboxylic acid ethyl ester This compound was prepared using a method analogous to that of Example 1, step 1.9, intermediate 376.1 replacing intermediate 1.8. The compound was however purified by preparative LC-MS (III).

LC-MS (B): $t_R$=1.13 min; [M+H]$^+$: 592.32.

Example 377

4-{(S)-2-[(6-benzenesulfonylmethyl-2-phenyl-pyrimidine-4-carbonyl)-amino]-4-carboxy-butyryl}-piperazine-1-carboxylic acid ethyl ester

377.1. 4-{(S)-2-[(6-benzenesulfonylmethyl-2-phenyl-pyrimidine-4-carbonyl)-amino]-4-tert-butoxycarbonyl-butyryl}-piperazine-1-carboxylic acid ethyl ester This compound was prepared using a method analogous to that of Example 375, step 375.2, intermediate 376.1 replacing intermediate 375.1.

LC-MS (B): $t_R$=1.19 min; [M+H]$^+$: 678.35.

377.2. 4-{(S)-2-[(6-benzenesulfonylmethyl-2-phenyl-pyrimidine-4-carbonyl)-amino]-4-carboxy-butyryl}-piperazine-1-carboxylic acid ethyl ester This compound was prepared using a method analogous to that of Example 1, step 1.9, intermediate 377.1 replacing intermediate 1.8. The compound was however purified by preparative LC-MS (III).

LC-MS (B): $t_R$=1.13 min; [M+H]$^+$: 592.32.

Example 378

4-{(S)-4-carboxy-2-[(6-cyclopentylsulfanylmethyl-2-phenyl-pyrimidine-4-carbonyl)-amino]-butyryl}-piperazine-1-carboxylic acid ethyl ester

378.1. 4-{(S)-4-tert-butoxycarbonyl-2-[(6-cyclopentylsulfanylmethyl-2-phenyl-pyrimidine-4-carbonyl)-amino]-butyryl}-piperazine-1-carboxylic acid ethyl ester This compound was prepared using a method analogous to that of Example 376, step 376.1, cyclopentylthiol replacing thiophenol.

LC-MS (B): $t_R$=1.29 min; [M+H]$^+$: 640.46.

378.2. 4-{(S)-4-carboxy-2-[(6-cyclopentylsulfanylm-ethyl-2-phenyl-pyrimidine-4-carbonyl)-amino]-butyryl}-piperazine-1-carboxylic acid ethyl ester This compound was prepared using a method analogous to that of Example 1, step 1.9, intermediate 378.1 replacing intermediate 1.8. The compound was however purified by preparative LC-MS (III).
LC-MS (B): $t_R$=1.15 min; [M+H]$^+$: 584.35.

Example 379

4-{(S)-4-carboxy-2-[(6-cyclopentanesulfonylmethyl-2-phenyl-pyrimidine-4-carbonyl)-amino]-butyryl}-piperazine-1-carboxylic acid ethyl ester 379.1. 4-{(S)-4-tert-butoxycarbonyl-2-[(6-cyclopentanesulfonylmethyl-2-phenyl-pyrimidine-4-carbonyl)-amino]-butyryl}-piperazine-1-carboxylic acid ethyl ester This compound was prepared using a method analogous to that of Example 375, step 375.2, intermediate 378.1 replacing intermediate 375.1.
LC-MS (B): $t_R$=1.20 min; [M+H]$^+$: 670.39.

379.2. 4-{(S)-4-carboxy-2-[(6-cyclopentanesulfonyl-methyl-2-phenyl-pyrimidine-4-carbonyl)-amino]-butyryl}-piperazine-1-carboxylic acid ethyl ester This compound was prepared using a method analogous to that of Example 1, step 1.9, intermediate 379.1 replacing intermediate 1.8. The compound was however purified by preparative LC-MS (III).
LC-MS (B): $t_R$=1.05 min; [M+H]$^+$: 624.32.

Example 380

4-{(S)-4-carboxy-2-[(2-phenyl-6-thiophen-3-yl-pyrimidine-4-carbonyl)-amino]-butyryl}-piperazine-1-carboxylic acid ethyl ester Intermediate 331.1 (50 mg), 3-thiopheneboronic acid (12.7 mg), tetrakis(triphenylphosphine)palladium (5.3 mg) and potassium phosphate (42 mg) were dissolved in anhydrous dioxane (1.5 ml) under argon. The mixture was refluxed for 4 h, filtered through Celite and evaporated off. Preparative LC-MS (IV) offered 2 mg of the desired compound.
LC-MS (C): $t_R$=0.98 min; [M+H]$^+$: 552.33.

Example 381

4-((S)-4-carboxy-2-{[6-(2-methoxy-phenyl)-2-phenyl-pyrimidine-4-carbonyl]-amino}-butyryl)-piperazine-1-carboxylic acid ethyl ester This compound was prepared using a method analogous to that of Example 380, 2-methoxyphenylboronic acid replacing 3-thiopheneboronic acid.
LC-MS (C): $t_R$=1.00 min; [M+H]$^+$: 576.38.

Example 382

4-((S)-4-carboxy-2-{[6-(4-methanesulfonyl-phenyl)-2-phenyl-pyrimidine-4-carbonyl]-amino}-butyryl)-piperazine-1-carboxylic acid ethyl ester This compound was prepared using a method analogous to that of Example 380, 4-(methanesulfonyl)phenylboronic acid replacing 3-thiopheneboronic acid.
LC-MS (C): $t_R$=0.94 min; [M+H]$^+$: 624.45.

Example 383

4-((S)-2-{[6-(4-Acetyl-phenyl)-2-phenyl-pyrimidine-4-carbonyl]-amino}-4-carboxy-butyryl)-piperazine-1-carboxylic acid ethyl ester This compound was prepared using a method analogous to that of Example 380, 4-acetylphenylboronic acid replacing 3-thiopheneboronic acid.
LC-MS (C): $t_R$=1.00 min; [M+H]$^+$: 588.47.

Example 384

4-((S)-4-carboxy-2-{[6-(2-fluoro-phenyl)-2-phenyl-pyrimidine-4-carbonyl]-amino}-butyryl)-piperazine-1-carboxylic acid ethyl ester This compound was prepared using a method analogous to that of Example 380, 2-fluorophenylboronic acid replacing 3-thiopheneboronic acid.
LC-MS (C): $t_R$=1.00 min; [M+H]$^+$: 564.32.

Example 385

4-((S)-4-carboxy-2-{[6-(3-cyano-phenyl)-2-phenyl-pyrimidine-4-carbonyl]-amino}-butyryl)-piperazine-1-carboxylic acid ethyl ester This compound was prepared using a method analogous to that of Example 380, 3-cyanophenylboronic acid replacing 3-thiopheneboronic acid.
LC-MS (C): $t_R$=0.99 min; [M+H]$^+$: 571.31.

Example 386

4-((S)-4-carboxy-2-{[6-(3-fluoro-phenyl)-2-phenyl-pyrimidine-4-carbonyl]-amino}-butyryl)-piperazine-1-carboxylic acid ethyl ester This compound was prepared using a method analogous to that of Example 380, 3-fluorophenylboronic acid replacing 3-thiopheneboronic acid.
LC-MS (C): $t_R$=1.01 min; [M+H]$^+$: 564.32.

Example 387

4-((S)-4-carboxy-2-{[6-(4-methoxy-phenyl)-2-phenyl-pyrimidine-4-carbonyl]-amino}-butyryl)-piperazine-1-carboxylic acid ethyl ester This compound was prepared using a method analogous to that of Example 380, 4-methoxyphenylboronic acid replacing 3-thiopheneboronic acid.
LC-MS (C): $t_R$=1.02 min; [M+H]$^+$: 576.41.

Example 388

4-{(S)-4-carboxy-2-[(6-furan-3-yl-2-phenyl-pyrimidine-4-carbonyl)-amino]-butyryl}-piperazine-1-carboxylic acid ethyl ester This compound was prepared using a method analogous to that of Example 380, 3-furanboronic acid replacing 3-thiopheneboronic acid.
LC-MS (C): $t_R$=0.97 min; [M+H]$^+$: 536.35.

Example 389

4-{(S)-2-[(6-benzo[1,3]dioxol-5-yl-2-phenyl-pyrimidine-4-carbonyl)-amino]-4-carboxy-butyryl}-piperazine-1-carboxylic acid ethyl ester This compound was prepared using a method analogous to that of Example 380, 3,4-methylenedioxyphenylboronic acid replacing 3-thiopheneboronic acid.
LC-MS (C): $t_R$=1.01 min; [M+H]$^+$: 590.31.

Example 390

4-((S)-4-carboxy-2-{[6-(3-methoxy-phenyl)-2-phenyl-pyrimidine-4-carbonyl]-amino}-butyryl)-piperazine-1-carboxylic acid ethyl ester This compound was prepared using a method analogous to that of Example 380, 3-methoxyphenylboronic acid replacing 3-thiopheneboronic acid.
LC-MS (C): $t_R$=1.02 min; [M+H]$^+$: 576.41.

Example 391

4-((S)-4-carboxy-2-{[6-(4-hydroxymethyl-phenyl)-2-phenyl-pyrimidine-4-carbonyl]-amino}-butyryl)-piperazine-1-carboxylic acid ethyl ester This compound was prepared using a method analogous to that of Example 380, 4-(hydroxymethyl)phenylboronic acid replacing 3-thiopheneboronic acid.
$^1$H-NMR (CDCl$_3$): 9.15 (d, 1H); 8.60 (m, 2H); 8.35 (s, 1H); 8.25 (m, 2H); 7.65 (m, 2H); 7.50 (m, 3H); 5.30 (m, 1H); 4.75 (s, 2H); 4.15 (q, 2H); 3.8 to 3.5 (m, 9H); 2.50 (m, 2H); 2.2 (m, 1H); 1.95 (m, 1H); 1.25 (t, 3H).

Example 392

4-{(S)-4-carboxy-2-[(2-phenyl-6-thiophen-2-yl-pyrimidine-4-carbonyl)-amino]-butyryl}-piperazine-1-carboxylic acid ethyl ester This compound was prepared using a method analogous to that of Example 380, 2-thiopheneboronic acid replacing 3-thiopheneboronic acid.
LC-MS (C): $t_R$=1.00 min; [M+H]$^+$: 552.32.

Example 393

4-((S)-4-carboxy-2-{[6-(4-cyano-phenyl)-2-phenyl-pyrimidine-4-carbonyl]-amino}-butyryl)-piperazine-1-carboxylic acid ethyl ester This compound was prepared using a method analogous to that of Example 380, 4-cyanophenylboronic acid replacing 3-thiopheneboronic acid.
LC-MS (C): $t_R$=1.01 min; [M+H]$^+$: 571.37.

Example 394

4-((S)-4-carboxy-2-{[6-(3-chloro-phenyl)-2-phenyl-pyrimidine-4-carbonyl]-amino}-butyryl)-piperazine-1-carboxylic acid ethyl ester This compound was prepared using a method analogous to that of Example 380, 3-chlorophenylboronic acid replacing 3-thiopheneboronic acid.
LC-MS (C): $t_R$=1.03 min; [M+H]$^+$: 580.28.

Example 395

4-{(S)-2-[(6-biphenyl-4-yl-2-phenyl-pyrimidine-4-carbonyl)-amino]-4-carboxy-butyryl}-piperazine-1-carboxylic acid ethyl ester This compound was prepared using a method analogous to that of Example 380, 4-biphenylboronic acid replacing 3-thiopheneboronic acid.
LC-MS (C): $t_R$=1.10 min; [M+H]$^+$: 622.40.

Example 396

4-((S)-4-carboxy-2-{[2-phenyl-6-(1H-pyrazol-4-yl)-pyrimidine-4-carbonyl]-amino}-butyryl)-piperazine-1-carboxylic acid ethyl ester This compound was prepared using a method analogous to that of Example 380, 4,4,5,5-tetramethyl-2-(1H-pyrazol-4-yl)-1,3,2-dioxaborolane replacing 3-thiopheneboronic acid.
LC-MS (C): $t_R$=0.94 min; [M+H]$^+$: 536.35.

Example 397

4-((S)-4-carboxy-2-{[2-phenyl-6-((E)-styryl)-pyrimidine-4-carbonyl]-amino}-butyryl)-piperazine-1-carboxylic acid ethyl ester This compound was prepared using a method analogous to that of Example 380, trans-2-phenylvinylboronic acid replacing 3-thiopheneboronic acid.
LC-MS (C): $t_R$=1.04 min; [M+H]$^+$: 572.45.

Example 398

4-((S)-4-carboxy-2-{[2-phenyl-6-(3-trifluoromethyl-phenyl)-pyrimidine-4-carbonyl]-amino}-butyryl)-piperazine-1-carboxylic acid ethyl ester This compound was prepared using a method analogous to that of Example 380, 3-(trifluoromethyl)phenylboronic acid replacing 3-thiopheneboronic acid.
LC-MS (C): $t_R$=1.06 min; [M+H]$^+$: 614.39.

Example 399

4-{(S)-4-carboxy-2-[(2-phenyl-6-pyridin-3-yl-pyrimidine-4-carbonyl)-amino]-butyryl}-piperazine-1-carboxylic acid ethyl ester 399.1. 4-{(S)-4-tert-butoxycarbonyl-2-[(2-phenyl-6-pyridin-3-yl-pyrimidine-4-carbonyl)-amino]-butyryl}-piperazine-1-carboxylic acid ethyl ester Intermediate 48.1 (100 mg), tetrakis(triphenylphosphine) palladium (5 mg) and a 2M solution of potassium carbonate (2 equivalents) were dissolved in 1,2-dimethoxyethane (1 ml) under argon. Pyridine-3-boronic acid in EtOH (1 ml) was added and the mixture was refluxed 2 h, filtered through Celite and evaporated off to give 53 mg of the crude desired compound.
LC-MS (C): $t_R$=0.99 min; [M+H]$^+$: 603.04.

399.2. 4-{(S)-4-carboxy-2-[(2-phenyl-6-pyridin-3-yl-pyrimidine-4-carbonyl)-amino]-butyryl}-piperazine-1-carboxylic acid ethyl ester This compound was prepared using a method analogous to that of Example 1, step 1.9, intermediate 399.1 replacing intermediate 1.8. The compound was however purified by preparative LC-MS (V).

LC-MS (C): $t_R$=0.80 min; [M+H]$^+$: 546.97.

Example 400

4-{(S)-4-carboxy-2-[(2-phenyl-6-pyridin-4-yl-pyrimidine-4-carbonyl)-amino]-butyryl}-piperazine-1-carboxylic acid ethyl ester 400.1. 4-{(S)-4-tert-butoxycarbonyl-2-[(2-phenyl-6-pyridin-4-yl-pyrimidine-4-carbonyl)-amino]-butyryl}-piperazine-1-carboxylic acid ethyl ester This compound was prepared using a method analogous to that of Example 399, step 399.1, pyridine-4-boronic acid replacing pyridine-3-boronic acid.

LC-MS (C): $t_R$=0.99 min; [M+H]$^+$: 603.60.

400.2. 4-{(S)-4-carboxy-2-[(2-phenyl-6-pyridin-4-yl-pyrimidine-4-carbonyl)-amino]-butyryl}-piperazine-1-carboxylic acid ethyl ester This compound was prepared using a method analogous to that of Example 1, step 1.9, intermediate 400.1 replacing intermediate 1.8. The compound was however purified by preparative LC-MS (V).

LC-MS (C): $t_R$=0.80 min; [M+H]$^+$: 546.97.

Example 401

4-{(S)-4-carboxy-2-[(2-phenyl-6-thiazol-2-yl-pyrimidine-4-carbonyl)-amino]-butyryl}-piperazine-1-carboxylic acid ethyl ester 401.1. 4-{(S)-4-tert-butoxycarbonyl-2-[(2-phenyl-6-thiazol-2-yl-pyrimidine-4-carbonyl)-amino]-butyryl}-piperazine-1-carboxylic acid ethyl ester Intermediate 48.1 (50 mg), tetrakis(triphenylphosphine)palladium (10 mg) and 2-tributylstannylthiazole (99 mg) were dissolved in toluene (2 ml) under argon. The mixture was refluxed 3 h, filtered and evaporated off. Preparative TLC (EA/Hept 5/3) afforded 52 mg of the desired compound.

LC-MS (B): $t_R$=1.22 min; [M+H]$^+$: 609.33.

401.2. 4-{(S)-4-carboxy-2-[(2-phenyl-6-thiazol-2-yl-pyrimidine-4-carbonyl)-amino]-butyryl}-piperazine-1-carboxylic acid ethyl ester This compound was prepared using a method analogous to that of Example 1, step 1.9, intermediate 399.1 replacing intermediate 1.8.

LC-MS (B): $t_R$=1.05 min; [M+H]$^+$: 553.22.

Example 402

4-{(S)-2-[(6-acetyl-2-phenyl-pyrimidine-4-carbonyl)-amino]-4-carboxy-butyryl}-piperazine-1-carboxylic acid ethyl ester 402.1. 4-((S)-4-tert-butoxycarbonyl-2-{[6-(1-ethoxy-vinyl)-2-phenyl-pyrimidine-4-carbonyl]-amino}-butyryl)-piperazine-1-carboxylic acid ethyl ester This compound was prepared using a method analogous to that of Example 401, step 401.1, 1-(ethoxyvinyl)-tributylstannane replacing 2-tributylstannylthiazole. The compound was however purified by column chromatography (EA/Hept 1/1).

LC-MS (B): $t_R$=1.25 min; [M+H]$^+$: 596.19.

402.2. 4-{(S)-2-[(6-acetyl-2-phenyl-pyrimidine-4-carbonyl)-amino]-4-tert-butoxycarbonyl-butyryl}-piperazine-1-carboxylic acid ethyl ester Intermediate 402.1 (160 mg) was dissolved in acetone (1.3 ml) and a 1M HCl solution (0.32 ml). The mixture was stirred at RT overnight and extracted with EA. The org. phases were washed with a NaHCO$_3$ solution, dried (Na$_2$SO$_4$) and evaporated off to give 200 mg of the desired product.

LC-MS (B): $t_R$=1.18 min; [M+H]$^+$: 568.16.

402.3. 4-{(S)-2-[(6-acetyl-2-phenyl-pyrimidine-4-carbonyl)-amino]-4-4-carboxy-butyryl}-piperazine-1-carboxylic acid ethyl ester This compound was prepared using a method analogous to that of Example 1, step 1.9, intermediate 402.2 replacing intermediate 1.8. The compound was however crystallised with Et$_2$O.

LC-MS (B): $t_R$=1.02 min; [M+H]$^+$: 512.15.

Example 403

4-((S)-4-carboxy-2-{[6-(1-hydroxy-ethyl)-2-phenyl-pyrimidine-4-carbonyl]-amino}-butyryl)-piperazine-1-carboxylic acid ethyl ester 403.1. 4-((S)-4-tert-butoxycarbonyl-2-{[6-(1-hydroxy-ethyl)-2-phenyl-pyrimidine-4-carbonyl]-amino}-butyryl)-piperazine-1-carboxylic acid ethyl ester Intermediate 402.2 (50 mg) was dissolved in MeOH (0.8 ml) and NaBH$_4$ (6.6 mg) was added at 0° C. After 2 h at 0° C., water and EA were added. The org. phase was dried (Na$_2$SO$_4$) and evaporated off to give 42 mg of the desired product.

LC-MS (B): $t_R$=1.10 min; [M+H]$^+$: 570.15.

403.2. 4-((S)-4-carboxy-2-{[6-(1-hydroxy-ethyl)-2-phenyl-pyrimidine-4-carbonyl]-amino}-butyryl)-piperazine-1-carboxylic acid ethyl ester This compound was prepared using a method analogous to that of Example 244, step 244.2, intermediate 403.1 replacing intermediate 244.1 and preparative LC-MS (II) replacing preparative LC-MS (III).

LC-MS (B): $t_R$=0.95 min; [M+H]$^+$: 514.18.

Example 404

4-((S)-4-carboxy-2-{[6-(1-methoxy-ethyl)-2-phenyl-pyrimidine-4-carbonyl]-amino}-butyryl)-piperazine-1-carboxylic acid ethyl ester

404.1. 4-((S)-4-tert-butoxycarbonyl-2-{[6-(1-methoxy-ethyl)-2-phenyl-pyrimidine-4-carbonyl]-amino}-butyryl)-piperazine-1-carboxylic acid ethyl ester This compound was prepared using a method analogous to that of Example 317, step 317.2, intermediate 403.1 replacing intermediate 317.1, no purification was however performed.
LC-MS (B): $t_R$=1.18 min; [M+H]$^+$: 582.45.

404.2. 4-((S)-4-carboxy-2-{[6-(1-methoxy-ethyl)-2-phenyl-pyrimidine-4-carbonyl]-amino}-butyryl)-piperazine-1-carboxylic acid ethyl ester This compound was prepared using a method analogous to that of Example 1, step 1.9, intermediate 404.1 replacing intermediate 1.8. The compound was however purified by preparative LC-MS (III).
LC-MS (B): $t_R$=1.02 min; [M+H]$^+$: 528.15.

Example 405

4-((S)-4-carboxy-2-{[6-(1-ethoxy-ethyl)-2-phenyl-pyrimidine-4-carbonyl]-amino}-butyryl)-piperazine-1-carboxylic acid ethyl ester

405.1. 4-((S)-4-tert-butoxycarbonyl-2-{[6-(1-ethoxy-ethyl)-2-phenyl-pyrimidine-4-carbonyl]-amino}-butyryl)-piperazine-1-carboxylic acid ethyl ester Intermediate 402.1 (50 mg) was dissolved in EtOH (3 ml) and Pd(OH)$_2$ (10 mg) was added. After stirring under hydrogen for 42 h, the suspension was filtered off and the solution evaporated to give 45 mg of the desired compound.
LC-MS (B): $t_R$=1.20 min; [M+H]$^+$: 620.28.

405.2. 4-((S)-4-carboxy-2-{[6-(1-ethoxy-ethyl)-2-phenyl-pyrimidine-4-carbonyl]-amino}-butyryl)-piperazine-1-carboxylic acid ethyl ester This compound was prepared using a method analogous to that of Example 1, step 1.9, intermediate 405.1 replacing intermediate 1.8. The compound was however purified by preparative LC-MS (III).
LC-MS (B): $t_R$=1.04 min; [M+H]$^+$: 542.09.

Example 406

4-((S)-4-carboxy-2-{[6-(1-hydroxy-1-methyl-ethyl)-2-phenyl-pyrimidine-4-carbonyl]-amino}-butyryl)-piperazine-1-carboxylic acid ethyl ester

406.1. 4-((S)-4-tert-butoxycarbonyl-2-{[6-(1-hydroxy-1-methyl-ethyl)-2-phenyl-pyrimidine-4-carbonyl]-amino}-butyryl)-piperazine-1-carboxylic acid ethyl ester Intermediate 402.2 (50 mg) was dissolved in Et$_2$O (0.2 ml) at −20° C. and a 3M methylmagnesium bromide solution in Et$_2$O (60 µl) was added. The mixture was allowed to warm to RT and stirred 1 h. A NH$_4$Cl solution and EA were added, the org. phase was dried (Na$_2$SO$_4$) and evaporated off to give 49 mg of the desired compound.
LC-MS (B): $t_R$=1.13 min; [M+H]$^+$: 583.91.

406.2. 4-((S)-4-carboxy-2-{[6-(1-hydroxy-1-methyl-ethyl)-2-phenyl-pyrimidine-4-carbonyl]-amino}-butyryl)-piperazine-1-carboxylic acid ethyl ester This compound was prepared using a method analogous to that of Example 244, step 244.2, intermediate 406.1 replacing intermediate 244.1 and preparative LC-MS (II) replacing preparative LC-MS (III).
LC-MS (B): $t_R$=0.97 min; [M+H]$^+$: 528.28.

Example 407

4-((S)-4-ethoxycarbonyl-2-{[6-(1-hydroxy-1-methyl-ethyl)-2-phenyl-pyrimidine-4-carbonyl]-amino}-butyryl)-piperazine-1-carboxylic acid ethyl ester The compound of Example 406 (900 mg) was dissolved in EtOH (30 ml) and concentrated H$_2$SO$_4$ (0.75 ml) was added. The mixture was heated at 60° C. for 2 h and evaporated off. The residue was taken up in EA/water. The organic phase was washed with a NaCl solution, dried (Na$_2$SO$_4$) and evaporated off. Column chromatography (DCM/MeOH 9/1) followed by preparative LC-MS (III) afforded 272 mg of the desired product.
LC-MS (B): $t_R$=1.11 min; [M+H]$^+$: 556.23.

Example 408

4-((S)-4-carboxy-2-{[6-(2-hydroxy-ethyl)-2-phenyl-pyrimidine-4-carbonyl]-amino}-butyryl)-piperazine-1-carboxylic acid ethyl ester

408.1. 4-{(S)-4-tert-butoxycarbonyl-2-[(2-phenyl-6-vinyl-pyrimidine-4-carbonyl)-amino]-butyryl}-piperazine-1-carboxylic acid ethyl ester This compound was prepared using a method analogous to that of Example 401, step 401.1, tributylvinylstannane replacing 2-tributylstannylthiazole. The compound was however purified by column chromatography (EA/Hept 1/1).
LC-MS (B): $t_R$=1.19 min; [M+H]$^+$: 552.32.

408.2. 4-((S)-4-tert-butoxycarbonyl-2-{[6-(2-hydroxy-ethyl)-2-phenyl-pyrimidine-4-carbonyl]-amino}-butyryl)-piperazine-1-carboxylic acid ethyl ester A 1M BH$_3$ solution in THF (0.28 ml) was added to a −10° C. solution of intermediate 408.1 (340 mg) in THF (0.1 ml). The mixture was stirred for 1 h at −10° C. and for 2 h at RT. A mixture of 6M NaOH solution (115 µl) and hydrogen peroxide (189 µl) in EtOH (0.5 ml) was added and the resulting solution was stirred at 50° C. for 24 h. A Na$_2$CO$_3$ solution and EA were added. The org. phases were dried (Na$_2$SO$_4$) and evaporated off. Preparative LC-MS (III) afforded a mixture of both regioisomers which were separated by preparative TLC (EA/Hept 5/1) to afford 16 mg of the desired product.
LC-MS (B): $t_R$=1.07 min; [M+H]$^+$: 570.26.

408.3. 4-((S)-4-carboxy-2-{[6-(2-hydroxy-ethyl)-2-phenyl-pyrimidine-4-carbonyl]-amino}-butyryl)-piperazine-1-carboxylic acid ethyl ester This compound was prepared using a method analogous to that of Example 244, step 244.2, intermediate 408.2 replacing intermediate 244.1 and preparative LC-MS (II) replacing preparative LC-MS (III).

LC-MS (C): $t_R$=0.81 min; [M+H]$^+$: 514.07.

Example 409

4-((S)-4-carboxy-2-{[6-(2-methoxy-ethyl)-2-phenyl-pyrimidine-4-carbonyl]-amino}-butyryl)-piperazine-1-carboxylic acid ethyl ester

409.1. 4-((S)-4-tert-butoxycarbonyl-2-{[6-(2-methoxy-ethyl)-2-phenyl-pyrimidine-4-carbonyl]-amino}-butyryl)-piperazine-1-carboxylic acid ethyl ester This compound was prepared using a method analogous to that of Example 317, step 317.2, intermediate 408.2 replacing intermediate 317.1.

LC-MS (B): $t_R$=1.04 min; [M+H]$^+$: 584.10.

409.2. 4-((S)-4-carboxy-2-{[6-(2-methoxy-ethyl)-2-phenyl-pyrimidine-4-carbonyl]-amino}-butyryl)-piperazine-1-carboxylic acid ethyl ester This compound was prepared using a method analogous to that of Example 1, step 1.9, intermediate 409.1 replacing intermediate 1.8. The compound was however purified by preparative LC-MS (II).

LC-MS (B): $t_R$=1.00 min; [M+H]$^+$: 528.56.

Example 410

4-((S)-4-carboxy-2-{[6-(2-hydroxy-cyclohexyl)-2-phenyl-pyrimidine-4-carbonyl]-amino}-butyryl)-piperazine-1-carboxylic acid ethyl ester

410.1. 4-{(S)-2-[(6-benzenesulfonyl-2-phenyl-pyrimidine-4-carbonyl)-amino]-4-tert-butoxycarbonyl-butyryl}-piperazine-1-carboxylic acid ethyl ester MCPBA (684 mg) was added to a 0° C. solution of intermediate 256.1 (800 mg) in DCM (40 ml). After 30 min stirring at 0° C., the mixture was allowed to warm to RT and was stirred at RT overnight. A Na$_2$CO$_3$ solution was added and the org. phase was dried (Na$_2$SO$_4$) and evaporated off. (RESULT???)

LC-MS (B): $t_R$=1.18 min; [M+H]$^+$: 666.25.

410.2. 4-((S)-4-tert-butoxycarbonyl-2-{[6-(2-oxo-cyclohexyl)-2-phenyl-pyrimidine-4-carbonyl]-amino}-butyryl)-piperazine-1-carboxylic acid ethyl ester Cyclohexanone (156 μl) was added to a suspension of NaH (24 mg) in THF (2.25 ml). After 1 h stirring at RT, NaH (24 mg) and cyclohexanone (156 μl) were again added. After 1 h at RT, the mixture was extracted with water/DCM. The org. phase was dried (Na$_2$SO$_4$) and evaporated off. Preparative LC-MS (V) afforded 75 mg of the desired product.

LC-MS (B): $t_R$=1.28 min; [M+H]$^+$: 622.36.

410.3. 4-((S)-4-tert-butoxycarbonyl-2-{[6-(2-hydroxy-cyclohexyl)-2-phenyl-pyrimidine-4-carbonyl]-amino}-butyryl)-piperazine-1-carboxylic acid ethyl ester This compound was prepared using a method analogous to that of Example 403, step 403.1, intermediate 410.2 replacing intermediate 402.2.

LC-MS (B): $t_R$=1.17 min; [M+H]$^+$: 624.36.

410.4. 4-((S)-4-carboxy-2-{[6-(2-hydroxy-cyclohexyl)-2-phenyl-pyrimidine-4-carbonyl]-amino}-butyryl)-piperazine-1-carboxylic acid ethyl ester This compound was prepared using a method analogous to that of Example 1, step 1.9, intermediate 410.3 replacing intermediate 1.8. The compound was however purified by preparative LC-MS (III).

LC-MS (B): $t_R$=1.05 min; [M+H]$^+$: 568.21.

Example 411

4-((S)-4-carboxy-2-{[6-(2-methoxy-cyclohexyl)-2-phenyl-pyrimidine-4-carbonyl]-amino}-butyryl)-piperazine-1-carboxylic acid ethyl ester

411.1. 4-((S)-4-tert-butoxycarbonyl-2-{[6-(2-methoxy-cyclohexyl)-2-phenyl-pyrimidine-4-carbonyl]-amino}-butyryl)-piperazine-1-carboxylic acid ethyl ester This compound was prepared using a method analogous to that of Example 317, step 317.2, intermediate 410.3 replacing intermediate 317.1. The compound was however purified by preparative LC-MS (V).

LC-MS (B): $t_R$=1.19 min; [M+H]$^+$: 639.10.

411.2. 4-((S)-4-carboxy-2-{[6-(2-methoxy-cyclohexyl)-2-phenyl-pyrimidine-4-carbonyl]-amino}-butyryl)-piperazine-1-carboxylic acid ethyl ester This compound was prepared using a method analogous to that of Example 1, step 1.9, intermediate 411.1 replacing intermediate 1.8. The compound was however purified by preparative LC-MS (III).

LC-MS (B): $t_R$=1.03 min; [M+H]$^+$: 580.27.

Example 412

4-((S)-4-carboxy-2-{[6-(2-hydroxy-cyclopentyl)-2-phenyl-pyrimidine-4-carbonyl]-amino}-butyryl)-piperazine-1-carboxylic acid ethyl ester

412.1. 4-((S)-4-tert-butoxycarbonyl-2-{[6-(2-oxo-cyclopentyl)-2-phenyl-pyrimidine-4-carbonyl]-amino}-butyryl)-piperazine-1-carboxylic acid ethyl ester This compound was prepared using a method analogous to that of Example 410, step 410.2, cyclopentanone replacing cyclohexanone. The compound was however purified by preparative LCMS (V).

LC-MS (C): $t_R$=1.06 min; [M+H]$^+$: 608.80.

412.2. 4-((S)-4-tert-butoxycarbonyl-2-{[6-(2-hydroxy-cyclopentyl)-2-phenyl-pyrimidine-4-carbonyl]-amino}-butyryl)-piperazine-1-carboxylic acid ethyl ester This compound was prepared using a method analogous to that of Example 410, step 410.3, intermediate 412.1 replacing intermediate 410.2.
LC-MS (C): $t_R$=1.04 min; [M+H]$^+$: 610.05.

412.3. 4-((S)-4-carboxy-2-{[6-(2-hydroxy-cyclopentyl)-2-phenyl-pyrimidine-4-carbonyl]-amino}-butyryl)-piperazine-1-carboxylic acid ethyl ester This compound was prepared using a method analogous to that of Example 1, step 1.9, intermediate 412.2 replacing intermediate 1.8. The compound was however purified by preparative LC-MS (III).
LC-MS (B): $t_R$=1.03 min; [M+H]$^+$: 554.15.

Example 413

4-((S)-4-carboxy-2-{[6-(2-hydroxy-propyl)-2-phenyl-pyrimidine-4-carbonyl]-amino}-butyryl)-piperazine-1-carboxylic acid ethyl ester 413.1. 4-((S)-4-tert-butoxycarbonyl-2-{[6-(2-oxo-propyl)-2-phenyl-pyrimidine-4-carbonyl]-amino}-butyryl)-piperazine-1-carboxylic acid ethyl ester This compound was prepared using a method analogous to that of Example 410, step 410.2, acetone replacing cyclohexanone. The compound was however purified by preparative LC-MS (IV).
LC-MS (C): $t_R$=1.01 min; [M+H]$^+$: 582.09.

413.2. 4-((S)-4-tert-butoxycarbonyl-2-{[6-(2-hydroxy-propyl)-2-phenyl-pyrimidine-4-carbonyl]-amino}-butyryl)-piperazine-1-carboxylic acid ethyl ester This compound was prepared using a method analogous to that of Example 410, step 410.3, intermediate 413.1 replacing intermediate 410.2.
LC-MS (C): $t_R$=0.98 min; [M+H]$^+$: 584.05.

413.3. 4-((S)-4-carboxy-2-{[6-(2-hydroxy-propyl)-2-phenyl-pyrimidine-4-carbonyl]-amino}-butyryl)-piperazine-1-carboxylic acid ethyl ester This compound was prepared using a method analogous to that of Example 1, step 1.9, intermediate 413.2 replacing intermediate 1.8. The compound was however purified by preparative LC-MS (III).
LC-MS (B): $t_R$=0.96 min; [M+H]$^+$: 528.11.

Example 414

4-((S)-4-carboxy-2-{[6-(2-methoxy-propyl)-2-phenyl-pyrimidine-4-carbonyl]-amino}-butyryl)-piperazine-1-carboxylic acid ethyl ester 414.1. 4-((S)-4-tert-butoxycarbonyl-2-{[6-(2-methoxy-propyl)-2-phenyl-pyrimidine-4-carbonyl]-amino}-butyryl)-piperazine-1-carboxylic acid ethyl ester This compound was prepared using a method analogous to that of Example 317, step 317.2, intermediate 413.2 replacing intermediate 317.1.
LC-MS (B): $t_R$=1.20 min; [M+H]$^+$: 598.27.

414.2. 4-((S)-4-carboxy-2-{[6-(2-methoxy-propyl)-2-phenyl-pyrimidine-4-carbonyl]-amino}-butyryl)-piperazine-1-carboxylic acid ethyl ester This compound was prepared using a method analogous to that of Example 1, step 1.9, intermediate 414.1 replacing intermediate 1.8. The compound was however purified by preparative LC-MS (III).
LC-MS (B): $t_R$=1.05 min; [M+H]$^+$: 542.17.

Example 415

4-((S)-4-carboxy-2-{[6-(3,6-dihydro-2H-pyran-4-yl)-2-phenyl-pyrimidine-4-carbonyl]-amino}-butyryl)-piperazine-1-carboxylic acid ethyl ester 415.1. Trifluoro-methanesulfonic acid 3,6-dihydro-2H-pyran-4-yl ester This compound was prepared using a method analogous to that of Example 311, step 311.1, tetrahydro-4H-pyran-4-one replacing 1,4-dioxaspiro[4,5]decan-8-one.
$^1$H-NMR (CDCl$_3$): 6.80 (m, 4H); 5.6 (s, 1H); 4.00 (m, 2H); 3.85 (m, 2H); 3.65 (m, 2H); 2.20 (m, 2H); 1.75 (s, 3H).

415.2. 4-(4,4,5,5-tetramethyl-[1,3,2]dioxaborolan-2-yl)-3,6-dihydro-2H-pyran

This compound was prepared using a method analogous to that of Example 311, step 311.2, intermediate 415.1 replacing intermediate 311.1. The compound was used in the next step without purification or characterisation.

415.3. 4-((S)-4-tert-butoxycarbonyl-2-{[6-(3,6-dihydro-2H-pyran-4-yl)-2-phenyl-pyrimidine-4-carbonyl]-amino}-butyryl)-piperazine-1-carboxylic acid ethyl ester This compound was prepared using a method analogous to that of Example 86, step 86.1, intermediate 415.2 replacing phenylboronic acid and intermediate 48.1 replacing 2-chloro-6-methyl-pyrimidine-4-carboxylic acid methyl ester. The compound was however purified by preparative TLC (EA/Hept 1/2).
LC-MS (A): $t_R$=1.30 min; [M+H]$^-$: 606.63.

415.4. 4-((S)-4-carboxy-2-{[6-(3,6-dihydro-2H-pyran-4-yl)-2-phenyl-pyrimidine-4-carbonyl]-amino}-butyryl)-piperazine-1-carboxylic acid ethyl ester This compound was prepared using a method analogous to that of Example 1, step 1.9, intermediate 415.3 replacing intermediate 1.8. The compound was however purified by preparative LC-MS (III).
LC-MS (A): $t_R$=1.06 min; [M+H]$^+$: 551.90.

Example 416

4-((S)-4-carboxy-2-{[2-phenyl-6-(tetrahydro-pyran-4-yl)-pyrimidine-4-carbonyl]-amino}-butyryl)-piperazine-1-carboxylic acid ethyl ester 416.1. 4-((S)-4-tert-butoxycarbonyl-2-{[2-phenyl-6-(tetraydro-pyran-4-yl)-pyrimidine-4-carbonyl]-amino}-butyryl)-piperazine-1-carboxylic acid ethyl ester This compound was prepared using a method analogous to that of Example 312, step 312.1, intermediate 415.3 replacing intermediate 311.3.
LC-MS (A): $t_R$=1.28 min; [M+H]$^+$: 610.44.

416.2. 4-((S)-4-carboxy-2-{[2-phenyl-6-(tetrahydropyran-4-yl)-pyrimidine-4-carbonyl]-amino}-butyryl)-piperazine-1-carboxylic acid ethyl ester This compound was prepared using a method analogous to that of Example 1, step 1.9, intermediate 416.1 replacing intermediate 1.8.
LC-MS (A): $t_R$=1.03 min; [M+H]$^+$: 554.19.

Example 417

4-((S)-4-carboxy-2-{[6-(2-ethoxycarbonyl-cyclohexyl)-2-phenyl-pyrimidine-4-carbonyl]-amino}-butyryl)-piperazine-1-carboxylic acid ethyl ester

417.1. 2-trifluoromethanesulfonyloxy-cyclohex-1-enecarboxylic acid ethyl ester At −78° C., a 1.6M n-butyllithium solution in hexane (2.6 ml) was added to diisopropylamine (0.6 ml) in THF (5 ml). The mixture was warmed to −30° C. and stirred for 30 min. The mixture was cooled down to −78° C. and 1,3-dimethyl-3,4,5,6-tetrahydro-2(1H)-pyrimidinone (1.39 ml) in THF (5 ml) followed by ethyl 2-cyclohexanonecarboxylate (623 µl) in THF (3 ml) were added. The mixture was stirred at −78° C. for 2 h and N-phenyl-bis(trifluoromethanesulfonimide) (1.5 g) in THF (5 ml) was added. The mixture was allowed to 0° C. and was stirred at 0° C. for 6 h. The solvent was evaporated off and the crude purified by column chromatography (EA/Hept 1/3) to afford 1.09 g of the desired compound.
$^1$H-NMR (CDCl$_3$): 4.20 (q, 2H); 2.45 (m, 2H); 2.40 (m, 2H); 1.75 (m, 2H); 1.65 (m, 2H); 1.25 (t, 3H).

417.2. 4-(4,4,5,5-tetramethyl-[1, 3, 2]dioxaborolan-2-yl)-3,6-dihydro-2H-pyran Intermediate 417.1 (151 mg), bis(pinacolato)diboron (142 mg), bis(triphenylphosphine) palladium (II) dichloride (11 mg), triphenylphosphine (8 mg) and K$_2$CO$_3$ (104 mg) were dissolved in anhydrous dioxane (3 ml) under argon and refluxed overnight. After cooling down, a NaCl solution was added and the mixture was extracted with Hept. The org. layers were dried (Na$_2$SO$_4$) and evaporated off. The compound was used in the next step without purification or characterisation.

417.3. 4-((S)-4-tert-butoxycarbonyl-2-{[6-(2-ethoxycarbonyl-cyclohex-1-enyl)-2-phenyl-pyrimidine-4-carbonyl]-amino}-butyryl)-piperazine-1-carboxylic acid ethyl ester This compound was prepared using a method analogous to that of Example 311, step 311.3, intermediate 417.2 replacing intermediate 311.2. The compound was however purified by column chromatography (EA/Hept 1/2 to 1/1).
LC-MS (A): $t_R$=1.38 min; [M+H]$^-$: 676.39.

417.4. 4-((S)-4-tert-butoxycarbonyl-2-{[6-(2-ethoxycarbonyl-cyclohexyl)-2-phenyl-pyrimidine-4-carbonyl]-amino}-butyryl)-piperazine-1-carboxylic acid ethyl ester Intermediate 417.3 (41 mg), 20% palladium hydroxide on carbon (21 mg), NaHCO$_3$ (6.1 mg) were stirred in EtOH (72 µl) and THF (0.192 ml) under hydrogen for 48 h. The mixture was filtered through celite and evaporated off to give 28 mg of the desired product.
LC-MS (A): $t_R$=1.41 min; [M+H]$^+$: 680.41.

417.5. 4-((S)-4-carboxy-2-{[6-(2-ethoxycarbonyl-cyclohexyl)-2-phenyl-pyrimidine-4-carbonyl]-amino}-butyryl)-piperazine-1-carboxylic acid ethyl ester This compound was prepared using a method analogous to that of Example 1, step 1.9, intermediate 417.4 replacing intermediate 1.8.
LC-MS (A): $t_R$=1.20 min; [M+H]$^+$: 624.29.

Example 418

4-((S)-4-carboxy-2-{[6-(1-oxy-pyridin-3-yl)-2-phenyl-pyrimidine-4-carbonyl]-amino}-butyryl)-piperazine-1-carboxylic acid ethyl ester

418.1. 4-((S)-4-tert-butoxycarbonyl-2-{[6-(1-oxy-pyridin-3-yl)-2-phenyl-pyrimidine-4-carbonyl]-amino}-butyryl)-piperazine-1-carboxylic acid ethyl ester MCPBA (43 mg) was added to a solution of intermediate 399.1 (100 mg) in DCM (2 ml). The mixture was stirred at RT for 1 h. A NaHCO$_3$ solution was added and the mixture was extracted with DCM. The org. phase was dried (Na$_2$SO$_4$) and evaporated off to afford 80 mg of the desired product.
LC-MS (C): $t_R$=1.08 min; [M+H]$^+$: 619.30.

418.2. 4-((S)-4-carboxy-2-{[6-(1-oxy-pyridin-3-yl)-2-phenyl-pyrimidine-4-carbonyl]-amino}-butyryl)-piperazine-1-carboxylic acid ethyl ester This compound was prepared using a method analogous to that of Example 1, step 1.9, intermediate 418.1 replacing intermediate 1.8. The compound was however crystallised in MeOH.
LC-MS (C): $t_R$=0.87 min; [M+H]$^+$: 563.23.

Example 419

4-((S)-4-carboxy-2-{[6-((E)-2-ethoxycarbonyl-vinyl)-2-phenyl-pyrimidine-4-carbonyl]-amino}-butyryl)-piperazine-1-carboxylic acid ethyl ester

419.1. 4-((S)-4-tert-butoxycarbonyl-2-{[6-((E)-2-ethoxycarbonyl-vinyl)-2-phenyl-pyrimidine-4-carbonyl]-amino}-butyryl)-piperazine-1-carboxylic acid ethyl ester To intermediate 48.1 (1 g), palladium (II) acetate (20 mg), tri-(ortho-tolyl)-phosphine (54.5 mg), DIPEA (614 µl), and ethyl acrylate (1.94 ml) was added MeCN under argon. The mixture was heated overnight at 100° C., filtered through Celite and evaporated off. Column chromatography (EA/Hept 3/7) afforded 250 mg of the desired product.
LC-MS (C): $t_R$=1.10 min; [M+H]$^+$: 624.07.

419.2. 4-((S)-4-carboxy-2-{[6-((E)-2-ethoxycarbonyl-vinyl)-2-phenyl-pyrimidine-4-carbonyl]-amino}-butyryl)-piperazine-1-carboxylic acid ethyl ester This compound was prepared using a method analogous to that of Example 1, step 1.9, intermediate 419.1 replacing intermediate 1.8. The compound was however purified by preparative LC-MS (III).
LC-MS (C): $t_R$=0.96 min; [M+H]$^+$: 568.01.

Example 420

4-((S)-4-carboxy-2-{[2-phenyl-6-(tetrahydro-furan-2-ylmethyl)-pyrimidine-4-carbonyl]-amino}-butyryl)-piperazine-1-carboxylic acid ethyl ester 420.1. 4-((S)-4-tert-butoxycarbonyl-2-{[2-phenyl-6-(tetrahydro-furan-2-ylmethyl)-pyrimidine-4-carbonyl]-amino}-butyryl)-piperazine-1-carboxylic acid ethyl ester This compound was prepared using a method analogous to that of Example 419, step 419.1, 4-penten-1-ol replacing ethyl acrylate and NEt$_3$ replacing DIPEA, the reaction being heated at 120° C. for 48 h. The compound was however purified by column chromatography (EA/Hept 1/1).
LC-MS (C): $t_R$=1.04 min; [M+H]$^+$: 610.59.

420.2. 4-((S)-4-carboxy-2-{[2-phenyl-6-(tetrahydro-furan-2-ylmethyl)-pyrimidine-4-carbonyl]-amino}-butyryl)-piperazine-1-carboxylic acid ethyl ester This compound was prepared using a method analogous to that of Example 1, step 1.9, intermediate 420.1 replacing intermediate 1.8. The compound was however purified by preparative LC-MS (II).
LC-MS (C): $t_R$=0.91 min; [M+H]$^+$: 554.04.

Example 421

4-((S)-4-carboxy-2-{[6-((E)-4-hydroxy-but-1-enyl)-2-phenyl-pyrimidine-4-carbonyl]-amino}-butyryl)-piperazine-1-carboxylic acid ethyl ester This compound was prepared using a method analogous to that of Example 420, step 420.1, 4-buten-1-ol replacing 4-penten-1-ol. After cooling down, TFA was added and, after 2 h stirring at RT, the mixture was filtered through Celite and evaporated off. The compound was purified by preparative LC-MS (III).
LC-MS (C): $t_R$=0.84 min; [M+H]$^+$: 540.29.

Example 422

4-((S)-4-carboxy-2-{[6-(3-hydroxy-2-methyl-propyl)-2-phenyl-pyrimidine-4-carbonyl]-amino}-butyryl)-piperazine-1-carboxylic acid ethyl ester 422.1. 4-((S)-4-tert-butoxycarbonyl-2-{[6-(2-methyl-3-oxo-propyl)-2-phenyl-pyrimidine-4-carbonyl]-amino}-butyryl)-piperazine-1-carboxylic acid ethyl ester This compound was prepared using a method analogous to that of Example 420, step 420.1, 2-methyl-2-propen-1-ol replacing 4-penten-1-ol.
LC-MS (C): $t_R$=1.05 min; [M+H]$^+$: 596.07.

422.2. 4-((S)-4-tert-butoxycarbonyl-2-{[6-(3-hydroxy-2-methyl-propyl)-2-phenyl-pyrimidine-4-carbonyl]-amino}-butyryl)-piperazine-1-carboxylic acid ethyl ester This compound was prepared using a method analogous to that of Example 403, step 403.1, intermediate 422.1 replacing intermediate 402.2, the reaction being carried out at RT. The compound was however purified by column chromatography (EA/Hept 3/7).
LC-MS (C): $t_R$=1.00 min; [M+H]$^+$: 598.07.

422.3. 4-((S)-4-carboxy-2-{[6-(3-hydroxy-2-methyl-propyl)-2-phenyl-pyrimidine-4-carbonyl]-amino}-butyryl)-piperazine-1-carboxylic acid ethyl ester This compound was prepared using a method analogous to that of Example 1, step 1.9, intermediate 422.2 replacing intermediate 1.8. The compound was however purified by preparative TLC (DCM/MeOH 97/3).
LC-MS (C): $t_R$=0.87 min; [M+H]$^+$: 542.43.

Example 423

4-((S)-4-carboxy-2-{[2-phenyl-6-(tetrahydro-furan-3-yl)-pyrimidine-4-carbonyl]-amino}-butyryl)-piperazine-1-carboxylic acid ethyl ester 423.1. 4-((S)-4-tert-butoxycarbonyl-2-{[6-(4,5-dihydro-furan-3-yl)-2-phenyl-pyrimidine-4-carbonyl]-amino}-butyryl)-piperazine-1-carboxylic acid ethyl ester This compound was prepared using a method analogous to that of Example 419, step 419.1, 2,3-dihydrofuran replacing ethyl acrylate and NEt$_3$ being used in addition to DIPEA (same mol amount). The compound was however purified by column chromatography (EA/Hex 1/1).
LC-MS (C): $t_R$=1.08 min; [M+H]$^+$: 594.09.

423.2. 4-((S)-4-tert-butoxycarbonyl-2-{[2-phenyl-6-(tetrahydro-furan-3-yl)-pyrimidine-4-carbonyl]-amino}-butyryl)-piperazine-1-carboxylic acid ethyl ester This compound was prepared using a method analogous to that of Example 1, step 1.2, intermediate 423.1 replacing intermediate 1.1. The compound was however purified by column chromatography (EA/Hex 3/7 to 1/1).
LC-MS (C): $t_R$=1.07 min; [M+H]$^+$: 596.05.

423.3. 4-((S)-4-carboxy-2-{[2-phenyl-6-(tetrahydro-furan-3-yl)-pyrimidine-4-carbonyl]-amino}-butyryl)-piperazine-1-carboxylic acid ethyl ester This compound was prepared using a method analogous to that of Example 1, step 1.9, intermediate 423.2 replacing intermediate 1.8. The compound was however purified by preparative TLC (EA/Hept 1/1).
LC-MS (C): $t_R$=0.91 min; [M+H]$^+$: 541.49.

Example 424

4-((S)-4-carboxy-2-{[6-((E)-2-dimethylcarbamoyl-vinyl)-2-phenyl-pyrimidine-4-carbonyl]-amino}-butyryl)-piperazine-1-carboxylic acid ethyl ester 424.1. 4-((S)-4-tert-butoxycarbonyl-2-{[6-((E)-2-dimethylcarbamoyl-vinyl)-2-phenyl-pyrimidine-4-carbonyl]-amino}-butyryl)-piperazine-1-carboxylic acid ethyl ester This compound was prepared using a method analogous to that of Example 419, step 419.1, N,N-dimethylacrylamide replacing ethyl acrylate, the reaction being heated at 100° C. for 48 h.
LC-MS (C): $t_R$=1.04 min; [M+H]$^+$: 623.63.

424.2. 4-((S)-4-carboxy-2-{[6-((E)-2-dimethylcarbamoyl-vinyl)-2-phenyl-pyrimidine-4-carbonyl]-amino}-butyryl)-piperazine-1-carboxylic acid ethyl ester This compound was prepared using a method analogous to that of Example 1, step 1.9, intermediate 424.1 replacing intermediate 1.8.
LC-MS (C): $t_R$=0.89 min; [M+H]$^+$: 567.55.

Example 425

4-{(S)-4-carboxy-2-[(6-cyano-2-phenyl-pyrimidine-4-carbonyl)-amino]-butyryl}-piperazine-1-carboxylic acid ethyl ester KCN (129 mg), intermediate 331.1 (200 mg), tetrakis(triphenylphosphine) palladium (229 mg) and CuI (75.6 mg) were suspended in MeCN (1 ml). The reaction mixture was heated at reflux overnight and filtered through celite. Water/EA were added. The org. phase was washed with a NaCl solution, dried (MgSO$_4$) and evaporated off. Column chromatography (DCM/MeOH 97/3) followed by preparative LC-MS (I) afforded 37 mg of the desired product.

LC-MS (C): $t_R$=0.93 min; [M+H]$^+$: 495.46.

Example 426

4-((S)-4-carboxy-2-{[6-(1-hydroxy-propyl)-2-phenyl-pyrimidine-4-carbonyl]-amino}-butyryl)-piperazine-1-carboxylic acid ethyl ester 426.1. 6-(1-hydroxy-propyl)-2-phenyl-pyrimidine-4-carboxylic acid methyl ester To magnesium (9.5 mg) in THF (1 ml) was added bromoethane (28 µl) at RT (2-3 drops), then at reflux (few drops), then dropwise at RT. The reaction was heated to reflux for 15 min, then cooled down to RT. The obtained ethyl magnesium bromide solution was added to a –78° C. solution of intermediate 362.1 (90 mg) in THF (1 ml) and the reaction was stirred at –78° C. for 3 h. A 1M HCl solution was added and the mixture was extracted with DCM. The org. phases were dried (MgSO$_4$) and evaporated off to afford 15 mg of the desired crude product.
$^1$H-NMR (CDCl$_3$): 8.5 (m, 2H); 7.85 (s, 1H); 7.5 (m, 3H); 4.80 (m, 1H); 4.05 (s, 3H); 3.80 (br s, 1H); 2.00 (m, 1H); 1.80 (m, 1H); 1.00 (t, 3H).

426.2. 6-(1-hydroxy-propyl)-2-phenyl-pyrimidine-4-carboxylic acid

This compound was prepared using a method analogous to that of Example 86, step 86.2, intermediate 426.1 replacing intermediate 86.1.
LC-MS (C): $t_R$=0.81 min; [M+H]$^+$: 259.17.

426.3. 4-((S)-4-tert-butoxycarbonyl-2-{[6-(1-hydroxy-propyl)-2-phenyl-pyrimidine-4-carbonyl]-amino}-butyryl)-piperazine-1-carboxylic acid ethyl ester This compound was prepared using a method analogous to that of Example 86, step 86.3, intermediate 426.2 replacing intermediate 86.2, and intermediate 1.2 being dissolved in DCM. No work up was performed and the compound was purified by preparative TLC (EA/Hept 1/1).
LC-MS (C): $t_R$=1.03 min; [M+H]$^+$: 584.43.

426.4. 4-((S)-4-carboxy-2-{[6-(1-hydroxy-propyl)-2-phenyl-pyrimidine-4-carbonyl]-amino}-butyryl)-piperazine-1-carboxylic acid ethyl ester This compound was prepared using a method analogous to that of Example 1, step 1.9, intermediate 426.3 replacing intermediate 1.8. The compound was however purified by preparative LC-MS (III).
LC-MS (C): $t_R$=0.87 min; [M+H]$^+$: 528.10.

Example 427

4-((S)-4-carboxy-2-{[6-(1-hydroxy-butyl)-2-phenyl-pyrimidine-4-carbonyl]-amino}-butyryl)-piperazine-1-carboxylic acid ethyl ester 427.1. 6-(1-hydroxy-butyl)-2-phenyl-pyrimidine-4-carboxylic acid methyl ester The Grignard reagent was prepared using a method analogous to that of Example 426, step 426.1, bromopropane (387 µl) replacing bromoethane and Et$_2$O (5 ml) being used instead of THF. The resulting propyl magnesium bromide solution was added to a –20° C. solution of intermediate 362.1 (200 mg) in Et$_2$O (50 ml) and the reaction was stirred at –20° C. for 1 h. The mixture was allowed to warm to 0° C. and 0.5 equivalent of propyl magnesium bromide was added. After 1 h at 0° C., a 1M HCl solution was added and the mixture was extracted with DCM. The org. phases were dried (MgSO$_4$) and evaporated off. Column chromatography (DCM to DCM with 1% MeOH) followed by preparative TLC (DCM with 0.5% MeOH) afforded 17 mg of the desired product.
LC-MS (C): $t_R$=0.95 min; [M+H]$^+$: 287.22.

427.2. 6-(1-hydroxy-butyl)-2-phenyl-pyrimidine-4-carboxylic acid

This compound was prepared using a method analogous to that of Example 86, step 86.2, intermediate 427.1 replacing intermediate 86.1.
LC-MS (C): $t_R$=0.86 min; [M+H]$^+$: 273.20.

427.3. 4-((S)-4-tert-butoxycarbonyl-2-{[6-(1-hydroxy-butyl)-2-phenyl-pyrimidine-4-carbonyl]-amino}-butyryl)-piperazine-1-carboxylic acid ethyl ester This compound was prepared using a method analogous to that of Example 426, step 426.3, intermediate 427.2 replacing intermediate 426.2.
LC-MS (C): $t_R$=1.05 min; [M+H]$^+$: 598.37.

427.4. 4-((S)-4-carboxy-2-{[6-(1-hydroxy-butyl)-2-phenyl-pyrimidine-4-carbonyl]-amino}-butyryl)-piperazine-1-carboxylic acid ethyl ester This compound was prepared using a method analogous to that of Example 1, step 1.9, intermediate 427.3 replacing intermediate 1.8. The compound was however purified by preparative LC-MS (III).
LC-MS (C): $t_R$=0.90 min; [M+H]$^+$: 542.10.

Example 428

4-((S)-4-carboxy-2-{[6-(hydroxy-phenyl-methyl)-2-phenyl-pyrimidine-4-carbonyl]-amino}-butyryl)-piperazine-1-carboxylic acid ethyl ester

428.1. 6-(hydroxy-phenyl-methyl)-2-phenyl-pyrimidine-4-carboxylic acid methyl ester This compound was prepared using a method analogous to that of Example 427, step 427.1, bromobenzene replacing bromopropane. The compound was however purified by column chromatography (DCM/hexane 9/1 to DCM).
LC-MS (C): $t_R$=0.96 min; [M+H]$^+$: 321.18.

428.2. 6-(hydroxy-phenyl-methyl)-2-phenyl-pyrimidine-4-carboxylic acid

This compound was prepared using a method analogous to that of Example 86, step 86.2, intermediate 428.1 replacing intermediate 86.1.
LC-MS (C): $t_R$=0.88 min; [M+H]$^+$: 307.15.

428.3. 4-((S)-4-tert-butoxycarbonyl-2-{[6-(hydroxyl-phenyl-methyl)-2-phenyl-pyrimidine-4-carbonyl]-amino}-butyryl)-piperazine-1-carboxylic acid ethyl ester This compound was prepared using a method analogous to that of Example 426, step 426.3, intermediate 428.2 replacing intermediate 426.2.
LC-MS (C): $t_R$=1.06 min; [M+H]$^+$: 632.41.

428.4. 4-((S)-4-carboxy-2-2-{[6-(hydroxyl-phenyl-methyl)-2-phenyl-pyrimidine-4-carbonyl]-amino}-butyryl)-piperazine-1-carboxylic acid ethyl ester This compound was prepared using a method analogous to that of Example 1, step 1.9, intermediate 428.3 replacing intermediate 1.8. The compound formed was however 4-{2-[(6-benzoyl-2-phenyl-pyrimidine-4-carbonyl)-amino]-4-carboxy-butyryl}-piperazine-1-carboxylic acid ethyl ester. It was further reduced to the desired compound using a method analogous to that of Example 362, step 362.2. The compound was purified by preparative LC-MS (III).
LC-MS (C): $t_R$=0.91 min; [M+H]$^+$: 576.1.

Example 429

4-((S)-4-carboxy-2-{[6-(2-hydroxy-2-phenyl-ethyl)-2-phenyl-pyrimidine-4-carbonyl]-amino}-butyryl)-piperazine-1-carboxylic acid ethyl ester

429.1. 6-(2-hydroxy-2-phenyl-ethyl)-2-phenyl-pyrimidine-4-carboxylic acid

To a solution of intermediate 86.2 (300 mg) in THF (9 ml) was added dropwise at 0° C. a 1M sodium bis(trimethylsilyl) amide solution in THF (3 ml). The mixture was stirred for 20 min at 0° C. and brought at −78° C. A solution of benzaldehyde (356 µl) in THF (1 ml) was added dropwise and the mixture stirred for 4 h at −78° C. A NH$_4$Cl solution and DCM were added. The org. phases were dried (MgSO$_4$) and evaporated off to afford 250 mg of the desired compound.
LC-MS (C): $t_R$=0.88 min; [M+H]$^+$: 321.19.

429.2. 4-((S)-4-tert-butoxycarbonyl-2-{[6-(2-hydroxy-2-phenyl-ethyl)-2-phenyl-pyrimidine-4-carbonyl]-amino}-butyryl)-piperazine-1-carboxylic acid ethyl ester This compound was prepared using a method analogous to that of Example 108, step 108.1, intermediate 429.1 replacing intermediate 24.3 and intermediate 1.2 replacing intermediate 4.2.
LC-MS (C): $t_R$=1.05 min; [M+H]$^+$: 646.36.

429.3. 4-((S)-4-carboxy-2-{[6-(2-hydroxy-2-phenyl-ethyl)-2-phenyl-pyrimidine-4-carbonyl]-amino}-butyryl)-piperazine-1-carboxylic acid ethyl ester This compound was prepared using a method analogous to that of Example 1, step 1.9, intermediate 429.2 replacing intermediate 1.8. The compound was however purified by column chromatography (EA/Hept 7/3).
LC-MS (C): $t_R$=0.92 min; [M+H]$^+$: 590.04.

Example 430

4-{(S)-4-carboxy-2-[(6-ethoxymethyl-2-phenyl-pyrimidine-4-carbonyl)-amino]-butyryl}-piperazine-1-carboxylic acid ethyl ester Intermediate 362.5 (25 mg) was dissolved in MeCN (1 ml) and a 20% sodium ethanolate solution in EtOH (162 µl) was added. The mixture was stirred for 30 min at RT. A 1M HCl solution was added and the solvent was removed. The residue was purified by preparative LC-MS (III) to afford 11 mg of the desired product.
LC-MS (C): $t_R$=0.91 min; [M+H]$^+$: 528.11.

Example 431

4-{(S)-4-carboxy-2-[(2-phenyl-6-trifluoromethyl-pyrimidine-4-carbonyl)-amino]-butyryl}-piperazine-1-carboxylic acid ethyl ester

431.1. 4-methyl-2-phenyl-6-trifluoromethyl-pyrimidine

This compound was prepared using a method analogous to that of Example 1, step 1.3, 1,1,1-trifluoro-2,4-pentanedione replacing methyl-4-methoxyacetate, the reaction mixture being evaporated off instead of filtered off.
LC-MS (A): $t_R$=1.29 min; [M+H]$^+$: 239.11.

431.2. 2-phenyl-6-trifluoromethyl-pyrimidine-4-carboxylic acid

This compound was prepared using a method analogous to that of Example 23, step 23.4, intermediate 431.1 replacing intermediate 23.3.
LC-MS (A): $t_R$=1.11 min; [M+H]$^-$: 267.96.

431.3. 4-{(S)-4-tert-butoxycarbonyl-2-[(2-phenyl-6-trifluoromethyl-pyrimidine-4-carbonyl)-amino]-butyryl}-piperazine-1-carboxylic acid ethyl ester This compound was prepared using a method analogous to that of Example 108, step 108.1, intermediate 431.2 replacing intermediate 24.3 and intermediate 1.2 replacing intermediate 4.2. The compound was however purified by preparative TLC (EA/Hept 2/1) followed by preparative LC-MS (V).
LC-MS (A): $t_R$=1.33 min; [M+H]$^-$: 592.36.

431.4. 4-{(S)-4-carboxy-2-[(2-phenyl-6-trifluoromethyl-pyrimidine-4-carbonyl)-amino]-butyryl}-piperazine-1-carboxylic acid ethyl ester This compound was prepared using a method analogous to that of Example 1, step 1.9, intermediate 431.3 replacing intermediate 1.8.
LC-MS (A): $t_R$=1.11 min; [M+H]$^+$: 538.44.

Example 432

4-{(S)-2-[(6-tert-butyl-2-phenyl-pyrimidine-4-carbonyl)-amino]-4-carboxy-butyryl}-piperazine-1-carboxylic acid ethyl ester

432.1. Acetic acid 5,5-dimethyl-4-oxo-hex-2-ynyl ester

Pivaloyl chloride (612 µl), propargyl acetate (644 µl), cupper iodide (12 mg) and bis-(triphenylphosphine) palladium (II)-dichloride (9.1 mg) in NEt$_3$ (10 ml) were stirred at RT for 24 h. MeOH was added and the mixture was evaporated off. The residue was taken up in Et$_2$O and the resulting suspension filtered off. The solution was washed with a 1M HCl solution, water, dried (Na$_2$SO$_4$) and evaporated off. Column chromatography (EA/Hept 1/3) afforded 343 mg of the desired compound.
$^1$H-NMR (CDCl$_3$): 4.85 (s, 2H); 2.15 (s, 3H); 1.20 (s, 9H).

432.2. Acetic acid 6-tert-butyl-2-phenyl-pyrimidin-4-ylmethyl ester

Intermediate 432.1, (161 mg), benzamidine (212 mg) and sodium carbonate (187 mg) were refluxed in MeCN (5 ml) and water (1 drop) for 16 h. Water was added and it was extracted Et$_2$O. The org. phase was dried (Na$_2$SO$_4$) and evaporated off. Column chromatography (EA/Hept 1/3) afforded 180 mg of the desired compound.
LC-MS (C): $t_R$=1.11 min; [M+H]$^-$: 285.11.

432.3. (6-tert-butyl-2-phenyl-pyrimidin-4-yl)-methanol

Intermediate 432.2 (180 mg) and K$_2$CO$_3$ (175 mg) were dissolved in MeOH/water (8 ml/2 ml) and the mixture was stirred at RT for 1 h. MeOH was evaporated off and the residue extracted with EA. The org. phase was dried (Na$_2$SO$_4$) and evaporated off to give 155 mg of the desired compound.
LC-MS (A): $t_R$=0.99 min; [M+H]$^-$: 243.09.

432.4. 6-tert-butyl-2-phenyl-pyrimidine-4-carboxylic acid

This compound was prepared using a method analogous to that of Example 24, step 24.3, intermediate 432.3 replacing intermediate 24.2.
LC-MS (C): $t_R$=0.98 min; [M+H]$^+$: 257.27.

432.5. 4-{(S)-2-[(6-tert-butyl-2-phenyl-pyrimidine-4-carbonyl)-amino]-4-tert-butyloxycarbonyl-butyryl}-piperazine-1-carboxylic acid ethyl ester This compound was prepared using a method analogous to that of Example 1, step 1.1, intermediate 432.4 replacing Z-(L)Glu(OtBu)—OH, intermediate 1.2 replacing 1-ethoxycarbonylpiperazine and DIPEA being used as base.
LC-MS (C): $t_R$=1.13 min; [M+H]$^+$: 582.33.

432.6 4-{(S)-2-[(6-tert-butyl-2-phenyl-pyrimidine-4-carbonyl)-amino]-4-carboxy-butyryl}-piperazine-1-carboxylic acid ethyl ester This compound was prepared using a method analogous to that of Example 1, step 1.9, intermediate 432.5 replacing intermediate 1.8.
LC-MS (C): $t_R$=0.99 min; [M+H]$^+$: 526.40.

Example 433

4-{(S)-4-carboxy-2-[(6-phenoxy-2-phenyl-pyrimidine-4-carbonyl)-amino]-butyryl}-piperazine-1-carboxylic acid ethyl ester

433.1. 4-{(S)-4-tert-butoxycarbonyl-2-[(6-phenoxy-2-phenyl-pyrimidine-4-carbonyl)-amino]-butyryl}-piperazine-1-carboxylic acid ethyl ester Phenol (199 mg) was dissolved in DMF (3 ml) and NaH (81 mg) was added. After 5 min, intermediate 48.1 (215 mg) was added and the mixture was stirred at RT for 1 h. Et$_2$O was added and the mixture was washed with a NaHSO$_4$ solution, NaOH solution, NaCl solution, dried (MgSO$_4$) and evaporated off to give 234 mg of the desired compound.
LC-MS (C): $t_R$=1.10 min; [M+H]$^+$: 618.05.

433.2. 4-{(S)-4-carboxy-2-[(6-phenoxy-2-phenyl-pyrimidine-4-carbonyl)-amino]-butyryl}-piperazine-1-carboxylic acid ethyl ester This compound was prepared using a method analogous to that of Example 1, step 1.9, intermediate 433.1 replacing intermediate 1.8. The compound was however purified by preparative LC-MS (III).
LC-MS (C): $t_R$=0.97 min; [M+H]$^-$: 561.98.

Example 434

4-((S)-4-carboxy-2-{[2-phenyl-6-(pyridin-3-yloxy)-pyrimidine-4-carbonyl]-amino}-butyryl)-piperazine-1-carboxylic acid ethyl ester This compound was prepared using a method analogous to that of Example 433, step 433.1, 3-hydroxypyridine replacing phenol and intermediate 331.1 replacing intermediate 48.1. The compound was however purified by preparative LC-MS (III).
LC-MS (C): $t_R$=0.89 min; [M+H]$^+$: 563.53.

Example 435

(S)-5-(4-tert-butylcarbamoyl-piperazin-1-yl)-4-[(6-cyclopentyloxy-2-phenyl-pyrimidine-4-carbonyl)-amino]-5-oxo-pentanoic acid Intermediate 34.4 (50 mg) was dissolved in THF (1.5 ml) and tert-butyl isocyanate (10 mg) was added. The mixture was stirred for 16 h at RT. The solvent was removed, the residue was redissolved in DCM/TFA (0.5 ml/0.5 ml) and the solution was stirred at RT for 16 h. The solvent was removed and the residue was purified by preparative LC-MS (IV).
LC-MS (C): $t_R$=1.00 min; [M+H]$^+$: 581.16.

Example 436

(S)-4-[(6-cyclopentyloxy-2-phenyl-pyrimidine-4-carbonyl)-amino]-5-(4-isopropylcarbamoyl-piperazin-1-yl)-5-oxo-pentanoic acid This compound was prepared using a method analogous to that of Example 435, isopropyl isocyanate replacing tert-butyl isocyanate. The compound was however purified by preparative LC-MS (IV).

LC-MS (C): $t_R$=0.97 min; [M+H]$^+$: 567.16.

Example 437

(S)-4-[(6-cyclopentyloxy-2-phenyl-pyrimidine-4-carbonyl)-amino]-5-oxo-5-[4-(thiophene-2-carbonyl)-piperazin-1-yl]-pentanoic acid HOBT (19 mg) was added to a solution of thiophene-2-carboxylic acid (12 mg) in DCM (1 ml). After 15 min stirring, EDCI (21.5 mg) was added and the mixture was stirred for 15 min. Intermediate 34.4 (50 mg) dissolved in DCM (0.5 ml) was added and the mixture was stirred at RT for 16 h. The mixture was passed through a ISOLUTE® SCX-2 SPE column (eluent: DCM) and the solution evaporated. TFA was added to the residue and the mixture was stirred at RT for 16 h. The solvent was removed and the residue was purified by preparative LC-MS (IV).

LC-MS (C): $t_R$=1.00 min; [M+H]$^+$: 592.09.

Example 438

(S)-5-(4-cyclopentanecarbonyl-piperazin-1-yl)-4-[(6-cyclopentyloxy-2-phenyl-pyrimidine-4-carbonyl)-amino]-5-oxo-pentanoic acid This compound was prepared using a method analogous to that of Example 437, cyclopentanecarboxylic acid replacing thiophene-2-carboxylic acid. The compound was however purified by preparative LC-MS (IV).

LC-MS (C): $t_R$=1.02 min; [M+H]$^+$: 578.18.

Example 439

(S)-4-[(6-cyclopentyloxy-2-phenyl-pyrimidine-4-carbonyl)-amino]-5-oxo-5-[4-(piperidine-1-carbonyl)-piperazin-1-yl]-pentanoic acid 1-piperidinecarbonyl chloride (27 mg) was added to an ice-cold solution of intermediate 34.4 (50 mg) and DIPEA (32 µl) in THF (1.5 ml). After 15 min stirring at 0° C., the mixture was allowed to warm to RT and was stirred at RT for 16 h. TFA (0.5 ml) was added and the mixture was stirred at RT for 16 h. The solvent was removed and the residue was purified by preparative LC-MS (IV).

LC-MS (C): $t_R$=1.02 min; [M+H]$^+$: 593.17.

The compounds of Examples 440 to 492 were prepared using a method analogous to that of the Example indicated between brackets, except that the last step of the corresponding Example was not carried out.

Example 440

4-(4-tert-butoxycarbonyl-2-{[6-((S)-3-methoxy-pyrrolidin-1-yl)-2-phenyl-pyrimidine-4-carbonyl]-amino}-butyryl)-piperazine-1-carboxylic acid ethyl ester (Example 317). LC-MS (C): $t_R$=1.07 min; [M+H]$^+$: 625.25.

Example 441

4-((S)-4-tert-butoxycarbonyl-2-{[6-((S)-2-methoxy-1-methyl-ethylamino)-2-phenyl-pyrimidine-4-carbonyl]-amino}-butyryl)-piperazine-1-carboxylic acid ethyl ester (Example 318). LC-MS (C): $t_R$=1.05 min; [M+H]$^+$: 613.23.

Example 442

4-((S)-4-tert-butoxycarbonyl-2-{[6-(4-methoxy-piperidin-1-yl)-2-phenyl-pyrimidine-4-carbonyl]-amino}-butyryl)-piperazine-1-carboxylic acid ethyl ester (Example 319). LC-MS (C): $t_R$=1.08 min; [M+H]$^+$: 639.28.

Example 443

4-(4-tert-butoxycarbonyl-2-{[6-((R)-3-methoxy-pyrrolidin-1-yl)-2-phenyl-pyrimidine-4-carbonyl]-amino}-butyryl)-piperazine-1-carboxylic acid ethyl ester (Example 320). LC-MS (C): $t_R$=1.07 min; [M+H]$^+$: 625.25.

Example 444

4-((S)-4-tert-butoxycarbonyl-2-{[6-((R)-2-methoxy-1-methyl-ethylamino)-2-phenyl-pyrimidine-4-carbonyl]-amino}-butyryl)-piperazine-1-carboxylic acid ethyl ester (Example 321). LC-MS (C): $t_R$=1.04 min; [M+H]$^+$: 613.22.

Example 445

4-((S)-4-tert-butoxycarbonyl-2-{[6-(2-methoxymethyl-piperidin-1-yl)-2-phenyl-pyrimidine-4-carbonyl]-amino}-butyryl)-piperazine-1-carboxylic acid ethyl ester (Example 322). LC-MS (C): $t_R$=1.11 min; [M+H]$^+$: 653.28.

Example 446

4-((S)-4-tert-butoxycarbonyl-2-{[6-((S)-2-methoxymethyl-pyrrolidin-1-yl)-2-phenyl-pyrimidine-4-carbonyl]-amino}-butyryl)-piperazine-1-carboxylic acid ethyl ester (Example 323). LC-MS (C): $t_R$=1.10 min; [M+H]$^+$: 639.28.

Example 447

4-((S)-4-tert-butoxycarbonyl-2-{[6-((R)-2-methoxymethyl-pyrrolidin-1-yl)-2-phenyl-pyrimidine-4-carbonyl]-amino}-butyryl)-piperazine-1-carboxylic acid ethyl ester (Example 324). LC-MS (C): $t_R$=1.09 min; [M+H]$^+$: 639.28.

Example 448

4-((S)-4-tert-butoxycarbonyl-2-{[6-(2-methoxy-1,1-dimethyl-ethylamino)-2-phenyl-pyrimidine-4-carbonyl]-amino}-butyryl)-piperazine-1-carboxylic acid ethyl ester (Example 325). LC-MS (B): $t_R$=1.19 min; [M+H]$^+$: 627.29.

Example 449

4-((S)-4-tert-butoxycarbonyl-2-{[6-(4,5-dihydro-pyrazol-1-yl)-2-phenyl-pyrimidine-4-carbonyl]-amino}-butyryl)-piperazine-1-carboxylic acid ethyl ester (Example 326). LC-MS (B): $t_R$=1.18 min; [M+H]$^+$: 594.26.

Example 450

4-((S)-4-tert-butoxycarbonyl-2-{[6-(2-methyl-4,5-dihydro-imidazol-1-yl)-2-phenyl-pyrimidine-4-carbonyl]-amino}-butyryl)-piperazine-1-carboxylic acid ethyl ester (Example 327). LC-MS (B): $t_R$=0.86 min; [M+H]$^+$: 608.32.

Example 451

4-{(S)-4-tert-butoxycarbonyl-2-[(2-phenyl-6-[1,2,4]triazol-1-yl-pyrimidine-4-carbonyl)-amino]-butyryl}-piperazine-1-carboxylic acid ethyl ester (Example 328). LC-MS (C): $t_R$=1.17 min; [M+H]$^+$: 593.24.

Example 452

4-((S)-4-tert-butoxycarbonyl-2-{[6-(4-methyl-pyrazol-1-yl)-2-phenyl-pyrimidine-4-carbonyl]-amino}-butyryl)-piperazine-1-carboxylic acid ethyl ester;

(Example 329). LC-MS (B): $t_R$=1.27 min; [M+H]$^+$: 606.24.

Example 453

4-((S)-4-tert-butoxycarbonyl-2-{[6-(3-methyl-pyrazol-1-yl)-2-phenyl-pyrimidine-4-carbonyl]-amino}-butyryl)-piperazine-1-carboxylic acid ethyl ester;

(Example 330). LC-MS (B): $t_R$=1.26 min; [M+H]$^+$: 606.24.

Example 454

4-((S)-2-{[6-(4-butyl-[1,2,3]triazol-1-yl)-2-phenyl-pyrimidine-4-carbonyl]-amino}-4-tert-butoxycarbonyl-butyryl)-piperazine-1-carboxylic acid ethyl ester;

(Example 332). LC-MS (C): $t_R$=1.14 min; [M+H]$^+$: 649.30.

Example 455

4-{(S)-2-[(6-amino-2-phenyl-pyrimidine-4-carbonyl)-amino]-4-tert-butoxycarbonyl-butyryl}-piperazine-1-carboxylic acid ethyl ester;

(Example 333). LC-MS (C): $t_R$=0.96 min; [M+H]$^+$: 541.13.

Example 456

4-((S)-4-tert-butoxycarbonyl-2-{[6-(3-methyl-5-oxo-2,5-dihydro-pyrazol-1-yl)-2-phenyl-pyrimidine-4-carbonyl]-amino}-butyryl)-piperazine-1-carboxylic acid ethyl ester;

(Example 359). LC-MS (C): $t_R$=1.01 min; [M+H]$^+$: 622.08.

Example 457

4-{(S)-4-tert-butoxycarbonyl-2-[(6-ethanesulfonylmethyl-2-phenyl-pyrimidine-4-carbonyl)-amino]-butyryl}-piperazine-1-carboxylic acid ethyl ester;

(Example 375). LC-MS (A): $t_R$=1.16 min; [M+H]$^+$: 630.39.

Example 458

4-{(S)-4-tert-butoxycarbonyl-2-[(6-ethylsulfanylmethyl-2-phenyl-pyrimidine-4-carbonyl)-amino]-butyryl}-piperazine-1-carboxylic acid ethyl ester (Example 376). LC-MS (B): $t_R$=1.27 min; [M+H]$^+$: 648.56.

Example 459

4-{(S)-2-[(6-benzenesulfonylmethyl-2-phenyl-pyrimidine-4-carbonyl)-amino]-4-tert-butoxycarbonyl-butyryl}-piperazine-1-carboxylic acid ethyl ester;

(Example 377). LC-MS (B): $t_R$=1.19 min; [M+H]$^+$: 678.35.

Example 460

4-{(S)-4-tert-butoxycarbonyl-2-[(6-cyclopentylsulfanylmethyl-2-phenyl-pyrimidine-4-carbonyl)-amino]-butyryl}-piperazine-1-carboxylic acid ethyl ester;

(Example 378). LC-MS (B): $t_R$=1.29 min; [M+H]$^+$: 640.46.

Example 461

4-{(S)-4-tert-butoxycarbonyl-2-[(6-cyclopentanesulfonylmethyl-2-phenyl-pyrimidine-4-carbonyl)-amino]-butyryl}-piperazine-1-carboxylic acid ethyl ester;

(Example 379). LC-MS (B): $t_R$=1.20 min; [M+H]$^+$: 670.39.

Example 462

4-{(S)-4-tert-butoxycarbonyl-2-[(2-phenyl-6-pyridin-3-yl-pyrimidine-4-carbonyl)-amino]-butyryl}-piperazine-1-carboxylic acid ethyl ester;

(Example 399). LC-MS (C): $t_R$=0.99 min; [M+H]$^+$: 603.04.

Example 463

4-{(S)-4-tert-butoxycarbonyl-2-[(2-phenyl-6-pyridin-4-yl-pyrimidine-4-carbonyl)-amino]-butyryl}-piperazine-1-carboxylic acid ethyl ester;

(Example 400). LC-MS (C): $t_R$=0.99 min; [M+H]$^+$: 603.60.

Example 464

4-{(S)-4-tert-butoxycarbonyl-2-[(2-phenyl-6-thiazol-2-yl-pyrimidine-4-carbonyl)-amino]-butyryl}-piperazine-1-carboxylic acid ethyl ester;

(Example 401). LC-MS (B): $t_R$=1.22 min; [M+H]$^+$: 609.33.

Example 465

4-{(S)-2-[(6-acetyl-2-phenyl-pyrimidine-4-carbonyl)-amino]-4-tert-butoxycarbonyl-butyryl}-piperazine-1-carboxylic acid ethyl ester;

(Example 402). LC-MS (B): $t_R$=1.18 min; [M+H]$^+$: 568.16.

Example 466

4-((S)-4-tert-butoxycarbonyl-2-{[6-(1-hydroxy-ethyl)-2-phenyl-pyrimidine-4-carbonyl]-amino}-butyryl)-piperazine-1-carboxylic acid ethyl ester;

(Example 403). LC-MS (B): $t_R$=1.10 min; [M+H]$^+$: 570.15.

Example 467

4-((S)-4-tert-butoxycarbonyl-2-{[6-(1-methoxy-ethyl)-2-phenyl-pyrimidine-4-carbonyl]-amino}-butyryl)-piperazine-1-carboxylic acid ethyl ester;

(Example 404). LC-MS (B): $t_R$=1.18 min; [M+H]$^+$: 582.45.

Example 468

4-((S)-4-tert-butoxycarbonyl-2-{[6-(1-ethoxy-ethyl)-2-phenyl-pyrimidine-4-carbonyl]-amino}-butyryl)-piperazine-1-carboxylic acid ethyl ester;

(Example 405). LC-MS (B): $t_R$=1.20 min; [M+H]$^+$: 620.28.

Example 469

4-((S)-4-tert-butoxycarbonyl-2-{[6-(1-hydroxy-1-methyl-ethyl)-2-phenyl-pyrimidine-4-carbonyl]-amino}-butyryl)-piperazine-1-carboxylic acid ethyl ester;

(Example 406). LC-MS (B): $t_R$=1.13 min; [M+H]$^+$: 583.91.

Example 470

4-((S)-4-tert-butoxycarbonyl-2-{[6-(2-hydroxy-ethyl)-2-phenyl-pyrimidine-4-carbonyl]-amino}-butyryl)-piperazine-1-carboxylic acid ethyl ester;

(Example 408). LC-MS (B): $t_R$=1.07 min; [M+H]$^+$: 570.26.

Example 471

4-((S)-4-tert-butoxycarbonyl-2-{[6-(2-methoxy-ethyl)-2-phenyl-pyrimidine-4-carbonyl]-amino}-butyryl)-piperazine-1-carboxylic acid ethyl ester;

(Example 409). LC-MS (B): $t_R$=1.04 min; [M+H]$^+$: 584.10.

Example 472

4-((S)-4-tert-butoxycarbonyl-2-{[6-(2-hydroxy-cyclohexyl)-2-phenyl-pyrimidine-4-carbonyl]-amino}-butyryl)-piperazine-1-carboxylic acid ethyl ester;

(Example 410). LC-MS (B): $t_R$=1.17 min; [M+H]$^+$: 624.36.

Example 473

4-((S)-4-tert-butoxycarbonyl-2-{[6-(2-methoxy-cyclohexyl)-2-phenyl-pyrimidine-4-carbonyl]-amino}-butyryl)-piperazine-1-carboxylic acid ethyl ester;

(Example 411). LC-MS (B): $t_R$=1.19 min; [M+H]$^+$: 639.10.

Example 474

4-((S)-4-tert-butoxycarbonyl-2-{[6-(2-hydroxy-cyclopentyl)-2-phenyl-pyrimidine-4-carbonyl]-amino}-butyryl)-piperazine-1-carboxylic acid ethyl ester;

(Example 412). LC-MS (C): $t_R$=1.04 min; [M+H]$^+$: 610.05.

Example 475

4-((S)-4-tert-butoxycarbonyl-2-{[6-(2-hydroxy-propyl)-2-phenyl-pyrimidine-4-carbonyl]-amino}-butyryl)-piperazine-1-carboxylic acid ethyl ester (Example 413). LC-MS (C): $t_R$=0.98 min; [M+H]$^+$: 584.05.

Example 476

4-((S)-4-tert-butoxycarbonyl-2-{[6-(2-methoxy-propyl)-2-phenyl-pyrimidine-4-carbonyl]-amino}-butyryl)-piperazine-1-carboxylic acid ethyl ester (Example 414). LC-MS (B): $t_R$=1.20 min; [M+H]$^+$: 598.27.

Example 477

4-((S)-4-tert-butoxycarbonyl-2-{[6-(3,6-dihydro-2H-pyran-4-yl)-2-phenyl-pyrimidine-4-carbonyl]-amino}-butyryl)-piperazine-1-carboxylic acid ethyl ester (Example 415). LC-MS (A): $t_R$=1.30 min; [M+H]$^-$: 606.63.

Example 478

4-((S)-4-tert-butoxycarbonyl-2-{[2-phenyl-6-(tetrahydro-pyran-4-yl)-pyrimidine-4-carbonyl]-amino}-butyryl)-piperazine-1-carboxylic acid ethyl ester (Example 416). LC-MS (A): $t_R$=1.28 min; [M+H]$^+$: 610.44.

Example 479

4-((S)-4-tert-butoxycarbonyl-2-{[6-(2-ethoxycarbonyl-cyclohexyl)-2-phenyl-pyrimidine-4-carbonyl]-amino}-butyryl)-piperazine-1-carboxylic acid ethyl ester (Example 417). LC-MS (A): $t_R$=1.41 min; [M+H]$^+$: 680.41.

Example 480

4-((S)-4-tert-butoxycarbonyl-2-{[6-(1-oxy-pyridin-3-yl)-2-phenyl-pyrimidine-4-carbonyl]-amino}-butyryl)-piperazine-1-carboxylic acid ethyl ester (Example 418). LC-MS (C): $t_R$=1.08 min; [M+H]$^+$: 619.30.

Example 481

4-((S)-4-tert-butoxycarbonyl-2-{[6-((E)-2-ethoxycarbonyl-vinyl)-2-phenyl-pyrimidine-4-carbonyl]-amino}-butyryl)-piperazine-1-carboxylic acid ethyl ester (Example 419). LC-MS (C): $t_R$=1.10 min; [M+H]$^+$: 624.07.

Example 482

4-((S)-4-tert-butoxycarbonyl-2-{[2-phenyl-6-(tetrahydro-furan-2-ylmethyl)-pyrimidine-4-carbonyl]-amino}-butyryl)-piperazine-1-carboxylic acid ethyl ester (Example 420). LC-MS (C): $t_R$=1.04 min; [M+H]$^+$: 610.59.

Example 483

4-((S)-4-tert-butoxycarbonyl-2-{[6-(3-hydroxy-2-methyl-propyl)-2-phenyl-pyrimidine-4-carbonyl]-amino}-butyryl)-piperazine-1-carboxylic acid ethyl ester (Example 422). LC-MS (C): $t_R$=1.00 min; [M+H]$^+$: 598.07.

Example 484

4-((S)-4-tert-butoxycarbonyl-2-{[2-phenyl-6-(tetrahydro-furan-3-yl)-pyrimidine-4-carbonyl]-amino}-butyryl)-piperazine-1-carboxylic acid ethyl ester (Example 423). LC-MS (C): $t_R$=1.07 min; [M+H]$^+$: 596.05.

Example 485

4-((S)-4-tert-butoxycarbonyl-2-{[6-((E)-2-dimethylcarbamoyl-vinyl)-2-phenyl-pyrimidine-4-carbonyl]-amino}-butyryl)-piperazine-1-carboxylic acid ethyl ester (Example 424). LC-MS (C): $t_R$=1.04 min; [M+H]$^+$: 623.63.

Example 486

4-((S)-4-tert-butoxycarbonyl-2-{[6-(1-hydroxy-propyl)-2-phenyl-pyrimidine-4-carbonyl]-amino}-butyryl)-piperazine-1-carboxylic acid ethyl ester (Example 426). LC-MS (C): $t_R$=1.03 min; [M+H]$^+$: 584.43.

Example 487

4-((S)-4-tert-butoxycarbonyl-2-{[6-(1-hydroxy-butyl)-2-phenyl-pyrimidine-4-carbonyl]-amino}-butyryl)-piperazine-1-carboxylic acid ethyl ester (Example 427). LC-MS (C): $t_R$=1.05 min; [M+H]$^+$: 598.37.

Example 488

4-((S)-4-tert-butoxycarbonyl-2-{[6-(hydroxy-phenyl-methyl)-2-phenyl-pyrimidine-4-carbonyl]-amino}-butyryl)-piperazine-1-carboxylic acid ethyl ester (Example 428). LC-MS (C): $t_R$=1.06 min; [M+H]$^+$: 632.41.

Example 489

4-((S)-4-tert-butoxycarbonyl-2-{[6-(2-hydroxy-2-phenyl-ethyl)-2-phenyl-pyrimidine-4-carbonyl]-amino}-butyryl)-piperazine-1-carboxylic acid ethyl ester (Example 429). LC-MS (C): $t_R$=1.05 min; [M+H]$^+$: 646.36.

Example 490

4-{(S)-4-tert-butoxycarbonyl-2-[(2-phenyl-6-trifluoromethyl-pyrimidine-4-carbonyl)-amino]-butyryl}-piperazine-1-carboxylic acid ethyl ester (Example 431). LC-MS (A): $t_R$=1.33 min; [M+H]$^-$: 592.36.

Example 491

4-{(S)-2-[(6-tert-butyl-2-phenyl-pyrimidine-4-carbonyl)-amino]-4-tert-butyloxycarbonyl-butyryl}-piperazine-1-carboxylic acid ethyl ester (Example 432). LC-MS (C): $t_R$=1.13 min; [M+H]$^+$: 582.33.

Example 492

4-{(S)-4-tert-butoxycarbonyl-2-[(6-phenoxy-2-phenyl-pyrimidine-4-carbonyl)-amino]-butyryl}-piperazine-1-carboxylic acid ethyl ester (Example 433). LC-MS (C): $t_R$=1.10 min; [M+H]$^+$: 618.05.

Example 493

4-((S)-4-carboxy-2-{[6-(1-oxy-pyridin-2-yl)-2-phenyl-pyrimidine-4-carbonyl]-amino}-butyryl)-piperazine-1-carboxylic acid ethyl ester 493.1. 4-((S)-4-tert-butoxycarbonyl-2-{[6-(1-oxy-pyridin-2-yl)-2-phenyl-pyrimidine-4-carbonyl]-amino}-butyryl)-piperazine-1-carboxylic acid ethyl ester A solution of intermediate 48.1 (300 mg) in toluene (3 ml) was syringed into a flask containing K$_2$CO$_3$ (212 mg), tri-(tert-butylphosphonium) tetrafluoroborate (23 mg), palladium(II) acetate (28 mg) and pyridine N-oxide (203 mg) under argon. The mixture was refluxed for 16 h, cooled down, filtered through Celite and evaporated off. Column chromatography (EA/Hept 3/7) afforded 110 mg of the desired product.

$^1$H-NMR (CD$_3$OD): 9.25 (d, 1H); 9.2 (s, 1H); 8.60 (m, 2H); 8.45 (m, 2H); 7.65 (m, 2H); 7.50 (m, 3H); 5.20 (m, 1H); 4.15 (q, 2H); 3.8 to 3.5 (m, 8H); 2.40 (m, 2H); 2.2 (m, 1H); 2.05 (m, 1H); 1.4 (s, 9H); 1.25 (t, 3H).

493.2. 4-((S)-4-carboxy-2-{[6-(1-oxy-pyridin-2-yl)-2-phenyl-pyrimidine-4-carbonyl]-amino}-butyryl)-piperazine-1-carboxylic acid ethyl ester This compound was prepared using a method analogous to that of Example 1, step 1.9, intermediate 493.1 replacing intermediate 1.8. The compound was however purified by preparative LC-MS (II).

LC-MS (C): $t_R$=0.85 min; [M+H]$^+$: 563.20.

Example 494

4-((S)-4-carboxy-2-{[6-(1-oxy-pyridin-4-yl)-2-phenyl-pyrimidine-4-carbonyl]-amino}-butyryl)-piperazine-1-carboxylic acid ethyl ester 494.1. 4-((S)-4-tert-butoxycarbonyl-2-{[6-(1-oxy-pyridin-4-yl)-2-phenyl-pyrimidine-4-carbonyl]-amino}-butyryl)-piperazine-1-carboxylic acid ethyl ester This compound was prepared using a method analogous to that of Example 418, step 418.1, intermediate 400.1 replacing intermediate 399.1.

LC-MS (C): $t_R$=1.09 min; [M+H+CH$_3$CN]$^+$: 660.31.

494.2. 4-((S)-4-carboxy-2-{[6-(1-oxy-pyridin-4-yl)-2-phenyl-pyrimidine-4-carbonyl]-amino}-butyryl)-piperazine-1-carboxylic acid ethyl ester This compound was prepared using a method analogous to that of Example 1, step 1.9, intermediate 494.1 replacing intermediate 1.8. The compound was however purified by preparative LC-MS (II).

LC-MS (C): $t_R$=0.87 min; [M+H+CH$_3$CN]$^+$: 605.21.

Example 495

4-((S)-4-carboxy-2-{[6-(2-hydroxy-1,1-dimethyl-ethyl)-2-phenyl-pyrimidine-4-carbonyl]-amino}-butyryl)-piperazine-1-carboxylic acid ethyl ester 495.1. 3-(tert-butyl-dimethyl-silanyloxy)-2,2-dimethyl-propionic acid methyl ester Methyl 2,2-dimethyl-3-hydroxypropionate (1.32 g), tert-butyldimethylsilyl chloride (1.8 g), 4-dimethylaminopyridine (122 mg) and NEt$_3$ (1.67 ml) were dissolved in DCM (100 ml) and stirred for 16 h at RT. A NaHSO$_4$ solution was added, and the org. phase was further washed with water, dried (Na$_2$SO$_4$) and evaporated off. Column chromatography (EA/Hept 1/4) afforded 800 mg of the desired compound.

$^1$H-NMR (CDCl$_3$): 3.65 (s, 3H); 3.55 (s, 2H); 1.15 (s, 6H); 0.85 (s, 9H); 0.0 (s, 6H).

495.2. 3-(tert-butyl-dimethyl-silanyloxy)-2,2-dimethyl-propionic acid

Intermediate 495.1 (800 mg) was dissolved in a mixture of THF (15 ml), MeOH (8 ml) and a 1M NaOH solution (10 ml). After 3 h at reflux, Et$_2$O and a 1M HCl solution were added. The org. phase was dried (Na$_2$SO$_4$) and evaporated off to give 486 mg of the desired product.

¹H-NMR (CDCl₃): 3.50 (s, 2H); 1.10 (s, 6H); 0.80 (s, 9H); 0.0 (s, 6H).

495.3. 3-(tert-butyl-dimethyl-silanyloxy)-2,2-dimethyl-propionyl chloride

Intermediate 495.2 (200 mg) was dissolved in DCM (12 ml) and DMF (7 μl), and oxalyl chloride (365 μl) was added. After stirring at RT for 3 h, the solvents were removed and the crude was used in the next step without any characterisation or purification.

495.4. Acetic acid 6-(tert-butyl-dimethyl-silanyloxy)-5,5-dimethyl-4-oxo-hex-2-ynyl ester This compound was prepared using a method analogous to that of Example 432, step 432.1, intermediate 495.3 replacing pivaloyl chloride.
¹H-NMR (CDCl₃): 4.80 (s, 2H); 3.60 (s, 2H); 2.05 (s, 3H); 1.15 (s, 6H); 0.90 (s, 9H); 0.10 (s, 6H).

495.5. Acetic acid 6-[2-(tert-butyl-dimethyl-silanyloxy)-1,1-dimethyl-ethyl]-2-phenyl-pyrimidin-4-ylmethyl ester This compound was prepared using a method analogous to that of Example 432, step 432.2, intermediate 495.4 replacing intermediate 432.1.
LC-MS (C): $t_R$=1.22 min; [M+H]⁻: 415.42.

495.6. {6-[2-(tert-butyl-dimethyl-silanyloxy)-1,1-dimethyl-ethyl]-2-phenyl-pyrimidin-4-yl}-methanol This compound was prepared using a method analogous to that of Example 432, step 432.3, intermediate 495.5 replacing intermediate 432.2.
LC-MS (C): $t_R$=1.17 min; [M+H]⁻: 373.41.

495.7. 6-[2-(tert-butyl-dimethyl-silanyloxy)-1,1-dimethyl-ethyl]-2-phenyl-pyrimidine-4-carboxylic acid This compound was prepared using a method analogous to that of Example 24, step 24.3, intermediate 495.6 replacing intermediate 24.2.
¹H-NMR (CDCl₃): 8.60 (br s, 2H); 8.15 (s, 1H); 7.60 (br s, 3H); 3.9 (s, 2H); 1.55 (s, 6H); 0.8 (s, 9H); 0.0 (s, 6H).

495.8. 4-{(S)-4-tert-butoxycarbonyl-2-({6-[2-(tert-butyl-dimethyl-silanyloxy)-1,1-dimethyl-ethyl]-2-phenyl-pyrimidine-4-carbonyl}-amino)-butyryl}-piperazine-1-carboxylic acid ethyl ester This compound was prepared using a method analogous to that of Example 108, step 108.1, intermediate 495.7 replacing intermediate 24.3, the reaction being carried out at RT instead of 0° C. The compound was however purified by column chromatography (EA/Hept 1/1).
LC-MS (C): $t_R$=1.25 min; [M+H]⁺: 712.54.

495.9. 4-((S)-4-tert-butoxycarbonyl-2-{[6-(2-hydroxy-1,1-dimethyl-ethyl)-2-phenyl-pyrimidine-4-carbonyl]-amino}-butyryl)-piperazine-1-carboxylic acid ethyl ester Intermediate 495.8 (9 mg) was dissolved in THF (0.5 ml) and a 1M solution of TBAF in THF (25 μl) was added. After stirring 16 h at RT, EA/NH₄Cl was added. After extraction, the org. phase was dried (Na₂SO₄) and evaporated off to give 12 mg of the desired product.
LC-MS (C): $t_R$=1.03 min; [M+H]⁺: 598.32.

495.10. 4-((S)-4-carboxy-2-{[6-(2-hydroxy-1,1-dimethyl-ethyl)-2-phenyl-pyrimidine-4-carbonyl]-amino}-butyryl)-piperazine-1-carboxylic acid ethyl ester This compound was prepared using a method analogous to that of Example 1, step 1.9, intermediate 495.9 replacing intermediate 1.8.
LC-MS (C): $t_R$=0.89 min; [M+H]⁺: 542.22.

The compounds of Examples 496 to 498 were prepared using a method analogous to that of the Example indicated between brackets, except that the last step of the corresponding Example was not carried out.

Example 496

4-((S)-4-tert-butoxycarbonyl-2-{[6-(1-oxy-pyridin-2-yl)-2-phenyl-pyrimidine-4-carbonyl]-amino}-butyryl)-piperazine-1-carboxylic acid ethyl ester (Example 493). ¹H-NMR (CD₃OD): 9.25 (d, 1H); 9.2 (s, 1H); 8.60 (m, 2H); 8.45 (m, 2H); 7.65 (m, 2H); 7.50 (m, 3H); 5.20 (m, 1H); 4.15 (q, 2H); 3.8 to 3.5 (m, 8H); 2.40 (m, 2H); 2.2 (m, 1H); 2.05 (m, 1H); 1.4 (s, 9H); 1.25 (t, 3H).

Example 497

4-((S)-4-tert-butoxycarbonyl-2-{[6-(1-oxy-pyridin-4-yl)-2-phenyl-pyrimidine-4-carbonyl]-amino}-butyryl)-piperazine-1-carboxylic acid ethyl ester;

(Example 494). LC-MS (C): $t_R$=1.09 min; [M+H+CH₃CN]⁺: 660.31.

Example 498

4-((S)-4-tert-butoxycarbonyl-2-{[6-(2-hydroxy-1,1-dimethyl-ethyl)-2-phenyl-pyrimidine-4-carbonyl]-amino}-butyryl)-piperazine-1-carboxylic acid ethyl ester;

(Example 495). LC-MS (C): $t_R$=1.03 min; [M+H]⁺: 598.32.

Example 499

4-((S)-4-tert-butoxycarbonyl-2-{[6-(2-hydroxymethyl-cyclopropyl)-2-phenyl-pyrimidine-4-carbonyl]-amino}-butyryl)-piperazine-1-carboxylic acid ethyl ester

499.1. 3-tributylstannanyl-prop-2-en-1-ol

To neat propargyl alcohol (1 ml) were added tributyl stannane (5.8 ml) followed by 1,1'-azobis(cyclohexanecarbonitrile) (213 mg). The mixture was heated for 2 h at 80° C., cooled to RT, and directly purified by column chromatography (EA/Hept 4/96 to 5/95) to afford 2.98 g of the desired product.
¹H-NMR (CDCl₃): 6.2 (m, 2H); 4.15 (m, 2H); 1.55-1.25 (m, 18H); 0.90 (t, 9H).

499.2. (2-tributylstannanyl-cyclopropyl)-methanol

To a stirred solution of diethylzinc (3.32 ml) in anhydrous DCM (5 ml) at 0° C. was added diiodomethane (538 µl). The mixture was stirred at 0° C. for 10 min and a solution of intermediate 499.1 (514 mg) in DCM (10 ml) was added slowly. The mixture was stirred at RT for 2 h, cooled down to 0° C. and quenched with a $NH_4Cl$ solution. The org. phase was separated and the aq. phase was extracted with EA. The resulting org. phases were dried ($Na_2SO_4$) and evaporated off. Column chromatography (EA/Hept 5/95) afforded 434 mg of the desired product.

$^1$H-NMR ($CDCl_3$): 3.55 (m, 1H); 3.39 (m, 1H); 1.55-1.25 (m, 18H); 1.10 (m, 1H); 0.90 (t, 9H); 0.75 (m, 1H); 0.52 (m, 2H).

499.93. 4-((S)-4-tert-butoxycarbonyl-2-{[6-(2-hydroxymethyl-cyclopropyl)-2-phenyl-pyrimidine-4-carbonyl]-amino}-butyryl)-piperazine-1-carboxylic acid ethyl ester This compound was prepared using a method analogous to that of Example 401, step 401.1, intermediate 499.2 replacing 2-tributylstannylthiazole. The compound was however purified by column chromatography (EA/Hept 1/1 to 7/3 to 1/0).

LC-MS (C): $t_R$=1.00 min; [M+H]$^+$: 596.32.

Example 500

4-((S)-4-carboxy-2-{[6-(2-hydroxymethyl-cyclopropyl)-2-phenyl-pyrimidine-4-carbonyl]-amino}-butyryl)-piperazine-1-carboxylic acid ethyl ester The compound of Example 499 (200 mg) was dissolved in TFA/DCM (1/2, 6 ml), and the mixture was stirred at RT for 3 h. Toluene (3 ml) was added and the mixture was evaporated off. The residue was taken up in EA/solution of $NaHCO_3$. The aq. phase was acidified with a 1M HCl solution and extracted with EA. The resulting org. phases were evaporated off. The residue was taken up in THF/solution of LiOH (7 mg) (2/1, 3 ml) in order to cleave off the trifluoroacetic ester. After 1 h, the desired compound was obtained. The mixture was diluted with a 1M NaOH solution and extracted several times with EA. The basic aq. solution was acidified (AcOH) and extracted twice with EA. The org. phases were dried ($Na_2SO_4$) and evaporated off to afford 91 mg of the desired compound.

LC-MS (C): $t_R$=0.86 min; [M+H]$^+$: 540.29.

Biological Tests
$P2Y_{12}$ Receptor Binding Assay
Procedure

Chinese Hamster Ovary (CHO) cells with recombinant expression of the human $P2Y_{12}$ receptor were cultured in 24 well cell-culture plates. Cells were washed three times with binding buffer (50 mM Tris pH 7.4, 100 mM NaCl, 1 mM EDTA, 0.5% BSA). The cells were then incubated with 0.5 ml per well binding buffer containing tritium-labeled 2-methyl-thio-adenosine 5'-diphosphate (2-methyl-S-ADP) (between 100'000 and 300'000 dpm per well) and various concentrations of test compounds. After incubation at room temperature for 2 hours, cells were washed three times with binding buffer. Then, cells were solubilized by addition of 0.5 ml solubilization buffer (SDS, NaOH, EDTA). The content of each well was then transferred into beta-counter vials and 2.0 ml of Ultima Gold Scintillation liquid was added. After quantification of the cell-associated signal, extent of inhibition was calculated relative to maximal possible inhibition demonstrated by addition of excess of cold 2-methyl-S-ADP.

Results Obtained for the Compounds of Formula I

The following results could be obtained for the example compounds using the procedure described above for the $P2Y_{12}$ receptor binding assay:

| Example No. | IC$_{50}$ at $P2Y_{12}$ receptor binding assay (nM) |
|---|---|
| 1 | 117 |
| 2 | 243 |
| 10 | 307 |
| 19 | 127 |
| 21 | 201 |
| 27 | 193 |
| 31 | 592 |
| 38 | 95 |
| 46 | 510 |
| 59 | 276 |
| 66 | 202 |
| 79 | 121 |
| 88 | 98 |
| 94 | 200 |
| 105 | 940 |
| 115 | 390 |
| 121 | 127 |
| 132 | 8114 |
| 223 | 97 |
| 225 | 100 |
| 231 | 174 |
| 243 | 223 |
| 247 | 142 |
| 249 | 101 |
| 251 | 624 |
| 258 | 253 |
| 261 | 126 |
| 266 | 273 |
| 267 | 216 |
| 324 | 61 |
| 333 | 161 |
| 341 | 169 |
| 362 | 86 |
| 375 | 108 |
| 378 | 157 |
| 396 | 73 |
| 402 | 72 |
| 408 | 207 |
| 418 | 129 |
| 421 | 75 |
| 430 | 188 |
| 431 | 170 |
| 435 | 94 |

The invention claimed is:

1. A compound selected from the group consisting of a compound of the formula I

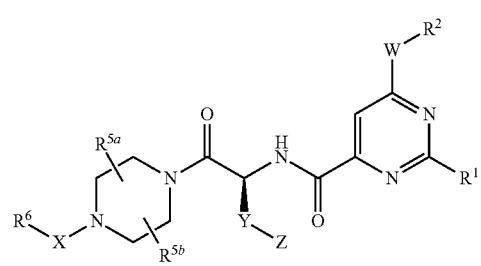

wherein
R$^1$ represents phenyl optionally substituted 1 to 3 times by substituents each independently selected from the group consisting of halogen, methyl, methoxy, trifluoromethyl and trifluoromethoxy;

W represents a bond, and R$^2$ represents alkyl, haloalkyl, cyano, hydroxyalkyl, hydroxyalkyl substituted on its alkyl chain with an unsubstituted phenyl group, alkoxyalkyl, heterocyclyl, heterocyclylalkyl, cycloalkyl, cycloalkylalkyl, aryl, heteroaryl, or one of the radicals

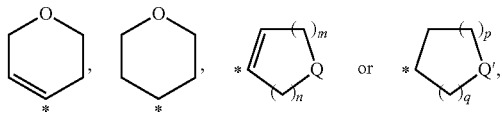

wherein:
m is 0 and n is 2 or 3, or m is 1 and n is 2,
p is 0 and q is 2 or 3, or p is 1 and q is 2, or p is 2 or 3 and q is 0,
Q is —CO— or —CH(OR$^a$)—, R$^a$ being hydrogen or alkyl, and
Q' is —CO—; or W represents —CH$_2$— and R$^2$ represents —NR$^7$R$^8$, —SR$^9$ or —SO$_2$R$^{10}$;

W represents —O— or —S— and R$^2$ represents alkyl, carboxyalkyl, alkoxycarbonylalkyl, hydroxyalkyl, alkoxyalkyl, heterocyclylalkyl, cycloalkyl, cycloalkylalkyl, aryl, aralkyl, heteroaryl or heteroarylalkyl;

W represents —NR$^3$— and R$^2$ represents hydrogen, alkyl, dialkylaminoalkyl, alkoxycarbonylalkyl, carboxyalkyl, carboxyalkyl substituted on its alkyl part with an unsubstituted phenyl group, hydroxyalkyl, alkoxyalkyl, heterocyclyl, heterocyclylalkyl, cycloalkyl, cycloalkylalkyl, aryl, 2-phenylcyclopropyl, aralkyl, diphenylalkyl, heteroarylalkyl wherein the heteroaryl is a monocyclic heteroaryl, —COR$^{11}$ or —SO$_2$R$^{12}$;

W represents —CH═CH— and R$^2$ represents alkyl, hydroxyalkyl, alkoxyalkyl, alkoxycarbonyl, phenyl or —CO—NR$^{13}$R$^{14}$; or W represents —C≡C— and R$^2$ represents hydrogen, alkyl, hydroxyalkyl or alkoxyalkyl; or W represents —CO— and R$^2$ represents alkyl;

R$^3$ represents hydrogen or alkyl;

R$^7$ represents alkyl or arylalkyl;

R$^8$ represents alkyl;

or R$^7$ and R$^8$ form, together with the nitrogen that carries them, a heterocyclic ring of 4 to 7 members wherein the members needed to complete said heterocyclic ring are each independently selected from —CH$_2$—, —CH(CH$_3$)—, —CHR$^y$—, —O—, —S—, —CO— and —NR$^z$—, and said heterocyclic ring does not contain more than one member selected from the group consisting of —CHR$^y$—, —O—, —S—, —CO— and —NR$^z$—, R$^y$ representing hydroxy, hydroxymethyl, alkoxymethyl, alkoxycarbonyl or alkoxy and R$^z$ representing hydrogen, alkyl or alkoxycarbonyl;

R$^9$ represents cycloalkyl or aryl;

R$^{10}$ represents alkyl, cycloalkyl or aryl;

R$^{11}$ represents alkyl, alkoxyalkyl, cycloalkyl, cycloalkylalkyl, aryl, monocyclic heteroaryl or aralkyl;

R$^{12}$ represents alkyl or aryl;

R$^{13}$ represents alkyl;

R$^{14}$ represents alkyl;

or W represents —NR$^3$— and R$^2$ and R$^3$ form, together with the nitrogen that carries them, a heterocyclic ring of 4 to 7 members wherein the members needed to complete said heterocyclic ring are each independently selected from —CH$_2$—, —CHR$^x$—, —O—, —S—, —CO— and —NR$^4$—, and said heterocyclic ring does not contain more than one member selected from the group consisting of —CHR$^x$—, —O—, —S—, —CO— and —NR$^4$—, R$^x$ representing hydroxy, hydroxymethyl, alkoxymethyl or alkoxy and R$^4$ representing hydrogen or alkyl;

or W represents —NR$^3$—, and R$^2$ and R$^3$ form, together with the nitrogen that carries them, either an imidazolyl, pyrazolyl, 1,2,3-triazolyl or 1,2,4-triazolyl ring, which ring may be substituted by an alkyl group, or a 4-oxo-4H-pyridin-1-yl, 4,5-dihydro-pyrazol-1-yl, 2-methyl-4,5-dihydro-imidazol-1-yl or 3-methyl-5-oxo-2,5-dihydro-pyrazol-1-yl ring;

each of R$^{5a}$ and R$^{5b}$ represents independently hydrogen or methyl;

X represents —CO— and R$^6$ represents alkyl, cycloalkyl, alkoxy, alkynyloxy, aryloxy, aralkoxy, aryl, monocyclic heteroaryl, aralkyl or NR$^{15}$R$^{16}$, or X represents —SO$_2$— and R$^6$ represents alkyl;

R$^{15}$ represents alkyl;

R$^{16}$ represents hydrogen or alkyl;

or R$^{15}$ and R$^{16}$ form, together with the nitrogen that carries them, a heterocyclic ring of 4 to 7 members, wherein the members needed to complete said heterocyclic ring are each independently selected from —CH$_2$—, —O—, —S— and —NR$^w$—, R$^w$ representing hydrogen or alkyl, and said heterocyclic ring does not contain more than one member selected from the group consisting of —O—, —S— and —NR$^w$—; and Y represents a bond and Z represents hydrogen or aryl substituted by carboxyalkoxy;

or Y represents alkylene, alkoxyalkylene, phenylalkylene, alkoxyphenylene or alkoxyphenylalkylene and Z represents hydrogen, —OH, —NH$_2$, —COOH, tetrazolyl, —CO—NH$_2$, —COOR$^{17}$, —NH—CO—R$^{17}$, —NH—COOR$^{17}$ or —NH—SO$_2$—R$^{17}$, R$^{17}$ representing alkyl;

or an optically pure enantiomer, a mixture of enantiomers, a racemate, an optically pure diastereoisomer, a mixture of diastereoisomers, a diastereoisomeric racemate, a mixture of diastereoisomeric racemates, or a pharmaceutically acceptable salt thereof.

2. The compound according to claim 1, wherein W represents a bond; or a pharmaceutically acceptable salt thereof.

3. The compound according to claim 1, wherein W represents —CH$_2$—; or a pharmaceutically acceptable salt thereof.

4. The compound according to claim 1, wherein W represents —O—; or a pharmaceutically acceptable salt thereof.

5. The compound according to claim 1, wherein W represents —S—; or a pharmaceutically acceptable salt thereof.

6. The compound according to claim 1, wherein W represents —NR$^3$—; or a pharmaceutically acceptable salt thereof.

7. The compound according to claim 1, wherein W represents —CH═CH—; or a pharmaceutically acceptable salt thereof.

8. The compound according to claim 1, wherein W represents —C≡C—; or a pharmaceutically acceptable salt thereof.

9. The compound according to claim 1, wherein Y represents alkylene, alkoxyalkylene or phenylalkylene; or a pharmaceutically acceptable salt thereof.

10. The compound according to claim 1, wherein $R^1$ represents unsubstituted phenyl; or a pharmaceutically acceptable salt thereof.

11. The compound according to claim 1, wherein each of $R^{5a}$ and $R^{5b}$ represents hydrogen; or a pharmaceutically acceptable salt thereof.

12. The compound according to claim 1, wherein X represents —CO— and $R^6$ represents alkoxy, alkynyloxy or heteroaryl; or a pharmaceutically acceptable salt thereof.

13. The compound according to claim 1, which is selected from the group consisting of:

4-{(S)-4-carboxy-2-[(6-cyclopentyloxy-2-phenyl-pyrimidine-4-carbonyl)-amino]-butyryl}-piperazine-1-carboxylic acid ethyl ester;

4-{(S)-3-carboxy-2-[(6-cyclopentyloxy-2-phenyl-pyrimidine-4-carbonyl)-amino]-propionyl}-piperazine-1-carboxylic acid ethyl ester;

4-{(S)-5-carboxy-2-[(6-cyclopentyloxy-2-phenyl-pyrimidine-4-carbonyl)-amino]-pentanoyl}-piperazine-1-carboxylic acid ethyl ester;

4-{2-[(6-cyclopentyloxy-2-phenyl-pyrimidine-4-carbonyl)-amino]-acetyl}-piperazine-1-carboxylic acid ethyl ester;

4-{(S)-2-[(6-cyclopentyloxy-2-phenyl-pyrimidine-4-carbonyl)-amino]-3-methyl-butyryl}-piperazine-1-carboxylic acid ethyl ester;

4-{(S)-3-carbamoyl-2-[(6-cyclopentyloxy-2-phenyl-pyrimidine-4-carbonyl)-amino]-propionyl}-piperazine-1-carboxylic acid ethyl ester;

4-{(S)-4-carbamoyl-2-[(6-cyclopentyloxy-2-phenyl-pyrimidine-4-carbonyl)-amino]-butyryl}-piperazine-1-carboxylic acid ethyl ester;

4-{(S)-3-amino-2-[(6-cyclopentyloxy-2-phenyl-pyrimidine-4-carbonyl)-amino]-propionyl}-piperazine-1-carboxylic acid ethyl ester;

4-{(S)-6-amino-2-[(6-cyclopentyloxy-2-phenyl-pyrimidine-4-carbonyl)-amino]-hexanoyl}-piperazine-1-carboxylic acid ethyl ester;

4-{(S)-2-[(6-cyclopentyloxy-2-phenyl-pyrimidine-4-carbonyl)-amino]-3-hydroxy-propionyl}-piperazine-1-carboxylic acid ethyl ester;

4-{(S)-2-[(6-cyclopentyloxy-2-phenyl-pyrimidine-4-carbonyl)-amino]-4-hydroxy-butyryl}-piperazine-1-carboxylic acid ethyl ester;

4-{(S)-2-[(6-cyclopentyloxy-2-phenyl-pyrimidine-4-carbonyl)-amino]-5-hydroxy-pentanoyl}-piperazine-1-carboxylic acid ethyl ester;

4-{(S)-2-[(6-cyclopentyloxy-2-phenyl-pyrimidine-4-carbonyl)-amino]-6-hydroxy-hexanoyl}-piperazine-1-carboxylic acid ethyl ester;

4-{(S)-3-acetylamino-2-[(6-cyclopentyloxy-2-phenyl-pyrimidine-4-carbonyl)-amino]-propionyl}-piperazine-1-carboxylic acid ethyl ester;

4-{(S)-2-[(6-cyclopentyloxy-2-phenyl-pyrimidine-4-carbonyl)-amino]-3-methoxycarbonylamino-propionyl}-piperazine-1-carboxylic acid ethyl ester;

4-{(S)-2-[(6-cyclopentyloxy-2-phenyl-pyrimidine-4-carbonyl)-amino]-3-methanesulfonylamino-propionyl}-piperazine-1-carboxylic acid ethyl ester;

4-{(S)-4-carboxymethoxy-2-[(6-cyclopentyloxy-2-phenyl-pyrimidine-4-carbonyl)-amino]-butyryl}-piperazine-1-carboxylic acid ethyl ester;

4-[(S)-2-[(6-cyclopentyloxy-2-phenyl-pyrimidine-4-carbonyl)-amino]-3-(1H-tetrazol-5-yl)-propionyl]-piperazine-1-carboxylic acid ethyl ester;

4-[(S)-2-[(6-cyclopentyloxy-2-phenyl-pyrimidine-4-carbonyl)-amino]-4-(1H-tetrazol-5-yl)-butyryl]-piperazine-1-carboxylic acid ethyl ester;

4-{(S)-2-[(6-cyclopentyloxy-2-phenyl-pyrimidine-4-carbonyl)-amino]-3-[4-(1H-tetrazol-5-yl)-phenyl]-propionyl}-piperazine-1-carboxylic acid ethyl ester;

4-{(S)-3-(4-carboxy-phenyl)-2-[(6-cyclopentyloxy-2-phenyl-pyrimidine-4-carbonyl)-amino]-propionyl}-piperazine-1-carboxylic acid ethyl ester;

4-{(S)-3-(4-carboxymethoxy-phenyl)-2-[(6-cyclopentyloxy-2-phenyl-pyrimidine-4-carbonyl)-amino]-propionyl}-piperazine-1-carboxylic acid ethyl ester;

4-{(S)-4-carboxy-2-[(6-carboxymethoxy-2-phenyl-pyrimidine-4-carbonyl)-amino]-butyryl}-piperazine-1-carboxylic acid ethyl ester;

4-{(S)-4-carboxy-2-[(2-phenyl-6-propoxy-pyrimidine-4-carbonyl)-amino]-butyryl}-piperazine-1-carboxylic acid ethyl ester;

4-((S)-4-carboxy-2-{[6-(2-hydroxy-ethoxy)-2-phenyl-pyrimidine-4-carbonyl]-amino}-butyryl)-piperazine-1-carboxylic acid ethyl ester;

4-{(S)-2-[(6-benzyloxy-2-phenyl-pyrimidine-4-carbonyl)-amino]-4-carboxy-butyryl}-piperazine-1-carboxylic acid ethyl ester;

4-{(S)-4-carboxy-2-[(6-cyclopropylmethoxy-2-phenyl-pyrimidine-4-carbonyl)-amino]-butyryl}-piperazine-1-carboxylic acid ethyl ester;

4-{(S)-4-carboxy-2-[(6-cyclohexyloxy-2-phenyl-pyrimidine-4-carbonyl)-amino]-butyryl}-piperazine-1-carboxylic acid ethyl ester;

4-{(S)-4-carboxy-2-[(6-isopropoxy-2-phenyl-pyrimidine-4-carbonyl)-amino]-butyryl}-piperazine-1-carboxylic acid ethyl ester;

4-{(S)-4-carboxy-2-[(6-methoxy-2-phenyl-pyrimidine-4-carbonyl)-amino]-butyryl}-piperazine-1-carboxylic acid ethyl ester;

4-{3-(3-carboxymethoxy-phenyl)-2-[(6-cyclopentyloxy-2-phenyl-pyrimidine-4-carbonyl)-amino]-propionyl}-piperazine-1-carboxylic acid ethyl ester;

4-{3-(2-carboxymethoxy-phenyl)-2-[(6-cyclopentyloxy-2-phenyl-pyrimidine-4-carbonyl)-amino]-propionyl}-piperazine-1-carboxylic acid ethyl ester;

4-{(S)-2-(4-carboxymethoxy-phenyl)-2-[(6-cyclopentyloxy-2-phenyl-pyrimidine-4-carbonyl)-amino]-acetyl}-piperazine-1-carboxylic acid ethyl ester;

4-{(S)-4-carboxy-2-[(6-cyclopentyloxy-2-phenyl-pyrimidine-4 carbonyl)-amino]-butyryl}-piperazine-1-carboxylic acid prop-2-ynyl ester;

4-{(S)-4-carboxy-2-[(6-cyclopentyloxy-2-phenyl-pyrimidine-4-carbonyl)-amino]-butyryl}-piperazine-1-carboxylic acid butyl ester;

4-{(S)-4-carboxy-2-[(6-cyclopentyloxy-2-phenyl-pyrimidine-4-carbonyl)-amino]-butyryl}-piperazine-1-carboxylic acid isobutyl ester;

4-{(S)-4-carboxy-2-[(6-cyclopentyloxy-2-phenyl-pyrimidine-4-carbonyl)-amino]-butyryl}-piperazine-1-carboxylic acid 2,2-dimethyl-propyl ester;

4-{(S)-4-carboxy-2-[(6-cyclopentyloxy-2-phenyl-pyrimidine-4-carbonyl)-amino]-butyryl}-piperazine-1-carboxylic acid isopropyl ester;

(S)-4-[(6-cyclopentyloxy-2-phenyl-pyrimidine-4-carbonyl)-amino]-5-[4-(furan-2-carbonyl)-piperazin-1-yl]-5-oxo-pentanoic acid;

4-{(S)-4-carboxy-2-[(6-cyclopentyloxy-2-phenyl-pyrimidine-4-carbonyl)-amino]-butyryl}-piperazine-1-carboxylic acid phenyl ester;

(S)-5-(4-benzoyl-piperazin-1-yl)-4-[(6-cyclopentyloxy-2-phenyl-pyrimidine-4-carbonyl)-amino]-5-oxo-pentanoic acid;

4-{(S)-4-carboxy-2-[(6-cyclopentyloxy-2-phenyl-pyrimidine-4-carbonyl)-amino]-butyryl}-piperazine-1-carboxylic acid benzyl ester;

(S)-5-(4-butyryl-piperazin-1-yl)-4-[(6-cyclopentyloxy-2-phenyl-pyrimidine-4-carbonyl)-amino]-5-oxo-pentanoic acid;

(S)-4-[(6-cyclopentyloxy-2-phenyl-pyrimidine-4-carbonyl)-amino]-5-oxo-5-[4-(propane-1-sulfonyl)-piperazin-1-yl]-pentanoic acid;

4-{(S)-4-carboxy-2-[(6-cyclopentyloxy-2-phenyl-pyrimidine-4-carbonyl)-amino]-butyryl}-3-methyl-piperazine-1-carboxylic acid ethyl ester;

4-{(S)-4-carboxy-2-[(6-cyclopentyloxy-2-phenyl-pyrimidine-4-carbonyl)-amino]-butyryl}-2-methyl-piperazine-1-carboxylic acid ethyl ester;

4-{(S)-4-carboxy-2-[(6-cyclopentyloxy-2-phenyl-pyrimidine-4-carbonyl)-amino]-butyryl}-trans-2,5-dimethyl-piperazine-1-carboxylic acid ethyl ester;

4-{(S)-4-carboxy-2-[(6-methylamino-2-phenyl-pyrimidine-4-carbonyl)-amino]-butyryl}-piperazine-1-carboxylic acid ethyl ester;

4-{(S)-4-carboxy-2-[(2-phenyl-6-propylamino-pyrimidine-4-carbonyl)-amino]-butyryl}-piperazine-1-carboxylic acid ethyl ester;

4-{(S)-4-carboxy-2-[(6-isopropylamino-2-phenyl-pyrimidine-4-carbonyl)-amino]-butyryl}-piperazine-1-carboxylic acid ethyl ester;

4-{(S)-2-[(6-butylamino-2-phenyl-pyrimidine-4-carbonyl)-amino]-4-carboxy-butyryl}-piperazine-1-carboxylic acid ethyl ester;

4-{(S)-4-carboxy-2-[(6-isobutylamino-2-phenyl-pyrimidine-4-carbonyl)-amino]-butyryl}-piperazine-1-carboxylic acid ethyl ester;

4-{(S)-4-carboxy-2-[(6-cyclopropylamino-2-phenyl-pyrimidine-4-carbonyl)-amino]-butyryl}-piperazine-1-carboxylic acid ethyl ester;

4-{(S)-4-carboxy-2-[(6-cyclopentylamino-2-phenyl-pyrimidine-4-carbonyl)-amino]-butyryl}-piperazine-1-carboxylic acid ethyl ester;

4-{(S)-4-carboxy-2-[(6-cyclohexylamino-2-phenyl-pyrimidine-4-carbonyl)-amino]-butyryl}-piperazine-1-carboxylic acid ethyl ester;

4-((S)-4-carboxy-2-{[6-(ethoxycarbonyl methyl-amino)-2-phenyl-pyrimidine-4-carbonyl]-amino}-butyryl)-piperazine-1-carboxylic acid ethyl ester;

4-((S)-4-carboxy-2-{[6-(carboxymethyl-amino)-2-phenyl-pyrimidine-4-carbonyl]-amino}-butyryl)-piperazine-1-carboxylic acid ethyl ester;

4-((S)-4-carboxy-2-{[6-(2-hydroxy-ethylamino)-2-phenyl-pyrimidine-4-carbonyl]-amino}-butyryl)-piperazine-1-carboxylic acid ethyl ester;

4-((S)-4-carboxy-2-{[6-(2-ethoxycarbonyl-ethylamino)-2-phenyl-pyrimidine-4-carbonyl]-amino}-butyryl)-piperazine-1-carboxylic acid ethyl ester;

4-((S)-4-carboxy-2-{[6-(2-carboxy-ethylamino)-2-phenyl-pyrimidine-4-carbonyl]-amino}-butyryl)-piperazine-1-carboxylic acid ethyl ester;

4-((S)-4-carboxy-2-{[6-(3-hydroxy-propylamino)-2-phenyl-pyrimidine-4-carbonyl]-amino}-butyryl)-piperazine-1-carboxylic acid ethyl ester;

4-((S)-4-carboxy-2-{[6-(3-carboxy-propylamino)-2-phenyl-pyrimidine-4-carbonyl]-amino}-butyryl)-piperazine-1-carboxylic acid ethyl ester;

((S)-4-carboxy-2-{[6-(2-dimethylamino-ethylamino)-2-phenyl-pyrimidine-4-carbonyl]-amino}-butyryl)-piperazine-1-carboxylic acid ethyl ester;

4-((S)-4-carboxy-2-{[6-(3-dimethylamino-propylamino)-2-phenyl-pyrimidine-4-carbonyl]-amino}-butyryl)-piperazine-1-carboxylic acid ethyl ester;

4-((S)-4-carboxy-2-{[6-(2-morpholin-4-yl-ethylamino)-2-phenyl-pyrimidine-4-carbonyl]-amino}-butyryl)-piperazine-1-carboxylic acid ethyl ester;

4-((S)-4-carboxy-2-{[6-(3-morpholin-4-y-propylamino)-2-phenyl-pyrimidine-4-carbonyl]-amino}-butyryl)-piperazine-1-carboxylic acid ethyl ester;

4-{(S)-2-[(6-benzylamino-2-phenyl-pyrimidine-4-carbonyl)-amino]-4-carboxy-butyryl}-piperazine-1-carboxylic acid ethyl ester;

4-((S)-4-carboxy-2-{[2-phenyl-6-((S)-1-phenyl-ethylamino)-pyrimidine-4-carbonyl]-amino}-butyryl)-piperazine-1-carboxylic acid ethyl ester;

4-((S)-4-carboxy-2-{[2-phenyl-6-((R)-1-phenyl-ethylamino)-pyrimidine-4-carbonyl]-amino}-butyryl)-piperazine-1-carboxylic acid ethyl ester;

4-((S)-4-carboxy-2-{[6-((S)-2-carboxy-1-phenyl-ethylamino)-2-phenyl-pyrimidine-4-carbonyl]-amino}-butyryl)-piperazine-1-carboxylic acid ethyl ester;

4-((S)-4-carboxy-2-{[6-((R)-2-carboxy-1-phenyl-ethylamino)-2-phenyl-pyrimidine-4-carbonyl]-amino}-butyryl)-piperazine-1-carboxylic acid ethyl ester;

4-{(S)-4-carboxy-2-[(6-phenethylamino-2-phenyl-pyrimidine-4-carbonyl)-amino]-butyryl}-piperazine-1-carboxylic acid ethyl ester;

4-((S)-4-carboxy-2-{[2-phenyl-6-(2-phenyl-propylamino)-pyrimidine-4-carbonyl]-amino}-butyryl)-piperazine-1-carboxylic acid ethyl ester;

4-((S)-4-carboxy-2-{[6-(1,2-diphenyl-ethylamino)-2-phenyl-pyrimidine-4-carbonyl]-amino}-butyryl)-piperazine-1-carboxylic acid ethyl ester;

4-(4-carboxy-2-{[2-phenyl-6-(trans-2-phenyl-cyclopropylamino)-pyrimidine-4-carbonyl]-amino}-butyryl)-piperazine-1-carboxylic acid ethyl ester;

4-((S)-4-carboxy-2-{[6-(indan-1-ylamino)-2-phenyl-pyrimidine-4-carbonyl]-amino}-butyryl)-piperazine-1-carboxylic acid ethyl ester;

4-((S)-4-carboxy-2-{[6-((R)-indan-1-ylamino)-2-phenyl-pyrimidine-4-carbonyl]-amino}-butyryl)-piperazine-1-carboxylic acid ethyl ester;

4-((S)-4-carboxy-2-{[6-(indan-2-ylamino)-2-phenyl-pyrimidine-4-carbonyl]-amino}-butyryl)-piperazine-1-carboxylic acid ethyl ester;

4-{(S)-4-carboxy-2-[(6-dimethylamino-2-phenyl-pyrimidine-4-carbonyl)-amino]-butyryl}-piperazine-1-carboxylic acid ethyl ester;

4-{(S)-2-[(6-azetidin-1-yl-2-phenyl-pyrimidine-4-carbonyl)-amino]-4-carboxy-butyryl}-piperazine-1-carboxylic acid ethyl ester;

4-{(S)-4-carboxy-2-[(2-phenyl-6-pyrrolidin-1-yl-pyrimidine-4-carbonyl)-amino]-butyryl}-piperazine-1-carboxylic acid ethyl ester;

4-{(S)-4-carboxy-2-[(2-phenyl-6-piperidin-1-yl-pyrimidine-4-carbonyl)-amino]-butyryl}-piperazine-1-carboxylic acid ethyl ester;

4-((S)-2-{[6-(butyl-methyl-amino)-2-phenyl-pyrimidine-4-carbonyl]-amino}-4-carboxy-butyryl)-piperazine-1-carboxylic acid ethyl ester;

4-{(S)-4-carboxy-2-[(2-phenyl-6-phenylamino-pyrimidine-4-carbonyl)-amino]-butyryl}-piperazine-1-carboxylic acid ethyl ester;
4-((S)-4-carboxy-2-{[6-(4-fluoro-phenylamino)-2-phenyl-pyrimidine-4-carbonyl]-amino}-butyryl)-piperazine-1-carboxylic acid ethyl ester;
4-{(S)-4-carboxy-2-[(6-methyl-2-phenyl-pyrimidine-4-carbonyl)-amino]-butyryl}-piperazine-1-carboxylic acid ethyl ester;
4-{(S)-4-carboxy-2-[(6-isopropyl-2-phenyl-pyrimidine-4-carbonyl)-amino]-butyryl}-piperazine-1-carboxylic acid ethyl ester;
4-{(S)-2-[(6-butyl-2-phenyl-pyrimidine-4-carbonyl)-amino]-4-carboxy-butyryl}-piperazine-1-carboxylic acid ethyl ester;
4-{(S)-4-carboxy-2-[(6-isobutyl-2-phenyl-pyrimidine-4-carbonyl)-amino]-butyryl}-piperazine-1-carboxylic acid ethyl ester;
4-{(S)-4-carboxy-2-[(6-cyclopropyl-2-phenyl-pyrimidine-4-carbonyl)-amino]-butyryl}-piperazine-1-carboxylic acid ethyl ester;
4-{(S)-4-carboxy-2-[(6-cyclopentyl-2-phenyl-pyrimidine-4-carbonyl)-amino]-butyryl}-piperazine-1-carboxylic acid ethyl ester;
4-{(S)-4-carboxy-2-[(2,6-diphenyl-pyrimidine-4-carbonyl)-amino]-butyryl}-piperazine-1-carboxylic acid ethyl ester;
4-{(S)-4-carboxy-2-[(2-phenyl-6-o-tolyl-pyrimidine-4-carbonyl)-amino]-butyryl}-piperazine-1-carboxylic acid ethyl ester;
4-{(S)-4-carboxy-2-[(2-phenyl-6-m-tolyl-pyrimidine-4-carbonyl)-amino]-butyryl}-piperazine-1-carboxylic acid ethyl ester;
4-{(S)-4-carboxy-2-[(2-phenyl-6-p-tolyl-pyrimidine-4-carbonyl)-amino]-butyryl}-piperazine-1-carboxylic acid ethyl ester;
4-((S)-4-carboxy-2-{[6-(3-carboxy-phenyl)-2-phenyl-pyrimidine-4-carbonyl]-amino}-butyryl)-piperazine-1-carboxylic acid ethyl ester;
4-((S)-4-carboxy-2-{[6-(4-carboxy-phenyl)-2-phenyl-pyrimidine-4-carbonyl]-amino}-butyryl)-piperazine-1-carboxylic acid ethyl ester;
4-((S)-4-carboxy-2-{[2-(4-fluoro-phenyl)-6-methyl-pyrimidine-4-carbonyl]-amino}-butyryl)-piperazine-1-carboxylic acid ethyl ester;
4-((S)-4-carboxy-2-{[2-(3-fluoro-phenyl)-6-methyl-pyrimidine-4-carbonyl]-amino}-butyryl)-piperazine-1-carboxylic acid ethyl ester;
4-((S)-4-carboxy-2-{[2-(2-fluoro-phenyl)-6-methyl-pyrimidine-4-carbonyl]-amino}-butyryl)-piperazine-1-carboxylic acid ethyl ester;
4-((S)-4-carboxy-2-{[2-(4-chloro-phenyl)-6-methyl-pyrimidine-4-carbonyl]-amino}-butyryl)-piperazine-1-carboxylic acid ethyl ester;
4-((S)-4-carboxy-2-{[2-(3-chloro-phenyl)-6-methyl-pyrimidine-4-carbonyl]-amino}-butyryl)-piperazine-1-carboxylic acid ethyl ester;
4-((S)-4-carboxy-2-{[2-(2-chloro-phenyl)-6-methyl-pyrimidine-4-carbonyl]-amino}-butyryl)-piperazine-1-carboxylic acid ethyl ester;
4-{(S)-4-carboxy-2-[(6-methyl-2-p-tolyl-pyrimidine-4-carbonyl)-amino]-butyryl}-piperazine-1-carboxylic acid ethyl ester;
4-{(S)-4-carboxy-2-[(6-methyl-2-m-tolyl-pyrimidine-4-carbonyl)-amino]-butyryl}-piperazine-1-carboxylic acid ethyl ester;
4-((S)-4-carboxy-2-{[2-(4-methoxy-phenyl)-6-methyl-pyrimidine-4-carbonyl]-amino}-butyryl)-piperazine-1-carboxylic acid ethyl ester;
4-((S)-4-carboxy-2-{[2-(3-methoxy-phenyl)-6-methyl-pyrimidine-4-carbonyl]-amino}-butyryl)-piperazine-1-carboxylic acid ethyl ester;
4-{2-[(6-isopropylamino-2-phenyl-pyrimidine-4-carbonyl)-amino]-acetyl}-piperazine-1-carboxylic acid ethyl ester;
4-{2-[(6-benzylamino-2-phenyl-pyrimidine-4-carbonyl)-amino]-acetyl}-piperazine-1-carboxylic acid ethyl ester;
4-{2-[(2,6-diphenyl-pyrimidine-4-carbonyl)-amino]-acetyl}-piperazine-1-carboxylic acid ethyl ester;
4-{2-[(6-cyclopropyl-2-phenyl-pyrimidine-4-carbonyl)-amino]-acetyl}-piperazine-1-carboxylic acid ethyl ester;
4-{(S)-2-[(6-isopropylamino-2-phenyl-pyrimidine-4-carbonyl)-amino]-3-methyl-butyryl}-piperazine-1-carboxylic acid ethyl ester;
4-{(S)-2-[(6-benzylamino-2-phenyl-pyrimidine-4-carbonyl)-amino]-3-methyl-butyryl}-piperazine-1-carboxylic acid ethyl ester;
4-{(S)-2-[(2,6-diphenyl-pyrimidine-4-carbonyl)-amino]-3-methyl-butyryl}-piperazine-1-carboxylic acid ethyl ester;
4-{(S)-3-(4-carboxy-phenyl)-2-[(6-isopropylamino-2-phenyl-pyrimidine-4-carbonyl)-amino]-propionyl}-piperazine-1-carboxylic acid ethyl ester;
4-{(S)-2-[(6-benzylamino-2-phenyl-pyrimidine-4-carbonyl)-amino]-3-(4-carboxy-phenyl)-propionyl}-piperazine-1-carboxylic acid ethyl ester;
4-{(S)-3-(4-carboxy-phenyl)-2-[(2,6-diphenyl-pyrimidine-4-carbonyl)-amino]-propionyl}-piperazine-1-carboxylic acid ethyl ester;
4-{(S)-3-(4-carboxy-phenyl)-2-[(6-cyclopropyl-2-phenyl-pyrimidine-4-carbonyl)-amino]-propionyl}-piperazine-1-carboxylic acid ethyl ester;
4-{(S)-5-carboxy-2-[(6-isopropylamino-2-phenyl-pyrimidine-4-carbonyl)-amino]-pentanoyl}-piperazine-1-carboxylic acid ethyl ester;
4-{(S)-2-[(6-benzylamino-2-phenyl-pyrimidine-4-carbonyl)-amino]-5-carboxy-pentanoyl}-piperazine-1-carboxylic acid ethyl ester;
4-{(S)-5-carboxy-2-[(2,6-diphenyl-pyrimidine-4-carbonyl)-amino]-pentanoyl}-piperazine-1-carboxylic acid ethyl ester;
4-{(S)-5-carboxy-2-[(6-cyclopropyl-2-phenyl-pyrimidine-4-carbonyl)-amino]-pentanoyl}-piperazine-1-carboxylic acid ethyl ester;
4-{(S)-2-[(6-benzylamino-2-phenyl-pyrimidine-4-carbonyl)-amino]-3-carbamoyl-propionyl}-piperazine-1-carboxylic acid ethyl ester;
4-{(S)-2-[(6-benzylamino-2-phenyl-pyrimidine-4-carbonyl)-amino]-3-(2H-tetrazol-5-yl)-propionyl}-piperazine-1-carboxylic acid ethyl ester;
4-{(S)-3-(4-hydroxy-phenyl)-2-[(6-isopropylamino-2-phenyl-pyrimidine-4-carbonyl)-amino]-propionyl}-piperazine-1-carboxylic acid ethyl ester;
4-{(S)-4-tert-butoxycarbonyl-2-[(6-cyclopentyloxy-2-phenyl-pyrimidine-4-carbonyl)-amino]-butyryl}-piperazine-1-carboxylic acid ethyl ester;
4-{(S)-3-tert-butoxycarbonyl-2-[(6-cyclopentyloxy-2-phenyl-pyrimidine-4-carbonyl)-amino]-propionyl}-piperazine-1-carboxylic acid ethyl ester;

4-{(S)-5-tert-butoxycarbonyl-2-[(6-cyclopentyloxy-2-phenyl-pyrimidine-4-carbonyl)-amino]-pentanoyl}-piperazine-1-carboxylic acid ethyl ester;

4-{(S)-2-[(6-cyclopentyloxy-2-phenyl-pyrimidine-4-carbonyl)-amino]-4-ethoxycarbonylmethoxy-butyryl}-piperazine-1-carboxylic acid ethyl ester;

4-[(S)-2-[(6-cyclopentyloxy-2-phenyl-pyrimidine-4-carbonyl)-amino]-3-(4-methoxycarbonyl-phenyl)-propionyl]-piperazine-1-carboxylic acid ethyl ester;

4-[(S)-2-[(6-cyclopentyloxy-2-phenyl-pyrimidine-4-carbonyl)-amino]-3-(4-methoxycarbonylmethoxy-phenyl)-propionyl]-piperazine-1-carboxylic acid ethyl ester;

4-{(S)-4-tert-butoxycarbonyl-2-[(6-carboxymethoxy-2-phenyl-pyrimidine-4-carbonyl)-amino]-butyryl}-piperazine-1-carboxylic acid ethyl ester;

4-{(S)-4-tert-butoxycarbonyl-2-[(2-phenyl-6-propoxy-pyrimidine-4-carbonyl)-amino]-butyryl}-piperazine-1-carboxylic acid ethyl ester;

4-((S)-4-tert-butoxycarbonyl-2-{[6-(2-hydroxy-ethoxy)-2-phenyl-pyrimidine-4-carbonyl]-amino}-butyryl)-piperazine-1-carboxylic acid ethyl ester;

4-{(S)-2-[(6-benzyloxy-2-phenyl-pyrimidine-4-carbonyl)-amino]-4-tert-butoxycarbonyl-butyryl}-piperazine-1-carboxylic acid ethyl ester;

4-{(S)-4-tert-butoxycarbonyl-2-[(6-cyclopropylmethoxy-2-phenyl-pyrimidine-4-carbonyl)-amino]-butyryl}-piperazine-1-carboxylic acid ethyl ester;

4-{(S)-4-tert-butoxycarbonyl-2-[(6-cyclohexyloxy-2-phenyl-pyrimidine-4-carbonyl)-amino]-butyryl}-piperazine-1-carboxylic acid ethyl ester;

4-{(S)-4-tert-butoxycarbonyl-2-[(6-isopropoxy-2-phenyl-pyrimidine-4-carbonyl)-amino]-butyryl}-piperazine-1-carboxylic acid ethyl ester;

4-{(S)-4-tert-butoxycarbonyl-2-[(6-methoxy-2-phenyl-pyrimidine-4-carbonyl)-amino]-butyryl}-piperazine-1-carboxylic acid ethyl ester;

4-[2-[(6-cyclopentyloxy-2-phenyl-pyrimidine-4-carbonyl)-amino]-3-(3-ethoxy-carbonylmethoxy-phenyl)-propionyl]-piperazine-1-carboxylic acid ethyl ester;

4-[2-[(6-cyclopentyloxy-2-phenyl-pyrimidine-4-carbonyl)-amino]-3-(2-ethoxy-carbonylmethoxy-phenyl)-propionyl]-piperazine-1-carboxylic acid ethyl ester;

4-[(S)-2-[(6-cyclopentyloxy-2-phenyl-pyrimidine-4-carbonyl)-amino]-2-(4-ethoxycarbonylmethoxy-phenyl)-acetyl]-piperazine-1-carboxylic acid ethyl ester;

4-{(S)-4-tert-butoxycarbonyl-2-[(6-cyclopentyloxy-2-phenyl-pyrimidine-4-carbonyl)-amino]-butyryl}-piperazine-1-carboxylic acid prop-2-ynyl ester;

4-{(S)-4-tert-butoxycarbonyl-2-[(6-cyclopentyloxy-2-phenyl-pyrimidine-4-carbonyl)-amino]-butyryl}-piperazine-1-carboxylic acid butyl ester;

4-{(S)-4-tert-butoxycarbonyl-2-[(6-cyclopentyloxy-2-phenyl-pyrimidine-4-carbonyl)-amino]-butyryl}-piperazine-1-carboxylic acid isobutyl ester;

4-{(S)-4-tert-butoxycarbonyl-2-[(6-cyclopentyloxy-2-phenyl-pyrimidine-4-carbonyl)-amino]-butyryl}-piperazine-1-carboxylic acid 2,2-dimethyl-propyl ester;

4-{(S)-4-tert-butoxycarbonyl-2-[(6-cyclopentyloxy-2-phenyl-pyrimidine-4-carbonyl)-amino]-butyryl}-piperazine-1-carboxylic acid isopropyl ester;

4-[(S)-(6-cyclopentyloxy-2-phenyl-pyrimidine-4-carbonyl)-amino]-5-[4-(furan-2-carbonyl)-piperazin-1-yl]-5-oxo-pentanoic acid tert-butyl ester;

4-{(S)-4-tert-butoxycarbonyl-2-[(6-cyclopentyloxy-2-phenyl-pyrimidine-4-carbonyl)-amino]-butyryl}-piperazine-1-carboxylic acid phenyl ester;

5-((S)-4-benzoyl-piperazin-1-yl)-4-[(6-cyclopentyloxy-2-phenyl-pyrimidine-4-carbonyl)-amino]-5-oxo-pentanoic acid tert-butyl ester;

4-{(S)-4-tert-butoxycarbonyl-2-[(6-cyclopentyloxy-2-phenyl-pyrimidine-4-carbonyl)-amino]-butyryl}-piperazine-1-carboxylic acid benzyl ester;

5-((S)-4-butyryl-piperazin-1-yl)-4-[(6-cyclopentyloxy-2-phenyl-pyrimidine-4-carbonyl)-amino]-5-oxo-pentanoic acid tert-butyl ester;

(S)-4-[(6-cyclopentyloxy-2-phenyl-pyrimidine-4-carbonyl)-amino]-5-oxo-5-[4-(propane-1-sulfonyl)-piperazin-1-yl]-pentanoic acid tert-butyl ester;

4-{(S)-4-tert-butoxycarbonyl-2-[(6-cyclopentyloxy-2-phenyl-pyrimidine-4-carbonyl)-amino]-butyryl}-3-methyl-piperazine-1-carboxylic acid ethyl ester;

4-{(S)-4-tert-butoxycarbonyl-2-[(6-cyclopentyloxy-2-phenyl-pyrimidine-4-carbonyl)-amino]-butyryl}-2-methyl-piperazine-1-carboxylic acid ethyl ester;

4-{(S)-4-tert-butoxycarbonyl-2-[(6-cyclopentyloxy-2-phenyl-pyrimidine-4-carbonyl)-amino]-butyryl}-trans-2,5-dimethyl-piperazine-1-carboxylic acid ethyl ester;

4-{(S)-4-tert-butoxycarbonyl-2-[(6-methylamino-2-phenyl-pyrimidine-4-carbonyl)-amino]-butyryl}-piperazine-1-carboxylic acid ethyl ester;

4-{(S)-4-tert-butoxycarbonyl-2-[(2-phenyl-6-propylamino-pyrimidine-4-carbonyl)-amino]-butyryl}-piperazine-1-carboxylic acid ethyl ester;

4-{(S)-4-tert-butoxycarbonyl-2-[(6-isopropylamino-2-phenyl-pyrimidine-4-carbonyl)-amino]-butyryl}-piperazine-1-carboxylic acid ethyl ester;

4-{(S)-4-tert-butoxycarbonyl-2-[(6-butylamino-2-phenyl-pyrimidine-4-carbonyl)-amino]-butyryl}-piperazine-1-carboxylic acid ethyl ester;

4-{(S)-4-tert-butoxycarbonyl-2-[(6-isobutylamino-2-phenyl-pyrimidine-4-carbonyl)-amino]-butyryl}-piperazine-1-carboxylic acid ethyl ester;

4-{(S)-4-tert-butoxycarbonyl-2-[(6-cyclopropylamino-2-phenyl-pyrimidine-4-carbonyl)-amino]-butyryl}-piperazine-1-carboxylic acid ethyl ester;

4-{(S)-4-tert-butoxycarbonyl-2-[(6-cyclopentylamino-2-phenyl-pyrimidine-4-carbonyl)-amino]-butyryl}-piperazine-1-carboxylic acid ethyl ester;

4-{(S)-4-tert-butoxycarbonyl-2-[(6-cyclohexylamino-2-phenyl-pyrimidine-4-carbonyl)-amino]-butyryl}-piperazine-1-carboxylic acid ethyl ester;

4-((S)-4-tert-butoxycarbonyl-2-{[6-(ethoxycarbonylmethyl-amino)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(2-ethoxycarbonyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-propylamino)-2-phenyl-pyrimidine-4-carbonyl]-amino}-butyryl)-piperazine-1-carboxylic acid ethyl ester;

4-((S)-4-tert-butoxycarbonyl-2-{[6-(3-tert-butoxycarbonyl-propylamino)-2-phenyl-pyrimidine-4-carbonyl]-amino}-butyryl)-piperazine-1-carboxylic acid ethyl ester;

4-((S)-4-tert-butoxycarbonyl-2-{[6-(2-dimethylamino-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(3-dimethylamino-propylamino)-2-phenyl-pyrimidine-4-carbonyl]-amino}-butyryl)-piperazine-1-carboxylic acid ethyl ester;

4-((S)-4-tert-butoxycarbonyl-2-{[6-(2-morpholin-4-yl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(3-morpholin-4-yl-propylamino)-2-phenyl-pyrimidine-4-carbonyl]-amino}-butyryl)-piperazine-1-carboxylic acid ethyl ester;

4-{(S)-2-[(6-benzylamino-2-phenyl-pyrimidine-4-carbonyl)-amino]-4-tert-butoxycarbonyl-butyryl}-piperazine-1-carboxylic acid ethyl ester;

4-((S)-4-tert-butoxycarbonyl-2-{[2-phenyl-6-((S)-1-phenyl-ethylamino)-pyrimidine-4-carbonyl]-amino}-butyryl)-piperazine-1-carboxylic acid ethyl ester;

4-((S)-4-tert-butoxycarbonyl-2-{[2-phenyl-6-((R)-1-phenyl-ethylamino)-pyrimidine-4-carbonyl]-amino}-butyryl)-piperazine-1-carboxylic acid ethyl ester;

4-((S)-4-tert-butoxycarbonyl-2-{[6-((S)-2-tert-butoxycarbonyl-1-phenyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-((R)-2-tert-butoxycarbonyl-1-phenyl-ethylamino)-2-phenyl-pyrimidine-4-carbonyl]-amino}-butyryl)-piperazine-1-carboxylic acid ethyl ester;

4-{(S)-4-tert-butoxycarbonyl-2-[(6-phenethylamino-2-phenyl-pyrimidine-4-carbonyl)-amino]-butyryl}-piperazine-1-carboxylic acid ethyl ester;

4-((S)-4-tert-butoxycarbonyl-2-{[2-phenyl-6-(2-phenyl-propylamino)-pyrimidine-4-carbonyl]-amino}-butyryl)-piperazine-1-carboxylic acid ethyl ester;

4-((S)-4-tert-butoxycarbonyl-2-{[6-(1,2-diphenyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[2-phenyl-6-(trans-2-phenyl-cyclopropylamino)-pyrimidine-4-carbonyl]-amino}-butyryl)-piperazine-1-carboxylic acid ethyl ester;

4-((S)-4-tert-butoxycarbonyl-2-{[6-(indan-1-ylamino)-2-phenyl-pyrimidine-4-carbonyl]-amino}-butyryl)-piperazine-1-carboxylic acid ethyl ester;

4-((S)-4-tert-butoxycarbonyl-2-{[6-((R)-indan-1-ylamino)-2-phenyl-pyrimidine-4-carbonyl]-amino}-butyryl)-piperazine-1-carboxylic acid ethyl ester;

4-((S)-4-tert-butoxycarbonyl-2-{[6-(indan-2-ylamino)-2-phenyl-pyrimidine-4-carbonyl]-amino}-butyryl)-piperazine-1-carboxylic acid ethyl ester;

4-{(S)-4-tert-butoxycarbonyl-2-[(6-dimethylamino-2-phenyl-pyrimidine-4-carbonyl)-amino]-butyryl}-piperazine-1-carboxylic acid ethyl ester;

4-{(S)-2-[(6-azetidin-1-yl-2-phenyl-pyrimidine-4-carbonyl)-amino]-4-tert-butoxycarbonyl-butyryl}-piperazine-1-carboxylic acid ethyl ester;

4-{(S)-4-tert-butoxycarbonyl-2-[(2-phenyl-6-pyrrolidin-1-yl-pyrimidine-4-carbonyl)-amino]-butyryl}-piperazine-1-carboxylic acid ethyl ester;

4-{(S)-4-tert-butoxycarbonyl-2-[(2-phenyl-6-piperidin-1-yl-pyrimidine-4-carbonyl)-amino]-butyryl}-piperazine-1-carboxylic acid ethyl ester;

4-((S)-4-tert-butoxycarbonyl-2-{[6-(butyl-methyl-amino)-2-phenyl-pyrimidine-4-carbonyl]-amino}-butyryl)-piperazine-1-carboxylic acid ethyl ester;

4-{(S)-4-tert-butoxycarbonyl-2-[(2-phenyl-6-phenylamino-pyrimidine-4-carbonyl)-amino]-butyryl}-piperazine-1-carboxylic acid ethyl ester;

4-((S)-4-tert-butoxycarbonyl-2-{[6-(4-fluoro-phenylamino)-2-phenyl-pyrimidine-4-carbonyl]-amino}-butyryl)-piperazine-1-carboxylic acid ethyl ester;

4-{(S)-4-tert-butoxycarbonyl-2-[(6-methyl-2-phenyl-pyrimidine-4-carbonyl)-amino]-butyryl}-piperazine-1-carboxylic acid ethyl ester;

4-{(S)-4-tert-butoxycarbonyl-2-[(6-isopropyl-2-phenyl-pyrimidine-4-carbonyl)-amino]-butyryl}-piperazine-1-carboxylic acid ethyl ester;

4-{4-tert-butoxycarbonyl-2-[(6-butyl-2-phenyl-pyrimidine-4-carbonyl)-amino]-butyryl}-piperazine-1-carboxylic acid ethyl ester;

4-{(S)-4-tert-butoxycarbonyl-2-[(6-isobutyl-2-phenyl-pyrimidine-4-carbonyl)-amino]-butyryl}-piperazine-1-carboxylic acid ethyl ester;

4-{(S)-4-tert-butoxycarbonyl-2-[(6-cyclopropyl-2-phenyl-pyrimidine-4-carbonyl)-amino]-butyryl}-piperazine-1-carboxylic acid ethyl ester;

4-{(S)-4-tert-butoxycarbonyl-2-[(6-cyclopentyl-2-phenyl-pyrimidine-4-carbonyl)-amino]-butyryl}-piperazine-1-carboxylic acid ethyl ester;

4-{(S)-4-tert-butoxycarbonyl-2-[(2,6-diphenyl-pyrimidine-4-carbonyl)-amino]-butyryl}-piperazine-1-carboxylic acid ethyl ester;

4-{(S)-4-tert-butoxycarbonyl-2-[(2-phenyl-6-o-tolyl-pyrimidine-4-carbonyl)-amino]-butyryl}-piperazine-1-carboxylic acid ethyl ester;

4-{(S)-4-tert-butoxycarbonyl-2-[(2-phenyl-6-m-tolyl-pyrimidine-4-carbonyl)-amino]-butyryl}-piperazine-1-carboxylic acid ethyl ester;

4-{(S)-4-tert-butoxycarbonyl-2-[(2-phenyl-6-p-tolyl-pyrimidine-4-carbonyl)-amino]-butyryl}-piperazine-1-carboxylic acid ethyl ester;

4-((S)-4-tert-butoxycarbonyl-2-{[6-(3-carboxy-phenyl)-2-phenyl-pyrimidine-4-carbonyl]-amino}-butyryl)-piperazine-1-carboxylic acid ethyl ester;

4-((S)-4-tert-butoxycarbonyl-2-{[6-(4-carboxy-phenyl)-2-phenyl-pyrimidine-4-carbonyl]-amino}-butyryl)-piperazine-1-carboxylic acid ethyl ester;

4-((S)-4-tert-butoxycarbonyl-2-{[2-(4-fluoro-phenyl)-6-methyl-pyrimidine-4-carbonyl]-amino}-butyryl)-piperazine-1-carboxylic acid ethyl ester;

4-((S)-4-tert-butoxycarbonyl-2-{[2-(3-fluoro-phenyl)-6-methyl-pyrimidine-4-carbonyl]-amino}-butyryl)-piperazine-1-carboxylic acid ethyl ester;

4-((S)-4-tert-butoxycarbonyl-2-{[2-(2-fluoro-phenyl)-6-methyl-pyrimidine-4-carbonyl]-amino}-butyryl)-piperazine-1-carboxylic acid ethyl ester;

4-((S)-4-tert-butoxycarbonyl-2-{[2-(4-chloro-phenyl)-6-methyl-pyrimidine-4-carbonyl]-amino}-butyryl)-piperazine-1-carboxylic acid ethyl ester;

4-((S)-4-tert-butoxycarbonyl-2-{[2-(3-chloro-phenyl)-6-methyl-pyrimidine-4-carbonyl]-amino}-butyryl)-piperazine-1-carboxylic acid ethyl ester;

4-((S)-4-tert-butoxycarbonyl-2-{[2-(2-chloro-phenyl)-6-methyl-pyrimidine-4-carbonyl]-amino}-butyryl)-piperazine-1-carboxylic acid ethyl ester;

4-{(S)-4-tert-butoxycarbonyl-2-[(6-methyl-2-p-tolyl-pyrimidine-4-carbonyl)-amino]-butyryl}-piperazine-1-carboxylic acid ethyl ester;

4-{(S)-4-tert-butoxycarbonyl-2-[(6-methyl-2-m-tolyl-pyrimidine-4-carbonyl)-amino]-butyryl}-piperazine-1-carboxylic acid ethyl ester;

4-((S)-4-tert-butoxycarbonyl-2-{[2-(4-methoxy-phenyl)-6-methyl-pyrimidine-4-carbonyl]-amino}-butyryl)-piperazine-1-carboxylic acid ethyl ester;

4-((S)-4-tert-butoxycarbonyl-2-{[2-(3-methoxy-phenyl)-6-methyl-pyrimidine-4-carbonyl]-amino}-butyryl)-piperazine-1-carboxylic acid ethyl ester;

4-[(S)-2-[(6-isopropylamino-2-phenyl-pyrimidine-4-carbonyl)-amino]-3-(4-methoxycarbonyl-phenyl)-propionyl]-piperazine-1-carboxylic acid ethyl ester;

4-[(S)-2-[(6-benzylamino-2-phenyl-pyrimidine-4-carbonyl)-amino]-3-(4-methoxycarbonyl-phenyl)-propionyl]-piperazine-1-carboxylic acid ethyl ester;

4-(S)-[2-[(2,6-diphenyl-pyrimidine-4-carbonyl)-amino]-3-(4-methoxycarbonyl-phenyl)-propionyl]-piperazine-1-carboxylic acid ethyl ester;

4-[(S)-2-[(6-cyclopropyl-2-phenyl-pyrimidine-4-carbonyl)-amino]-3-(4-methoxycarbonyl-phenyl)-propionyl]-piperazine-1-carboxylic acid ethyl ester;

4-{(S)-5-tert-butoxycarbonyl-2-[(6-isopropylamino-2-phenyl-pyrimidine-4-carbonyl)-amino]-pentanoyl}-piperazine-1-carboxylic acid ethyl ester;

4-{(S)-2-[(6-benzylamino-2-phenyl-pyrimidine-4-carbonyl)-amino]-5-tert-butoxycarbonyl-pentanoyl}-piperazine-1-carboxylic acid ethyl ester;

4-{(S)-5-tert-butoxycarbonyl-2-[(2,6-diphenyl-pyrimidine-4-carbonyl)-amino]-pentanoyl}-piperazine-1-carboxylic acid ethyl ester;

4-{(S)-5-tert-butoxycarbonyl-2-[(6-cyclopropyl-2-phenyl-pyrimidine-4-carbonyl)-amino]-pentanoyl}-piperazine-1-carboxylic acid ethyl ester;

4-((S)-4-carboxy-2-{[6-(2-methoxy-1-methyl-ethylamino)-2-phenyl-pyrimidine-4-carbonyl]-amino}-butyryl)-piperazine-1-carboxylic acid ethyl ester;

4-((S)-4-carboxy-2-{[6-(isopropyl-methyl-amino)-2-phenyl-pyrimidine-4-carbonyl]-amino}-butyryl)-piperazine-1-carboxylic acid ethyl ester;

4-{(S)-4-carboxy-2-[(6-morpholin-4-yl-2-phenyl-pyrimidine-4-carbonyl)-amino]-butyryl}-piperazine-1-carboxylic acid ethyl ester;

4-{(S)-4-carboxy-2-[(2-phenyl-6-thiazolidin-3-yl-pyrimidine-4-carbonyl)-amino]-butyryl}-piperazine-1-carboxylic acid ethyl ester;

4-((S)-4-carboxy-2-{[6-(4-hydroxy-piperidin-1-yl)-2-phenyl-pyrimidine-4-carbonyl]-amino}-butyryl)-piperazine-1-carboxylic acid ethyl ester;

4-((S)-4-carboxy-2-{[6-(piperazin-1-yl)-2-phenyl-pyrimidine-4-carbonyl]-amino}-butyryl-piperazine-1-carboxylic acid ethyl ester;

4-((S)-4-carboxy-2-{[6-(2-hydroxy-1-methyl-ethylamino)-2-phenyl-pyrimidine-4-carbonyl]-amino}-butyryl)-piperazine-1-carboxylic acid ethyl ester;

4-((S)-4-carboxy-2-{[6-(4-hydroxy-butylamino)-2-phenyl-pyrimidine-4-carbonyl]-amino}-butyryl)-piperazine-1-carboxylic acid ethyl ester;

4-((S)-4-carboxy-2-{[6-(2-hydroxy-propylamino)-2-phenyl-pyrimidine-4-carbonyl]-amino}-butyryl)-piperazine-1-carboxylic acid ethyl ester;

4-[(S)-4-carboxy-2-({2-phenyl-6-[(tetrahydro-furan-2-yl-methyl)-amino]-pyrimidine-4-carbonyl}-amino)-butyryl]-piperazine-1-carboxylic acid ethyl ester;

4-((S)-4-carboxy-2-{[6-((R)-2-hydroxymethyl-pyrrolidin-1-yl)-2-phenyl-pyrimidine-4-carbonyl]-amino}-butyryl)-piperazine-1-carboxylic acid ethyl ester;

4-((S)-4-carboxy-2-{[6-((S)-2-hydroxymethyl-pyrrolidin-1-yl)-2-phenyl-pyrimidine-4-carbonyl]-amino}-butyryl)-piperazine-1-carboxylic acid ethyl ester;

4-((S)-4-carboxy-2-{[6-((S)-3-hydroxy-pyrrolidin-1-yl)-2-phenyl-pyrimidine-4-carbonyl]-amino}-butyryl)-piperazine-1-carboxylic acid ethyl ester;

4-((S)-4-carboxy-2-{[6-((R)-3-hydroxy-pyrrolidin-1-yl)-2-phenyl-pyrimidine-4-carbonyl]-amino}-butyryl)-piperazine-1-carboxylic acid ethyl ester;

4-[(S)-4-carboxy-2-({2-phenyl-6-[(R)-(tetrahydro-furan-3-yl)amino]-pyrimidine-4-carbonyl}-amino)-butyryl]-piperazine-1-carboxylic acid ethyl ester;

4-{(S)-4-carboxy-2-[(6-imidazol-1-yl-2-phenyl-pyrimidine-4-carbonyl)-amino]-butyryl}-piperazine-1-carboxylic acid ethyl ester;

4-{(S)-4-carboxy-2-[(2-phenyl-6-pyrazol-1-yl-pyrimidine-4-carbonyl)-amino]-butyryl}-piperazine-1-carboxylic acid ethyl ester;

4-((S)-4-carboxy-2-{[6-((S)-2-hydroxy-1-methyl-ethylamino)-2-phenyl-pyrimidine-4-carbonyl]-amino}-butyryl)-piperazine-1-carboxylic acid ethyl ester;

4-((S)-4-carboxy-2-{[6-((R)-2-hydroxy-1-methyl-ethylamino)-2-phenyl-pyrimidine-4-carbonyl]-amino}-butyryl)-piperazine-1-carboxylic acid ethyl ester;

4-((S)-4-carboxy-2-{[6-(2-hydroxy-1,1-dimethyl-ethylamino)-2-phenyl-pyrimidine-4-carbonyl]-amino}-butyryl)-piperazine-1-carboxylic acid ethyl ester;

4-((S)-4-carboxy-2-{[6-(trans-4-hydroxy-cyclohexylamino)-2-phenyl-pyrimidine-4-carbonyl]-amino}-butyryl)-piperazine-1-carboxylic acid ethyl ester;

4-((S)-4-carboxy-2-{[6-(3-hydroxy-piperidin-1-yl)-2-phenyl-pyrimidine-4-carbonyl]-amino}-butyryl)-piperazine-1-carboxylic acid ethyl ester;

4-((S)-4-carboxy-2-{[6-(2-hydroxymethyl-piperidin-1-yl)-2-phenyl-pyrimidine-4-carbonyl]-amino}-butyryl)-piperazine-1-carboxylic acid ethyl ester;

4-((S)-4-carboxy-2-{[6-(trans-2-hydroxy-cyclohexylamino)-2-phenyl-pyrimidine-4 carbonyl]-amino}-butyryl)-piperazine-1-carboxylic acid ethyl ester;

4-{(S)-4-carboxy-2-[(2-phenyl-6-propylsulfanyl-pyrimidine-4-carbonyl)-amino]-butyryl}-piperazine-1-carboxylic acid ethyl ester;

4-{(S)-4-carboxy-2-[(6-isopropylsulfanyl-2-phenyl-pyrimidine-4-carbonyl)-amino]-butyryl}-piperazine-1-carboxylic acid ethyl ester;

4-{(S)-4-carboxy-2-[(6-cyclopentylsulfanyl-2-phenyl-pyrimidine-4-carbonyl)-amino]-butyryl}-piperazine-1-carboxylic acid ethyl ester;

4-{(S)-4-carboxy-2-[(6-isopropylsulfanyl-2-phenyl-pyrimidine-4-carbonyl)-amino]-butyryl}-piperazine-1-carboxylic acid ethyl ester;

4-{(S)-4-carboxy-2-[(6-cyclohexylsulfanyl-2-phenyl-pyrimidine-4-carbonyl)-amino]-butyryl}-piperazine-1-carboxylic acid ethyl ester;

4-{(S)-4-carboxy-2-[(6-ethoxycarbonylmethylsulfanyl-2-phenyl-pyrimidine-4-carbonyl)-amino]-butyryl}-piperazine-1-carboxylic acid ethyl ester;

4-((S)-4-carboxy-2-{[6-(2-ethoxycarbonyl-ethylsulfanyl)-2-phenyl-pyrimidine-4-carbonyl]-amino}-butyryl)-piperazine-1-carboxylic acid ethyl ester;

4-{(S)-4-carboxy-2-[(6-carboxymethylsulfanyl-2-phenyl-pyrimidine-4-carbonyl)-amino]-butyryl}-piperazine-1-carboxylic acid ethyl ester;

4-((S)-4-carboxy-2-{[6-(2-carboxy-ethylsulfanyl)-2-phenyl-pyrimidine-4-carbonyl]-amino}-butyryl)-piperazine-1-carboxylic acid ethyl ester;

4-{(S)-4-carboxy-2-[(2-phenyl-6-phenylsulfanyl-pyrimidine-4-carbonyl)-amino]-butyryl}-piperazine-1-carboxylic acid ethyl ester;

4-[(S)-2-[(6-benzylsulfanyl-2-phenyl-pyrimidine-4-carbonyl)-amino]-4-carboxy-butyryl]-piperazine-1-carboxylic acid ethyl ester;

4-{(S)-4-carboxy-2-[(6-ethynyl-2-phenyl-pyrimidine-4-carbonyl)-amino]-butyryl}-piperazine-1-carboxylic acid ethyl ester;

4-((S)-4-carboxy-2-{[6-(3-hydroxy-prop-1-ynyl)-2-phenyl-pyrimidine-4-carbonyl]-amino}-butyryl)-piperazine-1-carboxylic acid ethyl ester;

4-((S)-4-carboxy-2-{[6-(3-hydroxy-but-1-ynyl)-2-phenyl-pyrimidine-4-carbonyl]-amino}-butyryl)-piperazine-1-carboxylic acid ethyl ester;

4-((S)-4-carboxy-2-{[6-(3-hydroxy-pent-1-ynyl)-2-phenyl-pyrimidine-4-carbonyl]-amino}-butyryl)-piperazine-1-carboxylic acid ethyl ester;

4-((S)-4-carboxy-2-{[6-(3-hydroxy-3-methyl-but-1-ynyl)-2-phenyl-pyrimidine-4-carbonyl]-amino}-butyryl)-piperazine-1-carboxylic acid ethyl ester;

4-((S)-4-carboxy-2-{[6-(3-hydroxy-propyl)-2-phenyl-pyrimidine-4-carbonyl]-amino}-butyryl)-piperazine-1-carboxylic acid ethyl ester;

4-((S)-4-carboxy-2-{[6-(3-hydroxy-butyl)-2-phenyl-pyrimidine-4-carbonyl]-amino}-butyryl)-piperazine-1-carboxylic acid ethyl ester;

4-((S)-4-carboxy-2-{[6-(3-hydroxy-pentyl)-2-phenyl-pyrimidine-4-carbonyl]-amino}-butyryl)-piperazine-1-carboxylic acid ethyl ester;

4-((S)-4-carboxy-2-{[6-(3-hydroxy-3-methyl-butyl)-2-phenyl-pyrimidine-4-carbonyl]-amino}-butyryl)-piperazine-1-carboxylic acid ethyl ester;

4-((S)-4-carboxy-2-{[6-((E)-3-hydroxy-but-1-enyl)-2-phenyl-pyrimidine-4-carbonyl]-amino}-butyryl)-piperazine-1-carboxylic acid ethyl ester;

4-((S)-4-tert-butoxycarbonyl-2-{[6-(2-methoxy-1-methyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(isopropyl-methyl-amino)-2-phenyl-pyrimidine-4-carbonyl]-amino}-butyryl)-piperazine-1-carboxylic acid ethyl ester;

4-{(S)-4-tert-butoxycarbonyl-2-[(6-morpholin-4-yl-2-phenyl-pyrimidine-4-carbonyl)-amino]-butyryl}-piperazine-1-carboxylic acid ethyl ester;

4-{(S)-4-tert-butoxycarbonyl-2-[(2-phenyl-6-thiazolidin-3-yl-pyrimidine-4-carbonyl)-amino]-butyryl}-piperazine-1-carboxylic acid ethyl ester;

4-((S)-4-tert-butoxycarbonyl-2-{[6-(4-hydroxy-piperidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-(piperazin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-1-methyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(4-hydroxy-butylamino)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-propylamino)-2-phenyl-pyrimidine-4-carbonyl]-amino}-butyryl)-piperazine-1-carboxylic acid ethyl ester;

4-[(S)-4-tert-butoxycarbonyl-2-({2-phenyl-6-[(tetrahydro-furan-2-ylmethyl)-amino]-pyrimidine-4-carbonyl}-amino)-butyryl]-piperazine-1-carboxylic acid ethyl ester;

4-((S)-4-tert-butoxycarbonyl-2-{[6-((R)-2-hydroxymethyl-pyrrolidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-((S)-2-hydroxymethyl-pyrrolidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-((S)-3-hydroxy-pyrrolidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-((R)-3-hydroxy-pyrrolidin-1-yl)-2-phenyl-pyrimidine-4-carbonyl]-amino}-butyryl)-piperazine-1-carboxylic acid ethyl ester;

4-[(S)-4-tert-butoxycarbonyl-2-({2-phenyl-6-[(R)-(tetrahydro-furan-3-yl)amino]-pyrimidine-4-carbonyl}-amino)-butyryl]-piperazine-1-carboxylic acid ethyl ester;

4-{(S)-4-tert-butoxycarbonyl-2-[(6-imidazol-1-yl-2-phenyl-pyrimidine-4-carbonyl)-amino]-butyryl}-piperazine-1-carboxylic acid ethyl ester;

4-{(S)-4-tert-butoxycarbonyl-2-[(2-phenyl-6-pyrazol-1-yl-pyrimidine-4-carbonyl)-amino]-butyryl}-piperazine-1-carboxylic acid ethyl ester;

4-((S)-4-tert-butoxycarbonyl-2-{[6-((S)-2-hydroxy-1-methyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-((R)-2-hydroxy-1-methyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxy-1,1-dimethyl-ethylamino)-2-phenyl-pyrimidine-4-carbonyl]-amino}-butyryl)-piperazine-1-carboxylic acid ethyl ester;

4-((S)-4-tert-butoxycarbonyl-2-{[6-(trans-4-hydroxy-cyclohexylamino)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-piperidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-(2-hydroxymethyl-piperidin-1-yl)-2-phenyl-pyrimidine-4-carbonyl]-amino}-butyryl)-piperazine-1-carboxylic acid ethyl ester;

4-((S)-4-tert-butoxycarbonyl-2-{[6-(trans-2-hydroxy-cyclohexylamino)-2-phenyl-pyrimidine-4-carbonyl]-amino}-butyryl)-piperazine-1-carboxylic acid ethyl ester;

4-{(S)-4-tert-butoxycarbonyl-2-[(2-phenyl-6-propylsulfanyl-pyrimidine-4-carbonyl)-amino]-butyryl}-piperazine-1-carboxylic acid ethyl ester;

4-{(S)-4-tert-butoxycarbonyl-2-[(6-isopropylsulfanyl-2-phenyl-pyrimidine-4-carbonyl)-amino]-butyryl}-piperazine-1-carboxylic acid ethyl ester;

4-{(S)-4-tert-butoxycarbonyl-2-[(6-cyclopentylsulfanyl-2-phenyl-pyrimidine-4-carbonyl)-amino]-butyryl}-piperazine-1-carboxylic acid ethyl ester;

4-{(S)-4-tert-butoxycarbonyl-2-[(6-isopropylsulfanyl-2-phenyl-pyrimidine-4-carbonyl)-amino]-butyryl}-piperazine-1-carboxylic acid ethyl ester;

4-{(S)-4-tert-butoxycarbonyl-2-[(6-cyclohexylsulfanyl-2-phenyl-pyrimidine-4-carbonyl)-amino]-butyryl}-piperazine-1-carboxylic acid ethyl ester;

4-{(S)-4-tert-butoxycarbonyl-2-[(6-ethoxycarbonylmethylsulfanyl-2-phenyl-pyrimidine-4-carbonyl)-amino]-butyryl}-piperazine-1-carboxylic acid ethyl ester;

4-((S)-4-tert-butoxycarbonyl-2-{[6-(2-ethoxycarbonyl-ethylsulfanyl)-2-phenyl-pyrimidine-4-carbonyl]-amino}-butyryl)-piperazine-1-carboxylic acid ethyl ester;

4-{(S)-4-tert-butoxycarbonyl-2-[(2-phenyl-6-phenylsulfanyl-pyrimidine-4-carbonyl)-amino]-butyryl}-piperazine-1-carboxylic acid ethyl ester;

4-{(S)-2-[(6-benzylsulfanyl-2-phenyl-pyrimidine-4-carbonyl)-amino]-4-tert-butoxycarbonyl-butyryl}-piperazine-1-carboxylic acid ethyl ester;

4-{(S)-4-tert-butoxycarbonyl-2-[(6-ethynyl-2-phenyl-pyrimidine-4-carbonyl)-amino]-butyryl}-piperazine-1-carboxylic acid ethyl ester;

4-((S)-4-tert-butoxycarbonyl-2-{[6-(3-hydroxy-prop-1-ynyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-but-1-ynyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-pent-1-ynyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-3-methyl-but-1-ynyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-propyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-butyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-pentyl)-2-phenyl-pyrimidine-4-carbonyl]-amino}-butyryl)-piperazine-1-carboxylic acid ethyl ester;

4-((S)-4-tert-butoxycarbonyl-2-{[6-(3-hydroxy-3-methyl-butyl)-2-phenyl-pyrimidine-4-carbonyl]-amino}-butyryl)-piperazine-1-carboxylic acid ethyl ester;

4-((S)-4-tert-butoxycarbonyl-2-{[6-((Z)-3-hydroxy-but-1-enyl)-2-phenyl-pyrimidine-4-carbonyl]-amino}-butyryl)-piperazine-1-carboxylic acid ethyl ester;

4-((S)-4-carboxy-2-{[6-(4-oxo-cyclohex-1-enyl)-2-phenyl-pyrimidine-4-carbonyl]-amino}-butyryl)-piperazine-1-carboxylic acid ethyl ester;

4-((S)-4-carboxy-2-{[6-(4-oxo-cyclohexyl)-2-phenyl-pyrimidine-4-carbonyl]-amino}-butyryl)-piperazine-1-carboxylic acid ethyl ester;

4-((S)-4-carboxy-2-{[6-(4-hydroxy-cyclohex-1-enyl)-2-phenyl-pyrimidine-4-carbonyl]-amino}-butyryl)-piperazine-1-carboxylic acid ethyl ester;

4-((S)-4-carboxy-2-{[6-(4-hydroxy-cyclohexyl)-2-phenyl-pyrimidine-4-carbonyl]-amino}-butyryl)-piperazine-1-carboxylic acid ethyl ester;

4-((S)-4-tert-butoxycarbonyl-2-{[6-(4-oxo-cyclohex-1-enyl)-2-phenyl-pyrimidine-4-carbonyl]-amino}-butyryl)-piperazine-1-carboxylic acid ethyl ester;

4-((S)-4-tert-butoxycarbonyl-2-{[6-(4-oxo-cyclohexyl)-2-phenyl-pyrimidine-4-carbonyl]-amino}-butyryl)-piperazine-1-carboxylic acid ethyl ester;

4-((S)-4-carboxy-2-{[6-((S)-3-methoxy-pyrrolidin-1-yl)-2-phenyl-pyrimidine-4-carbonyl]-amino}-butyryl)-piperazine-1-carboxylic acid ethyl ester;

4-((S)-4-carboxy-2-{[6-((S)-2-methoxy-1-methyl-ethylamino)-2-phenyl-pyrimidine-4-carbonyl]-amino}-butyryl)-piperazine-1-carboxylic acid ethyl ester;

4-((S)-4-carboxy-2-{[6-(4-methoxy-piperidin-1-yl)-2-phenyl-pyrimidine-4-carbonyl]-amino}-butyryl)-piperazine-1-carboxylic acid ethyl ester;

4-((S)-4-carboxy-2-{[6-((R)-3-methoxy-pyrrolidin-1-yl)-2-phenyl-pyrimidine-4-carbonyl]-amino}-butyryl)-piperazine-1-carboxylic acid ethyl ester;

4-((S)-4-carboxy-2-{[6-((R)-2-methoxy-1-methyl-ethylamino)-2-phenyl-pyrimidine-4-carbonyl]-amino}-butyryl)-piperazine-1-carboxylic acid ethyl ester;

4-((S)-4-carboxy-2-{[6-(2-methoxymethyl-piperidin-1-yl)-2-phenyl-pyrimidine-4-carbonyl]-amino}-butyryl)-piperazine-1-carboxylic acid ethyl ester;

4-((S)-4-carboxy-2-{[6-((S)-2-methoxymethyl-pyrrolidin-1-yl)-2-phenyl-pyrimidine-4-carbonyl]-amino}-butyryl)-piperazine-1-carboxylic acid ethyl ester;

4-((S)-4-carboxy-2-{[6-((R)-2-methoxymethyl-pyrrolidin-1-yl)-2-phenyl-pyrimidine-4-carbonyl]-amino}-butyryl)-piperazine-1-carboxylic acid ethyl ester;

4-((S)-4-carboxy-2-{[6-(2-methoxy-1,1-dimethyl-ethylamino)-2-phenyl-pyrimidine-4-carbonyl]-amino}-butyryl)-piperazine-1-carboxylic acid ethyl ester;

4-((S)-4-carboxy-2-{[6-(4,5-dihydro-pyrazol-1-yl)-2-phenyl-pyrimidine-4-carbonyl]-amino}-butyryl)-piperazine-1-carboxylic acid ethyl ester;

4-((S)-4-carboxy-2-{[6-(2-methyl-4,5-dihydro-imidazol-1-yl)-2-phenyl-pyrimidine-4-carbonyl]-amino}-butyryl)-piperazine-1-carboxylic acid ethyl ester;

4-{(S)-4-carboxy-2-[(2-phenyl-6-[1,2,4]triazol-1-yl-pyrimidine-4-carbonyl)-amino]-butyryl}-piperazine-1-carboxylic acid ethyl ester;

4-((S)-4-carboxy-2-{[6-(4-methyl-pyrazol-1-yl)-2-phenyl-pyrimidine-4-carbonyl]-amino}-butyryl)-piperazine-1-carboxylic acid ethyl ester;

4-((S)-4-carboxy-2-{[6-(3-methyl-pyrazol-1-yl)-2-phenyl-pyrimidine-4-carbonyl]-amino}-butyryl)-piperazine-1-carboxylic acid ethyl ester;

4-{(S)-4-carboxy-2-[(2-phenyl-6-[1,2,3]triazol-1-yl-pyrimidine-4-carbonyl)-amino]-butyryl}-piperazine-1-carboxylic acid ethyl ester;

4-((S)-2-{[6-(4-butyl-[1,2,3]triazol-1-yl)-2-phenyl-pyrimidine-4-carbonyl]-amino}-4-carboxy-butyryl)-piperazine-1-carboxylic acid ethyl ester;

4-{(S)-2-[(6-amino-2-phenyl-pyrimidine-4-carbonyl)-amino]-4-carboxy-butyryl}-piperazine-1-carboxylic acid ethyl ester;

4-((S)-4-carboxy-2-{[6-(cyclohexanecarbonyl-amino)-2-phenyl-pyrimidine-4-carbonyl]-amino}-butyryl)-piperazine-1-carboxylic acid ethyl ester;

4-[(S)-4-carboxy-2-({2-phenyl-6-[(thiophene-2-carbonyl)-amino]-pyrimidine-4-carbonyl}-amino)-butyryl]-piperazine-1-carboxylic acid ethyl ester;

4-[(S)-4-carboxy-2-({6-[(furan-2-carbonyl)-amino]-2-phenyl-pyrimidine-4-carbonyl}-amino)-butyryl]-piperazine-1-carboxylic acid ethyl ester;

4-{(S)-4-carboxy-2-[(2-phenyl-6-phenylacetylamino-pyrimidine-4-carbonyl)-amino]-butyryl}-piperazine-1-carboxylic acid ethyl ester;

4-((S)-4-carboxy-2-{[2-phenyl-6-(3-phenyl-propionylamino)-pyrimidine-4-carbonyl]-amino}-butyryl)-piperazine-1-carboxylic acid ethyl ester;

4-((S)-4-carboxy-2-{[6-(3-cyclopentyl-propionylamino)-2-phenyl-pyrimidine-4-carbonyl]-amino}-butyryl)-piperazine-1-carboxylic acid ethyl ester;

4-((S)-4-carboxy-2-{[6-(2,2-dimethyl-propionylamino)-2-phenyl-pyrimidine-4-carbonyl]-amino}-butyryl)-piperazine-1-carboxylic acid ethyl ester;

4-((S)-4-carboxy-2-{[2-phenyl-6-(2-propyl-pentanoylamino)-pyrimidine-4-carbonyl]-amino}-butyryl)-piperazine-1-carboxylic acid ethyl ester;

4-{(S)-2-[(6-benzoylamino-2-phenyl-pyrimidine-4-carbonyl)-amino]-4-carboxy-butyryl}-piperazine-1-carboxylic acid ethyl ester;

4-((S)-4-carboxy-2-{[6-(2-cyclopentyl-acetylamino)-2-phenyl-pyrimidine-4-carbonyl]-amino}-butyryl)-piperazine-1-carboxylic acid ethyl ester;

4-((S)-4-carboxy-2-{[6-(2-methoxy-acetylamino)-2-phenyl-pyrimidine-4-carbonyl]-amino}-butyryl)-piperazine-1-carboxylic acid ethyl ester;

4-((S)-4-carboxy-2-{[6-(cyclobutanecarbonyl-amino)-2-phenyl-pyrimidine-4-carbonyl]-amino}-butyryl)-piperazine-1-carboxylic acid ethyl ester;

4-((S)-4-carboxy-2-{[6-(cyclopentanecarbonyl-amino)-2-phenyl-pyrimidine-4-carbonyl]-amino}-butyryl)-piperazine-1-carboxylic acid ethyl ester;

4-{(S)-4-carboxy-2-[(6-pentanoylamino-2-phenyl-pyrimidine-4-carbonyl)-amino]-butyryl}-piperazine-1-carboxylic acid ethyl ester;

4-((S)-4-carboxy-2-{[6-(3-methyl-butyrylamino)-2-phenyl-pyrimidine-4-carbonyl]-amino}-butyryl)-piperazine-1-carboxylic acid ethyl ester;

4-((S)-4-carboxy-2-{[6-(cyclopropanecarbonyl-amino)-2-phenyl-pyrimidine-4-carbonyl]-amino}-butyryl)-piperazine-1-carboxylic acid ethyl ester;

4-{(S)-2-[(6-acetylamino-2-phenyl-pyrimidine-4-carbonyl)-amino]-4-carboxy-butyryl}-piperazine-1-carboxylic acid ethyl ester;

4-{(S)-2-[(6-butyrylamino-2-phenyl-pyrimidine-4-carbonyl)-amino]-4-carboxy-butyryl}-piperazine-1-carboxylic acid ethyl ester;

4-{(S)-4-carboxy-2-[(6-isobutyrylamino-2-phenyl-pyrimidine-4-carbonyl)-amino]-butyryl}-piperazine-1-carboxylic acid ethyl ester;

4-{(S)-4-carboxy-2-[(2-phenyl-6-propionylamino-pyrimidine-4-carbonyl)-amino]-butyryl}-piperazine-1-carboxylic acid ethyl ester;

4-((S)-4-carboxy-2-{[2-phenyl-6-(propane-1-sulfonylamino)-pyrimidine-4-carbonyl]-amino}-butyryl)-piperazine-1-carboxylic acid ethyl ester;

4-{(S)-4-carboxy-2-[(6-ethanesulfonylamino-2-phenyl-pyrimidine-4-carbonyl)-amino]-butyryl}-piperazine-1-carboxylic acid ethyl ester;

4-{(S)-2-[(6-benzenesulfonylamino-2-phenyl-pyrimidine-4-carbonyl)-amino]-4-carboxy-butyryl}-piperazine-1-carboxylic acid ethyl ester;

4-((S)-4-carboxy-2-{[2-phenyl-6-(propane-2-sulfonylamino)-pyrimidine-4-carbonyl]-amino}-butyryl)-piperazine-1-carboxylic acid ethyl ester;

4-((S)-4-carboxy-2-{[6-(4-oxo-4H-pyridin-1-yl)-2-phenyl-pyrimidine-4-carbonyl]-amino}-butyryl)-piperazine-1-carboxylic acid ethyl ester;

4-((S)-4-carboxy-2-{[6-(3-methyl-5-oxo-2,5-dihydro-pyrazol-1-yl)-2-phenyl-pyrimidine-4-carbonyl]-amino}-butyryl)-piperazine-1-carboxylic acid ethyl ester;

4-((S)-4-carboxy-2-{[6-(2-hydroxy-1-methyl-propylsulfanyl)-2-phenyl-pyrimidine-4-carbonyl]-amino}-butyryl)-piperazine-1-carboxylic acid ethyl ester;

4-((S)-4-carboxy-2-{[6-(2-hydroxy-propylsulfanyl)-2-phenyl-pyrimidine-4-carbonyl]-amino}-butyryl)-piperazine-1-carboxylic acid ethyl ester;

4-[(S)-2-({6-[(benzyl-methyl-amino)-methyl]-2-phenyl-pyrimidine-4-carbonyl}-amino)-4-carboxy-butyryl]-piperazine-1-carboxylic acid ethyl ester;

4-((S)-4-carboxy-2-{[6-(4-ethoxycarbonyl-piperidin-1-ylmethyl)-2-phenyl-pyrimidine-4-carbonyl]-amino}-butyryl)-piperazine-1-carboxylic acid ethyl ester;

4-((S)-4-carboxy-2-{[6-((S)-2-hydroxymethyl-pyrrolidin-1-ylmethyl)-2-phenyl-pyrimidine-4-carbonyl]-amino}-butyryl)-piperazine-1-carboxylic acid ethyl ester;

4-((S)-4-carboxy-2-{[6-(4-methoxycarbonyl-piperidin-1-ylmethyl)-2-phenyl-pyrimidine-4-carbonyl]-amino}-butyryl)-piperazine-1-carboxylic acid ethyl ester;

4-((S)-4-carboxy-2-{[6-(3-hydroxy-piperidin-1-ylmethyl)-2-phenyl-pyrimidine-4-carbonyl]-amino}-butyryl)-piperazine-1-carboxylic acid ethyl ester;

4-((S)-4-carboxy-2-{[6-(2-hydroxymethyl-piperidin-1-ylmethyl)-2-phenyl-pyrimidine-4-carbonyl]-amino}-butyryl)-piperazine-1-carboxylic acid ethyl ester;

4-{(S)-4-carboxy-2-[(6-morpholin-4-ylmethyl-2-phenyl-pyrimidine-4-carbonyl)-amino]-butyryl}-piperazine-1-carboxylic acid ethyl ester;

4-((S)-4-carboxy-2-{[6-((R)-3-hydroxy-pyrrolidin-1-ylmethyl)-2-phenyl-pyrimidine-4-carbonyl]-amino}-butyryl)-piperazine-1-carboxylic acid ethyl ester;

4-{(S)-4-carboxy-2-[(2-phenyl-6-piperidin-1-ylmethyl-pyrimidine-4-carbonyl)-amino]-butyryl}-piperazine-1-carboxylic acid ethyl ester;

4-((S)-4-carboxy-2-{[6-(2,6-dimethyl-morpholin-4-ylmethyl)-2-phenyl-pyrimidine-4-carbonyl]-amino}-butyryl)-piperazine-1-carboxylic acid ethyl ester;

4-[(S)-4-carboxy-2-({6-[(ethyl-methyl-amino)-methyl]-2-phenyl-pyrimidine-4-carbonyl}-amino)-butyryl]-piperazine-1-carboxylic acid ethyl ester;

4-{(S)-4-carboxy-2-[(6-diethylaminomethyl-2-phenyl-pyrimidine-4-carbonyl)-amino]-butyryl}-piperazine-1-carboxylic acid ethyl ester;

4-{(S)-4-carboxy-2-[(2-phenyl-6-pyrrolidin-1-ylmethyl-pyrimidine-4-carbonyl)-amino]-butyryl}-piperazine-1-carboxylic acid ethyl ester;

4-{(S)-4-carboxy-2-[(6-ethanesulfonylmethyl-2-phenyl-pyrimidine-4-carbonyl)-amino]-butyryl}-piperazine-1-carboxylic acid ethyl ester;

4-{(S)-4-carboxy-2-[(2-phenyl-6-phenylsulfanylmethyl-pyrimidine-4-carbonyl)-amino]-butyryl}-piperazine-1-carboxylic acid ethyl ester;

4-{(S)-2-[(6-benzenesulfonylmethyl-2-phenyl-pyrimidine-4-carbonyl)-amino]-4-carboxy-butyryl}-piperazine-1-carboxylic acid ethyl ester;

4-{(S)-4-carboxy-2-[(6-cyclopentylsulfanylmethyl-2-phenyl-pyrimidine-4-carbonyl)-amino]-butyryl}-piperazine-1-carboxylic acid ethyl ester;

4-{(S)-4-carboxy-2-[(6-cyclopentanesulfonylmethyl-2-phenyl-pyrimidine-4-carbonyl)-amino]-butyryl}-piperazine-1-carboxylic acid ethyl ester;

4-{(S)-4-carboxy-2-[(2-phenyl-6-thiophen-3-yl-pyrimidine-4-carbonyl)-amino]-butyryl}-piperazine-1-carboxylic acid ethyl ester;

4-((S)-4-carboxy-2-{[6-(2-methoxy-phenyl)-2-phenyl-pyrimidine-4-carbonyl]-amino}-butyryl)-piperazine-1-carboxylic acid ethyl ester;

4-((S)-4-carboxy-2-{[6-(4-methanesulfonyl-phenyl)-2-phenyl-pyrimidine-4-carbonyl]-amino}-butyryl)-piperazine-1-carboxylic acid ethyl ester;

4-((S)-2-{[6-(4-Acetyl-phenyl)-2-phenyl-pyrimidine-4-carbonyl]-amino}-4-carboxy-butyryl)-piperazine-1-carboxylic acid ethyl ester;
4-((S)-4-carboxy-2-{[6-(2-fluoro-phenyl)-2-phenyl-pyrimidine-4-carbonyl]-amino}-butyryl)-piperazine-1-carboxylic acid ethyl ester;
4-((S)-4-carboxy-2-{[6-(3-cyano-phenyl)-2-phenyl-pyrimidine-4-carbonyl]-amino}-butyryl)-piperazine-1-carboxylic acid ethyl ester;
4-((S)-4-carboxy-2-{[6-(3-fluoro-phenyl)-2-phenyl-pyrimidine-4-carbonyl]-amino}-butyryl)-piperazine-1-carboxylic acid ethyl ester;
4-((S)-4-carboxy-2-{[6-(4-methoxy-phenyl)-2-phenyl-pyrimidine-4-carbonyl]-amino}-butyryl)-piperazine-1-carboxylic acid ethyl ester;
4-{(S)-4-carboxy-2-[(6-furan-3-yl-2-phenyl-pyrimidine-4-carbonyl)-amino]-butyryl}-piperazine-1-carboxylic acid ethyl ester;
4-{(S)-2-[(6-benzo[1,3]dioxol-5-yl-2-phenyl-pyrimidine-4-carbonyl)-amino]-4-carboxy-butyryl}-piperazine-1-carboxylic acid ethyl ester;
4-((S)-4-carboxy-2-{[6-(3-methoxy-phenyl)-2-phenyl-pyrimidine-4-carbonyl]-amino}-butyryl)-piperazine-1-carboxylic acid ethyl ester;
4-((S)-4-carboxy-2-{[6-(4-hydroxymethyl-phenyl)-2-phenyl-pyrimidine-4-carbonyl]-amino}-butyryl)-piperazine-1-carboxylic acid ethyl ester;
4-{(S)-4-carboxy-2-[(2-phenyl-6-thiophen-2-yl-pyrimidine-4-carbonyl)-amino]-butyryl}-piperazine-1-carboxylic acid ethyl ester;
4-((S)-4-carboxy-2-{[6-(4-cyano-phenyl)-2-phenyl-pyrimidine-4-carbonyl]-amino}-butyryl)-piperazine-1-carboxylic acid ethyl ester;
4-((S)-4-carboxy-2-{[6-(3-chloro-phenyl)-2-phenyl-pyrimidine-4-carbonyl]-amino}-butyryl)-piperazine-1-carboxylic acid ethyl ester;
4-{(S)-2-[(6-biphenyl-4-yl-2-phenyl-pyrimidine-4-carbonyl)-amino]-4-carboxy-butyryl}-piperazine-1-carboxylic acid ethyl ester;
4-((S)-4-carboxy-2-{[2-phenyl-6-(1H-pyrazol-4-yl)-pyrimidine-4-carbonyl]-amino}-butyryl)-piperazine-1-carboxylic acid ethyl ester;
4-((S)-4-carboxy-2-{[2-phenyl-6-((E)-styryl)-pyrimidine-4-carbonyl]-amino}-butyryl)-piperazine-1-carboxylic acid ethyl ester;
4-((S)-4-carboxy-2-{[2-phenyl-6-(3-trifluoromethyl-phenyl)-pyrimidine-4-carbonyl]-amino}-butyryl)-piperazine-1-carboxylic acid ethyl ester;
4-{(S)-4-carboxy-2-[(2-phenyl-6-pyridin-3-yl-pyrimidine-4-carbonyl)-amino]-butyryl}-piperazine-1-carboxylic acid ethyl ester;
4-{(S)-4-carboxy-2-[(2-phenyl-6-pyridin-4-yl-pyrimidine-4-carbonyl)-amino]-butyryl}-piperazine-1-carboxylic acid ethyl ester;
4-{(S)-4-carboxy-2-[(2-phenyl-6-thiazol-2-yl-pyrimidine-4-carbonyl)-amino]-butyryl}-piperazine-1-carboxylic acid ethyl ester;
4-{(S)-2-[(6-acetyl-2-phenyl-pyrimidine-4-carbonyl)-amino]-4-carboxy-butyryl}-piperazine-1-carboxylic acid ethyl ester;
4-((S)-4-carboxy-2-{[6-(1-hydroxy-ethyl)-2-phenyl-pyrimidine-4-carbonyl]-amino}-butyryl)-piperazine-1-carboxylic acid ethyl ester;
4-((S)-4-carboxy-2-{[6-(1-methoxy-ethyl)-2-phenyl-pyrimidine-4-carbonyl]-amino}-butyryl)-piperazine-1-carboxylic acid ethyl ester;
4-((S)-4-carboxy-2-{[6-(1-ethoxy-ethyl)-2-phenyl-pyrimidine-4-carbonyl]-amino}-butyryl)-piperazine-1-carboxylic acid ethyl ester;
4-((S)-4-carboxy-2-{[6-(1-hydroxy-1-methyl-ethyl)-2-phenyl-pyrimidine-4-carbonyl]-amino}-butyryl)-piperazine-1-carboxylic acid ethyl ester;
4-((S)-4-ethoxycarbonyl-2-{[6-(1-hydroxy-1-methyl-ethyl)-2-phenyl-pyrimidine-4-carbonyl]-amino}-butyryl)-piperazine-1-carboxylic acid ethyl ester;
4-((S)-4-carboxy-2-{[6-(2-hydroxy-ethyl)-2-phenyl-pyrimidine-4-carbonyl]-amino}-butyryl)-piperazine-1-carboxylic acid ethyl ester;
4-((S)-4-carboxy-2-{[6-(2-methoxy-ethyl)-2-phenyl-pyrimidine-4-carbonyl]-amino}-butyryl)-piperazine-1-carboxylic acid ethyl ester;
4-((S)-4-carboxy-2-{[6-(2-hydroxy-cyclohexyl)-2-phenyl-pyrimidine-4-carbonyl]-amino}-butyryl)-piperazine-1-carboxylic acid ethyl ester;
4-((S)-4-carboxy-2-{[6-(2-methoxy-cyclohexyl)-2-phenyl-pyrimidine-4-carbonyl]-amino}-butyryl)-piperazine-1-carboxylic acid ethyl ester;
4-((S)-4-carboxy-2-{[6-(2-hydroxy-cyclopentyl)-2-phenyl-pyrimidine-4-carbonyl]-amino}-butyryl)-piperazine-1-carboxylic acid ethyl ester;
4-((S)-4-carboxy-2-{[6-(2-hydroxy-propyl)-2-phenyl-pyrimidine-4-carbonyl]-amino}-butyryl)-piperazine-1-carboxylic acid ethyl ester;
4-((S)-4-carboxy-2-{[6-(2-methoxy-propyl)-2-phenyl-pyrimidine-4-carbonyl]-amino}-butyryl)-piperazine-1-carboxylic acid ethyl ester;
4-((S)-4-carboxy-2-{[6-(3,6-dihydro-2H-pyran-4-yl)-2-phenyl-pyrimidine-4-carbonyl]-amino}-butyryl)-piperazine-1-carboxylic acid ethyl ester;
4-((S)-4-carboxy-2-{[2-phenyl-6-(tetrahydro-pyran-4-yl)-pyrimidine-4-carbonyl]-amino}-butyryl)-piperazine-1-carboxylic acid ethyl ester;
4-((S)-4-carboxy-2-{[6-(2-ethoxycarbonyl-cyclohexyl)-2-phenyl-pyrimidine-4-carbonyl]-amino}-butyryl)-piperazine-1-carboxylic acid ethyl ester;
4-((S)-4-carboxy-2-{[6-(1-oxy-pyridin-3-yl)-2-phenyl-pyrimidine-4-carbonyl]-amino}-butyryl)-piperazine-1-carboxylic acid ethyl ester;
4-((S)-4-carboxy-2-{[6-((E)-2-ethoxycarbonyl-vinyl)-2-phenyl-pyrimidine-4-carbonyl]-amino}-butyryl)-piperazine-1-carboxylic acid ethyl ester;
4-((S)-4-carboxy-2-{[2-phenyl-6-(tetrahydro-furan-2-ylmethyl)-pyrimidine-4-carbonyl]-amino}-butyryl)-piperazine-1-carboxylic acid ethyl ester;
4-((S)-4-carboxy-2-{[6-((E)-4-hydroxy-but-1-enyl)-2-phenyl-pyrimidine-4-carbonyl]-amino}-butyryl)-piperazine-1-carboxylic acid ethyl ester;
4-((S)-4-carboxy-2-{[6-(3-hydroxy-2-methyl-propyl)-2-phenyl-pyrimidine-4-carbonyl]-amino}-butyryl)-piperazine-1-carboxylic acid ethyl ester;
4-((S)-4-carboxy-2-{[2-phenyl-6-(tetrahydro-furan-3-yl)-pyrimidine-4-carbonyl]-amino}-butyryl)-piperazine-1-carboxylic acid ethyl ester;
4-((S)-4-carboxy-2-{[6-((E)-2-dimethylcarbamoyl-vinyl)-2-phenyl-pyrimidine-4-carbonyl]-amino}-butyryl)-piperazine-1-carboxylic acid ethyl ester;
4-{(S)-4-carboxy-2-[(6-cyano-2-phenyl-pyrimidine-4-carbonyl)-amino]-butyryl}-piperazine-1-carboxylic acid ethyl ester;
4-((S)-4-carboxy-2-{[6-(1-hydroxy-propyl)-2-phenyl-pyrimidine-4-carbonyl]-amino}-butyryl)-piperazine-1-carboxylic acid ethyl ester;

4-((S)-4-carboxy-2-{[6-(1-hydroxy-butyl)-2-phenyl-pyrimidine-4-carbonyl]-amino}-butyryl)-piperazine-1-carboxylic acid ethyl ester;
4-((S)-4-carboxy-2-{[6-(hydroxy-phenyl-methyl)-2-phenyl-pyrimidine-4-carbonyl]-amino}-butyryl)-piperazine-1-carboxylic acid ethyl ester;
4-((S)-4-carboxy-2-{[6-(2-hydroxy-2-phenyl-ethyl)-2-phenyl-pyrimidine-4-carbonyl]-amino}-butyryl)-piperazine-1-carboxylic acid ethyl ester;
4-{(S)-4-carboxy-2-[(6-ethoxymethyl-2-phenyl-pyrimidine-4-carbonyl)-amino]-butyryl}-piperazine-1-carboxylic acid ethyl ester;
4-{(S)-4-carboxy-2-[(2-phenyl-6-trifluoromethyl-pyrimidine-4-carbonyl)-amino]-butyryl}-piperazine-1-carboxylic acid ethyl ester;
4-{(S)-2-[(6-tert-butyl-2-phenyl-pyrimidine-4-carbonyl)-amino]-4-carboxy-butyryl}-piperazine-1-carboxylic acid ethyl ester;
4-{(S)-4-carboxy-2-[(6-phenoxy-2-phenyl-pyrimidine-4-carbonyl)-amino]-butyryl}-piperazine-1-carboxylic acid ethyl ester;
4-((S)-4-carboxy-2-{[2-phenyl-6-(pyridin-3-yloxy)-pyrimidine-4-carbonyl]-amino}-butyryl)-piperazine-1-carboxylic acid ethyl ester;
(S)-5-(4-tert-butylcarbamoyl-piperazin-1-yl)-4-[(6-cyclopentyloxy-2-phenyl-pyrimidine-4-carbonyl)-amino]-5-oxo-pentanoic acid;
(S)-4-[(6-cyclopentyloxy-2-phenyl-pyrimidine-4-carbonyl)-amino]-5-(4-isopropylcarbamoyl-piperazin-1-yl)-5-oxo-pentanoic acid;
(S)-4-[(6-cyclopentyloxy-2-phenyl-pyrimidine-4-carbonyl)-amino]-5-oxo-5-[4-(thiophene-2-carbonyl)-piperazin-1-yl]-pentanoic acid;
(S)-5-(4-cyclopentanecarbonyl-piperazin-1-yl)-4-[(6-cyclopentyloxy-2-phenyl-pyrimidine-4-carbonyl)-amino]-5-oxo-pentanoic acid;
(S)-4-[(6-cyclopentyloxy-2-phenyl-pyrimidine-4-carbonyl)-amino]-5-oxo-5-[4-(piperidine-1-carbonyl)-piperazin-1-yl]-pentanoic acid;
4-(4-tert-butoxycarbonyl-2-{[6-((S)-3-methoxy-pyrrolidin-1-yl)-2-phenyl-pyrimidine-4-carbonyl]-amino}-butyryl)-piperazine-1-carboxylic acid ethyl ester;
4-((S)-4-tert-butoxycarbonyl-2-{[6-((S)-2-methoxy-1-methyl-ethylamino)-2-phenyl-pyrimidine-4-carbonyl]-amino}-butyryl)-piperazine-1-carboxylic acid ethyl ester;
4-((S)-4-tert-butoxycarbonyl-2-{[6-(4-methoxy-piperidin-1-yl)-2-phenyl-pyrimidine-4-carbonyl]-amino}-butyryl)-piperazine-1-carboxylic acid ethyl ester;
4-(4-tert-butoxycarbonyl-2-{[6-((R)-3-methoxy-pyrrolidin-1-yl)-2-phenyl-pyrimidine-4-carbonyl]-amino}-butyryl)-piperazine-1-carboxylic acid ethyl ester;
4-((S)-4-tert-butoxycarbonyl-2-{[6-((R)-2-methoxy-1-methyl-ethylamino)-2-phenyl-pyrimidine-4-carbonyl]-amino}-butyryl)-piperazine-1-carboxylic acid ethyl ester;
4-((S)-4-tert-butoxycarbonyl-2-{[6-(2-methoxymethyl-piperidin-1-yl)-2-phenyl-pyrimidine-4-carbonyl]-amino}-butyryl)-piperazine-1-carboxylic acid ethyl ester;
4-((S)-4-tert-butoxycarbonyl-2-{[6-((S)-2-methoxymethyl-pyrrolidin-1-yl)-2-phenyl-pyrimidine-4-carbonyl]-amino}-butyryl)-piperazine-1-carboxylic acid ethyl ester;
4-((S)-4-tert-butoxycarbonyl-2-{[6-((R)-2-methoxymethyl-pyrrolidin-1-yl)-2-phenyl-pyrimidine-4-carbonyl]-amino}-butyryl)-piperazine-1-carboxylic acid ethyl ester;
4-((S)-4-tert-butoxycarbonyl-2-{[6-(2-methoxy-1,1-dimethyl-ethylamino)-2-phenyl-pyrimidine-4-carbonyl]-amino}-butyryl)-piperazine-1-carboxylic acid ethyl ester;
4-((S)-4-tert-butoxycarbonyl-2-{[6-(4,5-dihydro-pyrazol-1-yl)-2-phenyl-pyrimidine-4-carbonyl]-amino}-butyryl)-piperazine-1-carboxylic acid ethyl ester;
4-((S)-4-tert-butoxycarbonyl-2-{[6-(2-methyl-4,5-dihydro-imidazol-1-yl)-2-phenyl-pyrimidine-4-carbonyl]-amino}-butyryl)-piperazine-1-carboxylic acid ethyl ester;
4-{(S)-4-tert-butoxycarbonyl-2-[(2-phenyl-6-[1,2,4]triazol-1-yl-pyrimidine-4-carbonyl)-amino]-butyryl}-piperazine-1-carboxylic acid ethyl ester;
4-((S)-4-tert-butoxycarbonyl-2-{[6-(4-methyl-pyrazol-1-yl)-2-phenyl-pyrimidine-4-carbonyl]-amino}-butyryl)-piperazine-1-carboxylic acid ethyl ester;
4-((S)-4-tert-butoxycarbonyl-2-{[6-(3-methyl-pyrazol-1-yl)-2-phenyl-pyrimidine-4-carbonyl]-amino}-butyryl)-piperazine-1-carboxylic acid ethyl ester;
4-((S)-2-{[6-(4-butyl-[1,2,3]triazol-1-yl)-2-phenyl-pyrimidine-4-carbonyl]-amino}-4-tert-butoxycarbonyl-butyryl)-piperazine-1-carboxylic acid ethyl ester;
4-{(S)-2-[(6-amino-2-phenyl-pyrimidine-4-carbonyl)-amino]-4-tert-butoxycarbonyl-butyryl}-piperazine-1-carboxylic acid ethyl ester;
4-((S)-4-tert-butoxycarbonyl-2-{[6-(3-methyl-5-oxo-2,5-dihydro-pyrazol-1-yl)-2-phenyl-pyrimidine-4-carbonyl]-amino}-butyryl)-piperazine-1-carboxylic acid ethyl ester;
4-{(S)-4-tert-butoxycarbonyl-2-[(6-ethanesulfonylmethyl-2-phenyl-pyrimidine-4-carbonyl)-amino]-butyryl}-piperazine-1-carboxylic acid ethyl ester;
4-{(S)-4-tert-butoxycarbonyl-2-[(6-ethylsulfanylmethyl-2-phenyl-pyrimidine-4-carbonyl)-amino]-butyryl}-piperazine-1-carboxylic acid ethyl ester;
4-{(S)-2-[(6-benzenesulfonylmethyl-2-phenyl-pyrimidine-4-carbonyl)-amino]-4-tert-butoxycarbonyl-butyryl}-piperazine-1-carboxylic acid ethyl ester;
4-{(S)-4-tert-butoxycarbonyl-2-[(6-cyclopentylsulfanylmethyl-2-phenyl-pyrimidine-4-carbonyl)-amino]-butyryl}-piperazine-1-carboxylic acid ethyl ester;
4-{(S)-4-tert-butoxycarbonyl-2-[(6-cyclopentanesulfonylmethyl-2-phenyl-pyrimidine-4-carbonyl)-amino]-butyryl}-piperazine-1-carboxylic acid ethyl ester;
4-{(S)-4-tert-butoxycarbonyl-2-[(2-phenyl-6-pyridin-3-yl-pyrimidine-4-carbonyl)-amino]-butyryl}-piperazine-1-carboxylic acid ethyl ester;
4-{(S)-4-tert-butoxycarbonyl-2-[(2-phenyl-6-pyridin-4-yl-pyrimidine-4-carbonyl)-amino]-butyryl}-piperazine-1-carboxylic acid ethyl ester;
4-{(S)-4-tert-butoxycarbonyl-2-[(2-phenyl-6-thiazol-2-yl-pyrimidine-4-carbonyl)-amino]-butyryl}-piperazine-1-carboxylic acid ethyl ester;
4-{(S)-2-[(6-acetyl-2-phenyl-pyrimidine-4-carbonyl)-amino]-4-tert-butoxycarbonyl-butyryl}-piperazine-1-carboxylic acid ethyl ester;
4-((S)-4-tert-butoxycarbonyl-2-{[6-(1-hydroxy-ethyl)-2-phenyl-pyrimidine-4-carbonyl]-amino}-butyryl)-piperazine-1-carboxylic acid ethyl ester;
4-((S)-4-tert-butoxycarbonyl-2-{[6-(1-methoxy-ethyl)-2-phenyl-pyrimidine-4-carbonyl]-amino}-butyryl)-piperazine-1-carboxylic acid ethyl ester;

4-((S)-4-tert-butoxycarbonyl-2-{[6-(1-ethoxy-ethyl)-2-phenyl-pyrimidine-4-carbonyl]-amino}-butyryl)-piperazine-1-carboxylic acid ethyl ester;
4-((S)-4-tert-butoxycarbonyl-2-{[6-(1-hydroxy-1-methyl-ethyl)-2-phenyl-pyrimidine-4-carbonyl]-amino}-butyryl)-piperazine-1-carboxylic acid ethyl ester;
4-((S)-4-tert-butoxycarbonyl-2-{[6-(2-hydroxy-ethyl)-2-phenyl-pyrimidine-4-carbonyl]-amino}-butyryl)-piperazine-1-carboxylic acid ethyl ester;
4-((S)-4-tert-butoxycarbonyl-2-{[6-(2-methoxy-ethyl)-2-phenyl-pyrimidine-4-carbonyl]-amino}-butyryl)-piperazine-1-carboxylic acid ethyl ester;
4-((S)-4-tert-butoxycarbonyl-2-{[6-(2-hydroxy-cyclohexyl)-2-phenyl-pyrimidine-4-carbonyl]-amino}-butyryl)-piperazine-1-carboxylic acid ethyl ester;
4-((S)-4-tert-butoxycarbonyl-2-{[6-(2-methoxy-cyclohexyl)-2-phenyl-pyrimidine-4-carbonyl]-amino}-butyryl)-piperazine-1-carboxylic acid ethyl ester;
4-((S)-4-tert-butoxycarbonyl-2-{[6-(2-hydroxy-cyclopentyl)-2-phenyl-pyrimidine-4-carbonyl]-amino}-butyryl)-piperazine-1-carboxylic acid ethyl ester;
4-((S)-4-tert-butoxycarbonyl-2-{[6-(2-hydroxy-propyl)-2-phenyl-pyrimidine-4-carbonyl]-amino}-butyryl)-piperazine-1-carboxylic acid ethyl ester;
4-((S)-4-tert-butoxycarbonyl-2-{[6-(2-methoxy-propyl)-2-phenyl-pyrimidine-4-carbonyl]-amino}-butyryl)-piperazine-1-carboxylic acid ethyl ester;
4-((S)-4-tert-butoxycarbonyl-2-{[6-(3,6-dihydro-2H-pyran-4-yl)-2-phenyl-pyrimidine-4-carbonyl]-amino}-butyryl)-piperazine-1-carboxylic acid ethyl ester;
4-((S)-4-tert-butoxycarbonyl-2-{[2-phenyl-6-(tetrahydro-pyran-4-yl)-pyrimidine-4-carbonyl]-amino}-butyryl)-piperazine-1-carboxylic acid ethyl ester;
4-((S)-4-tert-butoxycarbonyl-2-{[6-(2-ethoxycarbonyl-cyclohexyl)-2-phenyl-pyrimidine-4-carbonyl]-amino}-butyryl)-piperazine-1-carboxylic acid ethyl ester;
4-((S)-4-tert-butoxycarbonyl-2-{[6-(1-oxy-pyridin-3-yl)-2-phenyl-pyrimidine-4-carbonyl]-amino}-butyryl)-piperazine-1-carboxylic acid ethyl ester;
4-((S)-4-tert-butoxycarbonyl-2-{[6-((E)-2-ethoxycarbonyl-vinyl)-2-phenyl-pyrimidine-4-carbonyl]-amino}-butyryl)-piperazine-1-carboxylic acid ethyl ester;
4-((S)-4-tert-butoxycarbonyl-2-{[2-phenyl-6-(tetrahydro-furan-2-ylmethyl)-pyrimidine-4-carbonyl]-amino}-butyryl)-piperazine-1-carboxylic acid ethyl ester;
4-((S)-4-tert-butoxycarbonyl-2-{[6-(3-hydroxy-2-methyl-propyl)-2-phenyl-pyrimidine-4-carbonyl]-amino}-butyryl)-piperazine-1-carboxylic acid ethyl ester;
4-((S)-4-tert-butoxycarbonyl-2-{[2-phenyl-6-(tetrahydro-furan-3-yl)-pyrimidine-4-carbonyl]-amino}-butyryl)-piperazine-1-carboxylic acid ethyl ester;
4-((S)-4-tert-butoxycarbonyl-2-{[6-((E)-2-dimethylcarbamoyl-vinyl)-2-phenyl-pyrimidine-4-carbonyl]-amino}-butyryl)-piperazine-1-carboxylic acid ethyl ester;
4-((S)-4-tert-butoxycarbonyl-2-{[6-(1-hydroxy-propyl)-2-phenyl-pyrimidine-4-carbonyl]-amino}-butyryl)-piperazine-1-carboxylic acid ethyl ester;
4-((S)-4-tert-butoxycarbonyl-2-{[6-(1-hydroxy-butyl)-2-phenyl-pyrimidine-4-carbonyl]-amino}-butyryl)-piperazine-1-carboxylic acid ethyl ester;
4-((S)-4-tert-butoxycarbonyl-2-{[6-(hydroxy-phenyl-methyl)-2-phenyl-pyrimidine-4-carbonyl]-amino}-butyryl)-piperazine-1-carboxylic acid ethyl ester;
4-((S)-4-tert-butoxycarbonyl-2-{[6-(2-hydroxy-2-phenyl-ethyl)-2-phenyl-pyrimidine-4-carbonyl]-amino}-butyryl)-piperazine-1-carboxylic acid ethyl ester;
4-{(S)-4-tert-butoxycarbonyl-2-[(2-phenyl-6-trifluoromethyl-pyrimidine-4-carbonyl)-amino]-butyryl}-piperazine-1-carboxylic acid ethyl ester;
4-{(S)-2-[(6-tert-butyl-2-phenyl-pyrimidine-4-carbonyl)-amino]-4-tert-butyloxycarbonyl-butyryl}-piperazine-1-carboxylic acid ethyl ester;
4-{(S)-4-tert-butoxycarbonyl-2-[(6-phenoxy-2-phenyl-pyrimidine-4-carbonyl)-amino]-butyryl}-piperazine-1-carboxylic acid ethyl ester;
4-((S)-4-carboxy-2-{[6-(1-oxy-pyridin-2-yl)-2-phenyl-pyrimidine-4-carbonyl]-amino}-butyryl)-piperazine-1-carboxylic acid ethyl ester;
4-((S)-4-carboxy-2-{[6-(1-oxy-pyridin-4-yl)-2-phenyl-pyrimidine-4-carbonyl]-amino}-butyryl)-piperazine-1-carboxylic acid ethyl ester;
4-((S)-4-carboxy-2-{[6-(2-hydroxy-1,1-dimethyl-ethyl)-2-phenyl-pyrimidine-4-carbonyl]-amino}-butyryl)-piperazine-1-carboxylic acid ethyl ester;
4-((S)-4-tert-butoxycarbonyl-2-{[6-(1-oxy-pyridin-2-yl)-2-phenyl-pyrimidine-4-carbonyl]-amino}-butyryl)-piperazine-1-carboxylic acid ethyl ester;
4-((S)-4-tert-butoxycarbonyl-2-{[6-(1-oxy-pyridin-4-yl)-2-phenyl-pyrimidine-4-carbonyl]-amino}-butyryl)-piperazine-1-carboxylic acid ethyl ester;
4-((S)-4-tert-butoxycarbonyl-2-{[6-(2-hydroxy-1,1-dimethyl-ethyl)-2-phenyl-pyrimidine-4-carbonyl]-amino}-butyryl)-piperazine-1-carboxylic acid ethyl ester;
4-((S)-4-tert-butoxycarbonyl-2-{[6-(2-hydroxymethyl-cyclopropyl)-2-phenyl-pyrimidine-4-carbonyl]-amino}-butyryl)-piperazine-1-carboxylic acid ethyl ester; and
4-((S)-4-carboxy-2-{[6-(2-hydroxymethyl-cyclopropyl)-2-phenyl-pyrimidine-4-carbonyl]-amino}-butyryl)-piperazine-1-carboxylic acid ethyl ester, or a pharmaceutically acceptable salt thereof.

14. The compound of formula I according to claim 1 which is also a compound of formula $I_{CE}$

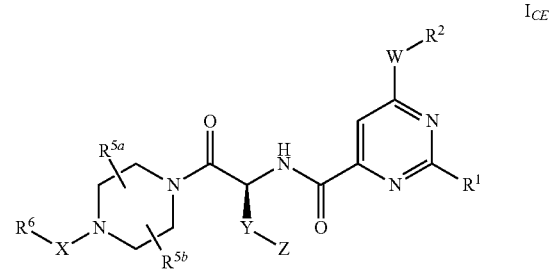

wherein
$R^1$ represents phenyl optionally substituted once by a substituent selected from the group consisting of halogen, methyl, methoxy, trifluoromethyl and trifluoromethoxy;
W represents a bond, and $R^2$ represents alkyl; haloalkyl; cyano; hydroxyalkyl;
hydroxyalkyl substituted on its alkyl chain with an unsubstituted phenyl group; alkoxyalkyl; heterocyclyl; heterocyclylalkyl; cycloalkyl of 3 to 7 carbon atoms optionally substituted once by a group selected from hydroxy, hydroxymethyl, alkoxy and alkoxycarbonyl; phenyl optionally substituted once by a group selected from halogen, alkyl, alkoxy, hydroxymethyl, acetyl, methanesulfonyl, trifluoromethyl, carboxy and cyano; biphenyl-4-yl; an unsubstituted monocyclic heteroaryl; 1-oxy-pyridin-2-yl; 1-oxy-pyridin-3-yl; 1-oxy-pyridin-4-yl; benzo[1,3]dioxol-5-yl; or one of the radicals

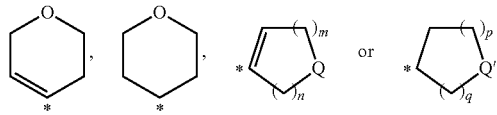

wherein:
m is 1 and n is 2,
p is 1 and q is 2,
Q is —CO— or —CH(OR$^a$)—, R$^a$ being hydrogen, and Q' is —CO—; or
W represents —CH$_2$— and R$^2$ represents —NR$^7$R$^8$, —SR$^9$ or —SO$_2$R$^{10}$; or
W represents —O— and R$^2$ represents alkyl, carboxyalkyl, hydroxyalkyl, cycloalkyl, cycloalkylalkyl, phenyl, phenylalkyl or an unsubstituted monocyclic heteroaryl; or
W represents —S— and R$^2$ represents alkyl, carboxyalkyl, alkoxycarbonylalkyl, hydroxyalkyl, unsubstituted cycloalkyl of 3 to 7 carbon atoms, phenyl, phenylalkyl or heteroarylalkyl wherein the heteroaryl is an unsubstituted monocyclic heteroaryl; or
W represents —NR$^3$— and R$^2$ represents hydrogen, alkyl, dialkylaminoalkyl, alkoxycarbonylalkyl, carboxyalkyl, carboxyalkyl substituted on its alkyl part with an unsubstituted phenyl group, hydroxyalkyl, alkoxyalkyl, heterocyclyl, heterocyclylalkyl, cycloalkyl, phenyl optionally substituted once by halogen, indan-1-yl, indan-2-yl, 2-phenylcyclopropyl, phenylalkyl, diphenylalkyl, —COR$^{11}$ or —SO$_2$R$^{12}$;
W represents —CH=CH— and R$^2$ represents hydroxyalkyl, alkoxycarbonyl, phenyl or —CO—NR$^{13}$R$^{14}$; or
W represents —C≡C— and R$^2$ represents hydrogen or hydroxyalkyl; or
W represents —CO— and R$^2$ represents alkyl;
R$^3$ represents hydrogen or alkyl;
R$^7$ represents alkyl or phenylalkyl;
R$^8$ represents alkyl;
or R$^7$ and R$^8$ form, together with the nitrogen that carries them, a heterocyclic ring of 4 to 7 members wherein the members needed to complete said heterocyclic ring are each independently selected from —CH$_2$—, —CH(CH$_3$)—, —CHR$^y$— or —O—, and said heterocyclic ring does not contain more than one member selected from the group consisting of —CHR$^y$— and —O—, R$^y$ representing hydroxy, hydroxymethyl or alkoxycarbonyl;
R$^9$ represents unsubstituted cycloalkyl of 3 to 7 carbon atoms or phenyl;
R$^{10}$ represents alkyl, unsubstituted cycloalkyl of 3 to 7 carbon atoms or phenyl;
R$^{11}$ represents alkyl, alkoxyalkyl, unsubstituted cycloalkyl of 3 to 7 carbon atoms, cycloalkylalkyl wherein the cycloalkyl is an unsubstituted cycloalkyl of 3 to 7 carbon atoms, phenyl, monocyclic heteroaryl or phenylalkyl;
R$^{12}$ represents alkyl or phenyl;
R$^{13}$ represents alkyl;
R$^{14}$ represents alkyl;
or, when W represents —NR$^3$—, R$^2$ and R$^3$ can form, together with the nitrogen that carries them, a heterocyclic ring of 4 to 7 members wherein the members needed to complete said heterocyclic ring are each independently selected from —CH$_2$—, —CHR$^x$—, —O—, —S— and —NR$^4$—, and said heterocyclic ring does not contain more than one member selected from the group consisting of —CHR$^x$—, —O—, —S— and —NR$^4$, R$^x$ representing hydroxy, methoxy, hydroxymethyl or methoxymethyl and R$^4$ representing hydrogen;
or, when W represents —NR$^3$—, R$^2$ and R$^3$ can form, together with the nitrogen that carries them, either an imidazolyl, pyrazolyl, 1,2,3-triazolyl or 1,2,4-triazolyl ring, which ring may be substituted by an alkyl group, or a 4-oxo-4H-pyridin-1-yl, 4,5-dihydro-pyrazol-1-yl, 2-methyl-4,5-dihydro-imidazol-1-yl or 3-methyl-5-oxo-2,5-dihydro-pyrazol-1-yl;
each of R$^{5a}$ and R$^{5b}$ represents independently hydrogen or methyl;
X represents —CO— and R$^6$ represents alkoxy, alkynyloxy, phenoxy, phenyl, heteroaryl of 5 ring members, phenylalkyl or NR$^{15}$R$^{16}$, or X represents —SO$_2$— and R$^6$ represents alkyl;
R$^{15}$ represents alkyl;
R$^{16}$ represents hydrogen;
or R$^{15}$ and R$^{16}$ form, together with the nitrogen that carries them, a heterocyclic ring of 4 to 7 members, wherein the members needed to complete said heterocyclic ring are each —CH$_2$—; and
Y represents a bond and Z represents hydrogen or phenyl substituted by carboxyalkoxy;
or Y represents alkylene, alkoxyalkylene, phenylalkylene, alkoxyphenylene or alkoxyphenylalkylene and Z represents hydrogen, —OH, —NH$_2$, —COOH, tetrazolyl, —CO—NH$_2$, —NH—CO—R$^{17}$, —NH—COOR$^{17}$ or —NH—SO$_2$—R$^{17}$, R$^{17}$ representing alkyl;
or a pharmaceutically acceptable salt thereof.

15. A pharmaceutical composition containing at least one compound of formula I as defined in claim 1, or a pharmaceutically acceptable salt thereof, and a pharmaceutically acceptable carrier, diluent or excipient.

16. A method for treating thrombosis, comprising administering to a subject in need thereof the compound of formula I as defined in claim 1, or of a pharmaceutically acceptable salt thereof.

\* \* \* \* \*